(12) United States Patent
Brizgys et al.

(10) Patent No.: US 9,873,680 B2
(45) Date of Patent: Jan. 23, 2018

(54) THERAPEUTIC COMPOUNDS

(71) Applicant: Gilead Sciences, Inc., Foster City, CA (US)

(72) Inventors: Gediminas Brizgys, Menlo Park, CA (US); Eda Canales, San Mateo, CA (US); Randall L. Halcomb, Foster City, CA (US); Yunfeng Eric Hu, San Mateo, CA (US); Darryl Kato, San Francisco, CA (US); John O. Link, San Francisco, CA (US); Qi Liu, Union City, CA (US); Roland D. Saito, San Mateo, CA (US); Winston C. Tse, Redwood City, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/836,774

(22) Filed: Aug. 26, 2015

(65) Prior Publication Data

US 2016/0083368 A1    Mar. 24, 2016

Related U.S. Application Data

(60) Provisional application No. 62/044,135, filed on Aug. 29, 2014.

(51) Int. Cl.

| | |
|---|---|
| *C07D 401/14* | (2006.01) |
| *C07D 403/14* | (2006.01) |
| *C07D 405/14* | (2006.01) |
| *C07D 413/14* | (2006.01) |
| *C07D 471/04* | (2006.01) |
| *C07D 493/04* | (2006.01) |
| *C07D 498/04* | (2006.01) |
| *A61K 31/4439* | (2006.01) |
| *A61K 31/444* | (2006.01) |
| *A61K 31/4709* | (2006.01) |
| *A61K 31/496* | (2006.01) |
| *A61K 31/506* | (2006.01) |
| *A61K 31/5377* | (2006.01) |
| *A61K 45/06* | (2006.01) |
| *C07D 519/00* | (2006.01) |

(52) U.S. Cl.
CPC .......... *C07D 401/14* (2013.01); *A61K 31/444* (2013.01); *A61K 31/4439* (2013.01); *A61K 31/4709* (2013.01); *A61K 31/496* (2013.01); *A61K 31/506* (2013.01); *A61K 31/5377* (2013.01); *A61K 45/06* (2013.01); *C07D 403/14* (2013.01); *C07D 405/14* (2013.01); *C07D 413/14* (2013.01); *C07D 471/04* (2013.01); *C07D 493/04* (2013.01); *C07D 498/04* (2013.01); *C07D 519/00* (2013.01)

(58) Field of Classification Search
CPC .. C07D 401/14; C07D 403/14; C07D 405/14; C07D 413/14; C07D 471/04; C07D 493/04; C07D 498/04
See application file for complete search history.

(56) References Cited

U.S. PATENT DOCUMENTS

| | | | |
|---|---|---|---|
| 9,012,441 | B2 | 4/2015 | Bondy et al. |
| 9,050,344 | B2 | 6/2015 | Brizgys et al. |
| 9,220,710 | B2 | 12/2015 | Bondy et al. |
| 9,540,343 | B2 | 1/2017 | Bondy et al. |
| 2014/0142085 | A1 | 5/2014 | Bondy et al. |
| 2014/0296266 | A1 | 10/2014 | Hu et al. |
| 2016/0067224 | A1 | 3/2016 | Bondy et al. |
| 2016/0108030 | A1 | 4/2016 | Brizgys et al. |
| 2016/0368881 | A1 | 12/2016 | Bondy et al. |

FOREIGN PATENT DOCUMENTS

| | | |
|---|---|---|
| WO | WO-2013006738 A1 | 1/2013 |
| WO | WO-2014110297 A1 | 7/2014 |
| WO | WO-2014134566 A2 | 9/2014 |

OTHER PUBLICATIONS

International Search Report and Written Opinion dated Oct. 12, 2015 for PCT/US2015/047040.
International Preliminary Report on Patentability dated Feb. 28, 2017 for PCT/US2015/047040.

*Primary Examiner* — Rebecca L Anderson

(57) ABSTRACT

Compounds of formula I:

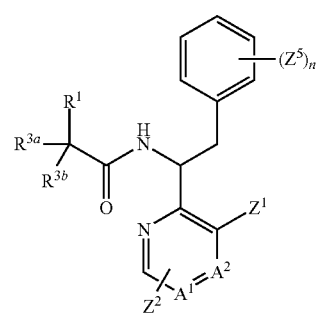

or salts thereof are disclosed. Also disclosed are pharmaceutical compositions comprising a compound of formula I, processes for preparing compounds of formula I, intermediates useful for preparing compounds of formula I and therapeutic methods for treating a Retroviridae viral infection including an infection caused by the HIV virus.

40 Claims, No Drawings

THERAPEUTIC COMPOUNDS

CROSS REFERENCE TO RELATED APPLICATIONS

This application claims the benefit of and priority to U.S. Provisional Patent Application Ser. No. 62/044,135, filed Aug. 29, 2014, the disclosure of which is hereby incorporated by reference in its entirety.

BACKGROUND

Positive-single stranded RNA viruses comprising the Retroviridae family include those of the subfamily Orthoretrovirinae and genera *Alpharetrovirus, Betaretrovirus, Gamaretrovirus, Deltaretrovirus, Epsilonretrovirus, Lentivirus*, and *Spumavirus* which cause many human and animal diseases. Among the *Lentivirus*, HIV-1 infection in humans leads to depletion of T helper cells and immune dysfunction, producing immunodeficiency and vulnerability to opportunistic infections. Though progress has been made in treating HIV-1 infections (Hammer, S. M., et al.; *JAMA* 2008, 300: 555-570), HIV infections remain a global health concern. As such, there remains a pressing need to discover new antiretroviral agents that are active against HIV.

SUMMARY

Provided herein are compounds and methods for the treatment of HIV (i.e., human immunodeficiency virus) infection.

One embodiment provides a compound of formula I:

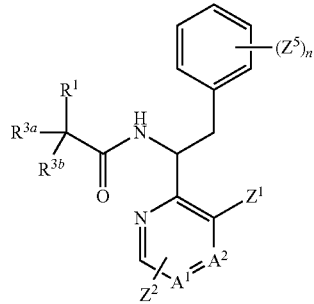

wherein
$A^1$ is C—$Z^3$ or nitrogen;
$A^2$ is C—$Z^3$ or nitrogen;
$R^1$ is 6-12 membered aryl, 5-12 membered heteroaryl, or 3-12 membered heterocycle, wherein any 6-12 membered aryl, 5-12 membered heteroaryl, or 3-12 membered heterocycle of $R^1$ is optionally substituted with 1, 2, 3, 4 or 5 $Z^4$ groups, wherein the $Z^4$ groups are the same or different;
each $R^{3a}$ and $R^{3b}$ is independently H or $(C_1\text{-}C_3)$alkyl;
$Z^1$ is 6-12 membered aryl, 5-14 membered heteroaryl, or 3-14 membered heterocycle, wherein any 6-12 membered aryl, 5-14 membered heteroaryl, or 3-14 membered heterocycle of $Z^1$ is optionally substituted with 1, 2, 3, 4 or 5 $Z^{1a}$ or $Z^{1b}$, wherein the $Z^{1a}$ and $Z^{1b}$ groups are the same or different;
each $Z^{1a}$ is independently oxo, $(C_3\text{-}C_7)$carbocycle, 5-12 membered heteroaryl, 3-12 membered heterocycle, halogen, —CN, —$OR^{n1}$, —$OC(O)R^{p1}$, —$OC(O)NR^{q1}R^{r1}$, —$SR^{n1}$, —$S(O)R^{p1}$, —$S(O)_2OH$, —$S(O)_2R^{p1}$, —$S(O)_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2OR^{p1}$, —$NR^{n1}S(O)_2NR^{q1}R^{r1}$, —$C(O)R^{n1}$, —$C(O)OR^{n1}$, —$C(O)NR^{q1}R^{r1}$ and —$S(O)_2NR^{n1}COR^{p1}$, wherein any $(C_3\text{-}C_7)$ carbocycle, 5-12 membered heteroaryl and 3-12 membered heterocycle of $Z^{1a}$ is optionally substituted with 1, 2, 3, 4 or 5 $Z^{1c}$ or $Z^{1d}$ groups, wherein the $Z^{1c}$ and $Z^{1d}$ groups are the same or different;
each $Z^{1b}$ is independently $(C_1\text{-}C_8)$alkyl optionally substituted with 1, 2, 3, 4 or 5 halogen, which are the same or different;
each $Z^{1c}$ is independently halogen, —CN, —OH, —$NH_2$, —$C(O)NR^{q2}R^{r2}$, or $(C_1\text{-}C_8)$heteroalkyl;
each $Z^{1d}$ is independently $(C_1\text{-}C_8)$alkyl or $(C_1\text{-}C_8)$haloalkyl;
each $R^{n1}$ is independently H, $(C_1\text{-}C_8)$alkyl, $(C_3\text{-}C_7)$carbocycle, 3-7 membered heterocycle, or 5-6 membered monocyclic-heteroaryl, wherein any $(C_3\text{-}C_7)$carbocycle, 3-7 membered heterocycle, or 5-6 membered monocyclic-heteroaryl of $R^{n1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1\text{-}C_8)$alkyl of $R^{n1}$ is optionally substituted with 1, 2, 3, 4 or 5 $Z^{1c}$ groups, wherein the $Z^{1c}$ groups are the same or different;
each $R^{p1}$ is independently $(C_1\text{-}C_8)$alkyl, $(C_3\text{-}C_7)$carbocycle, 3-7 membered heterocycle, or 5-6 membered monocyclic-heteroaryl, wherein any $(C_3\text{-}C_7)$carbocycle, 3-7 membered heterocycle, or 5-6 membered monocyclic-heteroaryl of $R^{p1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1\text{-}C_8)$alkyl of $R^{p1}$ is optionally substituted with 1, 2, 3, 4 or 5 $Z^{1c}$ groups, wherein the $Z^{1c}$ groups are the same or different;
each $R^{q1}$ and $R^{r1}$ is independently H, $(C_1\text{-}C_8)$alkyl, $(C_3\text{-}C_7)$carbocycle, 3-7 membered heterocycle, or 5-6 membered monocyclic-heteroaryl, wherein any $(C_3\text{-}C_7)$carbocycle, 3-7 membered heterocycle, or 5-6 membered monocyclic-heteroaryl of $R^{q1}$ or $R^{r1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1\text{-}C_8)$alkyl of $R^{q1}$ or $R^{r1}$ is optionally substituted with 1, 2, 3, 4 or 5 $Z^{1c}$ groups, wherein the $Z^{1c}$ groups are the same or different, or $R^{q1}$ and $R^{r1}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups, wherein the $Z^{1c}$ and $Z^{1d}$ groups are the same or different;
each $R^{q2}$ and $R^{r2}$ is independently H, $(C_1\text{-}C_8)$alkyl, $(C_3\text{-}C_7)$carbocycle, or $R^{q2}$ and $R^{r2}$ together with the nitrogen to which they are attached form a 5, 6, or 7-membered heterocycle;
$Z^2$ is $(C_2\text{-}C_8)$alkenyl, $(C_2\text{-}C_8)$alkynyl, 6-12 membered aryl, 5-12 membered heteroaryl, 3-12 membered heterocycle, wherein any $(C_2\text{-}C_8)$alkenyl, $(C_2\text{-}C_8)$alkynyl, 6-12 membered aryl, 5-12 membered heteroaryl, or 3-12 membered heterocycle of $Z^2$ is substituted with 1 or 2 $Z^{2b}$ groups and optionally 1, 2, or 3 $Z^{2c}$ groups, wherein the $Z^{2b}$ and $Z^{2c}$ groups are the same or different;
each $R^{n3}$ is independently H or $(C_1\text{-}C_4)$alkyl;
each $R^{q3}$ and $R^{r3}$ is independently H or $(C_1\text{-}C_4)$alkyl;
each $Z^{2b}$ is independently 6-12 membered aryl, 5-12 membered heteroaryl, 3-9 membered carbocycle, 3-12 membered heterocycle, or amino substituted with 3-12 membered heterocycle, 5-12 membered C-linked-heteroaryl, 3-9 membered carbocycle, or 3-12 membered heterocycle, wherein any 6-12 membered aryl, 5-12 membered heteroaryl, 3-9 membered carbocycle, or 3-12 membered heterocycle of $Z^{2b}$ is optionally substituted with 1, 2, 3, 4, or 5 $Z^{2d}$ groups;

each $Z^{2c}$ is independently oxo, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, —C(O)NR$^{q4}$R$^{r4}$, or (C$_1$-C$_4$) alkyl optionally substituted with 1, 2, or 3 halogen or —OR$^{n4}$;

each $Z^{2d}$ is independently oxo, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, —C(O)NR$^{q4}$R$^{r4}$, or (C$_1$-C$_4$) alkyl optionally substituted with 1, 2, or 3 halogen or —OR$^{n4}$;

each R$^{n4}$ is independently H, (C$_1$-C$_4$)alkyl optionally substituted with 1, 2, or 3 —OH groups, (C$_1$-C$_4$)haloalkyl, or (C$_1$-C$_4$)heteroalkyl;

each R$^{p4}$ is independently (C$_1$-C$_8$)alkyl, (C$_1$-C$_4$)haloalkyl, or (C$_1$-C$_4$)heteroalkyl;

each R$^{q4}$ and R$^{r4}$ is independently H, (C$_1$-C$_4$)alkyl, (C$_1$-C$_4$)haloalkyl, or (C$_1$-C$_4$)heteroalkyl;

each $Z^3$ is independently H or —NR$^{q4}$R$^{r4}$;

each $Z^4$ is independently oxo, (C$_1$-C$_8$)alkyl, (C$_3$-C$_7$)carbocycle, halogen, —CN, —OR$^{n5}$, —NR$^{q5}$R$^{r5}$, —NR$^{n5}$COR$^{p5}$, —NR$^{n5}$CO$_2$R$^{p5}$, —C(O)R$^{n5}$, —C(O)OR$^{n5}$, or —C(O)NR$^{q5}$R$^{r5}$, wherein any (C$_3$-C$_7$)carbocycle or (C$_1$-C$_8$)alkyl of $Z^4$ is optionally substituted with 1, 2, 3, 4 or 5 $Z^{4a}$ groups, wherein the $Z^{4a}$ groups are the same or different;

each $Z^{4a}$ is independently halogen, —CN, or —OR$^{n6}$;

each R$^{n5}$, R$^{p5}$, R$^{q5}$, R$^{r5}$, and R$^{n6}$ is independently H or (C$_1$-C$_4$)alkyl;

each $Z^5$ is independently halogen, which may be same or different; and n is 0, 1, 2, or 3; or a pharmaceutically acceptable salt thereof.

One embodiment provides a pharmaceutical composition comprising a compound as detailed herein, including a compound of formula I (e.g. a compound of any one of formulas I, Ia, Ib, Ic, Id, II, III, IV, V, VI, VII, VIIa, VIIb, VIIc, or VIId), or a pharmaceutically acceptable salt thereof, and a pharmaceutically acceptable carrier.

One embodiment provides a pharmaceutical composition comprising a compound of formula I, Ia, Ib, Ic, Id, II, III, IV, V, VI, VII, VIIa, VIIb, VIIc, or VIId, or a pharmaceutically acceptable salt thereof; and an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor and combinations thereof.

One embodiment provides a method for treating a Retroviridae viral infection (e.g., an HIV viral infection) in a mammal (e.g., a human), comprising administering a compound as detailed herein, including a compound of any one of formulas I, Ia, Ib, Ic, Id, II, III, IV, V, VI, VII, VIIa, VIIb, VIIc, or VIId, or a pharmaceutically acceptable salt thereof, to the mammal. Another embodiment provides a method for treating a HIV infection in a patient in need thereof comprising administering a therapeutically effective amount of a compound as detailed herein, or a pharmaceutically acceptable salt thereof, to the patient.

One embodiment provides a method for inhibiting the proliferation of the HIV virus, treating AIDS or delaying the onset of AIDS or ARC symptoms in a mammal (e.g., a human), comprising administering a compound of any one of formulas I, Ia, Ib, Ic, Id, II, III, IV, V, VI, VII, VIIa, VIIb, VIIc, or VIId, or a pharmaceutically acceptable salt thereof, to the mammal.

One embodiment provides a method for treating an HIV infection in a mammal (e.g., a human), comprising administering a compound of formula I, or a pharmaceutically acceptable salt thereof, to the mammal. Another embodiment provides a method for treating an HIV infection in a mammal (e.g., a human), comprising administering a compound as detailed herein, including a compound of any one of formulas I, Ia, Ib, Ic, Id, II, III, IV, V, VI, VII, VIIa, VIIb, VIIc, or VIId, or a pharmaceutically acceptable salt thereof, to the mammal.

One embodiment provides a method for treating an HIV infection in a mammal (e.g., a human), comprising administering to the mammal in need thereof a therapeutically effective amount of a compound of any one of formulas I, Ia, Ib, Ic, Id, II, III, IV, V, VI, VII, VIIa, VIIb, VIIc, or VIId, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof. Another embodiment provides a method for treating an HIV infection in a patient in need thereof comprising administering to the patient a therapeutically effective amount of a compound as described herein, or a pharmaceutically acceptable salt thereof, in combination with a therapeutically effective amount of an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase site inhibitor and combinations thereof.

One embodiment provides a method for treating an HIV infection in a mammal (e.g., a human), comprising administering to the mammal in need thereof a therapeutically effective amount of a compound as detailed herein, including a compound of any one of formulas I, Ia, Ib, Ic, Id, II, III, IV, V, VI, VII, VIIa, VIIb, VIIc, or VIId, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and non-catalytic site HIV integrase inhibitors, and combinations thereof.

One embodiment provides a compound as detailed herein, including a compound of any one of formulas I, Ia, Ib, Ic, Id, II, III, IV, V, VI, VII, VIIa, VIIb, VIIc, or VIId, or a pharmaceutically acceptable salt thereof, for use in medical therapy (e.g., for use in treating a Retroviridae viral infection (e.g., an HIV viral infection) or the proliferation of the HIV virus or AIDS or delaying the onset of AIDS or ARC symptoms in a mammal (e.g., a human)).

One embodiment provides a compound as detailed herein, including a compound of any one of formulas I, Ia, Ib, Ic, Id, II, III, IV, V, VI, VII, VIIa, VIIb, VIIc, or VIId, or a pharmaceutically acceptable salt thereof, for use in the manufacture of a medicament for treating a Retroviridae viral infection (e.g., an HIV viral infection) or the proliferation of the HIV virus or AIDS or delaying the onset of AIDS or ARC symptoms in a mammal (e.g., a human).

One embodiment provides a compound as detailed herein, including a compound of any one of formulas I, Ia, Ib, Ic, Id, II, III, IV, V, VI, VII, VIIa, VIIb, VIIc, or VIId, or a pharmaceutically acceptable salt thereof, for use in the prophylactic or therapeutic treatment of the proliferation of a Retroviridae virus, an HIV virus or AIDS or for use in the therapeutic treatment of delaying the onset of AIDS or ARC symptoms.

One embodiment provides a compound as detailed herein, including a compound of any one of formulas I, Ia, Ib, Ic, Id, II, III, IV, V, VI, VII, VIIa, VIIb, VIIc, or VIId, or a pharmaceutically acceptable salt thereof, for use in the prophylactic or therapeutic treatment of a Retroviridae virus infection (e.g., an HIV virus infection).

One embodiment provides a compound as detailed herein, including a compound of any one of formulas I, Ia, Ib, Ic, Id, II, III, IV, V, VI, VII, VIIa, VIIb, VIIc, or VIId, or a pharmaceutically acceptable salt thereof, for the manufacture of a medicament for a Retroviridae virus infection (e.g., an HIV virus infection) in a mammal (e.g., a human).

One embodiment provides processes and intermediates disclosed herein that are useful for preparing compounds of any one of formulas I, Ia, Ib, Ic, Id, II, III, IV, V, VI, VII, VIIa, VIIb, VIIc, or VIId, or salts thereof.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

The description below is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. A prefix such as "$C_{u-v}$" or ($C_u$-$C_v$) indicates that the following group has from u to v carbon atoms. For example, "$C_{1-6}$alkyl" indicates that the alkyl group has from 1 to 6 carbon atoms.

Unless stated otherwise, the following terms and phrases as used herein are intended to have the following meanings:

When trade names are used herein, applicants intend to independently include the tradename product and the active pharmaceutical ingredient(s) of the tradename product.

"Alkyl" is a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms (i.e., ($C_1$-$C_4$)alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

"Alkenyl" is a straight or branched hydrocarbon with at least one carbon-carbon, $sp^2$ double bond. For example, an alkenyl group can have 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$) and 5-hexenyl (—$CH_2CH_2CH_2CH_2$CH=$CH_2$).

"Alkynyl" is a straight or branched hydrocarbon with at least one carbon-carbon, sp triple bond. For example, an alkynyl group can have 2 to 8 carbon atoms (i.e., $C_2$-$C_8$ alkyne) or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms of the alkyl are each independently replaced by a halo substituent. For example, ($C_1$-$C_6$)haloalkyl is a ($C_1$-$C_6$)alkyl wherein one or more of the hydrogen atoms of the ($C_1$-$C_6$)alkyl have been replaced by a halo substituent. Examples of haloalkyls include but are not limited to fluoromethyl, fluorochloromethyl, difluoromethyl, difluorochloromethyl, trifluoromethyl, 1,1,1, trifluoroethyl and pentafluoroethyl.

The term "heteroalkyl" as used herein refers to an alkyl as defined herein, wherein one or more of the carbon atoms of the alkyl are replaced by an O, S, or $NR^q$, (or if the carbon atom being replaced is a terminal carbon with an OH, SH or N($R^q$)$_2$) wherein each $R^q$ is independently H or ($C_1$-$C_6$) alkyl. For example, ($C_1$-$C_8$)heteroalkyl includes a heteroalkyl of one to eight carbons and one or more heteroatoms (e.g., O, S, N$R^q$, OH, SH or N($R^q$)$_2$). Thus, for example, a $C_1$ heteroalkyl encompasses, e.g., —$CH_2$—$NH_2$. Examples of heteroalkyls include but are not limited to methoxymethyl, ethoxymethyl, methoxy, 2-hydroxyethyl and N,N'-dimethylpropyl amine.

The terms "hydroxyl" or "hydroxyl" refer to —OH.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. It is also to be understood that when reference is made to a certain atom-range membered aryl (e.g., 6-12 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5-14 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole.

The term "C-linked-heteroaryl" (carbon-linked heteroaryl) as used herein refers to a heteroaryl that is linked at a carbon atom of the heteroaryl to the remainder of the compound of formula I.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). It is also to be understood that when reference is made to a certain atom-range membered heterocycle (e.g., a 3-14 membered heterocycle), the atom range is for the total ring atoms of the heterocycle and includes carbon atoms and heteroatoms. For example, a 3-membered heterocycle would include an aziridinyl and a 10-membered heterocycle would include a 1,2,3,4-tetrahydroquinolyl. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one and pyrrolidin-2-one.

The term "C-linked-heterocycle" (carbon-linked heterocycle) as used herein refers to a "heterocycle that is linked at a carbon atom of the heterocycle to the remainder of the compound of formula I.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e., ($C_3$-$C_7$)carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocycles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). The "carbocycle" or "carbocyclyl" can also be optionally substituted with one or more (e.g., 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "halophenyl" as used herein refers to phenyl, wherein one or more (e.g., 1, 2, 3, 4 or 5) hydrogen atoms of the phenyl are each replaced independently by a halo substituent. Examples of halophenyl include but are not limited to fluorophenyl, 2,3-dichlorophenyl, 3-bromo-4-fluorophenyl and pentafluorophenyl.

The term "haloheteroaryl" as used herein refers to a heteroaryl, wherein one or more (e.g., 1, 2, 3, 4 or 5) hydrogen atoms of the heteroaryl are each replaced independently by a halo substituent. Examples of haloheteroaryl include but are not limited to 2-fluorofuryl, 2,3-dichloropyridinyl and 8-chloro-3-fluoroquinolinyl.

The term "haloheterocycle" as used herein refers to a heterocycle, wherein one or more (e.g., 1, 2, 3, 4 or 5) hydrogen atoms of the heterocycle are each replaced independently by a halo substituent. Examples of haloheteroaryl include but are not limited to 2-fluoropiperidinyl, 2-chloro-3-fluoropiperazinyl and 3-bromopyrrolidinyl.

The term "oxo" as used herein refers to =O.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present disclosure. Similarly, one skilled in the art will recognize that substituents and other moieties of the compounds detailed herein, including a compound of any one of formulas I, Ia, Ib, Ic, Id, II, III, IV, V, VI, VII, VIIa, VIIb, VIIc, or VIId, or a pharmaceutically acceptable salt thereof, should be selected in order to provide a compound which is sufficiently stable to provide a pharmaceutically useful compound which can be formulated into an acceptably stable pharmaceutical composition. Compounds as detailed herein which have such stability are contemplated as falling within the scope of the present disclosure.

The modifier "about" used in connection with a quantity is inclusive of the stated value and has the meaning dictated by the context (e.g., includes the degree of error associated with measurement of the particular quantity). The word "about" may also be represented symbolically by "~" in the context of a chemical measurement (e.g., ~50 mg or pH~7).

The term "treatment" or "treating," to the extent it relates to a disease or condition includes preventing the disease or condition from occurring, inhibiting the disease or condition, eliminating the disease or condition, and/or relieving one or more symptoms of the disease or condition.

In one embodiment, "treatment" or "treating" include one or more of the following: a) inhibiting the disease or condition (e.g., decreasing one or more symptoms resulting from the disease or condition, and/or diminishing the extent of the disease or condition); b)

slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

Chemical names for certain compounds were generated using ChemBioDraw 12.0 software.

Stereoisomers

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The compounds disclosed herein may have chiral centers, e.g., chiral carbon atoms. Such compounds thus include racemic mixtures of all stereoisomers, including enantiomers, diastereomers, and atropisomers. In addition, the compounds disclosed herein include enriched or resolved optical isomers at any or all asymmetric, chiral atoms. Similarly, compositions disclosed herein also include racemic mixtures of all stereoisomers, including enantiomers, diastereomers, and atropisomers of compounds disclosed herein. In addition, the compounds and compositions disclosed herein include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the present disclosure. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

The present disclosure includes any or all of the stereochemical forms, including any enantiomeric or diastereomeric forms and geometric isomers of the compounds described, or mixtures thereof. Unless stereochemistry is explicitly indicated in a chemical structure or name, the structure or name is intended to embrace all possible stereoisomers, including geometric isomers, of a compound depicted. Compositions comprising a compound of the present disclosure are also intended, such as a composition of substantially pure compound, including a specific stereochemical form, including a specific geometric isomer, thereof. Compositions comprising a mixture of compounds of the present disclosure in any ratio are also embraced by the present disclosure, including mixtures of two or more stereochemical forms of a compound of the present disclosure in any ratio, such that racemic, non-racemic, enantio-enriched and scalemic mixtures of a compound are embraced, or mixtures thereof.

It is to be understood that for compounds disclosed herein when a bond is drawn in a non-stereochemical manner (e.g., flat) the atom to which the bond is attached includes all stereochemical possibilities. It is also to be understood that when a bond is drawn in a stereochemical manner (e.g., bold, bold-wedge, dashed or dashed-wedge) the atom to which the stereochemical bond is attached has the stereochemistry as shown unless otherwise noted. Accordingly, in one embodiment, a compound disclosed herein is greater than 50% a single enantiomer. In another embodiment, a compound disclosed herein is at least 80% a single enantiomer. In another embodiment, a compound disclosed herein is at least 90% a single enantiomer. In another embodiment, a compound disclosed herein is at least 98% a single enantiomer. In another embodiment, a compound disclosed herein is at least 99% a single enantiomer. In another embodiment, a compound disclosed herein is greater than 50% a single diastereomer. In another embodiment, a compound disclosed herein is at least 80% a single diastereomer. In another embodiment, a compound disclosed herein is at least 90% a single diastereomer. In another embodiment, a compound disclosed herein is at least 98% a single diastereomer. In another embodiment, a compound disclosed herein is at least 99% a single diastereomer.

Accordingly, in one embodiment, a composition disclosed herein is greater than 50% a single enantiomer. In another embodiment, a composition disclosed herein is at least 80% a single enantiomer. In another embodiment, a composition disclosed herein is at least 90% a single enantiomer. In another embodiment, a composition disclosed herein is at least 98% a single enantiomer. In another embodiment, a composition disclosed herein is at least 99% a single enantiomer. In another embodiment, a composition disclosed herein is greater than 50% a single diastereomer. In another embodiment, a composition disclosed herein is at least 80% a single diastereomer. In another embodiment, a composition disclosed herein is at least 90% a single diastereomer. In another embodiment, a composition disclosed herein is at least 98% a single diastereomer. In another embodiment, a composition disclosed herein is at least 99% a single diastereomer.

In certain embodiments, the compounds disclosed herein display atropisomerism resulting from steric hindrance affecting the axial rotation rate around a single bond. In certain circumstances, the resultant conformational isomers are observed as distinct entities by characterization techniques such as NMR and HPLC. In certain embodiments, the compounds disclosed herein exist as a mixture of atropisomers. The synthetic examples provided herein note where such mixtures of atropisomers have been observed. However, the detection of atropisomers is dependent on factors such as temperature, solvent, conditions of purification, and timescale of spectroscopic technique. Characterization data presented herein may not represent the equilibrium state depending on the conditions of purification, isolation, handling, solvents used, and temperature.

Tautomers

The compounds disclosed herein can also exist as tautomeric isomers in certain cases. Although only one delocalized resonance structure may be depicted, all such forms are contemplated within the scope of the present disclosure. For example, ene-amine tautomers can exist for purine, pyrimidine, imidazole, guanidine, amidine, and tetrazole systems and all their possible tautomeric forms are within the scope of the present disclosure. Another non-limiting example includes keto-enol tautomers of heteroaryls. Such tautomers are exemplified by T1/T1', T2/T2' and T3/T3'. All such tautomeric forms are also within the scope of the present disclosure.

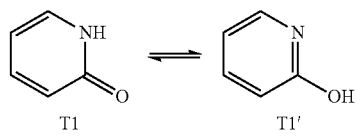

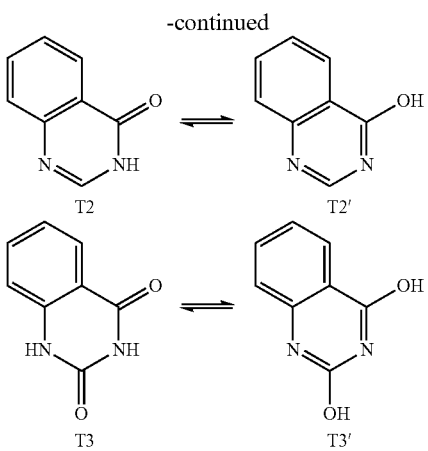

Protecting Groups

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Salts and Hydrates

"Pharmaceutically acceptable salt" refers to a salt of a compound that is pharmaceutically acceptable and that possesses (or can be converted to a form that possesses) the desired pharmacological activity of the parent compound. Pharmaceutically acceptable salts are generally regarded as safe and suitable for use without undue toxicity, irritation, allergic response, and the like, commensurate with a reasonable benefit/risk ratio. Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, camphorsulfonic, citric, glucoheptonic, gluconic, lactic, fumaric, tartaric, maleic, malonic, malic, mandelic, isethionic, lactobionic, succinic, 2-napththalenesulfonic, oleic, palmitic, propionic, stearic, and trimethylacetic acids; organic sulfonic acids, such as methanesulfonic, ethanesulfonic, benzenesulfonic and p-toluenesulfonic acids; and inorganic acids, such as hydrochloric, hydrobromic, sulfuric, nitric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group). Pharmaceutically acceptable salts also include salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of formula I or another compound disclosed herein. All salts, whether or not derived from a physiologically acceptable acid or base, are within the scope of the present present disclosure.

Metal salts typically are prepared by reacting the metal hydroxide with a compound disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, such as amines. Finally, it is to be understood that the compositions herein comprise compounds disclosed herein in their unionized, as well as zwitterionic form, and combinations with stoichiometric amounts of water as in hydrates.

Often crystallizations produce a solvate of the compound of the present disclosure. As used herein, the term "solvate" refers to an aggregate that comprises one or more molecules of a compound of the present disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the present disclosure may be true solvates, while in other cases, the compound of the present disclosure may merely retain adventitious water or be a mixture of water plus some adventitious solvent.

Isotopes

It is understood by one skilled in the art that this disclosure also includes any compound claimed that may be enriched at any or all atoms above naturally occurring isotopic ratios with one or more isotopes such as, but not limited to, deuterium ($^2H$ or D). As a non-limiting example, in certain embodiments, a —$CH_3$ group is replaced with —$CD_3$.

Specific values listed below for radicals, substituents, and ranges in the embodiments of the present disclosure are for illustration only; they do not exclude other defined values or other values within defined ranges for the radicals and substituents.

Compounds of Formula I.

In certain embodiments, a compound of formula I:

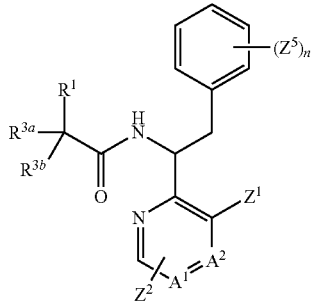

wherein
A$^1$ is C—Z$^3$ or nitrogen;
A$^2$ is C—Z$^3$ or nitrogen;
R$^1$ is 6-12 membered aryl, 5-12 membered heteroaryl, or 3-12 membered heterocycle, wherein any 6-12 membered aryl, 5-12 membered heteroaryl, or 3-12 membered heterocycle of R$^1$ is optionally substituted with 1, 2, 3, 4 or 5 Z$^4$ groups, wherein the Z$^4$ groups are the same or different;
each R$^{3a}$ and R$^{3b}$ is independently H or (C$_1$-C$_3$)alkyl;
Z$^1$ is 6-12 membered aryl, 5-14 membered heteroaryl, or 3-14 membered heterocycle, wherein any 6-12 membered aryl, 5-14 membered heteroaryl, or 3-14 membered heterocycle of Z$^1$ is optionally substituted with 1, 2, 3, 4 or 5 Z$^{1a}$ or Z$^{1b}$, wherein the Z$^{1a}$ and Z$^{1b}$ groups are the same or different;
each Z$^{1a}$ is independently oxo, (C$_3$-C$_7$)carbocycle, 5-12 membered heteroaryl, 3-12 membered heterocycle, halogen, —CN, —OR$^{n1}$, —OC(O)R$^{p1}$, —OC(O)NR$^{q1}$R$^{r1}$, —SR$^{n1}$, —S(O)R$^{p1}$, —S(O)$_2$OH, —S(O)$_2$R$^{p1}$, —S(O)$_2$NR$^{q1}$R$^{r1}$, —NR$^{q1}$R$^{r1}$, —NR$^{n1}$COR$^{p1}$, —NR$^{n1}$CO$_2$R$^{p1}$, —NR$^{n1}$CONR$^{q1}$R$^{r1}$, —NR$^{n1}$S(O)$_2$R$^{p1}$, —NR$^{n1}$S(O)$_2$OR$^{p1}$, —NR$^{n1}$S(O)$_2$NR$^{q1}$R$^{r1}$, —C(O)R$^{n1}$, —C(O)OR$^{n1}$, —C(O)NR$^{q1}$R$^{r1}$ and —S(O)$_2$NR$^{n1}$COR$^{p1}$, wherein any (C$_3$-C$_7$)carbocycle, 5-12 membered heteroaryl and 3-12 membered heterocycle of Z$^{1a}$ is optionally substituted with 1, 2, 3, 4 or 5 Z$^{1c}$ or Z$^{1d}$ groups, wherein the Z$^{1c}$ and Z$^{1d}$ groups are the same or different;
each Z$^{1b}$ is independently (C$_1$-C$_8$)alkyl optionally substituted with 1, 2, 3, 4 or 5 halogen, which are the same or different;
each Z$^{1c}$ is independently halogen, —CN, —OH, —NH$_2$, —C(O)NR$^{q2}$R$^{r2}$, or (C$_1$-C$_8$)heteroalkyl;
each Z$^{1d}$ is independently (C$_1$-C$_8$)alkyl or (C$_1$-C$_8$)haloalkyl;
each R$^{n1}$ is independently H, (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{n1}$ is optionally substituted with 1, 2, 3, 4 or 5 Z$^{1c}$ or Z$^{1d}$ groups, wherein the Z$^{1c}$ and Z$^{1d}$ groups are the same or different, and wherein any (C$_1$-C$_8$)alkyl of R$^{n1}$ is optionally substituted with 1, 2, 3, 4 or 5 Z$^{1c}$ groups, wherein the Z$^{1c}$ groups are the same or different;
each R$^{p1}$ is independently (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{p1}$ is optionally substituted with 1, 2, 3, 4 or 5 Z$^{1c}$ or Z$^{1d}$ groups, wherein the Z$^{1c}$ and Z$^{1d}$ groups are the same or different, and wherein any (C$_1$-C$_8$)alkyl of R$^{p1}$ is optionally substituted with 1, 2, 3, 4 or 5 Z$^{1c}$ groups, wherein the Z$^{1c}$ groups are the same or different;
each R$^{q1}$ and R$^{r1}$ is independently H, (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{q1}$ or R$^{r1}$ is optionally substituted with 1, 2, 3, 4 or 5 Z$^{1c}$ or Z$^{1d}$ groups, wherein the Z$^{1c}$ and Z$^{1d}$ groups are the same or different, and wherein any (C$_1$-C$_8$)alkyl of R$^{q1}$ or R$^{r1}$ is optionally substituted with 1, 2, 3, 4 or 5 Z$^{1c}$ groups, wherein the Z$^{1c}$ groups are the same or different, or R$^{q1}$ and R$^{r1}$ together with the nitrogen to which they are attached form a 5, 6 or 7-membered heterocycle, wherein the 5, 6 or 7-membered heterocycle is optionally substituted with 1, 2, 3, 4 or 5 Z$^{1c}$ or Z$^{1d}$ groups, wherein the Z$^{1c}$ and Z$^{1d}$ groups are the same or different;
each R$^{q2}$ and R$^{r2}$ is independently H, (C$_1$-C$_8$)alkyl, (C$_3$-C$_7$)carbocycle, or R$^{q2}$ and R$^{r2}$ together with the nitrogen to which they are attached form a 5, 6, or 7-membered heterocycle;
Z$^2$ is (C$_2$-C$_8$)alkenyl, (C$_2$-C$_8$)alkynyl, 6-12 membered aryl, 5-12 membered heteroaryl, 3-12 membered heterocycle, wherein any (C$_2$-C$_8$)alkenyl, (C$_2$-C$_8$)alkynyl, 6-12 membered aryl, 5-12 membered heteroaryl, or 3-12 membered heterocycle of Z$^2$ is substituted with 1 or 2 Z$^{2b}$ groups and optionally 1, 2, or 3 Z$^{2c}$ groups, wherein the Z$^{2b}$ and Z$^{2c}$ groups are the same or different;
each R$^{n3}$ is independently H or (C$_1$-C$_4$)alkyl;
each R$^{q3}$ and R$^{r3}$ is independently H or (C$_1$-C$_4$)alkyl;
each Z$^{2b}$ is independently 6-12 membered aryl, 5-12 membered heteroaryl, 3-9 membered carbocycle, 3-12 membered heterocycle, or amino substituted with 3-12 membered heterocycle, 5-12 membered heteroaryl, 3-9 membered carbocycle, or 3-12 membered heterocycle, wherein any 6-12 membered aryl, 5-12 membered heteroaryl, 3-9 membered carbocycle, or 3-12 membered heterocycle of Z$^{2b}$ is optionally substituted with 1, 2, 3, 4, or 5 Z$^{2d}$ groups;
each Z$^{2c}$ is independently oxo, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, —C(O)NR$^{q4}$R$^{r4}$, or (C$_1$-C$_4$) alkyl optionally substituted with 1, 2, or 3 halogen or —OR$^{n4}$;
each Z$^{2d}$ is independently oxo, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, —C(O)NR$^{q4}$R$^{r4}$, or (C$_1$-C$_4$) alkyl optionally substituted with 1, 2, or 3 halogen or —OR$^{n4}$;
each R$^{n4}$ is independently H, (C$_1$-C$_4$)alkyl optionally substituted with 1, 2, or 3 —OH groups, (C$_1$-C$_4$)haloalkyl, or (C$_1$-C$_4$)heteroalkyl;
each R$^{p4}$ is independently (C$_1$-C$_8$)alkyl, (C$_1$-C$_4$)haloalkyl, or (C$_1$-C$_4$)heteroalkyl;
each R$^{q4}$ and R$^{r4}$ is independently H, (C$_1$-C$_4$)alkyl, (C$_1$-C$_4$)haloalkyl, or (C$_1$-C$_4$)heteroalkyl;
each Z$^3$ is independently H or —NR$^{q4}$R$^{r4}$;
each Z$^4$ is independently oxo, (C$_1$-C$_8$)alkyl, (C$_3$-C$_7$)carbocycle, halogen, —CN, —OR$^{n5}$, —NR$^{q5}$R$^{r5}$, —NR$^{n5}$COR$^{p5}$, —NR$^{n5}$CO$_2$R$^{p5}$, —C(O)R$^{n5}$, —C(O)OR$^{n5}$, or —C(O)NR$^{q5}$R$^{r5}$, wherein any (C$_3$-C$_7$)carbocycle or (C$_1$-

$C_8$)alkyl of $Z^4$ is optionally substituted with 1, 2, 3, 4 or 5 $Z^{4a}$ groups, wherein the $Z^{4a}$ groups are the same or different;

each $Z^{4a}$ is independently halogen, —CN, or —$OR^{n6}$;

each $R^{n5}$, $R^{p5}$, $R^{q5}$, $R^{r5}$, and $R^{n6}$ is independently H or ($C_1$-$C_4$)alkyl;

each $Z^5$ is independently halogen, which may be same or different; and n is 0, 1, 2, or 3; or a pharmaceutically acceptable salt thereof, is provided Specific values listed below are values for compounds of formula I as well as all related formulas (e.g., formulas I, Ia, Ib, Ic, Id, II, III, IV, V, VI, VII, VIIa, VIIb, VIIc, or VIId). It is to be understood that two or more values may combined. Thus, it is to be understood that any variable for compounds of formula I may be combined with any other variable for compounds of formula I the same as if each and every combination of variables were specifically and individually listed. For example, it is understood that any specific value of $R^1$ detailed herein for compounds of formula I may be combined with any other specific value for one or more of the variables (e.g. $A^1$, $Z^1$, $Z^2$, $R^{3a}$ or $R^{3b}$) the same as if each and every combination were specifically and individually listed. Further, the present disclosure includes compounds of formula I as well as all related formulas (e.g., formulas I, Ia, Ib, Ic, Id, II, III, IV, V, VI, VII, VIIa, VIIb, VIIc, or VIId), or a pharmaceutically acceptable salt thereof.

In certain embodiments of the compound of formula I, $A^1$ is C—$Z^3$ and $A^2$ is nitrogen. In certain embodiments of the compound of formula I, $A^1$ is nitrogen and $A^2$ is C—$Z^3$. In certain embodiments of the compound of formula I, $A^1$ is C—$Z^3$ and $A^2$ is C—$Z^3$.

In certain embodiments, the compound of formula I is a compound of formula Ia,

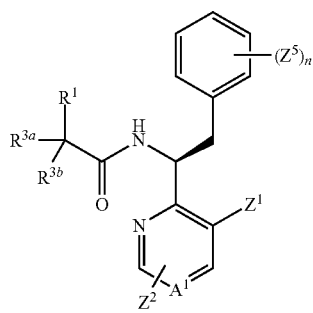

Ia or a pharmaceutically acceptable salt thereof, wherein $R^1$, $R^{3a}$, $R^{3b}$, $Z^1$, $Z^2$, $A^1$, $Z^5$ and n are as described herein.

In certain embodiments, the compound of formula I is a compound of formula Ib,

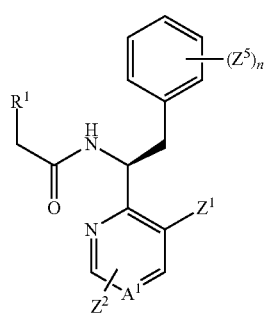

Ib or a pharmaceutically acceptable salt thereof, wherein $R^1$, $Z^1$, $Z^2$, $A^1$, $Z^5$ and n are as described herein.

In certain embodiments, the compound of formula I, Ia, or Ib is a compound of formula Ic.

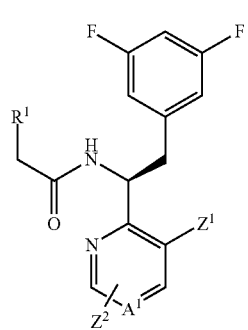

Ic or a pharmaceutically acceptable salt thereof, wherein $R^1$, $Z^1$, $Z^2$, and $A^1$ are as described herein.

In certain embodiments, the compound of formula I, Ia, or Ib is a compound of formula Id

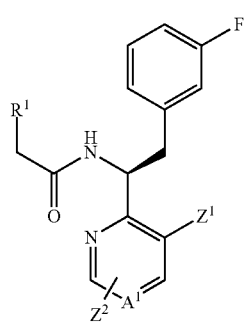

Id or a pharmaceutically acceptable salt thereof, wherein $R^1$, $Z^1$, $Z^2$, and $A^1$ are as described herein.

In certain embodiments of a compound of formula I, Ia, Ib, Ic, Id, VII, VIIa, VIIb, VIIc, or VIId, $A^1$ is N.

In certain embodiments of a compound of formula I, Ia, Ib, Ic, Id, VII, VIIa, VIIb, VIIc, or VIId, $A^1$ is C—$Z^3$.

In certain embodiments of a compound of formula I, Ia, Ib, Ic, Id, VII, VIIa, VIIb, VIIc, or VIId, $Z^3$ is H or $NH_2$. In certain embodiments of a compound of formula I, Ia, Ib, Ic, Id, VII, VIIa, VIIb, VIIc, or VIId $Z^3$ is H. In certain embodiments of a compound of formula I, Ia, Ib, Ic, Id, VII, VIIa, VIIb, VIIc, or VIId, $Z^3$ is $NH_2$.

In certain embodiments of a compound of formula I, Ia, Ib, Ic, Id, VII, or VIIa the moiety

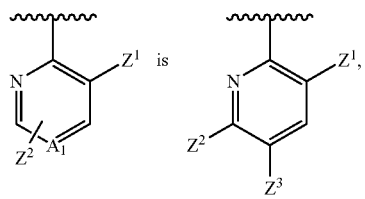

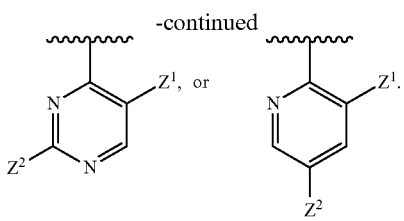

In certain embodiments of a compound of formula I, Ia, or Ib, the moiety

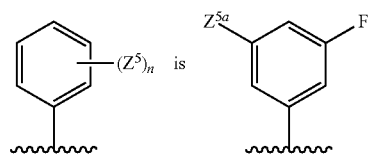

wherein $Z^{5a}$ is H or halogen. In certain embodiments, $Z^{5a}$ is H or fluoro.

In certain embodiments of a compound of formula I or Ia, each of $R^{3a}$ and $R^{3b}$ is independently selected from H, halogen, $(C_1-C_3)$alkyl, and $(C_1-C_3)$haloalkyl. In certain embodiments of a compound of formula I or Ia, each of $R^{3a}$ and $R^{3b}$ is independently selected from H, $(C_1-C_3)$alkyl, and $(C_1-C_3)$haloalkyl. In certain embodiments of a compound of formula I or Ia, each of $R^{3a}$ and $R^{3b}$ is independently selected from H and $(C_1-C_3)$alkyl. In certain embodiments of a compound of formula I or Ia, each of $R^{3a}$ and $R^{3b}$ is independently selected from H, methyl and ethyl. In certain embodiments of a compound of formula I or Ia, each of $R^{3a}$ and $R^{3b}$ is independently selected from H and methyl.

In certain embodiments of a compound of formula I or Ia, $R^{3a}$ is H and $R^{3b}$ is $(C_1-C_3)$alkyl. In certain embodiments of a compound of formula I or Ia, $R^{3a}$ is H and $R^{3b}$ is methyl or ethyl. In certain embodiments of a compound of formula I or Ia, $R^{3a}$ is H and $R^{3b}$ is methyl.

In certain embodiments of a compound of formula I or Ia, $R^{3a}$ and $R^{3b}$ is H.

In certain embodiments, the compound of formula I, Ia, or Ib, is a compound of formula II

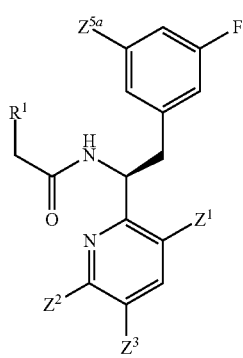

or a pharmaceutically acceptable salt thereof, wherein $Z^{5a}$ is H or halogen, $Z^3$ is —H or —NH$_2$ and $R^1$, $Z^1$, $Z^2$, and $Z^{5a}$ are as described herein.

In certain embodiments, the compound of formula I, Ia, or Ib, is a compound of formula III

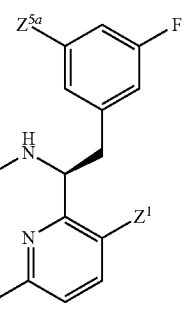

or a pharmaceutically acceptable salt thereof, wherein $Z^{5a}$ is H or halogen and $R^1$, $Z^1$, $Z^{2b}$, and $Z^{5a}$ are as described herein.

In certain embodiments, the compound of formula I, Ia, or Ib, is a compound of formula IV

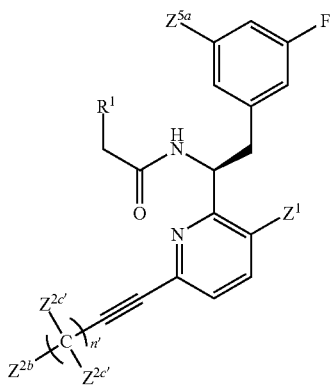

or a pharmaceutically acceptable salt thereof, wherein $Z^{5a}$ is H or halogen, each $Z^{2c'}$ is independently hydrogen, $(C_1-C_4)$ alkyl, or $OR^{n4}$ where $R^{n4}$ is hydrogen or $(C_1-C_4)$ alkyl, n' is 1, 2, or 3 and $R^1$. $Z^1$, and $Z^{2b}$ are as described herein. In certain embodiments of a compound of formula IV, each $Z^{2c'}$ is independently hydrogen, methyl, or —OH. In certain embodiments of a compound of formula IV, n is 1. In certain embodiments of a compound of formula IV, n is 2. In certain embodiments of a compound of formula IV, n' is 1. In certain embodiments of a compound of formula IV, n' is 2.

In certain embodiments, the compound of formula I, Ia, or Ib is a compound of formula V

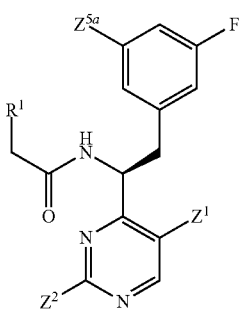

or a pharmaceutically acceptable salt thereof, wherein $Z^{5a}$ is H or halogen and $R^1$, $Z^1$, and $Z^2$ are as described herein.

In certain embodiments, the compound of formula I, Ia, or Ib is a compound of formula VI

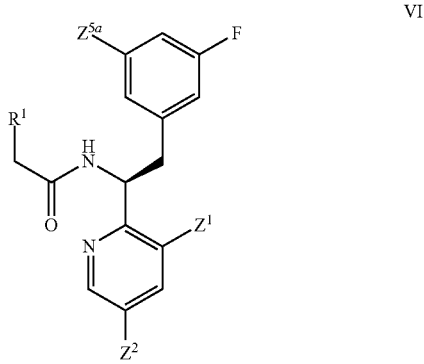

VI or a pharmaceutically acceptable salt thereof, wherein $Z^{5a}$ is H or halogen and $R^1$, $Z^1$, and $Z^2$ are as described herein.

In certain embodiments of a compound of formula I, Ia, Ib, Ic, Id, II, III, IV, V, VI, VII, VIIa, or VIIb, $Z^2$ is $(C_2-C_8)$alkynyl, 6-12 membered aryl, 5-12 membered C-linked-heteroaryl, or 3-12 membered C-linked-heterocycle, wherein any $(C_2-C_8)$alkynyl, 6-12 membered aryl, 5-12 membered C-linked-heteroaryl, or 3-12 membered C-linked-heterocycle of $Z^2$ is substituted with 1 or 2 $Z^{2b}$ groups and optionally 1, 2, or 3 $Z^{2c}$ groups, wherein the $Z^{2b}$ and $Z^{2c}$ groups are the same or different.

In certain embodiments of a compound of formula I, Ia, Ib, Ic, Id, II, II, IV, V, VI, VII, VIIa, or VIIb, wherein $Z^2$ is $(C_2-C_8)$alkynyl or 5-6 membered C-linked-monocyclic-heteroaryl, wherein any $(C_2-C_8)$alkynyl or 5-6 membered C-linked-monocyclic-heteroaryl of $Z^2$ is substituted with 1 or 2 $Z^{2b}$ groups and optionally substituted with 1, 2, or 3 $Z^{2c}$ groups.

In certain embodiments of a compound of formula I, Ia, Ib, Ic, Id, II, III, IV, V, VI, VII, VIIa, or VIIb, $Z^2$ is $(C_2-C_8)$alkynyl substituted with 1 or 2 $Z^{2b}$ groups and optionally substituted with 1, 2, or 3 $Z^{2c}$ groups. In certain embodiments of a compound of formula I, Ia, Ib, Ic, Id, II, III, IV, V, VI, VII, VIIa, or VIIb, $Z^2$ is $(C_2-C_5)$alkynyl substituted with 1 or 2 $Z^{2b}$ groups and optionally substituted with 1, 2, or 3 $Z^{2c}$ groups.

In certain embodiments of a compound of formula I, Ia, Ib, Ic, Id, II, III, IV, V, VI, VII, VIIa, or VIIb, $Z^2$ is 6-10 membered aryl substituted with 1 or 2 $Z^{2b}$ groups and optionally 1, 2, or 3 $Z^{2c}$ groups, wherein the $Z^{2b}$ and $Z^{2c}$ groups are the same or different. In certain embodiments of a compound of formula I, Ia, Ib, I, Ic, II, III, IV, V, VI, VII, VIIa, or VIIb, $Z^2$ is 6 membered aryl substituted with 1 or 2 $Z^{2b}$ groups and optionally 1, 2, or 3 $Z^{2c}$ groups, wherein the $Z^{2b}$ and $Z^{2c}$ groups are the same or different. In certain embodiments of a compound of formula I, Ia, Ib, Ic, Id, II, III, IV, V, VI, VII, VIIa, or VIIb, $Z^2$ is phenyl substituted with 1 or 2 $Z^{2b}$ groups and optionally 1, 2, or 3 $Z^{2c}$ groups, wherein the $Z^{2b}$ and $Z^{2c}$ groups are the same or different.

In certain embodiments of a compound of formula I, Ia, Ib, Ic, Id, II, III, IV, V, VI, VII, VIIa, or VIIb, $Z^2$ is 5-10 membered C-linked-heteroaryl substituted with 1 or 2 $Z^{2b}$ groups and optionally 1, 2, or 3 $Z^{2c}$ groups, wherein the $Z^{2b}$ and $Z^{2c}$ groups are the same or different. In certain embodiments of a compound of formula I, Ia, Ib, Ic, Id, II, III, IV, V, VI, VII, VIIa, or VIIb, $Z^2$ is 5-10 membered C-linked-heteroaryl substituted with 1 or 2 $Z^{2b}$ groups and optionally 1, 2, or 3 $Z^{2c}$ groups, wherein the $Z^{2b}$ and $Z^{2c}$ groups are the same or different, wherein the 5-10 membered C-linked-heteroaryl has 1-9 carbon atoms and 1-3 heteroatoms in the ring system. In certain embodiments of a compound of formula I, Ia, Ib, Ic, Id, II, III, IV, V, VI, VII, VIIa, or VIIb, $Z^2$ is 5-6 membered C-linked-heteroaryl substituted with 1 or 2 $Z^{2b}$ groups and optionally 1, 2, or 3 $Z^{2c}$ groups, wherein the $Z^{2b}$ and $Z^{2c}$ groups are the same or different, wherein the 5-6 membered C-linked-heteroaryl has 1-4 carbon atoms and 1-3 heteroatoms in the ring system. In certain embodiments of a compound of formula I, Ia, Ib, Ic, Id, II, III, IV, V, VI, VII, VIIa, or VIIb, $Z^2$ is pyrazolyl substituted with 1 or 2 $Z^{2b}$ groups and optionally 1, 2, or 3 $Z^{2c}$ groups, wherein the $Z^{2b}$ and $Z^{2c}$ groups are the same or different.

In certain embodiments of a compound of formula I, Ia, Ib, Ic, Id, II, III, IV, V, VI, VII, VIIa, or VIIb, $Z^2$ is 3-12 membered C-linked-heterocycle substituted with 1 or 2 $Z^{2b}$ groups and optionally 1, 2, or 3 $Z^{2c}$ groups, wherein the $Z^{2b}$ and $Z^{2c}$ groups are the same or different. In certain embodiments of a compound of formula I, Ia, Ib, Ic, Id, II, III, IV, V, VI, VII, VIIa, or VIIb, $Z^2$ is 4-10 membered C-linked-heterocycle substituted with 1 or 2 $Z^{2b}$ groups and optionally 1, 2, or 3 $Z^{2c}$ groups, wherein the $Z^{2b}$ and $Z^{2c}$ groups are the same or different. In certain embodiments of a compound of formula I, Ia, Ib, Ic, Id, II, III, IV, V, VI, VII, VIIa, or VIIb, $Z^2$ is 4-10 membered C-linked-heterocycle substituted with 1 or 2 $Z^{2b}$ groups and optionally 1, 2, or 3 $Z^{2c}$ groups, wherein the $Z^{2b}$ and $Z^{2c}$ groups are the same or different wherein the 4-10 membered C-linked-heterocycle has 3-9 carbon atoms and 1-3 heteroatoms in the ring system. In certain embodiments of a compound of formula I, Ia, Ib, Ic, Id, II, III, IV, V, VI, VII, VIIa, or VIIb, $Z^2$ is 4-8 membered C-linked-heterocycle substituted with 1 or 2 $Z^{2b}$ groups and optionally 1, 2, or 3 $Z^{2c}$ groups, wherein the $Z^{2b}$ and $Z^{2c}$ groups are the same or different wherein the 4-8 membered C-linked-heterocycle has 3-7 carbon atoms and 1-3 heteroatoms in the ring system.

In certain embodiments of a compound of formula I, Ia, Ib, Ic, Id, II, III, IV, V, VI, VII, VIIa, or VIIb, each $Z^2$ is independently halogen, —$OR^{n4}$, $NR^{q4}R^{r4}$, —$NR^{n4}CO_2R^{p4}$, —$C(O)OR^{n4}$, or —$C(O)NR^{q4}R^{r4}$.

In certain embodiments of a compound of formula I, Ia, Ib, Ic, Id, II, III, IV, V, VI, VII, VIIa, or VIIb, $Z^2$ is substituted with one $Z^{2b}$.

In certain embodiments of a compound of formula I, Ia, Ib, Ic, Id, II, III, IV, V, VI, VII, VIIa, or VIIb each $Z^{2b}$ is independently 6-12 membered aryl, 5-12 membered C-linked-heteroaryl, 3-9 membered carbocycle, 3-12 membered C-linked-heterocycle, or amino substituted with 3-12 membered C-linked-heterocycle, 5-12 membered C-linked-heteroaryl, or 3-12 membered —C-linked-heterocycle, wherein any 6-12 membered aryl, 5-12 membered C-linked-heteroaryl, 3-7 membered carbocycle, or 3-12 membered heterocycle of $Z^{2b}$ is optionally substituted with 1, 2, 3, 4, or 5 $Z^{2d}$ groups.

In certain embodiments of a compound of formula I, Ia, Ib, Ic, Id, II, III, IV, V, VI, VII, VIIa, or VIIb each $Z^{2b}$ is independently 6-10 membered aryl optionally substituted with 1, 2, 3, 4, or 5 $Z^{2d}$ groups. In certain embodiments of a compound of formula I, Ia, Ib, Ic, Id, II, III, IV, V, VI, VII, VIIa, or VIIb each $Z^{2b}$ is independently phenyl optionally substituted with 1, 2, 3, 4, or 5 $Z^{2d}$ groups.

In certain embodiments of a compound of formula I, Ia, Ib, Ic, Id, II, III, IV, V, VI, VII, VIIa, or VIIb each $Z^{2b}$ is independently 5-12 membered C-linked-heteroaryl optionally substituted with 1, 2, 3, 4, or 5 $Z^{2d}$ groups. In certain embodiments of a compound of formula I, Ia, Ib, Ic, Id, II, III, IV, V, VI, VII, VIIa, or VIIb each $Z^{2b}$ is independently 5-10 membered C-linked-heteroaryl optionally substituted with 1, 2, 3, 4, or 5 $Z^{2d}$ groups. In certain embodiments of a compound of formula I, Ia, Ib, Ic, Id, II, III, IV, V, VI, VII, VIIa, or VIIb each $Z^{2b}$ is independently 5-10 membered C-linked-heteroaryl optionally substituted with 1, 2, 3, 4, or 5 $Z^{2d}$ groups, wherein the 5-10 membered C-linked-heteroaryl has 2-9 carbon atoms and 1-3 heteroatoms in the ring system. In certain embodiments of a compound of formula I, Ia, Ib, Ic, Id, II, III, IV, V, VI, VII, VIIa, or VIIb each $Z^{2b}$ is independently 5-8 membered C-linked-heteroaryl optionally substituted with 1, 2, 3, 4, or 5 $Z^{2d}$ groups, wherein the 5-8 membered C-linked-heteroaryl has 2-7 carbon atoms and 1-3 heteroatoms in the ring system. In certain embodiments of a compound of formula I, Ia, Ib, Ic, Id, II, III, IV, V, VI, VII, VIIa, or VIIb each $Z^{2b}$ is independently 5-8 membered C-linked-heteroaryl optionally substituted with 1, 2, 3, 4, or 5 $Z^{2d}$ groups, wherein the 5-8 membered C-linked-heteroaryl has 2-7 carbon atoms and 1-3 heteroatoms in the ring system.

In certain embodiments of a compound of formula I, Ia, Ib, Ic, Id, II, III, IV, V, VI, VII, VIIa, or VIIb each $Z^{2b}$ is independently 3-9 membered carbocycle optionally substituted with 1, 2, 3, 4, or 5 $Z^{2d}$ groups. In certain embodiments of a compound of formula I, Ia, Ib, Ic, Id, II, III, IV, V, VI, VII, VIIa, or VIIb each $Z^{2b}$ is independently 3-7 membered carbocycle optionally substituted with 1, 2, 3, 4, or 5 $Z^{2d}$ groups. In certain embodiments of a compound of formula I, Ia, Ib, Ic, Id, II, III, IV, V, VI, VII, VIIa, or VIIb each $Z^{2b}$ is independently 3-6 membered carbocycle optionally substituted with 1, 2, 3, 4, or 5 $Z^{2d}$ groups. In certain embodiments of a compound of formula I, Ia, Ib, Ic, Id, II, III, IV, V, VI, VII, VIIa, or VIIb each $Z^{2b}$ is independently cyclopropyl, cyclobutyl, cyclopentyl, or cyclohexyl, optionally substituted with 1, 2, 3, 4, or 5 $Z^{2d}$ groups.

In certain embodiments of a compound of formula I, Ia, Ib, Ic, Id, II, III, IV, V, VI, VII, VIIa, or VIIb each $Z^{2b}$ is independently 3-12 membered C-linked heterocycle optionally substituted with 1, 2, 3, 4, or 5 $Z^{2d}$ groups. In certain embodiments of a compound of formula I, Ia, Ib, Ic, Id, II, III, IV, V, VI, VII, VIIa, or VIIb each $Z^{2b}$ is independently 4-10 membered C-linked heterocycle optionally substituted with 1, 2, 3, 4, or 5 $Z^{2d}$ groups, wherein the 4-10 membered C-linked heterocycle has 3-9 carbon atoms and 1-3 heteroatoms in the ring system. In certain embodiments of a compound of formula I, Ia, Ib, Ic, Id, II, III, IV, V, VI, VII, VIIa, or VIIb each $Z^{2b}$ is independently 4-8 membered C-linked heterocycle optionally substituted with 1, 2, 3, 4, or 5 $Z^{2d}$ groups, wherein the 4-8 membered C-linked heterocycle has 3-7 carbon atoms and 1-3 heteroatoms in the ring system. In certain embodiments of a compound of formula I, Ia, Ib, Ic, Id, II, III, IV, V, VI, VII, VIIa, or VIIb each $Z^{2b}$ is independently dihydroquinolinyl, dihydropyridinyl, oxetanyl, azetidinyl, pyrrolidinyl, tetrahydropyranyl, tetrahydrofuranyl, piperidinyl, piperazinyl, morpholinyl, hexahydrofuro[2,3-b]furanyl, oxaspiro[3.3]heptanyl, oxazolidinyl, dioxanyl, dihydroimidazo[2,1-c][1,4]oxazinyl, or oxotriazolyl optionally substituted with 1, 2, 3, 4, or 5 $Z^{2d}$ groups.

In certain embodiments of a compound of formula I, Ia, Ib, Ic, Id, II, III, IV, V, VI, VII, VIIa, VIIb, VIIc or VIId, each $Z^{2b}$ is independently phenyl, 5-10 membered C-linked-heteroaryl, 3-7 membered carbocycle, 4-6 membered C-linked-heterocycle or amino substituted with 4-5 membered heterocycle, wherein any phenyl, 5-10 membered C-linked-heteroaryl, 3-7 membered carbocycle, 4-6 membered C-linked-heterocycle, or 4-5 membered heterocycle of $Z^{2b}$ is optionally substituted with 1, 2, 3, 4, or 5 $Z^{2d}$ groups, wherein each $Z^{2d}$ is independently oxo, halogen, —CN, —$OR^{n4}$, —OC(O)$R^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, —C(O)NR$^{q4}$R$^{p4}$, or (C$_1$-C$_4$)alkyl optionally substituted with 1, 2, or 3 halogen or —OR$^{n4}$.

In certain embodiments of a compound of formula I, Ia, Ib, Ic, Id, II, III, IV, V, VI, VII, VIIa, VIIb, VIIc or VIId, each $Z^{2b}$ is cyclopropyl, cyclobutyl, cyclopentyl, cyclohexyl, dihydroquinolinyl, dihydropyridinyl, oxetanyl, azetidinyl, pyrrolidinyl, tetrahydropyranyl, tetrahydrofuranyl, piperidinyl, piperazinyl, morpholinyl, hexahydrofuro[2,3-b]furanyl, oxaspiro[3.3]heptanyl, oxazolidinyl, dioxanyl, dihydroimidazo[2,1-c][1,4]oxazinyl, oxotriazolyl, phenyl, pyridinyl, pyrimidinyl, pyrrolo[2,3-b]pyridinyl, imidazolyl, furanyl, or triazolyl, wherein each $Z^{2b}$ is optionally substituted with 1, 2 or 3 $Z^{2d}$ groups.

In certain embodiments oaf a compound of formula I, Ia, Ib, Ic, Id, II, III, IV, V, VI, VII, VIIa, VIIb, VIIc, or VIId, each $Z^{2b}$ is cyclopropyl, cyclobutyl, cyclopentyl, cyclohexyl, 2-oxo-1,2-dihydroquinolin-6-yl, 6-oxo-1,6-dihydropyridin-3-yl, oxetan-3-yl, azetidin-3-yl, pyrrolidin-2-yl, pyrrolidin-3-yl, tetrahydro-2H-pyran-4-yl, tetrahydropyran-4-yl, tetrahydrofuran-3-yl, piperidin-2-yl, piperidin-3-yl, piperidin-4-yl, piperazin-1-yl, morpholin-2-yl, morpholin-3-yl, hexahydrofuro[2,3-b]furan-3-yl, oxaspiro[3.3]heptan-6-yl, oxazolidin-3-yl, oxazolidin-4-yl, dioxan-5-yl, 5H-imidazo[2,1-c][1,4]oxazin-8-yl, oxotriazol-1-yl, phenyl, pyridin-3-yl, pyridin-4-yl, pyrimidin-5-yl, 1H-pyrrolo[2,3-b]pyridin-6-yl, 1H-imidazol-1-yl, imidazol-2-yl, 1H-imidazol-4-yl, 1H-imidazol-5-yl, furan-2-yl, triazol-1-yl, or triazol-4-yl, wherein each $Z^{2b}$ is optionally substituted with 1, 2, or 3 $Z^{2d}$ groups.

In certain embodiments of a compound of formula I, Ia, Ib, Ic, Id, II, III, IV, V, VI, VII, VIIa, VIIb, VIIc, or VIId, each $Z^{2b}$ optionally substituted with 1, 2 or 3 $Z^{2d}$ groups is

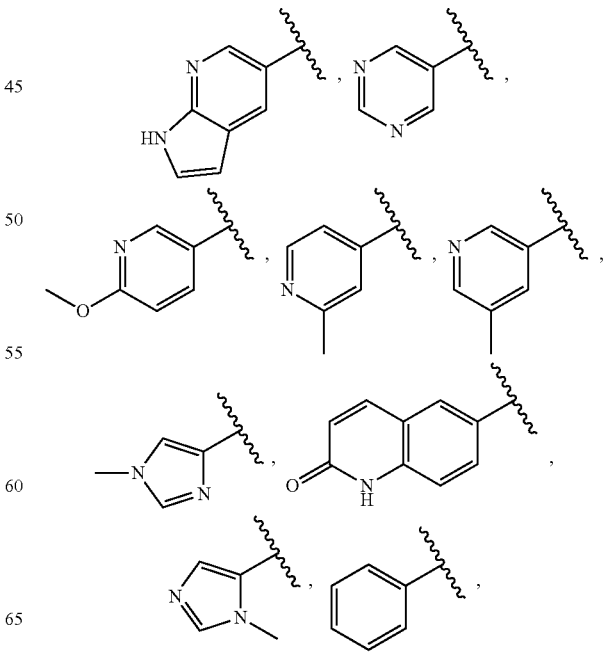

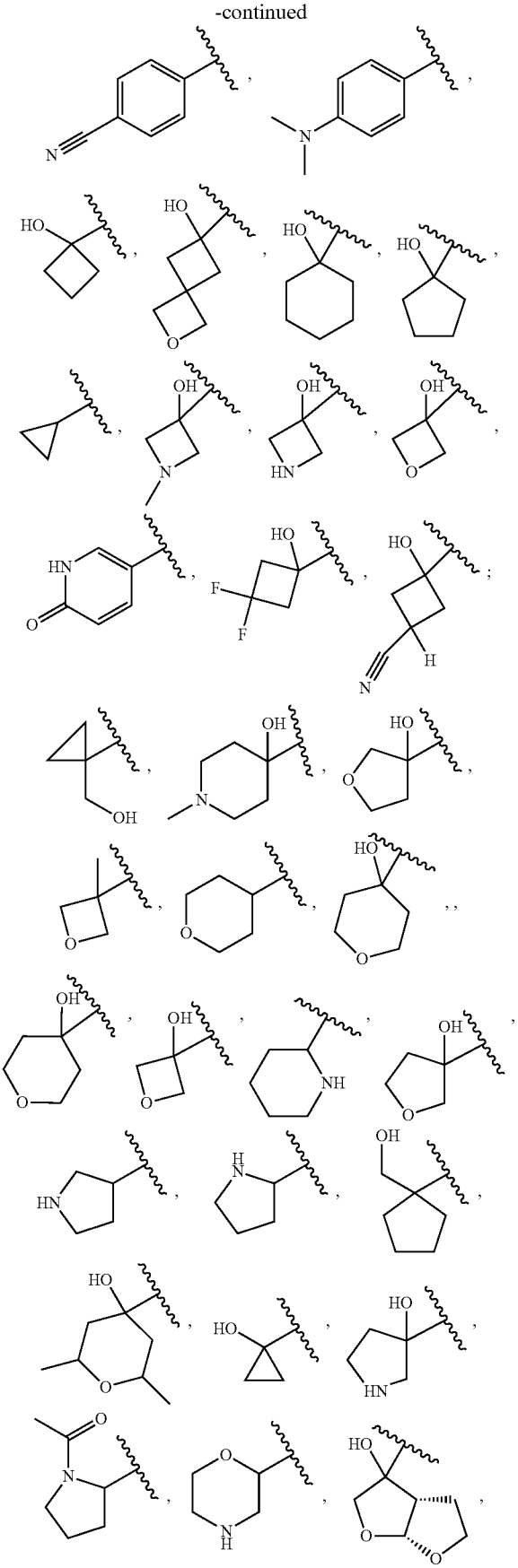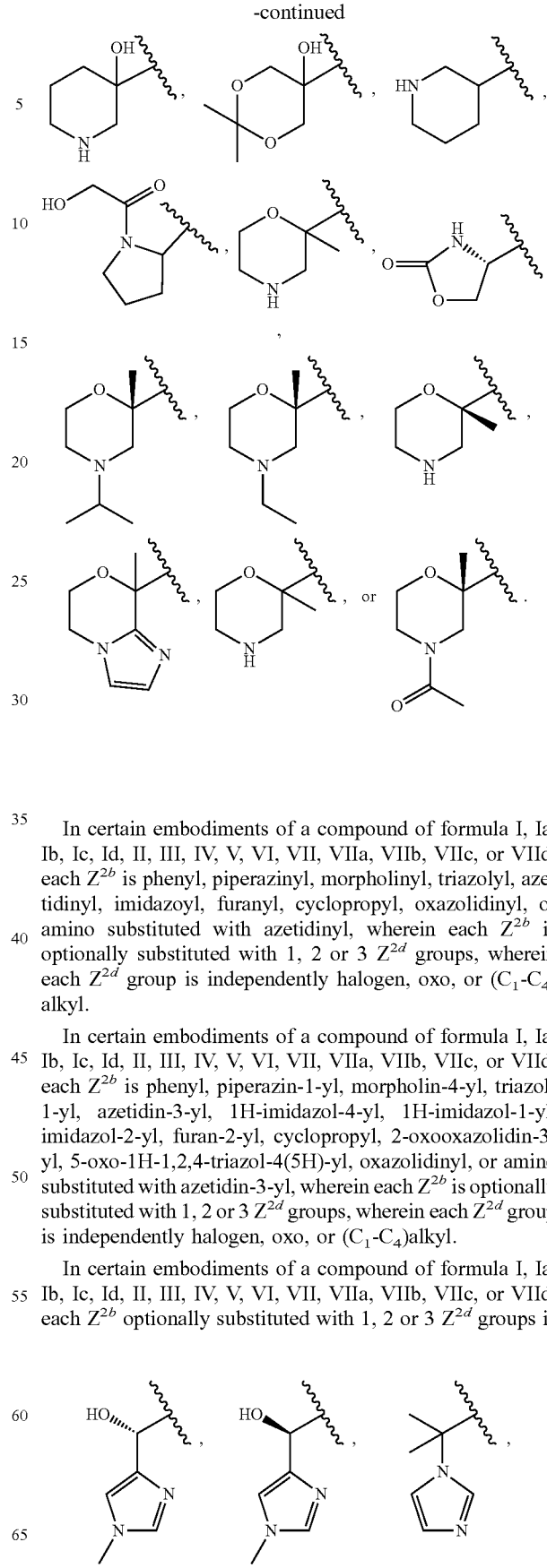

In certain embodiments of a compound of formula I, Ia, Ib, Ic, Id, II, III, IV, V, VI, VII, VIIa, VIIb, VIIc, or VIId, each $Z^{2b}$ is phenyl, piperazinyl, morpholinyl, triazolyl, azetidinyl, imidazoyl, furanyl, cyclopropyl, oxazolidinyl, or amino substituted with azetidinyl, wherein each $Z^{2b}$ is optionally substituted with 1, 2 or 3 $Z^{2d}$ groups, wherein each $Z^{2d}$ group is independently halogen, oxo, or $(C_1$-$C_4)$ alkyl.

In certain embodiments of a compound of formula I, Ia, Ib, Ic, Id, II, III, IV, V, VI, VII, VIIa, VIIb, VIIc, or VIId, each $Z^{2b}$ is phenyl, piperazin-1-yl, morpholin-4-yl, triazol-1-yl, azetidin-3-yl, 1H-imidazol-4-yl, 1H-imidazol-1-yl, imidazol-2-yl, furan-2-yl, cyclopropyl, 2-oxooxazolidin-3-yl, 5-oxo-1H-1,2,4-triazol-4(5H)-yl, oxazolidinyl, or amino substituted with azetidin-3-yl, wherein each $Z^{2b}$ is optionally substituted with 1, 2 or 3 $Z^{2d}$ groups, wherein each $Z^{2d}$ group is independently halogen, oxo, or $(C_1$-$C_4)$alkyl.

In certain embodiments of a compound of formula I, Ia, Ib, Ic, Id, II, III, IV, V, VI, VII, VIIa, VIIb, VIIc, or VIId, each $Z^{2b}$ optionally substituted with 1, 2 or 3 $Z^{2d}$ groups is

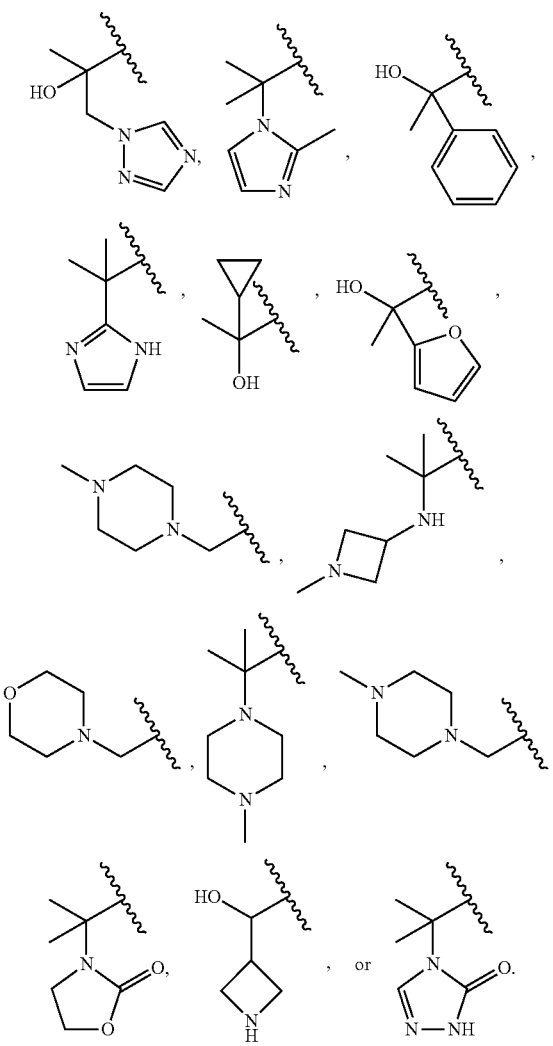

In certain embodiments of a compound of formula IV or VII, the moiety

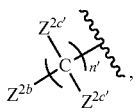

wherein $Z^{2b}$ is optionally substituted with 1, 2 or 3 $Z^{2d}$ groups, is

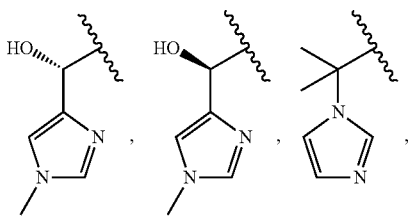

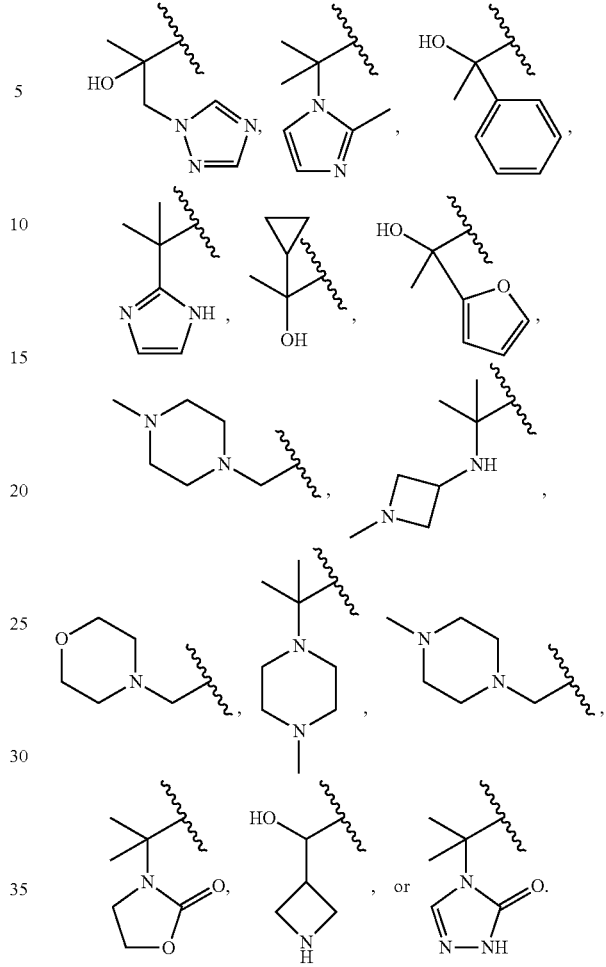

In certain embodiments of a compound of formula I, Ia, Ib, Ic, Id, II, III, IV, V, VI, VII, VIIa, or VIIb, $Z^2$ is 5-6 membered C-linked-monocyclic-heteroaryl substituted with one $Z^{2b}$ and optionally 1, 2, or 3 $Z^{2c}$ groups. In certain embodiments of a compound of formula I, Ia, Ib, Ic, Id, II, III, IV, V, VI, VII, VIIa, or VIIb, $Z^2$ is pyrazolyl optionally substituted 1, 2, or 3 $Z^{2d}$ groups. In certain embodiments of a compound of formula I, Ia, Ib, Ic, Id, II, III, IV, V, VI, VII, VIIa, or VIIb, $Z^{2b}$ is 4-6 membered C-linked-heterocycle. In certain embodiments of a compound of I, Ia, Ib, Ic, Id, II, III, IV, V, VI, VII, VIIa, or VIIb, $Z^{2b}$ is oxetanyl, tetrahydrofuranyl, or tetrahydropyranyl. In certain embodiments of a compound of formula I, Ia, Ib, Ic, Id, II, III, IV, V, or VI, $Z^{2b}$ is oxetan-3-yl, tetrahydrofuranyl, or tetrahydropyran-4-yl.

In certain embodiments of a compound of formula I, Ia, Ib, Ic, Id, II, III, IV, V, VI, VII, VIIa, VIIb, VIIc, or VIId, $Z^{2b}$ is optionally substituted with 1, 2 or 3 $Z^{2d}$ groups, wherein each $Z^{2d}$ group is independently halogen, —CN, $OR^{n4}$, —$NR^{q4}R^{r4}$, oxo, (C$_1$-C$_4$)alkyl optionally substituted with —OH, or C(O)$R^{n4}$, where $R^{n4}$ is (C$_1$-C$_4$)alkyl optionally substituted with 1, 2, or 3 —OH groups.

In certain embodiments of a compound of formula I, Ia, Ib, Ic, Id, II, III, IV, V, VI, VII, VIIa, VIIb, VIIc, or VIId, each $Z^{2d}$ group is independently halogen, —CN, $OR^{n4}$, —$NR^{q4}R^{r4}$, oxo, (C$_1$-C$_4$)alkyl optionally substituted with —OH, or C(O)$R^{n4}$, where $R^{n4}$ is (C$_1$-C$_4$)alkyl optionally substituted with 1, 2, or 3 —OH groups.

In certain embodiments of a compound of formula I, Ia, Ib, Ic, Id, II, III, IV, V, VI, VII, VIIa, VIIb, VIIc, or VIId, each $Z^{2d}$ group is independently methyl, halogen or —OH.

In certain embodiments of a compound of formula I, Ia, Ib, Ic, Id, II, III, IV, V, VI, VII, VIIa, VIIb, VIIc, or VIId, each $Z^{2d}$ group is independently halogen or —OH.

In certain embodiments of a compound of formula I, Ia, Ib, Ic, Id, II, III, IV, V, VI, VII, VIIa, VIIb, VIIc, or VIId, each $Z^{2d}$ group is independently halogen, oxo, or $(C_1$-$C_4)$ alkyl.

In certain embodiments of a compound of formula I, Ia, Ib, Ic, Id, II, III, IV, V, VI, VIIa, or VIIb, $Z^2$ substituted with 1 or 2 $Z^{2b}$ groups, and optionally 1, 2, or 3 $Z^{2c}$ groups is selected from:

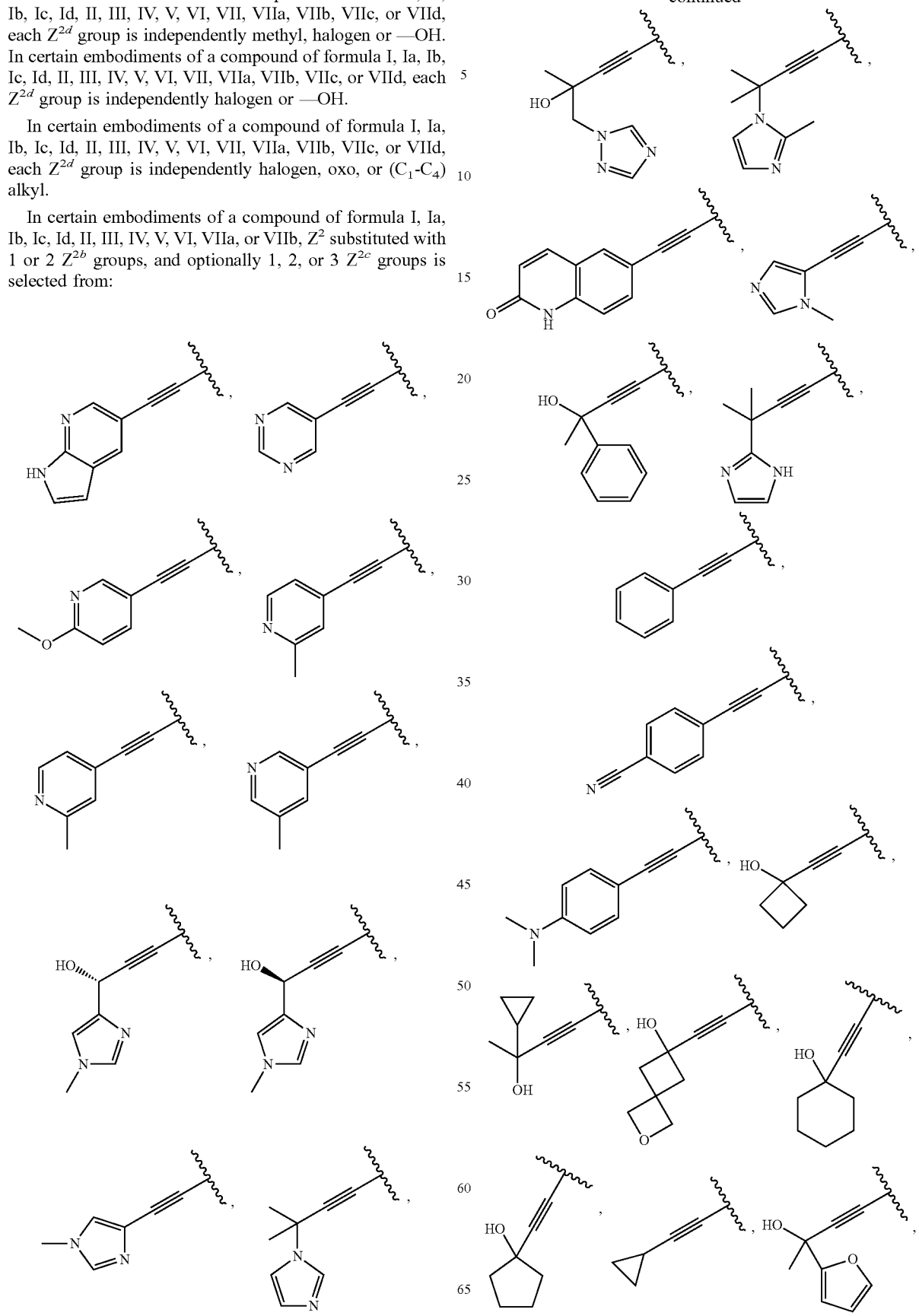

31
-continued
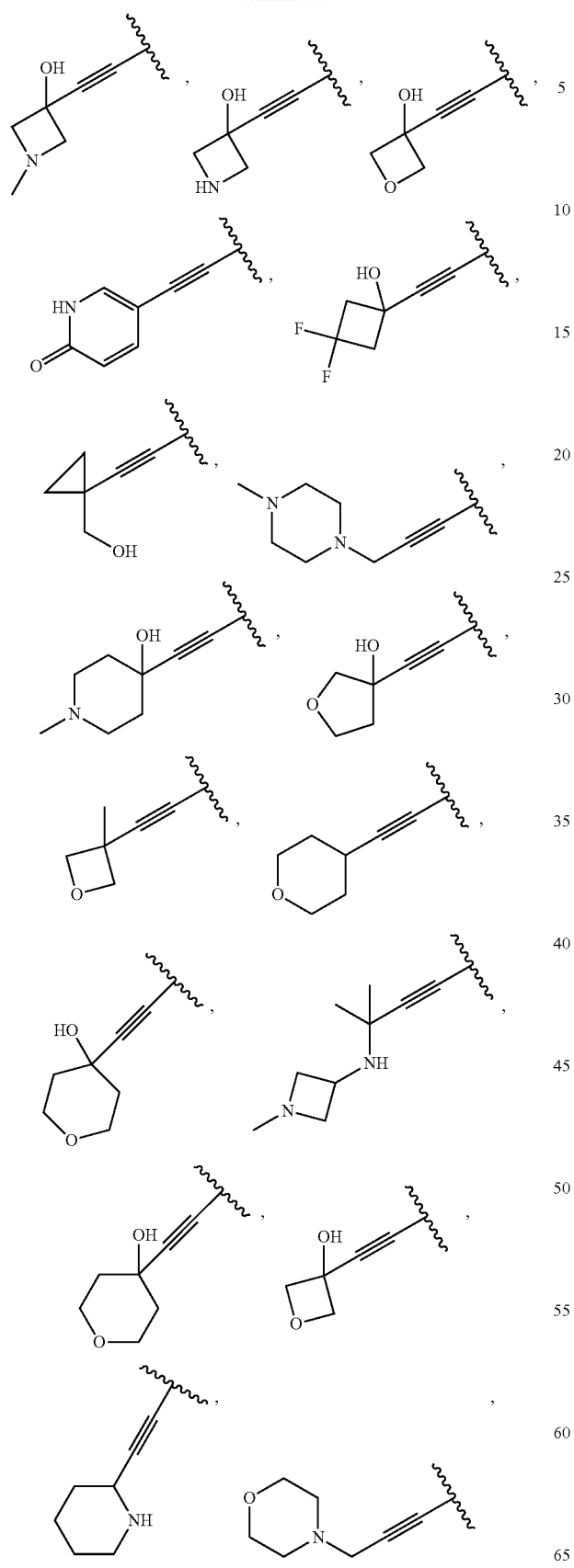
32
-continued
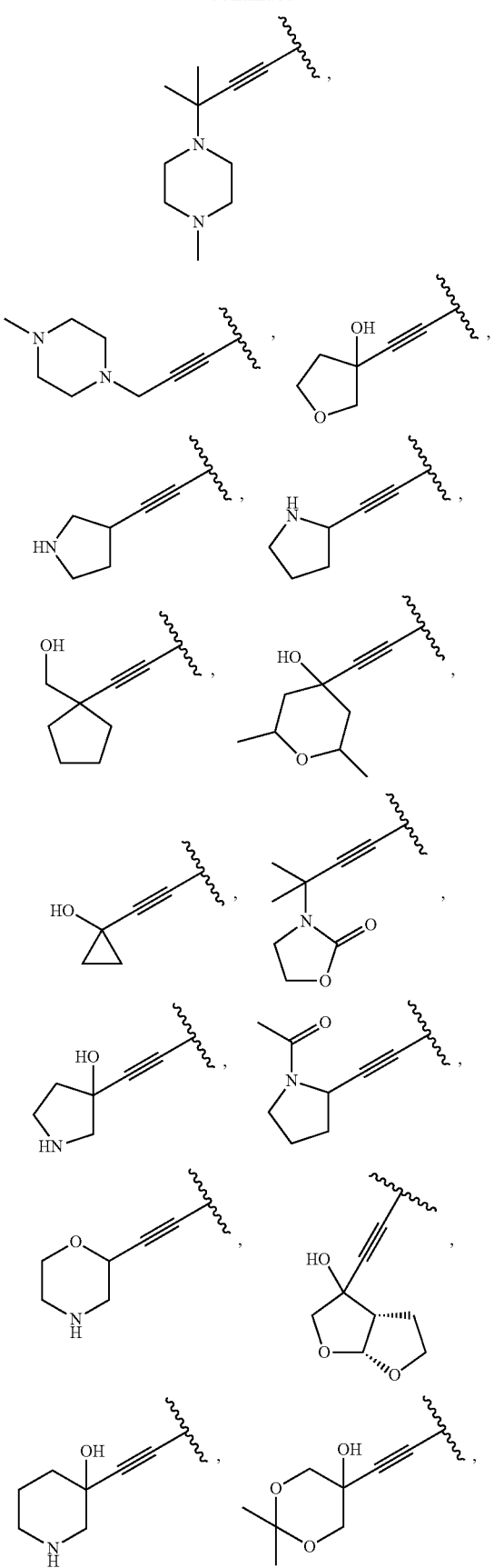

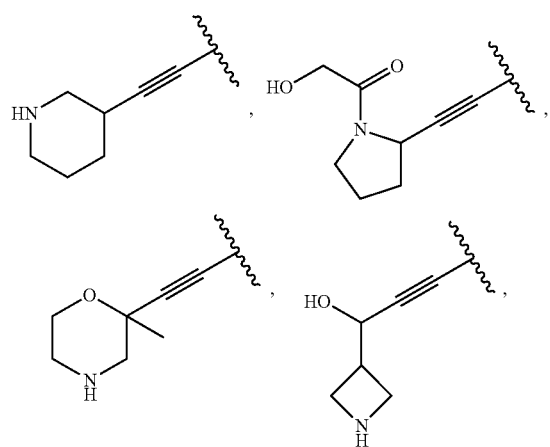
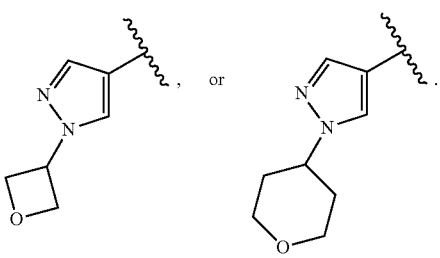
In certain embodiments of a compound of formula I, Ia, Ib, Ic, Id, II, III, IV, V, VI, VIIa, or VIIb, $Z^2$ substituted with 1 or 2 $Z^{2b}$ groups, and optionally 1, 2, or 3 $Z^{2c}$ groups is selected from
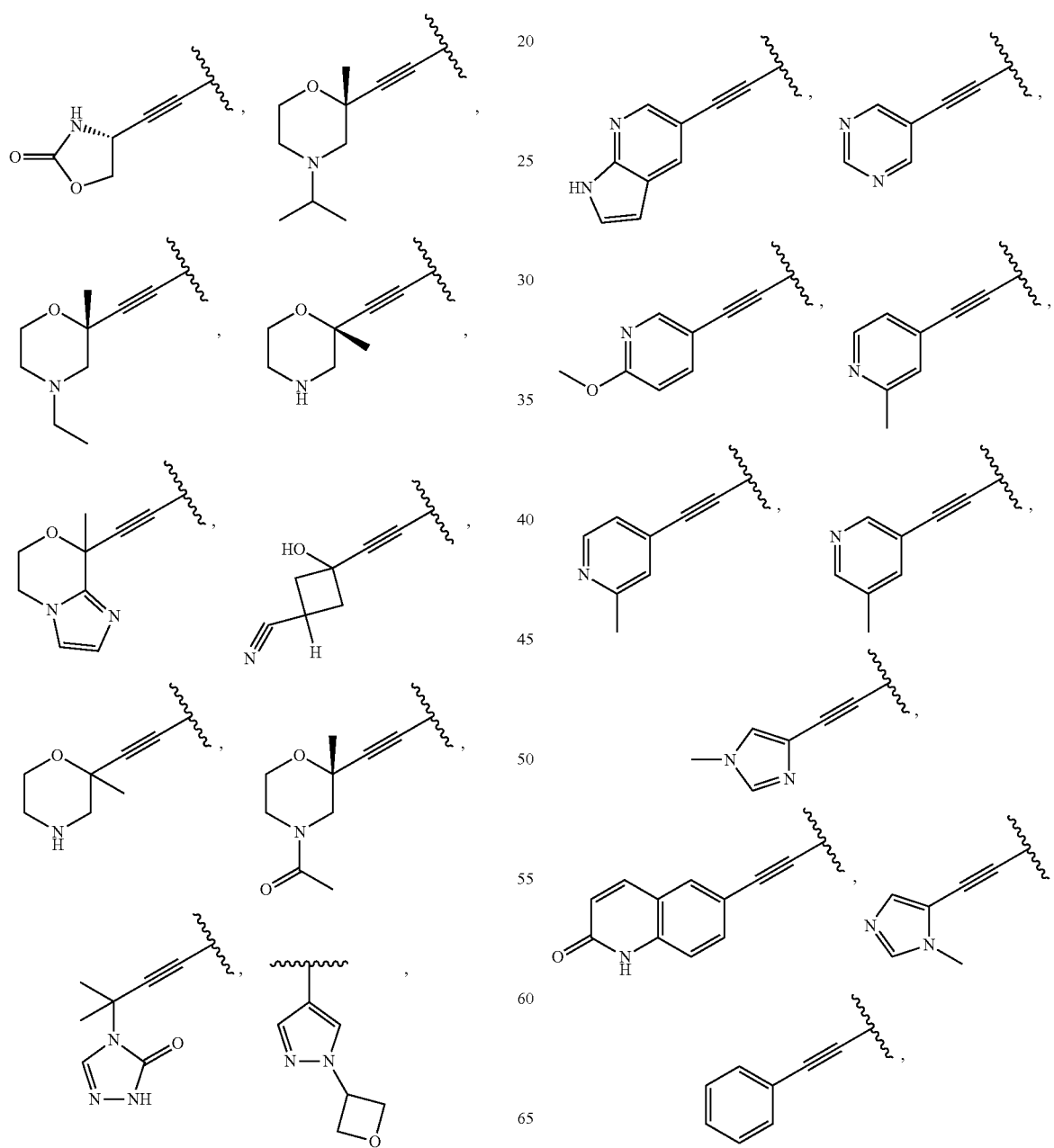

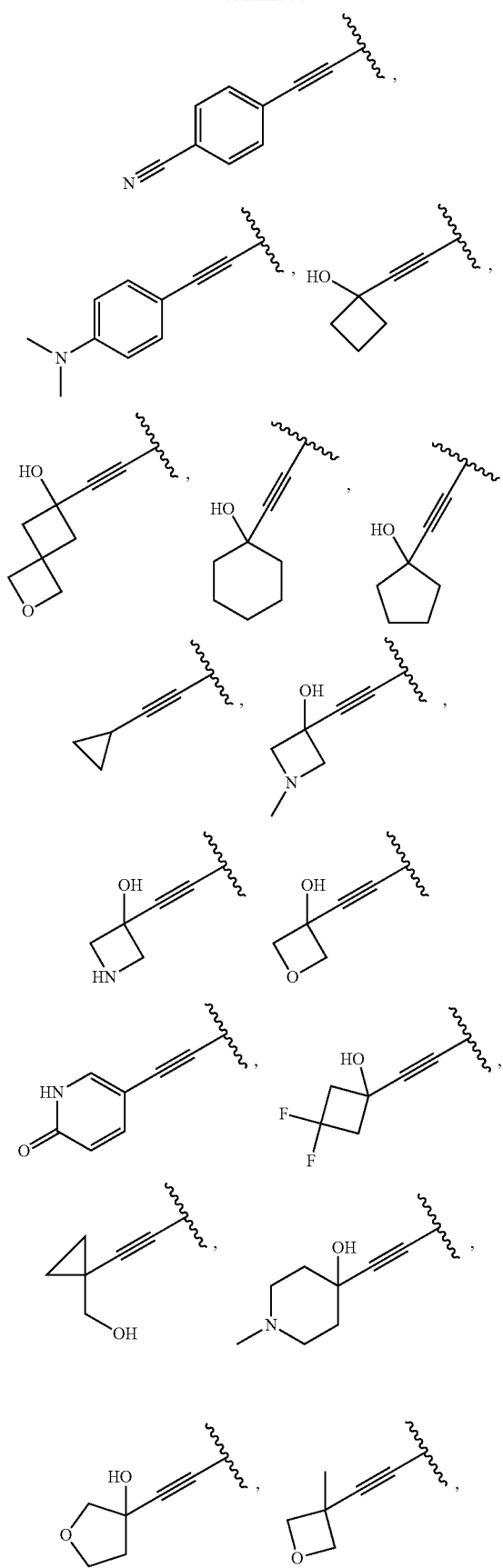
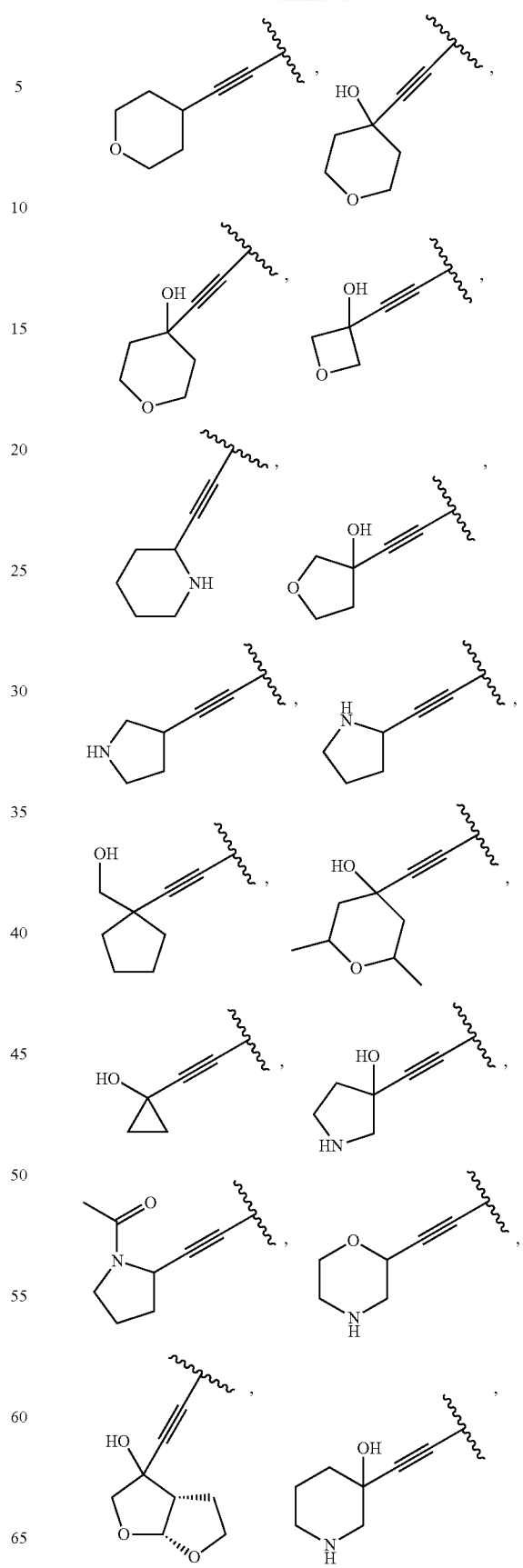

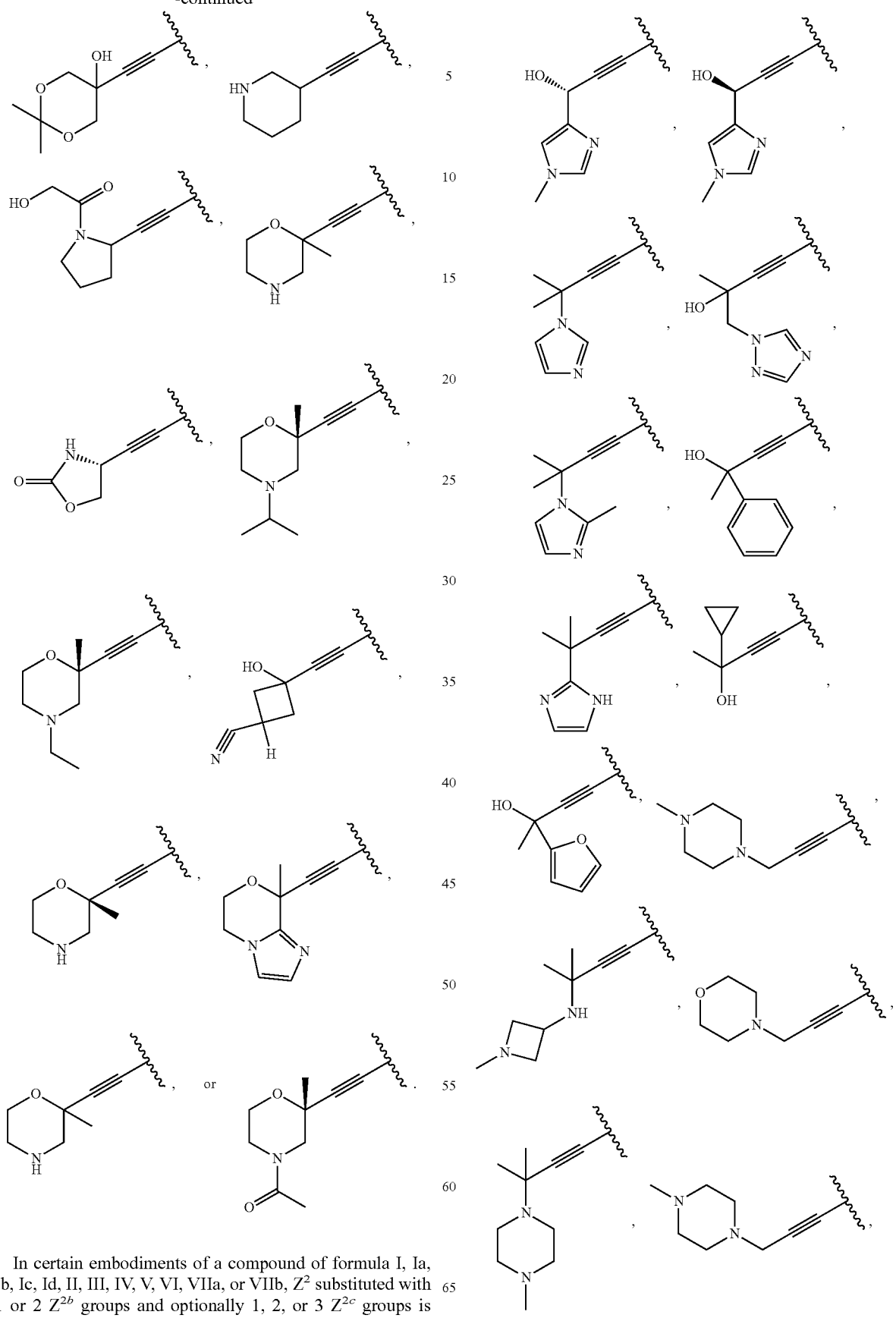
In certain embodiments of a compound of formula I, Ia, Ib, Ic, Id, II, III, IV, V, VI, VIIa, or VIIb, $Z^2$ substituted with 1 or 2 $Z^{2b}$ groups and optionally 1, 2, or 3 $Z^{2c}$ groups is selected from

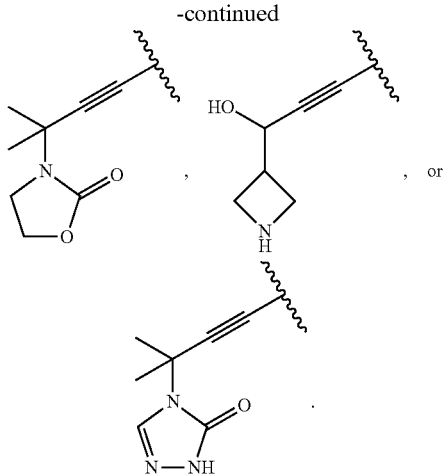

In certain embodiments of a compound of formula I, Ia, Ib, Ic, Id, II, III, IV, V, or VI, $R^1$ is a 5-12 membered heteroaryl, wherein any 5-12 membered heteroaryl of $R^1$ is optionally substituted with one or more (e.g., 1, 2, 3, 4, or 5) $Z^4$ groups.

In certain embodiments of a compound of formula I, Ia, Ib, Ic, Id, II, III, IV, V, or VI, $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with one or more (e.g., 1, 2, 3, 4, or 5) $Z^4$ groups.

In certain embodiments of a compound of formula I, Ia, Ib, Ic, Id, II, III, IV, V, or VI, $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl have 4-10 carbon atoms and 1-5 heteroatoms in the ring system, and wherein any 8-12 membered bicyclic-heteroaryl or 8-12 membered tricyclic-heteroaryl of $R^1$ is optionally substituted with one or more (e.g., 1, 2, 3, 4, or 5) $Z^4$ groups.

In certain embodiments of a compound of formula I, Ia, Ib, Ic, Id, II, III, IV, V, or VI, $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl contains at least one partially unsaturated ring, and wherein any 8-12 membered bicyclic-heteroaryl or 8-12 membered tricyclic-heteroaryl of $R^1$ is optionally substituted with one or more (e.g., 1, 2, 3, 4 or 5) $Z^4$ groups.

In certain embodiments of a compound of formula I, Ia, Ib, Ic, Id, II, III, IV, V, or VI, $R^1$ has the following formula

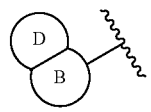

wherein:
D together with the two carbon atoms of ring B to which it is attached forms a 3-7 membered monocyclic-carbocycle, 5-8 membered bicyclic-carbocycle, 3-7 membered monocyclic-heterocycle or 5-8 membered bicyclic heterocycle, wherein any 3-7 membered monocyclic-carbocycle, 5-8 membered bicyclic-carbocycle, 3-7 membered monocyclic-heterocycle or 5-8 membered bicyclic heterocycle of D is optionally substituted with one or more (e.g. 1, 2, 3, 4 or 5) $Z^4$ groups; and B is a 5 or 6 membered monocyclic-heteroaryl with 1, 2 or 3 nitrogen atoms, wherein B is optionally substituted with one or more or (e.g. 1, 2, 3, 4 or 5) $Z^4$ groups.

In certain embodiments of a compound of formula I, Ia, Ib, Ic, Id, II, III, IV, V, or VI, $R^1$ has the following formula

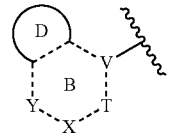

wherein:
D together with the two carbon atoms of ring B to which it is attached forms a 3-7 membered monocyclic-carbocycle, 5-8 membered bicyclic-carbocycle, 3-7 membered monocyclic-heterocycle or 5-8 membered bicyclic heterocycle, wherein any 3-7 membered monocyclic-carbocycle, 5-8 membered bicyclic-carbocycle, 3-7 membered monocyclic-heterocycle or 5-8 membered bicyclic heterocycle of D is optionally substituted with one or more (e.g. 1, 2, 3, 4 or 5) $Z^4$ groups; and B is a 5 or 6 membered monocyclic-heteroaryl having 1, 2 or 3 nitrogen atoms;
V is C or N;
T is $CZ^{4c}$, $NZ^{4c}$ or N;
X is $CZ^{4c}$, $NZ^{4c}$ or N;
Y is $CZ^{4c}$, N or absent;
the dashed bonds are selected from single bonds and double bonds, wherein the dashed bonds, V, T, X and Y are selected so that the 5 or 6 membered monocyclic-heteroaryl B is aromatic; and
each $Z^{4c}$ is independently selected from H or $Z^4$.

In certain embodiments of a compound of formula I, Ia, Ib, Ic, Id, II, III, IV, V, or VI, $R^1$ has the following formula

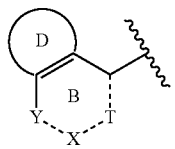

wherein:
D together with the two carbon atoms of ring B to which it is attached forms a 3-7 membered monocyclic-carbocycle, 5-8 membered bicyclic-carbocycle, 3-7 membered monocyclic-heterocycle or 5-8 membered bicyclic heterocycle, wherein any 3-7 membered monocyclic-carbocycle, 5-8 membered bicyclic-carbocycle, 3-7 membered monocyclic-heterocycle or 5-8 membered bicyclic heterocycle of D is optionally substituted with one or more (e.g. 1, 2, 3, 4 or 5) $Z^4$ groups; and B is a 5 or 6 membered monocyclic-heteroaryl having 1, 2 or 3 nitrogen atoms;
V is C or N;
T is $CZ^{4c}$ or N;
X is $CZ^{4c}$, $NZ^{4c}$ or N;
Y is $CZ^{4c}$, N or absent;
the dashed bonds are selected from single bonds and double bonds, wherein the dashed bonds, V, T, X and Y are selected so that the 5 or 6 membered monocyclic-heteroaryl B is aromatic; and
each $Z^{4c}$ is independently selected from H or $Z^4$.

In certain embodiments of a compound of formula I, Ia, Ib, Ic, Id, II, III, IV, V, or VI, $R^1$ has the following formula:

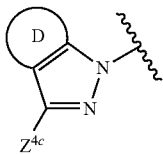

wherein:

D together with the two carbon atoms to which it is attached forms a 3-7 membered monocyclic-carbocycle, 5-9 membered bicyclic-carbocycle, 3-7 membered monocyclic-heterocycle or 5-9 membered bicyclic heterocycle, wherein any 3-7 membered monocyclic-carbocycle, 5-9 membered bicyclic-carbocycle, 3-7 membered monocyclic-heterocycle or 5-9 membered bicyclic heterocycle of D is optionally substituted with one or more (e.g. 1, 2, 3, 4 or 5) $Z^4$ groups; and each $Z^{4c}$ is independently selected from H or $Z^4$.

In certain embodiments of a compound of formula I, Ia, Ib, Ic, Id, II, III, IV, V, VI, VII, VIIa, VIIb, VIIc, or VIId, each $Z^4$ is independently ($C_1$-$C_6$)alkyl, —CN, or halogen, wherein any ($C_1$-$C_6$)alkyl of $Z^4$ is optionally substituted with one or more (e.g., 1, 2, 3, 4, or 5) halogen.

In certain embodiments of a compound of formula I, Ia, Ib, Ic, Id, II, III, IV, V, VI, VII, VIIa, VIIb, VIIc, or VIId, each $Z^4$ is independently fluoro, trifluoromethyl or difluoromethyl.

In certain embodiments of a compound of formula I, Ia, Ib, Ic, Id, II, III, IV, V, or VI, $R^1$ is selected from:

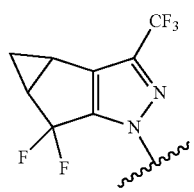 and 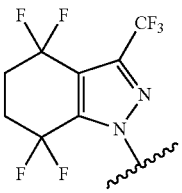

In certain embodiments of a compound of formula I, Ia, Ib, Ic, Id, II, III, IV, V, or VI, $R^1$ is selected from:

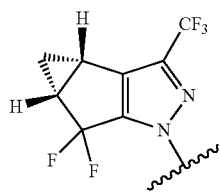 and 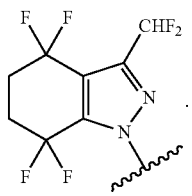

In certain embodiments of a compound of formula I, Ia, Ib, Ic, Id, II, III, IV, V, or VI, $R^1$ is

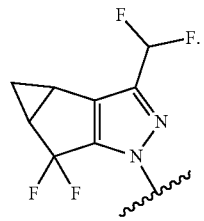 [SMILES: *n1nc(C(F)F)c2c1C(F)(F)C1CC21]

In certain embodiments of a compound of formula I, Ia, Ib, Ic, Id, II, III, IV, V, or VI, $R^1$ is

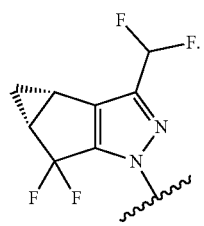 [SMILES: *n1nc(C(F)F)c2c1C(F)(F)[C@@H]1C[C@H]21]

In certain embodiments of a compound of formula I, Ia, Ib, Ic, Id, II, III, IV, V, or VI, $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl has 4-9 carbon atoms and 1-5 heteroatoms in the ring system, and wherein any 8-12 membered bicyclic-heteroaryl or 8-12 membered tricyclic-heteroaryl of $R^1$ is optionally substituted with one or more (e.g., 1, 2, 3, 4 or 5) $Z^4$ groups.

In certain embodiments of a compound of formula I, Ia, Ib, Ic, Id, II, III, IV, V, or VI, $R^1$ is a 8-12 membered bicyclic-heteroaryl, wherein the 8-12 membered bicyclic-heteroaryl has 6-9 carbon atoms and 1-3 heteroatoms in the ring system, and wherein any 8-12 membered bicyclic-heteroaryl of $R^1$ is optionally substituted with one or more (e.g., 1, 2, 3, 4 or 5) $Z^4$ groups.

In certain embodiments of a compound of formula I, Ia, Ib, Ic, Id, II, III, IV, V, or VI, $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl has 6-9 carbon atoms and 1-3 heteroatoms in the ring system, and wherein any 8-12 membered bicyclic-heteroaryl or 8-12 membered tricyclic-heteroaryl of $R^1$ is optionally substituted with one or more (e.g., 1, 2, 3, 4 or 5) $Z^4$ groups.

In certain embodiments of a compound of formula I, Ia, Ib, Ic, Id, II, II, IV, V, or VI, $R^1$ is selected from indolyl, indazolyl, and 4,5,6,7-tetrahydro-indazolyl, wherein any indolyl, indazolyl, and 4,5,6,7-tetrahydro-indazolyl of $R^1$ is optionally substituted with one or more (e.g., 1, 2, 3, 4 or 5) $Z^4$ groups.

In certain embodiments of a compound of formula I, Ia, Ib, Ic, Id, II, III, IV, V, or VI, $R^1$ is selected from indolyl, 4,5,6,7-tetrahydro-indazolyl, 3b,4,4a,5-tetrahydro-cyclopropa[3,4]cyclopenta[1,2-c]pyrazole and 1,4,5,5a,6,6a-hexahydrocyclopropa[g]indazole, wherein any indolyl, 4,5,6,7-tetrahydro-indazolyl, 3b,4,4a,5-tetrahydro-cyclopropa[3,4]cyclopenta[1,2-c]pyrazole and 1,4,5,5a,6,6a-hexahydrocyclopropa[g]indazole of $R^1$ is optionally substituted with one or more (e.g., 1, 2, 3, 4 or 5) $Z^4$ groups.

In certain embodiments of a compound of formula I, Ia, Ib, Ic, Id, II, III, IV, V, or VI, $R^1$ is selected from indol-3-yl and 4,5,6,7-tetrahydro-1H-indazol-1-yl, wherein any indol-3-yl and 4,5,6,7-tetrahydro-1H-indazol-1-yl of $R^1$ is optionally substituted with one or more (e.g., 1, 2, 3, 4 or 5) $Z^4$ groups.

In certain embodiments of a compound of formula I, Ia, Ib, Ic, Id, II, III, IV, V, or VI, $R^1$ is selected from indazolyl, 4,5,6,7-tetrahydro-indazolyl, or 3b,4,4a,5-tetrahydro-cyclopropa[3,4]cyclopenta[1,2-c]pyrazole wherein any indazolyl, 4,5,6,7-tetrahydro-indazolyl, or 3b,4,4a,5-tetrahydro-cyclopropa[3,4]cyclopenta[1,2-c]pyrazole of $R^1$ is optionally substituted with one or more (e.g., 1, 2, 3, 4 or 5) $Z^4$ groups.

In certain embodiments of a compound of formula I, Ia, Ib, Ic, Id, II, III, IV, V, or VI, $R^1$ is selected from 1H-indazol-1-yl, 4,5,6,7-tetrahydro-indazol-1-yl, or 3b,4,4a,5-tetrahydro-1H-cyclopropa[3,4]cyclopenta[1,2-c]pyrazol-1-yl wherein any 1H-indazol-1-yl, 4,5,6,7-tetrahydro-1H-indazol-1-yl, or 3b,4,4a,5-tetrahydro-1H-cyclopropa[3,4]cyclopenta[1,2-c]pyrazol-1-yl of $R^1$ is optionally substituted with one or more (e.g., 1, 2, 3, 4 or 5) $Z^4$ groups.

In certain embodiments of a compound of formula I, Ia, Ib, Ic, Id, II, III, IV, V, or VI, $R^1$ is selected from indol-3-yl, 4,5,6,7-tetrahydro-1H-indazol-1-yl, 3b,4,4a,5-tetrahydro-1H-cyclopropa[3,4]cyclopenta[1,2-c]pyrazol-1-yl and 1,4,5,5a,6,6a-hexahydrocyclopropa[g]indazol-1-yl, wherein any indol-3-yl, 4,5,6,7-tetrahydro-1H-indazol-1-yl, 3b,4,4a,5-tetrahydro-1H-cyclopropa[3,4]cyclopenta[1,2-c]pyrazol-1-yl and 1,4,5,5a,6,6a-hexahydrocyclopropa[g]indazol-1-yl of $R^1$ is optionally substituted with one or more (e.g., 1, 2, 3, 4 or 5) $Z^4$ groups.

In certain embodiments of a compound of formula I, Ia, Ib, Ic, Id, II, III, IV, V, VI, $R^1$ is

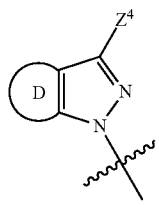

wherein
D, together with the two carbon atoms to which it is attached, forms a 3-7 membered monocyclic-carbocycle, 6 membered aryl, 6 membered heteroaryl, or 5-9 membered bicyclic-carbocycle, wherein any 3-7 membered monocyclic-carbocycle, 6 membered aryl, 6 membered heteroaryl, or 5-9 membered bicyclic-carbocycle of D is optionally substituted with 1, 2, 3, 4 or 5 $Z^4$ groups, wherein the $Z^4$ groups are the same or different. In certain embodiments of a compound of formula I, Ia, Ib, Ic, Id, II, III, IV, V, VI, VII, VIIa, VIIb, VIIc, or VIId, D, together with the two carbon atoms to which it is attached, forms a 5-6 membered monocyclic-carbocycle, 6 membered aryl, or 6 membered bicyclic-carbocycle, wherein any 5-6 membered monocyclic-carbocycle, 6 membered aryl, or 6 membered bicyclic-carbocycle of D is optionally substituted with 1, 2, 3, 4 or 5 $Z^4$ groups, wherein the $Z^4$ groups are the same or different. In certain embodiments of a compound of formula I, Ia, Ib, Ic, Id, II, III, IV, V, VI, VII, VIIa, VIIb, VIIc or VIId, D, together with the two carbon atoms to which it is attached, forms a phenyl, cyclohexyl, cyclopentyl, or bicyclohexyl group, wherein any phenyl, cyclohexyl, cyclopentyl, or bicyclohexyl group of D is optionally substituted with 1, 2, 3, 4 or 5 $Z^4$ groups, wherein the $Z^4$ groups are the same or different.

In certain embodiments of a compound of formula I, Ia, Ib, Ic, Id, II, III, IV, V, VI, VII, VIIa, VIIb, VIIc, or VIId, each $Z^4$ is independently $(C_1-C_6)$alkyl, —CN, or halogen, wherein any $(C_1-C_6)$alkyl of $Z^4$ is optionally substituted with 1, 2, 3, 4 or 5 halogen, which may be the same or different. In certain embodiments of a compound of formula I, Ia, Ib, Ic, Id, II, III, IV, V, VI, VII, VIIa, VIIb, VIIc, or VIId, each $Z^4$ is independently $(C_1-C_3)$alkyl, —CN, or halogen, wherein any $(C_1-C_3)$alkyl of $Z^4$ is optionally substituted with 1, 2, 3, 4 or 5 halogen, which may be the same or different. In certain embodiments of a compound of formula I, Ia, Ib, Ic, Id, II, III, IV, V, VI, VII, VIIa, VIIb, VIIc, or VIId, each $Z^4$ is independently selected from fluoro, —CN trifluoromethyl and difluoromethyl.

In certain embodiments of a compound of formula I, Ia, Ib, Ic, Id, II, III, IV, V, or VI, each $R^1$ is

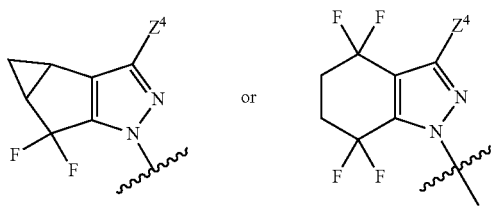

In certain embodiments of a compound of formula VII, VIIa, VIIb, VIIc, or VIId, the moiety

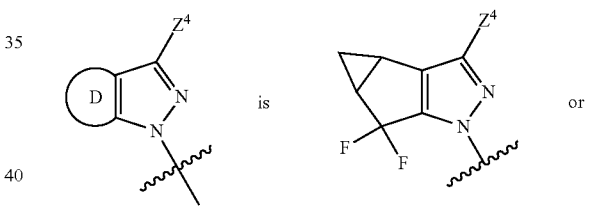

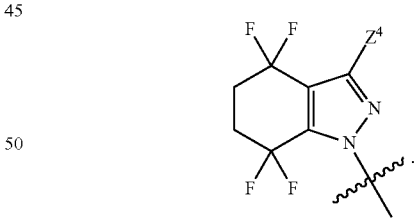

In certain embodiments of a compound of formula I, Ia, Ib, Ic, Id, II, III, IV, V, or VI, each $R^1$ is

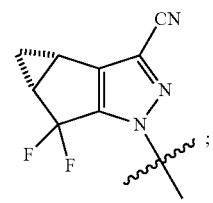

-continued
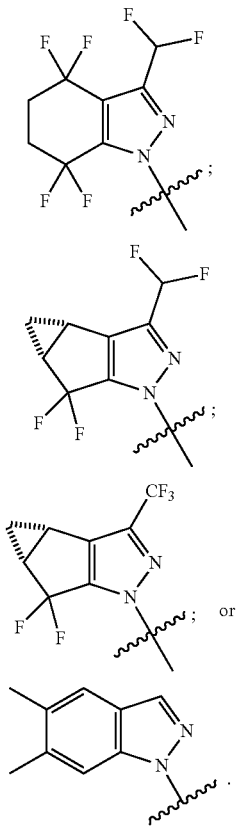
In certain embodiments of a compound of formula VII, VIIa, VIIb, VIIc, or VIId, the moiety
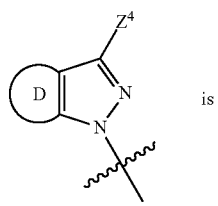 is
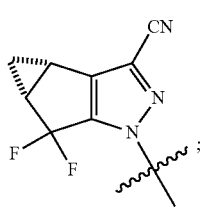
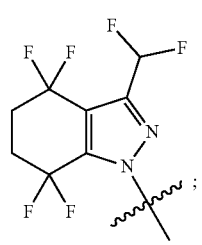
-continued
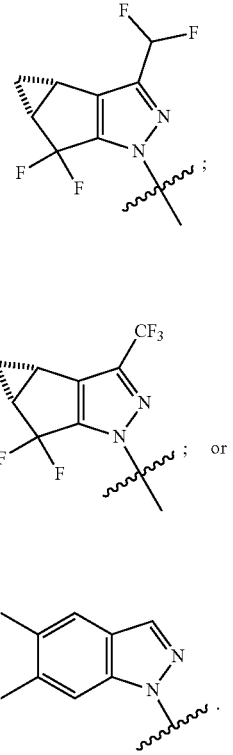
In certain embodiments of a compound of formula I, Ia, Ib, Ic, Id, II, III, IV, V, or VI, each $R^1$ is
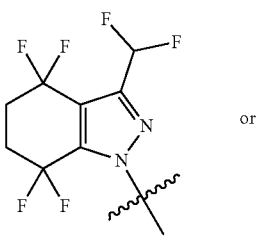
In certain embodiments of a compound of formula VII, VIIa, VIIb, VIIc, or VIId, the moiety
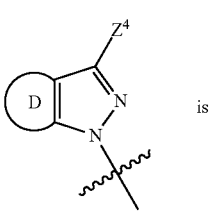 is

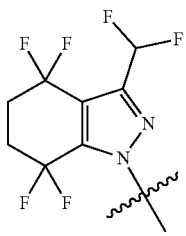
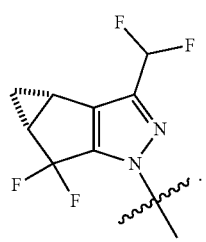
or
In certain embodiments of a compound of formula I, Ia, Ib, Ic, Id, II, III, IV, V, or VI, each R¹ is
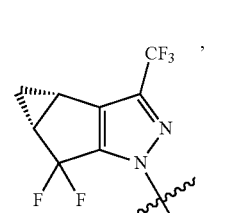
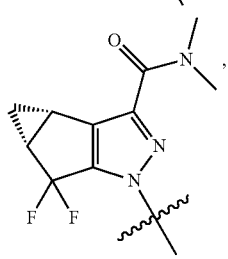
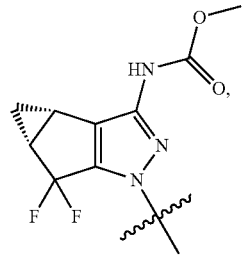
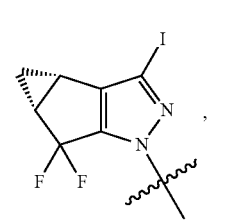
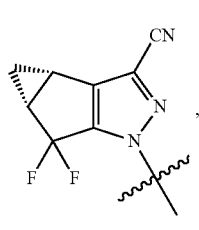
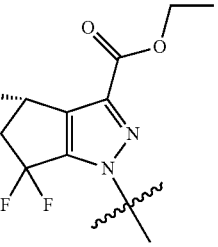
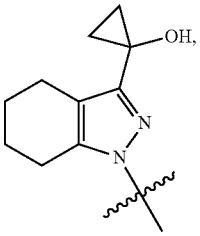
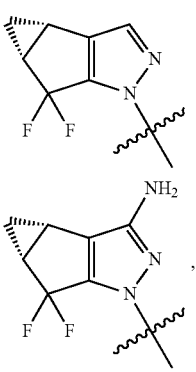
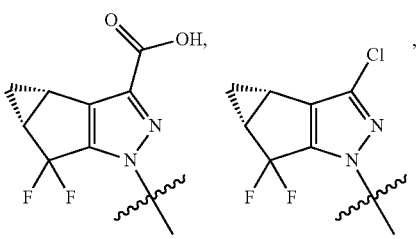
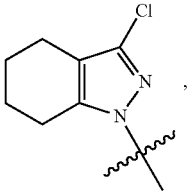
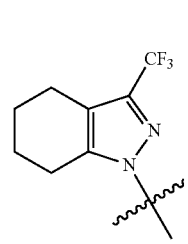
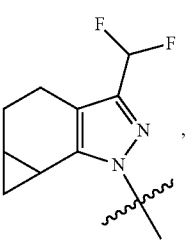
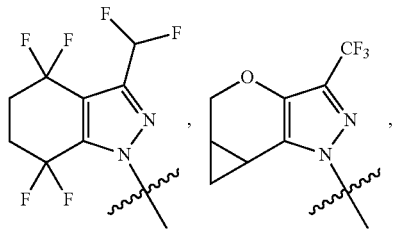

-continued

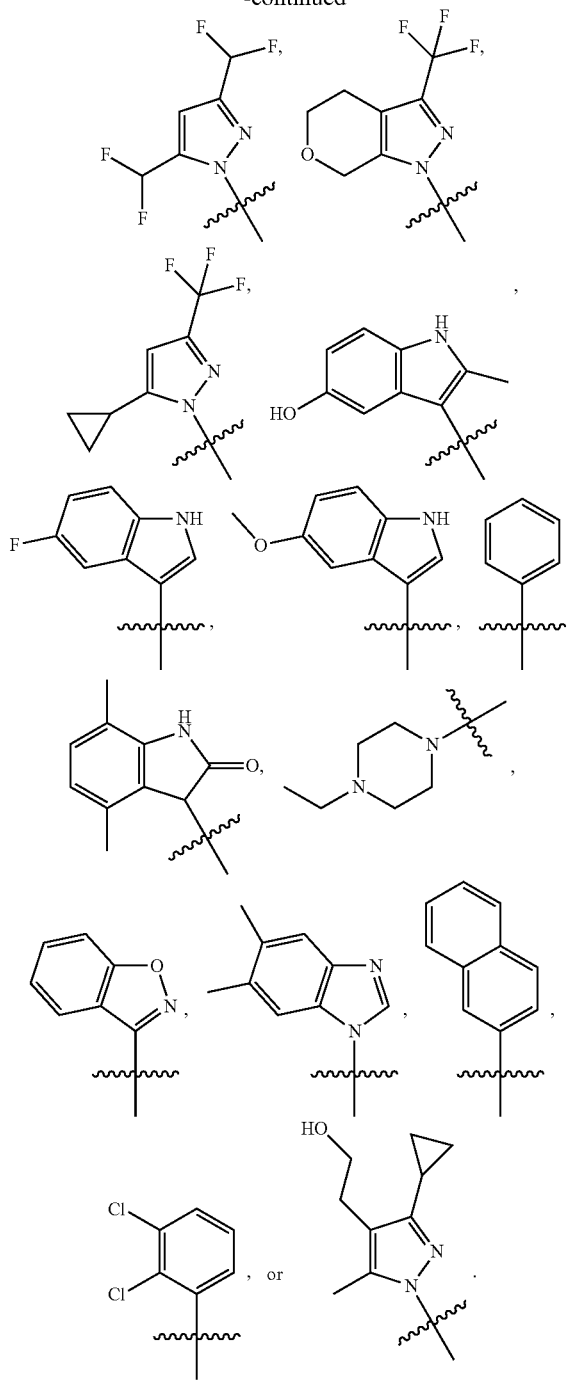

In certain embodiments of a compound of formula I, Ia, Ib, Ic, Id, II, III, IV, V, or VI, $Z^1$ is 6-12 membered aryl, 5-14 membered heteroaryl, or 3-14 membered heterocycle, wherein any 6-12 membered aryl, 5-14 membered heteroaryl, or 3-14 membered heterocycle of $Z^1$ is optionally substituted with 1, 2, 3, 4 or 5 $Z^{1a}$ or $Z^{1b}$, wherein the $Z^{1a}$ and $Z^{1b}$ groups are the same or different.

In certain embodiments of a compound of formula I, Ia, Ib, Ic, Id, II, III, IV, V, or VI, $Z^1$ is phenyl, 8-10 membered bicyclic-heteroaryl, 8-10 membered bicyclic-heterocycle, or 9-12 membered tricyclic-heterocycle, wherein any phenyl, 8-10 membered bicyclic-heteroaryl, 8-10 membered bicyclic-heterocycle, or 9-12 membered tricyclic-heterocycle of $Z^1$ is optionally substituted with 1, 2, 3, 4, or 5 $Z^{1a}$ or $Z^{1b}$ groups.

In certain embodiments of a compound of formula I, Ia, Ib, Ic, Id, II, III, IV, V, or VI, $Z^1$ is phenyl, 8-10 membered bicyclic-heteroaryl or 8-10 membered bicyclic-heterocycle, wherein any 8-10 membered bicyclic-heteroaryl or 8-10 membered bicyclic-heterocycle has 3-9 carbon atoms and 1-5 heteroatoms in the ring system, and wherein any phenyl, 8-10 membered bicyclic-heteroaryl, or 8-10 membered bicyclic-heterocycle of $Z^1$ is optionally substituted with 1, 2, 3, 4, or 5 $Z^{1a}$ or $Z^{1b}$ groups.

In certain embodiments of a compound of formula I, Ia, Ib, Ic, Id, II, III, IV, V, or VI, $Z^1$ is phenyl, 8-10 membered bicyclic-heteroaryl, or 8-10 membered bicyclic-heterocycle, wherein any phenyl, 8-10 membered bicyclic-heteroaryl, or 8-10 membered bicyclic-heterocycle of $Z^1$ is optionally substituted with 1, 2, 3, 4, or 5 $Z^{1a}$ or $Z^{1b}$ groups.

In certain embodiments of a compound of formula I, Ia, Ib, Ic, Id, II, III, IV, V, or VI, $Z^1$ is phenyl, 1H-indazolyl, 2,3-dihydro-[1,2,4]triazolo[4,3-a]pyridinyl, 1H-pyrrolo[2,3-c]pyridinyl, isoindolinyl, or spiro[cyclopropane-1,1'-isoindolin]yl, as shown by the following formulas

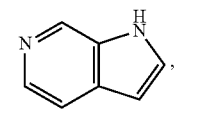

1H-pyrrolo[2,3-c]pyridinyl

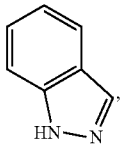

1H-indazolyl

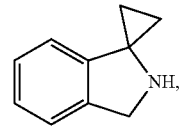

spirocyclopropane-1,1'-isoindolinyl

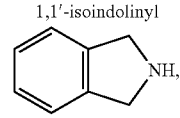

isoindolinyl

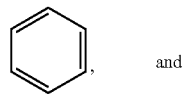

and phenyl

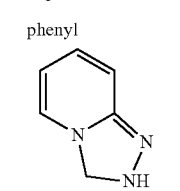

2,3-dihydro-[1,2,4]triazolo[4,3-a]pyridinyl each of which is optionally substituted with 1, 2, 3, 4 or 5 $Z^{1a}$ or $Z^{1b}$.

In certain embodiments of a compound of formula I, Ia, Ib, Ic, Id, II, III, IV, V, or VI, $Z^1$ is phenyl, 1H-indazolyl, 3-oxo-2,3-dihydro-[1,2,4]triazolo[4,3-a]pyridinyl, 1H-pyrrolo[2,3-c]pyridinyl, 3-oxoisoindolinyl, or 3-oxospiro[cyclopropane-1,1'-isoindolin]yl, as shown by the following formulas

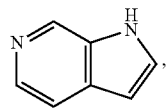

1H-pyrrolo[2,3-c]pyridinyl

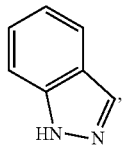

1H-indazolyl

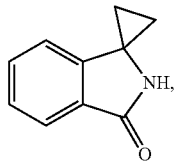

3-oxospiro[cyclopropane-1,1'-isoindolin]-yl

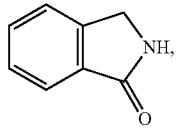

3-oxoisoindolinyl

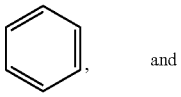

phenyl

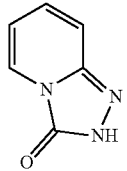

3-oxo-2,3-dihyrdo-[1,2,4]triazolo[4,3-a]pyridinyl each of which is optionally substituted with 1, 2, 3, or 4 $Z^{1a}$ or $Z^{1b}$.

In certain embodiments of a compound of formula I, Ia, Ib, Ic, Id, II, III, IV, V, or VI, $Z^1$ is $Z^1$ is

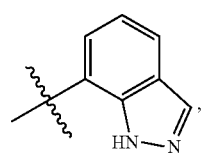

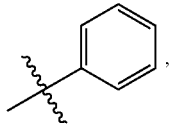

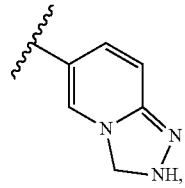

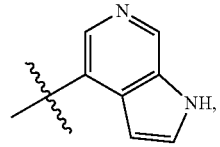

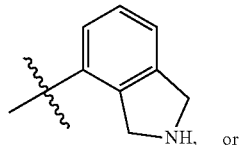

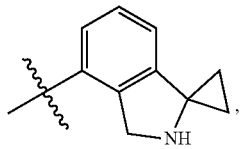

optionally substituted with 1, 2, 3, 4 or 5 $Z^{1a}$ or $Z^{1b}$.

In certain embodiments of a compound of formula I, Ia, Ib, Ic, Id, II, III, IV, V, or VI, $Z^1$ is $Z^1$ $Z^1$ optionally substituted with 1, 2, 3, 4, or 5 $Z^{1a}$ or $Z^{1b}$ groups is

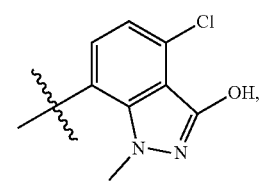

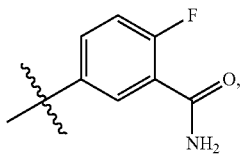

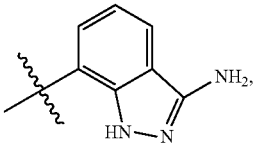

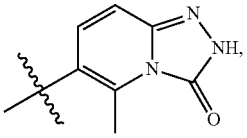

-continued
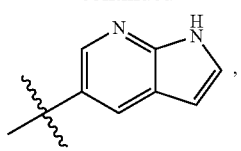
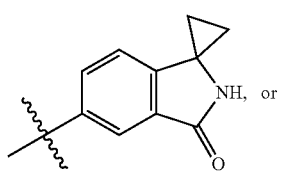
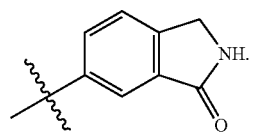
In certain embodiments of a compound of formula I, Ia, Ib, Ic, Id, II, III, IV, V, or VI, $Z^1$ optionally substituted with 1, 2, 3, 4, or 5 $Z^{1a}$ or $Z^{1b}$ groups is
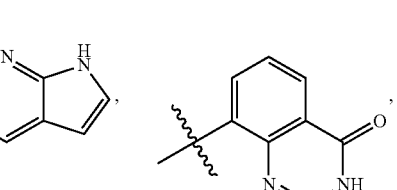
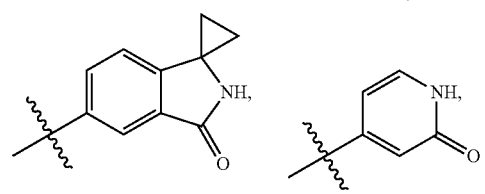
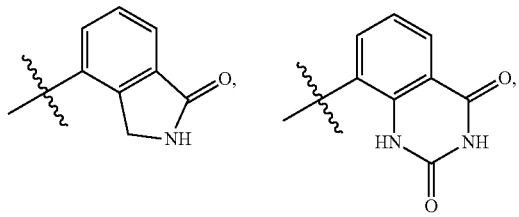
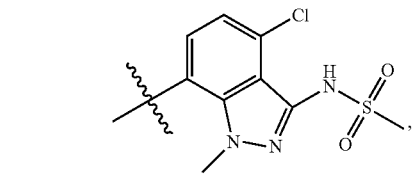
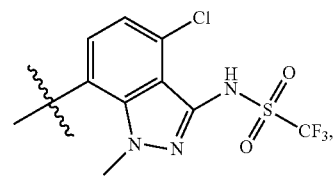
-continued
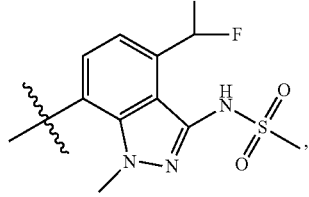
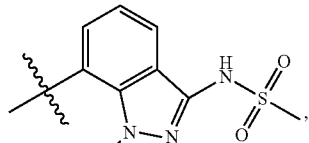
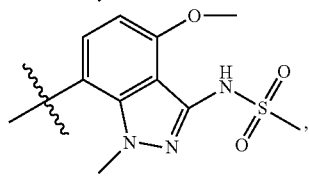
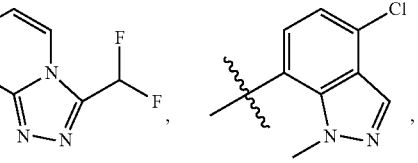
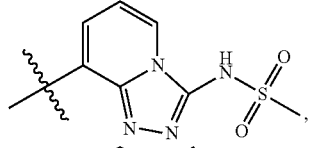
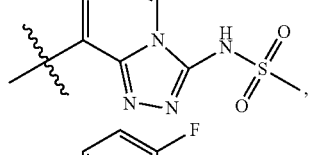
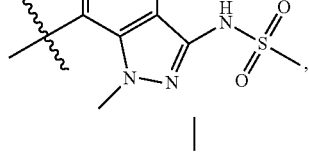
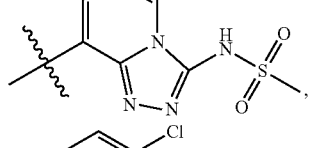
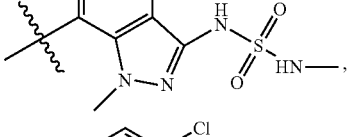
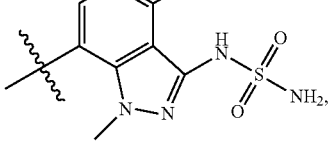

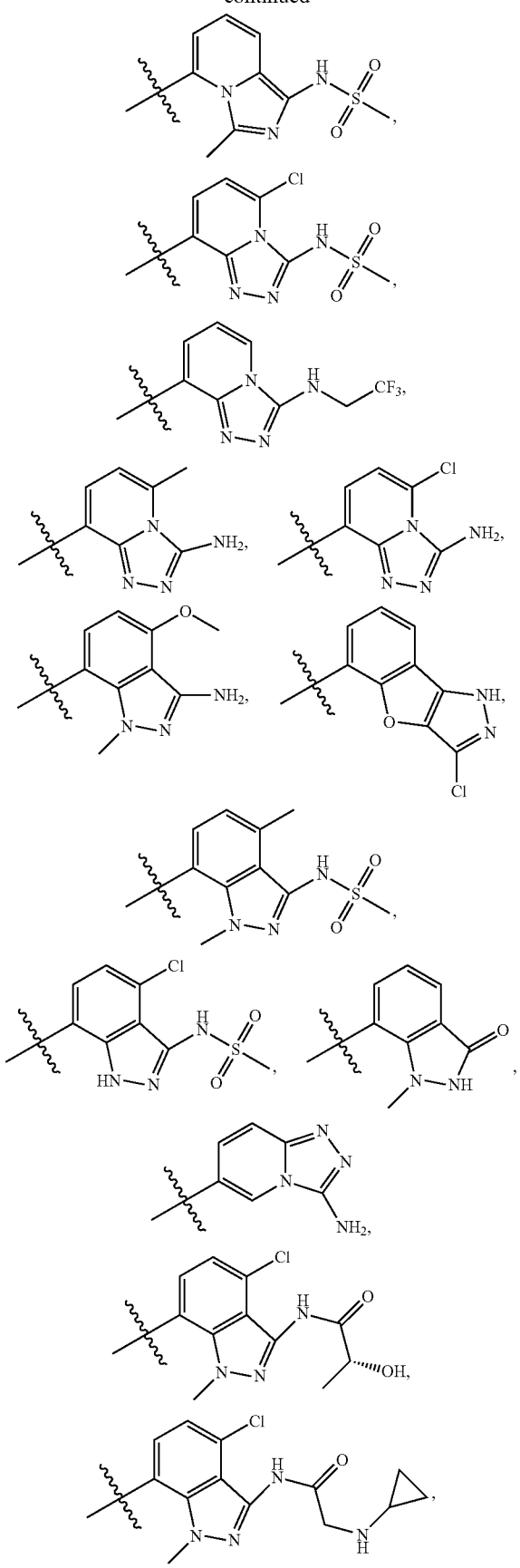
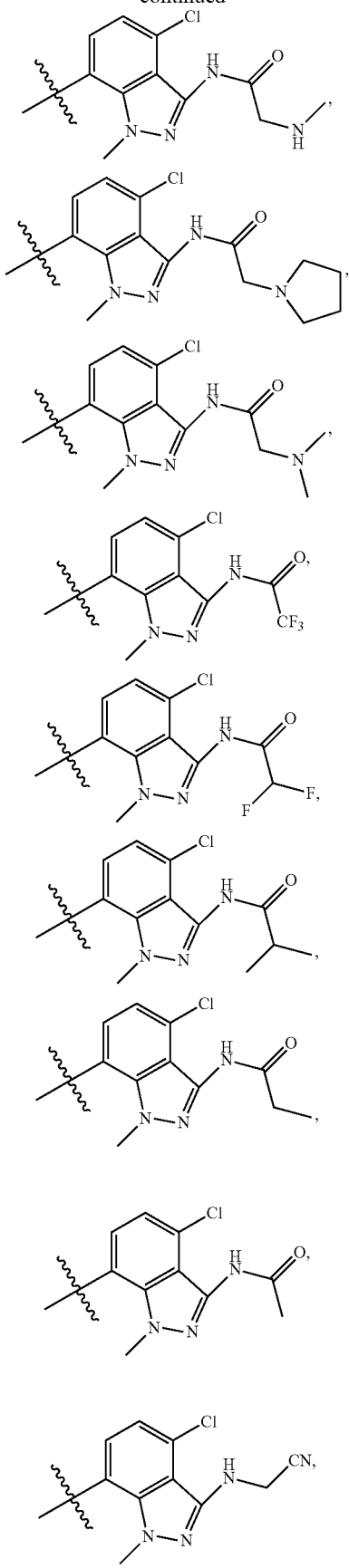

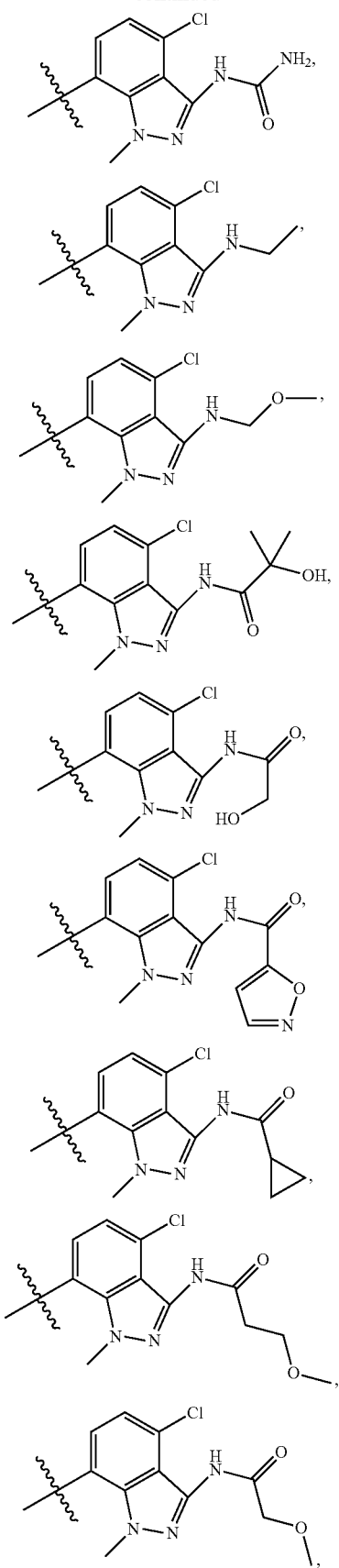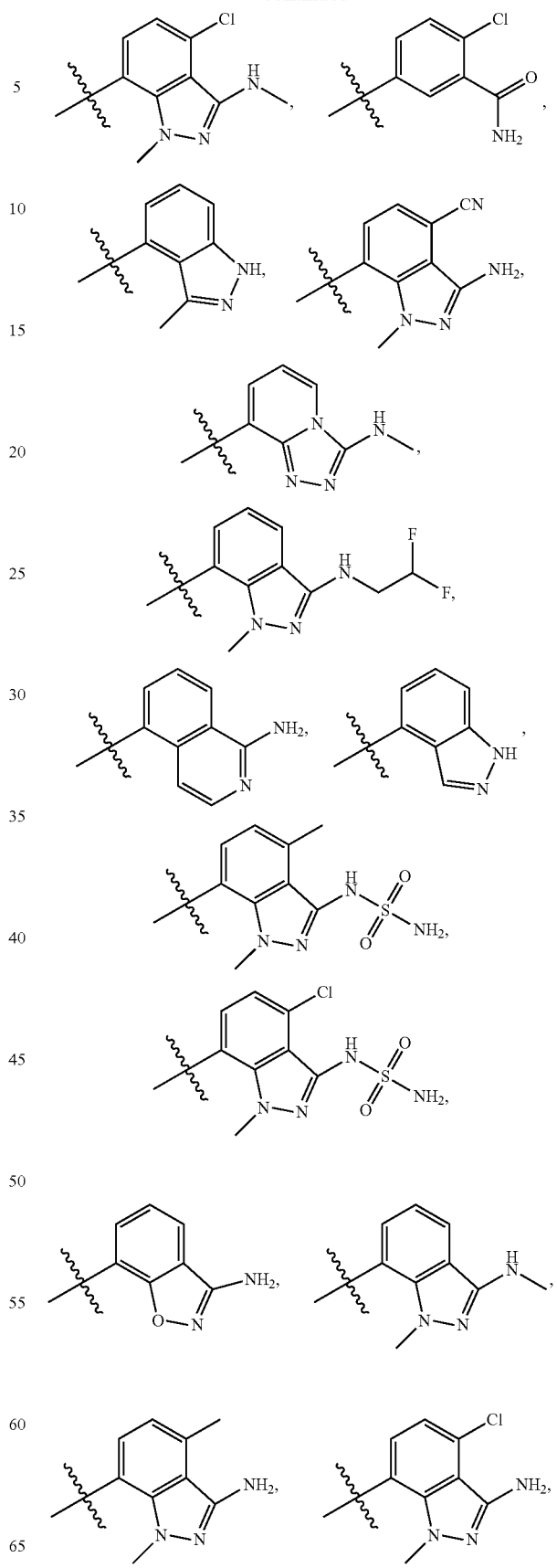

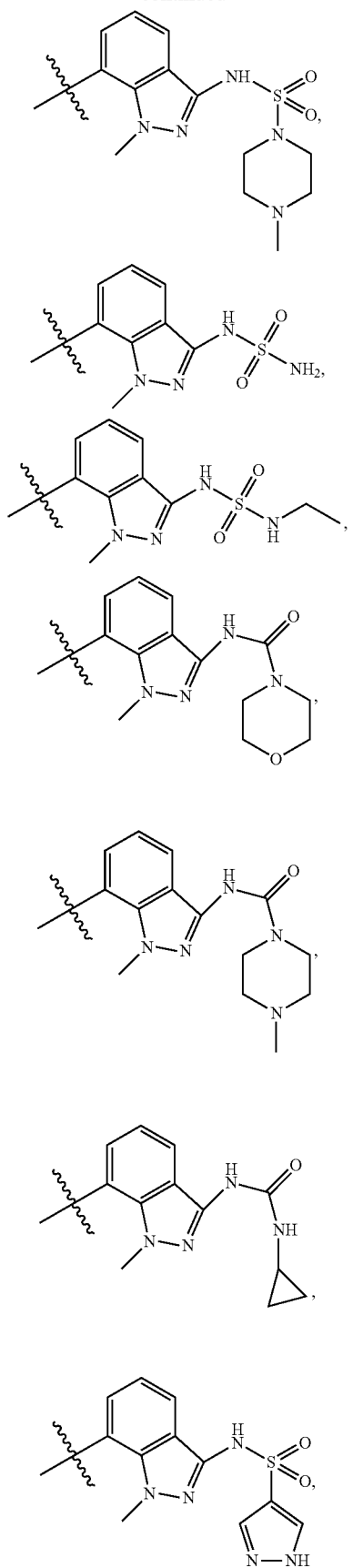

-continued

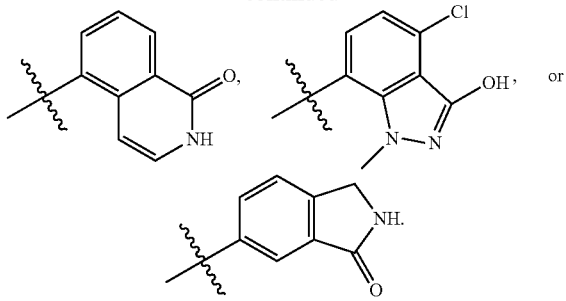

In certain embodiments of a compound of formula I, Ia, Ib, Ic, Id, II, III, IV, V, or VI, $Z^1$ is

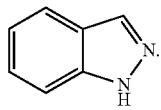

In certain embodiments of a compound of formula I, Ia, Ib, Ic, Id, II, III, IV, V, or VI, $Z^1$ is

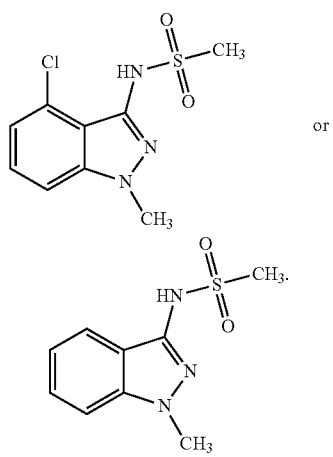

In certain embodiments of formula, I, Ia, Ib, Ic, Id, II, III, IV, V, VI, $Z^1$ is

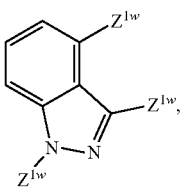

wherein each $Z^{1w}$ is $Z^{1a}$ or $Z^{1b}$.

In certain embodiments of a compound of formula I, Ia, Ib, Ic, Id, II, III, IV, V, VI, $Z^1$ is not substituted with $Z^{1b}$.

In certain embodiments of a compound of formula I, Ia, Ib, Ic, Id, II, III, IV, V, VI, VII, VIIa, VIIb, VIIc or VIId, each $Z^{1a}$ is independently oxo, $(C_3-C_7)$carbocycle, halogen, —CN, —OH, —O—$(C_1-C_8)$alkyl, —NR$^{q1}$R$^{r1}$, —NR$^{n1}$COR$^{p1}$, —NR$^{n1}$CO$_2$R$^{p1}$, —NR$^{n1}$CONR$^{q1}$R$^{r1}$, —NR$^{n1}$S(O)$_2$R$^{p1}$, —NR$^{n1}$S(O)$_2$NR$^{q1}$R$^{r1}$, or —C(O)NR$^{q1}$R$^{r1}$.

In certain embodiments of a compound of formula I, Ia, Ib, Ic, Id, II, III, IV, V, VI, VII, VIIa, VIIc or VIId, each $Z^{1a}$ is independently oxo, —OH, —NR$^{q1}$R$^{r1}$—NR$^{n1}$S(O)$_2$R$^{p1}$, —NR$^{n1}$S(O)$_2$NR$^{q1}$R$^{r1}$, C(O)NR$^{q1}$R$^{r1}$, or halogen.

In certain embodiments of a compound of formula I, Ia, Ib, Ic, Id, II, III, IV, V, VI, VII, VIIa, VIIb, VIIc or VIId, each $Z^{1a}$ is independently oxo, —NR$^{q1}$R$^{r1}$, —OH, halogen, or —NR$^{n1}$S(O)$_2$R$^{p1}$.

In certain embodiments of a compound of formula I, Ia, Ib, Ic, Id, II, III, IV, V, VI, VII, VIIa, VIIb, VIIc or VIId, each $Z^{1a}$ is independently selected from halogen, —OR$^{r1}$ and —C(O)NR$^{q1}$R$^{r1}$.

In certain embodiments of a compound of formula I, Ia, Ib, Ic, Id, II, III, IV, V, VI, VII, VIIa, VIIb, VIIc or VIId, each $Z^{1a}$ is independently selected from halogen and —C(O)NR$^{q1}$R$^{r1}$.

In certain embodiments of a compound of formula I, Ia, Ib, Ic, Id, II, III, IV, V, VI, VII, VIIa, VIIb, VIIc or VIId, each $R^{n1}$, $R^{q1}$ and $R^{r1}$ are H.

In certain embodiments of a compound of formula I, Ia, Ib, Ic, Id, II, III, IV, V, VI, VII, VIIa, VIIb, VIIc or VIId, each $Z^{1a}$ is independently selected from halogen, —OH and —C(O)NH$_2$.

In certain embodiments of a compound of formula I, Ia, Ib, Ic, Id, II, III, IV, V, VI, VII, VIIa, VIIb, VIIc or VIId, each $Z^{1a}$ is independently selected from fluoro, —OH and —C(O)NH$_2$.

In certain embodiments of a compound of formula I, Ia, Ib, Ic, Id, II, III, IV, V, VI, VII, VIIa, VIIb, VIIc or VIId, $R^{q1}$ and $R^{r1}$ are each H.

In certain embodiments of a compound of formula I, Ia, Ib, Ic, Id, II, III, IV, V, VI, VII, VIIa, VIIb, VIIc or VIId, each $Z^{1a}$ is independently selected from halogen and —NR$^{n1}$S(O)$_2$R$^{p1}$.

In certain embodiments of a compound of formula I, Ia, Ib, Ic, Id, II, III, IV, V, VI, VII, VIIa, VIIb, VIIc or VIId, each $Z^{1b}$ is $(C_1-C_8)$alkyl, which may be same or different.

In certain embodiments of a compound of formula I, Ia, Ib, Ic, Id, II, III, IV, V, VI, VII, VIIa, VIIb, VIIc or VIId, each $Z^{1a}$ is independently selected from halogen and —NR$^{n1}$S(O)$_2$R$^{p1}$ and each $Z^{1b}$ is $(C_1-C_8)$alkyl, which may be same or different.

In certain embodiments of formula I, Ia, Ib, Ic, Id, II, III, IV, V, or VI, $R^1$ is

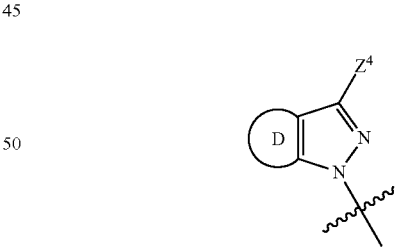

wherein

D, together with the two carbon atoms to which it is attached, forms a 3-7 membered monocyclic-carbocycle, 6 membered aryl, 6 membered heteroaryl, or 5-9 membered bicyclic-carbocycle, wherein any 3-7 membered monocyclic-carbocycle, 6 membered aryl, 6 membered heteroaryl, or 5-9 membered bicyclic-carbocycle of D is optionally substituted with 1, 2, 3, 4 or 5 $Z^4$ groups, wherein the $Z^4$ groups are the same or different;

$Z^1$ is phenyl, 8-10 membered bicyclic-heteroaryl, 8-10 membered bicyclic-heterocycle, or 9-12 membered tricyclic-heterocycle, wherein any phenyl, 8-10 membered bicyclic-heteroaryl, 8-10 membered bicyclic-heterocycle, or 9-12 membered tricyclic-heterocycle of $Z^1$ is optionally substituted with 1, 2, 3, 4, or 5 $Z^{1a}$ or $Z^{1b}$ groups; and $Z^2$ is $(C_2-C_8)$alkynyl or 5-6 membered C-linked-monocyclic-heteroaryl, wherein any $(C_2-C_8)$alkynyl or 5-6 membered C-linked-monocyclic-heteroaryl of $Z^2$ is substituted with 1 or 2 $Z^{2b}$ groups and optionally substituted with 1, 2, or 3 $Z^{2c}$ groups.

In certain embodiments of formula I, Ia, Ib, Ic, Id, II, III, IV, V, or VI, $R^1$ is

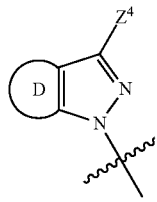

wherein:
D, together with the two carbon atoms to which it is attached, forms a 5-6 membered monocyclic-carbocycle, 6 membered aryl, or 6 membered bicyclic-carbocycle, wherein any 5-6 membered monocyclic-carbocycle, 6 membered aryl, or 6 membered bicyclic-carbocycle of D is optionally substituted with 1, 2, 3, 4 or 5 $Z^4$ groups, wherein the $Z^4$ groups are the same or different;

$Z^1$ is phenyl, 8-10 membered bicyclic-heteroaryl, 8-10 membered bicyclic-heterocycle, or 9-12 membered tricyclic-heterocycle, wherein any phenyl, 8-10 membered bicyclic-heteroaryl, 8-10 membered bicyclic-heterocycle, or 9-12 membered tricyclic-heterocycle of $Z^1$ is optionally substituted with 1, 2, 3, 4, or 5 $Z^{1a}$ or $Z^{1b}$ groups; and $Z^2$ is $(C_2-C_8)$alkynyl or 5-6 membered C-linked-monocyclic-heteroaryl, wherein any $(C_2-C_8)$alkynyl or 5-6 membered C-linked-monocyclic-heteroaryl of $Z^2$ is substituted with 1 or 2 $Z^{2b}$ groups and optionally substituted with 1, 2, or 3 $Z^{2c}$ groups.

In certain embodiments of formula I, Ia, Ib, Ic, Id, II, III, IV, V, or VI, $R^1$ is

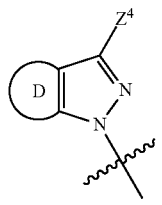

wherein:
D, together with the two carbon atoms to which it is attached, forms a phenyl, cyclohexyl, cyclopentyl, or bicyclohexyl group, wherein any phenyl, cyclohexyl, cyclopentyl, or bicyclohexyl group of D is optionally substituted with 1, 2, 3, 4 or 5 $Z^4$ groups, wherein the $Z^4$ groups are the same or different;

$Z^1$ is phenyl, 8-10 membered bicyclic-heteroaryl, 8-10 membered bicyclic-heterocycle, or 9-12 membered tricyclic-heterocycle, wherein any phenyl, 8-10 membered bicyclic-heteroaryl, 8-10 membered bicyclic-heterocycle, or 9-12 membered tricyclic-heterocycle of $Z^1$ is optionally substituted with 1, 2, 3, 4, or 5 $Z^{1a}$ or $Z^{1b}$ groups; and $Z^2$ is $(C_2-C_8)$alkynyl or 5-6 membered C-linked-monocyclic-heteroaryl, wherein any $(C_2-C_8)$alkynyl or 5-6 membered C-linked-monocyclic-heteroaryl of $Z^2$ is substituted with 1 or 2 $Z^{2b}$ groups and optionally substituted with 1, 2, or 3 $Z^{2c}$ groups.

In certain embodiments of formula I, Ia, Ib, Ic, Id, II, III, IV, V, or VI, $R^1$ is

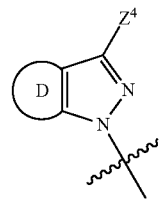

wherein
D, together with the two carbon atoms to which it is attached, forms a 3-7 membered monocyclic-carbocycle, 6 membered aryl, 6 membered heteroaryl, or 5-9 membered bicyclic-carbocycle, wherein any 3-7 membered monocyclic-carbocycle, 6 membered aryl, 6 membered heteroaryl, or 5-9 membered bicyclic-carbocycle of D is optionally substituted with 1, 2, 3, 4 or 5 $Z^4$ groups, wherein the $Z^4$ groups are the same or different;

$Z^1$ is phenyl, 8-10 membered bicyclic-heteroaryl, 8-10 membered bicyclic-heterocycle, or 9-12 membered tricyclic-heterocycle, wherein any phenyl, 8-10 membered bicyclic-heteroaryl, 8-10 membered bicyclic-heterocycle, or 9-12 membered tricyclic-heterocycle of $Z^1$ is optionally substituted with 1, 2, 3, 4, or 5 $Z^{1a}$ or $Z^{1b}$ groups; and $Z^2$ is 5-6 membered C-linked-monocyclic-heteroaryl substituted with 1 or 2 $Z^{2b}$ groups and optionally substituted with 1, 2, or 3 $Z^{2c}$ groups.

In certain embodiments of formula I, Ia, Ib, Ic, Id, II, III, IV, V, or VI, $R^1$ is

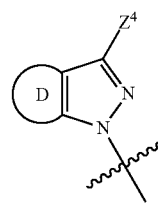

wherein
D, together with the two carbon atoms to which it is attached, forms a 5-6 membered monocyclic-carbocycle, 6 membered aryl, or 6 membered bicyclic-carbocycle, wherein any 5-6 membered monocyclic-carbocycle, 6 membered aryl, or 6 membered bicyclic-carbocycle of D is optionally substituted with 1, 2, 3, 4 or 5 $Z^4$ groups, wherein the $Z^4$ groups are the same or different; $Z^1$ is phenyl, 8-10 membered bicyclic-heteroaryl or 8-10 membered bicyclic-heterocycle, wherein any 8-10 membered bicyclic-heteroaryl or 8-10 membered bicyclic-heterocycle has 3-9 carbon atoms and 1-5 heteroatoms in the ring system, and wherein any phenyl, 8-10 membered bicyclic-heteroaryl, or 8-10 membered bicyclic-heterocycle of $Z^1$ is optionally substituted with 1, 2, 3, 4, or 5 $Z^{1a}$ or $Z^{1b}$ groups; and $Z^2$ is 5-6 membered C-linked-monocyclic-heteroaryl substituted with 1 $Z^{2b}$ group and optionally substituted with 1, 2, or 3 $Z^{2c}$ groups.

In certain embodiments of formula I, Ia, Ib, Ic, Id, II, III, IV, V, or VI, $R^1$ is

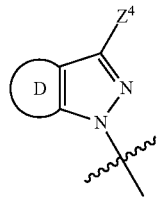

wherein

D, together with the two carbon atoms to which it is attached, forms a phenyl, cyclohexyl, cyclopentyl, or bicyclohexyl group, wherein any phenyl, cyclohexyl, cyclopentyl, or bicyclohexyl group of D is optionally substituted with 1, 2, 3, 4 or 5 $Z^4$ groups, wherein the $Z^4$ groups are the same or different;

$Z^1$ is phenyl, 8-10 membered bicyclic-heteroaryl, 8-10 membered bicyclic-heterocycle, or 9-12 membered tricyclic-heterocycle, wherein any phenyl, 8-10 membered bicyclic-heteroaryl, 8-10 membered bicyclic-heterocycle, or 9-12 membered tricyclic-heterocycle of $Z^1$ is optionally substituted with 1, 2, 3, 4, or 5 $Z^{1a}$ or $Z^{1b}$ groups; and $Z^2$ is 5-6 membered C-linked-monocyclic-heteroaryl substituted with 1 $Z^{2b}$ group and optionally substituted with 1, 2, or 3 $Z^{2c}$ groups.

In certain embodiments of formula I, Ia, Ib, Ic, Id, II, III, IV, V, or VI, $R^1$ is

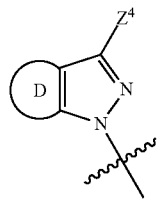

wherein

D, together with the two carbon atoms to which it is attached, forms a 3-7 membered monocyclic-carbocycle, 6 membered aryl, 6 membered heteroaryl, or 5-9 membered bicyclic-carbocycle, wherein any 3-7 membered monocyclic-carbocycle, 6 membered aryl, 6 membered heteroaryl, or 5-9 membered bicyclic-carbocycle of D is optionally substituted with 1, 2, 3, 4 or 5 $Z^4$ groups, wherein the $Z^4$ groups are the same or different;

$Z^1$ is phenyl, 8-10 membered bicyclic-heteroaryl, 8-10 membered bicyclic-heterocycle, or 9-12 membered tricyclic-heterocycle, wherein any phenyl, 8-10 membered bicyclic-heteroaryl, 8-10 membered bicyclic-heterocycle, or 9-12 membered tricyclic-heterocycle of $Z^1$ is optionally substituted with 1, 2, 3, 4, or 5 $Z^{1a}$ or $Z^{1b}$ groups; and $Z^2$ is $(C_2-C_8)$alkynyl substituted with 1 $Z^{2b}$ group and optionally substituted with 1, 2, or 3 $Z^{2c}$ groups.

In certain embodiments of formula I, Ia, Ib, Ic, Id, II, III, IV, V, or VI, $R^1$ is

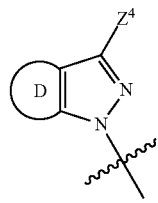

wherein

D, together with the two carbon atoms to which it is attached, forms a 5-6 membered monocyclic-carbocycle, 6 membered aryl, or 6 membered bicyclic-carbocycle, wherein any 5-6 membered monocyclic-carbocycle, 6 membered aryl, or 6 membered bicyclic-carbocycle of D is optionally substituted with 1, 2, 3, 4 or 5 $Z^4$ groups, wherein the 4 groups are the same or different;

$Z^1$ is phenyl, 8-10 membered bicyclic-heteroaryl, 8-10 membered bicyclic-heterocycle, or 9-12 membered tricyclic-heterocycle, wherein any phenyl, 8-10 membered bicyclic-heteroaryl, 8-10 membered bicyclic-heterocycle, or 9-12 membered tricyclic-heterocycle of $Z^1$ is optionally substituted with 1, 2, 3, 4, or 5 $Z^{1b}$ or $Z^{1b}$ groups; and $Z^2$ is $(C_2-C_8)$alkynyl substituted with 1 $Z^{2b}$ group and optionally substituted with 1, 2, or 3 $Z^{2c}$ groups.

In certain embodiments of formula I, Ia, Ib, Ic, Id, II, III, IV, V, or VI, $R^1$ is

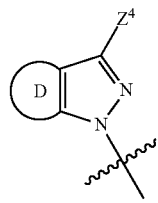

wherein:

D, together with the two carbon atoms to which it is attached, forms a phenyl, cyclohexyl, cyclopentyl, or bicyclohexyl group, wherein any phenyl, cyclohexyl, cyclopentyl, or bicyclohexyl group of D is optionally substituted with 1, 2, 3, 4 or 5 $Z^4$ groups, wherein the $Z^4$ groups are the same or different;

$Z^1$ is phenyl, 8-10 membered bicyclic-heteroaryl, 8-10 membered bicyclic-heterocycle, or 9-12 membered tricyclic-heterocycle, wherein any phenyl, 8-10 membered bicyclic-heteroaryl, 8-10 membered bicyclic-heterocycle, or 9-12 membered tricyclic-heterocycle of $Z^1$ is optionally substituted with 1, 2, 3, 4, or 5 $Z^{1a}$ or $Z^{1b}$ groups; and $Z^2$ is $(C_2-C_8)$alkynyl substituted with 1 $Z^{2b}$ group and optionally substituted with 1, 2, or 3 $Z^{2c}$ groups.

In certain embodiments, the compound of formula I, is a compound of formula VII:

VII

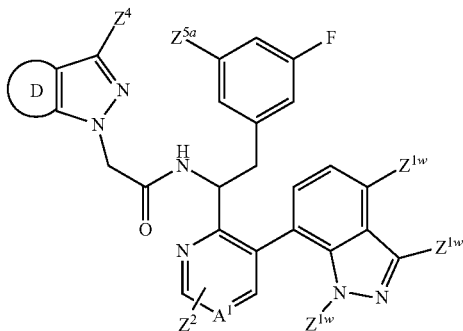

or a pharmaceutically acceptable salt thereof
wherein
$A^1$ is C—$Z^3$ or nitrogen;
D, together with the two carbon atoms to which it is attached, forms a 3-7 membered monocyclic-carbocycle, 6 membered aryl, 6 membered heteroaryl, or 5-9 membered bicyclic-carbocycle, wherein any 3-7 membered monocyclic-carbocycle, 6 membered aryl, 6 membered heteroaryl, or 5-9 membered bicyclic-carbocycle of D is optionally substituted with 1, 2, 3, 4 or 5 $Z^4$ groups, wherein the $Z^4$ groups are the same or different;
each $Z^{1w}$ is independently $Z^{1a}$, $Z^{1b}$ or H;
each $Z^{1a}$ is independently oxo, $(C_3-C_7)$carbocycle, 5-12 membered heteroaryl, 3-12 membered heterocycle, halogen, —CN, —$OR^{n1}$, —$OC(O)R^{p1}$, —$OC(O)NR^{q1}R^{r1}$, —$SR^{n1}$, —$S(O)R^{p1}$, —$S(O)_2OH$, —$S(O)_2R^{p1}$, —$S(O)_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)R^{p1}$, —$NR^{n1}S(O)_2NR^{q1}R^{r1}$, —$C(O)R^{n1}$, —$C(O)OR^{n1}$, —$C(O)NR^{q1}R^{r1}$ and —$S(O)_2NR^{n1}COR^{p1}$, wherein any $(C_3-C_7)$carbocycle, 5-12 membered heteroaryl and 3-12 membered heterocycle of $Z^{1a}$ is optionally substituted with 1, 2, 3, 4 or 5 $Z^{1c}$ or $Z^{1d}$ groups, wherein the $Z^{1c}$ and $Z^{1d}$ groups are the same or different;
each $Z^{1b}$ is independently $(C_1-C_8)$alkyl optionally substituted with 1, 2, 3, 4 or 5 halogen, which are the same or different;
each $Z^{1c}$ is independently halogen, —CN, —OH, —$NH_2$, —$C(O)NR^{q2}R^{r2}$, or $(C_1-C_8)$heteroalkyl;
each $Z^{1d}$ is independently $(C_1-C_8)$alkyl or $(C_1-C_8)$haloalkyl;
each $R^{n1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{n1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{n1}$ is optionally substituted with 1, 2, 3, 4 or 5 $Z^{1c}$ groups, wherein the $Z^{1c}$ groups are the same or different;
each $R^{p1}$ is independently $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{p1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{p1}$ is optionally substituted with 1, 2, 3, 4 or 5 $Z^{1c}$ groups, wherein the $Z^{1c}$ groups are the same or different;
each $R^{q1}$ and $R^{r1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{q1}$ or $R^{r1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{q1}$ or $R^{r1}$ is optionally substituted with 1, 2, 3, 4 or 5 $Z^{1c}$ groups, wherein the $Z^{1c}$ groups are the same or different, or $R^{q1}$ and $R^{r1}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups, wherein the $Z^{1c}$ and $Z^{1d}$ groups are the same or different;
each $R^{q2}$ and $R^{r2}$ is independently H, $(C_1-C_8)$alkyl, $(C_3-C_7)$carbocycle, or $R^{q2}$ and $R^{r2}$ together with the nitrogen to which they are attached form a 5, 6, or 7-membered heterocycle;
$Z^2$ is $(C_2-C_8)$alkynyl or 5-12 membered C-linked-heteroaryl wherein any $(C_2-C_8)$alkynyl or 5-12 membered C-linked-heteroaryl of $Z^2$ is substituted with 1 or 2 $Z^{2b}$ groups and optionally 1, 2, or 3 $Z^{2c}$ groups, wherein the $Z^{2b}$ and $Z^{2c}$ groups are the same or different;
each $R^{n3}$ is independently H or $(C_1-C_4)$alkyl;
each $R^{q3}$ and $R^{r3}$ is independently H or $(C_1-C_4)$alkyl;
each $Z^{2b}$ is independently 6-12 membered aryl, 5-12 membered C-linked-heteroaryl, 3-9 membered carbocycle, 3-12 membered heterocycle, or amino substituted with 3-12 membered heterocycle, 5-12 membered C-linked-heteroaryl, 3-9 membered carbocycle, or 3-12 membered heterocycle, wherein any 6-12 membered aryl, 5-12 membered C-linked-heteroaryl, 3-9 membered carbocycle, or 3-12 membered heterocycle of $Z^{2b}$ is optionally substituted with 1, 2, 3, 4, or 5 $Z^{2d}$ groups;
each $Z^{2c}$ is independently oxo, halogen, —CN, —$OR^{n4}$, —$OC(O)R^{p4}$, —$OC(O)NR^{q4}R^{r4}$, —$SR^{n4}$, —$S(O)R^{p4}$, —$S(O)_2OH$, —$S(O)_2R^{p4}$, —$S(O)_2NR^{q4}R^{r4}$, —$NR^{q4}R^{r4}$, —$NR^{n4}COR^{p4}$, —$NR^{n4}CO_2R^{p4}$, —$NR^{n4}CONR^{q4}R^{r4}$, —$NR^{n4}S(O)_2R^{p4}$, —$NR^{n4}S(O)_2OR^{p4}$, —$NR^{n4}S(O)_2NR^{q4}R^{r4}$, —$NO_2$, —$C(O)R^{n4}$, —$C(O)OR^{n4}$, —$C(O)NR^{q4}R^{r4}$, or $(C_1-C_4)$ alkyl optionally substituted with 1, 2, or 3 halogen or —$OR^{n4}$;
each $Z^{2d}$ is independently oxo, halogen, —CN, —$OR^{n4}$, —$OC(O)R^{p4}$, —$OC(O)NR^{q4}R^{r4}$, —$SR^{n4}$, —$S(O)R^{p4}$, —$S(O)_2OH$, —$S(O)_2R^{p4}$, —$S(O)_2NR^{q4}R^{r4}$, —$NR^{q4}R^{r4}$, —$NR^{n4}COR^{p4}$, —$NR^{n4}CO_2R^{p4}$, —$NR^{n4}CONR^{q4}R^{r4}$, —$NR^{n4}S(O)_2R^{p4}$, —$NR^{n4}S(O)_2OR^{p4}$, —$NR^{n4}S(O)_2NR^{q4}R^{r4}$, —$NO_2$, —$C(O)R^{n4}$, —$C(O)OR^{n4}$, —$C(O)NR^{q4}R^{r4}$, or $(C_1-C_4)$ alkyl optionally substituted with 1, 2, or 3 halogen or —$OR^{n4}$;
each $R^{n4}$ is independently H, $(C_1-C_4)$alkyl optionally substituted with 1, 2, or 3 —OH groups, $(C_1-C_4)$haloalkyl, or $(C_1-C_4)$heteroalkyl;
each $R^{p4}$ is independently $(C_1-C_8)$alkyl, $(C_1-C_4)$haloalkyl, or $(C_1-C_4)$heteroalkyl;
each $R^{q4}$ and $R^{r4}$ is independently H, $(C_1-C_4)$alkyl, $(C_1-C_4)$haloalkyl, or $(C_1-C_4)$heteroalkyl;
each $Z^3$ is independently H or —$NR^{q4}R^{r4}$;
each $Z^4$ is independently oxo, $(C_1-C_8)$alkyl, $(C_3-C_7)$carbocycle, halogen, —CN, —$OR^{n5}$, —$NR^{q5}R^{r5}$, —$NR^{n5}COR^{p5}$, —$NR^{n5}CO_2R^{p5}$, —$C(O)R^{n5}$, —$C(O)OR^{n5}$, or —$C(O)NR^{q5}SR^{r5}$, wherein any $(C_3-C_7)$carbocycle or $(C_1-C_8)$alkyl of $Z^4$ is optionally substituted with 1, 2, 3, 4 or 5 $Z^{4a}$ groups, wherein the $Z^{4a}$ groups are the same or different;
each $Z^{4a}$ is independently halogen, —CN, or —$OR^{n6}$;
each $R^{n5}$, $R^{p5}$, $R^{q5}$, $R^{r5}$, and $R^{n6}$ is independently H or $(C_1-C_4)$alkyl; and
$Z^{5a}$ is H or halogen;
or a pharmaceutically acceptable salt thereof.

In certain embodiments, the compound of formula I or VII is a compound of formula VIIa

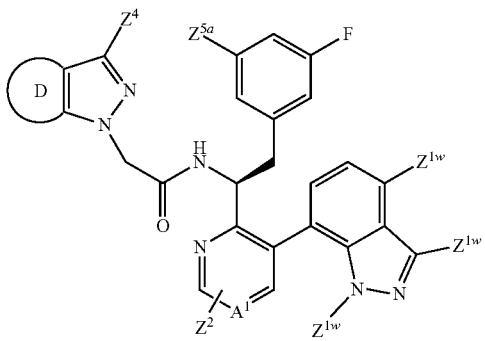

VIIa or a pharmaceutically acceptable salt thereof, wherein each $Z^{1w}$, $A^1$, $Z^2$, $Z^4$, and $Z^{5a}$ are as disclosed herein. In certain embodiments, each $Z^{1w}$, $A^1$, $Z^2$, $Z^4$, and $Z^{5a}$ and D is as disclosed herein.

In certain embodiments, the compound of formula I, VII, or VIIa is a compound of formula VIIb

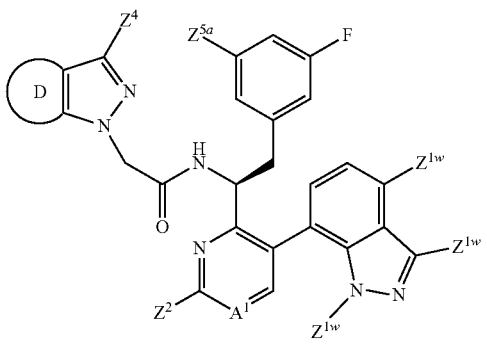

VIIb or a pharmaceutically acceptable salt thereof wherein each $Z^{1w}$, $A^1$, $Z^2$, $Z^4$, and $Z^{5a}$ are as disclosed herein. In certain embodiments, each $Z^{1w}$, $A^1$, $Z^2$, $Z^4$, and $Z^{5a}$ and D is as disclosed herein.

In certain embodiments, the compound of formula I, formula VII, VIIa, or VIIb is a compound of formula VIIc

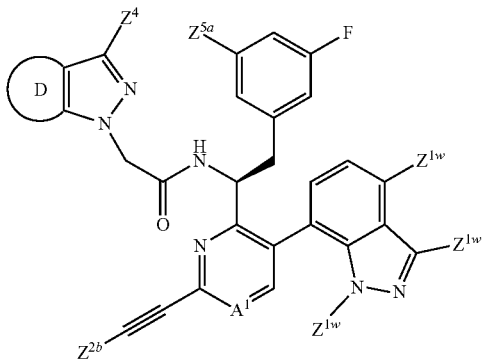

VIIc or a pharmaceutically acceptable salt thereof, wherein each $Z^{1w}$, $A^1$, $Z^{2b}$, $Z^4$, and $Z^{5a}$ are as disclosed herein. In certain embodiments, each $Z^{1w}$, $A^1$, $Z^{2b}$, $Z^4$, D, and $Z^{5a}$ are as disclosed herein.

In certain embodiments, the compound of formula I, formula VII, VIIa, or VIIb is a compound of formula VIId

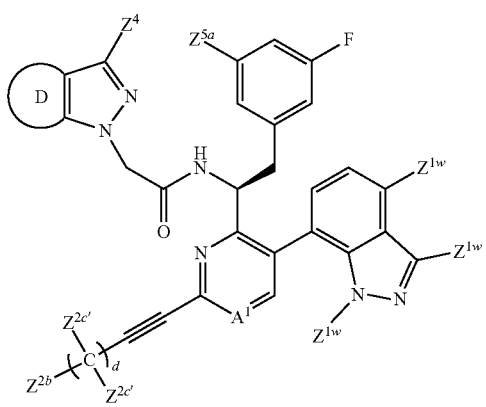

VIId wherein each $Z^{2c'}$ independently hydrogen, $(C_1-C_4)$alkyl, or $OR^{n4}$ where $R^{n4}$ is hydrogen or $(C_1-C_4)$ alkyl, n' is 1, 2, or 3, and each $Z^{1w}$, $A^1$, $Z^{2b}$, $Z^4$, and $Z^{5a}$ are as disclosed herein. In certain embodiments, D is as disclosed herein. In certain embodiments of a compound of formula VII, each $Z^{2c'}$ independently hydrogen, methyl, or —OH. In certain embodiments of a compound of formula VII, n is 1. In certain embodiments of a compound of formula VII, n is 2. In certain embodiments of a compound of formula VII, n' is 1. In certain embodiments of a compound of formula VII, n' is 2. In certain embodiments of a compound of formula VIId, each $Z^{2c'}$ independently hydrogen, methyl, or —OH. In certain embodiments of a compound of formula VIId, n is 1. In certain embodiments of a compound of formula VIId, n is 2. In certain embodiments of a compound of formula VIId, n' is 1. In certain embodiments of a compound of formula VIId, n' is 2.

In certain embodiments a compound of formula I, or a pharmaceutically acceptable salt thereof, which is

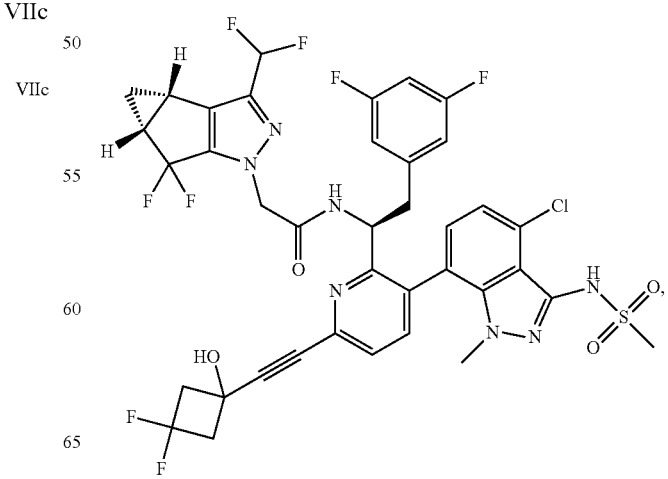

71
-continued
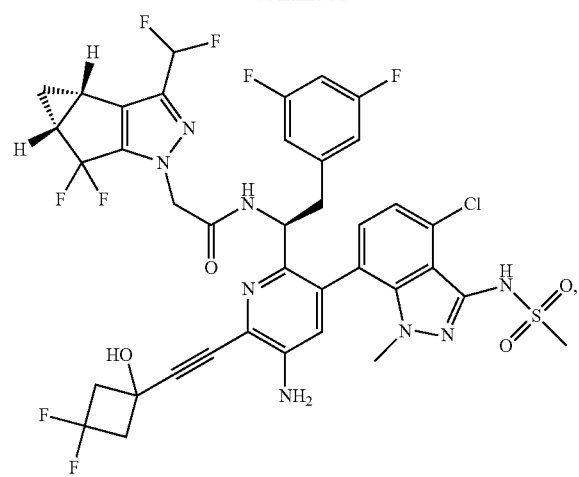
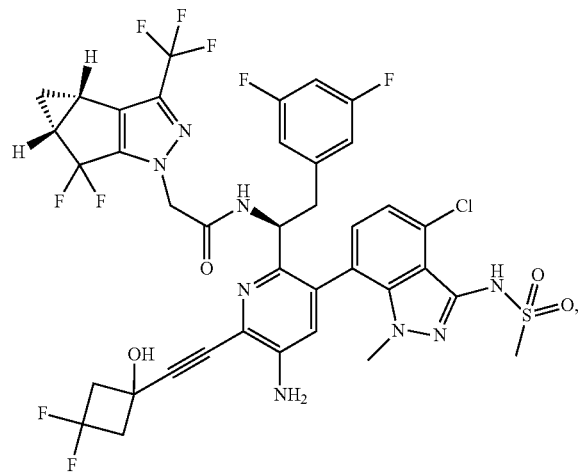
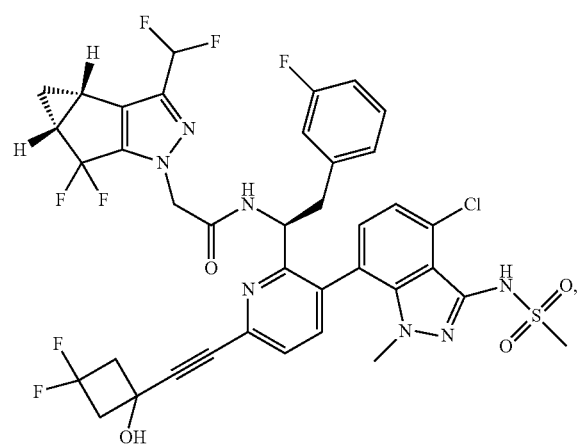
72
-continued
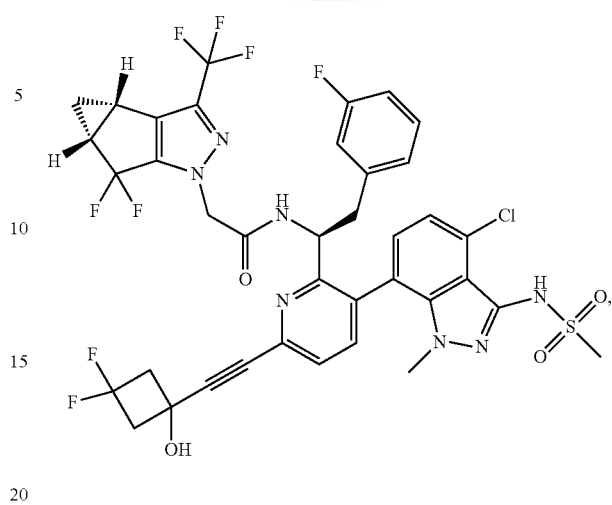
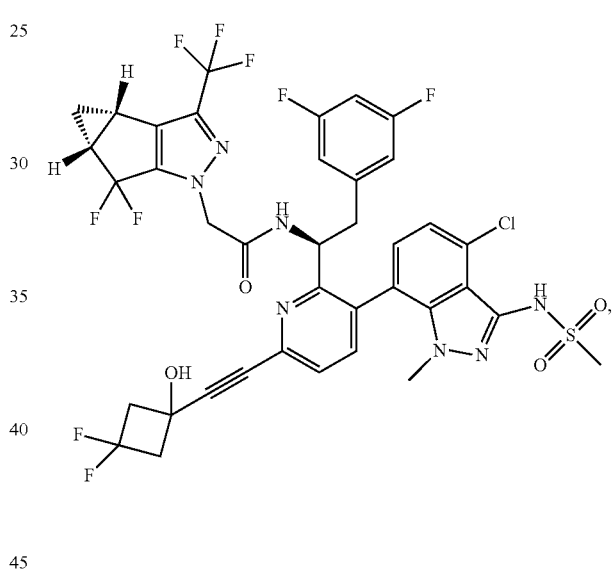
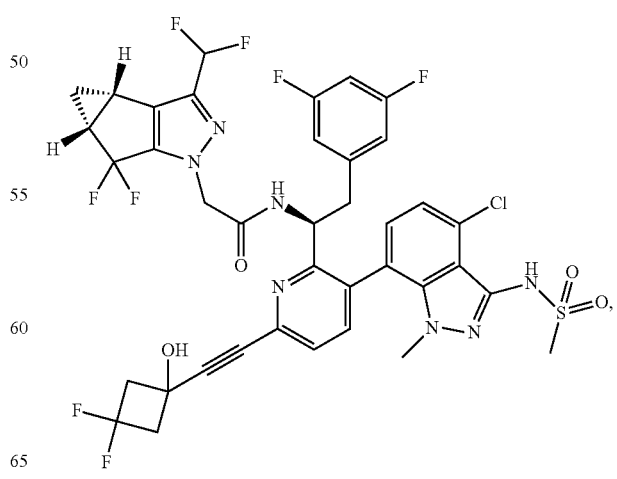

-continued
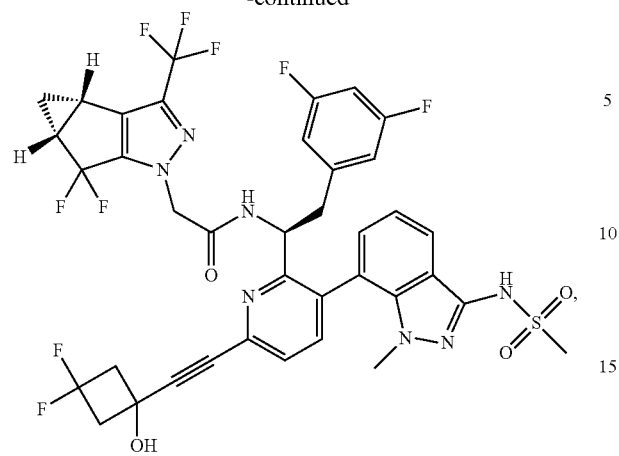
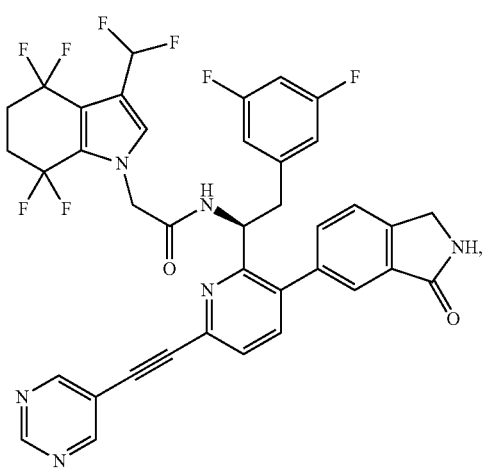
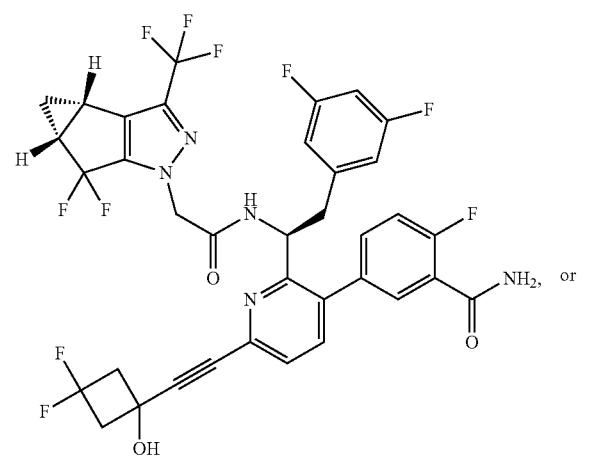
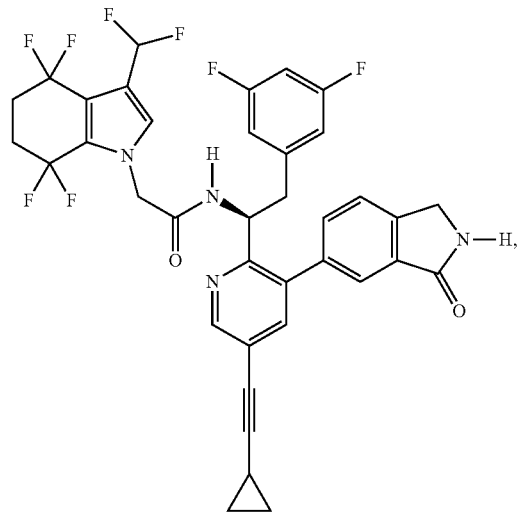
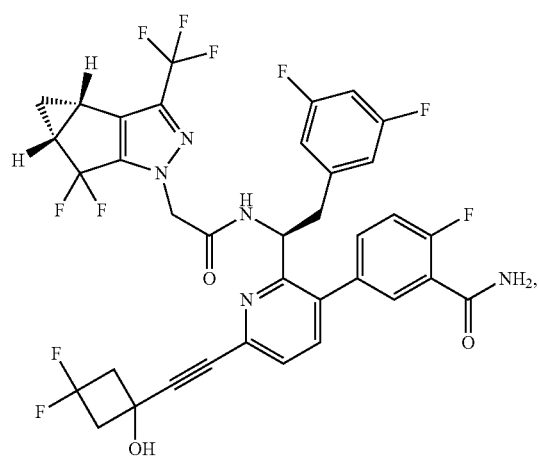 [SMILES: NC(=O)c1cc(-c2ccc(C#CC3(O)CC(F)(F)C3)nc2[C@H](Cc2cc(F)cc(F)c2)NC(=O)Cn2nc(C(F)(F)F)c3c2C(F)(F)[C@@H]2C[C@H]32)ccc1F]
is provided.
In certain embodiments a compound of formula I, or a pharmaceutically acceptable salt thereof, which is
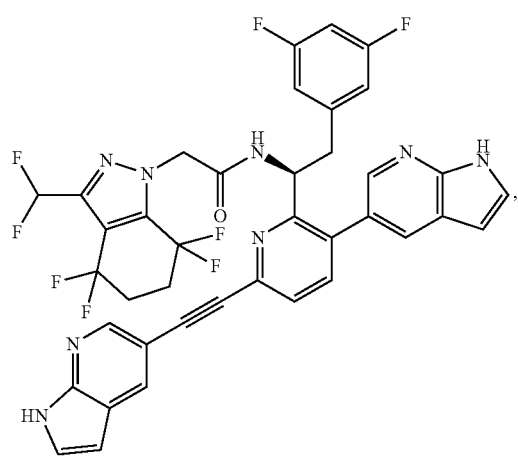

75
-continued
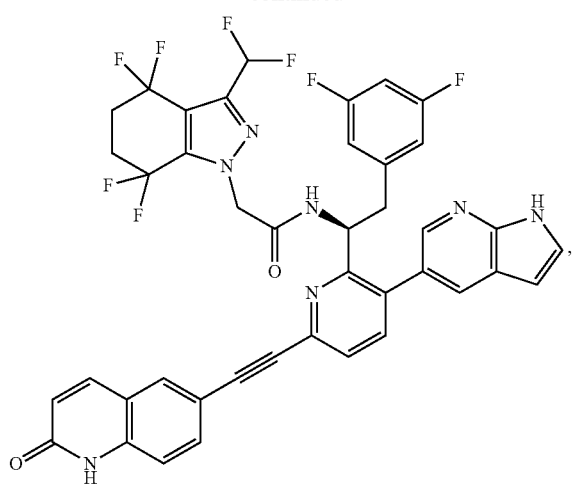
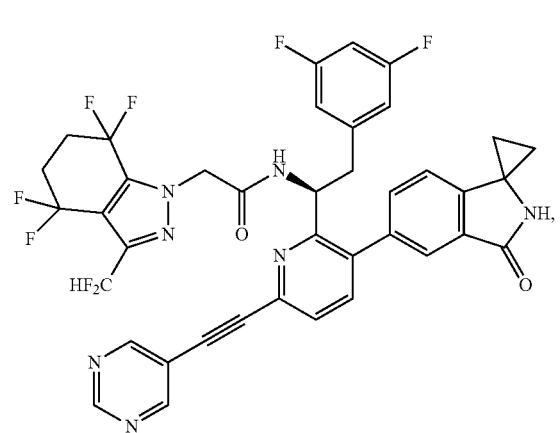
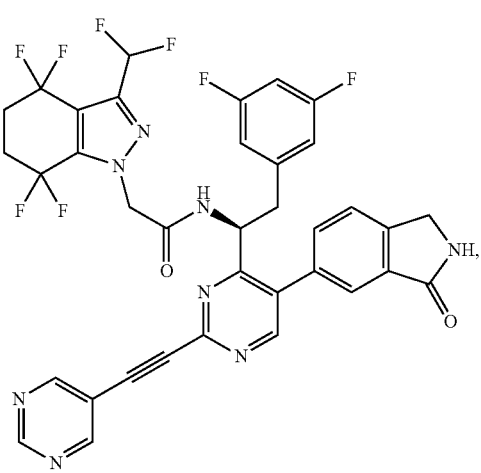
76
-continued
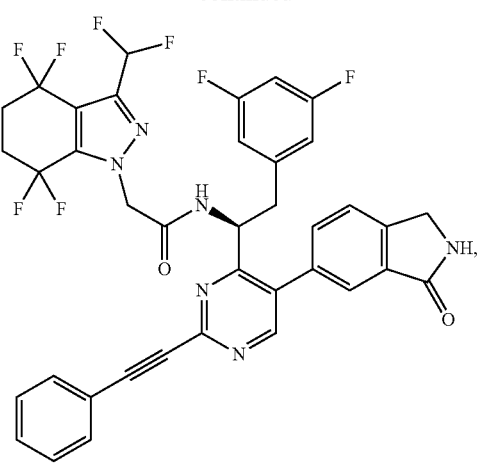
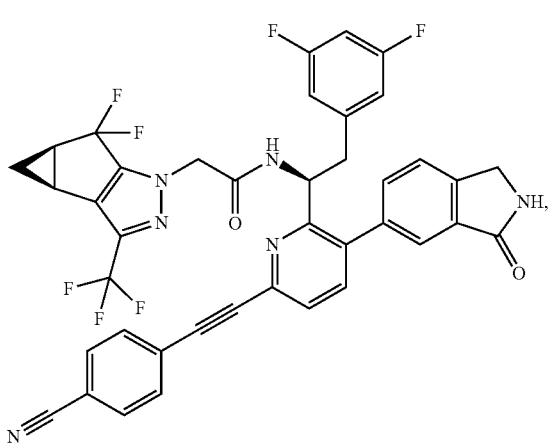
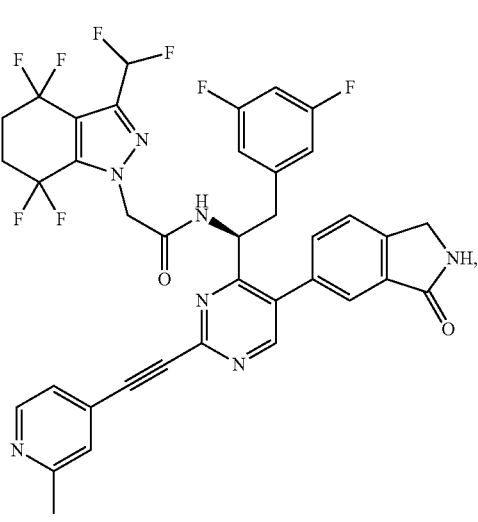

77
-continued
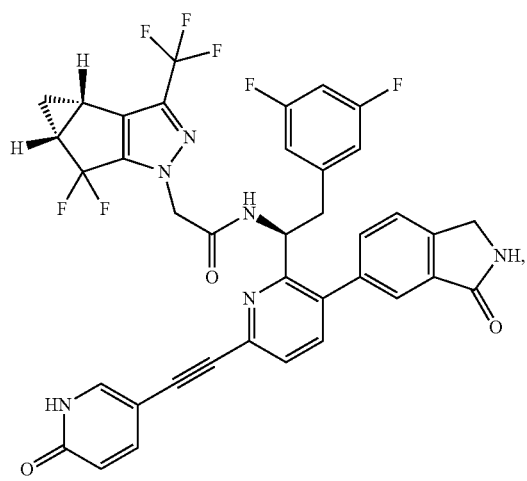
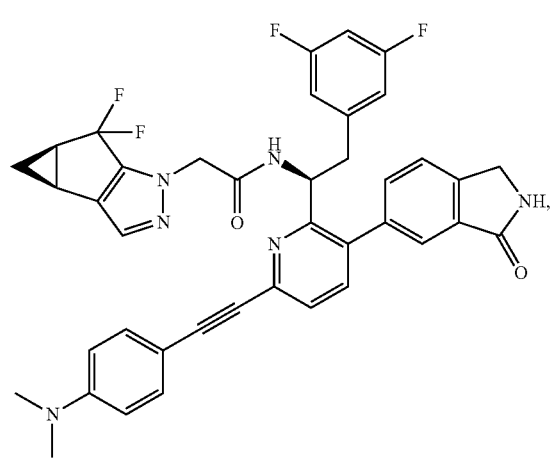
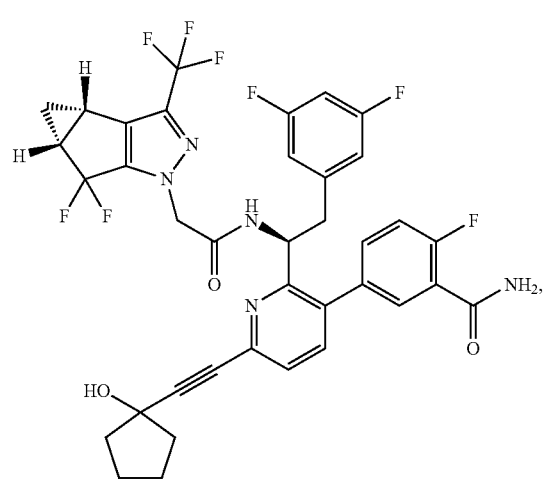
78
-continued
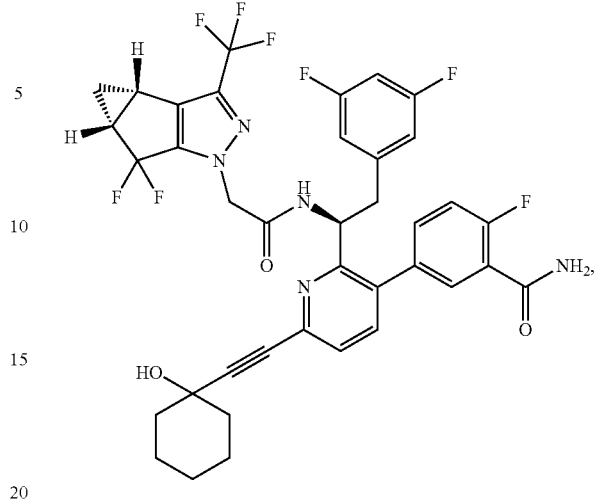
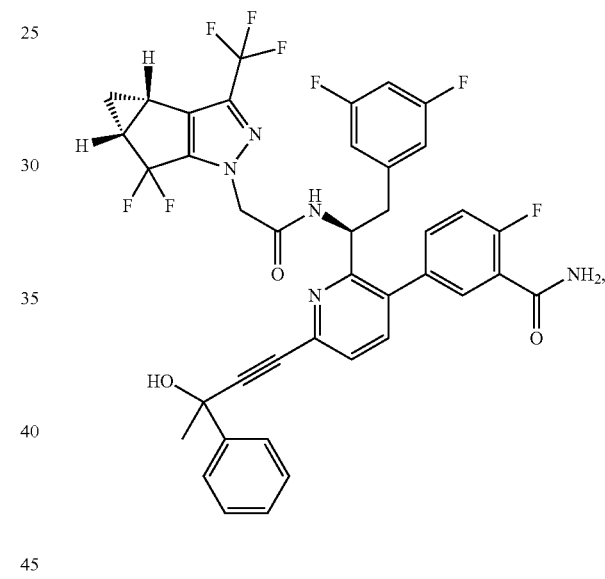
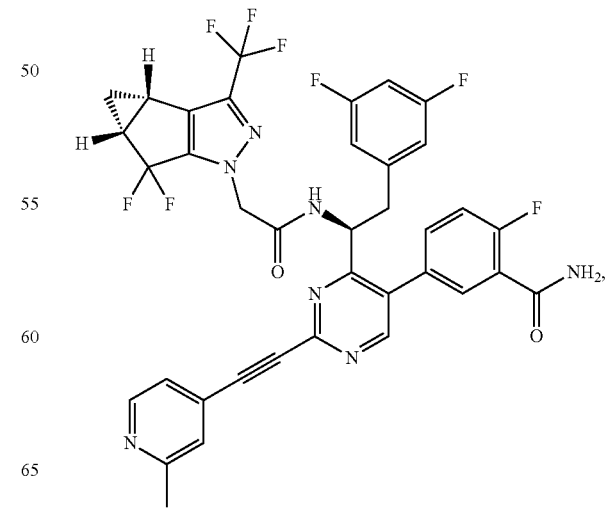

79
-continued
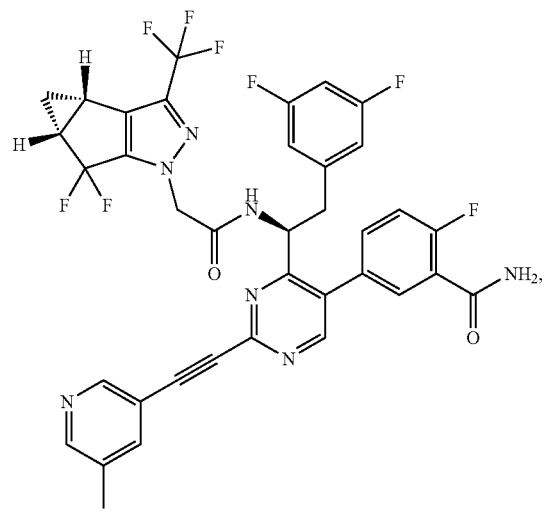
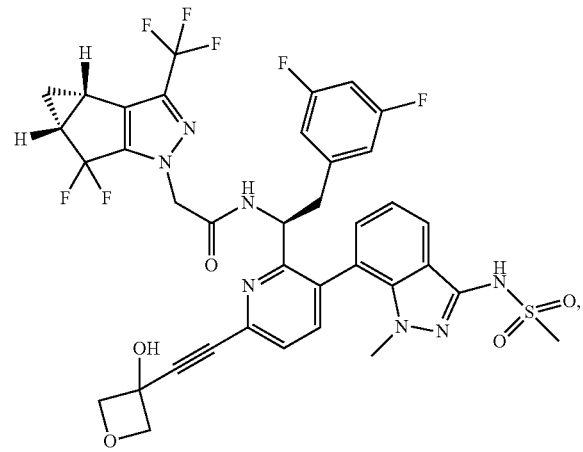
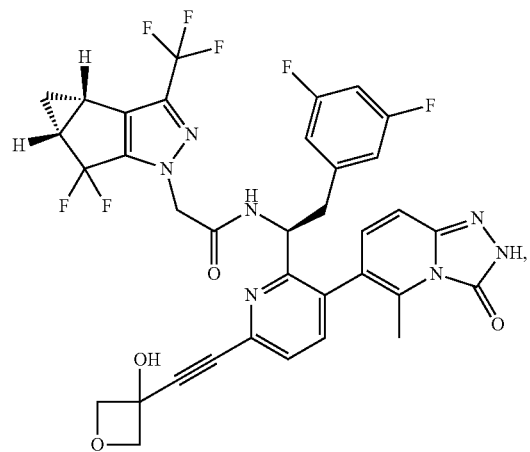
80
-continued
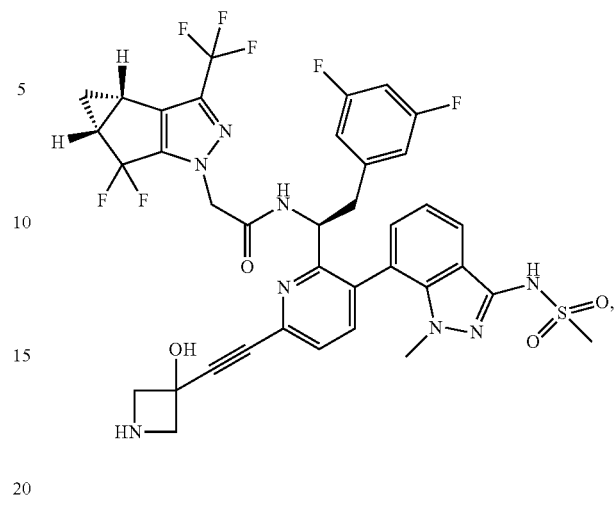
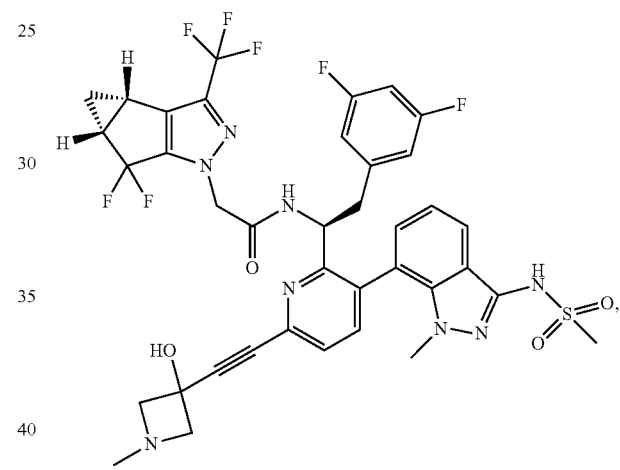

-continued
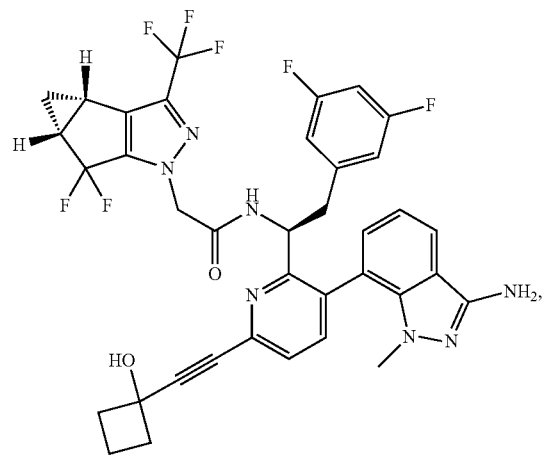
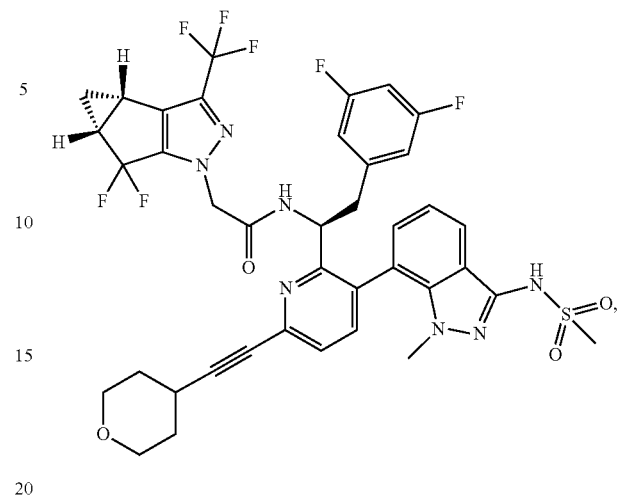
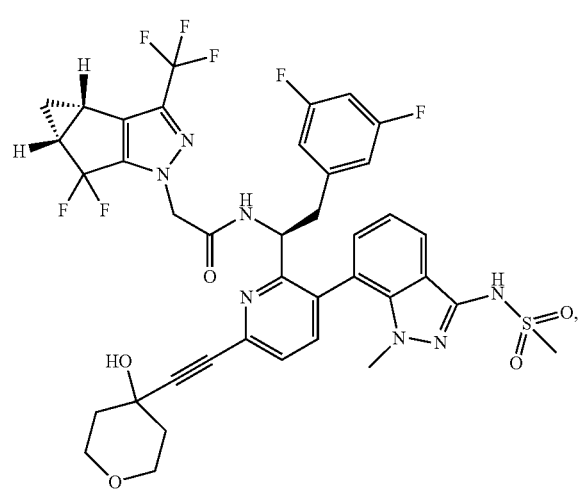
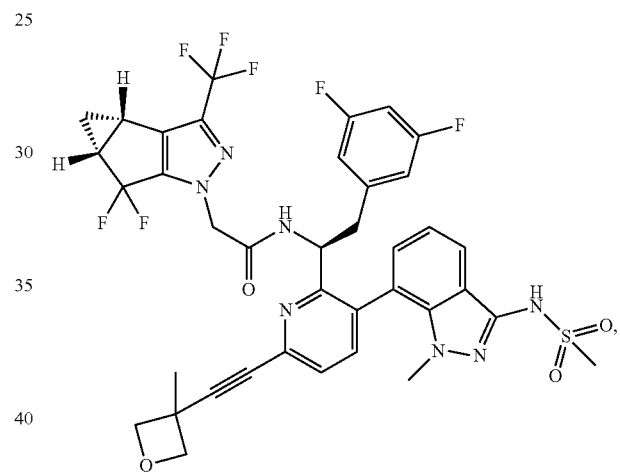
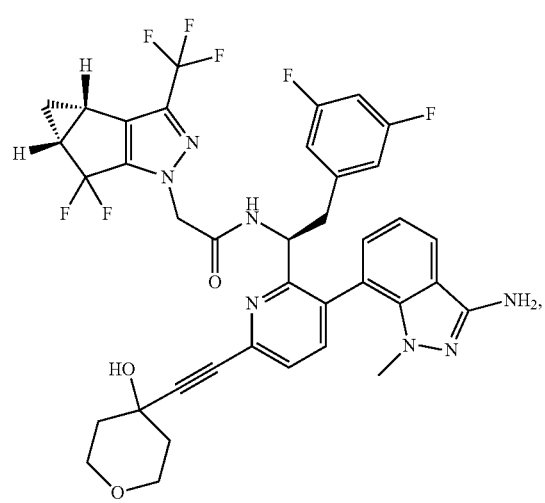
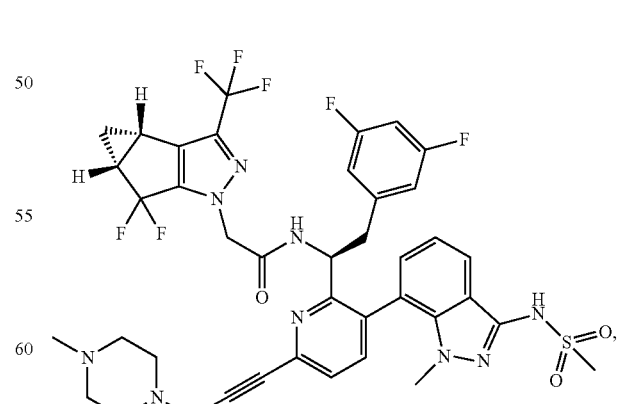

83
-continued
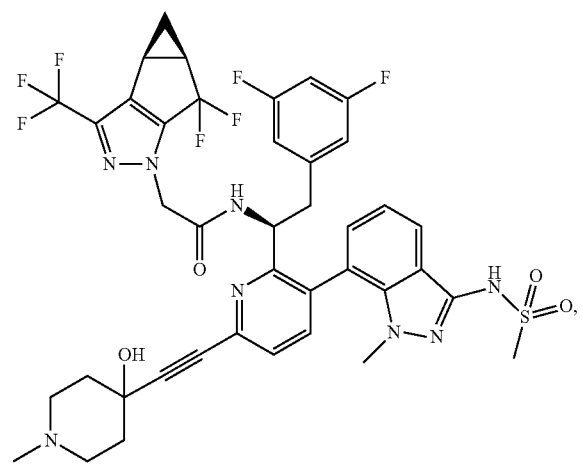
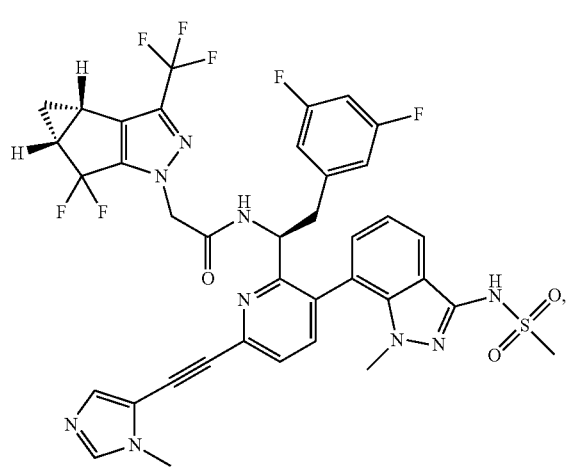
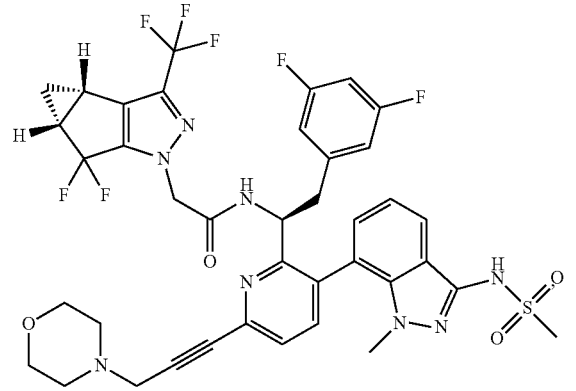
84
-continued
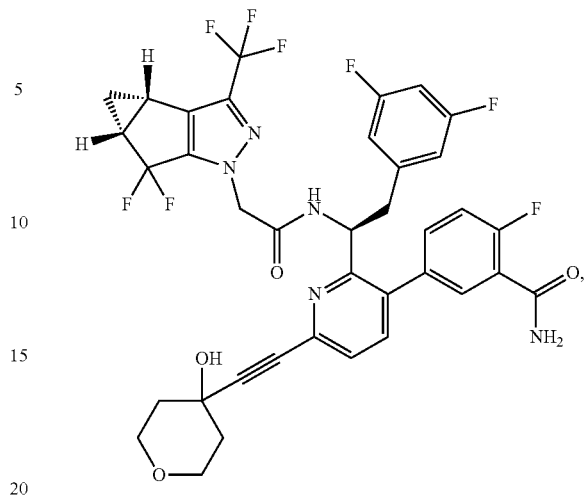
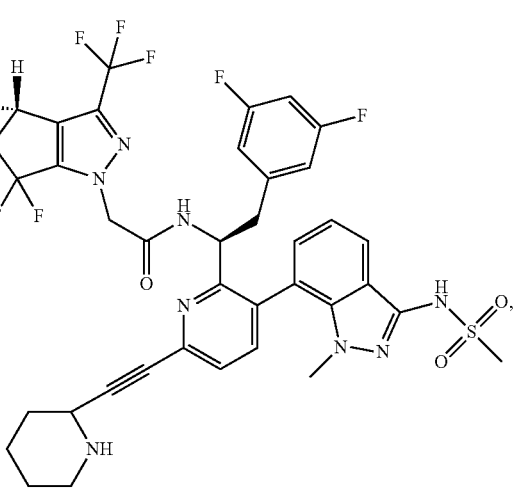
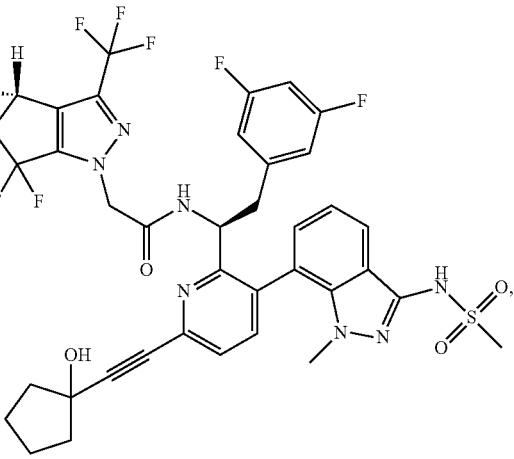

85
-continued
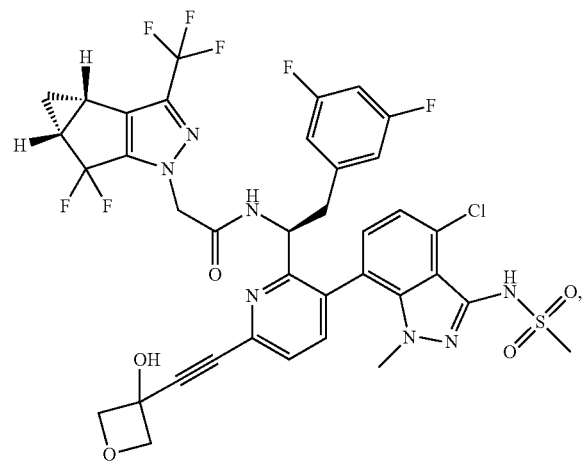
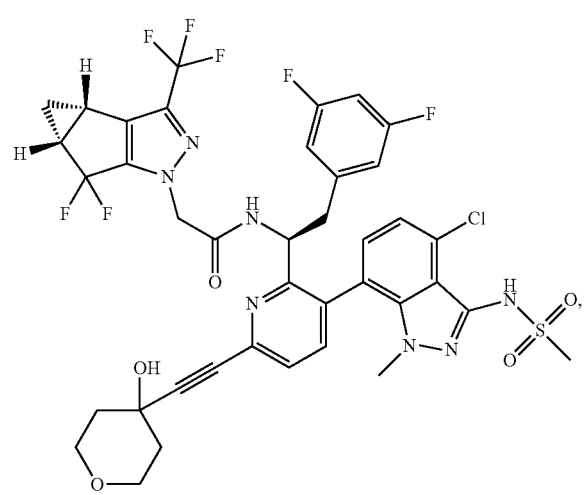
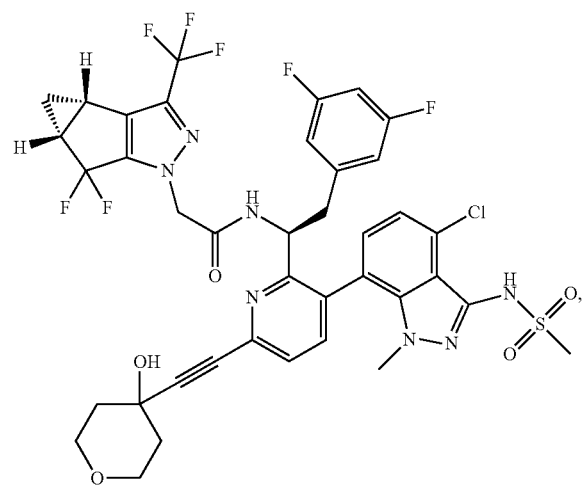
86
-continued
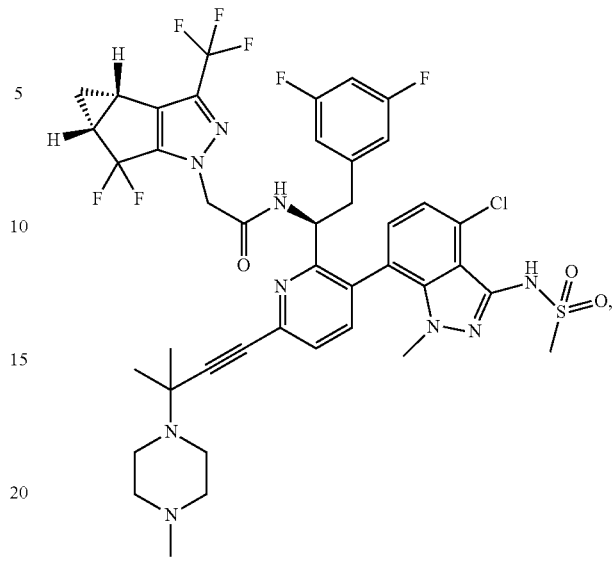
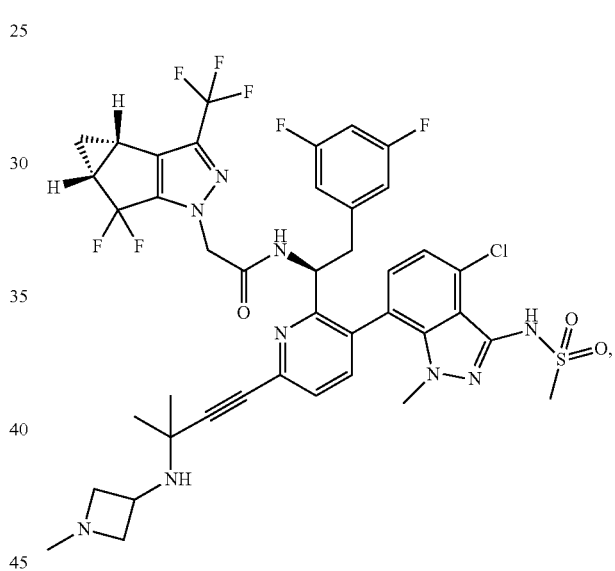
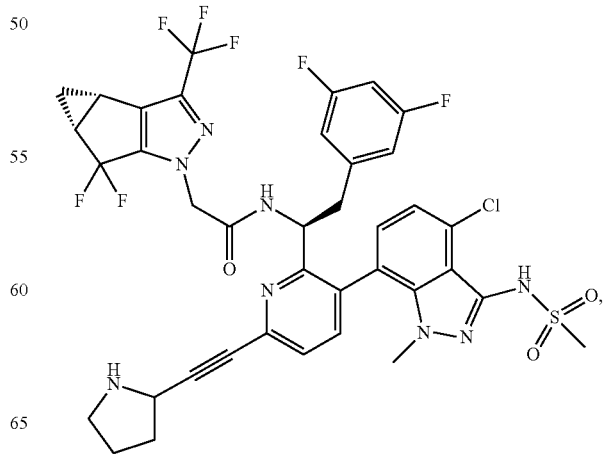

-continued
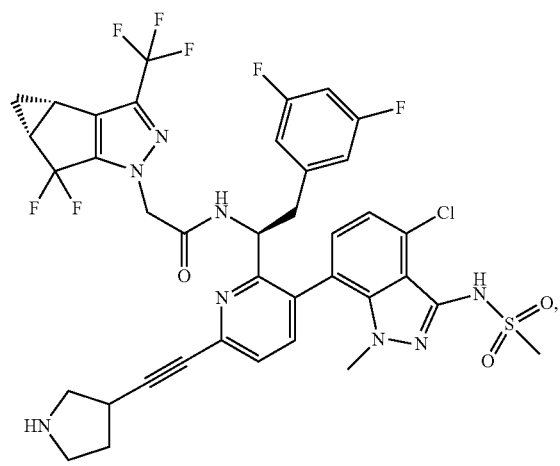
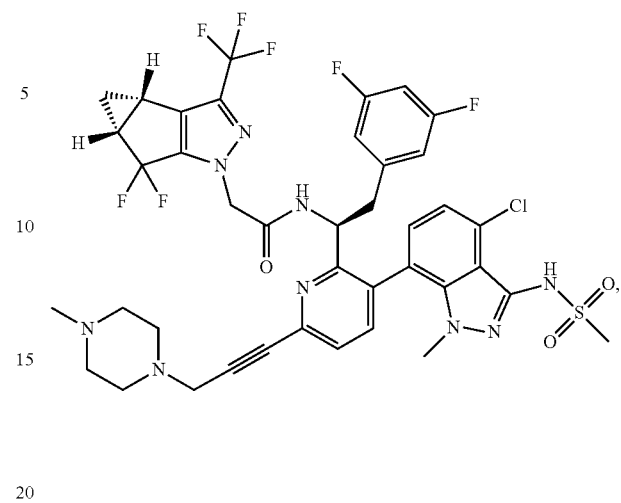
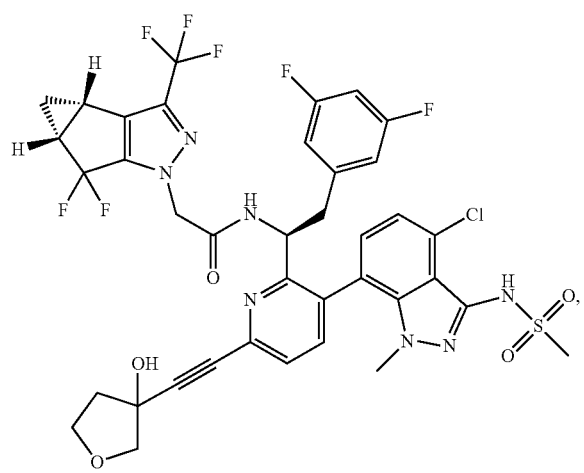
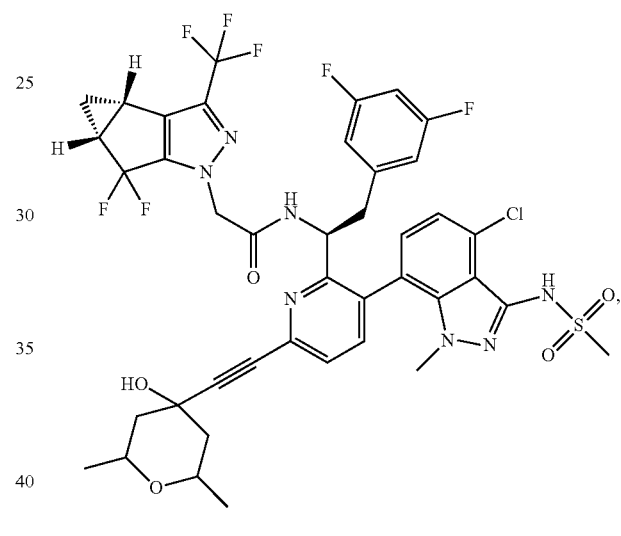
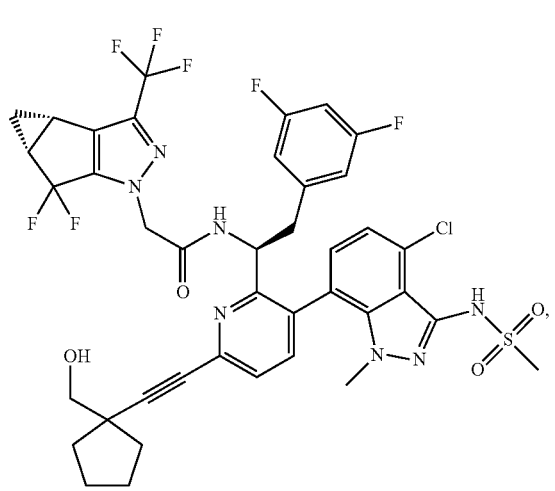
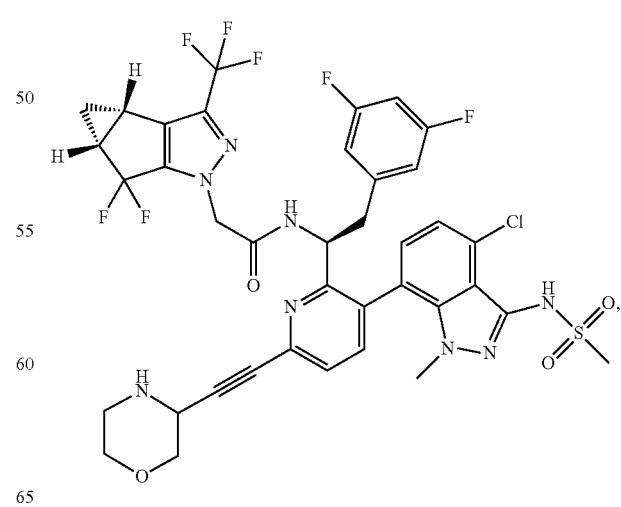

89
-continued
90
-continued
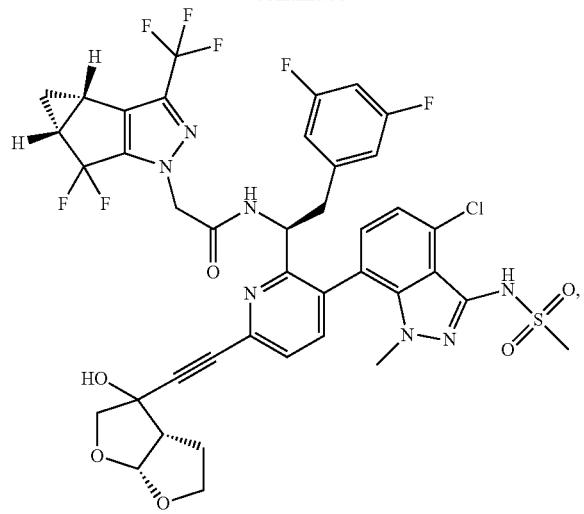
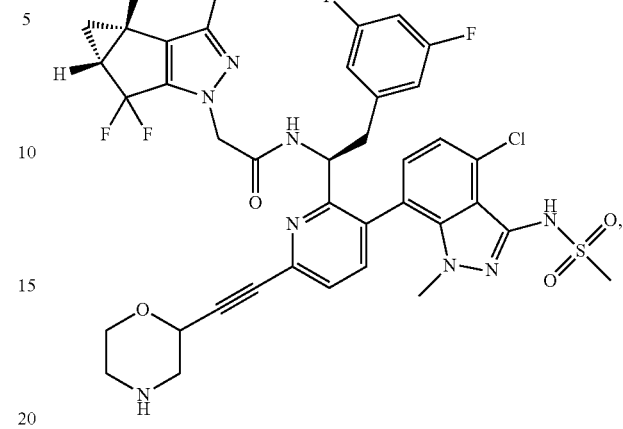
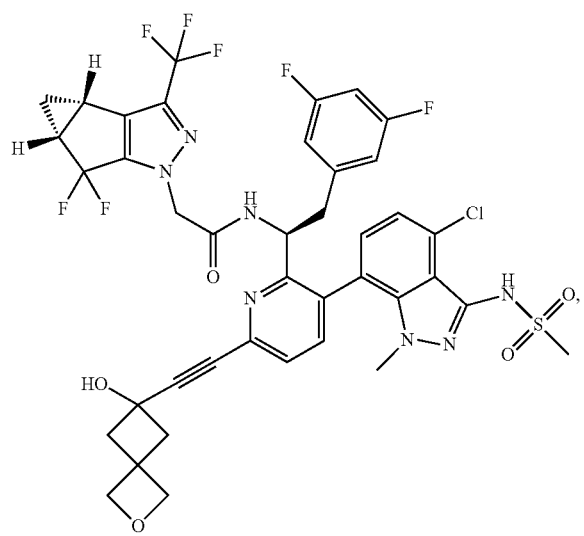
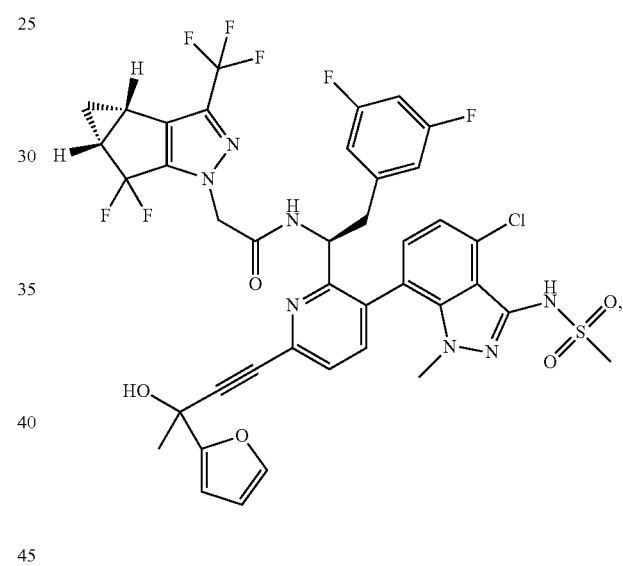
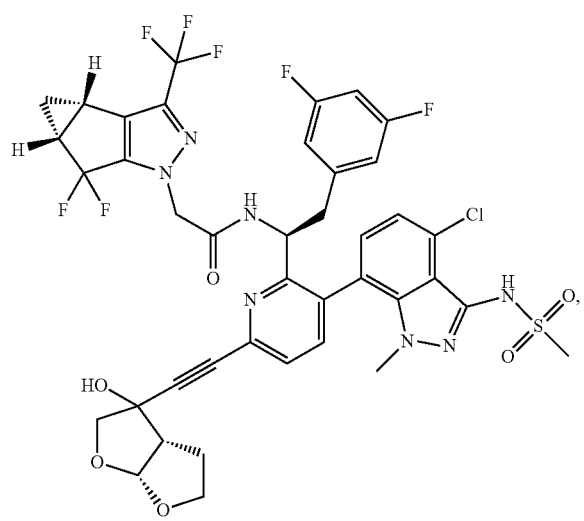
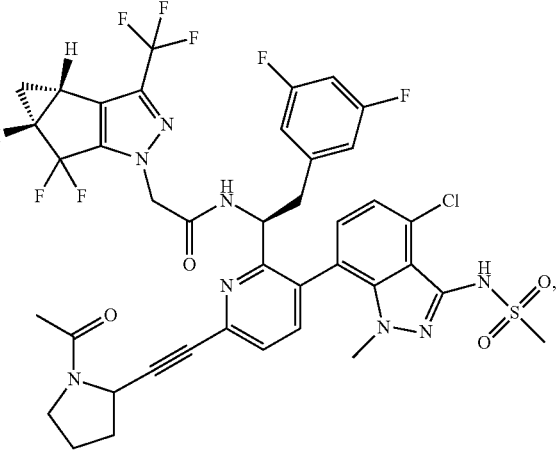

91
-continued
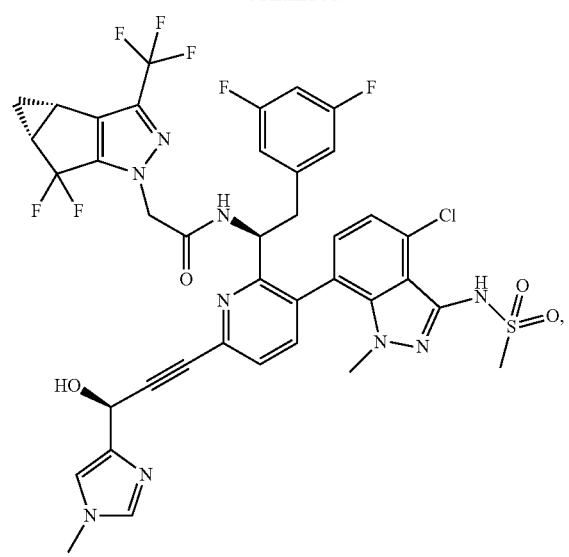
92
-continued
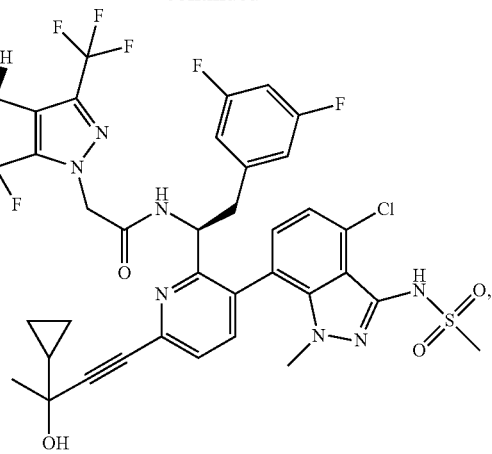
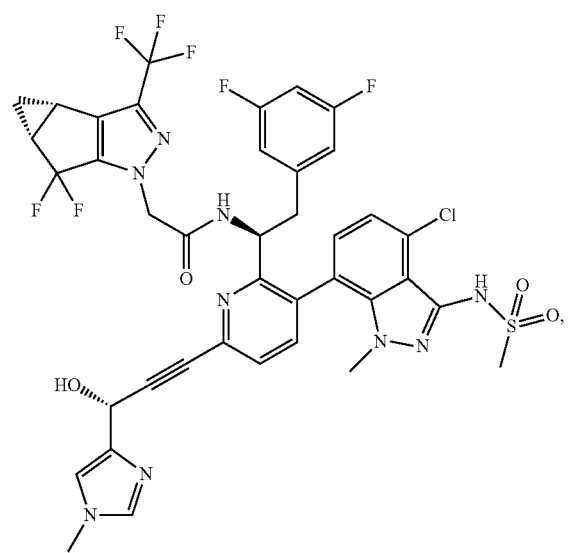
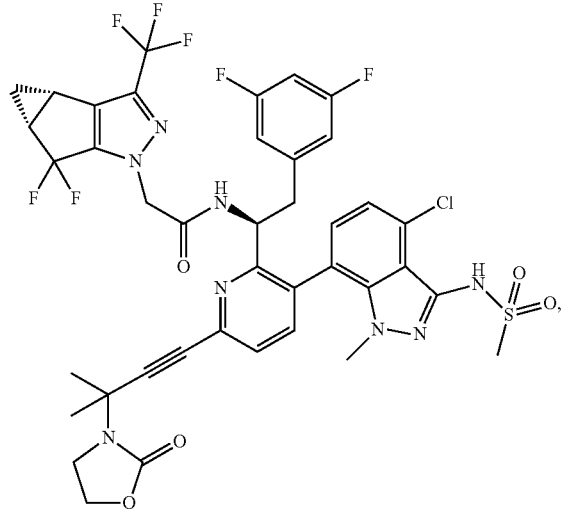
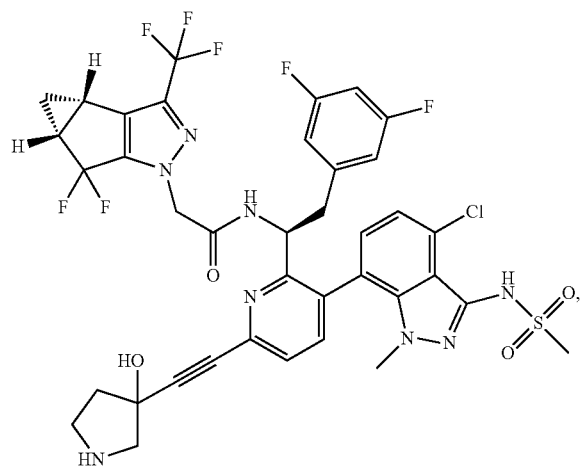

93
-continued
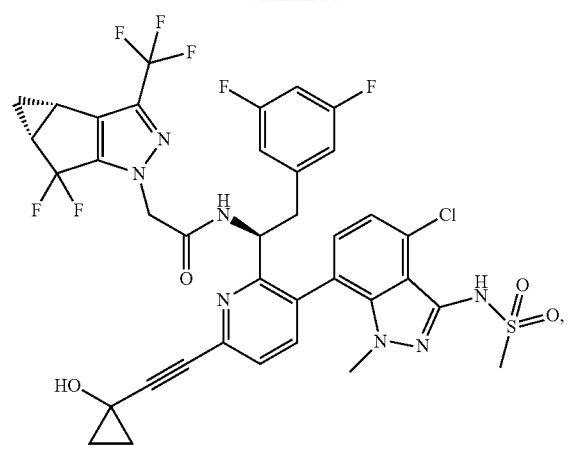
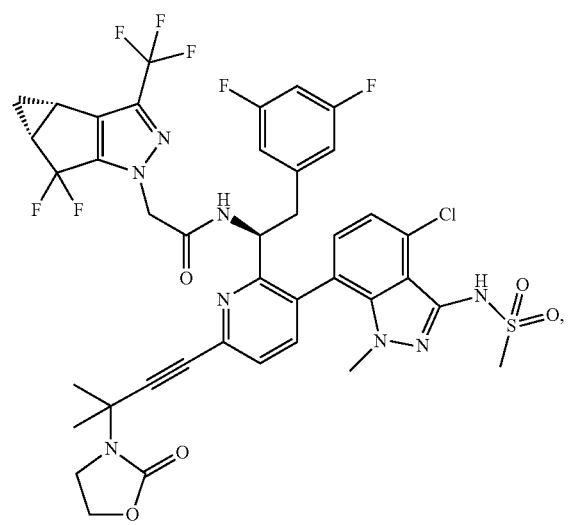
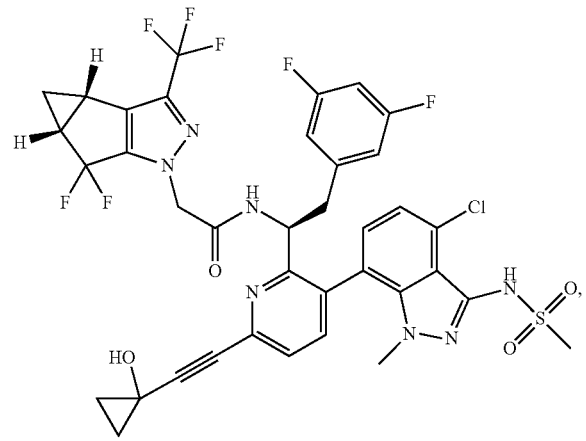
94
-continued
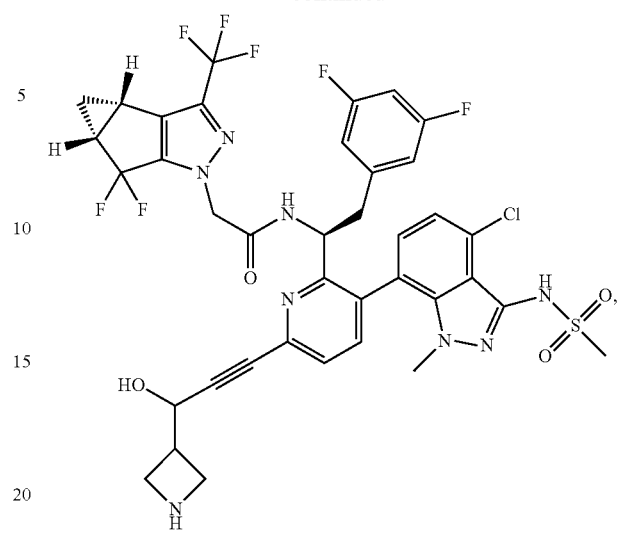
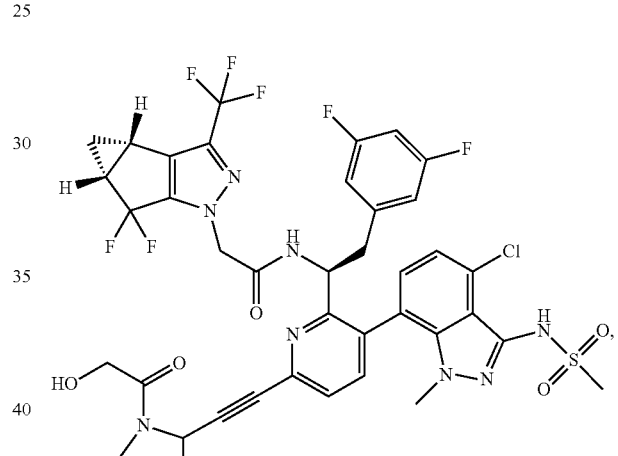
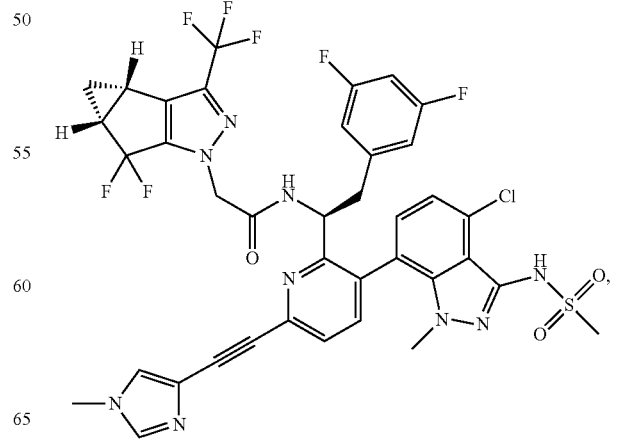

95
-continued
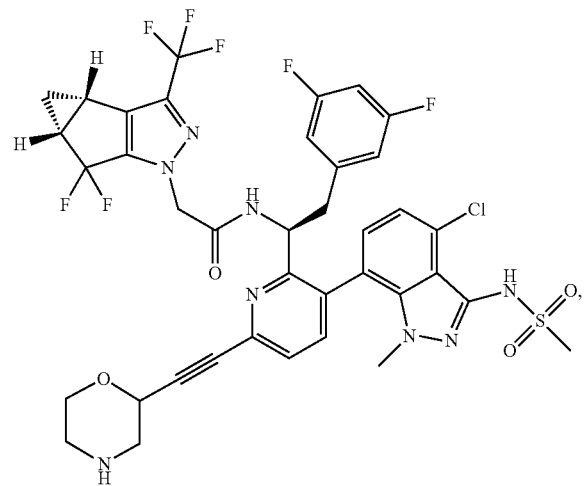
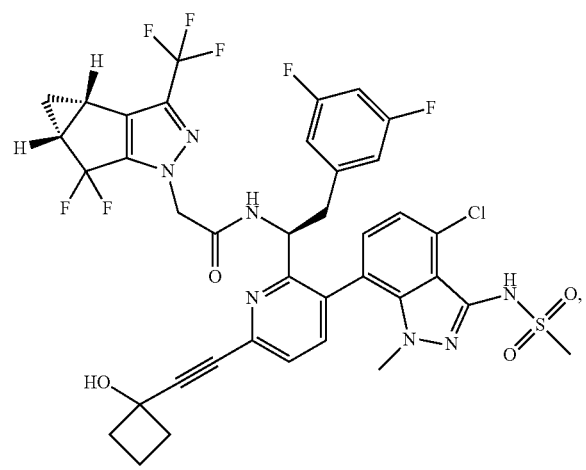
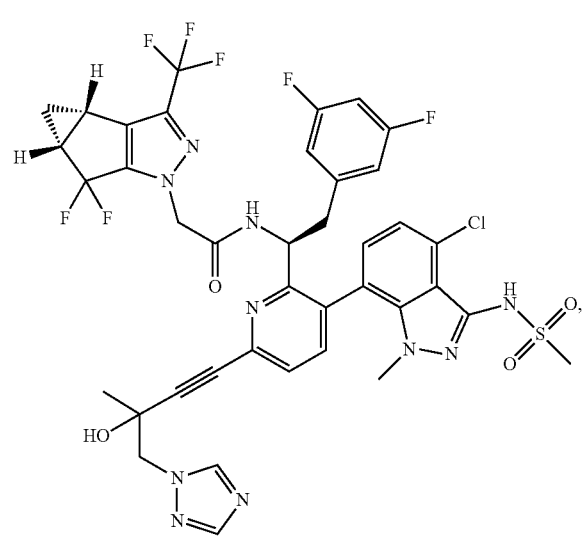
96
-continued
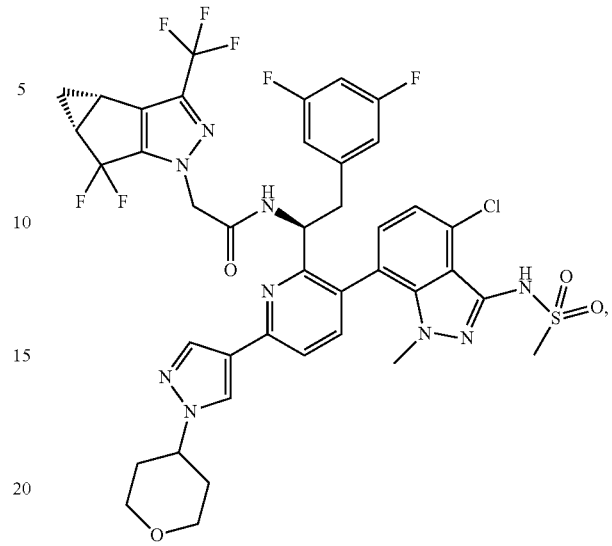
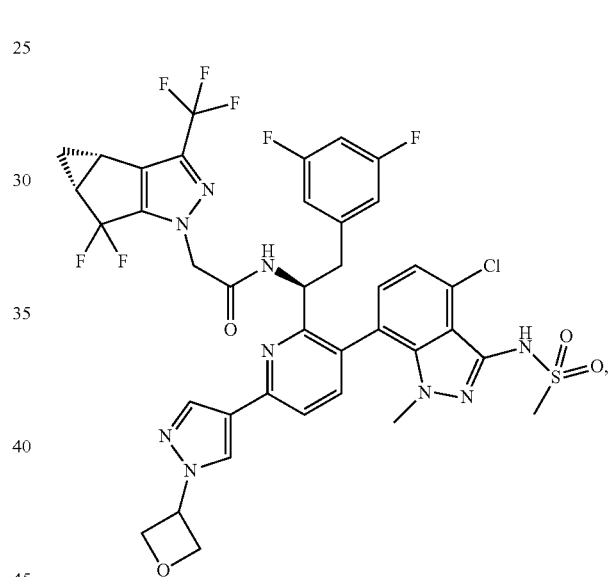
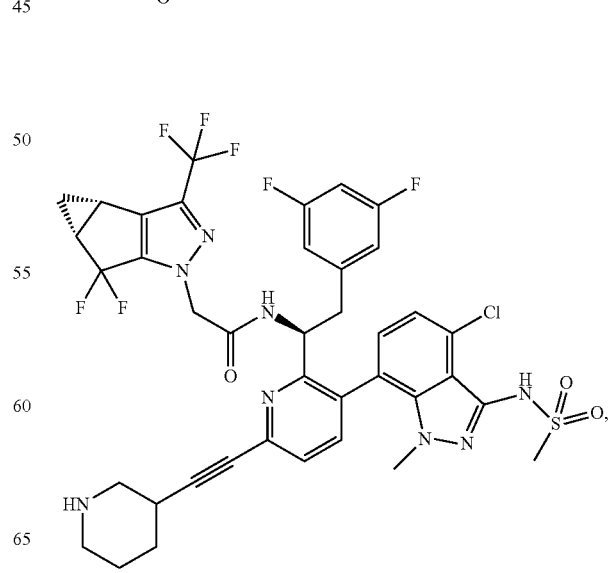

97
-continued
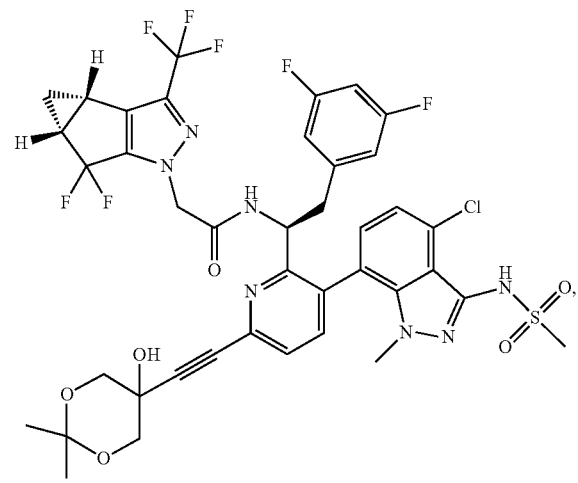
98
-continued
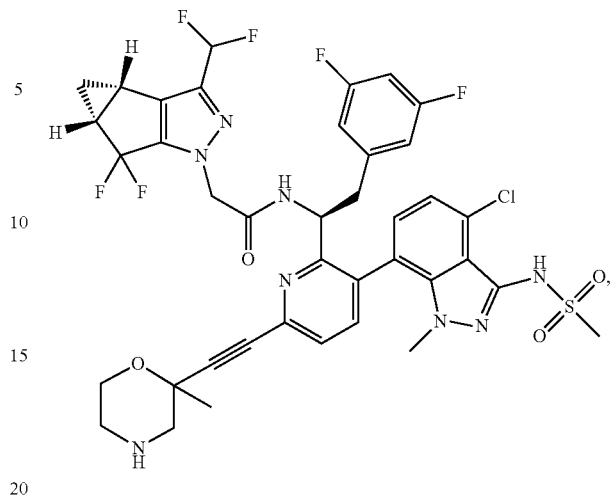
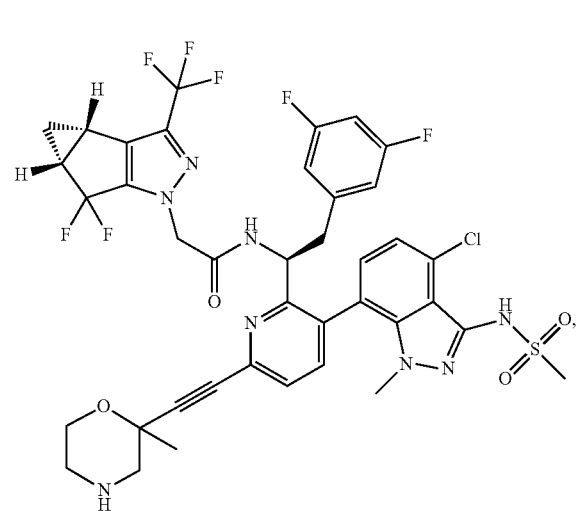
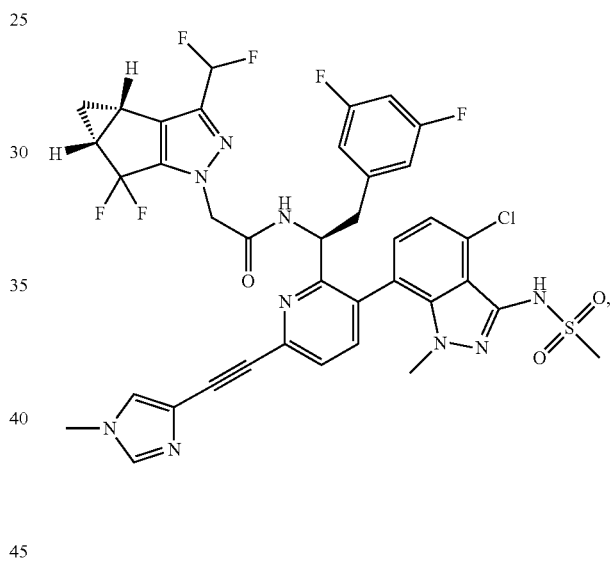
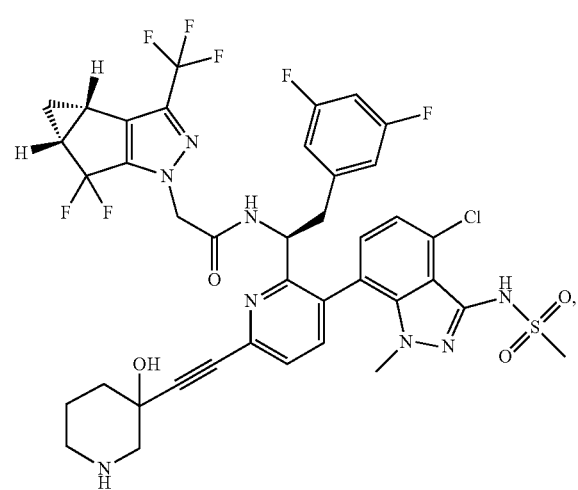
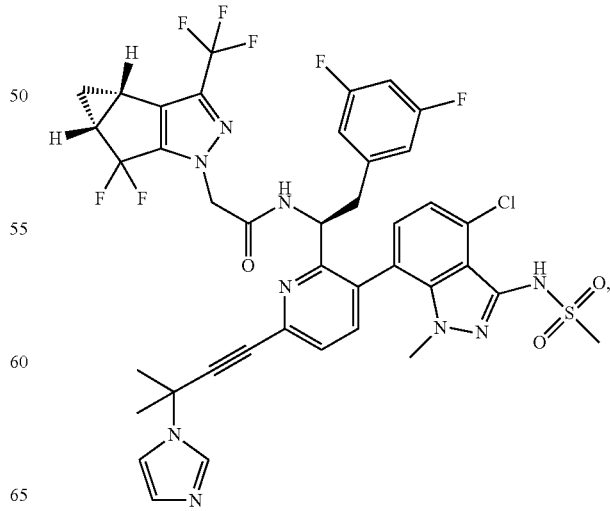

99
-continued
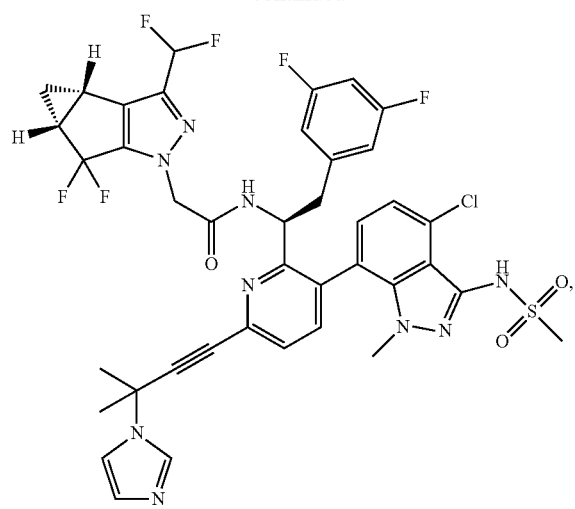
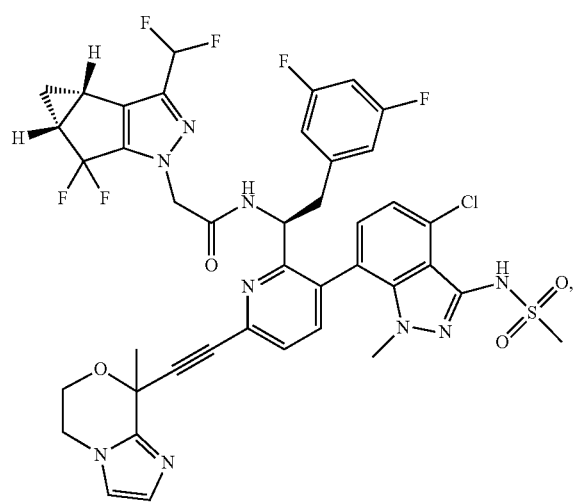
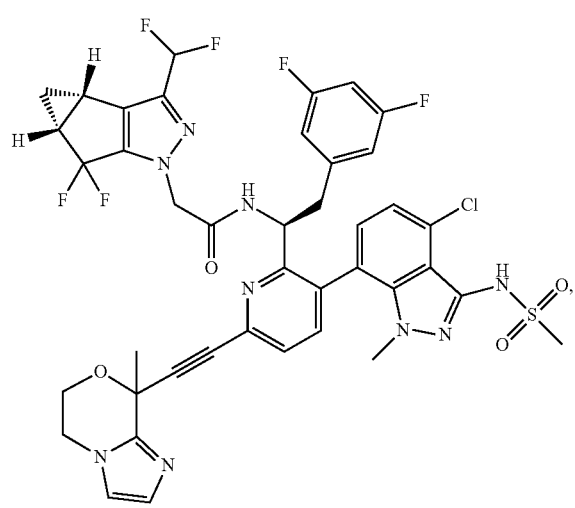
100
-continued
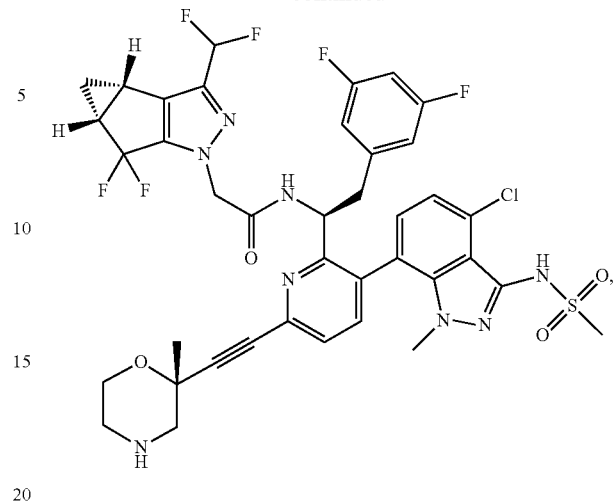
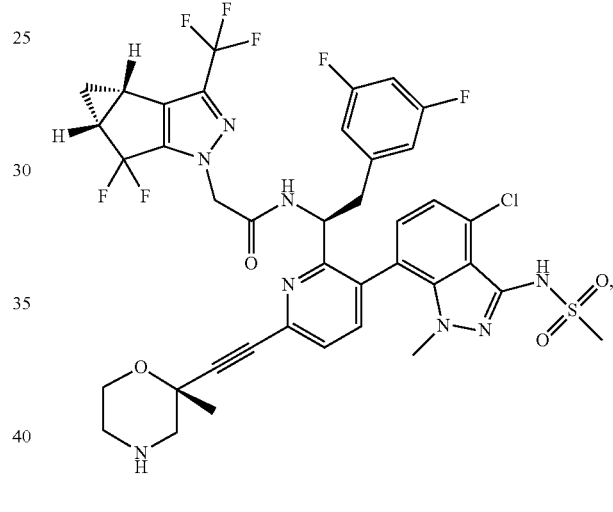
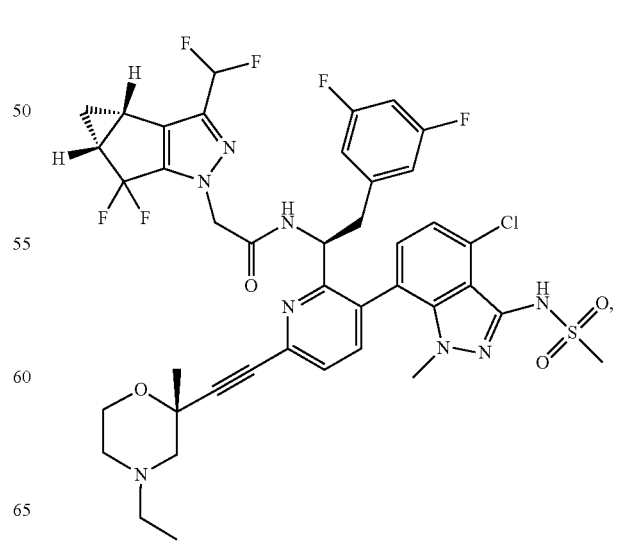

101
-continued
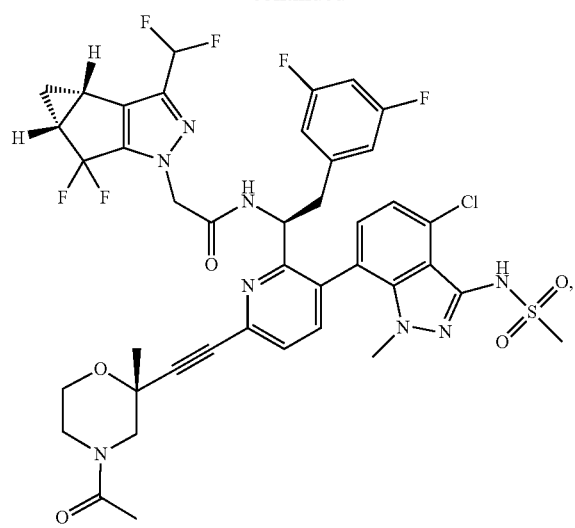
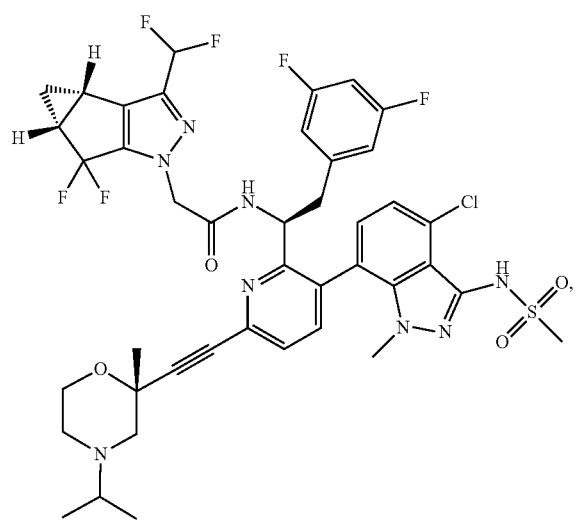
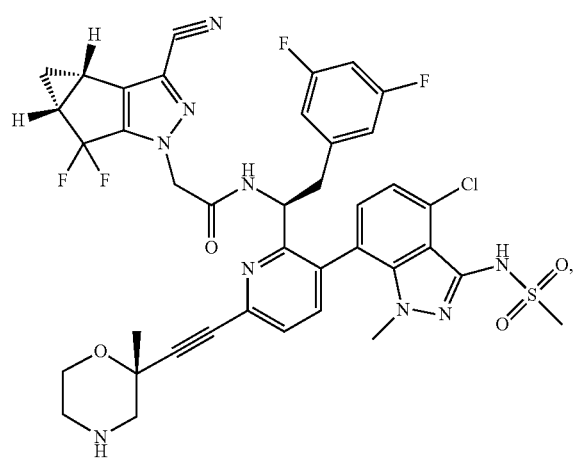
102
-continued
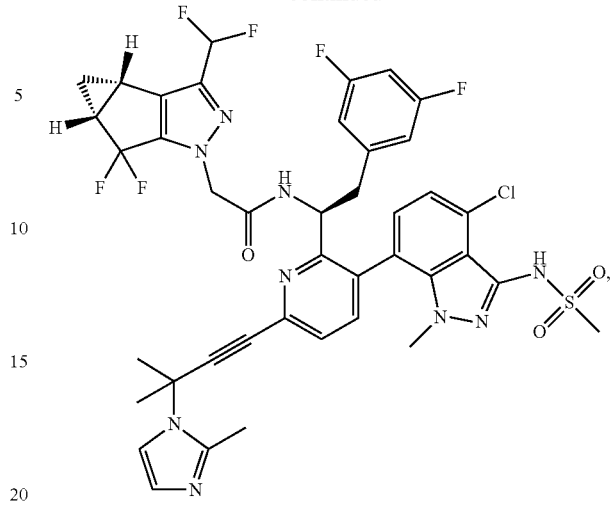
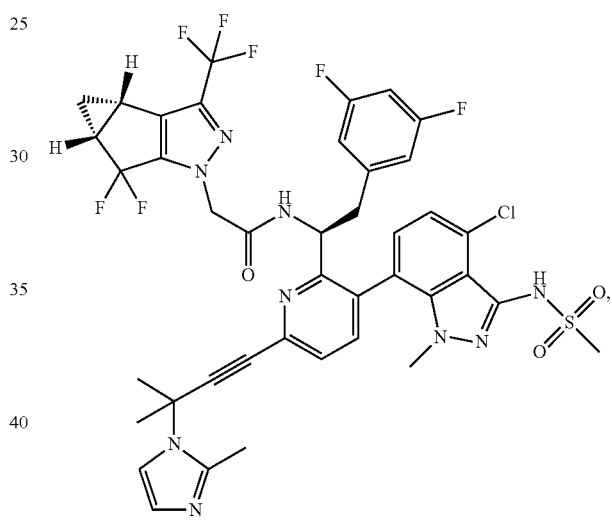
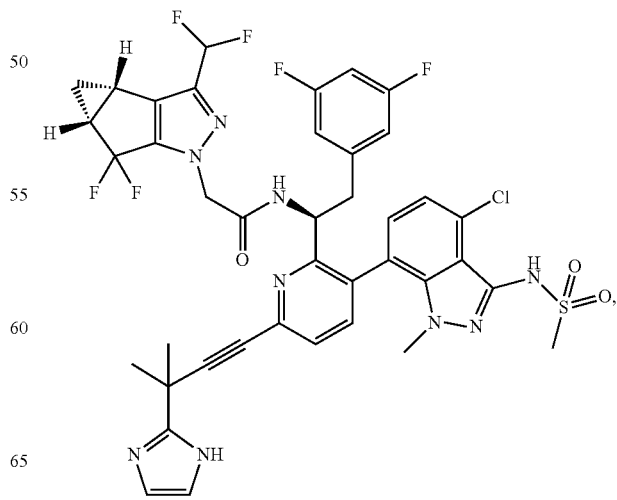

103
-continued
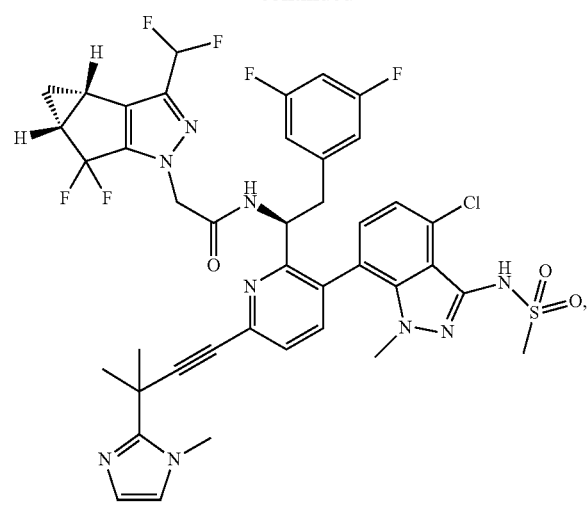
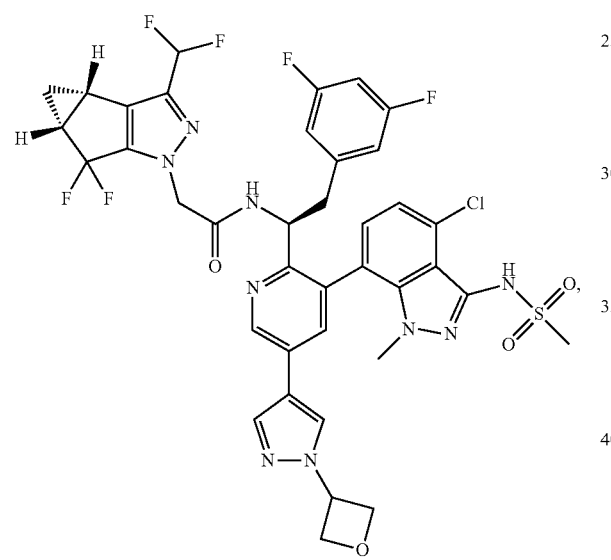
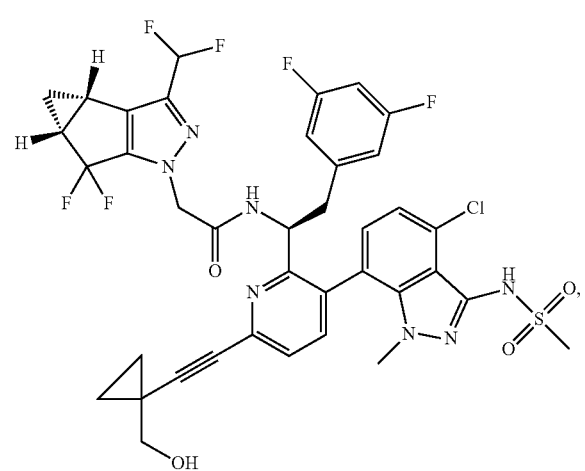
104
-continued
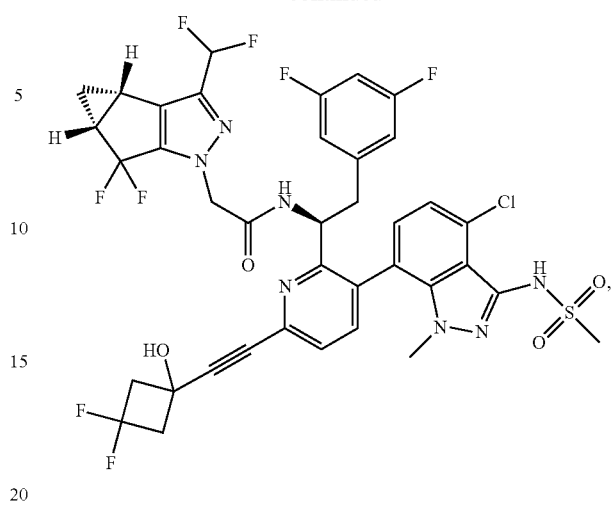
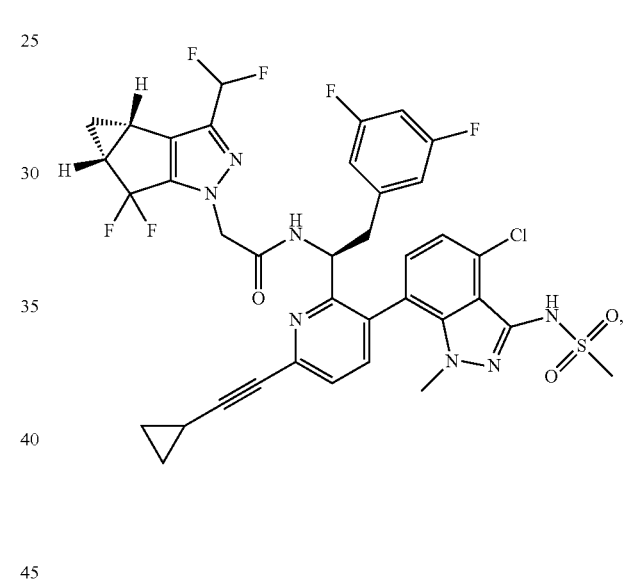
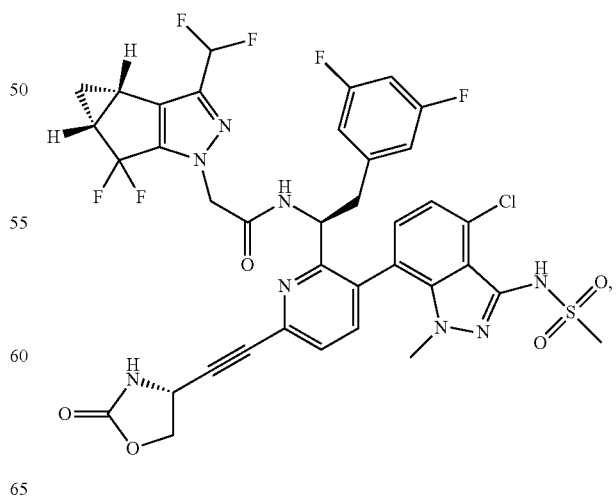

105
-continued
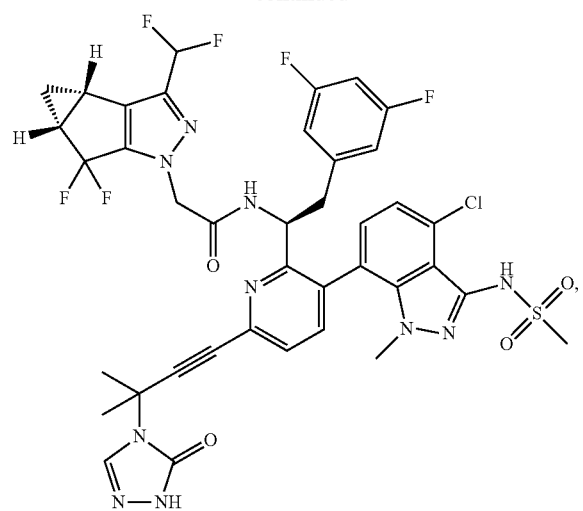
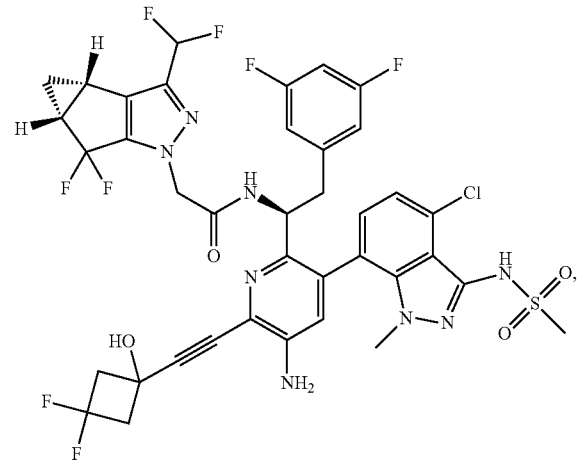
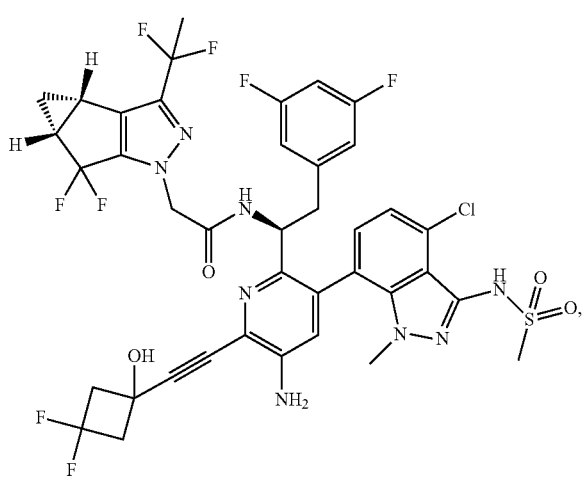
106
-continued
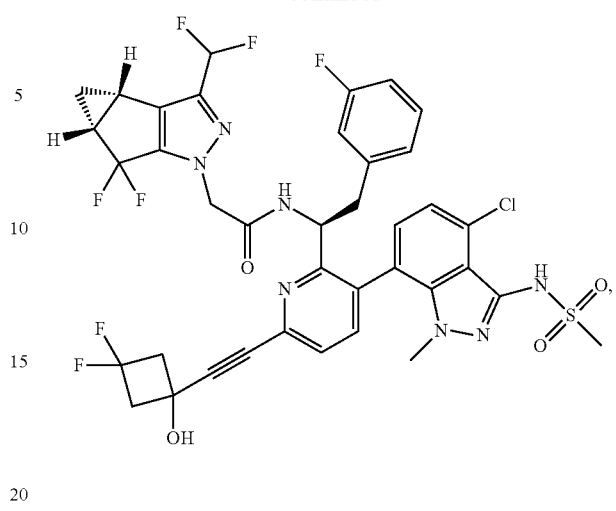
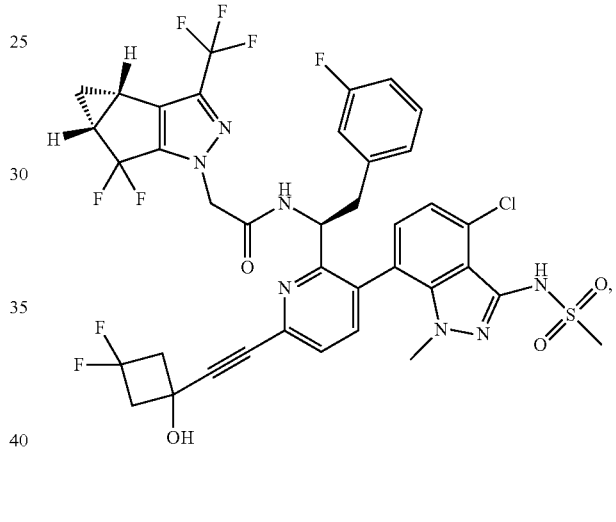
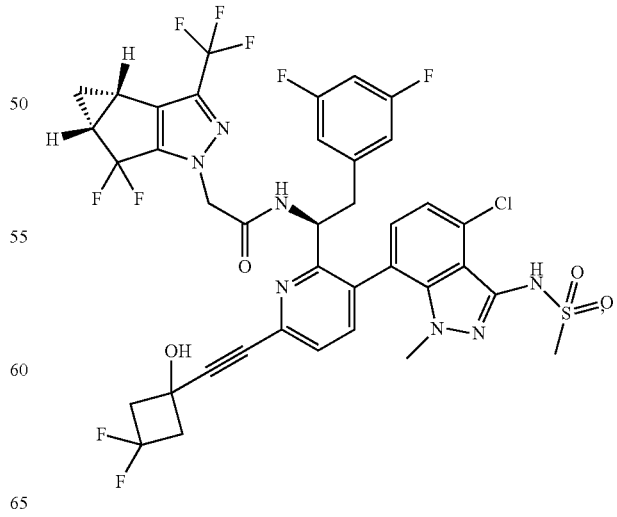

107
-continued
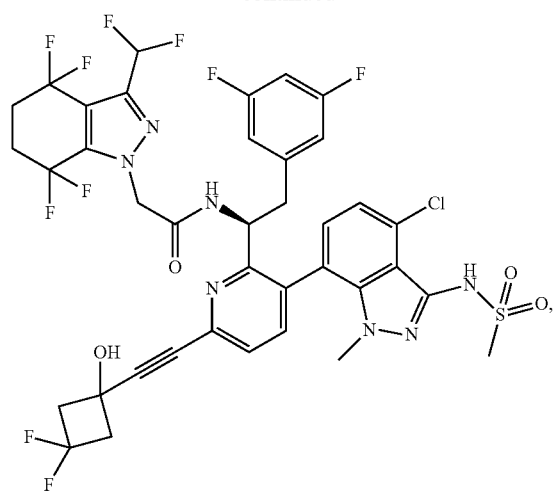
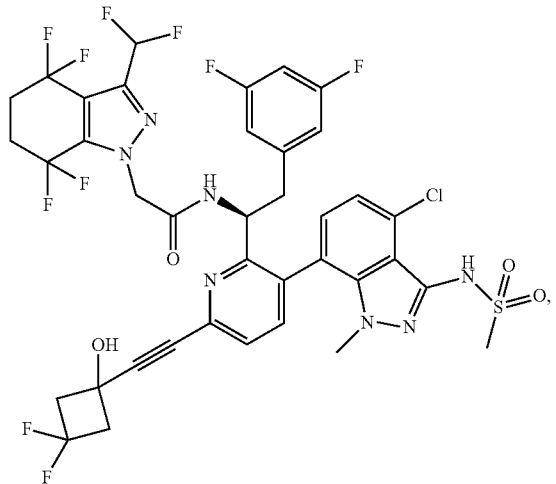
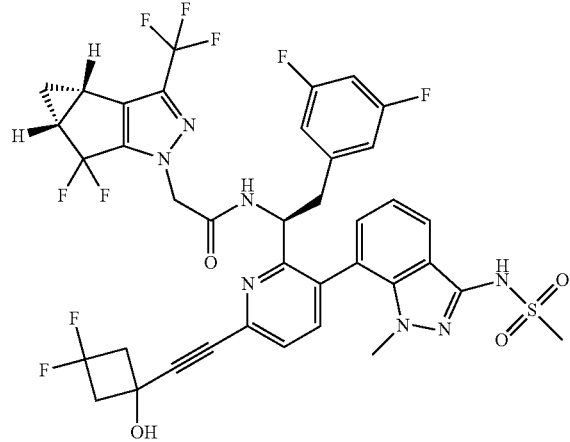
108
-continued
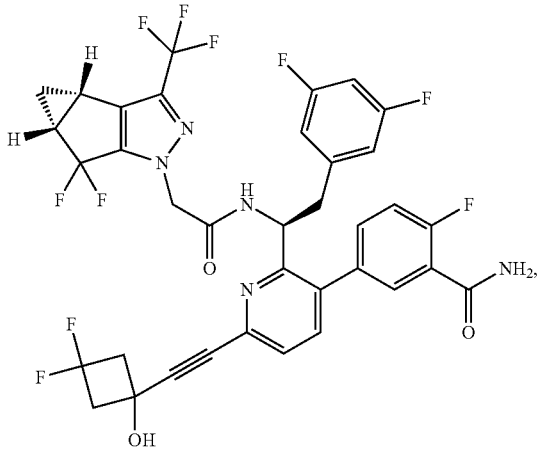
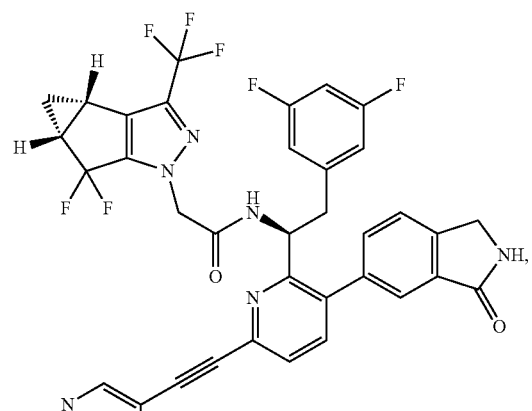

109
-continued
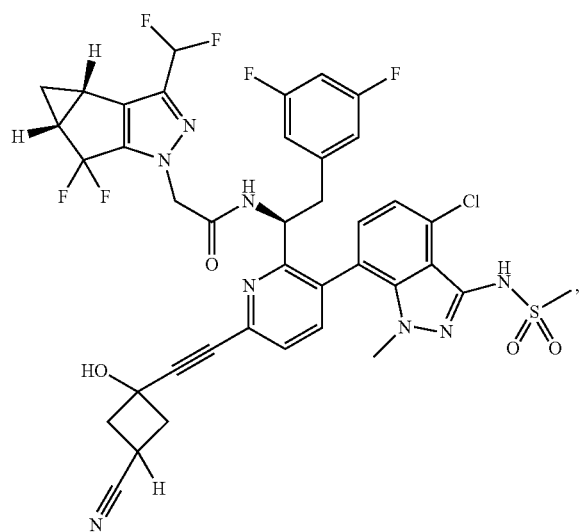
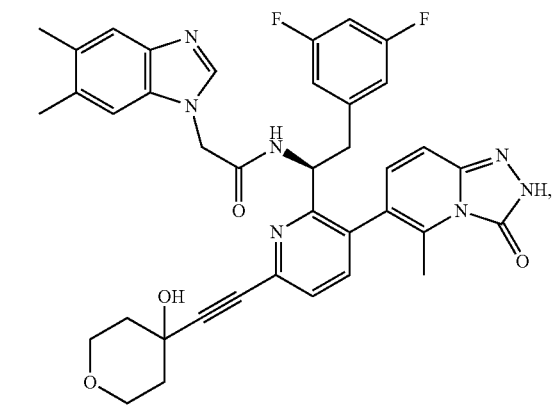
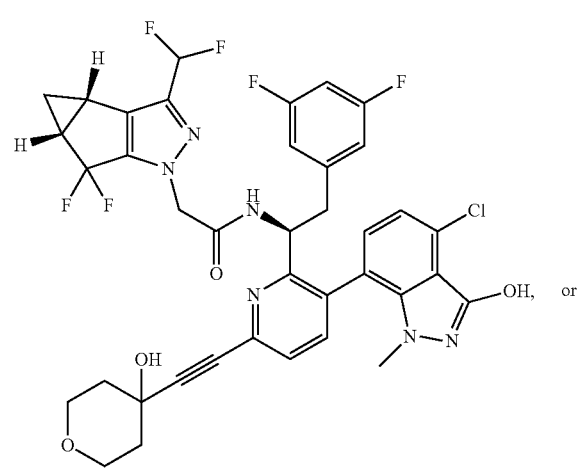
110
-continued
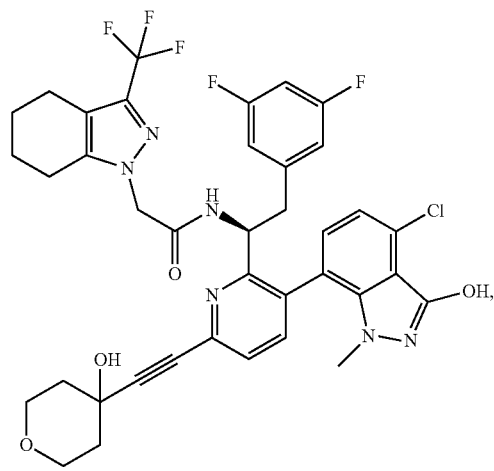 [SMILES: Cn1nc(O)c2c(Cl)ccc(-c3ccc(C#CC4(O)CCOCC4)nc3[C@H](Cc3cc(F)cc(F)c3)NC(=O)Cn3nc(C(F)(F)F)c4c3CCCC4)c21]
is provided.
General Synthetic Procedures
The following schemes describe methods that are useful for preparing compounds of formula I.
Scheme 1
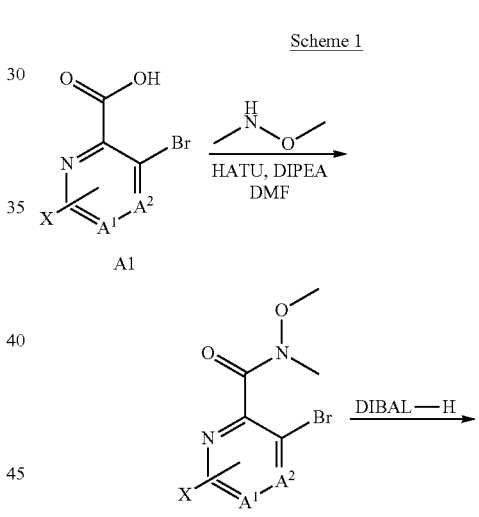
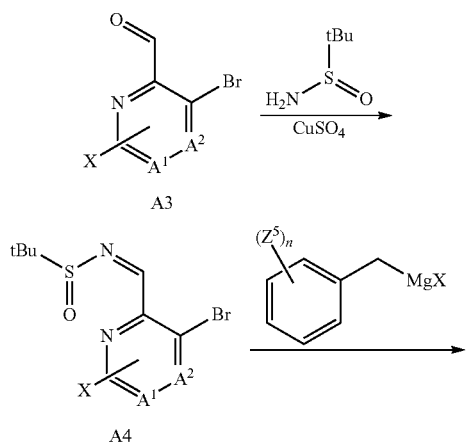

-continued

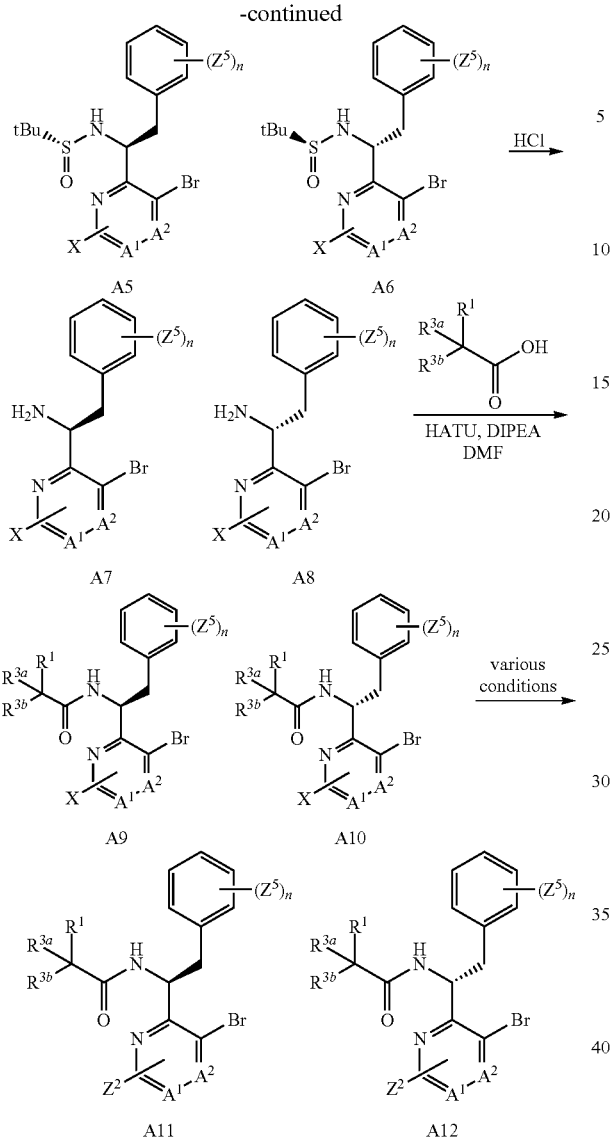

112

Scheme 2 describes a general stereoselective route which can be used to prepare certain compounds of formula I.

Scheme 2

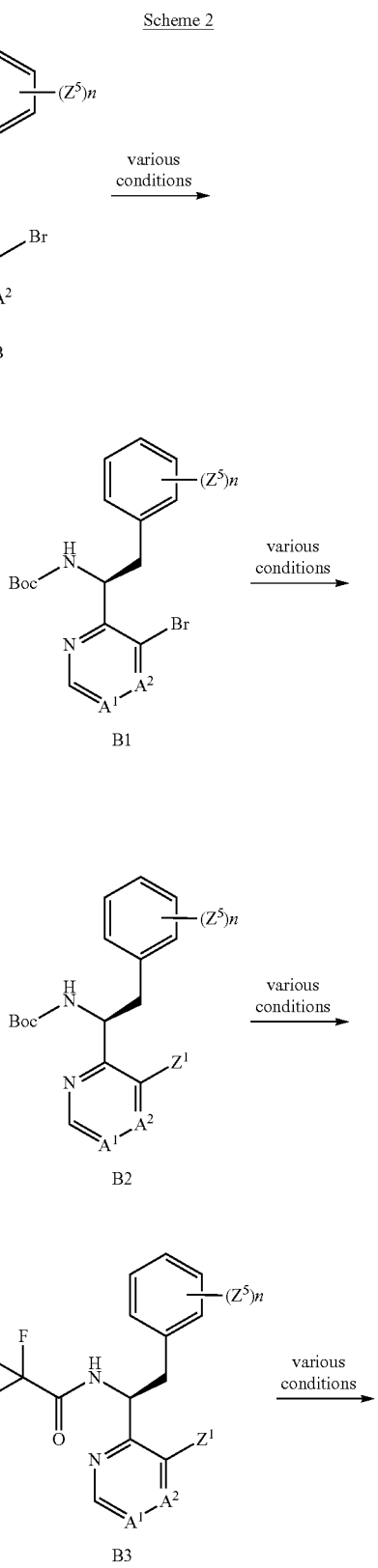

Scheme 1 describes a general stereoselective route which is used to prepare compounds of formula I. Heteroaryl acids of formula A1 (where X represents diversifiable chemical group such as $NH_2$, SH, or halogen that are suitably protected) are converted to the corresponding aldehydes then condensed with a chiral auxiliary to provide a stereoselective addition of a nucleophilic reagent. Depicted in Scheme 1 is the conversion of a heteroaryl acid A1 containing two diversifiable functional groups (e.g., X and Br) to the corresponding aldehyde. This is followed by the condensation of the aldehyde A3 with (S) tert-butane sulfinamide and the addition of a Grignard reagent to provide a mixture of A5 and A6 enriched in A5. This mixture is separated by column chromatography on silica gel to provide pure diastereomers. Removal of the auxiliary provides amines A7 and A8 which are coupled to a variety of carboxylic acids to provide heteroaryl compounds of formula A9 and A10. Diversification of A9 and A10 is accomplished by a variety of methods including alkylation, acylation, cyanation, nucleophilic aromatic displacement, and metal catalyzed cross coupling reactions such as Suzuki couplings, Buchwald-Hartwig type couplings, and Sonogashira couplings.

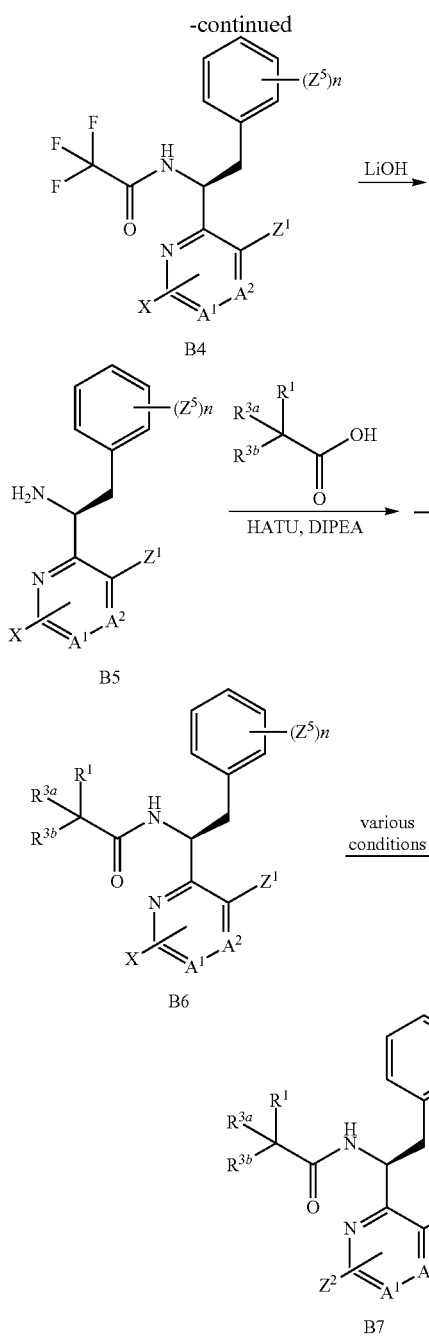

B4

B5

B6

B7

Scheme 3

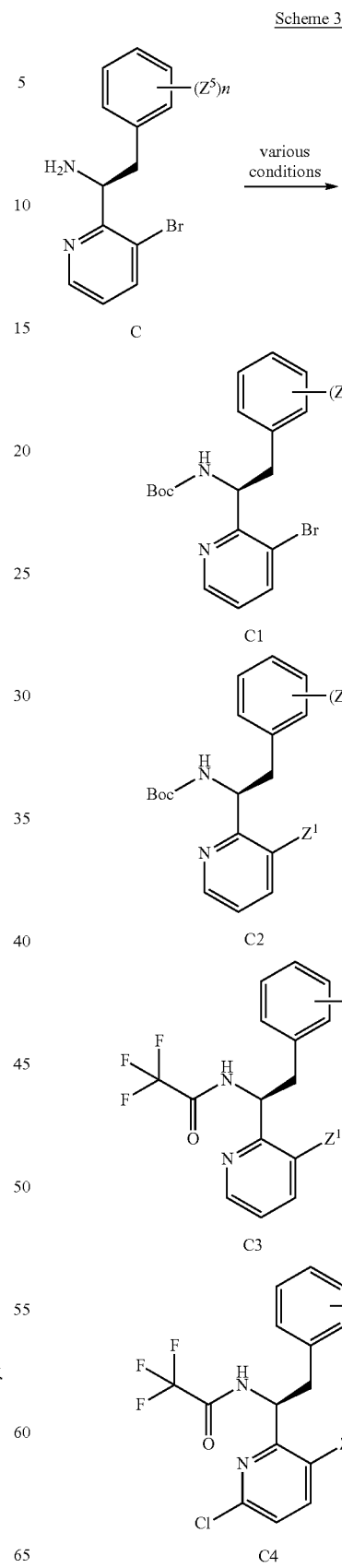

C

C1

C2

C3

C4

Depicted in Scheme 2 is the protection of amine B to a compound of formula B1. Diversification of the halide may then be accomplished to introduce a suitable Z1 group include metal catalyzed cross coupling reactions such as Suzuki couplings. After conversion of the amine protecting group, functional group X may be introduced as depicted in formula B4. After unblocking the amine, compounds of formula B5 are coupled to a variety of carboxylic acids to provide heteroaryl compounds of formula B6. Diversification of B6 is accomplished by a variety of methods including cyanation, nucleophilic aromatic displacement, and metal catalyzed cross coupling reactions such as Suzuki couplings, Buchwald-Hartwig type couplings, and Sonogashira couplings provides compounds of formula I.

Scheme 3 describes a general stereoselective route which can be used to prepare certain compounds of formula I.

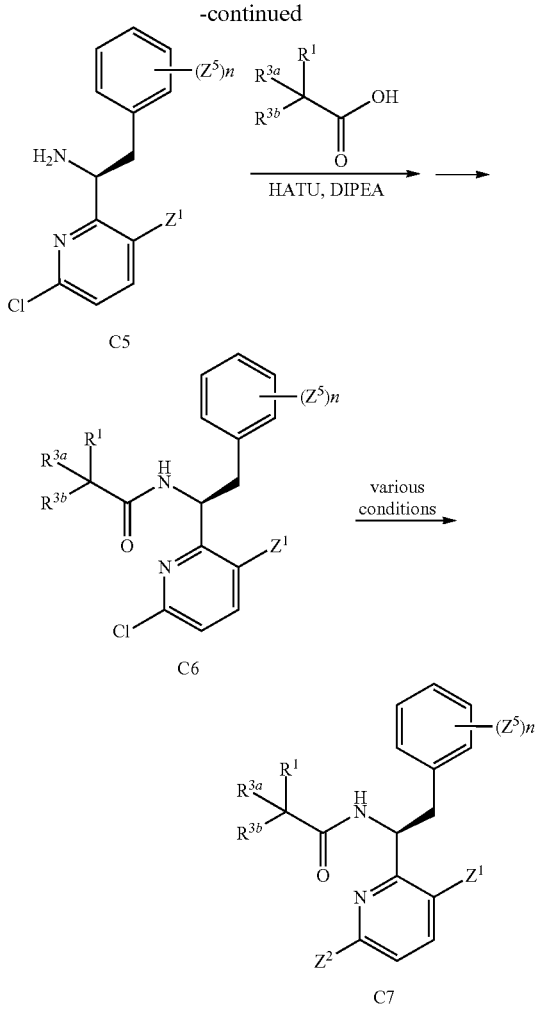

Depicted in Scheme 3 is the protection of amine C to a compound of formula C1. Diversification of the halide may then be accomplished to introduce a suitable Z1 group include metal catalyzed cross coupling reactions such as Suzuki couplings. After conversion of the amine protecting group, a halide may be introduced such as a Cl depicted in formula C4. After unblocking the amine, compounds of formula C5 are coupled to a variety of carboxylic acids to provide heteroaryl compounds of formula C6. Diversification of C6 is accomplished by a variety of methods including cyanation, nucleophilic aromatic displacement, and metal catalyzed cross coupling reactions such as Suzuki couplings, Buchwald-Hartwig type couplings, and Sonogashira couplings provides compounds of formula I.

Combination Therapy

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating an HIV infection, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection.

A compound as disclosed herein (e.g., any compound of Formula (I)) may be combined with one or more additional therapeutic agents in any dosage amount of the compound of Formula I (e.g., from 50 mg to 1000 mg of compound).

In certain embodiments, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent or excipient are provided.

In certain embodiments, kits comprising a compound disclosed herein, or a pharmaceutically acceptable salt thereof, in combination with one or more (e.g., one, two, three, one or two, or one to three) additional therapeutic agents are provided.

In certain of the above embodiments, the additional therapeutic agent may be an anti-HIV agent. For example, in some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV nucleotide competing inhibitors of reverse transcriptase such as those disclosed in WO 2013/091096A1 (Boehringer Ingelheim), HIV integrase inhibitors, HIV non-catalytic site (or allosteric) integrase inhibitors, HIV entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, HIV vaccines, HIV maturation inhibitors, latency reversing agents (e.g., histone deacetylase inhibitors, proteasome inhibitors, protein kinase C (PKC) activators, and BRD4 inhibitors), compounds that target the HIV capsid ("capsid inhibitors"; e.g., capsid polymerization inhibitors or capsid disrupting compounds, HIV nucleocapsid p7 (NCp7) inhibitors, HIV p24 capsid protein inhibitors), pharmacokinetic enhancers, immune-based therapies (e.g., Pd-1 modulators, Pd-L1 modulators, toll like receptors modulators, IL-15 agonists, HIV antibodies, bispecific antibodies and "antibody-like" therapeutic proteins (e.g., DARTs®, Duobodies®, Bites®, XmAbs®, TandAbs®, Fab derivatives) including those targeting HIV gp120 or gp41, combination drugs for HIV, HIV p17 matrix protein inhibitors, IL-13 antagonists, Peptidyl-prolyl cis-trans isomerase A modulators, Protein disulfide isomerase inhibitors, Complement C5a receptor antagonists, DNA methyltransferase inhibitor, HIV vif gene modulators, HIV-1 viral infectivity factor inhibitors, TAT protein inhibitors, HIV-1 Nef modulators, Hck tyrosine kinase modulators, mixed lineage kinase-3 (MLK-3) inhibitors, Rev protein inhibitors, Integrin antagonists, Nucleoprotein inhibitors, Splicing factor modulators, COMM domain containing protein 1 modulators, HIV Ribonuclease H inhibitors, Retrocyclin modulators, CDK-9 inhibitors, Dendritic ICAM-3 grabbing nonintegrin 1 inhibitors, HIV GAG protein inhibitors, HIV POL protein inhibitors, Complement Factor H modulators, Ubiquitin ligase inhibitors, Deoxycytidine kinase inhibitors, Cyclin dependent kinase inhibitors Proprotein convertase PC9 stimulators, ATP dependent RNA helicase DDX3X inhibitors, compounds such as those disclosed in WO 2013/006738 (Gilead Sciences), US 2013/0165489 (University of Pennsylvania), WO 2009/062285 (Boehringer Ingelheim), WO 2010/130034 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences) and WO 2013/006792 (Pharma Resources), and other drugs for treating HIV, and combinations thereof.

In certain embodiments, the additional therapeutic is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments a compound of Formula (I) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof. In certain embodiments, such tablets are suitable for once daily dosing.

In certain embodiments, the additional therapeutic agent is selected from one or more of:

(1) Combination drugs selected from the group consisting of ATRIPLA® (efavirenz+tenofovir disoproxil fumarate+emtricitabine), COMPLERA® (EVIPLERA®, rilpivirine+tenofovir disoproxil fumarate+emtricitabine), STRIBILD® (elvitegravir+cobicistat+tenofovir disoproxil fumarate+entricitabine), dolutegravir+abacavir sulfate+lamivudine, dolutegravir+abacavir sulfate+lamivudine, lamivudine+nevirapine+zidovudine, dolutegravir+rilpivirine, atazanavir sulfate+cobicistat, darunavir+cobicistat, efavirenz+lamivudine+tenofovir disoproxil fumarate, tenofovir alafenanlide hemifumarate+emtricitabine+cobicistat+elvitegravir, Vacc-4x+romidepsin, darunavir+tenofovir alafenamide hemifumarate+emtricitabine+cobicistat, APH-0812, raltegravir+lamivudine, KALETRA® (ALUVIA®, lopinavir+ritonavir), atazanavir sulfate+ritonavir, COMBIVIR® (zidovudine+lamivudine, AZT+3TC), EPZICOM® (Livexa®, abacavir sulfate+lamivudine, ABC+3TC), TRIZIVIR® (abacavir sulfate+zidovudine+lamivudine, ABC+AZT+3TC), TRUVADA® (tenofovir disoproxil fumarate+emtricitabine, TDF+FTC), tenofovir+lamivudine and lamivudine+tenofovir disoproxil fumarate;

(2) HIV protease inhibitors selected from the group consisting of amprenavir, atazanavir, fosamprenavir, fosamprenavir calcium, indinavir, indinavir sulfate, lopinavir, ritonavir, nelfinavir, nelfinavir mesylate, saquinavir, saquinavir mesylate, tipranavir, brecanavir, darunavir, DG-17, TMB-657 (PPL-100), TMC-310911, and TMB-657;

(3) HIV non-nucleoside or non-nucleotide inhibitors of reverse transcriptase selected from the group consisting of delavirdine, delavirdine mesylate, nevirapine, etravirine, dapivirine, doravirine, rilpivirine, efavirenz, KM-023, VM-1500, lentinan and AIC-292;

(4) HIV nucleoside or nucleotide inhibitors of reverse transcriptase selected from the group consisting of VIDEX® and VIDEX® EC (didanosine, ddI), zidovudine, emtricitabine, didanosine, stavudine, zalcitabine, lamivudine, censavudine, abacavir, abacavir sulfate, amdoxovir, elvucitabine, alovudine, phosphazid, fozivudine tidoxil, apricitabine, amdoxovir, KP-1461, fosalvudine tidoxil, tenofovir, tenofovir disoproxil, tenofovir disoproxil fumarate, tenofovir disoproxil hemifumarate, tenofovir alafenamide, tenofovir alafenamide hemifumarate, tenofovir alafenamide fumarate, adefovir, adefovir dipivoxil, and festinavir;

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, elvitegravir, dolutegravir and cabotegravir;

(6) HIV non-catalytic site, or allosteric, integrase inhibitors (NCINI) selected from the group consisting of CX-05168, CX-05045 and CX-14442;

(7) HIV gp41 inhibitors selected from the group consisting of enfuvirtide, sifuvirtide and albuvirtide;

(8) HIV entry inhibitors selected from the group consisting of cenicriviroc;

(9) HIV gp120 inhibitors selected from the group consisting of Radha-108 (Receptol) and BMS-663068;

(10) CCR5 inhibitors selected from the group consisting of aplaviroc, vicriviroc, maraviroc, cenicriviroc, PRO-140, Adaptavir (RAP-101), TBR-220 (TAK-220) and vMIP (Haimipu);

(11) CD4 attachment inhibitors selected from the group consisting of ibalizumab;

(12) CXCR4 inhibitors selected from the group consisting of plerixafor, ALT-1188, vMIP and Haimipu;

(13) Pharmacokinetic enhancers selected from the group consisting of cobicistat and ritonavir;

(14) Immune-based therapies selected from the group consisting of dermaVir, interleukin-7, lexgenleucel-T (VRX-496), plaquenil (hydroxychloroquine), proleukin (aldesleukin, IL-2), interferon alfa, interferon alfa-2b, interferon alfa-n3, pegylated interferon alfa, interferon gamma, hydroxyurea, mycophenolate mofetil (MPA) and its ester derivative mycophenolate mofetil (MMF), WF-10, ribavirin, IL-2, IL-2 XL, IL-12, polymer polyethyleneimine (PEI), Gepon, VGV-1, MOR-22, toll-like receptors modulators (tlr1, tlr2, tlr3, tlr4, tlr5, tlr6, tlr7, tlr8, tlr9, tlr10, tlr11, tlr12 and tlr13), rintatolimod and IR-103;

(15) HIV vaccines selected from the group consisting of peptide vaccines, recombinant subunit protein vaccines, live vector vaccines. DNA vaccines, virus-like particle vaccines (pseudovirion vaccine), CD4-derived peptide vaccines, vaccine combinations, rgp120 (AIDSVAX), ALVAC HIV (vCP1521)/AIDSVAX B/E (gp120) (RV144), Remune, ITV-1, Contre Vir, Ad5-ENVA-48, DCVax-001 (CDX-2401), PEP-6409, Vacc-4x, Vacc-C5, VAC-3S, multiclade DNA recombinant adenovirus-5 (rAd5), Pennvax-G, VRC-HIV MAB060-00-AB, AVX-101, Tat Oyi vaccine, AVX-201, HIV-LAMP-vax, Ad35, Ad35-GRIN, NAcGM3/VSSP ISA-51, poly-ICLC adjuvanted vaccines, TatImmune, GTUmultiHIV (FIT-06), AGS-004, gp140[delta]V2.TV1+ MF-59, rVSVIN HIV-1 gag vaccine, SeV-Gag vaccine, AT-20, DNK-4, Ad35-GRIN/ENV, TBC-M4, HIVAX, HIVAX-2, NYVAC-HIV-PT1, NYVAC-HIV-PT4, DNA-HIV-PT123, Vichrepol, rAAV1-PG9DP, GOVX-B11, GOVX-B21, ThV-01, TUTI-16, VGX-3300, TVI-HIV-1, Ad-4 (Ad4-env Clade C+ Ad4-mGag), EN41-FPA2, PreVaxTat, TL-01, SAV-001, AE-H, MYM-V101, CombiHIVvac, ADVAX, MYM-V201 and DNA-Ad5 gag/pol/nef/nev (HVTN505);

(16) HIV antibodies, bispecific antibodies and "antibody-like" therapeutic proteins (such as DARTs®, Duobodies®, Bites®, XmAbs®, TandAbs®, Fab derivatives) including those targeting HIV gp120 or gp41 selected from the group consisting of bavituximab, UB-421, C2F5, C2G12, C4E10, C2F5+C2G12+C4E10, 3-BNC-117, KD-247, PGT145, PGT121, MDX010 (ipilimumab), VRC01, A32, 7B2, 10E8 and VRC07;

(17) latency reversing agents selected from the group consisting of Histone deacetylase inhibitors such as Romidepsin, vorinostat, panobinostat; Proteasome inhibitors such as Velcade; protein kinase C (PKC) activators such as Indolactam, Prostratin, Ingenol B and DAG-lactones, Ionomycin, GSK-343, PMA, SAHA, BRD4 inhibitors, IL-15, JQ1 and disulfram;

(18) HIV nucleocapsid p7 (NCp7) inhibitors selected from the group consisting of azodicarbonamide;

(19) HIV maturation inhibitors selected from the group consisting of BMS-955176 and GSK-2838232;

(20) the compounds disclosed in WO 2004/096286 (Gilead Sciences), WO 2006/110157 (Gilead Sciences), WO 2006/015261 (Gilead Sciences), WO 2013/006738 (Gilead Sciences), US 2013/0165489 (University of Pennsylvania), WO 2013/006792 (Pharma Resources), WO 2009/062285 (Boehringer Ingelheim), WO 2010/130034 (Boehringer Ingelheim), WO 2013/091096A1 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences);

and

(21) other drugs for treating HIV selected from the group consisting of REP 9, Cytolin, CYT-107, alisporivir, NOV-205, IND-02, metenkefalin, PGN-007, Acemannan, Gamimune, SCY-635, Prolastin, 1,5-dicaffeoylquinic acid, BIT-225, RPI-MN, VSSP, Hiviral, IMO-3100, SB-728-T, RPI-MN, VIR-576, HGTV-43, MK-1376, rHIV7-sh1-TAR-CCR5RZ, MazF gene therapy, BlockAide and PA-1050040 (PA-040).

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In certain embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In a further embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with one, two, three, four or more additional therapeutic agents selected from raltegravir, Truvada® (tenofovir disoproxil fumarate+emtricitabine, TDF+FTC), maraviroc, enfuvirtide, Epzicom® (Livexa®, abacavir sulfate+lamivudine, ABC+3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+emtricitabine), rilpivirine, rilpivirine hydrochloride, Complera® (Eviplera®, rilpivirine+tenofovir disoproxil fumarate+emtricitabine), Cobicistat, Atripla® (efavirenz+tenofovir disoproxil fumarate+emtricitabine), atazanavir, atazanavir sulfate, dolutegravir, elvitegravir, Aluvia® (Kaletra®, lopinavir+ritonavir), ritonavir, emtricitabine, atazanavir sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, abacavir, abacavir sulfate, tenofovir, tenofovir disoproxil, tenofovir disoproxil fumarate, tenofovir alafenamide and tenofovir alafenamide hemifumarate.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of: tenofovir, tenofovir disoproxil, tenofovir disoproxil fumarate, tenofovir alafenamide, and tenofovir alafenamide hemifumarate and a second additional therapeutic agent, wherein the second additional therapeutic agent is emtricitabine.

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide and 200 mg emtricitabine. A compound as disclosed herein (e.g., a compound of formula (I)) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof is combined with 200-400 mg tenofovir disoproxil fumarate, tenofovir disoproxil hemifumarate, or tenofovir disoproxil and 200 mg emtricitabine. In certain embodiments, a compound disclosed herein, or a pharmaceutically acceptable salt thereof, is combined with 200-250; 200-300; 200-350; 250-350; 250-400; 350-400; 300-400; or 250-400 mg tenofovir disoproxil fumarate, tenofovir disoproxil hemifumarate, or tenofovir disoproxil and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil and 200 mg emtricitabine. A compound as disclosed herein (e.g., a compound of formula (I)) may be combined with the agents provided herein in any dosage amount of the compound (e.g., from 50 mg to 500 mg of compound) the same as if each combination of dosages were specifically and individually listed.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In some embodiments, one or more of the compounds disclosed herein are combined with one or more other active therapeutic agents in a unitary dosage form for simultaneous or sequential administration to a patient. In certain embodiments, a pharmaceutical composition including one or more of the compounds disclosed herein combined with one or more other active therapeutic agents is provided. In certain embodiments, the compounds disclosed herein are combined with one or more other active therapeutic agents in a solid dosage form. The combination therapy may be administered as a simultaneous or sequential regimen. When administered sequentially, the combination may be administered in two or more administrations.

In some embodiments, one or more of the compounds disclosed herein are co-administered with one or more other active therapeutic agents. Co-administration of a compound disclosed herein with one or more other active therapeutic agents generally refers to simultaneous or sequential administration of a compound disclosed herein and one or more other active therapeutic agents, such that therapeutically effective amounts of disclosed herein and one or more other active therapeutic agents are both present in the body of the patient.

In yet another embodiment, the present application provides a method for treating an HIV infection comprising administering to a patient in need thereof a therapeutically effective amount of a compound disclosed herein, or a pharmaceutically acceptable salt thereof, in combination with a therapeutically effective amount of one or more additional therapeutic agents such as those disclosed above.

Pharmaceutical Formulations

The compounds disclosed herein are formulated with conventional carriers (e.g., inactive ingredient or excipient material) which will be selected in accord with ordinary practice. Tablets will contain excipients including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). The formulations, both for veterinary and for human use, of the present disclosure comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipients, etc.) which constitutes one or more accessory ingredients. In general the formulations are prepared by uniformly and intimately bringing into association the active ingredient with liquid carriers or finely divided solid carriers or both, and then, if necessary, shaping the product.

Formulations described herein that are suitable for oral administration may be presented as discrete units including but not limited to capsules, cachets or tablets each containing a predetermined amount of the active ingredient.

Pharmaceutical formulations disclosed herein comprise one or more compounds disclosed herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in certain embodiments, a dosage form for oral administration to humans contains approximately 1 to 1000 mg of active material formulated with an appropriate and convenient amount of carrier material (e.g., inactive ingredient or excipient material). In certain embodiments, a dosage form (e.g., for oral administration to humans) contains: from 10 mg to 1000 mg or from 50 mg to 1000 mg or from 100 mg to 1000 mg or from 200 mg to 1000 mg or from 300 mg to 1000 mg or from 10 mg to 800 mg or from 10 mg to 600 mg or from 10 mg to 500 mg or from 10 mg to 400 mg or from 10 mg to 300 mg or from 50 mg to 800 mg or from 100 mg to 600 mg or from 150 mg to 500 mg or from 200 mg to 400 mg or from 50 mg to 500 mg or from 10 mg to 300 mg or from 50 mg to 300 mg or from 10 mg to 200 mg or from 50 mg to 200 mg or from 100 mg to 300 mg or from 100 mg to 200 mg or from 200 mg to 300 mg of active material (e.g., a compound of formula I). In certain embodiments, a dosage form for oral administration to humans contains at least any of 10, 25, 50, 100, 150, 200, 250 or 300 mg and no more than 500 or 800 or 1000 mg of active material (e.g., from at least 50 mg to no more than 500 mg). In some embodiments, a dosage form for oral administration to humans contains at least any of 10, 25, 50, 100, 150, 200, 250 or 300 mg or no more than 500 or 800 or 1000 mg of active material. In some embodiments, a dosage form for oral administration to humans contains any of 10, 25, 50, 100, 150, 200, 250, 300, 350, 400, 450, 500, 550, 600, 650, 700, 750, 800, 850, 900, 950, or 1000 mg of active material. It is understood that a dosage form in an amount provided herein may be administered to a patient (e.g., a human in need thereof) in accordance with a dosing regimen provided herein, such as once, twice or thrice daily dosing. In one aspect, a dosing regimen provides for administration of at least 10 mg and no more that 1,000 mg of active material (e.g., a compound of formula I) daily, and it is understood that the amount may be provided in any suitable dosage form and amount (e.g., 500 mg twice daily or 1,000 mg once daily would provide the same amount of 1,000 mg/day dosing). The present disclosure embraces once daily dosing to an individual (e.g., a human in need thereof) of a dosage form of compound (e.g., a compound of formula I) containing at least 50 mg and not more than 300 mg of compound. In certain embodiments, the carrier material varies from about 5 to about 95% of the total compositions (weight:weight).

It should be understood that in addition to the ingredients particularly mentioned above the formulations of the present disclosure may include other agents conventional in the art having regard to the type of formulation in question, for example those suitable for oral administration may include flavoring agents.

The present disclosure further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds disclosed herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds disclosed herein is that they are orally bioavailable and can be dosed orally.

Dosing Regimen

The compound, such as a compound of Formulas I, may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of Formulas I may be adjusted over the course of the treatment, e.g., based on the judgment of the administering physician.

The compound may be administered to an individual (e.g., a human) in an effective amount. In one aspect, the compound is administered once daily. In one aspect, the compound is administered twice a day. In one aspect, the compound is administered three times daily. It is understood that the compound may be administered in any dosage amount provided herein, such as a dosage amount that would provide at least 10 mg/day dosing and no more than 1,000 mg/day dosing. Once daily oral dosing is embraced, such as by administering a dosage form containing from 50 mg to 300 mg of compound.

The antiviral properties of a compound as disclosed herein may be determined using Test A described below.

Test A: Antiviral Assay in MT4 Cells

For the antiviral assay, 40 µL of a concentration required to achieve a final effective 1× test concentration of 3-fold serially diluted compound in culture medium with 10% FBS was added to each well of a 384-well plate (10 concentrations) in quadruplicate. MT-4 cells were next mixed with HIV-IIIb at an m.o.i of 0.003 for 1 hour, after which time 35 µL of virus/cell mixture (2000 cells) was immediately added to each well containing 40 µL of diluted compound. The plates were then incubated at 37° C. for 5 days. After 5 days of incubation, 25 µl of 2× concentrated CellTiter-Glo™ Reagent (catalog #G7571, Promega Biosciences, Inc., Madison, Wis.) was added to each well containing MT-4 cells. Cell lysis was carried out by incubating at room temperature for 10 min and then chemiluminescence was read. EC50 values were calculated as the compound concentration that caused a 50% decrease in luminescence signal, a measure of HIV-1 replication. Percent inhibition of virus-induced cell killing calculated from the dose response curve at 0.2 µM drug concentration is shown in the table below.

Test B: Cytotoxicity Assay

Compound cytotoxicity and the corresponding CC50 values was determined using the same protocol as described in the antiviral assay (Test A) except that uninfected cells were used.

Compounds of the present invention demonstrate antiviral activity (Test A) as depicted in the table below. Shown below are the corresponding values for CC50 and percent inhibition of virus-induced cell killing in the presence of 0.2 µM drug concentration.

| Compound | % inhibition at 0.2 µM | $CC_{50}$ (nM) |
| --- | --- | --- |
| 1J | 81 | >53192 |
| 2G | 0 | 38400 |
| 3D | 91 | 31644 |
| 4C | 0 | 1267 |
| 5 | 5 | >53192 |
| 6 | 0 | 1656 |
| 7H | 94 | 534 |
| 8 | 102 | >53192 |
| 9 | 25 | >53192 |
| 10C | 21 | >51889 |
| 11 | 69 | 761 |
| 12 | 70 | 7703 |
| 13C | 87 | >53192 |
| 14 | 1 | >53192 |
| 15B | 68 | 3016 |
| 16 | 76 | 3003 |
| 17 | 66 | 3057 |
| 18C | 90 | 2310 |
| 19 | 83 | 4627 |
| 20E | 94 | 27704 |
| 21 | 100 | 11723 |
| 22C | 93 | 17690 |
| 23C | 100 | 9191 |
| 24D | 100 | 15847 |
| 25 | 91 | 9920 |
| 26 | 94 | 15933 |
| 27 | 92 | 15848 |
| 28B | 92 | 6065 |
| 29 | 100 | 12379 |
| 30B | 100 | 19487 |
| 31 | 93 | 20174 |
| 32 | 95 | 8533 |
| 33 | 93 | 12542 |
| 34 | 87 | 10179 |
| 35 | 86 | 10105 |
| 36B | 83 | 6572 |
| 37 | 80 | 8715 |
| 38 | 97 | 14276 |
| 39 | 95 | 10748 |
| 40 | 96 | 17047 |
| 41 | 98 | 2076 |
| 42 | 90 | 2768 |
| 43H | 99 | 4344 |
| 44 | 100 | 5644 |
| 45B | 93 | 7349 |
| 46 | 96 | 17554 |
| 47 | 94 | 7968 |
| 48C | 92 | 7273 |
| 49 | 92 | 20599 |
| 50B | 92 | 10047 |
| 51B | 89 | 19789 |
| 52 | 96 | 17131 |
| 53B | 100 | 6807 |
| 54 | 100 | 11559 |
| 55 | 88 | 9938 |
| 56B | 84 | 9017 |
| 57 | 100 | 20956 |
| 58 | 91 | 5192 |
| 59 | 95 | 10180 |
| 60D | 94 | >27757 |
| 61C | 93 | 7887 |
| 62B | 93 | 14937 |
| 63 | 90 | 20655 |
| 64 | 98 | 16069 |
| 65 | 37 | 19307 |
| 66 | 92 | 11633 |
| 67 | 87 | >53192 |
| 68 | 100 | 7509 |
| 69 | 96 | 13605 |
| 70B | 96 | 14185 |
| 71 | 97 | >53192 |
| 72 | 93 | 50313 |
| 73 | 100 | 6001 |
| 74 | 77 | 8621 |
| 75 | 81 | 5593 |
| 76 | 93 | 6674 |
| 77 | 90 | 7702 |
| 78 | 87 | >36630 |
| 79B | 93 | 11505 |

-continued

| Compound | % inhibition at 0.2 µM | CC$_{50}$ (nM) |
|---|---|---|
| 80 | 89 | 20855 |
| 81E | 87 | >57039 |
| 82 | 90 | 29592 |
| 83G | 90 | 6574 |
| 84 | 88 | 6900 |
| 85 | 100 | 28557 |
| 86 | 93 | 21384 |
| 87 | 100 | 19465 |
| 88L | 97 | 5788 |
| 89B | 87 | 8312 |
| 90 | 98 | 3036 |
| 91F | 98 | 14580 |
| 92B | 100 | 25872 |
| 93D | 93 | 18297 |
| 94B | 91 | 12354 |
| 95E | 96 | 8749 |
| 96 | 82 | 20141 |
| 97C | 89 | 15168 |
| 98D | 94 | 10362 |
| 99C | | |
| 100 | 87 | 8197 |
| 101H | 91 | 9095 |
| 102 | 88 | 7173 |
| 103 | 100 | 9214 |
| 104 | 100 | 8415 |
| 105D | 88 | 6458 |
| 106C | 100 | 2855 |
| 107 | 99 | 3642 |
| 108F | | |
| 109E | 100 | 22334 |

The data above represent an average over time of each assay for each compound. For certain compounds, multiple assays have been conducted. In the above table, percent inhibition values have been normalized to 100% where the calculation of percent inhibition would have resulted in a value greater than 100.

In one embodiment, the compounds demonstrate >10% inhibition at 2 µM. In one embodiment, the compounds demonstrate >30% inhibition at 2 µM. In one embodiment, the compounds demonstrate >50% inhibition at 2 µM. In one embodiment, the compounds demonstrate >70% inhibition at 2 µM. In one embodiment, the compounds demonstrate >75% inhibition at 2 µM. In one embodiment, the compounds demonstrate >80% inhibition at 2 µM. In one embodiment, the compounds demonstrate >85% inhibition at 2 µM. In one embodiment, the compounds demonstrate >90% inhibition at 2 µM. In one embodiment, the compounds demonstrate >95% inhibition at 2 µM. It is to be understood that the compounds disclosed herein can be grouped according to their % inhibition as described above.

In one embodiment, the compounds demonstrate >10% inhibition at 0.2 µM. In one embodiment, the compounds demonstrate >30% inhibition at 0.2 µM. In one embodiment, the compounds demonstrate >50% inhibition at 0.2 µM. In one embodiment, the compounds demonstrate >70% inhibition at 0.2 µM. In one embodiment, the compounds demonstrate >75% inhibition at 0.2 µM. In one embodiment, the compounds demonstrate >80% inhibition at 0.2 µM. In one embodiment, the compounds demonstrate >85% inhibition at 0.2 µM. In one embodiment, the compounds demonstrate >90% inhibition at 0.2 µM. In one embodiment, the compounds demonstrate >95% inhibition at 0.2 µM. It is to be understood that the compounds disclosed herein can be grouped according to their % inhibition as described above.

In one variation, a compound is of any formulae provided herein, wherein the compound exhibits from 85%-100% inhibition of virus-induced cell killing at 2 µM. In one variation, a compound is of any formulae provided herein, wherein the compound exhibits from 85%-100% inhibition of virus-induced cell killing at 0.2 µM. In other embodiments, a compound is of any formulae provided herein wherein the compound exhibits from 50-100, 60-100, 70-100, 80-100, or 90-100% inhibition of virus-induced cell killing at 2 µM or at 0.2 µM.

It is understood that % inhibition may be evaluated by techniques known in the art. In a particular variation, a compound is of any formulae provided herein wherein the compound exhibits from 85%-110% inhibition of virus-induced cell killing at 2 µM or at 0.2 µM as measured by the method provided in the Test A and Test B sections discussed above.

Percent inhibition was also calculated for certain compounds as compared to previously published compounds (WO 2013/006738, cmpds X2 and 53) and is shown below. Additional inhibition data from certain compounds of PCT Application No. US2014/019663 (cmpd 18 below). Structures are depicted for compounds not disclosed in the present application. The percent inhibition of virus-induced cell killing at 2 µM and 0.2 µM was measured by the method provided in the Test A and Test B sections discussed above.

| Compound | Response at 2 µM | Response at 0.2 µM |
|---|---|---|
| 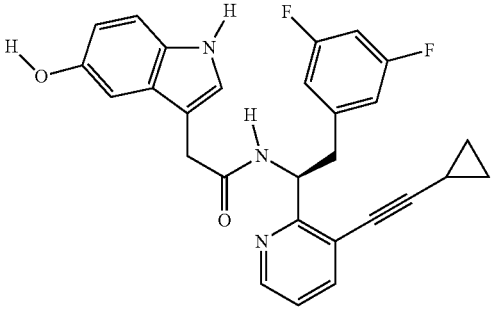 [SMILES: O=C(Cc1c[nH]c2ccc(O)cc12)N[C@@H](Cc1cc(F)cc(F)c1)c1ncccc1C#CC1CC1] 53 | 33 | 0 |
| 2G | 6 | 0 |
| 96 | 82 | 82 |

| Compound | Response at 2 μM | Response at 0.2 μM |
|---|---|---|
| 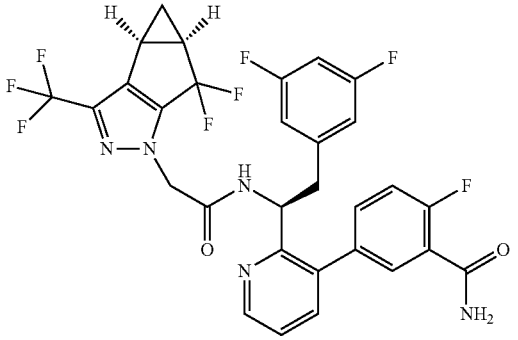 X2 | 91 | 65 |
| 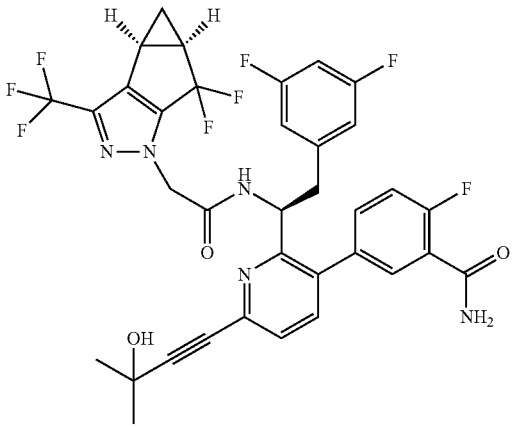 18 | 96 | 96 |
| 15B | 68 | 68 |
| 16 | 77 | 76 |
| 17 | 73 | 66 |
| 18C | 94 | 90 |
| 19 | 88 | 83 |
| 35 | 86 | 86 |
| 107 | 99 | 99 |

The specific pharmacological responses observed may vary according to and depending on the particular active compound selected and whether there are present pharmaceutical carriers and/or pharmaceutically active compounds, as well as the type of formulation and mode of administration employed, and such expected variations or differences in the results are contemplated in accordance with practice of the present disclosure.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

Example 1

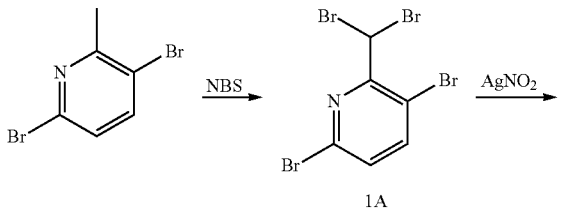

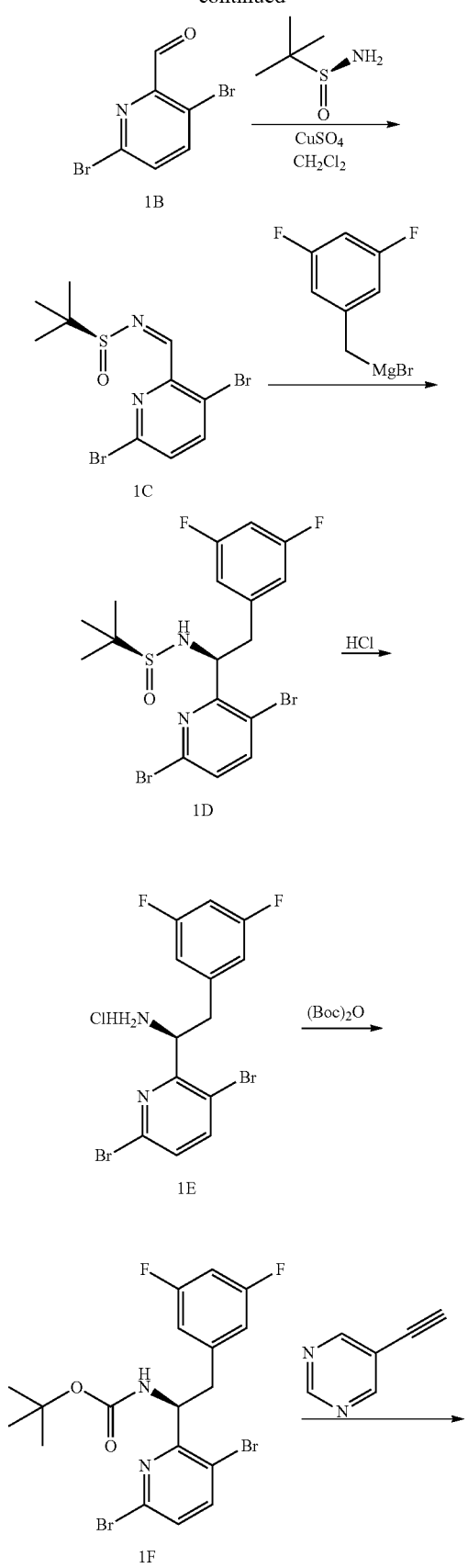
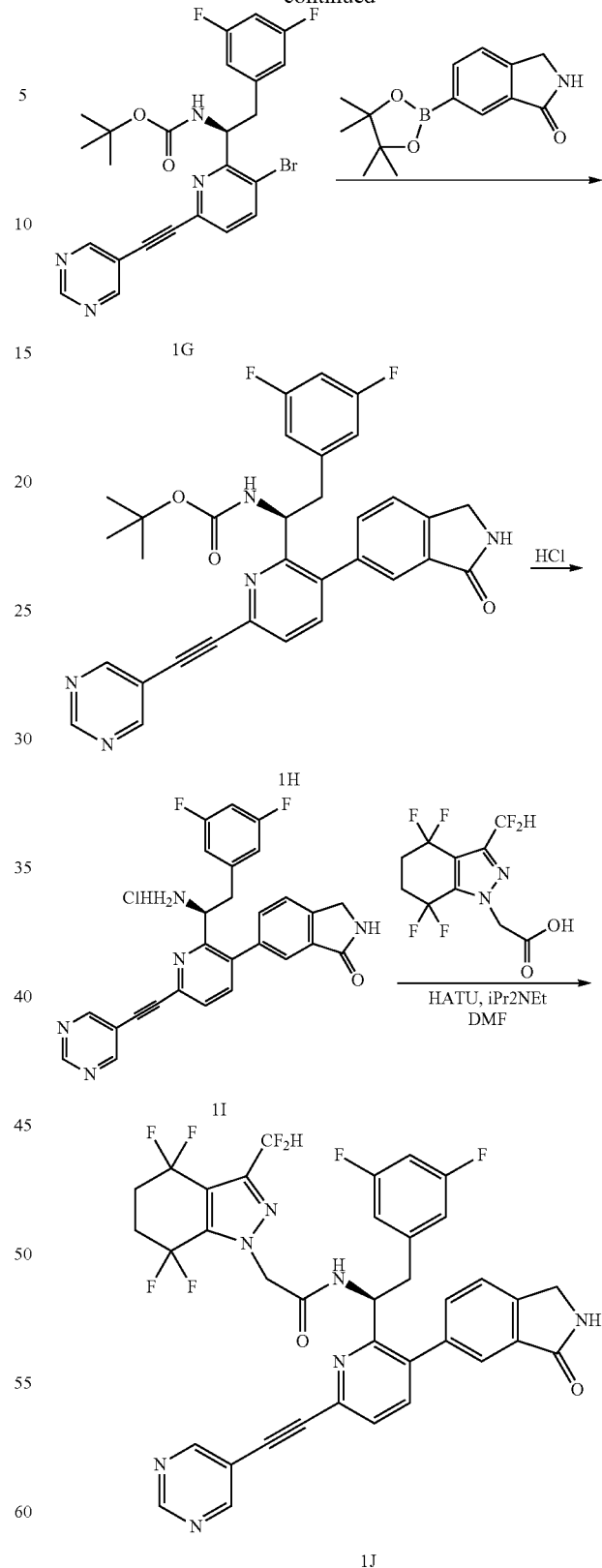
Synthesis of 3,6-dibromo-2-(dibromomethyl)pyridine (1A): To a solution of 3,6-dibromo-2-methylpyridine (5.2 g, 21 mmol) in CCl$_4$ (50 mL) was added N-bromosuccinimide (7.57 g, 42 mmol) and 2,2'-azobis(2-methylpropionitrile) (0.70 g, 4.3 mmol). The mixture was heated at 80° C. overnight and cooled to room temperature. The solid was removed by filtration and the filtrate was concentrated under reduced pressure. The product (1A) was obtained after flash chromatography. MS (m/z): 409.66 [M+H]$^+$ Synthesis of 3,6-dibromopicolinaldehyde (1B): A solution of silver nitrate (7.6 g, 45 mmol) in water (24 mL) was added dropwise to a solution of 1A (7.36 g, 18 mmol) in refluxing EtOH (90 mL). The reaction mixture was stirred at 80° C. for 5 hours then cooled to room temperature. To it was added water (100 mL) then extracted with EtOAc (3 times). The organic layer was separated, dried over Na$_2$SO$_4$, filtered and concentrated under reduced pressure to afford the title product 1B. MS (m/z): 265.96. [M+H]$^+$ Synthesis of (S,Z)—N-((3,6-dibromopyridin-2-yl)methylene)-2-methylpropane-2-sulfinamide (1C): The title compound (1C) was prepared according to the method presented for the synthesis of compound 7C of Example 7 utilizing compound 1B. MS (m/z) 368.86 [M+H]$^+$ Synthesis of (S)—N—((S)-1-(3,6-dibromopyridin-2-yl)-2-(3,5-difluorophenyl)ethyl)-2-methylpropane-2-sulfinamide (1D): The title compound (1D) was prepared according to the method presented for the synthesis of compound 7D of Example 7 utilizing 1C. MS (m/z) 496.99 [M+H]$^+$ Synthesis of (S)-1-(3,6-dibromopyridin-2-yl)-2-(3,5-difluorophenyl)ethanamine hydrochloride (1E): The title compound (1E) was prepared according to the method presented for the synthesis of compound 7E of Example 7 utilizing 1D. MS (m/z) 393.29 [M+H]$^+$ Synthesis of (S)-tert-butyl(1-(3,6-dibromopyridin-2-yl)-2-(3,5-difluorophenyl)ethyl)carbamate (1F): (S)-1-(3,6-dibromopyridin-2-yl)-2-(3,5-difluorophenyl)ethanamine hydrochloride (1E, 236 mg, 0.55 mmol) was combined with di-tert-butyl dicarbonate (120 mg, 0.55 mmol) and TEA (153 µL, 1.1 mmol) in DCM (2 mL). The reaction was stirred for 2 hr at ambient temperature. The reaction was partitioned between EtOAc and H$_2$O. The organics were separated, dried, and removed in vacuo. The residue purified by column chromatography on silica to provide the title compound. MS (m/z) 492.81 [M+H]$^+$.

Synthesis of (S)-tert-butyl(1-(3-bromo-6-(pyrimidin-5-ylethynyl)pyridin-2-yl)-2-(3,5-difluorophenyl)ethyl)carbamate (1G): (S)-tert-butyl(1-(3,6-dibromopyridin-2-yl)-2-(3,5-difluorophenyl)ethyl)carbamate (1G, 50 mg, 0.1 mmol) and 5-ethynylpyrimidine (11.5 mg, 0.11 mmol) in THF (0.2 mL) was degassed and purged with argon. To it was added TEA (0.05 mL), Pd(PPh$_3$)$_2$Cl$_2$ (7 mg, 0.01 mmol) and CuI (2 mg, 0.01 mmol). The reaction was stirred for 2 hr at 40° C. and then cooled to ambient temperature. The reaction mixture was partitioned between EtOAc and H$_2$O (plus 0.1 mL of ammonia). The organics were separated, dried, and removed in vacuo. The residue purified by column chromatography on silica to provide the title compound. MS (m/z) 516.66 [M+H]$^+$.

Synthesis of (S)-tert-butyl(2-(3,5-difluorophenyl)-1-(3-(3-oxoisoindolin-5-yl)-6-(pyrimidin-5-ylethynyl)pyridin-2-yl)ethyl)carbamate (1H): To a mixture of (S)-tert-butyl(1-(3-bromo-6-(pyrimidin-5-ylethynyl)pyridin-2-yl)-2-(3,5-difluorophenyl)ethyl)carbamate (26 mg, 0.05 mmol), 6-(4,4,5,5-tetramethyl-1,3,2-dioxaborolan-2-yl)isoindolin-1-one (20 mg, 0.075 mmol), LiCl (6 mg), and Na$_2$CO$_3$ (8.4 mg, 0.1 mmol) was added DME/DMF/H$_2$O (4/1/1, 2 mL) and Pd(PPh$_3$)$_2$Cl$_2$ (5 mg). The reaction was heated in a microwave reactor to 150° C. for 20 min then purified by RP HPLC to provide the desired product. MS (m/z) 567.89 [M+H]$^+$.

Synthesis of (S)-6-(2-(1-amino-2-(3,5-difluorophenyl)ethyl)-6-(pyrimidin-5-ylethynyl)pyridin-3-yl)isoindolin-1-one hydrochloride (1I): To (S)-tert-butyl(2-(3,5-difluorophenyl)-1-(3-(3-oxoisoindolin-5-yl)-6-(pyrimidin-5-ylethynyl)pyridin-2-yl)ethyl)carbamate (1H, 5 mg, 0.009 mmol) was added 1 mL of 4N HCl in dioxane. The reaction mixture was stirred at ambient temperature for 15 min then removed the solvent to afford the title product. MS (m/z) 468.10 [M+H]$^+$.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(3-(3-oxoisoindolin-5-yl)-6-(pyrimidin-5-ylethynyl)pyridin-2-yl)ethyl)acetamidehydrochloride (1J): To a mixture of 2-(3-(difluoromethyl)-4,4,7,7-tetrafluoro-4,5,6,7-tetrahydro-1H-indazol-1-yl)acetic acid (3 mg, 0.009 mmol), Compound 1I (0.009 mmol) and HATU (4 mg, 0.011 mmol) in 0.5 mL of DMF was added N,N-diisopropylethylamine (4.7 µL, 0.027 mmol). The reaction mixture was allowed to stir at ambient temperature for 5 minutes then purified by RP HPLC to provide the title product. $^1$H NMR (400 MHz, Methanol-d$_4$) δ 9.18 (s), 9.03 (s), 8.84 (d), 7.73-7.57 (m), 7.49 (d), 7.34 (s), 6.99-6.55 (m), 6.30 (d), 5.45 (t), 5.07 (s), 4.49 (s), 3.16-2.93 (m), 2.63-2.40 (m). MS (m/z): 752.01 [M+H]$^+$.

Example 2

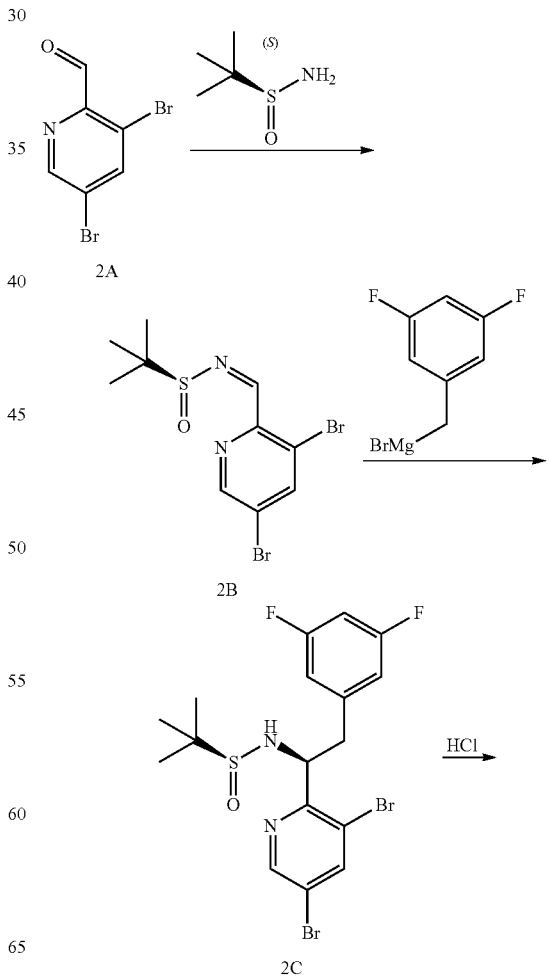

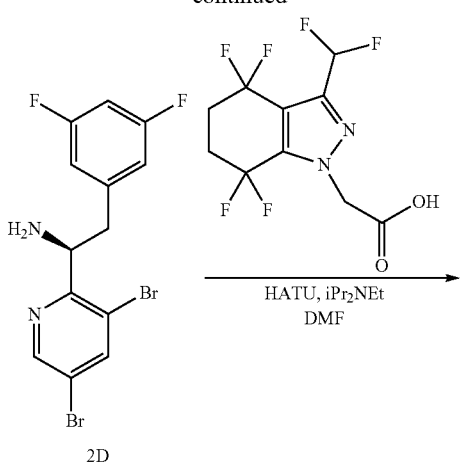

2D

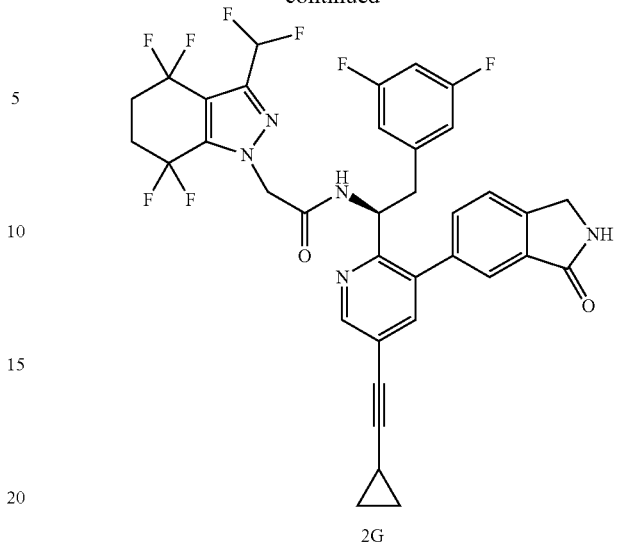

2G

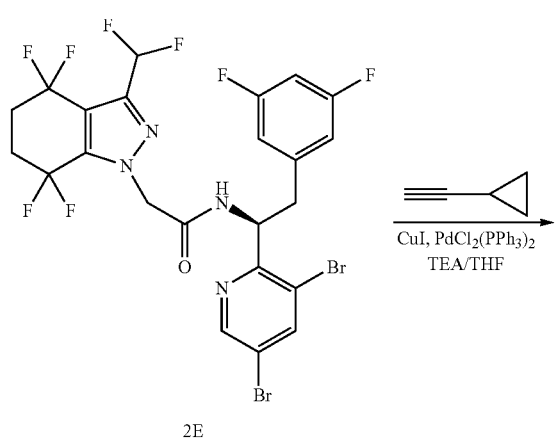

2E

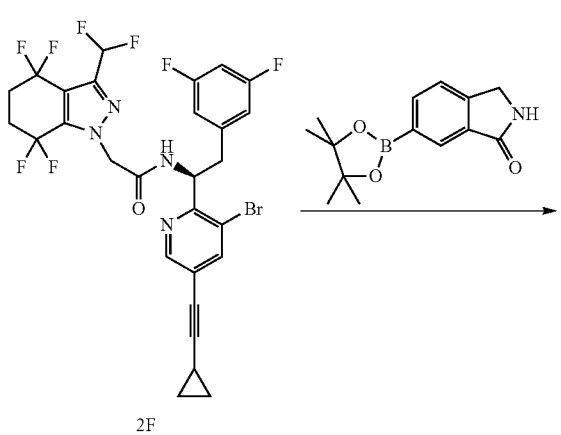

2F

Synthesis of (S)—N-((3,5-dibromopyridin-2-yl)methylene)-2-methylpropane-2-sulfinamide (2B): To 3,5-dibromopicolinaldehyde (1.9 g, 7.17 mmol) in DCM (30 mL) was added (S)-2-methylpropane-2-sulfinamide (870 mg, 7.17 mmol) and CuSO$_4$ (2.29 g, 14.3 mmol). The reaction mixture was stirred for 15 h. Solids were filtered over celite. The solvents were removed in vacuo and the residue purified by column chromatography on silica to provide 2.6 g of the title compound. MS (m/z) 368.9 [M+H]$^+$.

Synthesis of (S)—N—((S)-1-(3,5-dibromopyridin-2-yl)-2-(3,5-difluorophenyl)ethyl)-2-methylpropane-2-sulfinamide (2C): (S)—N-((3,5-dibromopyridin-2-yl)methylene)-2-methylpropane-2-sulfinamide (2.6 g, 7.1 mmol) was dissolved in THF (24 mL) and cooled to −78° C. (3,5-difluorobenzyl)magnesium bromide (34 mL, 0.25 M in Et$_2$O) was added dropwise. The reaction was stirred at −78° C. for 3 hr then let warm to 0° C. and quenched. The reaction was partitioned between EtOAc and aq. NH$_4$Cl. The organics were separated, dried, and removed in vacuo. The residue purified by column chromatography on silica to provide the title compound. MS (m/z) 496.6 [M+H]$^+$.

Synthesis of (S)-1-(3,5-dibromopyridin-2-yl)-2-(3,5-difluorophenyl)ethanamine (2D): To (S)—N—((S)-1-(3,5-dibromopyridin-2-yl)-2-(3,5-difluorophenyl)ethyl)-2-methylpropane-2-sulfinamide (650 mg) dissolved in DCM (3 mL) was added 4N HCl in dioxanes (4 mL). The reaction was stirred for 2 hr at ambient temperature. Solvents were removed in vacuo and the crude desired product was used without further purification. MS (m/z) 393.0 [M+H]$^+$.

Synthesis of (S)-tert-butyl 1-(3,5-dibromopyridin-2-yl)-2-(3,5-difluorophenyl)ethylcarbamate (2E): (S)-1-(3,5-Dibromopyridin-2-yl)-2-(3,5-difluorophenyl)ethanamine (780 mg, 1.84 mmol) was combined with di-tert-butyl dicarbonate (400 mg, 1.84 mmol) and TEA (515 μL, 3.7 mmol) in DCM (9 mL). The reaction was stirred for 2 hr at ambient temperature. The reaction was partitioned between EtOAc and H$_2$O. The organics were separated, dried, and removed in vacuo. The residue purified by column chromatography on silica to provide the title compound. MS (m/z) 492.9 [M+H]$^+$.

Synthesis of (S)—N-(1-(3-bromo-5-(cyclopropylethynyl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (2F): The title compound (2F) was prepared according to the method presented for the synthesis of compound 1G of Example 1 utilizing 2E and ethynylcyclopropane. MS (m/z) 662.6 [M+H]⁺.

Synthesis of (S)—N-(1-(5-(cyclopropylethynyl)-3-(3-oxoisoindolin-5-yl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (2G): The title compound (2G) was prepared according to the method presented for the synthesis of compound 1H of Example 1 utilizing 2F. MS (m/z) 714.1 [M+H]⁺.

Example 3

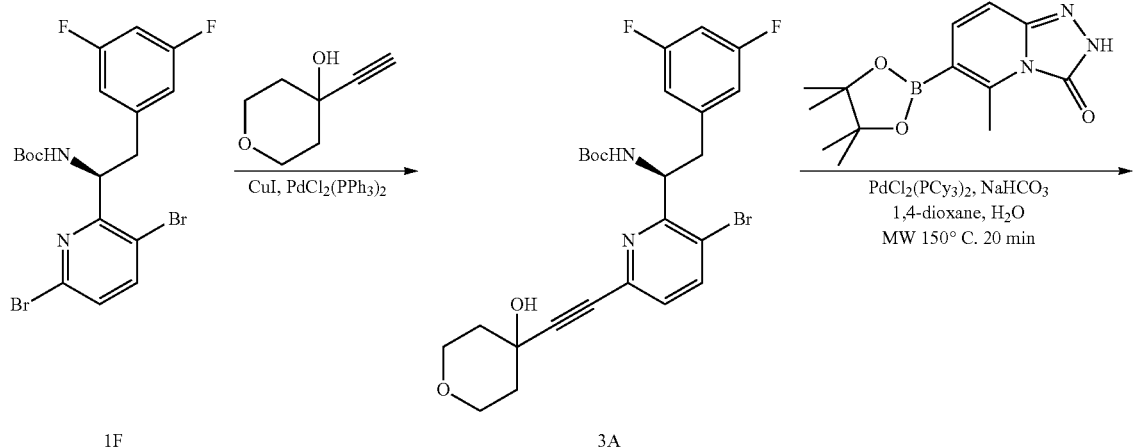

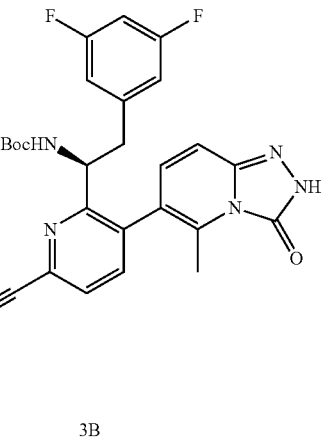

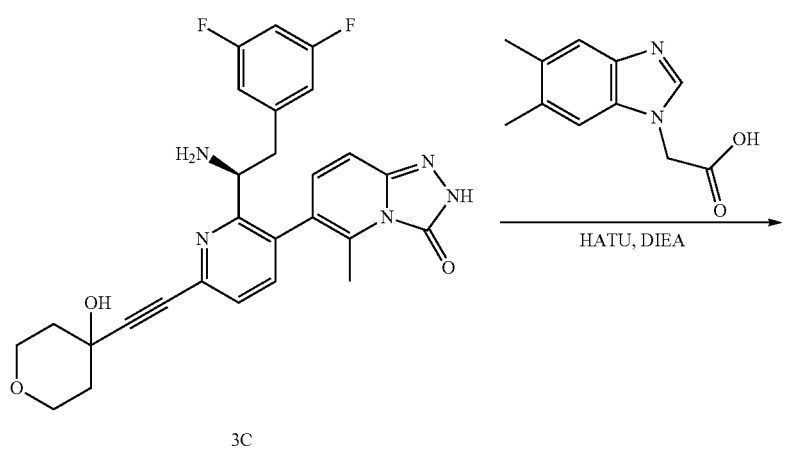

-continued

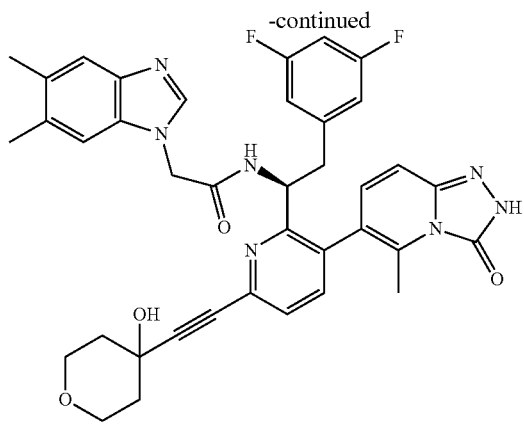

3D (S)-tert-butyl(1-(3-bromo-6-((4-hydroxytetrahydro-2H-pyran-4-yl)ethynyl)pyridin-2-yl)-2-(3,5-difluorophenyl)ethyl)carbamate (3A): Compound 1F (300 mg, 0.61 mmol) was dissolved in Methyl-THF (degassed by bubbling $N_2$ for 10 minutes), TEA (0.25 ml, 1.83 mmol) and 4-ethynyltetrahydro-2H-pyran-4-ol (115 mg, 0.91 mmol) were added, followed by CuI (6 mg, 0.03 mmol) and $PdCl_2(PPh_3)_2$ (21 mg, 0.03 mmol). The reaction was stirred for 1 hour and then partitioned between EtOAc and water. The organics were separated, dried with $MgSO_4$ and concentrated. The resultant crude was purified by column chromatography on silica (20-80% EtOAc/hexane) to afford compound 3A. MS (m/z) 537 [M+H]$^+$.

(S)-tert-butyl(2-(3,5-difluorophenyl)-1-(6-((4-hydroxytetrahydro-2H-pyran-4-yl)ethynyl)-3-(5-methyl-3-oxo-2,3-dihydro-[1,2,4]triazolo[4,3-a]pyridin-6-yl)pyridin-2-yl)ethyl)carbamate (3B): Compound 3A (41 mg, 0.076 mmol), 5-methyl-6-(4,4,5,5-tetramethyl-1,3,2-dioxaborolan-2-yl)-[1,2,4]triazolo[4,3-a]pyridin-3(2H)-one (31 mg, 0.11 mmol), $PdCl_2(PCy_3)_2$ (6 mg, 0.008 mmol), $NaHCO_3$ (19 mg, 0.23 mmol), 1,4-dioxane (1.5 ml) and water (0.3 ml) were added to a microwave tube. $N_2$ was bubbled into the reaction mixture for 2 minutes, and then heated in a microwave reactor at 150° C. for 20 minutes. The reaction was partitioned between EtOAc and water. The organics were separated, dried with $MgSO_4$, and concentrated. The resultant crude was purified by column chromatography on silica (10-80% EtOAc/hexane) to afford compound 3B. MS (m/z) 606 [M+H]$^+$.

Synthesis of (S)-6-(2-(1-amino-2-(3,5-difluorophenyl)ethyl)-6-((4-hydroxytetrahydro-2H-pyran-4-yl)ethynyl)pyridin-3-yl)-5-methyl-[1,2,4]triazolo[4,3-a]pyridin-3(2H)-one (3C);

Compound 3B (33 mg, 0.054 mmol) was dissolved in dichloromethane (1 ml). TFA (0.5 ml) was added. The reaction was stirred for 45 minutes and then concentrated to afford compound 3C. MS (m/z) 506 [M+H]$^+$.

Synthesis of (S)—N-(2-(3,5-difluorophenyl)-1-(6-((4-hydroxytetrahydro-2H-pyran-4-yl)ethynyl)-3-(5-methyl-3-oxo-2,3-dihydro-[1,2,4]triazolo[4,3-a]pyridin-6-yl)pyridin-2-yl)ethyl)-2-(5,6-dimethyl-1H-benzo[d]imidazol-1-yl)acetamide (3D): Compound 3D was prepared as a mixture of atropisomers according to the method presented for the synthesis of compound 108F of Example 108 utilizing compound 3C and 2-(5,6-dimethyl-1H-benzo[d]imidazol-1-yl)acetic acid. 1H NMR (400 MHz, DMSO-d6) δ 12.40-12.30 (m), 9.24 (dd), 9.06 (s), 7.70-7.51 (m), 7.18 (s), 7.07-6.90 (m), 6.85 (s), 6.76-6.63 (m), 5.89-5.84 (m), 5.74 (s), 5.15-4.94 (m), 4.01 (q), 3.87-3.77 (m), 3.67-3.57 (m), 3.37 (q), 3.15 (s), 3.06 (t), 2.37-2.09 (m), 2.00-1.91 (m), 1.83-1.72 (m), 1.24-1.03 (m), 0.87-0.79 (m). MS (m/z) 692 [M+H]$^+$.

Example 4

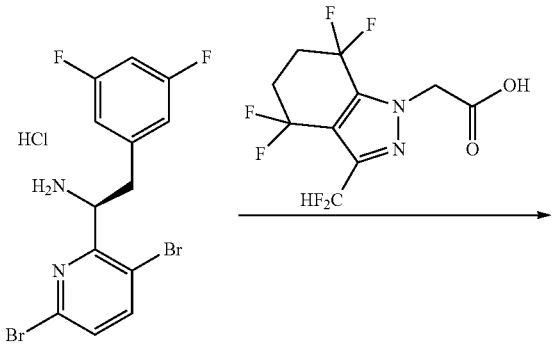

1E

-continued

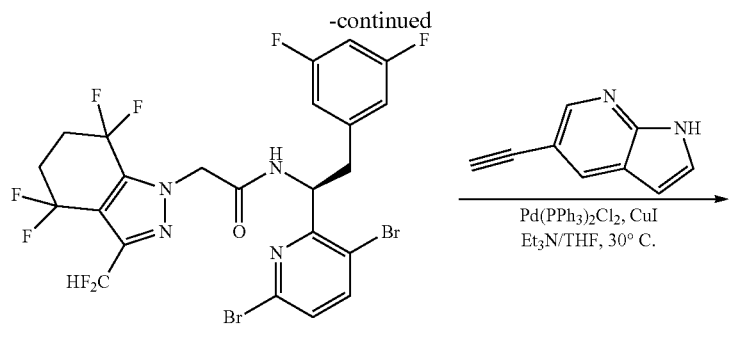

4A

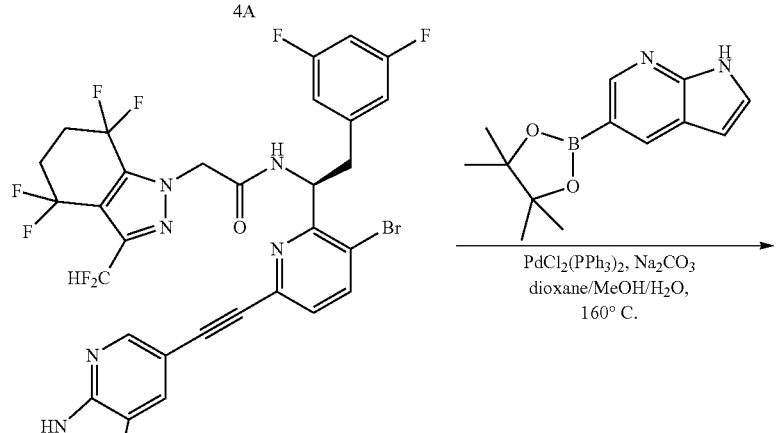

4B

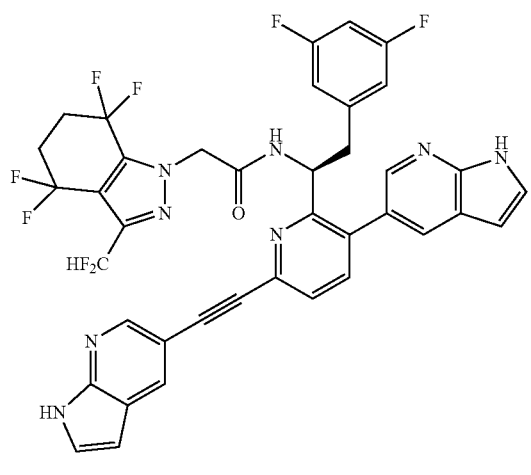

4C

Synthesis of (S)—N-(1-(3,6-dibromopyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (4A): The title compound (4A) was prepared according to the method presented for the synthesis of compound 1J of Example 1 utilizing 1E.

Synthesis of (S)—N-(1-(6-((1H-pyrrolo[2,3-b]pyridin-5-yl)ethynyl)-3-bromopyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (4B): To (S)—N-(1-(3,6-dibromopyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (67 mg, 0.1 mmol) in THF (2 mL) was added triethylamine (0.6 mL), alkyne (16 mg, 0.11 mmol), CuI (0.95 mg, 0.005 mmol), and trans-dichlorobis(triphenylphosphine)palladium (II) (3.51 mg, 0.005 mmol). The reaction mixture was degassed with argon and stirred at 30° C. overnight. The reaction was cooled, diluted with EtOAc, and then the solids were filtered off over Celite and silica gel eluting with EtOAc. The mixture was concentrated and the resulting crude material was used in the next step without further purification. MS (m/z) 737.54 [M+H]$^+$.

Synthesis of (S)—N-(1-(6-((1H-pyrrolo[2,3-b]pyridin-5-yl)ethynyl)-3-(1H-pyrrolo[2,3-b]pyridin-5-yl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (4C): The title compound (4C) was prepared according to the method presented for the synthesis of compound 1H of Example 1 utilizing 4B and 5-(4,4,5,5-tetramethyl-1,3,2-dioxaborolan-2-yl)-1H-pyrrolo[2,3-b]pyridine. ¹H NMR (400 MHz, Methanol-d₄) δ 8.92 (d, 1H), 8.59-8.10 (m, 2H), 7.95-7.58 (m, 4H), 7.58-7.31 (m, 4H), 7.05-6.49 (m, 4H), 6.32 (d, 3H), 5.42 (s, 1H), 5.19-5.04 (m, 2H), 2.51 (d, 4H). MS (m/z) 775.21 [M+H]⁺.

Example 5

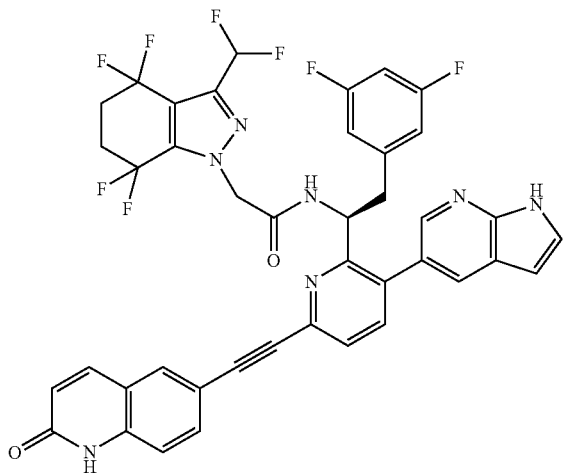

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(6-((2-oxo-1,2-dihydroquinolin-6-yl)ethynyl)-3-(1H-pyrrolo[2,3-b]pyridin-5-yl)pyridin-2-yl)ethyl)acetamide (5): The title compound (5) was prepared according to the method presented for the synthesis of compound 4C of Example 4 utilizing 6-((trimethylsilyl)ethynyl)quinolin-2(1H)-one. MS (m/z) 802.10 [M+H]⁺.

Example 6

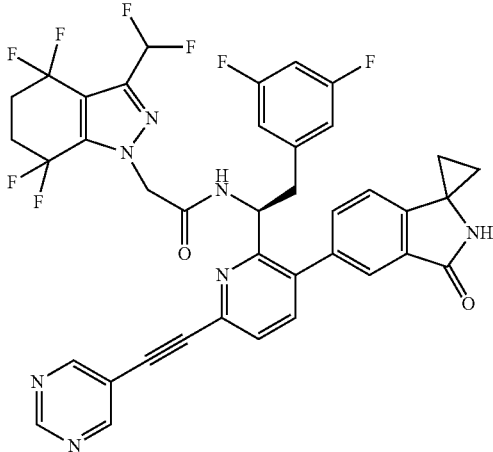

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(3-(3'-oxospiro[cyclopropane-1,1'-isoindolin]-5'-yl)-6-(pyrimidin-5-ylethynyl)pyridin-2-yl)ethyl)acetamide (6): The title compound (6) was prepared according to the method presented for the synthesis of compound 4C of Example 4 utilizing 5-ethynylpyrimidine and 5'-(4,4,5,5-tetramethyl-1,3,2-dioxaborolan-2-yl)spiro[cyclopropane-1,1'-isoindolin]-3'-one. ¹H NMR (400 MHz, Methanol-d₄) δ 9.18 (s, 1H), 9.03 (s, 2H), 7.82-7.61 (m, 2H), 7.45 (d, 1H), 7.40-7.19 (m, 2H), 7.02-6.56 (m, 2H), 6.29 (d, 3H), 5.46 (d, 1H), 5.08 (s, 2H), 3.15-2.98 (m, 2H), 2.71-2.41 (m, 4H), 1.68-1.44 (m, 4H). MS (m/z) 778.67 [M+H]⁺.

Example 7

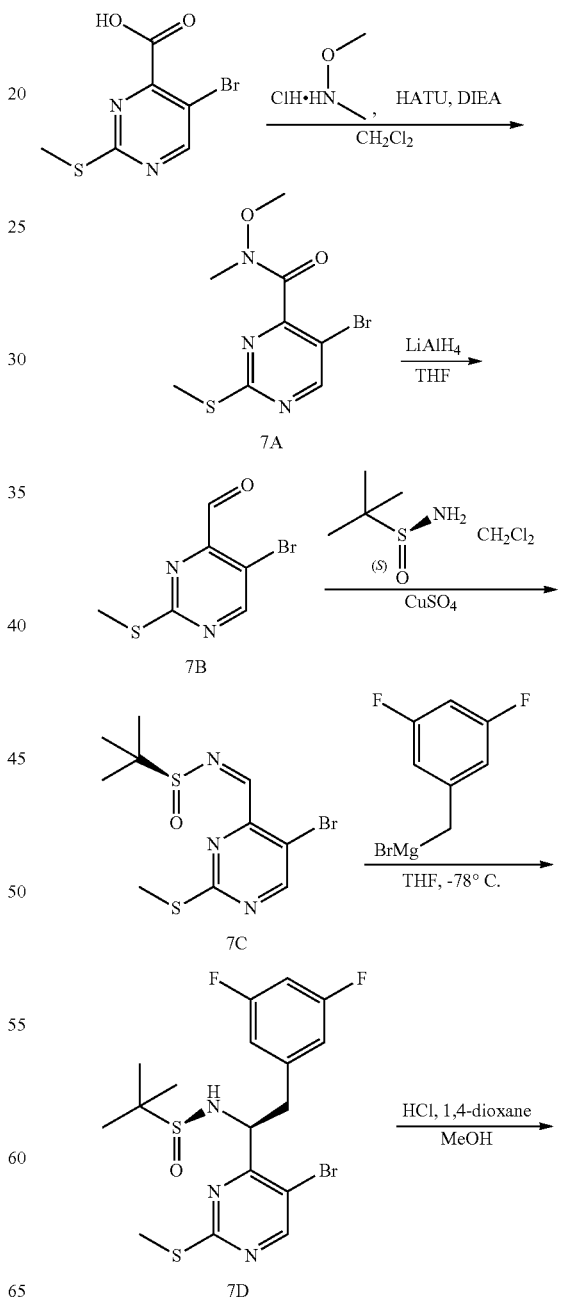

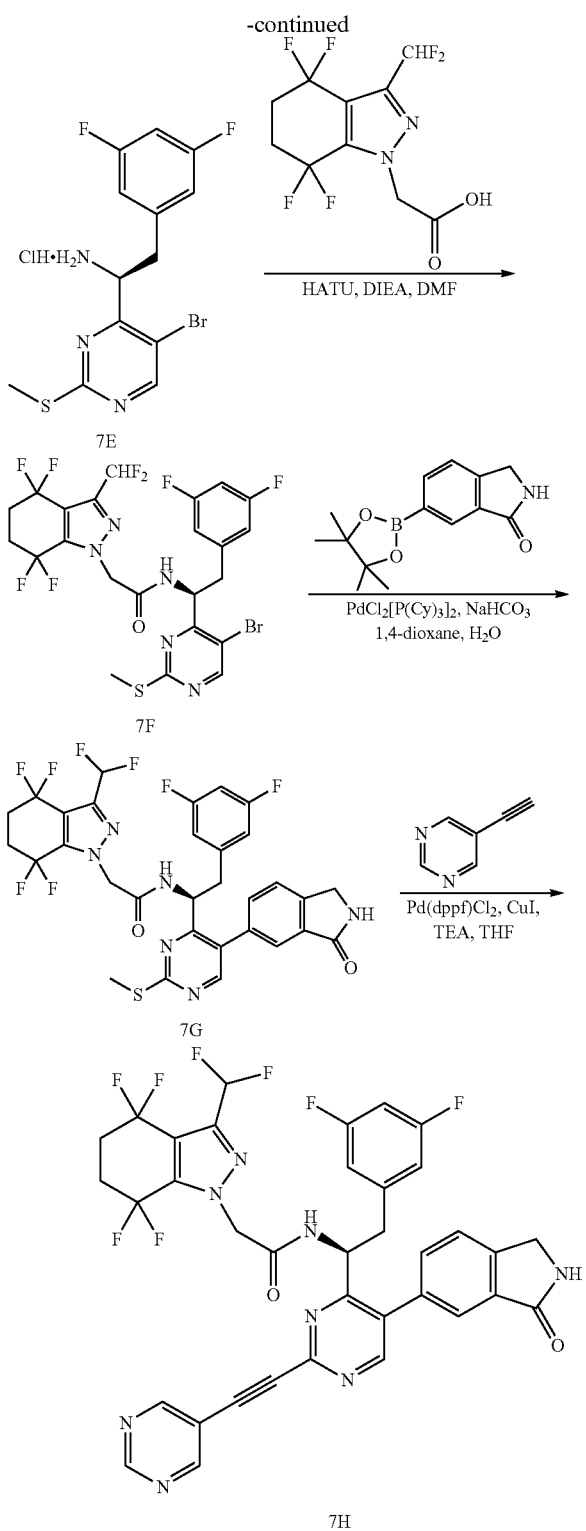

Synthesis of 5-bromo-N-methoxy-N-methyl-2-(methylthio)pyrimidine-4-carboxamide (7A): To a mixture of 5-bromo-2-(methylthio)pyrimidine-4-carboxylic acid (5 g, 20 mmol), N,O-dimethylhydroxylamine hydrochloride (2.9 g, 30 mmol) and HATU (9.1 g, 24 mmol) in 100 mL of CH$_2$Cl$_2$ at 0° C. was added N,N-diisopropylethylamine (17.4 mL, 100 mmol). The reaction mixture was allowed to stir at 0° C. for 30 min and then diluted with CH$_2$Cl$_2$. It was washed with water and half brine. The organic layer was separated, dried over MgSO$_4$, filtered and concentrated. The crude product was purified by silica gel chromatography to afford the title compound 7A. MS (m/z) 292.16 [M+H]$^+$.

Synthesis of 5-bromo-2-(methylthio)pyrimidine-4-carbaldehyde (7B): A solution of 5-bromo-N-methoxy-N-methyl-2-(methylthio)pyrimidine-4-carboxamide (7A, 8.2 g, 28 mmol) in THF (120 mL) was added dropwise to a suspension of lithium aluminum hydride (1.06 g, 28 mmol) and THF (120 mL) at −78° C. The mixture was stirred for 10 minutes after addition finish. H$_2$O (1.06 mL), 15% aqueous NaOH solution (1.06 mL) and H$_2$O (3.18 mL) were successively added to the mixture at 0° C. very slowly. The resulting precipitate was filtered and washed with THF. The filtrate was concentrated in vacuo to afford crude of the title compound. MS (m/z): 233.14, [M+H]$^+$.

Synthesis of (S)—N-((5-bromo-2-(methylthio)pyrimidin-4-yl)methylene)-2-methylpropane-2-sulfinamide (7C): Copper(II) sulfate (anhydrous, 8.9 g, 56 mmol) was added to a solution of 5-bromo-2-(methylthio)pyrimidine-4-carbaldehyde (7B, ~28 mmol) and (S)-2-methylpropane-2-sulfinamide (3.4 g, 28 mmol) in CH$_2$Cl$_2$ (100 mL). The suspension was stirred for 3 days at room temperature. The reaction was filtered and washed with CH$_2$Cl$_2$ (3×20 ml). The filtrate was concentrated. The crude product was purified by silica gel chromatography to yield the title compound 7C. MS (m/z) 337.7 [M+H]$^+$ Synthesis of (S)—N—((S)-1-(5-bromo-2-(methylthio)pyrimidin-4-yl)-2-(3,5-difluorophenyl)ethyl)-2-methylpropane-2-sulfinamide (7D): To a solution of(S)—N-((5-bromo-2-(methylthio)pyrimidin-4-yl)methylene)-2-methylpropane-2-sulfinamide (7C, 2.97 g, 8.8 mmol) in THF (18 mL) cooled to −78° C. was drop wise added 3,5-difluorobenzylmagnesium bromide (53 mL, 0.25 M in diethyl ether, 13.3 mmol). The reaction mixture was allowed to stir at −78° C. for 10 min, NH$_4$Cl (sat. aq., 10 ml) was added to the reaction and warmed up to ambient temperature. Extracted with EtOAc and the organic layer was dried over Na$_2$SO$_4$(s). The solvent was removed and the residue was purified by silica gel chromatography to yield the title compound 7D. MS (m/z) 465.87 [M+H]$^+$ Synthesis of(S)-1-(5-bromo-2-(methylthio)pyrimidin-4-yl)-2-(3,5-difluorophenyl)ethanamine hydrochloride (7E): Compound 7D (8 g, 17.23 mmol) was dissolved in 35 mL of methanol and cooled to 0° C. To it was added 4N HCl/1,4-dioxane (10.7 mL). The reaction mixture was allowed to stir for 20 minutes and to it was added diethyl ether. The resulting precipitate was collected by vacuum filtration then dried to afford the title product 7E. MS (m/z) 362.02 [M+H]$^+$.

Synthesis of(S)—N-(1-(5-bromo-2-(methylthio)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (7F): A mixture of 2-(3-(difluoromethyl)-4,4,7,7-tetrafluoro-4,5,6,7-tetrahydro-1H-indazol-1-yl)acetic acid (604 mg, 2 mmol), Compound 7E (793 mg, 2 mmol) and HATU (912 mg, 2.4 mmol) in 10 mL of DMF was cooled to 0° C. To it was drop wise added N,N-diisopropylethylamine (1.05 mL, 6 mmol). The reaction mixture was allowed to stir at 0° C. for 10 minutes then slowly poured it into ice water with stirring. The resulting precipitate was collected by vacuum filtration then dried to afford the title product 7F. MS (m/z) 644.22 [M+H]$^+$.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(2-(methylthio)-5-(3-oxoisoindolin-5-yl)pyrimidin-4-yl)ethyl)acetamide (7G): A microwave tube was charged with compound 7F (300 mg, 0.47 mmol), 6-(4,4,5,5-tetramethyl-1,3,2-dioxaborolan-2-yl)isoindolin-1-one (181 mg, 0.7 mmol) and PdCl$_2$[P(cy)$_3$]$_2$ (17 mg, 0.023 mmol). To it was added 10 mL of 1,4-dioxane and 1.4 mL of sodium bicarbonate aqueous solution (1M). The reaction mixture was heated to 155° C. for 25 min in a microwave synthesizer. After cooled to room temperature, it was partitioned between EtOAc and water. The organic layer was separated and washed with brine, then dried over MgSO$_4$, filtered and concentrated. The residue was purified by silica gel chromatography to afford the title compound 7G. MS (m/z) 697.32 [M+H]$^+$.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(2-(3-hydroxy-3-methylbut-1-yn-1-yl)-5-(3-oxoisoindolin-5-yl)pyrimidin-4-yl)ethyl)acetamide (7H): To a mixture of CuI (2 mg, 0.01 mmol), [Pd(dppf)Cl$_2$] (4 mg, 0.005 mmol), 5-ethynylpyrimidine (10.5 mg, 0.1 mmol) and compound 7G (35 mg, 0.05 mmol) was added THF (0.5 mL) and Et$_3$N (0.04 mL, 0.03 mmol). The reaction mixture was heated in a microwave at 150° C. for 30 min. After cooled to room temperature it was diluted with EtOAc. To it was added Si-Thiol (130 mg, 1.37 mmol/g) and the mixture was stirred at 40° C. for 1 hour. Then it was filtered and the filtrate was washed with 10% aq NH$_4$OH, H$_2$O and brine. The organic layer was dried over MgSO$_4$, filtered, concentrated and purified by reverse phase HPLC to afford the title product. $^1$H NMR (400 MHz, Methanol-d4): δ 9.22 (s), 9.08 (d), 8.65 (s), 7.70-7.59 (m), 7.44 (d), 6.98-6.59 (m), 6.38 (d), 5.47 (q), 5.06 (s), 4.51 (s), 3.09 (d), 2.54-2.45 (m). MS (m/z) 752.97 [M+H]$^+$.

Example 8

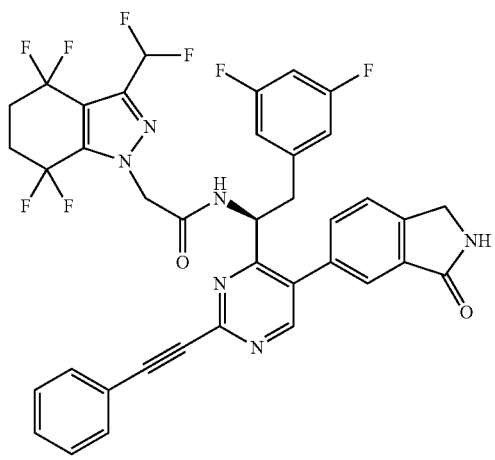

8

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(5-(3-oxoisoindolin-5-yl)-2-(phenylethynyl)pyrimidin-4-yl)ethyl)acetamide (8): The title compound (8) was prepared according to the method presented for the synthesis of compound 7H of Example 7 utilizing compound 7G and ethynylbenzene. $^1$H NMR (400 MHz, Methanol-d$_4$) δ 9.10 (d), 8.60 (s), 7.71-7.58 (m), 7.54-7.42 (m), 6.95-6.55 (m), 6.39 (d), 5.45 (q), 5.07 (d), 4.51 (s), 3.09 (d), 2.56-2.42 (m). MS (m/z) 751.2 [M+H]$^+$.

Example 9

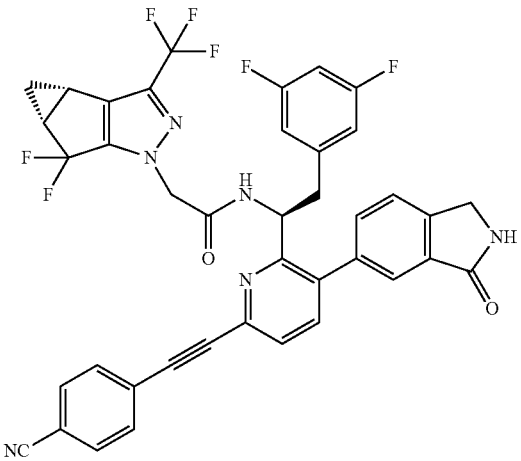

9

Synthesis of N—((S)-1-(6-((4-cyanophenyl)ethynyl)-3-(3-oxoisoindolin-5-yl)pyridin-2-yl)-2-(3,5-difluorophenyl)ethyl)-2-((3bS,4aR)-5,5-difluoro-3-(trifluromethyl)-3b,4,4a,5-tetrahydro-1H-cyclopropa[3,4]cyclopenta[1,2-c]pyrazol-1-yl)acetamide (9): The title compound (9) was prepared according to the method presented for the synthesis of compound 10C of Example 10 utilizing 4-ethynylbenzonitrile. $^1$H NMR (400 MHz, Methanol-d$_4$) δ 8.78 (d, 1H), 7.92-7.74 (m, 4H), 7.74-7.55 (m, 3H), 7.50 (s, 1H), 7.30 (s, 1H), 6.63 (d, 1H), 6.28 (d, 2H), 5.45 (d, 1H), 4.87 (d, 2H), 4.49 (s, 2H), 3.06 (d, 2H), 2.47 (s, 2H), 1.38 (s, 1H), 1.11 (s, 1H). MS (m/z) 755.03 [M+H]$^+$.

Example 10

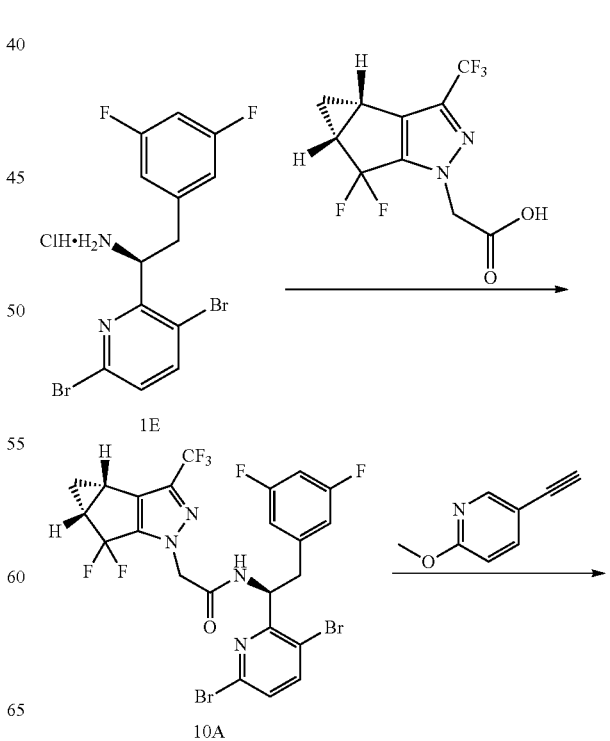

-continued

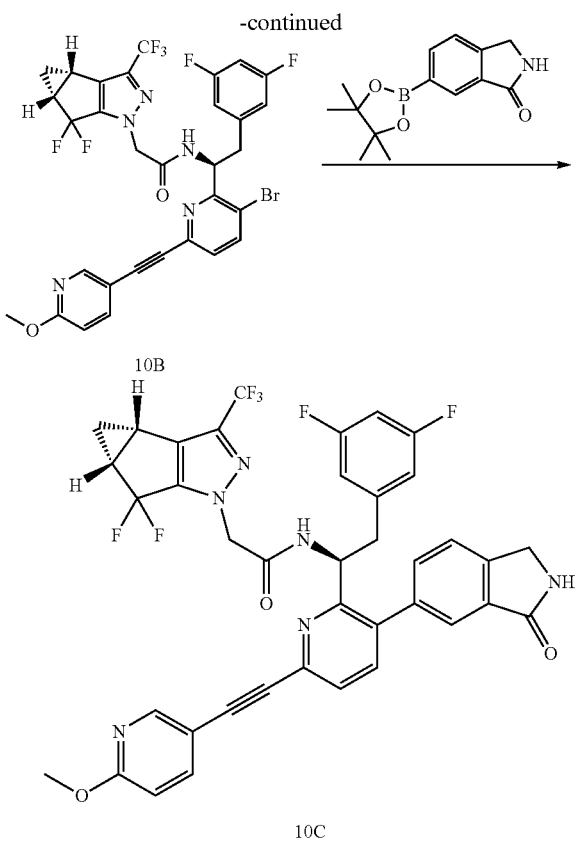

10B

10C

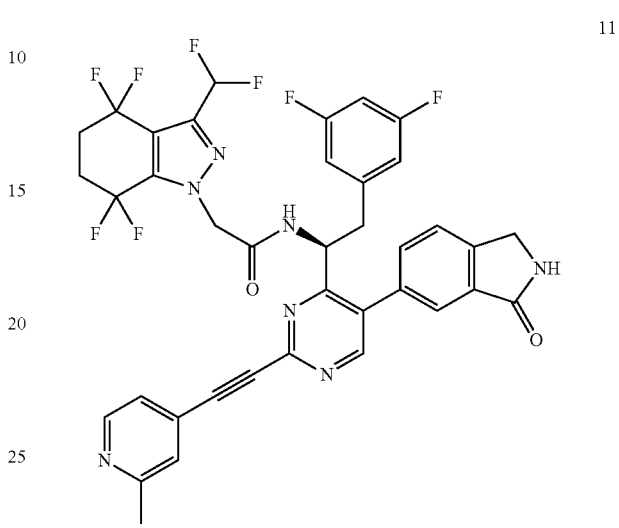

(s), 3.12-2.99 (m), 2.54-2.41 (m), 1.44-1.34 (m), 1.15-1.10 (m). MS (m/z) 761.41 [M+H]⁺.

Example 11

11

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(2-((2-methylpyridin-4-yl)ethynyl)-5-(3-oxoisoindolin-5-yl)pyrimidin-4-yl)ethyl)acetamide (11): The title compound (11) was prepared according to the method presented for the synthesis of compound 7H of Example 7 utilizing compound 7G and 4-ethynyl-2-methylpyridine. ¹H NMR (400 MHz, Methanol-d₄) δ 9.08 (d), 8.70-8.63 (m), 7.90 (s), 7.80 (dd), 7.71-7.60 (m), 7.44 (s), 7.03-6.57 (m), 6.41-6.34 (m), 5.52-5.41 (m), 5.05 (s), 4.51 (s), 3.15-3.04 (m), 2.72 (s), 2.54-2.43 (m). MS (m/z) 766.11 [M+H]⁺.

Example 12

12

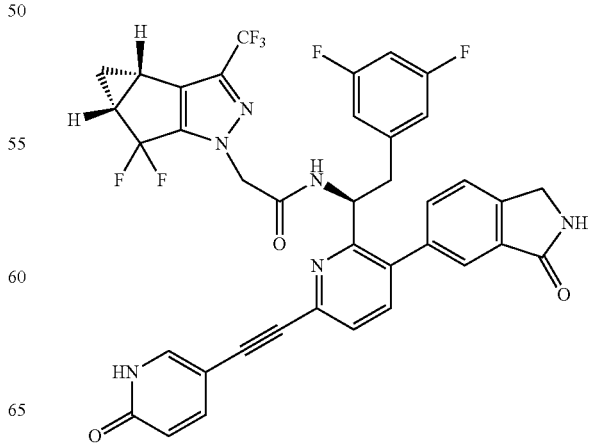

Synthesis of N—((S)-1-(3,6-dibromopyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (10A): Compound 1E (590 mg, 1.5 mmol) and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (424 mg, 1.5 mmol) were dissolved in 5 mL DMF and cooled to 0° C. To it was added HATU (686 mg, 1.8 mmol) then DIEA (1.08 mL, 6 mmol) added dropwise. After stirred at 0° C. for 5 min, the mixture was added dropwise into 100 mL of ice water and stirred for 1 h at ambient temperature. The resulting while solid was collected by filtration and washed with water then dried under high vacuum for overnight to afford the title product. MS (m/z) 656.86 [M+H]⁺.

Synthesis of N—((S)-1-(3-bromo-6-((6-methoxypyridin-3-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (10B): The title compound (10B) was prepared according to the method presented for the synthesis of compound 1G of Example 1 utilizing compound 10A and 5-ethynyl-2-methoxypyridine. MS (m/z) 708.06 [M+H]⁺.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-((6-methoxypyridin-3-yl)ethynyl)-3-(3-oxoisoindolin-5-yl)pyridin-2-yl)ethyl)acetamide (10C): The title compound (10C) was prepared according to the method presented for the synthesis of compound 1H of Example 1 utilizing compound 10B. ¹H NMR (400 MHz, Methanol-d₄) δ 8.46-8.40 (m), 7.88 (dd), 7.65-7.55 (m), 7.47 (d), 7.29 (d), 6.87 (dd), 6.69-6.59 (m), 6.28 (d), 5.44 (t), 4.88 (d), 4.49 (s), 3.96

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-((6-oxo-1,6-dihydropyridin-3-yl)ethynyl)-3-(3-oxoisoindolin-5-yl)pyridin-2-yl)ethyl)acetamide (12): In a microwave tube was charged with 10 mg of compound 10C. To it was added 0.3 mL of ethanol and 0.3 mL of HCl in 1,4-dioxane (4N). The reaction mixture was heated at 100° C. for 20 min in a Microwave Synthesizer. After cooling down the solvent was removed and the residue was dissolved in 1 mL of methanol and to it was added potassium hydroxide (4 mg). The reaction mixture was heated at 100° C. for 10 min in a Microwave Synthesizer. After cooling down the solvent was removed and the residue was purified by reverse phase HPLC to afford the title product. $^1$H NMR (400 MHz, Methanol-$d_4$) δ 8.72 (d), 7.81 (dd), 7.72 (dd), 7.63-7.52 (m), 7.46 (d), 7.28 (s), 6.69-6.54 (m), 6.30-6.23 (m), 5.43 (q), 4.87 (s), 4.49 (s), 3.07-3.00 (m), 2.54-2.43 (m), 1.45-1.34 (m), 1.17-1.09 (m). MS (m/z) 746.97 [M+H]$^+$.

Example 13

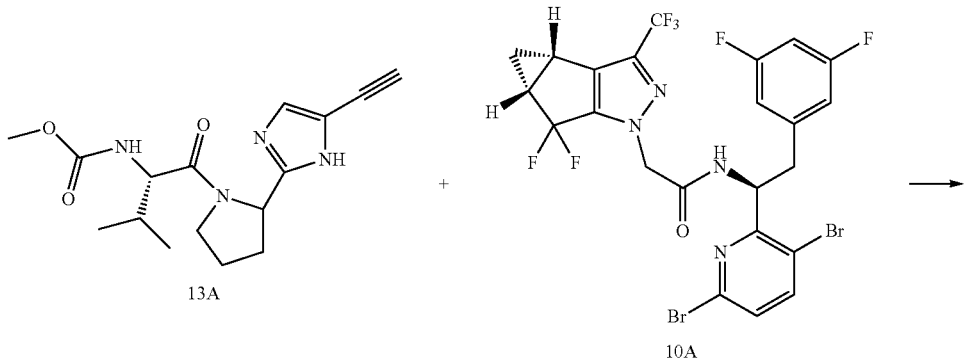

13A

10A

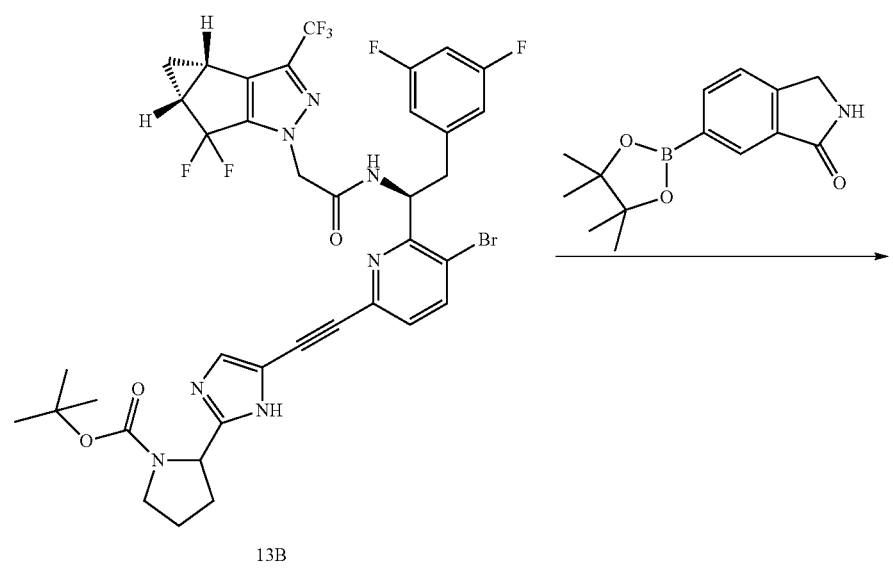

13B

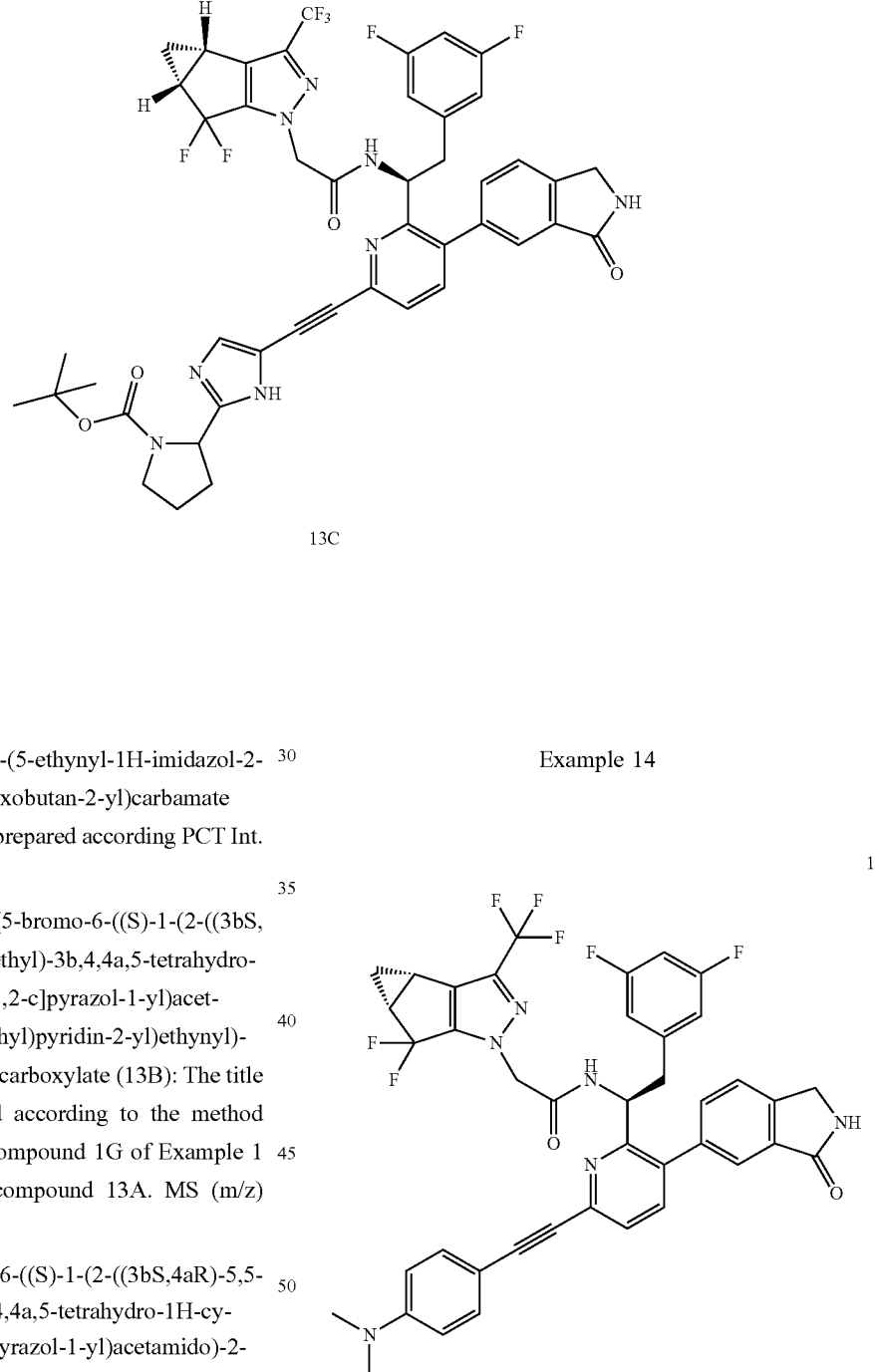

13C

Synthesis of methyl((2S)-1-(2-(5-ethynyl-1H-imidazol-2-yl)pyrrolidin-1-yl)-3-methyl-1-oxobutan-2-yl)carbamate (13A): The title compound was prepared according PCT Int. Appl. WO2010132601.

Synthesis of tert-butyl 2-(5-((5-bromo-6-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-2-yl)ethynyl)-1H-imidazol-2-yl)pyrrolidine-1-carboxylate (13B): The title compound (13B) was prepared according to the method presented for the synthesis of compound 1G of Example 1 utilizing compound 10A and compound 13A. MS (m/z) 837.75 [M+H]+.

Synthesis of tert-butyl 2-(5-((6-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-5-(3-oxoisoindolin-5-yl)pyridin-2-yl)ethynyl)-1H-imidazol-2-yl)pyrrolidine-1-carboxylate (13C): The title compound (13C) was prepared according to the method presented for the synthesis of compound 1H of Example 1 utilizing compound 13B and 6-(4,4,5,5-tetramethyl-1,3,2-dioxaborolan-2-yl)isoindolin-1-one. 1H NMR (400 MHz, Methanol-d4) δ 8.76 (d), 7.80 (s), 7.69-7.55 (m), 7.49 (d), 7.29 (s), 6.85-6.55 (m), 6.27 (d), 5.42 (t), 5.013-4.95 (m), 4.49 (s), 3.73-3.60 (m), 3.57-3.44 (m), 3.15-2.95 (m), 2.47 (dd), 2.20-1.86 (m), 1.71-1.02 (m). MS (m/z) 888.92 [M+H]+.

Example 14

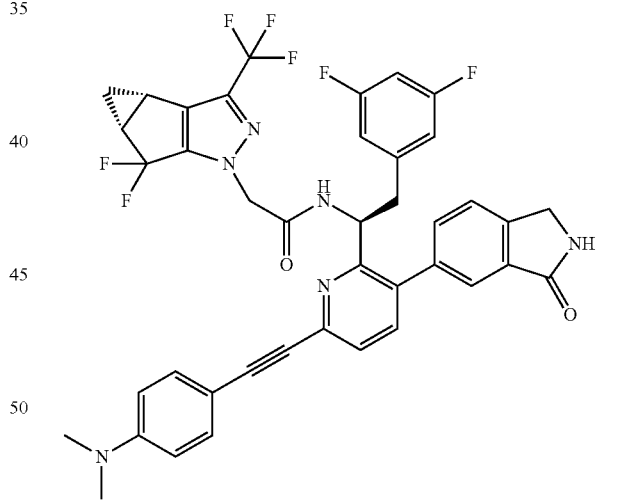

14

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-((4-(dimethylamino)phenyl)ethynyl)-3-(3-oxoisoindolin-5-yl)pyridin-2-yl)ethyl)acetamide (14): The title compound (14) was prepared according to the method presented for the synthesis of compound 13C of Example 13 utilizing 10A and 4-ethynyl-N,N-dimethylaniline. 1H NMR (400 MHz, Methanol-d4) δ 7.67-7.41 (m, 6H), 7.28 (s, 1H), 6.83 (d, 2H), 6.69-6.54 (m, 1H), 6.28 (d, 2H), 5.43 (dd, 1H), 4.99-4.86 (m, 2H), 4.49 (s, 2H), 3.04 (s, 6H), 2.48 (dd, 2H), 1.59-1.32 (m, 1H), 1.22-1.03 (m, 1H). MS (m/z) 773.11 [M+H]+.

Example 15

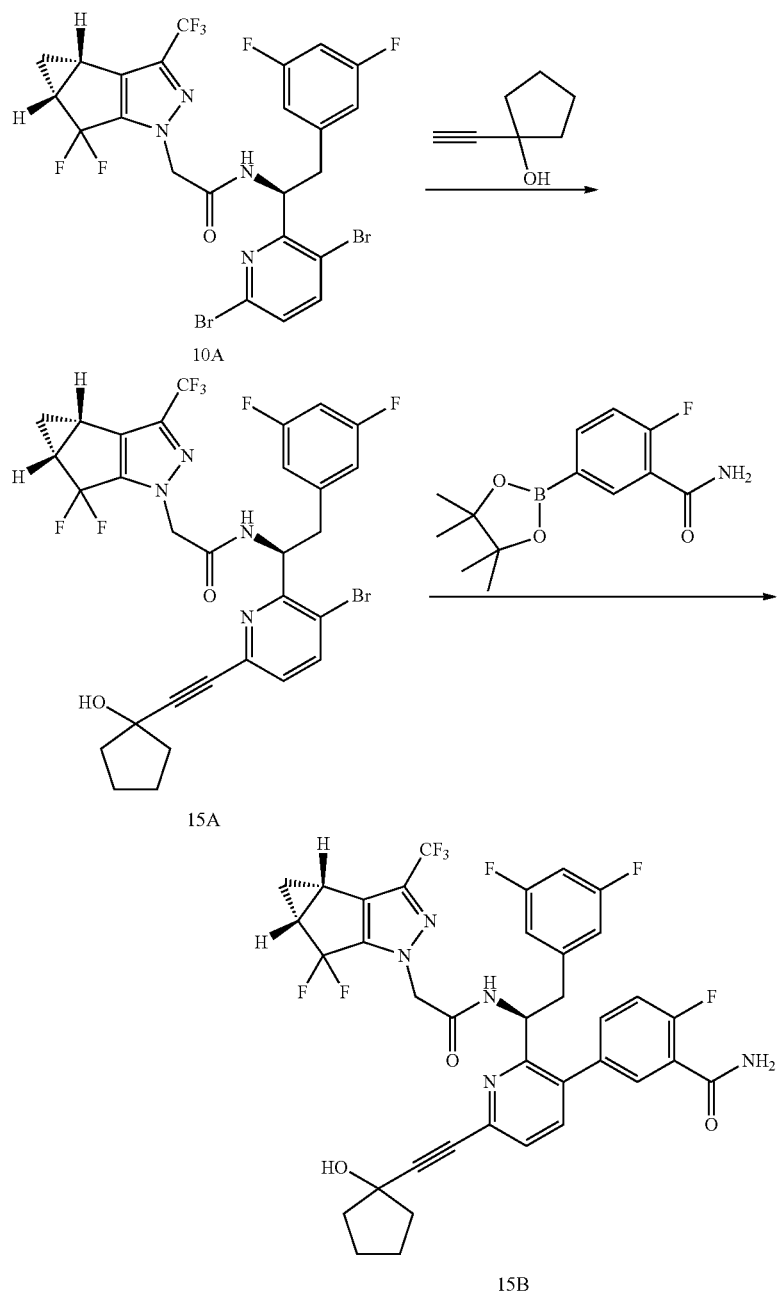

Synthesis of N—((S)-1-(3-bromo-6-((1-hydroxycyclopentyl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (15A): The title compound (15A) was prepared according to the method presented for the synthesis of compound 1G of Example 1 utilizing compound 10A and 1-ethynylcyclopentanol. MS (m/z) 685.22 [M+H]$^+$.

Synthesis of 5-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-((1-hydroxycyclopentyl)ethynyl)pyridin-3-yl)-2-fluorobenzamide (15B): A microwave tube was charged with compound 15A (20 mg, 0.029 mmol), (3-carbamoyl-4-fluorophenyl)boronic acid (8 mg, 0.044 mmol), LiCl (2.5 mg, 0.058 mmol), Na$_2$CO$_3$ (9 mg, 0.088 mmol) and PdCl$_2$(PPh$_3$)$_2$ (2 mg, 0.003 mmol). To the mixture was added 0.7 mL of 1,4-dioxane and 0.1 mL of H$_2$O. The system was purged with argon and then the microwave tube was sealed and the reaction mixture was heated in a 130° C. bath for 40 min. After cooling to ambient temperature the reaction mixture was partitioned between EtOAc and water. The organic layer was separated and washed with brine, then dried over MgSO$_4$, filtered and concentrated. The residue was purified by reverse phase HPLC to afford the title product. $^1$H NMR (400 MHz, Methanol-$d_4$) δ 7.52 (d), 7.45 (d), 7.39-7.25 (m), 7.20 ( ), 6.71-6.58 (m), 6.38-6.28 (m), 5.34 (dd), 4.86 (s), 3.16-2.89 (m), 2.55-2.39 (m), 2.20-1.97 (m), 1.98-1.69 (m), 1.58-1.23 (m), 1.15-1.04 (m). MS (m/z) 744.35 [M+H]$^+$.

Example 16

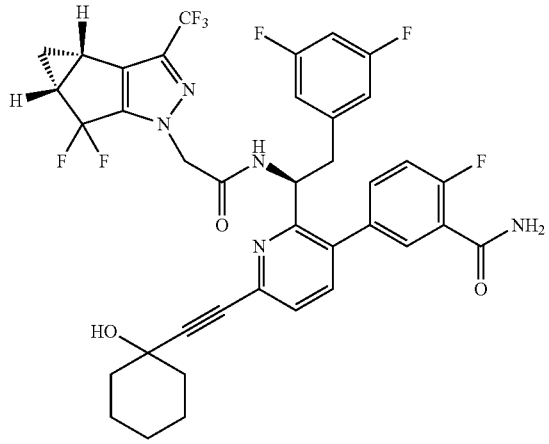

Synthesis of 5-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-((1-hydroxycyclohexyl)ethynyl)pyridin-3-yl)-2-fluorobenzamide (16): The title compound (16) was prepared according to the method presented for the synthesis of compound 15B of Example 15 utilizing compound 10A and 1-ethynylcyclohexanol and then Suzuki reaction with 2-fluoro-5-(4,4,5,5-tetramethyl-1,3,2-dioxaborolan-2-yl)benzamide to afford title product. $^1$H NMR (400 MHz, Methanol-d4) δ 7.53 (d), 7.46 (d), 7.42-7.27 (m), 7.20 (dd), 6.65 (tt), 6.41-6.21 (m), 5.34 (dd), 4.85 (s), 3.16-2.97 (m), 2.60-2.35 (m), 2.13-1.95 (m), 1.87-1.51 (m), 1.46-1.22 (m), 1.16-1.02 (m). MS (m/z) 758.41 [M+H]$^+$.

Example 17

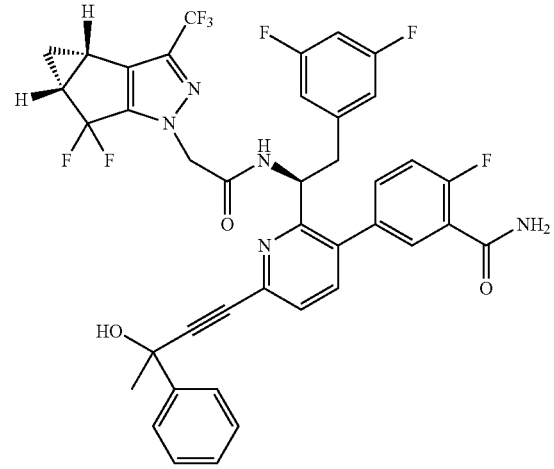

Synthesis of 5-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-phenylbut-1-yn-1-yl)pyridin-3-yl)-2-fluorobenzamide (17): The title compound (17) was prepared according to the method presented for the synthesis of compound 15B of Example 15 utilizing compound 10A and 2-phenylbut-3-yn-2-ol and then Suzuki reaction with 2-fluoro-5-(4,4,5,5-tetramethyl-1,3,2-dioxaborolan-2-yl)benzamide to afford the title product. $^1$H NMR (400 MHz, Methanol-$d_4$) δ 7.84-7.68 (m), 7.63-7.47 (m), 7.47-7.27 (m), 7.21 (dd), 6.73-6.57 (m), 6.39-6.24 (m), 5.35 (dd), 1.26-1.23 (m), 4.84 (s), 3.06 (qd), 2.56-2.30 (m), 1.86-1.38 (q), 1.10 (m). MS (m/z) 780.34 [M+H]$^+$.

Example 18

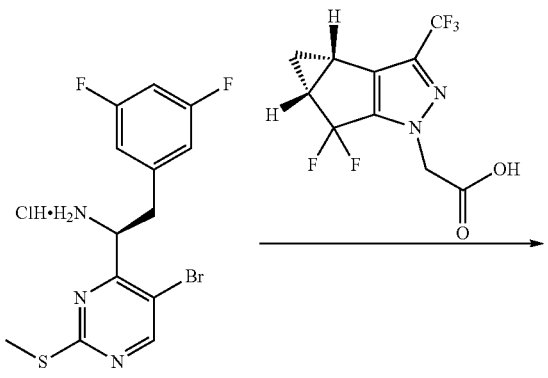

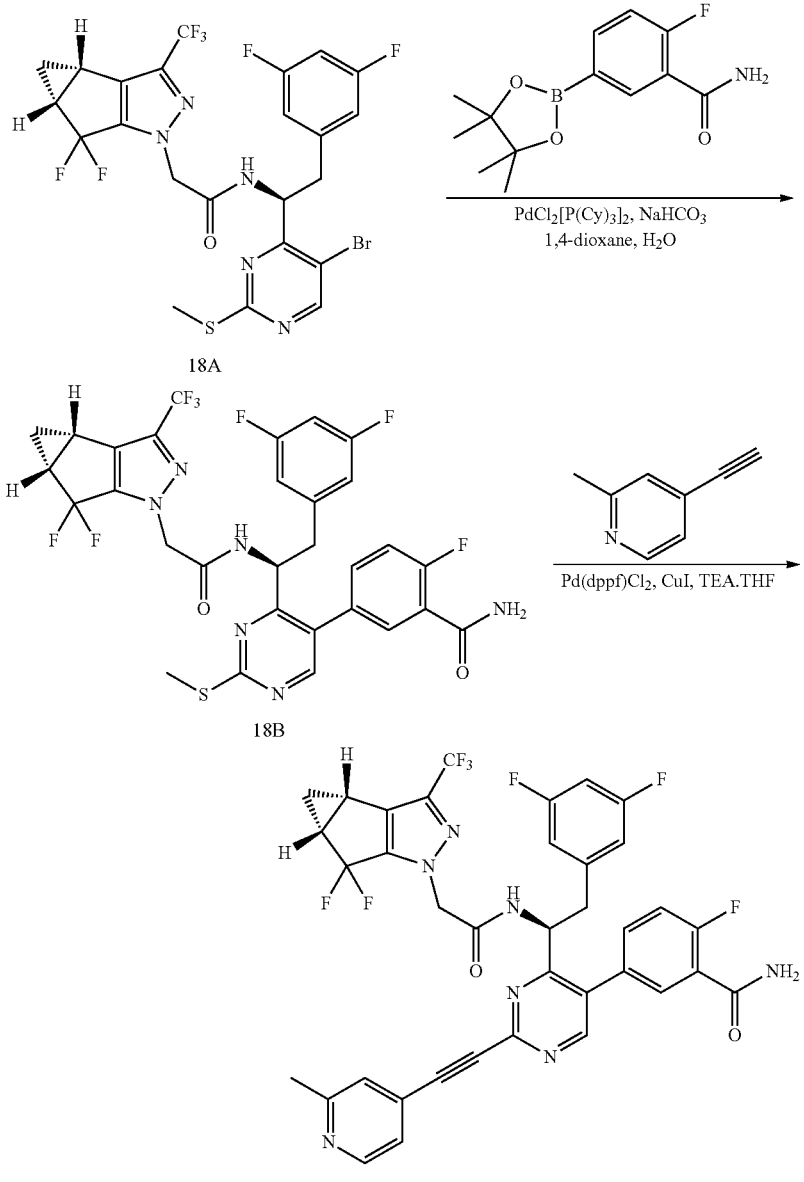

Synthesis of N—((S)-1-(5-bromo-2-(methylthio)pyrimidin-4-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (18A): The title compound (18A) was prepared according to the method presented for the synthesis of compound 10A of Example 10 utilizing compound 7E. MS (m/z) 624.13 [M+H]+.

Synthesis of 5-(4-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(methylthio)pyrimidin-5-yl)-2-fluorobenzamide (18B): A microwave tube was charged with compound 18A (282 mg, 0.45 mmol), (3-carbamoyl-4-fluorophenyl)boronic acid (91 mg, 0.5 mmol) and PdCl2[P(cy)3]2 (17 mg, 0.023 mmol). To the mixture was added 10 mL of 1,4-dioxane and 1.4 mL of sodium bicarbonate aqueous solution (1M). The system was purged with argon and then the microwave tube was sealed and the reaction mixture was heated in a 130° C. bath for 40 min. After cooled to ambient temperature it was partitioned between EtOAc and water. The organic layer was separated and washed with brine, then dried over MgSO4, filtered and concentrated. The residue was purified by silica gel chromatography to afford title product. MS (m/z) 683.06 [M+H]+.

Synthesis of 5-(4-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-((2-methylpyridin-4-yl)ethynyl)pyrimidin-5-yl)-2-fluorobenzamide (18C): The title compound (18C) was prepared according to the method presented for the synthesis of compound 7H of Example 7 utilizing compound 18B and 4-ethynyl-2-methylpyridine. $^1$H NMR (400 MHz, Methanol-$d_4$) δ 9.11 (d), 8.69 (d), 8.64, 7.95 (d), 7.86 (dd), 7.52 (dd), 7.30 (dd), 6.70 (tt), 6.53-6.32 (m), 5.41 (q), 4.85 (s), 3.19-3.01 (m), 2.97 (s), 2.89-2.80 (m), 2.74 (s), 2.60-2.31 (m), 1.38 (q), 1.15-0.99 (m). MS (nm/z) 752.12 [M+H]+.

Example 19

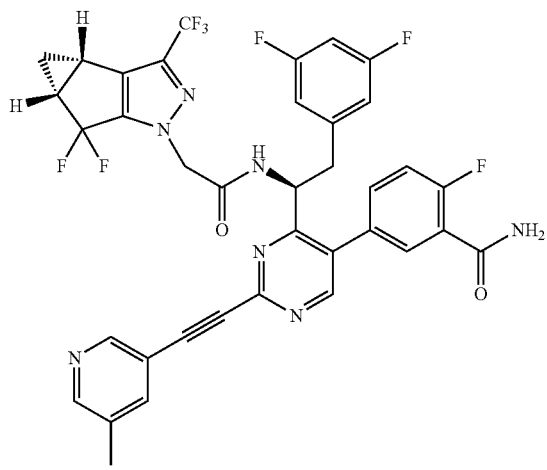

Synthesis of 5-(4-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-((5-methylpyridin-3-yl)ethynyl)pyrimidin-5-yl)-2-fluorobenzamide (19): The title compound (19) was prepared according to the method presented for the synthesis of compound 7H of Example 7 utilizing compound 18B and 3-ethynyl-5-methylpyridine. $^1$H NMR (400 MHz, Methanol-$d_4$) δ 9.09 (d), 8.75 (s), 8.59 (d), 8.17 (dd), 7.65-7.43 (m), 7.29 (dd), 6.70 (tt), 6.51-6.18 (m), 5.40 (q), 4.83 (s), 3.17-2.97 (m), 2.59-2.31 (m), 1.38 (td), 1.15-0.99 (m). MS (m/z) 752.11 [M+H]$^+$.

Example 20

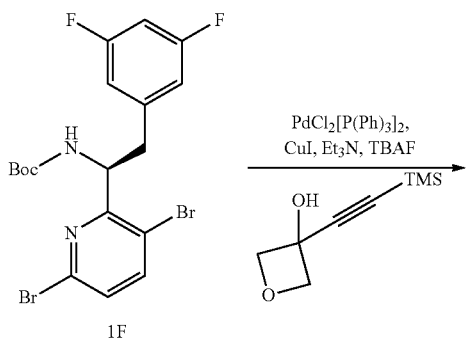

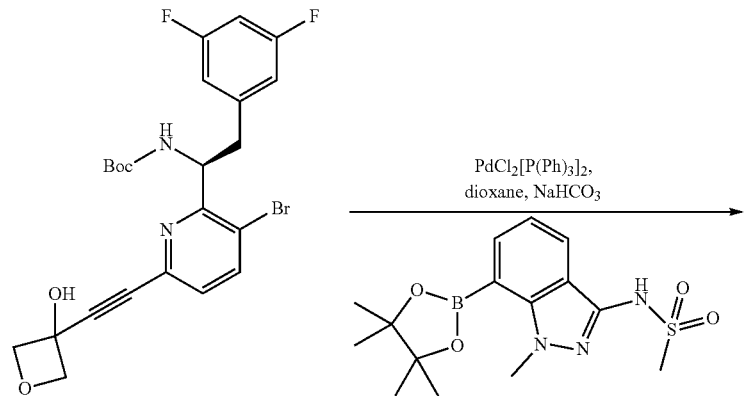

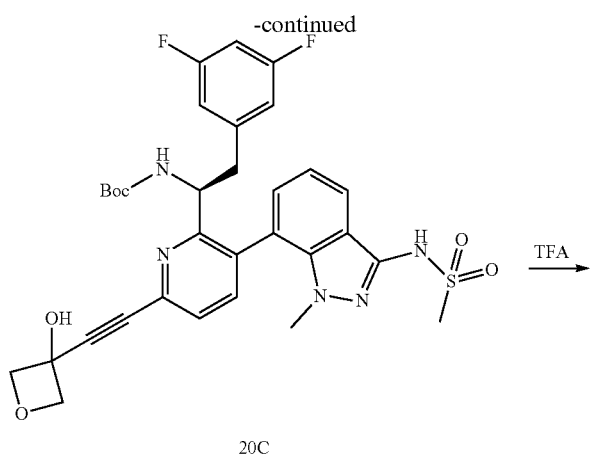
20C
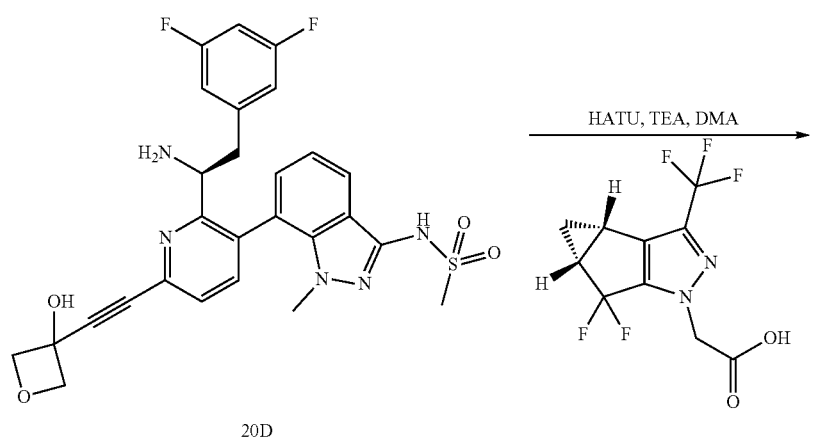
20D
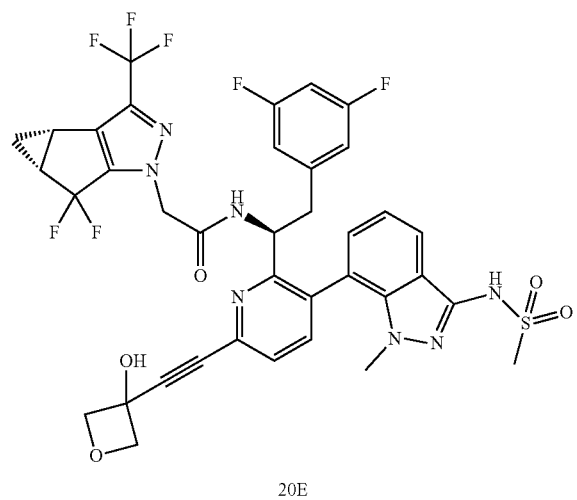 [SMILES: Cn1nc(NS(C)(=O)=O)c2cccc(-c3ccc(C#CC4(O)CNC4)nc3[C@H](Cc3cc(F)cc(F)c3)NC(=O)Cn3nc(C(F)(F)F)c4c3C(F)(F)[C@@H]3C[C@H]43)c21]
20E
Synthesis of (S)-tert-butyl(1-(3-bromo-6-((3-hydroxyoxetan-3-yl)ethynyl)pyridin-2-yl)-2-(3,5-difluorophenyl)ethyl)carbamate (20A): To 1F (300 mg, 0.61 mmol) in THF (3 mL) was added 3-((trimethylsilyl)-ethynyl)oxetan-3-ol (207 mg, 1.22 mmol), triethylamine (0.84 mL, 6.1 mmol), CuI (5.8 mg, 0.03 mmol) and PdCl$_2$[P(Ph)$_3$]$_2$ (21 mg, 0.03 mmol). The contents were flushed with argon gas for 5-10 min followed by the addition of TBAF (1 M in THF, 0.61 mmol). The reaction mixture sealed and stirred for 2 h at rt. The reaction mixture was concentrated in vacuo, and purified by silica gel column chromatography, eluting with 0-50% EtOAc in hexanes to give the title compound 20A.

Synthesis of(S)-tert-butyl(2-(3,5-difluorophenyl)-1-(6-((3-hydroxyoxetan-3-yl)ethynyl)-3-(1-methyl-3-(methylsulfonamido)-1H-indazol-7-yl)pyridin-2-yl)ethyl)carbamate (20C): To 20A (50 mg, 0.098 mmol) in dioxane (3 mL) was added N-(1-methyl-7-(4,4,5,5-tetramethyl-1,3,2-dioxaborolan-2-yl)-1H-indazol-3-yl)methanesulfonamide (20B) (48 mg, 0.13 mmol), $PdCl_2[P(Ph)_3]_2$ (6.8 mg, 0.009 mmol), and aq 1 M $NaHCO_3$ (0.3 mL, 0.3 mmol). The reaction mixture sealed and heated in a microwave reactor to 150° C. for 20 min. Upon cooling, the reaction mixture was diluted with EtOAc and washed with two portions of brine. The organic layer were dried over $Na_2SO_4$, filtered, concentrated in vacuo, and purified by silica gel column chromatography, eluting with 0-100% EtOAc in hexanes to give the title compound 20C.

Synthesis of(S)—N-(7-(2-(1-amino-2-(3,5-difluorophenyl)ethyl)-6-((3-hydroxyoxetan-3-yl)ethynyl)pyridin-3-yl)-1-methyl-1H-indazol-3-yl)methanesulfonamide (20D): To a solution of 20C (38 mg, 0.05 mmol) in DCM (1 mL) was added neat TFA (1 mL). The reaction mixture was stirred at room temperature for 0.5 hours. Upon complete removal of the Boc protecting group, the reaction was concentrated in vacuo to give the title compound 20D.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-((3-hydroxyoxetan-3-yl)ethynyl)-3-(1-methyl-3-(methylsulfonamido)-1H-indazol-7-yl)pyridin-2-yl)ethyl) acetamide (20E): To a solution of 20D (0.05 mmol assuming 100% purity) in DMA (1 mL) was added triethylamine (0.02 mL, 0.143 mmol), followed by 2-((3bS,4aR)-3-(trifluoromethyl)-5,5-difluoro-3b,4,4a,5-tetrahydro-1H-cyclopropa[3,4]cyclopenta[1,2-c]pyrazol-1-yl)acetic acid (18 mg, 0.06 mmol) and HATU (26 mg, 0.06 mmol). After stirring for 5 minutes, the reaction mixture was filtered and purified by reverse phase HPLC. Fractions containing the product were pooled and lyophilized to provide the product 20E. HPLC retention time 6.83 and 7.01 min (2-98% acetonitrile: water with 0.1% trifluoroacetic acid, 8.5 min gradient on a Phenomonex Kinetex C18 column). MS (m/z) 818.1 $[M+H]^+$.

Example 21

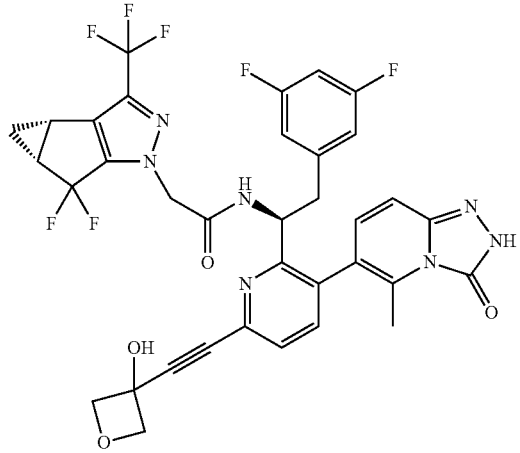

21

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-((3-hydroxyoxetan-3-yl)ethynyl)-3-(5-methyl-3-oxo-2,3-dihydro-[1,2,4]triazolo[4,3-a]pyridin-6-yl)pyridin-2-yl) ethyl)acetamide (21): The title compound (21) was prepared according to the method presented for the synthesis of compound 20E of Example 20 utilizing 5-methyl-6-(4,4,5,5-tetramethyl-1,3,2-dioxaborolan-2-yl)-[1,2,4]triazolo[4,3-a]pyridin-3(2H)-one in place of 20B. MS (m/z) 742.1 [M+H]+. HPLC retention time 6.27 min (2-98% acetonitrile: water with 0.1% trifluoroacetic acid, 8.5 min gradient on a Phenomonex Kinetex C18 column). MS (m/z) 742.1 $[M+H]^+$.

Example 22

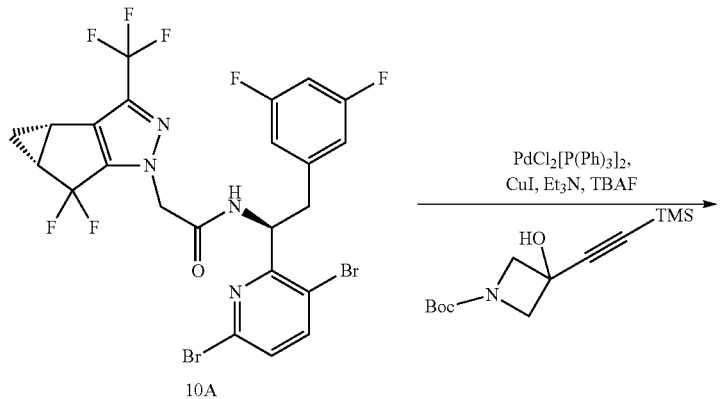

10A

-continued

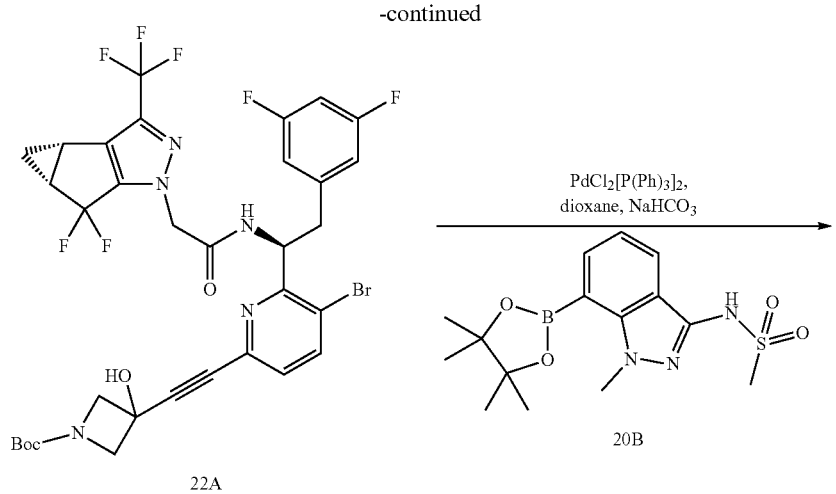

22A

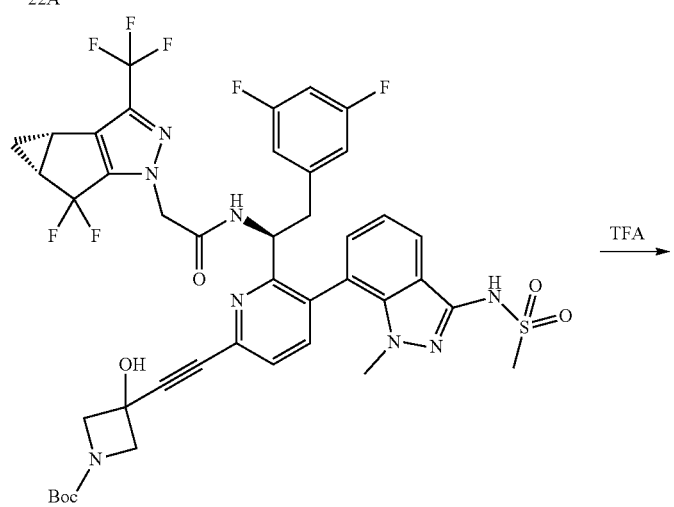

22B

22C

Synthesis of tert-butyl 3-((5-bromo-6-((S)-1-(2-((3bS, 4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-2-yl)ethynyl)-3-hydroxyazetidine-1-carboxylate (22A): To 10A (200 mg, 0.3 mmol) in THF (8 mL) was added tert-butyl 3-hydroxy-3-((trimethylsilyl)ethynyl)azetidine-1-carboxylate (222 mg, 0.8 mmol), triethylamine (0.85 mL, 0.61 mmol), CuI (1.1 mg, 0.006 mmol) and PdCl$_2$[P(Ph)$_3$]$_2$ (4 mg, 0.006 mmol). The contents were flushed with argon gas for 5-10 min followed by the addition of TBAF (1 M in THF, 0.39 mmol). The reaction mixture sealed and heated at 50° C. for 2 h. The reaction mixture was concentrated in vacuo, and purified by silica gel column chromatography, eluting with 0-100% EtOAc in hexanes to give the title compound 22A. MS (m/z) 656.7 [M+H]⁺.

Synthesis of tert-butyl 3-((6-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-5-(1-methyl-3-(methylsulfonamido)-1H-indazol-7-yl)pyridin-2-yl)ethynyl)-3-hydroxyazetidine-1-carboxylate (22B): To 22A (30 mg, 0.04 mmol) in dioxane (3 mL) was added N-(1-methyl-7-(4,4,5,5-tetramethyl-1,3,2-dioxaborolan-2-yl)-1H-indazol-3-yl)methanesulfonamide (20B) (17 mg, 0.05 mmol), PdCl$_2$[P(Ph)$_3$]$_2$ (2 mg, 0.003 mmol), and aq 1M NaHCO$_3$ (0.11 mL, 0.11 mmol). The reaction mixture sealed and heated in a microwave reactor to 150° C. for 20 min. Upon cooling, the reaction mixture was diluted with EtOAc and washed with two portions of brine. The organic layer was dried over Na$_2$SO$_4$, filtered, concentrated in vacuo, to give the crude title compound 22B. MS (m/z) 772.1 [M+H]⁺.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-((3-hydroxyazetidin-3-yl)ethynyl)-3-(1-methyl-3-(methylsulfonamido)-1H-indazol-7-yl)pyridin-2-yl)ethyl)acetamide (22C): To a solution of 22B (~0.04 mmol) in DCM (1 mL) was added neat TFA (1 mL). The reaction mixture was stirred at room temperature for 0.5 hours. After stirring, the reaction mixture was filtered and purified by reverse phase HPLC, eluting with 5-100% acetonitrile in water with 0.1% TFA. Fractions containing the product were pooled and lyophilized to provide the TFA salt of the product 22C. ¹H NMR (400 MHz, methanol-d$_4$) δ 8.86-8.69 (m), 7.96-7.81 (m), 7.72-7.62 (m), 7.60-7.47 (m), 7.27-7.02 (m), 6.82-6.51 (m), 6.42-6.27 (m), 5.36-5.26 (m), 5.11-5.00 (m), 4.87-4.71 (m), 3.19-3.05 (m), 3.04-2.85 (m), 2.57-2.38 (m), 1.50-1.32 (m), 1.21-0.98 (m). MS (m/z) 817.1 [M+H]⁺.

Example 23

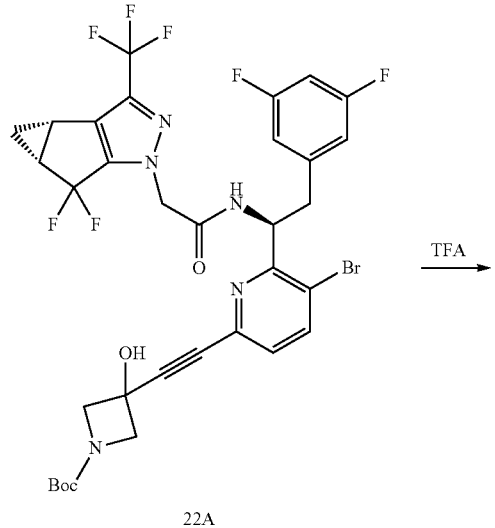

22A

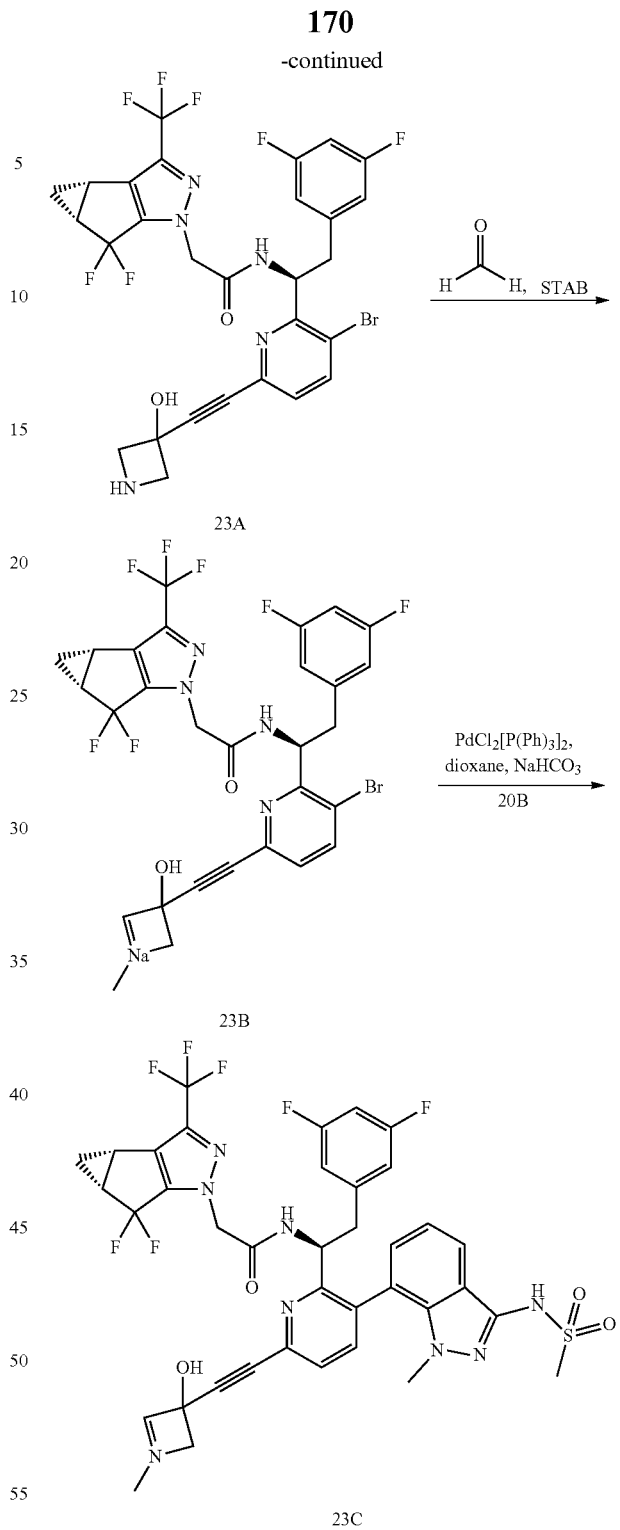

Synthesis of N—((S)-1-(3-bromo-6-((3-hydroxyazetidin-3-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (23A): To a solution of 22A (75 mg, 0.09 mmol) in DCM (1 mL) was added neat TFA (1 mL). The reaction mixture was stirred at room temperature for 0.5 hours. Upon complete removal of the Boc protecting group, the reaction was concentrated in vacuo to give the title compound 23A. MS (m/z) 674.0 [M+H]⁺.

Synthesis of N—((S)-1-(3-bromo-6-((3-hydroxy-1-methylazetidin-3-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (23B): A solution of 23A (50 mg, 0.007 mmol) in ACOH (2 mL) was treated with formaldehyde (0.166 mL, 37% in water) followed by sodium triacetoxy borohydride (79 mg, 0.03 mmol). The reaction was stirred at rt for 30 min. The reaction mixture was diluted with EtOAc, neutralized with saturated sodium bicarbonate solution, washed with two portions of brine. The organic layer was then dried over $Na_2SO_4$, filtered, and concentrated in vacuo to give the crude title compound 23B. MS (m/z) 688.0 $[M+H]^+$.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-((3-hydroxy-1-methylazetidin-3-yl)ethynyl)-3-(1-methyl-3-(methylsulfonamido)-1H-indazol-7-yl)pyridin-2-yl)ethyl)acetamide (23C): The title compound was prepared according to the method presented for the synthesis of compound 22B of Example 22 utilizing 23B in place of 22A. $^1$H NMR (400 MHz, methanol-$d_4$) δ 8.80-8.69 (m), 7.95-7.57 (m), 7.34-7.03 (m), 6.82-6.70 (m), 6.58-6.25 (m), 5.37-4.94 (m), 4.83-4.74 (m), 3.77-3.46 (m), 3.38-3.34 (m), 3.24-3.05 (m), 3.00-2.89 (m), 2.58-2.39 (m), 1.48-1.28 (m), 1.21-1.10 (m), 1.11-0.79 (m). MS (m/z) 831.1 $[M+H]^+$.

Example 24

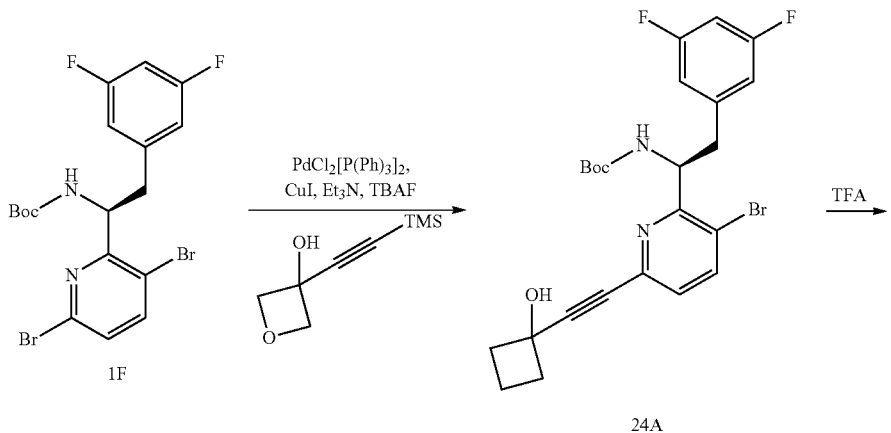

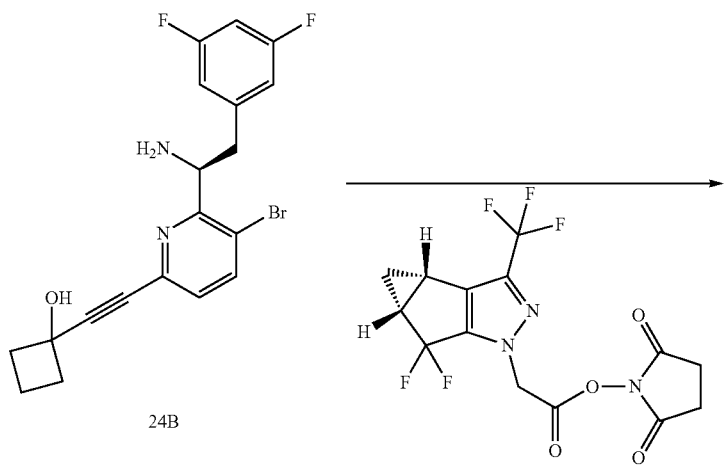

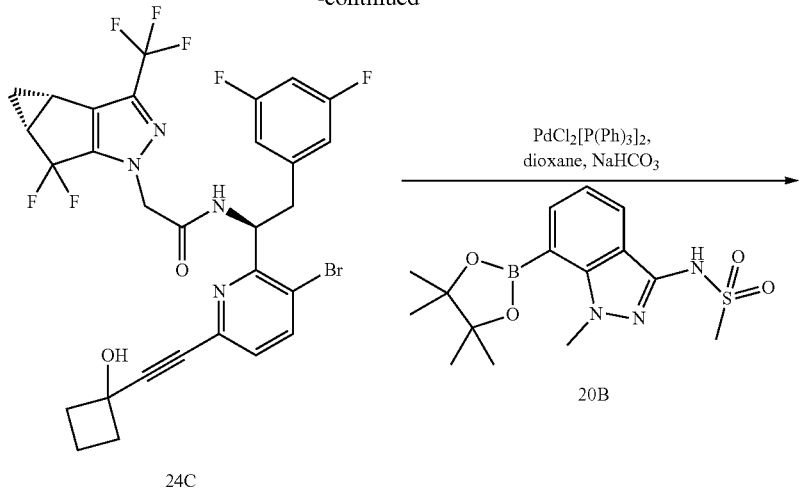

24C

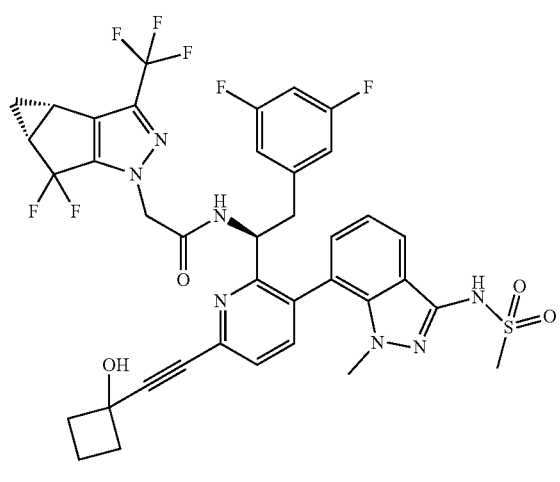

24D

Synthesis of (S)-tert-butyl(1-(3-bromo-6-((1-hydroxycyclobutyl)ethynyl)pyridin-2-yl)-2-(3,5-difluorophenyl)ethyl) carbamate (24A): The title compound was prepared according to the method presented for the synthesis of compound 20A of Example 20 utilizing 1-((trimethylsilyl)ethynyl)cyclobutanol in place of 3-((trimethylsilyl)-ethynyl)oxetan-3-ol. MS (m/z) 507.8 [M+H]+.

Synthesis of (S)-1-((6-(1-amino-2-(3,5-difluorophenyl)ethyl)-5-bromopyridin-2-yl)ethynyl)cyclobutanol (24B): To a solution of 24A (163 mg, 0.32 mmol) in DCM (1 mL) was added neat TFA (1 mL). The reaction mixture was stirred at room temperature for 0.5 hours. Upon complete removal of the Boc protecting group, the reaction was concentrated in vacuo to give the title compound 24B. MS (m/z) 407.0 [M+H]+.

Synthesis of N—((S)-1-(3-bromo-6-((1-hydroxycyclobutyl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (24C): A solution of 24B (~0.32 mmol) in acetonitrile (3 mL) was treated with 2,5-dioxopyrrolidin-1-yl 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetate (0.146 mg, 0.38 mmol) for 15 min at rt. The reaction mixture was diluted with EtOAc, washed with saturated sodium bicarbonate solution, followed by two portions of brine. The organic layer was then dried over Na2SO4, filtered, and concentrated in vacuo to give the crude title compound 24C. MS (m/z) 672.9 [M+H]+.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-((1-hydroxycyclobutyl)ethynyl)-3-(1-methyl-3-(methylsulfonamido)-1H-indazol-7-yl)pyridin-2-yl)ethyl) acetamide (24D): The title compound was prepared according to the method presented for the synthesis of compound 23C of Example 23 utilizing 24C in place of 23B. $^1$H NMR (400 MHz, methanol-d$_4$) δ 8.82-8.71 (m), 7.89-7.78 (m), 7.75-7.68 (m), 7.62-7.53 (m), 7.28-7.07 (m), 6.78-6.67 (m), 6.66-6.48 (m), 6.42-6.26 (m), 5.35-5.25 (m), 5.07-4.97 (m), 4.86-4.69 (m), 3.34 (s, OH), 3.23-3.06 (m), 3.04-2.85 (m), 2.64-2.27 (m), 2.03-1.84 (m), 1.57-1.32 (m), 1.17-0.98 (m). MS (m/z) 816.1 [M+H]+.

Example 25

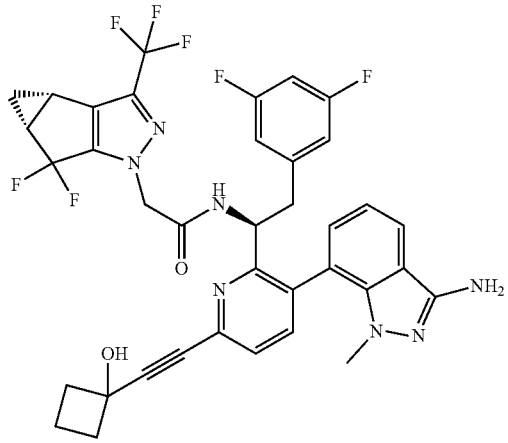

25

Synthesis of N—((S)-1-(3-(3-amino-1-methyl-1H-indazol-7-yl)-6-((1-hydroxy-cyclobutyl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (25): The title compound was prepared according to the method presented for the synthesis of compound 24D of Example 24, utilizing 1-methyl-7-(4,4,5,5-tetramethyl-1,3,2-dioxaborolan-2-yl)-1H-indazol-3-amine in place of N-(1-methyl-7-(4,4,5,5-tetramethyl-1,3,2-dioxaborolan-2-yl)-1H-indazol-3-yl)methanesulfonamide. ¹H NMR (400 MHz, methanol-d₄) δ 8.88-8.69 (m), 7.93-7.79 (m), 7.79-7.62 (m), 7.60-7.52 (m), 7.34-7.00 (m), 6.81-6.52 (m), 6.45-6.22 (m), 5.30-5.20 (m), 5.08-4.98 (m), 4.84-4.69 (m), 3.18 (s, OH), 3.15-3.05 (m), 3.01-2.91 (m), 2.86 (s, OH), 2.68-2.20 (m), 2.05-1.87 (m), 1.47-1.35 (m), 1.19-1.00 (m). MS (m/z) 738.2 [M+H]⁺.

Example 26

26

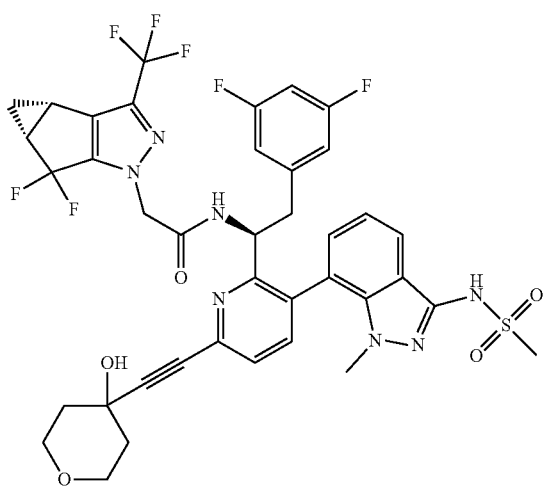

Synthesis of 2-((3bS,4aR)-5,5-difluoro-3-(trifluoromethyl)-3b,4,4a,5-tetrahydro-1H-cyclopropa[3,4]cyclopenta [1,2-c]pyrazol-1-yl)-N—((S)-2-(3,5-difluorophenyl)-1-(6-((4-hydroxytetrahydro-2H-pyran-4-yl)ethynyl)-3-(1-methyl-3-(methylsulfonamido)-1H-indazol-7-yl)pyridin-2-yl)ethyl)acetamide (26): The title compound was prepared according to the method presented for the synthesis of compound 24D of Example 24, utilizing 4-ethynyltetrahydro-2H-pyran-4-ol in place of 1-((trimethylsilyl)ethynyl)cyclobutanol and omitting the addition of TBAF. ¹H NMR (400 MHz, methanol-d₄) δ 8.84-8.66 (m), 7.88-7.76 (m), 7.76-7.67 (m), 7.66-7.53 (m), 7.33-7.02 (m), 6.83-6.68 (m), 6.68-6.52 (m), 6.42-6.27 (m), 5.37-5.22 (m), 5.08-4.94 (m), 4.85-4.69 (m), 4.03-3.90 (m), 3.91-3.71 (m), 3.36-3.31 (m), 3.20-3.08 (m), 3.03-2.88 (m), 2.56-2.35 (m), 2.17-1.99 (m), 1.98-1.78 (m), 1.46-1.35 (m), 1.21-0.92 (m). MS (m/z) 846.1 [M+H]⁺.

Example 27

27

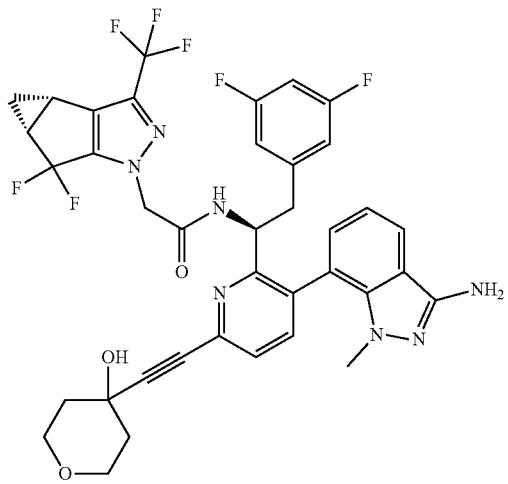

Synthesis of N—((S)-1-(3-(3-amino-1-methyl-1H-indazol-7-yl)-6-((4-hydroxytetrahydro-2H-pyran-4-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (27): The title compound was prepared according to the method presented for the synthesis of compound 25 of Example 25, utilizing 4-ethynyltetrahydro-2H-pyran-4-ol in place of 1-((trimethylsilyl)ethynyl)cyclobutanol and omitting the addition of TBAF. ¹H NMR (400 MHz, methanol-d₄) δ 8.88-8.63 (m), 7.89-7.75 (m), 7.75-7.67 (m), 7.62-7.53 (m), 7.32-7.20 (m), 7.23-7.05 (m), 6.86-6.58 (m), 6.46-6.27 (m), 5.29-5.18 (m), 5.12-4.97 (m), 4.85-4.71 (m), 4.05-3.87 (m), 3.85-3.68 (m), 3.22-3.03 (m), 3.02-2.88 (m), 2.88-2.79 (m), 2.64-2.36 (m), 2.16-2.03 (m), 1.96-1.81 (m), 1.47-1.34 (m), 1.18-1.00 (m). MS (m/z) 768.1 [M+H]⁺.

Example 28

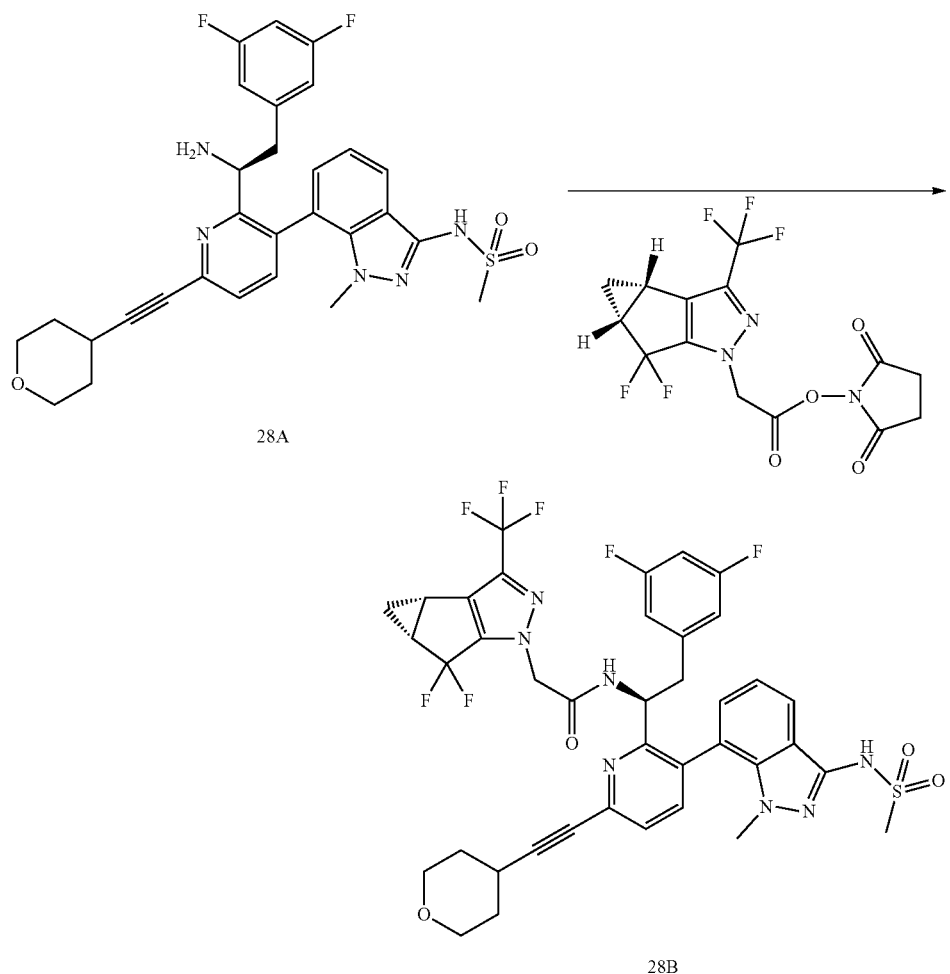

Synthesis of (S)—N-(7-(2-(1-amino-2-(3,5-difluorophenyl)ethyl)-6-((tetrahydro-2H-pyran-4-yl)ethynyl)pyridin-3-yl)-1-methyl-1H-indazol-3-yl)methanesulfonamide (28A): The title compound was prepared according to the method presented for the synthesis of compound 20D of Example 20, utilizing 4-ethynyltetrahydro-2H-pyran in place of 3-((trimethylsilyl)ethynyl)oxetan-3-ol and omitting TBAF. MS (m/z) 566.2 [M+H]+.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(3-(1-methyl-3-(methylsulfonamido)-1H-indazol-7-yl)-6-((tetrahydro-2H-pyran-4-yl)ethynyl)pyridin-2-yl)ethyl)acetamide (28B): A solution of 28A (70 mg, 0.10 mmol) in acetonitrile (1 mL) was treated with 2,5-dioxopyrrolidin-1-yl 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetate (44 mg, 0.11 mmol) for 15 min at rt. After stirring, the reaction mixture was filtered and purified by reverse phase HPLC. Fractions containing the product were pooled and lyophilized to provide the product 28B. 1H NMR (400 MHz, methanol-d4) δ 7.90-7.77 (m), 7.73-7.65 (m), 7.57-7.45 (m), 7.29-7.13 (m), 6.77-6.68 (m), 6.64-6.48 (m), 6.38-6.27 (m), 5.35-5.23 (m), 5.05-4.94 (m), 4.05-3.89 (m), 3.64-3.55 (m), 3.34-3.33 (m), 3.23-3.06 (m), 3.05-2.86 (m), 2.57-2.39 (m), 2.08-1.91 (m), 1.90-1.74 (m), 1.48-1.34 (m), 1.19-1.00 (m). MS (m/z) 830.2 [M+H]+.

Example 29

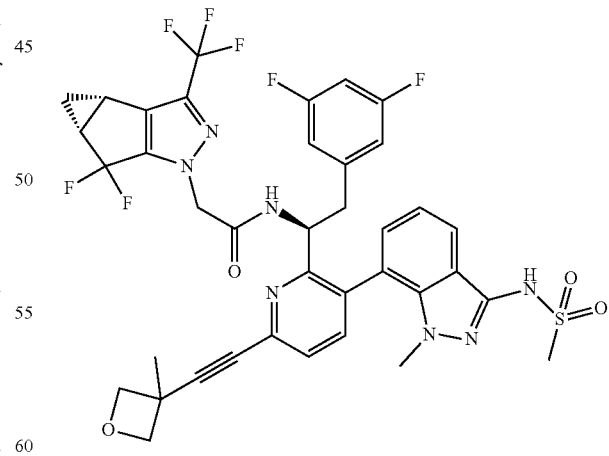

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(3-(1-methyl-3-(methylsulfonamido)-1H-indazol-7-yl)-6-((3-methyloxetan-3-yl)ethynyl)pyridin-2-yl)ethyl)acetamide (29): The title compound was prepared according to the method presented for the synthesis of compound 28B of Example 28, utilizing 3-ethynyl-3-methyloxetane in place of 4-ethynyltetrahydro-2H-pyran-4-ol. $^1$H NMR (400 MHz, methanol-d$_4$) δ 8.81-8.53 (m), 7.89-7.79 (m), 7.74-7.66 (m), 7.60-7.48 (m), 7.32-7.01 (m), 6.80-6.66 (m), 6.66-6.49 (m), 6.41-6.23 (m), 5.39-5.23 (m), 5.06-4.91 (m), 4.64-4.47 (m), 3.79-3.59 (m), 3.35-3.32 (m), 3.24-3.07 (m), 3.05-2.87 (m), 2.60-2.36 (m), 1.93-1.67 (m), 1.50-1.31 (m), 1.20-0.98 (m). MS (m/z) 816.3 [M+H]$^+$.

Example 30

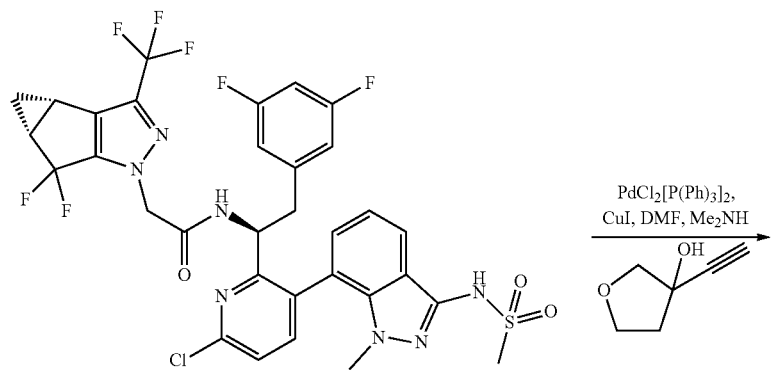

30A

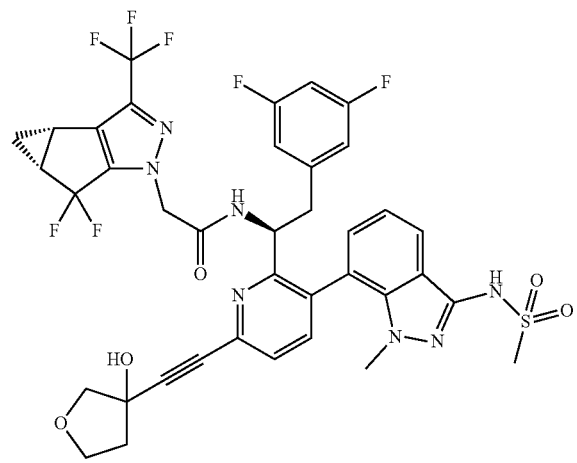

30B

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-((1S)-2-(3,5-difluorophenyl)-1-(6-((3-hydroxytetrahydrofuran-3-yl)ethynyl)-3-(1-methyl-3-(methylsulfonamido)-1H-indazol-7-yl)pyridin-2-yl)ethyl) acetamide (30B): To the reaction vial containing 30A (20 mg, 0.026 mmol) in DMF (1 mL) was added 3-ethynyltetrahydrofuran-3-ol (15 mg, 0.13 mmol), PdCl$_2$[P(Ph)$_3$]$_2$ (1.87 mg, 0.003 mmol), and diethylamine (19 mg, 0.26 mmol). The reaction mixture was flushed with argon gas for 5 min then sealed and heated in a microwave reactor to 125° C. for 15 min. Upon cooling, the reaction mixture was filtered and purified by reverse phase HPLC. Fractions containing the product were pooled and lyophilized to provide the title compound 30B. $^1$H NMR (400 MHz, methanol-d$_4$) δ 8.79-8.65 (m), 7.90-7.79 (m), 7.75-7.66 (m), 7.63-7.51 (m), 7.32-7.06 (m), 6.77-6.67 (m), 6.58-6.48 (m), 6.41-6.19 (m), 5.36-5.26 (m), 5.08-4.92 (m), 4.81-4.62 (m), 4.18-4.03 (m), 4.02-3.93 (m), 3.35-3.32 (m), 3.20-3.05 (m), 3.03-2.84 (m), 2.61-2.41 (m), 2.41-2.29 (m), 1.47-1.35 (m), 1.21-0.96 (m). MS (m/z) 832.1 [M+H]$^+$.

Example 31

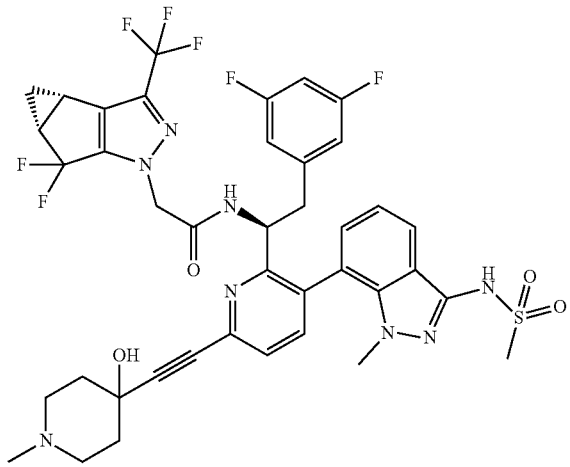

31

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-((4-hydroxy-1-methylpiperidin-4-yl)ethynyl)-3-(1-methyl-3-(methylsulfonamido)-1H-indazol-7-yl)pyridin-2-yl)ethyl)acetamide (31): The title compound (31) was prepared according to the method presented for the synthesis of compound 30B of Example 30 utilizing 4-ethynyl-1-methylpiperidin-4-ol. $^1$H NMR (400 MHz, Methanol-$d_4$) δ 8.70 (d, J=8.1 Hz, 1H), 7.93-7.82 (m, 3H), 7.79-7.63 (m, 5H), 7.57 (dd, 2H), 7.32-7.14 (m, 2H), 7.14-7.05 (m 2H), 6.79-6.67 (m, 2H), 6.68-6.46 (m, 3H), 6.33 (dd, 7H), 5.29 (dd, 1H), 5.00 (q, 2H), 4.81-4.69 (m, 6H), 3.69 (d, 2H), 3.57-3.36 (m, 11H), 3.15 (dd, 1211), 3.04-2.84 (m, 16H), 2.48 (ddd, 4H), 2.36-2.25 (m, 7H), 2.20-2.07 (m, 2H), 1.40 (dt, 3H), 1.09 (d, 3H). MS (m/z) 859.30 [M+H]$^+$.

Example 32

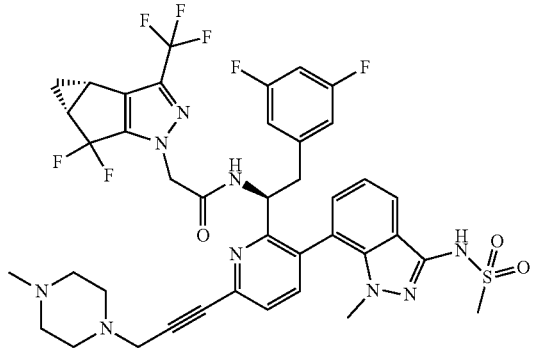

32

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(3-(1-methyl-3-(methylsulfonamido)-1H-indazol-7-yl)-6-(3-(4-methylpiperazin-1-yl)prop-1-yn-1-yl)pyridin-2-yl)ethyl)acetamide (32): The title compound was prepared according to the method presented for the synthesis of compound 30B of Example 30, utilizing 1-methyl-4-(prop-2-yn-1-yl)piperazine in place of 3-ethynyltetrahydrofuran-3-ol. $^1$H NMR (400 MHz, methanol-$d_4$) δ 8.72-8.54 (m), 7.91-7.79 (m), 7.78-7.67 (m), 7.65-7.50 (m), 7.31-7.00 (m), 6.84-6.57 (m), 6.57-6.47 (m), 6.42-6.19 (m), 5.38-5.22 (m), 5.04-4.93 (m), 4.82-4.67 (m), 3.92-3.70 (m), 3.34-3.31 (m), 3.21-3.10 (m), 3.01-2.88 (m), 2.58-2.37 (m), 1.50-1.34 (m), 1.16-1.02 (m). MS (m/z) 858.2 [M+H]$^+$.

Example 33

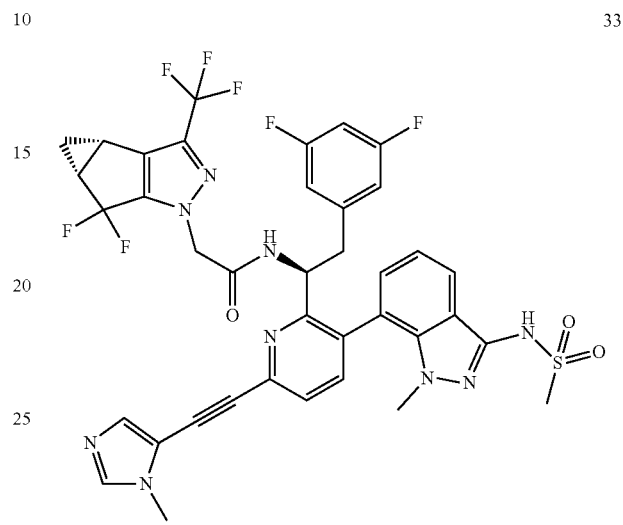

33

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-((1-methyl-1H-imidazol-5-yl)ethynyl)-3-(1-methyl-3-(methylsulfonamido)-1H-indazol-7-yl)pyridin-2-yl)ethyl)acetamide (33): The title compound was prepared according to the method presented for the synthesis of compound 30B of Example 30, utilizing 5-ethynyl-1-methyl-1H-imidazole in place of 3-ethynyltetrahydrofuran-3-ol. $^1$H NMR (400 MHz, methanol-$d_4$) δ 8.93-8.82 (m), 8.80-8.61 (m), 8.03-7.69 (m), 7.37-7.04 (m), 6.82-6.67 (m), 6.67-6.57 (m), 6.45-6.30 (m), 5.40-5.25 (m), 5.10-4.98 (m), 4.82-4.65 (m), 4.15-3.94 (m), 3.35 (s, OH), 3.24-3.11 (m), 3.06-2.88 (m), 2.59-2.33 (m), 1.52-1.31 (m), 1.19-0.91 (m). MS (m/z) 826.1 [M+H]$^+$.

Example 34

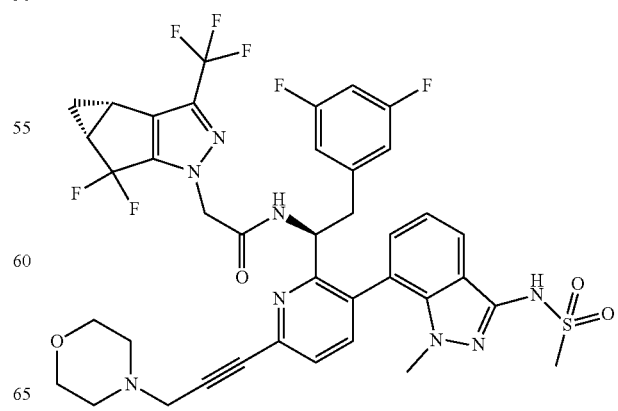

34

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(3-(1-methyl-3-(methylsulfonamido)-1H-indazol-7-yl)-6-(3-morpholinoprop-1-yn-1-yl)pyridin-2-yl)ethyl)acetamide (34): The title compound was prepared according to the method presented for the synthesis of compound 30B of Example 30, utilizing 4-(prop-2-yn-1-yl)morpholine in place of 3-ethynyltetrahydrofuran-3-ol. $^1$H NMR (400 MHz, methanol-d$_4$) δ 8.77-8.59 (m), 7.97-7.61 (m), 7.33-7.06 (m), 6.82-6.52 (m), 6.43-6.28 (m), 5.35-5.23 (m), 5.08-4.99 (m), 4.80-4.73 (m), 4.50-4.33 (m), 4.06-3.92 (m), 3.55-3.45 (m), 3.34-3.32 (m), 3.20-3.10 (m), 3.02-2.87 (m), 2.62-2.35 (m), 1.49-1.35 (m), 1.17-0.98 (m). MS (m/z) 845.1 [M+H]$^+$.

Example 35

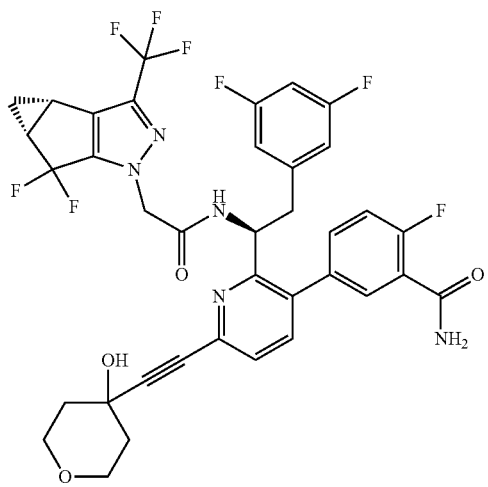

Synthesis of 5-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-((4-hydroxytetrahydro-2H-pyran-4-yl)ethynyl)pyridin-3-yl)-2-fluorobenzamide (35): The title compound (35) was prepared according to the method presented for the synthesis of compound 26 of Example 26 utilizing (3-carbamoyl-4-fluorophenyl)boronic acid. $^1$H NMR (400 MHz, methanol-d$_4$) δ 7.61-7.46 (m), 7.44-7.29 (m), 7.27-7.17 (m), 6.72-6.60 (m), 6.40-6.28 (m), 5.42-5.29 (m), 4.86 (s, OH), 4.01-3.89 (m), 3.85-3.72 (m), 3.15-2.96 (m), 2.58-2.40 (m), 2.16-2.00 (m), 1.95-1.77 (m), 1.48-1.33 (m), 1.20-1.00 (m). MS (m/z) 760.2 [M+H]$^+$.

Example 36

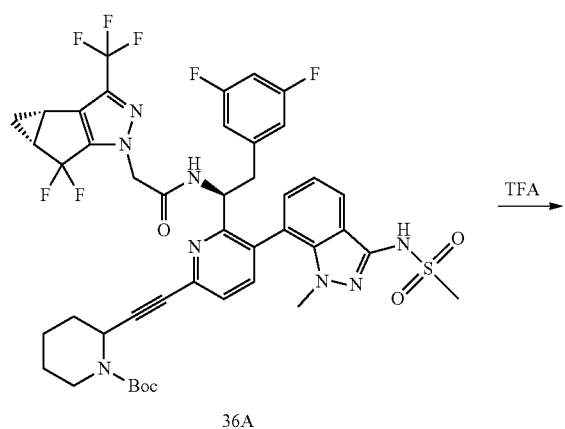

36A

TFA →

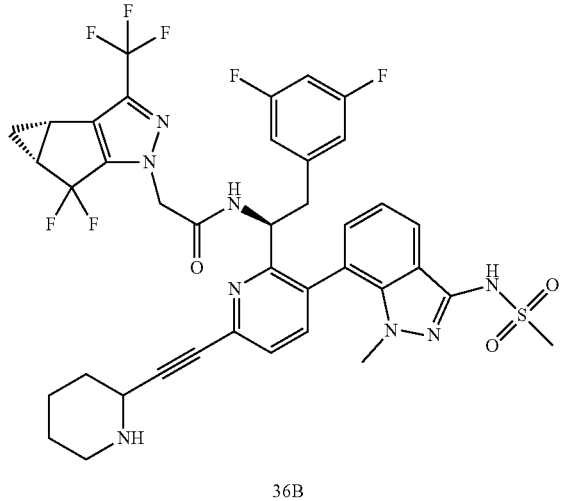

36B

Synthesis of tert-butyl 2-((6-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-5-(1-methyl-3-(methylsulfonamido)-1H-indazol-7-yl)pyridin-2-yl)ethynyl)piperidine-1-carboxylate (36A): The title compound was prepared according to the method presented for the synthesis of compound 30B of Example 30, utilizing tert-butyl 2-ethynylpiperidine-1-carboxylate in place of 3-ethynyltetrahydrofuran-3-ol. MS (m/z) 929.0 [M+H]$^+$.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-((1S)-2-(3,5-difluorophenyl)-1-(3-(1-methyl-3-(methylsulfonamido)-1H-indazol-7-yl)-6-(piperidin-2-ylethynyl)pyridin-2-yl)ethyl)acetamide (36B): To the reaction vial containing 36B (30 mg, 0.03 mmol) in DCM (1 mL) was added TFA (1 mL) The reaction mixture was stirred for 1 h at rt, concentrated, filtered and purified by reverse phase HPLC, eluting with 5-100% acetonitrile in water with 0.1% TFA. Fractions containing the product were pooled and lyophilized to provide the TFA salt of the title compound 36B. $^1$H NMR (400 MHz, methanol-d$_4$) δ 8.76-8.64 (m), 7.95-7.73 (m), 7.71-7.55 (m), 7.33-7.05 (m), 6.83-6.59 (m), 6.61-6.50 (m), 6.44-6.19 (m), 5.32-5.23 (m), 5.07-4.94 (m), 4.81-4.72 (m), 4.65-4.47 (m), 3.57-3.46 (m), 3.33-3.32 (m), 3.26-3.08 (m), 3.01-2.87 (m), 2.58-2.37 (m), 2.34-2.24 (m), 2.04 (s, OH), 1.95-1.68 (m), 1.51-1.31 (m), 1.21-0.98 (m). MS (m/z) 829.3 [M+H]$^+$.

Example 37

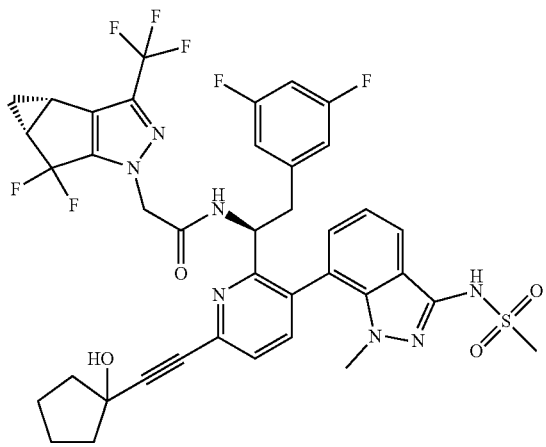

37

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-((1-hydroxycyclopentyl)ethynyl)-3-(1-methyl-3-(methylsulfonamido)-1H-indazol-7-yl)pyridin-2-yl)ethyl)acetamide (37): The title compound was prepared according to the method presented for the synthesis of compound 30B of Example 30, utilizing 1-ethynylcyclopentanol in place of 3-ethynyltetrahydrofuran-3-ol. $^1$H NMR (400 MHz, methanol-d$_4$) δ 8.80-8.61 (m), 7.91-7.80 (m), 7.76-7.65 (m), 7.60-7.44 (m), 7.31-7.17 (m), 7.14-7.05 (m), 6.85-6.46 (m), 6.47-6.22 (m), 5.38-5.23 (m), 5.03-4.93 (m), 4.81-4.71 (m), 3.34-3.32 (m), 3.24-3.06 (m), 3.03-2.86 (m), 2.56-2.36 (m), 2.16-2.02 (m), 1.97-1.76 (m), 1.48-1.31 (m), 1.20-1.00 (m). MS (m/z) 830.2 [M+H]$^+$.

Example 38

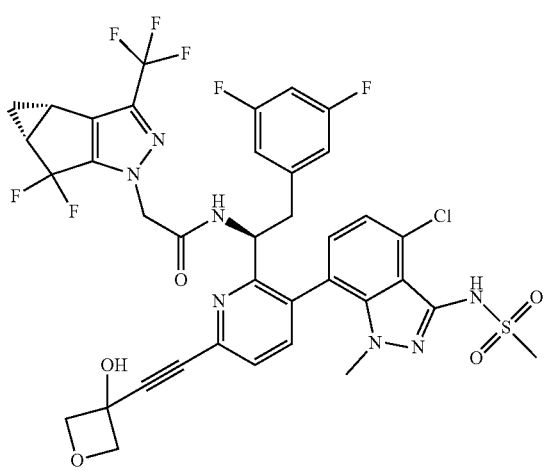

38

Synthesis of N—((S)-1-(3-(4-chloro-1-methyl-3-(methylsulfonamido)-1H-indazol-7-yl)-6-((3-hydroxyoxetan-3-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (38): The title compound (38) was prepared according to the method presented for the synthesis of compound 20E of Example 20 utilizing N-(4-chloro-1-methyl-7-(4,4,5,5-tetramethyl-1,3,2-dioxaborolan-2-yl)-1H-indazol-3-yl)methanesulfonamide in place of 20B. $^1$H NMR (400 MHz, methanol-d$_4$) δ 8.82-8.67 (m), 7.79-7.68 (m), 7.66-7.55 (m), 7.28-7.13 (m), 7.12-7.03 (m), 6.83-6.71 (m), 6.69-6.61 (m), 6.47-6.25 (m), 5.34-5.21 (m), 5.04-4.93 (m), 4.81-4.73 (m), 3.35-3.32 (m), 3.27-3.22 (m), 3.21-3.11 (m), 3.06-2.92 (m), 2.57-2.38 (m), 1.46-1.32 (m), 1.16-1.00 (m). MS (m/z) 852.1 [M+H]$^+$.

Example 39

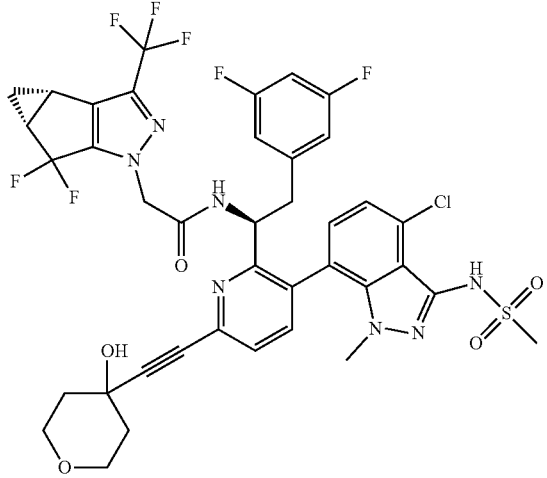

39

Synthesis of N—((S)-1-(3-(4-chloro-1-methyl-3-(methylsulfonamido)-1H-indazol-7-yl)-6-((4-hydroxytetrahydro-2H-pyran-4-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (39): The title compound (39) was prepared according to the method presented for the synthesis of compound 38 of Example 38 utilizing 4-ethynyltetrahydro-2H-pyran-4-ol in place of 3-((trimethylsilyl)ethynyl)oxetan-3-ol and omitting TBAF. $^1$H NMR (400 MHz, methanol-d$_4$) δ 8.88-8.74 (m), 7.76-7.65 (m), 7.65-7.50 (m), 7.23-7.12 (m), 7.11-7.03 (m), 6.83-6.58 (m), 6.50-6.28 (m), 5.32-5.22 (m), 5.03-4.95 (m), 4.83-4.70 (m), 4.03-3.88 (m), 3.83-3.72 (in), 3.35-3.33 (m), 3.27-3.22 (m), 3.20-3.10 (m), 3.07-2.93 (m), 2.62-2.39 (m), 2.15-2.04 (m), 1.98-1.83 (m), 1.47-1.30 (m), 1.19-1.03 (m). MS (m/z) 880.1 [M+H]$^+$.

Example 40

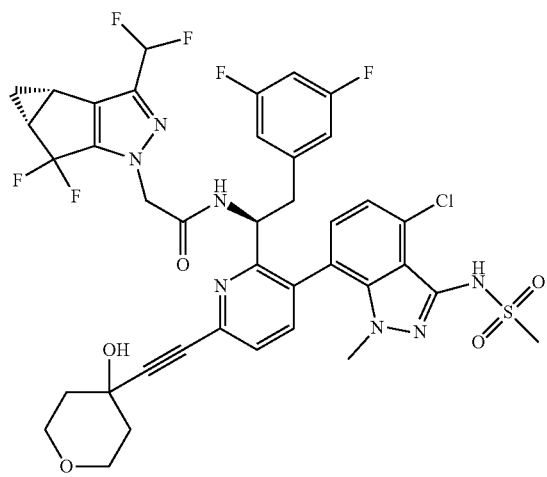

40

Synthesis of N—((S)-1-(3-(4-chloro-1-methyl-3-(methylsulfonamido)-1H-indazol-7-yl)-6-((4-hydroxytetrahydro-2H-pyran-4-yl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (40): The title compound (40) was prepared according to the method presented for the synthesis of compound 39 of Example 38 utilizing 2-((3bS,4aR)-5,5-difluoro-3-(difluoromethyl)-3b,4,4a,5-tetrahydro-1H-cyclopropa[3,4]cyclopenta[1,2-c]pyrazol-yl)acetic acid in place of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. $^1$H NMR (400 MHz, methanol-$d_4$) δ 8.77-8.62 (m), 7.79-7.65 (m), 7.63-7.54 (m), 7.16-7.01 (m), 6.88-6.49 (m), 6.49-6.32 (m), 5.33-5.22 (m), 5.08-4.91 (m), 4.81-4.65 (m), 4.00-3.88 (m), 3.86-3.72 (m), 3.35-3.33 (m), 3.26-3.21 (m), 3.21-3.07 (m), 3.06-2.91 (m), 2.77-2.62 (m), 2.51-2.37 (m), 2.14-2.00 (m), 1.96-1.83 (m), 1.77-1.52 (m), 1.44-1.28 (m), 1.08-0.86 (m), 0.72-0.56 (m). MS (m/z) 862.0 [M+H]$^+$.

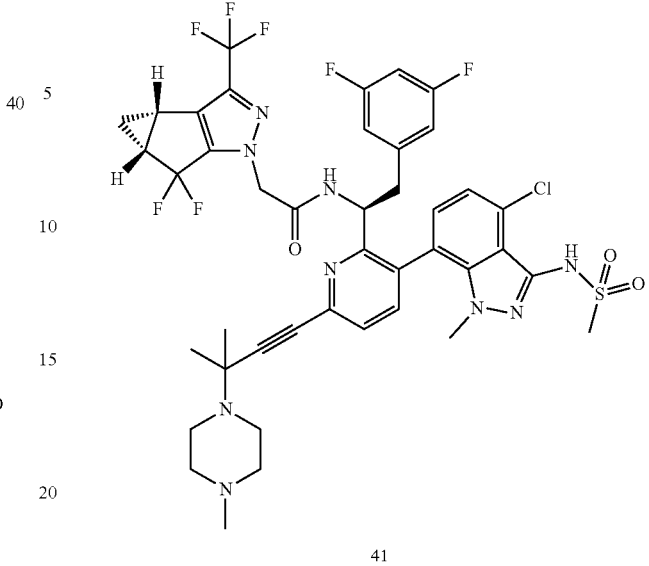

41

Synthesis of N—((S)-1-(3-(4-chloro-1-methyl-3-(methylsulfonamido)-1H-indazol-7-yl)-6-(3-methyl-3-(4-methylpiperazin-1-yl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (41): Argon was bubbled through a solution of 2-methylbut-3-yn-2-yl acetate (15.96 mg, 126.5 μmol), copper(I) chloride (0.25 mg, 2.53 μmol), triethylamine (17.63 μl, 126.5 μmol), and n-methylpiperazine (21.05 μl, 189.74 μmol) in DMF (0.4 ml). The mixture was sealed and heated in a microwave reactor at 110° C. for 5 minutes. To resulting mixture was added 43F (20 mg, 25.3 μmol), Cu(I) iodide (0.5 mg, 2.5 μmol), and Pd(Cl$_2$)(Ph$_3$)$_2$ (1.8 mg, 2.5 μmol). Argon was bubbled through the reaction and diethylamine (39.4 μl, 379 μmol) was added. The mixture was heated in a microwave reactor for 15 minutes at 125° C. The excess amines were removed under vacuum and the product was purified by reverse phase HPLC to give the title compound 41 as a mixture of atropisomers. $^1$H NMR (400 MHz, Methanol-$d_4$) δ 8.79-8.71 (m), 7.86-7.75 (m), 7.74-7.65 (m), 7.61-7.52 (m), 7.22-7.14 (m), 7.07 (d), 6.82-6.73 (m), 6.70-6.60 (m), 6.48-6.41 (m), 6.41-6.31 (m), 5.34-5.20 (m), 5.03-4.92 (m), 4.82-4.70 (m), 3.32 (s), 3.26 (s), 3.23 (s), 3.18-3.10 (m), 3.05-2.94 (m), 2.92 (s), 2.59-2.37 (m), 1.60 (s), 1.48-1.35 (m), 1.17-1.10 (m), 1.10-1.01 (m). MS (m/z) 920.3 [M+H]$^+$.

Example 41

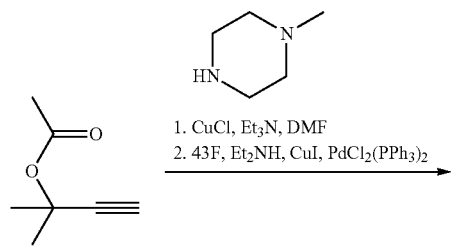

1. CuCl, Et$_3$N, DMF
2. 43F, Et$_2$NH, CuI, PdCl$_2$(PPh$_3$)$_2$

Example 42

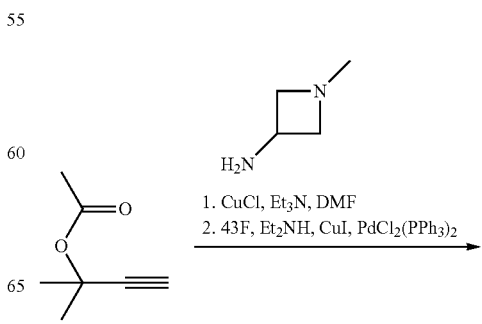

1. CuCl, Et$_3$N, DMF
2. 43F, Et$_2$NH, CuI, PdCl$_2$(PPh$_3$)$_2$

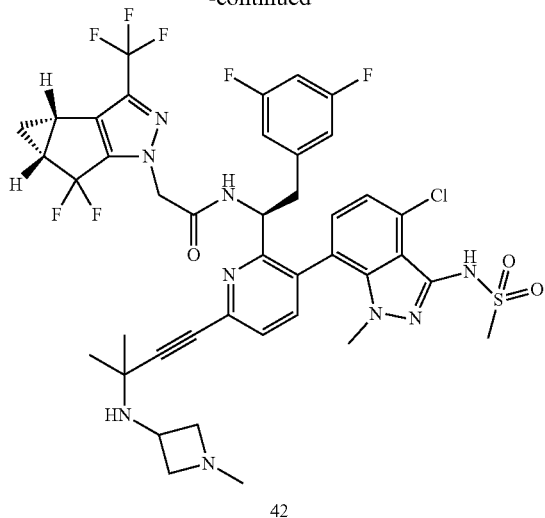

42

Synthesis of N—((S)-1-(3-(4-chloro-1-methyl-3-(methylsulfonamido)-1H-indazol-7-yl)-6-(3-methyl-3-((1-methylazetidin-3-yl)amino)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (42): The title compound (42) was prepared as a mixture of atropisomers according to the method presented for the synthesis of compound 41 of Example 41 utilizing 1-methylazetidin-3-amine. $^1$H NMR (400 MHz, cd$_3$od) δ 8.77-8.68 (m), 7.87-7.74 (m), 7.74-7.60 (m), 7.59-7.48 (m), 7.20-7.14 (m), 7.07 (d), 6.83-6.73 (m), 6.70-6.61 (m), 6.49-6.41 (m), 6.41-6.33 (m), 5.30-5.18 (m), 5.02-4.91 (m), 4.79-4.72 (m), 3.32 (s), 3.25 (s), 3.23 (s), 3.19-3.08 (m), 3.06-2.95 (m), 2.59-2.41 (m), 2.11-1.68 (m), 1.49-1.34 (m), 1.17-1.08 (m), 1.08-1.01 (m). MS (m/z) 906.3 [M+H]$^+$.

Example 43

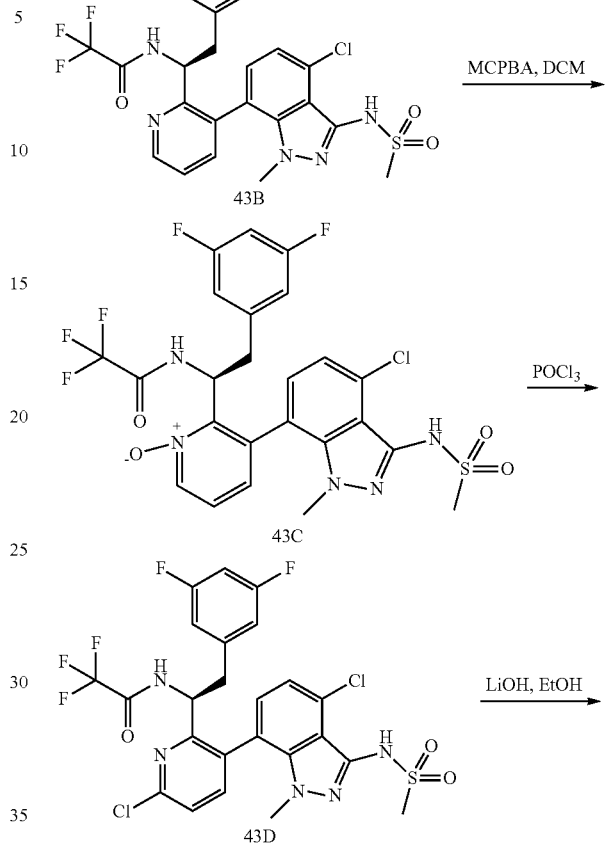

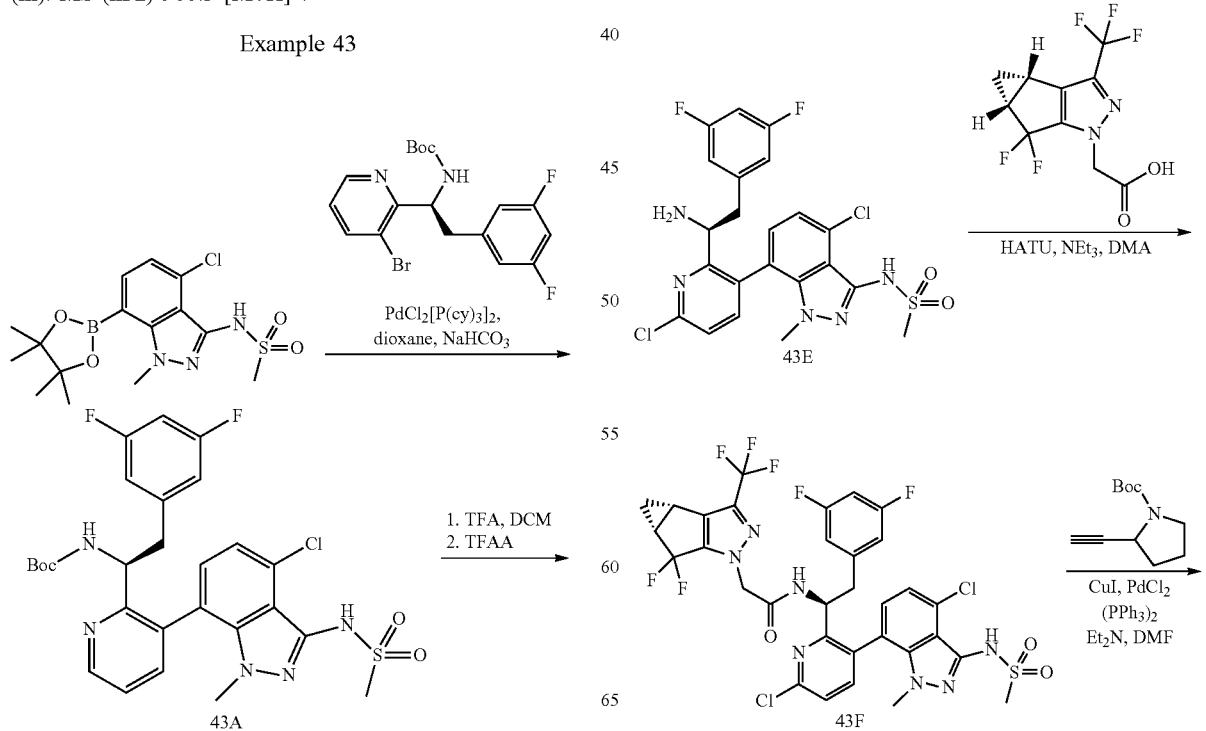

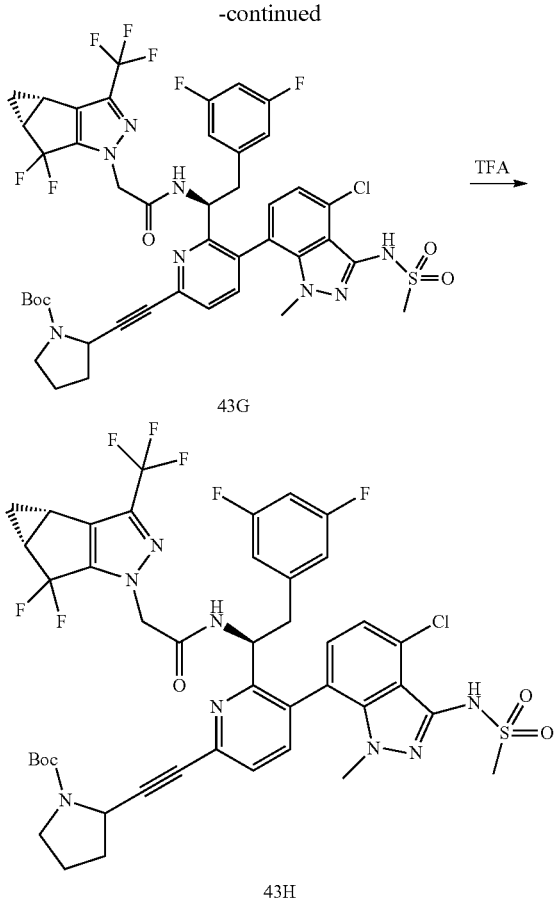

43G

43H

Synthesis of (S)-tert-butyl(1-(3-(4-chloro-1-methyl-3-(methylsulfonamido)-1H-indazol-7-yl)pyridin-2-yl)-2-(3,5-difluorophenyl)ethyl)carbamate (43A): (S)-tert-butyl(1-(3-bromopyridin-2-yl)-2-(3,5-difluorophenyl)ethyl)carbamate (1.0 g, 2.42 mmol), N-(4-chloro-1-methyl-7-(4,4,5,5-tetramethyl-1,3,2-dioxaborolan-2-yl)-1H-indazol-3-yl)methanesulfonamide (1.12 g, 2.90 mmol), and PdCl$_2$[P(cy)$_3$]$_2$ (89.0 mg, 0.121 mmol) were suspended in 1,4-dioxane (12 mL) and 1.0 M aqueous NaHCO$_3$ (4 mL). The reaction mixture was degassed by bubbling argon for 5 minutes then sealed and heated 150° C. for 15 minutes in a microwave reactor. Upon cooling, the reaction mixture was diluted with water and extracted with three portions of EtOAc. The combined organic layers were dried over Na$_2$SO$_4$, filtered, concentrated in vacuo, and purified by silica gel column chromatography to give the title compound 43A. MS (m/z) 591.72 [M+H]$^+$.

Synthesis of (S)—N-(1-(3-(4-chloro-1-methyl-3-(methylsulfonamido)-1H-indazol-7-yl)pyridin-2-yl)-2-(3,5-difluorophenyl)ethyl)-2,2,2-trifluoroacetamide (43B): To (S)-tert-butyl(1-(3-(4-chloro-1-methyl-3-(methylsulfonamido)-1H-indazol-7-yl)pyridin-2-yl)-2-(3,5-difluorophenyl)ethyl)carbamate (43A, 3.39 g, 5.73 mmol) in DCM (5 mL) was added trifluoroacetic acid (5 mL). The reaction mixture was stirred at room temperature for 2.5 hours. Upon complete removal of the Boc protecting group, trifluoroacetic anhydride (2.02 mL, 14.31 mmol) was added. The reaction mixture was stirred at room temperature for 30 minutes. Upon completion, the reaction mixture was filtered through celite, concentrated in vacuo, taken in EtOAc, and carefully neutralized with 1M aqueous NaHCO$_3$ until the aqueous layer was at pH 10. The organic layer was collected and the aqueous layer extracted once more with EtOAc. The combined organic layers were dried over Na$_2$SO$_4$, filtered, concentrated in vacuo, and purified by silica gel column chromatography to give the title compound 43B. MS (m/z) 588.14 [M+H]$^+$.

Synthesis of (S)-3-(4-chloro-1-methyl-3-(methylsulfonamido)-1H-indazol-7-yl)-2-(2-(3,5-difluorophenyl)-1-(2,2,2-trifluoroacetamido)ethyl)pyridine 1-oxide (43C): To a solution of (S)—N-(1-(3-(4-chloro-1-methyl-3-(methylsulfonamido)-1H-indazol-7-yl)pyridin-2-yl)-2-(3,5-difluorophenyl)ethyl)-2,2,2-trifluoroacetamide (43B, 8.0 g, 13.61 mmol) in DCM (70 mL) was added MCPBA (3.659 g, 16.33 mmol) in 4 portions over a 15 minute period. The reaction mixture was stirred at room temperature for 16 hours. Upon completion, the reaction was quenched with 1M aqueous NaHSO$_3$ and saturated aqueous NaHCO$_3$. The organic layer was collected and the aqueous layer was extracted an additional time with DCM. The combined organic layers were dried over Na$_2$SO$_4$, filtered, concentrated in vacuo, and purified by silica gel column chromatography to give the title compound 43C. MS (m/z) 604.10 [M+H]$^+$.

Synthesis of (S)—N-(1-(6-chloro-3-(4-chloro-1-methyl-3-(methylsulfonamido)-1H-indazol-7-yl)pyridin-2-yl)-2-(3,5-difluorophenyl)ethyl)-2,2,2-trifluoroacetamide (43D): (S)-3-(4-chloro-1-methyl-3-(methylsulfonamido)-1H-indazol-7-yl)-2-(2-(3,5-difluorophenyl)-1-(2,2,2-trifluoroacetamido)ethyl)pyridine 1-oxide (43C, 1.0 g, 1.66 mmol) was taken in POCl$_3$ (2.32 mL, 24.84 mmol). The reaction mixture was stirred at 115° C. for 2 hours. Upon cooling, the reaction was concentrated in vacuo, taken in DCM, and vigorously stirred with saturated aqueous NaHCO$_3$ for 1 hour. The organic layer was collected, and the aqueous layer was extracted an additional time with DCM. The combined organic layers were dried over Na$_2$SO$_4$, filtered, concentrated in vacuo, and purified by silica gel column chromatography to give the title compound 43D. MS (m/z) 622.13 [M+H]$^+$.

Synthesis of (S)—N-(7-(2-(1-amino-2-(3,5-difluorophenyl)ethyl)-6-chloropyridin-3-yl)-4-chloro-1-methyl-1H-indazol-3-yl)methanesulfonamide (43E): To a solution of (S)—N-(1-(6-chloro-3-(4-chloro-1-methyl-3-(methylsulfonamido)-1H-indazol-7-yl)pyridin-2-yl)-2-(3,5-difluorophenyl)ethyl)-2,2,2-trifluoroacetamide (43D, 870 mg, 1.40 mmol) in EtOH (16 mL) was added 2M aqueous LiOH (7.0 mL, 13.98 mmol). The reaction was heated at 130° C. for 10 minutes. Upon cooling, the reaction mixture was acidified with 2N aqueous HCl until at pH 5. The reaction mixture was then concentrated in vacuo and taken in EtOAc. To the solution was added saturated aqueous NaHCO$_3$ until the aqueous layer was at pH 10. The organic layer was collected, and the aqueous layer was extracted an additional time with EtOAc. The combined organic layers were dried over Na$_2$SO$_4$, filtered, concentrated in vacuo to give the title compound 43E which was used without further purification. MS (m/z) 526.06 [M+H]$^+$.

Synthesis of N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (43F): The title compound (43F) was prepared according to the method presented for the synthesis of compound 10A of Example 10 utilizing 43E. MS (m/z) 790.0 [M+H]$^+$.

Synthesis of tert-butyl 2-((5-(4-chloro-1-methyl-3-(methylsulfonamido)-1H-indazol-7-yl)-6-((S)-1-(2-((3bS,4aR)-5, 5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-2-yl)ethynyl)pyrrolidine-1-carboxylate (43G): To a reaction vial containing 43F (20 mg, 0.025 mmol) in DMF (1 mL) was added tert-butyl 2-ethynylpyrrolidine-1-carboxylate (15 mg, 0.076 mmol), PdCl2(P(Ph3)2 (1.8 mg, 0.003 mmol), and diethylamine (19 mg, 0.25 mmol). The reaction mixture was flushed with argon gas for 2 min then heated in a microwave reactor at 125° C. for 15 min. Upon cooling, the reaction mixture was filtered and the eluent concentrated in vacuo. The residue was partitioned between EtOAc and water. The organics were separated, dried and removed in vacuo. The residue was purified by column chromatography on silica to provide the desired product. MS (m/z) 949.1 [M+H]+.

Synthesis of N-((1S)-1-(3-(4-chloro-1-methyl-3-(methylsulfonamido)-1H-indazol-7-yl)-6-(pyrrolidin-2-ylethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (43H): tert-butyl 2-((5-(4-chloro-1-methyl-3-(methylsulfonamido)-1H-indazol-7-yl)-6-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-2-yl)ethynyl)pyrrolidine-1-carboxylate (20 mg) was dissolved in DCM and treated with TFA (0.5 mL). After 30 min stirring at ambient temperature, the solvents were removed in vacuo. The crude mixture was purified by RP HPLC to provide the desired product. 1H NMR (400 MHz, Methanol-d4) δ 7.97 (s), 7.78 (dd), 7.65 (dd), 7.25-7.13 (m), 7.07 (d), 6.78 (t), 6.65 (s), 6.42 (d), 6.39-6.31 (m), 5.25 (dd), 4.99 (t), 4.81-4.70 (m), 3.59-3.36 (in), 3.24 (d), 3.19-3.08 (m), 3.08-2.90 (m), 2.86 (d), 2.62-2.35 (m), 2.35-2.13 (m), 1.41 (dt), 1.16-1.01 (m).
MS (m/z) 849.2 [M+H]+.

Example 44

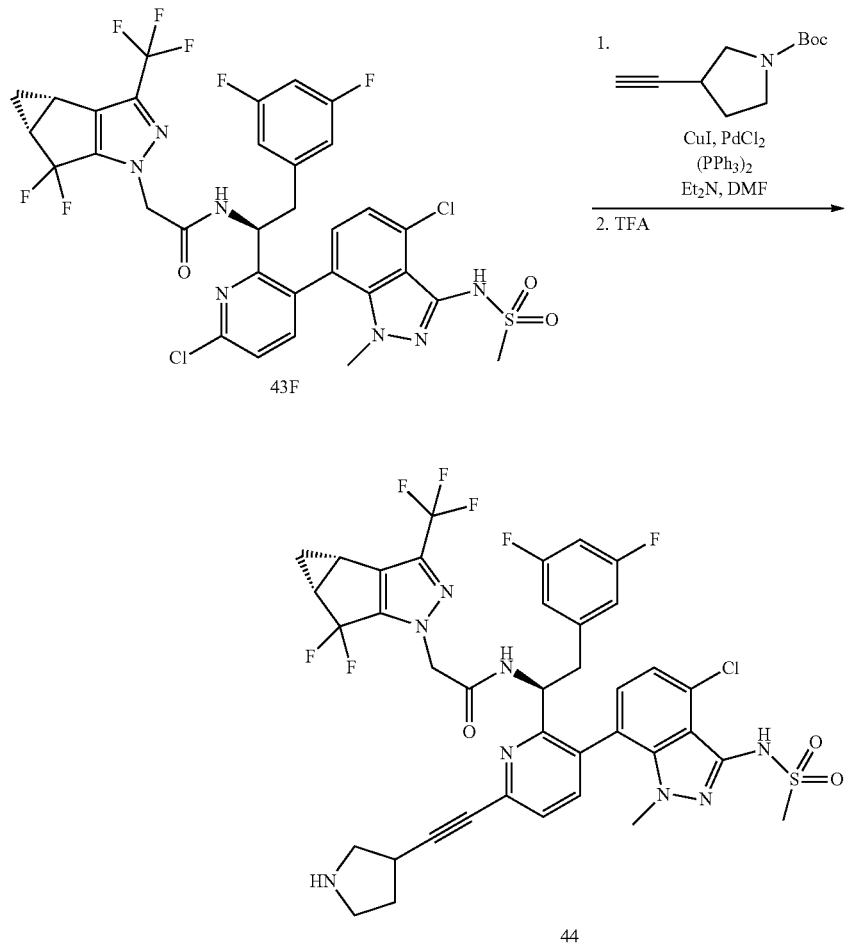

Synthesis of N-((1S)-1-(3-(4-chloro-1-methyl-3-(methylsulfonamido)-1H-indazol-7-yl)-6-(pyrrolidin-3-ylethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (44): The title compound (44) was prepared according to the method presented for the synthesis of compound 43H of Example 43 utilizing tert-butyl 3-ethynylpyrrolidine-1-carboxylate. 1H NMR (400 MHz, Methanol-d4) δ 8.66 (t), 7.72 (dd), 7.56 (dd), 7.18 (d), 7.06 (d), 6.78 (t), 6.64 (s), 6.39 (dd), 5.26 (d), 5.04-4.92 (m), 4.81-4.66 (m), 3.75-3.52 (m), 3.44 (dt), 3.24 (d), 3.20-3.09 (m), 3.07-2.93 (m), 2.86 (d), 2.50 (dt), 2.28 (dd), 1.42 (dd), 1.10 (d). MS (m/z) 849.1 [M+H]+.

Example 45

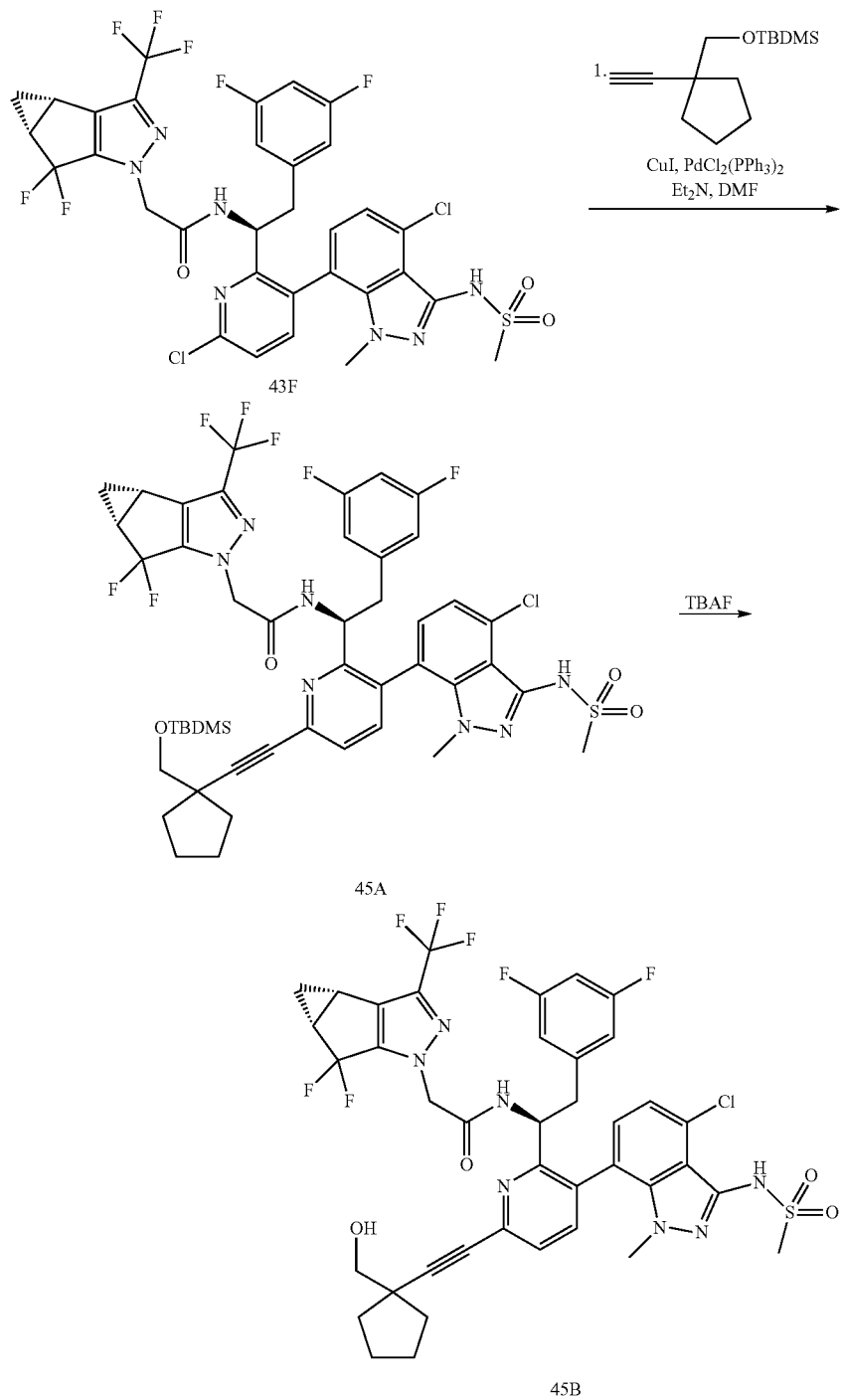

Synthesis of N—((S)-1-(6-((1-(((tert-butyldimethylsilyl)oxy)methyl)cyclopentyl)ethynyl)-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (45A): The title compound (44) was prepared according to the method presented for the synthesis of compound 43G of Example 43 utilizing tert-butyl((1-ethynylcyclopentyl)methoxy)dimethylsilane (prepared as described in US2012/214762). It was used in the following reaction without purification.

Synthesis of N—((S)-1-(3-(4-chloro-1-methyl-3-(methylsulfonamido)-1H-indazol-7-yl)-6-((1-(hydroxymethyl)cyclopentyl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]

pyrazol-1-yl)acetamide (45B): To compound 45A (20 mg, 0.02 mmol) in THF (1 mL) was added TBAF (1 mL). Solvents were removed in vacuo and the residue was purified by RP HPLC to provide the desired product. $^1$H NMR (400 MHz, Chloroform-d) δ 7.56-7.31 (m), 7.15 (q), 6.89 (d), 6.47 (t), 6.22 (d), 6.05 (d), 5.52 (q), 4.76 (d), 4.72 (d), 3.66 (s), 3.54 (d), 3.39 (d), 3.03 (s), 3.00-2.89 (m), 2.49 (s), 2.13-2.01 (m), 1.87 (dt), 1.75 (s), 1.49-1.37 (m), 1.30 (d), 1.19 (s), 0.90 (q). MS (m/z) 878.2 [M+H]$^+$.

Example 46

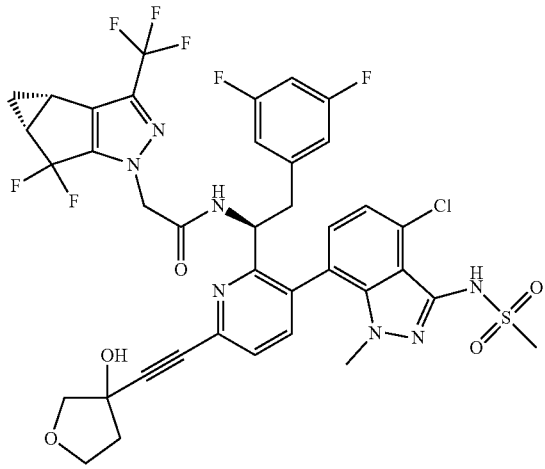

Synthesis of N-((1S)-1-(3-(4-chloro-1-methyl-3-(methyl-sulfonamido)-1H-indazol-7-yl)-6-((3-hydroxytetrahydrofuran-3-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (46): The title compound (46) was prepared according to the method presented for the synthesis of compound 43G of Example 43 utilizing 3-ethynyltetrahydrofuran-3-ol in place of tert-butyl 2-ethynylpyrrolidine-1-carboxylate. $^1$H NMR (400 MHz, methanol-d$_4$) δ 8.83-8.67 (m), 7.77-7.64 (m), 7.62-7.53 (m), 7.24-7.01 (m), 6.83-6.55 (m), 6.49-6.28 (m), 5.35-4.92 (m), 4.80-4.67 (m), 4.15-4.03 (m), 4.00-3.92 (m), 3.34-3.32 (m), 3.26-3.21 (m), 3.20-3.07 (m), 3.06-2.87 (m), 2.60-2.43 (m), 2.39-2.27 (m), 1.52-1.35 (m), 1.15-1.03 (m). MS (m/z) 866.1 [M+H]$^+$.

Example 47

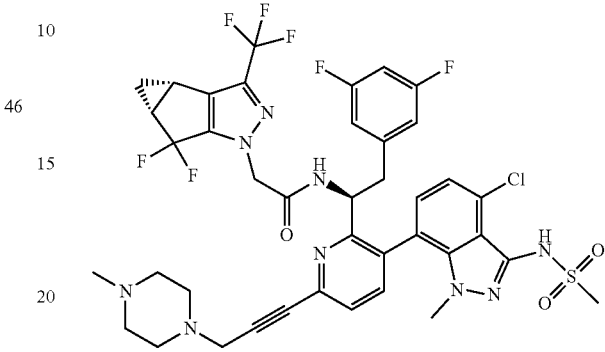

Synthesis of N—((S)-1-(3-(4-chloro-1-methyl-3-(methyl-sulfonamido)-1H-indazol-7-yl)-6-(3-(4-methylpiperazin-1-yl)prop-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (47): The title compound (47) was prepared according to the method presented for the synthesis of compound 43G of Example 43 utilizing 2-ethynylmorpholine in place of tert-butyl 2-ethynylpyrrolidine-1-carboxylate. $^1$H NMR (400 MHz, methanol-d$_4$) δ 8.74-8.56 (m), 7.80-7.64 (m), 7.62-7.48 (m), 7.22-6.98 (m), 6.84-6.57 (m), 6.49-6.30 (m), 5.32-4.92 (m), 4.78-4.72 (m), 3.88-3.73 (m), 3.56 (s, OH), 3.34-3.32 (m), 3.27-3.10 (m), 3.05-2.90 (m), 2.84-2.66 (m), 2.61-2.37 (m), 1.53-1.32 (m), 1.19-0.97 (m). MS (m/z) 892.3 [M+H]$^+$.

Example 48

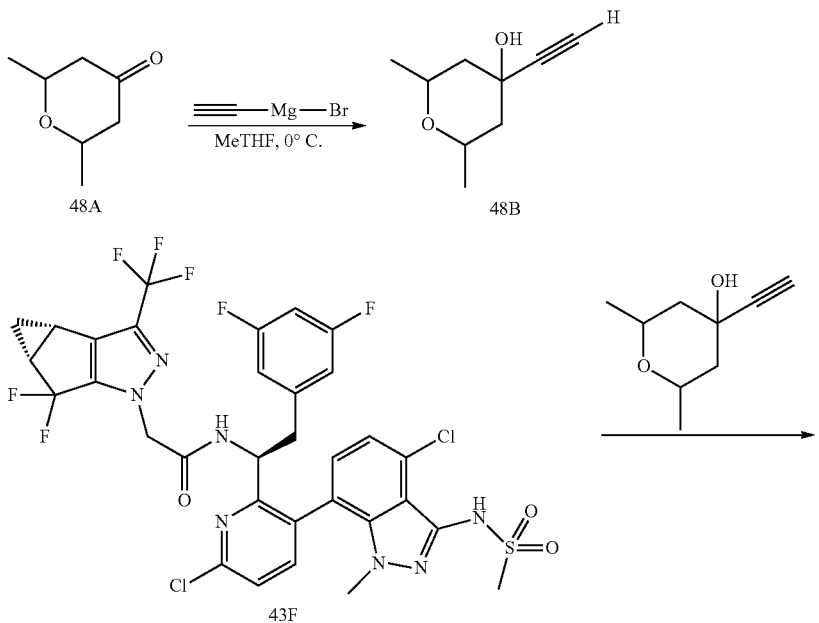

-continued

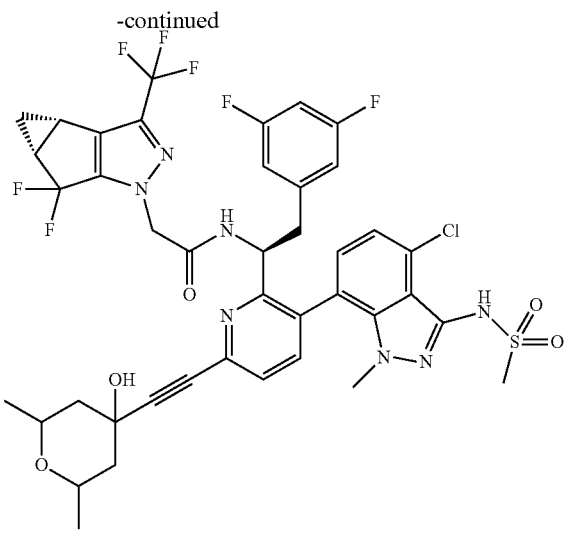

48C

Synthesis of N-((1S)-1-(3-(4-chloro-1-methyl-3-(methylsulfonamido)-1H-indazol-7-yl)-6-((4-hydroxy-2,6-dimethyltetrahydro-2H-pyran-4-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (48B): To a solution of ketone (1 g, 7.8 mmol) in methyl tetrahydrofuran (100 mL) was added ethynylmagnesium bromide (0.5 M in THF, 31 mL, 15.6 mmol) at 0° C. After 1 h, the reaction mixture was poured into a mixture of EtOAc and saturated NH4Cl solution. After separation, the organic layer was concentrated to give the alkyne as a solid. The crude material was used in the next step without further purification. $^1$H NMR (400 MHz, Chloroform-d) δ 3.90-3.61 (m, 2H), 2.50 (d, J=28.3 Hz, 1H), 2.09-1.87 (m, 2H), 1.47-1.31 (m, 2H), 1.23 (d, J=6.3 Hz, 5H), 1.17 (d, J=6.3 Hz, 1H).

Synthesis of N-((1S)-1-(3-(4-chloro-1-methyl-3-(methylsulfonamido)-1H-indazol-7-yl)-6-((4-hydroxy-2,6-dimethyltetrahydro-2H-pyran-4-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (48C): The title compound (48C) was prepared according to the method presented for the synthesis of compound 43G of Example 43 utilizing 48B and 43F. $^1$H NMR (400 MHz, Methanol-d4) δ 8.79 (t, 1H), 7.71 (dd, 1H), 7.57 (dd, 1H), 7.24-7.11 (m, 1H), 7.07 (d, 1H), 6.83-6.58 (m, 1H), 6.48-6.33 (m, 3H), 5.32-4.91 (m, 1H), 4.82-4.69 (m, 2H), 3.89 (dt, 2H), 3.33 (s, 2H), 3.24 (d, 4H), 2.97 (d, 2H), 2.59-2.38 (m, 1H), 2.11 (d, 2H), 1.53-1.36 (m, 3H), 1.27 (dd, 6H), 1.23-1.01 (m, 2H). MS (m/z) 908.85 [M+H]$^+$.

Example 49

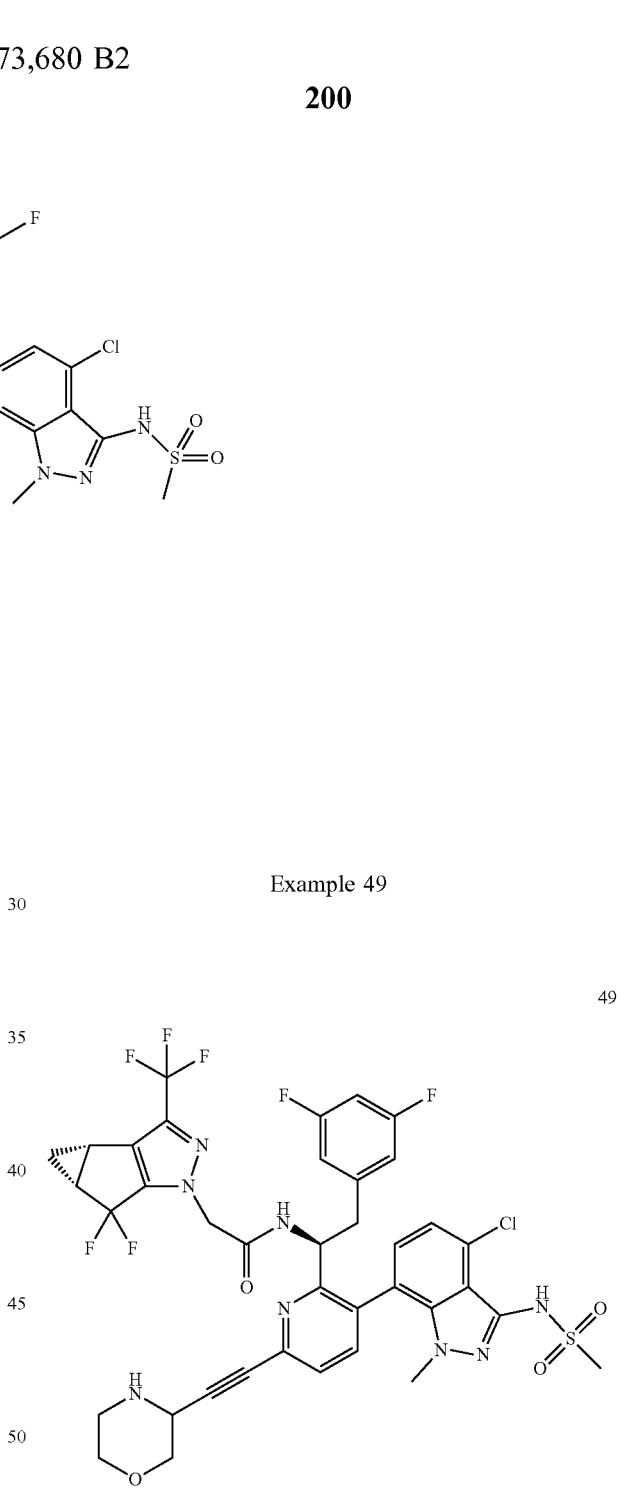

49

Synthesis of N-((1S)-1-(3-(4-chloro-1-methyl-3-(methylsulfonamido)-1H-indazol-7-yl)-6-(morpholin-3-ylethynyl)pyridin-2-yl)-2-(3,5-difluorophenyl)ethyl)-2-((3bS,4aR)-5,5-difluoro-3-(trifluoromethyl)-3b,4,4a,5-tetrahydro-1 I-cyclopropa[3,4]cyclopenta[1,2-c]pyrazol-1-yl)acetamide (49): The title compound (49) was prepared according to the method presented for the synthesis of compound 43G of Example 43 utilizing 2-ethynylmorpholine in place of tert-butyl 2-ethynylpyrrolidine-1-carboxylate. MS (m/z) 865.3 [M+H]+. HPLC retention time 6.27 min and 6.33 min (2-98% acetonitrile: water with 0.1% trifluoroacetic acid, 8.5 min gradient on a Phenomonex Kinetex C18 column). MS (m/z) 865.1 [M+H]$^+$.

Example 50

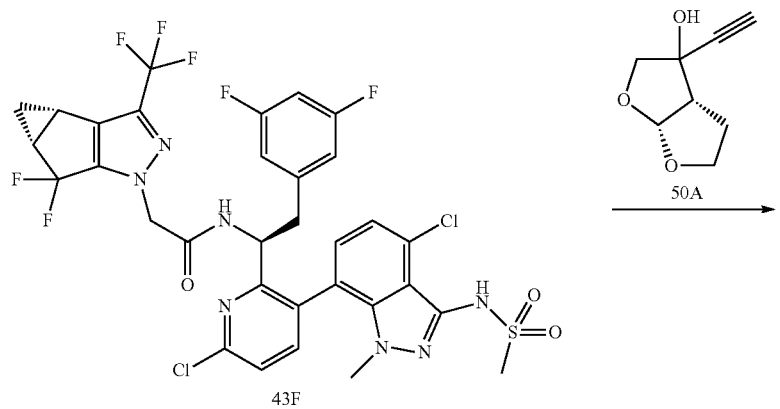

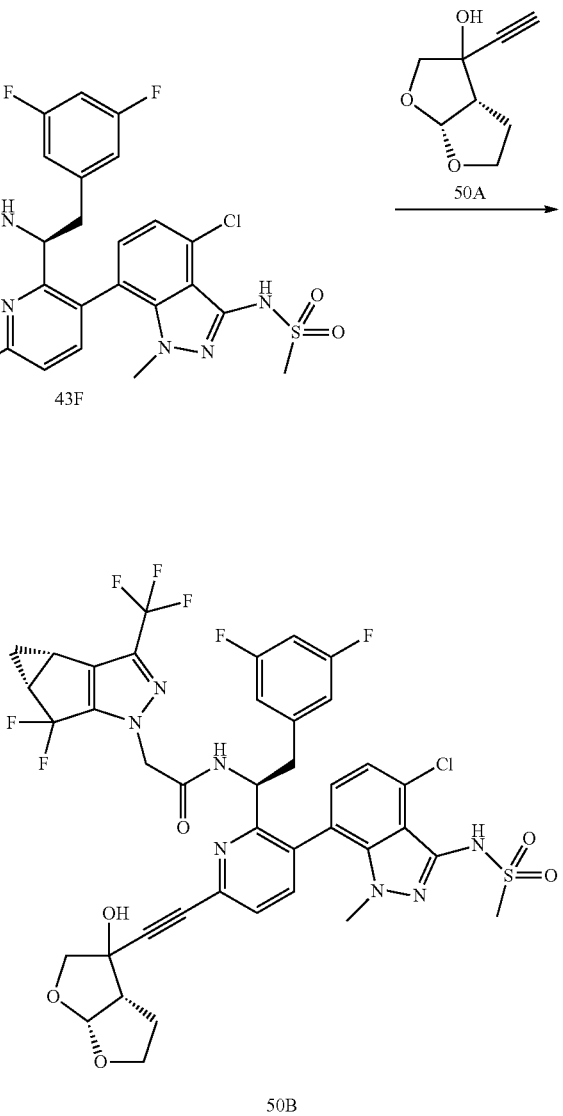

Synthesis of N-((1S)-1-(3-(4-chloro-1-methyl-3-(methylsulfonamido)-1H-indazol-7-yl)-6-(((3aS,6aR)-3-hydroxyhexahydrofuro[2,3-b]furan-3-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (50B): The title compound (50B) was prepared according to the method presented for the synthesis of compound 43G of Example 43 utilizing alkyne 50A (prepared according to the method presented for the synthesis of compound 48B of Example 48: $^1$H NMR (400 MHz, Chloroform-d) δ 5.79 (d, J=5.2 Hz, 1H), 4.10-3.90 (m, 3H), 3.86 (d, J=9.1 Hz, 1H), 3.05 (ddd, J=9.9, 5.2, 2.6 Hz, 1H), 2.58 (s, 1H), 2.33 (ddt, J=13.0, 5.5, 2.7 Hz, 1H), 1.92 (dtd, J=13.3, 10.0, 8.5 Hz, 1H)) and 43F. $^1$H NMR (400 MHz, Methanol-d$_4$) δ 8.77 (q, 1H), 7.71 (dd, 1H), 7.57 (dd, 1H), 7.28-6.99 (m, 1H), 6.88-6.57 (m, 1H), 6.38 (dd, 3H), 5.84 (dd, 1H), 5.38-4.91 (m, 1H), 4.82-4.66 (m, 2H), 4.15-3.77 (m, 4H), 3.20-2.91 (m, 4H), 2.86 (d, 1H), 2.61-2.33 (m, 4H), 2.03-1.87 (m, 1H), 1.47-1.24 (m, 2H). MS (m/z) 908.55 [M+H]$^+$

Example 51

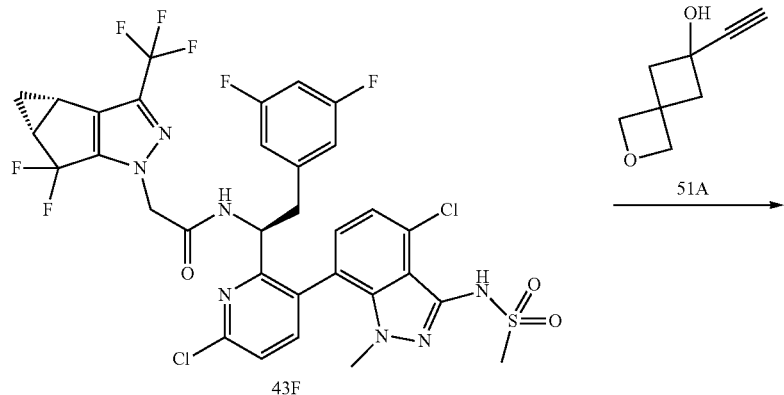

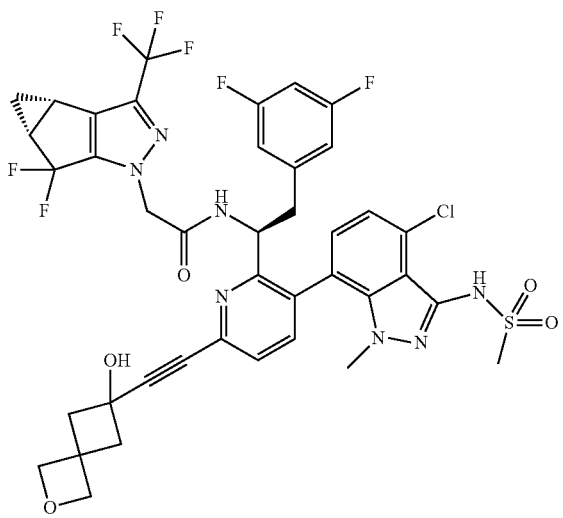

Synthesis of N—((S)-1-(3-(4-chloro-1-methyl-3-(methylsulfonamido)-1H-indazol-7-yl)-6-((6-hydroxy-2-oxaspiro[3.3]heptan-6-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (51): The title compound (51B) was prepared according to the method presented for the synthesis of compound 43G of Example 43 utilizing alkyne 51A (prepared according to the method presented for the synthesis of compound 48B of Example 48: $^1$H NMR (400 MHz, Chloroform-d) δ 4.76 (s, 2H), 4.67 (s, 2H), 2.81-2.65 (m, 2H), 2.51 (s, 1H), 2.49-2.37 (m, 2H)) and 43F. $^1$H NMR (400 MHz, Methanol-d$_4$) δ 8.74 (dd, 1H), 7.70 (dd, 1H), 7.53 (dd, 1H), 7.22-7.00 (m, 2H), 6.87-6.59 (m, 1H), 6.49-6.26 (m, 3H), 5.36-4.92 (m, 1H), 4.80-4.68 (m, 4H), 3.22-2.94 (m, 4H), 2.86 (dt, 2H), 2.63-2.37 (m, 5H), 1.41 (dt, 1H), 1.10 (d, 1H). MS (m/z) 892.76 [M+H]$^+$.

Example 52

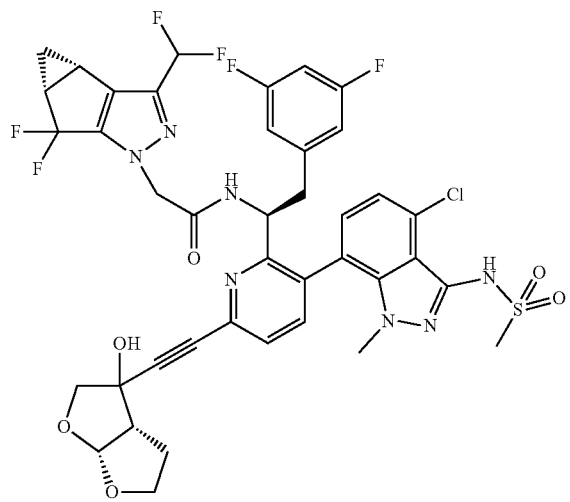

52

Synthesis of N-((1S)-1-(3-(4-chloro-1-methyl-3-(methylsulfonamido)-1H-indazol-7-yl)-6-(((3aS,6aR)-3-hydroxyhexahydrofuro[2,3-b]furan-3-yl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (52): The title compound (52) was prepared according to the method presented for the synthesis of compound 43G of Example 32 utilizing 60A and 50A. $^1$H NMR (400 MHz, Methanol-d4) δ 7.71 (dd, 1H), 7.57 (dd, 1H), 7.22-7.13 (m, 1H), 7.07 (d, 1H), 6.88-6.52 (m, 3H), 6.39 (dd, 4H), 5.84 (d, 1H), 4.97 (t, 1H), 4.78-4.64 (m, 3H), 4.09 (d, 1H), 4.02-3.85 (m, 4H), 3.24 (d, 6H), 3.19-3.08 (m, 1H), 3.07-2.92 (m, 4H), 2.86 (d, 1H), 2.46 (dt, 1H), 2.06-1.91 (m, 2H), 1.34 (dt, 2H), 1.02 (d, 1H). MS (m/z) 890.18 [M+H]$^+$.

Example 53

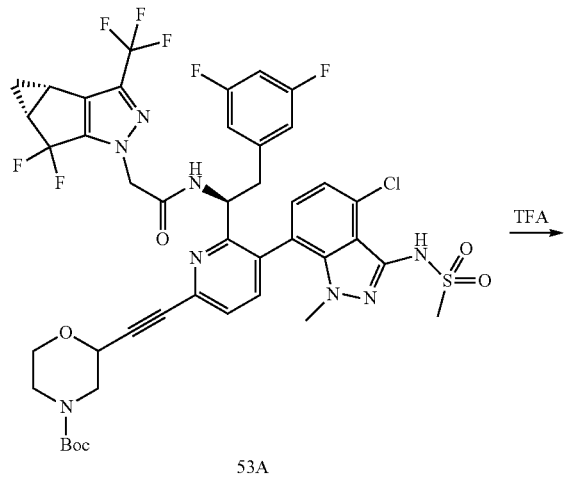

53A

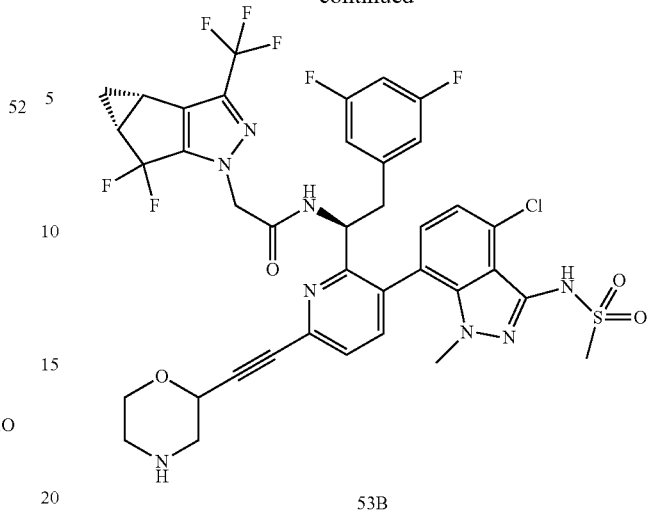

53B

Synthesis of tert-butyl 2-((5-(4-chloro-1-methyl-3-(methylsulfonamido)-1H-indazol-7-yl)-6-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-2-yl)ethynyl)morpholine-4-carboxylate (53A): The title compound was prepared according to the method presented for the synthesis of compound 43G of Example 43, utilizing tert-butyl 2-ethynylmorpholine-4-carboxylate in place of tert-butyl 2-ethynylpyrrolidine-1-carboxylate. MS (m/z) 965.9 [M+H]$^+$.

Synthesis of N-((1S)-1-(3-(4-chloro-1-methyl-3-(methylsulfonamido)-1H-indazol-7-yl)-6-(morpholin-2-ylethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (53B): To the reaction vial containing 53A (24 mg, 0.025 mmol) in DCM (1 mL) was added TFA (1 mL) The reaction mixture was stirred for 1 h at rt, concentrated, filtered and purified by reverse phase HPLC. Fractions containing the product were pooled and lyophilized to provide the title compound 36B. $^1$H NMR (400 MHz, methanol-d$_4$) δ 8.69-8.50 (m), 7.84-7.57 (m), 7.27-7.00 (m), 6.75-6.53 (m), 6.49-6.30 (m), 5.36-4.93 (m), 4.78-4.65 (m), 4.35-4.22 (m), 4.00-3.80 (m), 3.71-3.58 (m), 3.46-3.36 (m), 3.37-3.32 (m), 3.28-3.21 (m), 3.18-2.95 (m), 2.56-2.32 (m), 1.49-1.24 (m), 1.13-0.93 (m). MS (m/z) 865.2 [M+H]$^+$.

Example 54

54

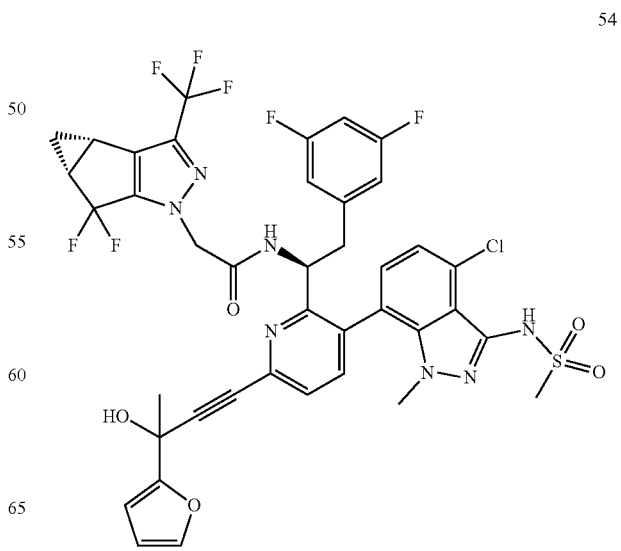

Synthesis of N-((1S)-1-(3-(4-chloro-1-methyl-3-(methyl-sulfonamido)-1H-indazol-7-yl)-6-(3-(furan-2-yl)-3-hydroxybut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (54): The title compound (54) was prepared according to the method presented for the synthesis of compound 43G of Example 43 utilizing 2-(furan-2-yl)but-3-yn-2-ol in place of tert-butyl 2-ethynylpyrrolidine-1-carboxylate. $^1$H NMR (400 MHz, methanol-d$_4$) δ 8.79-8.67 (m), 7.71 (m), 7.65-7.49 (m), 7.26-7.02 (m), 6.91-6.50 (m), 6.50-6.29 (m), 5.35-5.20 (m), 5.05-4.93 (m), 4.80-4.59 (m), 3.35-3.32 (m), 3.26-3.21 (m), 3.18-3.09 (m), 3.04-2.92 (m), 2.53-2.38 (m), 1.94 (s), 1.47-1.26 (m), 1.10-0.96 (m), 0.93-0.83 (m). MS (m/z) 890.1 [M+H]$^+$.

Example 55

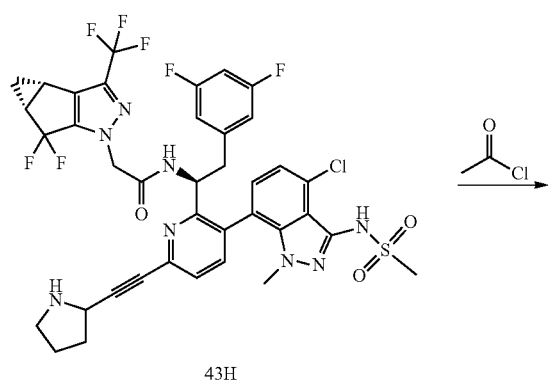

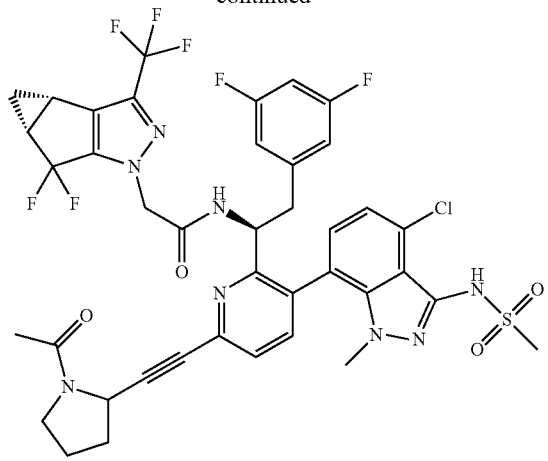

Synthesis of N-((1S)-1-(6-((1-acetylpyrrolidin-2-yl)ethynyl)-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (55): To the reaction vial containing 43H (21 mg, 0.025 mmol) in DCM (1 mL) was added acetylchloride (0.005 mL, 0.075 mmol)) followed by triethylamine (0.01 mL, 0.075 mmol) The reaction mixture was stirred for 1 h at rt, concentrated, filtered and purified by reverse phase HPLC, eluting with 5-100% acetonitrile in water with 0.1% TFA. Fractions containing the product were pooled and lyophilized to provide the TFA salt of the title compound 55. $^1$H NMR (400 MHz, methanol-d$_4$) δ 8.85-8.65 (m), 7.77-7.63 (m), 7.55 (ddd, OH), 7.25-7.12 (m), 7.07 (dd, OH), 6.85-6.70 (m), 6.62 (s, OH), 6.51-6.28 (m), 5.36-4.91 (m), 4.83-4.63 (m), 3.80-3.70 (m), 3.69-3.53 (m), 3.54-3.41 (m), 3.37-3.31 (m), 3.28-3.20 (m), 3.19-3.07 (m), 3.05-2.91 (m), 2.59-2.42 (m), 2.34-2.28 (m), 1.49-1.27 (m), 1.17-0.97 (m). MS (m/z) 891.1 [M+H]$^+$.

Example 56

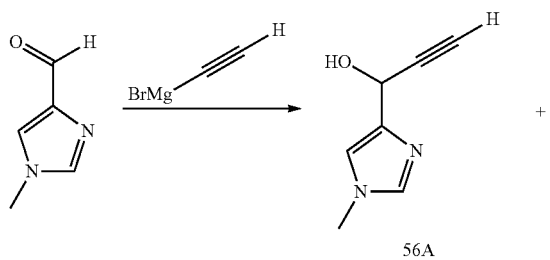

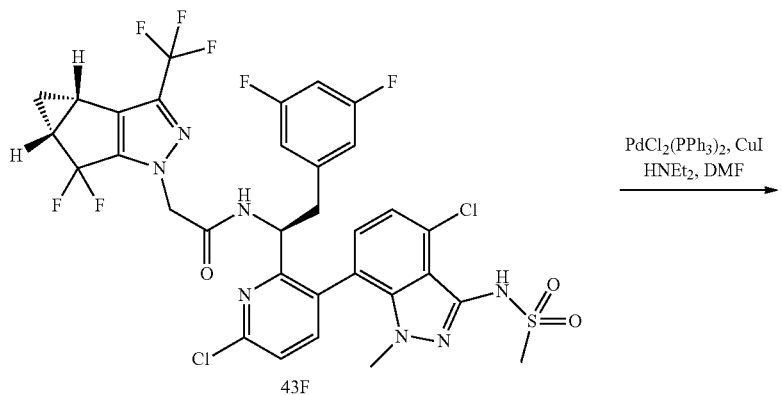

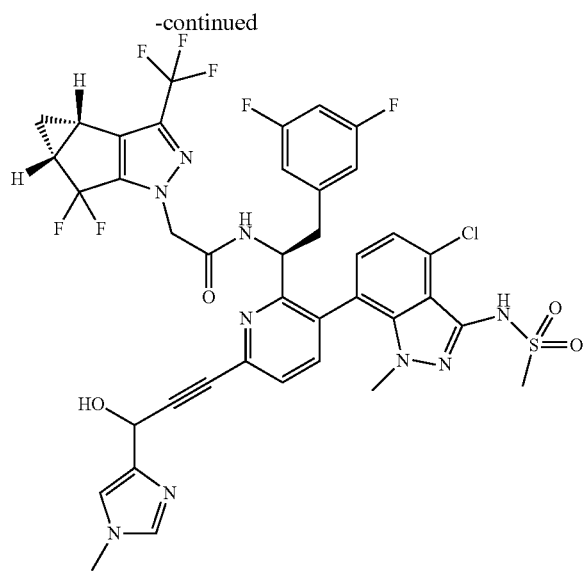

56B

Synthesis of 1-(1-methyl-1H-imidazol-4-yl)prop-2-yn-1-ol (56A): To ethynylmagnesium bromide (0.5 M, 4.0 mL, 2.0 mmol) at 0° C. was added 1-methyl-1H-imadazole-4-carbaldehyde (200.0 mg, 1.82 mmol). The reaction mixture was warmed to room temperature and allowed to stir at room temperature overnight. The reaction was quenched with saturated aqueous ammonium chloride and extracted with three portions of EtOAc. The combined organic layers were dried over $Na_2SO_4$, filtered, and concentrated in vacuo to give the title compound 56A which was used without additional purification.

Synthesis of N-((1S)-1-(3-(4-chloro-1-methyl-3-(methylsulfonamido)-1H-indazol-7-yl)-6-(3-hydroxy-3-(1-methyl-1H-imidazol-4-yl)prop-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (56B): N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (43F, 20.0 mg, 0.025 mmol), 1-(1-methyl-1H-imidazol-4-yl)prop-2-yn-1-ol (56A, 17.2 mg, 0.126 mmol), $PdCl_2(PPh_3)_2$ (1.8 mg, 0.003 mmol), and CuI (0.5 mg, 0.003 mmol) were taken in DMF (0.25 mL). To the reaction mixture was added diethylamine (26 µL, 0.253 mmol), and the reaction mixture was degassed by bubbling argon for 30 seconds then sealed and heated at 125° C. for 20 minutes in a microwave reactor. Upon cooling, the reaction mixture was filtered and purified by reverse phase HPLC to give the title compound 56B as a mixture of atropisomers. $^1$H NMR (400 MHz, Methanol-$d_4$) δ 8.97 (s), 8.77-8.67 (m), 7.82-7.73 (m), 7.73-7.62 (m), 7.28-6.99 (m), 6.83-6.58 (in), 6.47-6.35 (m), 6.07 (s), 5.34-4.94 (m), 4.81-4.69 (m), 4.13 (s), 3.34 (s), 3.28-3.23 (m), 3.21-3.08 (m), 3.07-2.91 (m), 2.57-2.41 (m), 1.52-1.36 (m), 1.18-1.02 (m). MS (m/z) 890.18 [M+H]$^+$.

Example 57

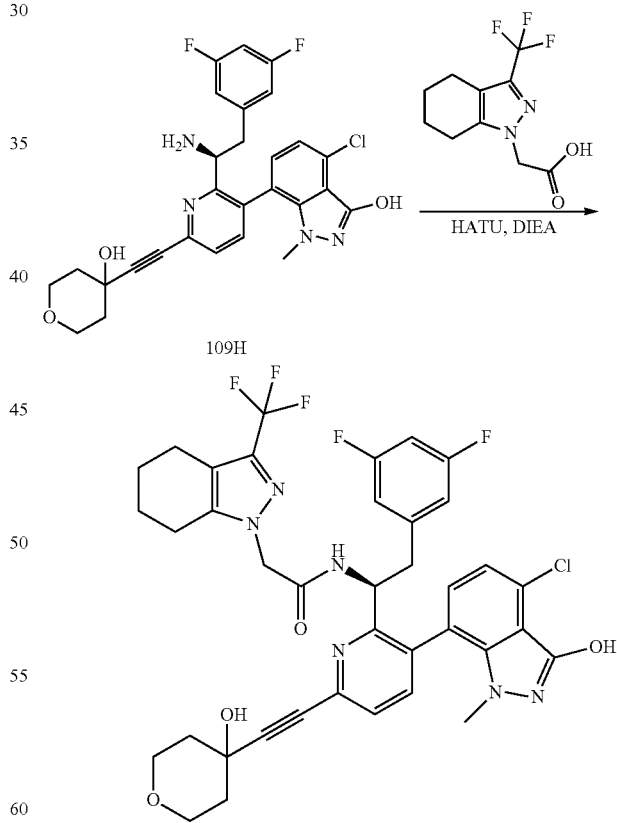

57

Synthesis of (S)—N-(1-(3-(4-chloro-3-hydroxy-1-methyl-1H-indazol-7-yl)-6-((4-hydroxytetrahydro-2H-pyran-4-yl)ethynyl)pyridin-2-yl)-2-(3,5-difluorophenyl)ethyl)-2-(3-(trifluoromethyl)-4,5,6,7-tetrahydro-1H-indazol-1-yl)acetamide (57): The compound 57 was prepared as a mixture of atropisomers according to the method presented for the synthesis of compound 108F of Example 108 utilizing compound 109H and 2-(3-(trifluoromethyl)-4,5,6,7-tetrahydro-1H-indazol-1-yl)acetic acid. 1H NMR (400 MHz, Acetonitrile-d3) δ 7.69 (d), 7.57 (dd), 7.24-6.96 (m), 6.88-6.72 (m), 6.73-6.59 (m), 6.51-6.33 (m), 5.47 (s), 5.25 (q), 5.01 (td), 4.70-4.56 (m), 3.97-3.81 (m), 3.74 (ddd), 3.60 (s), 3.41 (s), 3.14-2.78 (m), 2.57 (q), 2.46-2.23 (m), 2.13-1.97 (m), 1.96-1.65 (m), 1.40-1.17 (m), 0.95-0.82 (m). MS (m/z) 769 [M+H]+.

Example 58

58

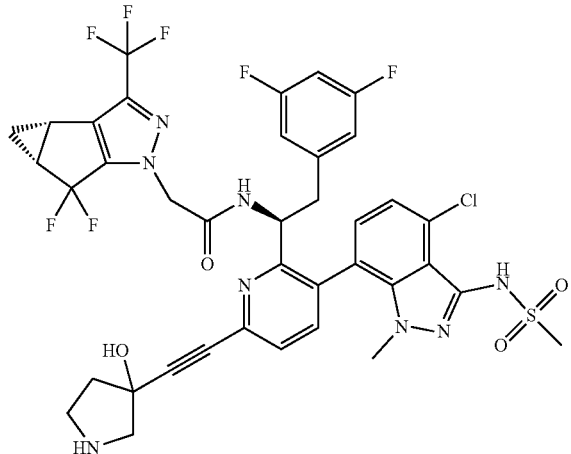

Synthesis of N-((1S)-1-(3-(4-chloro-1-methyl-3-(methylsulfonamido)-1H-indazol-7-yl)-6-((3-hydroxypyrrolidin-3-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (58): The title compound (58) was prepared according to the method presented for the synthesis of compound 53B of Example 53 utilizing tert-butyl 3-ethynyl-3-hydroxypyrrolidine-1-carboxylate in place of tert-butyl 2-ethynylmorpholine-4-carboxylate. 1H NMR (400 MHz, methanol-d4) δ 8.83-8.65 (m), 7.85-7.52 (m), 7.26-7.01 (m), 6.86-6.59 (m), 6.48-6.31 (m), 5.37-4.90 (m), 4.77-4.66 (m), 3.70-3.43 (m), 3.35-3.31 (m), 3.20-2.87 (m), 2.59-2.39 (m), 1.54-1.20 (m), 1.18-0.96 (m). MS (m/z) 865.2 [M+H]+

Example 59

59

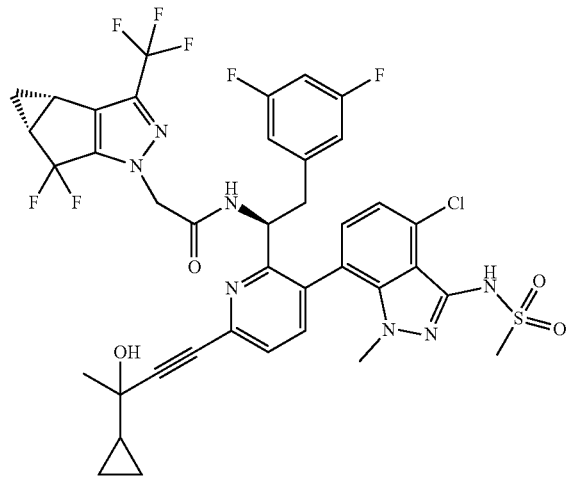

Synthesis of N-((1S)-1-(3-(4-chloro-1-methyl-3-(methylsulfonamido)-1H-indazol-7-yl)-6-(3-cyclopropyl-3-hydroxybut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (59): The title compound (59) was prepared according to the method presented for the synthesis of compound 43G of Example 43 utilizing 2-cyclopropylbut-3-yn-2-ol in place of tert-butyl 2-ethynylpyrrolidine-1-carboxylate. 1H NMR (400 MHz, methanol-d4) δ 8.86-8.64 (m, 1H), 7.77-7.41 (m, 2H), 7.23-6.99 (m, 2H), 6.84-6.58 (m, 1H), 6.51-6.31 (m, 2H), 5.32-4.92 (m, 1H), 4.79-4.68 (m, 2H), 3.36-3.32 (m, 3H), 3.28-3.21 (m, 3H), 3.19-2.85 (m, 3H), 2.61-2.36 (m, 3H), 2.14-1.61 (m, 3H), 1.48-1.34 (m, 1H), 1.32-1.19 (m, 1H), 1.17-0.99 (m, 1H), 0.88-0.66 (m, 1H), 0.67-0.47 (m, 3H). MS (m/z) 864.0 [M+H]+.

Example 60

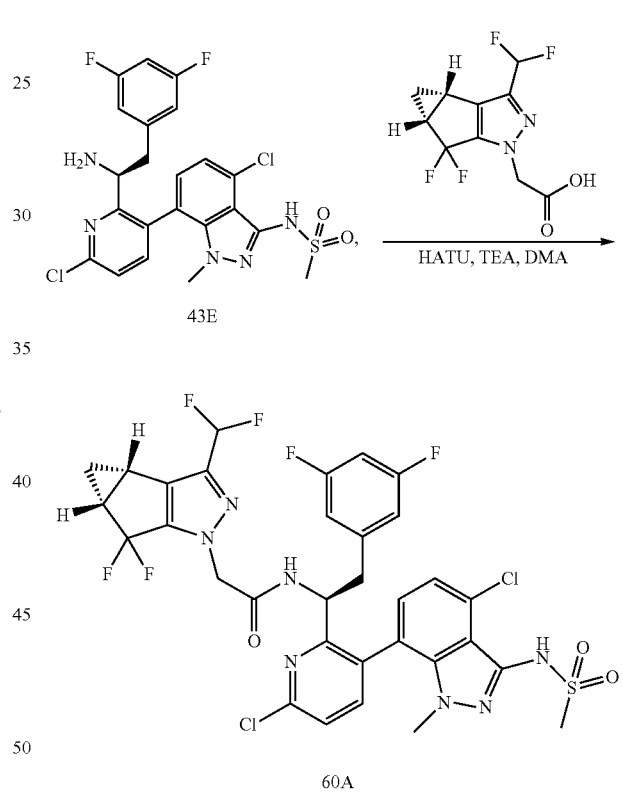

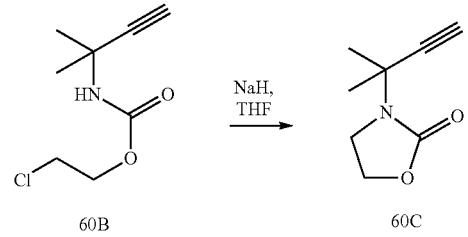

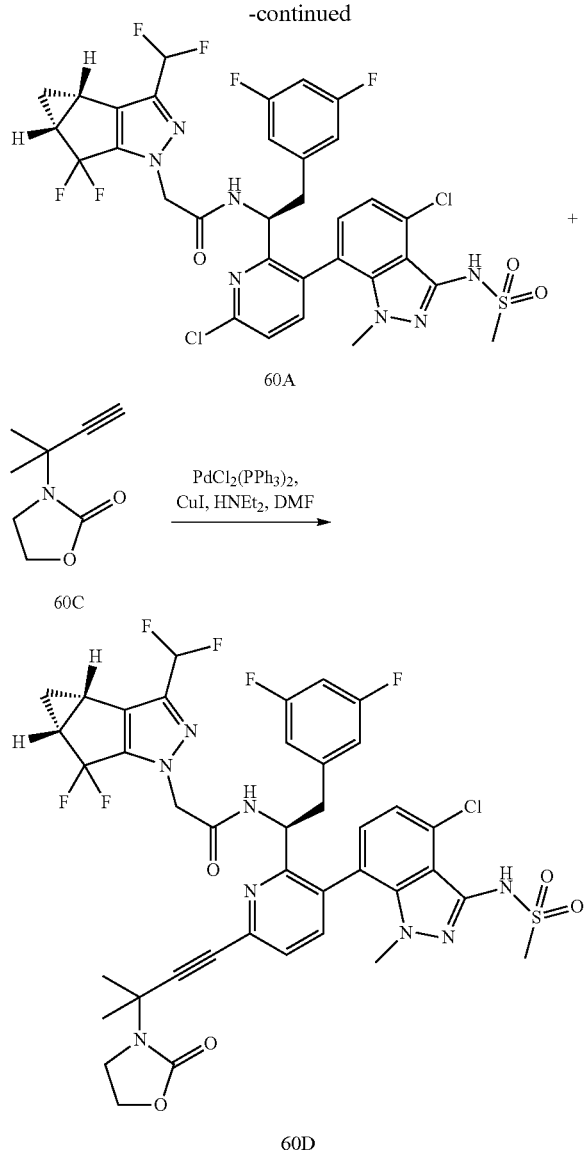

Synthesis of N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (60A): To a solution of crude (S)—N-(7-(2-(1-amino-2-(3,5-difluorophenyl)ethyl)-6-chloropyridin-3-yl)-4-chloro-1-methyl-1H-indazol-3-yl)methanesulfonamide (43E, 400 mg, 0.76 mmol) in DMA (6 mL) was added NEt₃ (0.32 mL, 2.28 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (160.6 mg, 0.61 mmol), then HATU (173.4 mg, 0.46 mmol). The reaction mixture was stirred at room temperature for 15 minutes, then additional HATU (86.7 mg, 0.23 mmol) was added. The reaction mixture was stirred at room temperature for an additional 15 minutes. Upon completion, the reaction mixture was concentrated in vacuo and purified by silica gel column chromatography to give the title compound 60A. MS (m/z) 772.03 [M+H]⁺.

Synthesis of 2-chloroethyl(2-methylbut-3-yn-2-yl)carbamate (60B): To a solution of 2-methyl-3-butyn-2-amine (500 mg, 6.01 mmol) in MeCN (25 mL) at 0° C. was added solid potassium carbonate followed by 2-chloroethyl chloroformate (0.65 mL, 6.32 mmol) in MeCN (10 mL) over 10 minutes. The reaction mixture was warmed to room temperature. After 4 hours, the reaction mixture was heated to 90° C. for 60 minutes. After cooling, the reaction mixture was diluted with EtOAc, filtered, concentrated, taken in EtOAc, and washed with water and brine. The organic layer was dried over Na₂SO₄, filtered, and concentrated to provide the title compound 60B which was used without further purification.

Synthesis of 3-(2-methylbut-3-yn-2-yl)oxazolidin-2-one (60C): To a solution of crude 2-chloroethyl(2-methylbut-3-yn-2-yl)carbamate (60B, 630 mg, 3.32 mmol) in dry THF (12 mL) was added sodium hydride (60% in mineral oil, 398.61 mg, 9.97 mmol). The reaction mixture was stirred at room temperature overnight. The reaction mixture was cooled to 0° C. and quenched by dropwise addition of 2N HCl. The reaction mixture was extracted with two portions of EtOAc, and the combined organic layers were washed with saturated aqueous NaCl. The organic layer was then dried over Na₂SO₄, filtered, concentrated, and purified by silica gel column chromatography to give the title compound 60C. ¹H NMR (400 MHz, Chloroform-d) δ 4.26 (q, J=7.5 Hz, 2H), 3.74 (q, J=7.2 Hz, 2H), 2.50-2.35 (m, 1H), 1.78-1.63 (m, 6H).

Synthesis of N—((S)-1-(3-(4-chloro-1-methyl-3-(methylsulfonamido)-1H-indazol-7-yl)-6-(3-methyl-3-(2-oxooxazolidin-3-yl)but-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (60D): The title compound (60D) was prepared according to the method presented for the synthesis of compound 56B of Example 56 utilizing N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (60A) and 3-(2-methylbut-3-yn-2-yl)oxazolidin-2-one (60C). ¹H NMR (400 MHz, Methanol-d₄) δ 7.75-7.65 (m), 7.63-7.48 (m), 7.23-7.02 (m), 6.94-6.28 (m), 5.08-4.89 (m), 4.78-4.65 (m), 4.43-4.30 (m), 3.96-3.85 (m), 3.33 (s), 3.30-3.20 (m), 3.19-3.10 (m), 3.06-2.91 (m), 2.55-2.35 (m), 1.86 (s), 1.48-1.29 (m), 1.14-0.95 (m). MS (m/z) 889.13 [M+H]⁺.

Example 61

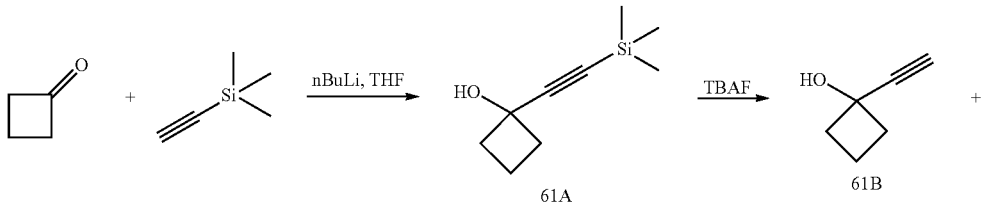

-continued

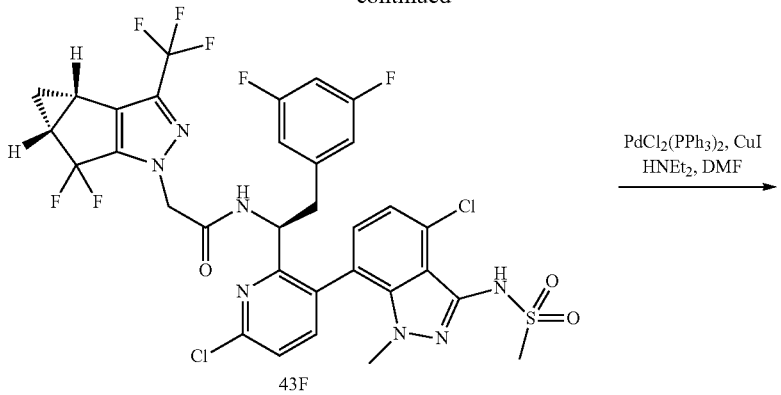

43F

PdCl₂(PPh₃)₂, CuI
HNEt₂, DMF
→

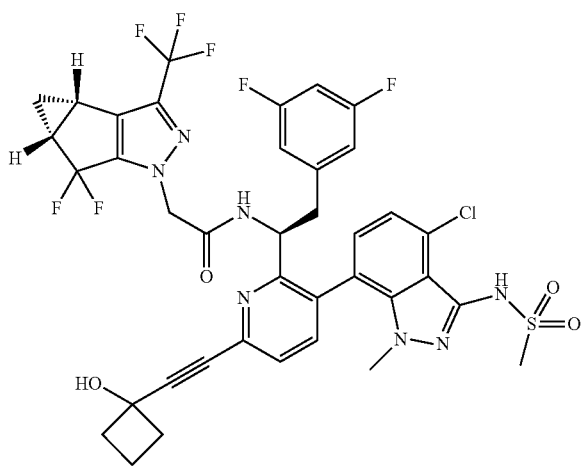

61C

Synthesis of 1-((trimethylsilyl)ethynyl)cyclobutanol (61A): To a solution of trimethylsilylacetylene (1.86 mL, 14.3 mmol) in THF (60 mL) at −78° C. was added nBuLi (2.5 M in hexanes, 5.1 mL, 12.8 mmol) dropwise. The reaction mixture was stirred at −78° C. for 30 minutes, then cyclobutanone (1.0 g, 14.3 mmol) was added. The reaction was slowly warmed to room temperature and stirred at room temperature overnight. The reaction was quenched with saturated aqueous ammonium chloride, and the aqueous layer was extracted with three portions of EtOAc. The combined organic layers were washed with saturated aqueous sodium chloride, dried over MgSO₄, filtered, and concentrated in vacuo to give the title compound 61A which was used without further purification.

Synthesis of 1-ethynylcyclobutanol (61B): To a solution of crude 1-((trimethylsilyl)ethynyl)cyclobutanol (61A, 300 mg, 1.8 mmol) in THF (1 mL) was added TBAF (1 M in THF, 2.14 mL, 2.1 mmol) at room temperature. The reaction mixture was stirred at room temperature for 30 minutes, then quenched with saturated aqueous ammonium chloride. The aqueous layer was extracted with 2 portions of diethyl ether, and the combined organic layers were dried over MgSO₄, filtered, and carefully concentrated in vacuo to give the title compound 61B which was used without further purification.

Synthesis of N—((S)-1-(3-(4-chloro-1-methyl-3-(methylsulfonamido)-1H-indazol-7-yl)-6-((1-hydroxycyclobutyl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (61C): The title compound (61C) was prepared according to the method presented for the synthesis of compound 56B of Example 56 utilizing N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (43F) and 1-ethynylcyclobutanol (61B). $^1$H NMR (400 MHz, Methanol-d₄) δ 8.86-8.70 (m), 7.71 (dd), 7.56 (dd), 7.26-6.98 (m), 6.88-6.52 (m), 6.50-6.30 (m), 5.32-4.94 (m), 4.83-4.71 (m), 3.35 (s), 3.28-3.22 (m), 3.21-3.13 (m), 3.07-2.94 (m), 2.66-2.29 (m), 2.07-1.84 (m), 1.51-1.24 (m), 1.20-1.00 (m). MS (m/z) 850.09 [M+H]⁺.

Example 62

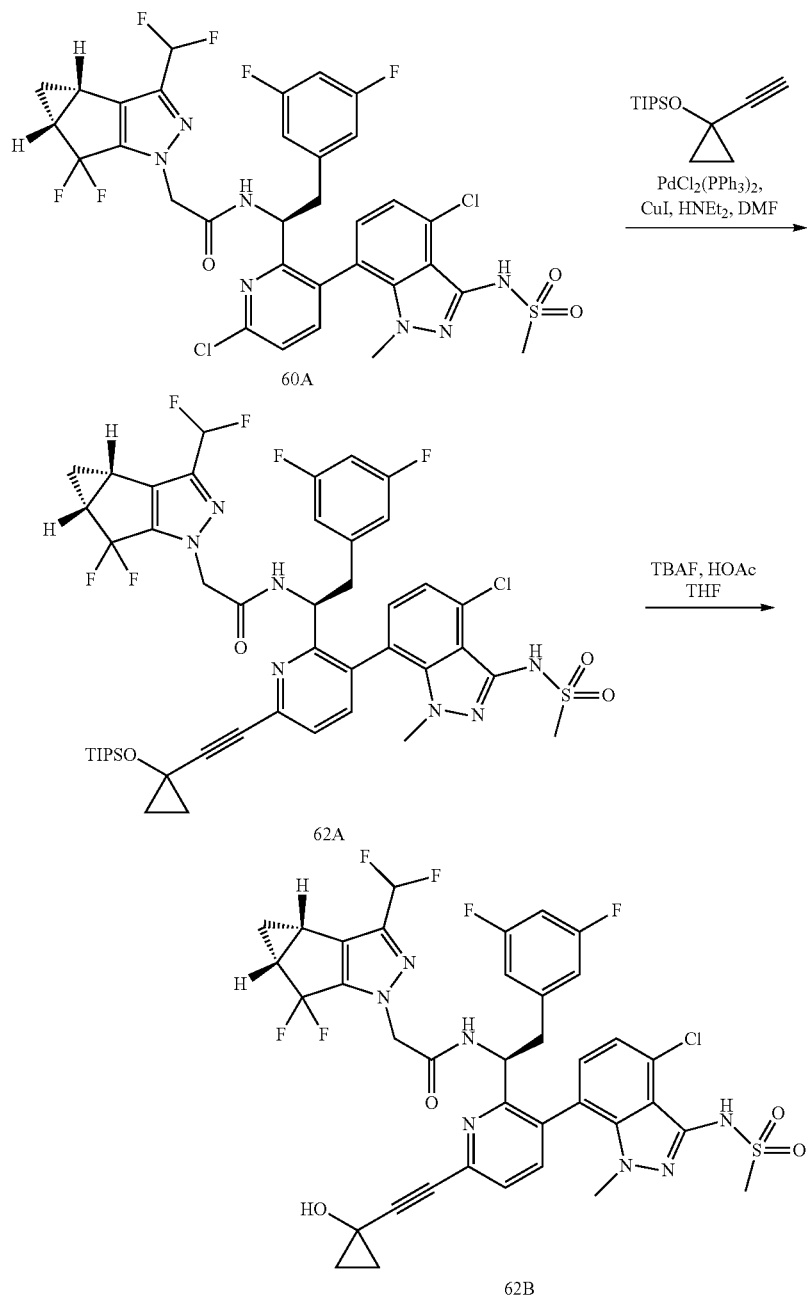

Synthesis of N—((S)-1-(3-(4-chloro-1-methyl-3-(methylsulfonamido)-1H-indazol-7-yl)-6-((1-((triisopropylsilyl)oxy)cyclopropyl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (62A): The title compound (62A) was prepared according to the method presented for the synthesis of compound 56B of Example 56 utilizing N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (60A) and (1-ethynylcyclopropoxy)triisopropylsilane. MS (m/z) 974.10 [M+H]+.

Synthesis of N—((S)-1-(3-(4-chloro-1-methyl-3-(methylsulfonamido)-1H-indazol-7-yl)-6-((1-hydroxycyclopropyl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (62B): To a solution of N—((S)-1-(3-(4-chloro-1-methyl-3-(methylsulfonamido)-1H-indazol-7-yl)-6-((1-((triisopropylsilyl)oxy)cyclopropyl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (62A, 20 mg, 0.021 mmol) in THF was added acetic acid (1.4 μL, 0.025 mmol) followed by TBAF (1M in THF, 24.6 μL, 0.025 mmol). The reaction mixture was stirred at room temperature for 24 hours. Upon completion, the reaction was concentrated, taken in DMF, and purified by reverse phase HPLC to give the title compound 62B as a mixture of atropisomers. $^1$H NMR (400 MHz, Methanol-d$_4$) δ 8.67-8.43 (m), 7.68 (dd), 7.50 (dd), 7.28-6.98 (m), 6.87-6.52 (m), 6.46-6.31 (m), 5.01-4.91 (m), 4.79-4.61 (m), 3.33 (s), 3.28-3.19 (m), 3.16-3.07 (m), 3.04-2.91 (m), 2.55-2.38 (m), 1.46-1.26 (m), 1.19-1.14 (m), 1.11-0.98 (m). MS (m/z) 818.12 [M+H]$^+$.

Example 63

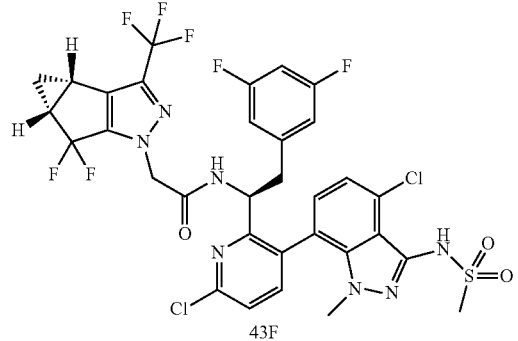

43F

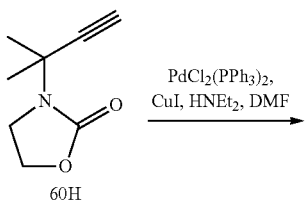

60H

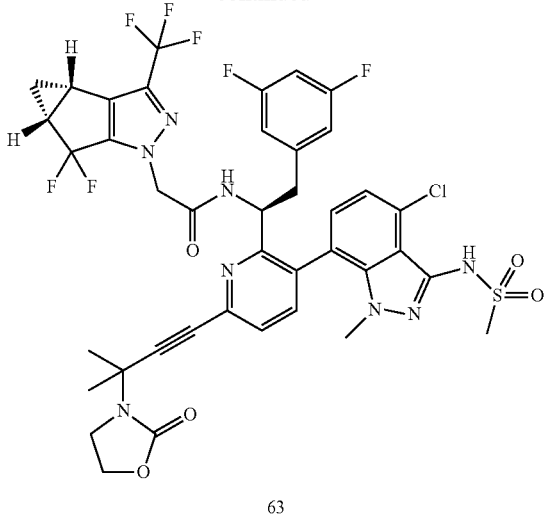

63

Synthesis of N—((S)-1-(3-(4-chloro-1-methyl-3-(methylsulfonamido)-1H-indazol-7-yl)-6-(3-methyl-3-(2-oxooxazolidin-3-yl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide: The title compound (63) was prepared according to the method presented for the synthesis of compound 56B of Example 56 utilizing N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (43F) and 3-(2-methylbut-3-yn-2-yl)oxazolidin-2-one (60H). $^1$H NMR (400 MHz, Methanol-d$_4$) δ 8.84-8.75 (m), 7.74-7.67 (m), 7.62-7.51 (m), 7.20-7.02 (m), 6.83-6.57 (m), 6.47-6.33 (m), 5.03-4.95 (m), 4.81-4.70 (m), 4.40-4.34 (m), 3.97-3.83 (m), 3.33 (s), 3.28-3.21 (m), 3.16-3.08 (m), 3.06-2.93 (m), 2.60-2.36 (m), 1.85 (s), 1.50-1.32 (m), 1.18-1.00 (m). MS (m/z) 907.09 [M+H]$^+$.

Example 64

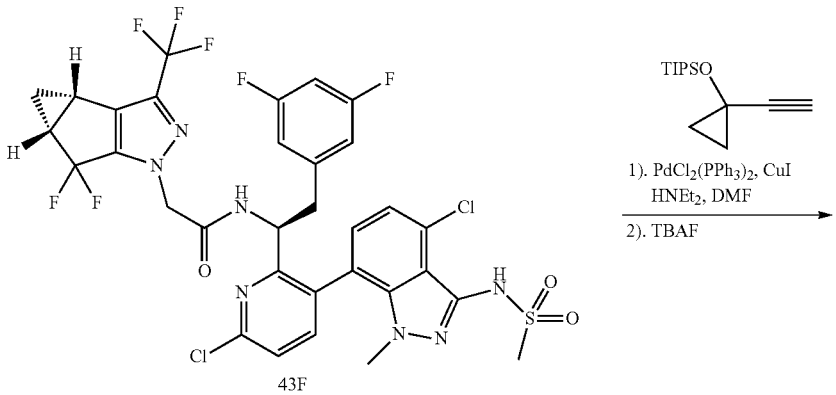

43F

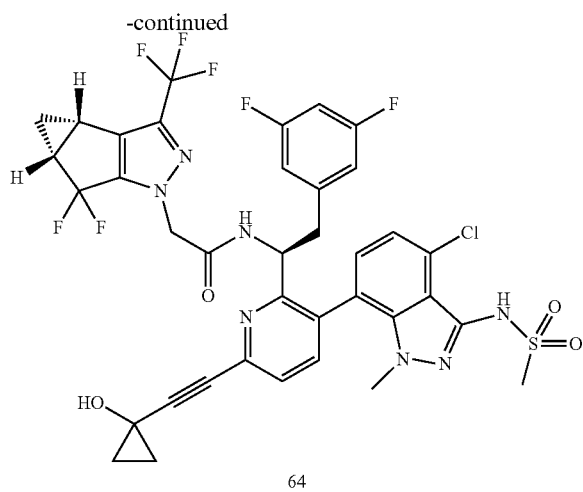

64

Synthesis N—((S)-1-(3-(4-chloro-1-methyl-3-(methylsulfonamido)-1H-indazol-7-yl)-6-((1-hydroxycyclopropyl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (64): The title compound (64) was prepared as a mixture of atropisomers according to the method presented for the synthesis of compound 56B of Example 56 utilizing (1-ethynylcyclopropoxy)triisopropylsilane and an additional work up step taking the concentrated organic fraction and running it through a silica gel plug eluting with EtOAc followed by concentration. The mixture was then treated with TBAF until done then concentrated and purified by HPLC. $^1$H NMR (Chloroform-d) δ: 7.55-7.39 (m), 7.30-7.19 (m), 7.12 (dd), 6.91 (d), 6.66 (t), 6.24-6.12 (m), 6.11-6.02 (m), 5.02-4.89 (m), 4.80-4.66 (m), 4.73 (d, 1H), 3.53 (d), 3.41 (s), 3.40 (s), 3.29-3.27 (m), 3.26 (s), 3.11 (s), 3.02-3.00 (m), 2.98-2.90 (m), 2.54-2.45 (m), 1.45 (q), 1.39-1.17 (m), 1.13 (d). MS (m/z) 836.0 [M+H]$^+$.

Example 65

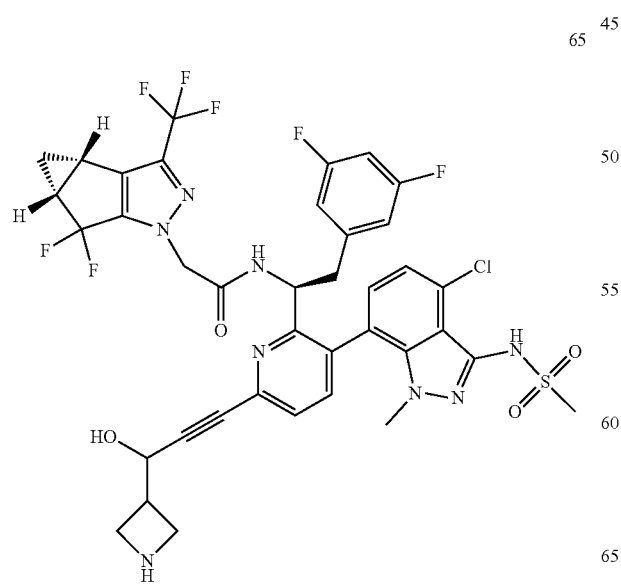

65

223

Synthesis of N-((1S)-1-(6-(3-(azetidin-3-yl)-3-hydroxyprop-1-yn-1-yl)-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (65): The title compound (65) was prepared according to the method presented for the synthesis of compound 53B of Example 53 utilizing tert-butyl 3-(1-hydroxyprop-2-yn-1-yl)azetidine-1-carboxylate in place of tert-butyl 2-ethynylmorpholine-4-carboxylate. $^1$H NMR (400 MHz, methanol-$d_4$) δ 8.85-8.60 (m, 1H), 7.81-7.45 (m, 2H), 7.25-6.98 (m, 1H), 6.87-6.55 (m, 1H), 6.49-6.32 (m, 3H), 5.31-4.92 (m, 1H), 4.79-4.73 (m, 2H), 4.30-4.09 (m, 4H), 3.33-3.32 (m, 4H), 3.27-3.21 (m, 4H), 3.18-2.94 (m, 3H), 2.69-2.33 (m, 2H), 1.56-1.33 (m, 1H), 1.15-1.01 (m, 1H). MS (m/z) 865.2 [M+H]$^+$

224

Synthesis of N-((1S)-1-(3-(4-chloro-1-methyl-3-(methylsulfonamido)-1H-indazol-7-yl)-6-((1-(2-hydroxyacetyl)pyrrolidin-2-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (66): To the reaction vial containing 43H (21 mg, 0.025 mmol) in DCM (1 mL) was added acetoxyacetyl chloride (7 mg, 0.05 mmol)) followed by DMAP (6 m, 0.05 mmol) The reaction mixture was stirred for 1 h at rt. Methanol (1 mL) was added to the reaction mixture followed by solid potassium carbonate (10 mg, 0.075 mmol), this heterogeneous solution was stirred for 30 min, filtered, concentrated and purified by reverse phase HPLC. Fractions containing the product were pooled and lyophilized to provide the title compound 66. MS (m/z) 907.4 [M+H]+. HPLC retention time 6.99 min and 7.18 min (2-98% acetonitrile: water with 0.1% trifluoroacetic acid, 8.5 min gradient on a Phenomonex Kinetex C18 column).

Example 66

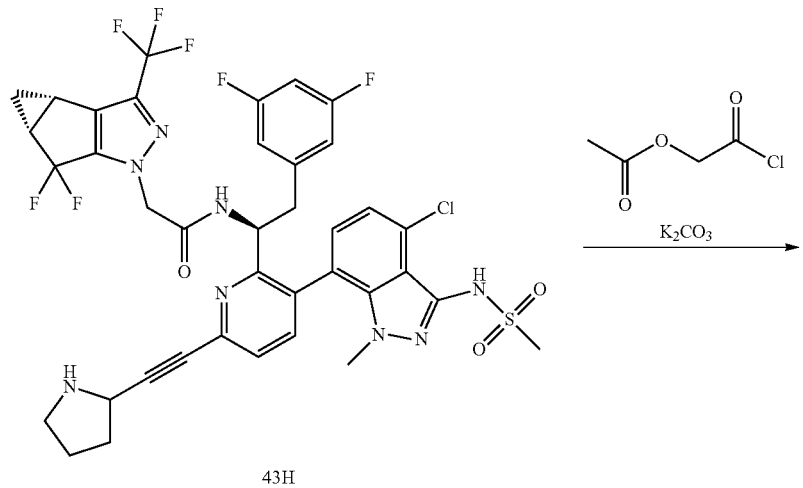

43H

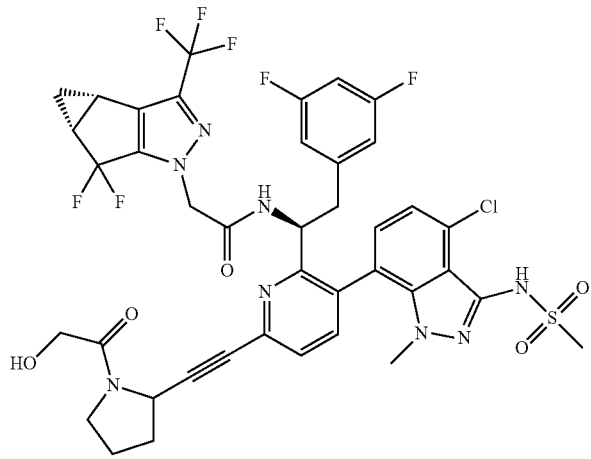

66

Example 67

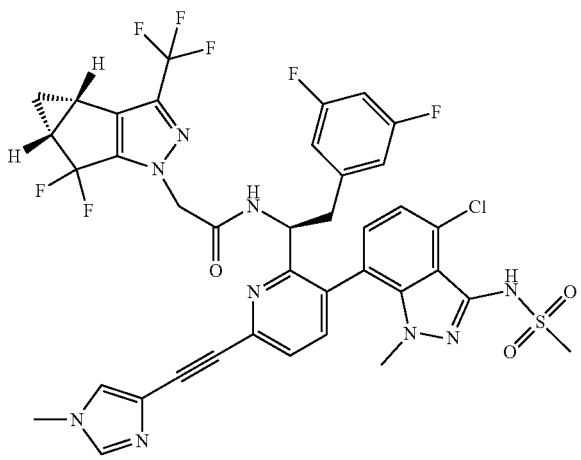

Synthesis of N—((S)-1-(3-(4-chloro-1-methyl-3-(methylsulfonamido)-1H-indazol-7-yl)-6-((1-methyl-1H-imidazol-4-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (67): The title compound (67) was prepared according to the method presented for the synthesis of compound 43G of Example 43 utilizing 4-ethynyl-1-methyl-1H-imidazole in place of tert-butyl 2-ethynylpyrrolidine-1-carboxylate. ¹H NMR (400 MHz, methanol-d₄) δ 8.95-8.78 (s, 1H), 8.77-8.73 (m, 1H), 8.10-8.00 (s, 1H), 7.97-7.63 (m, 2H), 7.35-7.02 (m, 1H), 6.87-6.60 (m, 2H), 6.55-6.31 (m, 2H), 5.28-4.98 (m, 1H), 4.82-4.62 (m, 2H), 4.04 (s, 3H), 3.36-3.29 (m, 3H), 3.26-3.24 (m, 3H), 3.11-2.95 (m, 2H), 2.62-2.37 (m, 2H), 1.46-1.30 (m, 1H), 1.15-1.01 (m, 1H). MS (m/z) 860.1 [M+H]⁺

Example 68

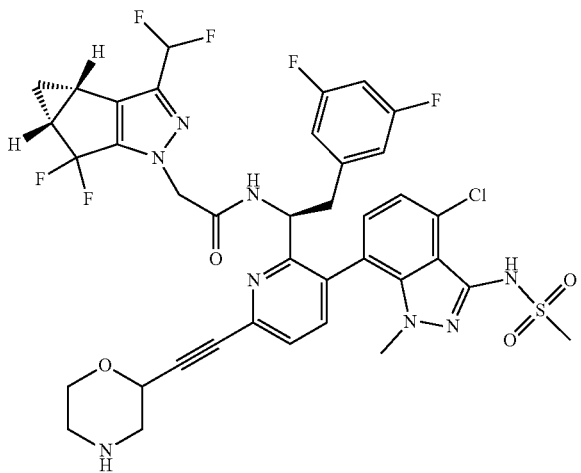

Synthesis of N-((1S)-1-(3-(4-chloro-1-methyl-3-(methylsulfonamido)-1H-indazol-7-yl)-6-(morpholin-2-ylethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (68): The title compound (68) was prepared according to the method presented for the synthesis of compound 60D of Example 60 utilizing tert-butyl 2-ethynylmorpholine-4-carboxylate in place of 3-(2-methylbut-3-yn-2-yl)oxazolidin-2-one followed by the addition of TFA (1 mL) prior to purification. ¹H NMR (400 MHz, methanol-d₄) δ 8.69-8.50 (m, 1H), 7.84-7.57 (m, 2H), 7.27-7.00 (m, 1H), 6.90-6.53 (m, 2H), 6.49-6.30 (m, 3H), 5.36-4.93 (m, 2H), 4.78-4.65 (m, 2H), 4.35-4.22 (m, 1H), 4.03-3.87 (m, 1H), 3.71-3.58 (m, 1H), 3.46-3.36 (m, 1H), 3.37-3.32 (m, 4H), 3.28-3.21 (m, 3H), 3.18-2.90 (m, 3H), 2.56-2.32 (m, 2H), 1.49-1.24 (m, 2H), 1.13-0.93 (m, 1H). MS (m/z) 847.1 [M+H]⁺

Example 69

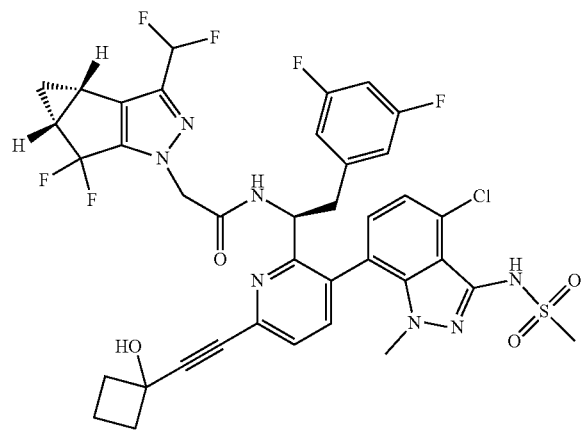

Synthesis of N—((S)-1-(3-(4-chloro-1-methyl-3-(methylsulfonamido)-1H-indazol-7-yl)-6-((1-hydroxycyclobutyl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (69): The title compound (69) was prepared according to the method presented for the synthesis of compound 60D of Example 60 utilizing 1-ethynylcyclobutanol in place of 3-(2-methylbut-3-yn-2-yl)oxazolidin-2-one. ¹H NMR (400 MHz, methanol-d₄) δ 8.80-8.57 (m, 1H), 7.82-7.47 (m, 2H), 7.26-6.98 (m, 1H), 6.90-6.50 (m, 2H), 6.49-6.30 (m, 3H), 5.38-4.89 (m, 1H), 4.80-4.64 (m, 2H), 3.36-3.32 (m, 2H), 3.28-3.21 (m, 3H), 3.19-2.92 (m, 3H), 2.64-2.30 (m, 7H), 2.07-1.85 (m, 2H), 1.52-1.24 (m, 1H), 1.14-0.94 (m, 1H). MS (m/z) 832.1 [M+H]⁺

Example 70

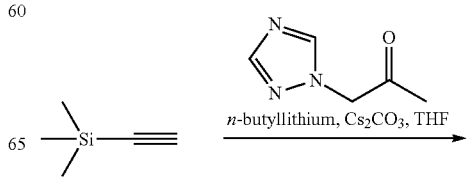

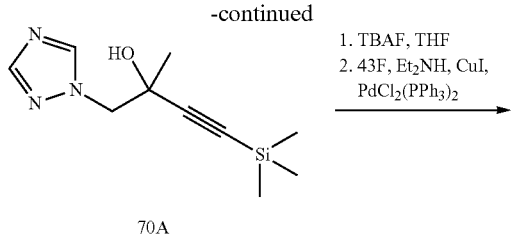

70A

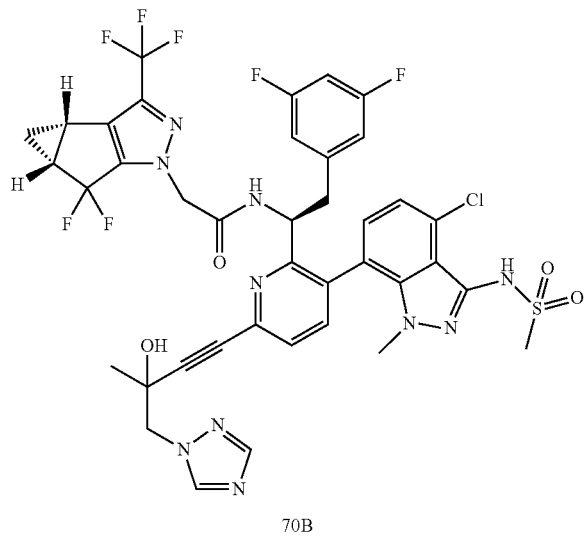

70B

Synthesis of 2-methyl-1-(1H-1,2,4-triazol-1-yl)-4-(trimethylsilyl)but-3-yn-2-ol (70A): To a solution of trimethylsilylacetylene (0.64 ml, 4.50 mmol) in THF (5 mil) 2.5M n-butyllithium in hexanes (1.8 ml, 4.50 mmol) was added dropwise at −78° C. After stirring for 45 minutes, cerium (III) chloride (1.11 g, 4.50 mmol) was added and the mixture was stirred for 45 minutes at −78° C. To the reaction was added 1-(1H-1,2,4-triazol-1-yl)propan-2-one (112 mg, 0.90 mmol) and the resulting mixture was stirred at −78° C. for 3 hours then, gradually warmed to 0° C. The reaction was quenched with 4.0M ammonium chloride, slurried in celite, and filtered. The product was extracted with 2MeTHF and washed with brine. The organics were dried with Na2SO4, filtered, and concentrated in vacuo. The crude product was taken to next step without further purification. MS (m/z) 224.1 [M+H]+.

Synthesis of N-((1S)-1-(3-(4-chloro-1-methyl-3-(methylsulfonamido)-1H-indazol-7-yl)-6-(3-hydroxy-3-methyl-4-(1H-1,2,4-triazol-1-yl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (70B): To 70A (28.3 mg, 126.5 mol) was added 1M tetrabutylammonium fluoride in THF (126 µl). After stirring at room temperature for 10 minutes, 43F (20 mg, 25.3 µmol), copper(I) iodide (1.9 mg, 10.1 µmol), Pd(C2)(Ph3)2 (3.6 mg, 5.1 µmol) and diethylamine (39.4 µl, 379.5 µmol) in DMF (0.4 mL) was added to the reaction. Argon was bubbled through the reaction for 1 minute and the mixture was heated in a microwave reactor for 15 minutes at 125° C. The excess amines were removed under vacuum and the product was purified by reverse phase HPLC to give the title compound 70B as a mixture of atropisomers. $^1$H NMR (400 MHz, cd$_3$od) δ 8.90-8.75 (m), 8.19 (s), 7.75-7.66 (m), 7.56-7.47 (m), 7.20-7.11 (m), 7.06 (dd), 6.81-6.71 (m), 6.68-6.59 (m), 6.47-6.39 (m), 6.39-6.32 (m), 5.25 (dd), 5.10 (s), 4.97 (t), 4.84-4.73 (m), 4.66-4.53 (m), 3.51-3.35 (m), 3.35-3.31 (m), 3.25 (s), 3.22 (s), 3.18-3.10 (m), 3.04-2.95 (m), 2.95-2.93 (m), 2.57-2.36 (m), 1.65 (s), 1.64 (s), 1.48-1.28 (m), 1.29-1.21 (m), 1.16-1.10 (m), 1.08-1.03 (m). MS (m/z) 905.1 [M+H]+.

Example 71

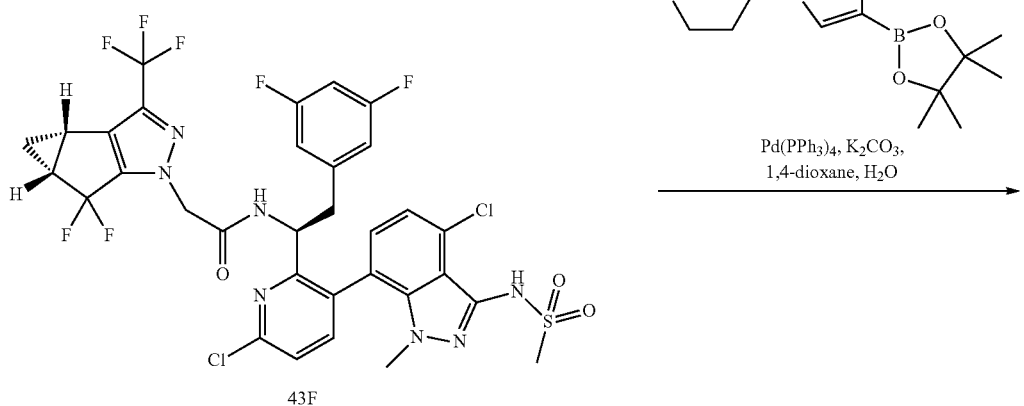

-continued

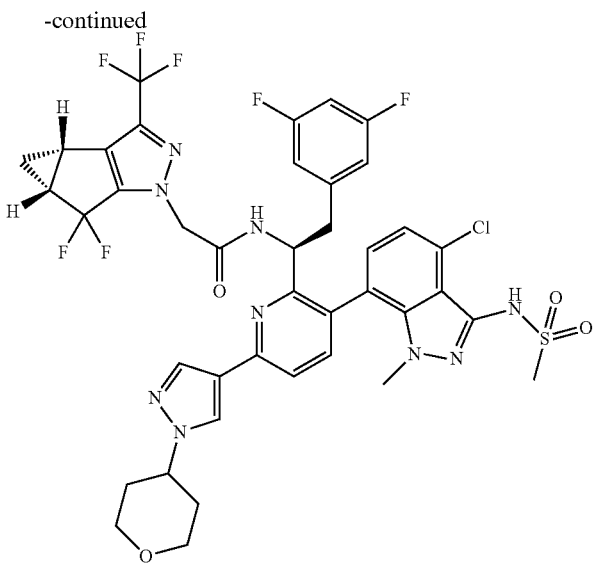

71

Synthesis of N—((S)-1-(3-(4-chloro-1-methyl-3-(methylsulfonamido)-1H-indazol-7-yl)-6-(1-(tetrahydro-2H-pyran-4-yl)-1H-pyrazol-4-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (71): N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (43F, 20 mg, 0.025 mmol), 1-(tetrahydro-2H-pyran-4-yl)-4-(4,4,5,5-tetramethyl-1,3,2-dioxaborolan-2-yl)-1H-pyrazole (8.4 mg, 0.030 mmol), Pd(PPh$_3$)$_4$ (1.5 mg, 0.0013 mmol), and K$_2$CO$_3$ (10.5 mg, 0.076 mmol) were suspended in a mixture of 1,4-dioxane (0.2 mL) and water (0.05 mL). The reaction mixture was degassed with argon for 60 seconds, then heated at 110° C. thermally for 2 hours. Upon completion, the reaction mixture was cooled and concentrated in vacuo. The crude residue was taken in DMF, filtered, and purified by reverse phase HPLC to give the title compound 71 as a mixture of atropisomers. $^1$H NMR (400 MHz, Methanol-d$_4$) δ 8.54-8.45 (m), 8.28-8.21 (m), 7.75-7.59 (m), 7.18-7.02 (m), 6.81-6.56 (m), 6.48-6.31 (m), 5.32-4.97 (m), 4.60-4.46 (m), 4.19-4.08 (m), 3.64 (td), 3.47-3.37 (m), 3.28-3.18 (m), 3.08-2.91 (m), 2.62-2.37 (m), 2.28-2.11 (m), 1.49-1.35 (m), 1.20-1.02 (m). MS (m/z) 906.22 [M+H]$^+$.

Example 72

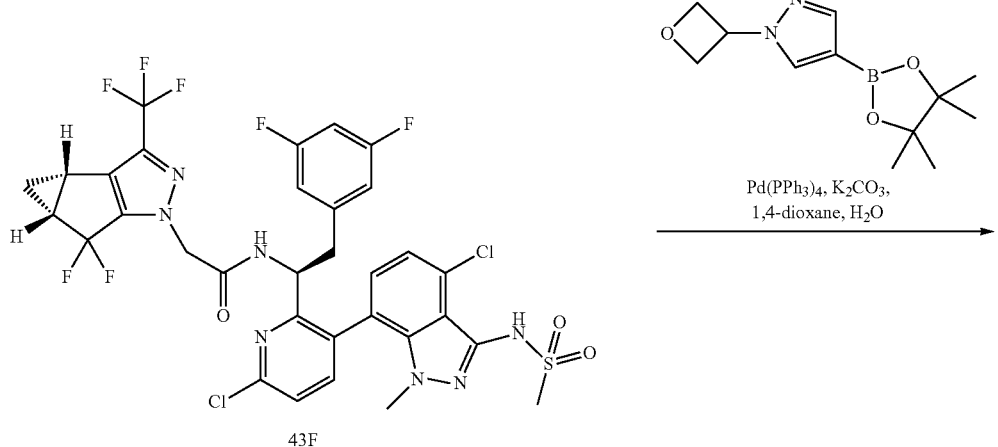

-continued

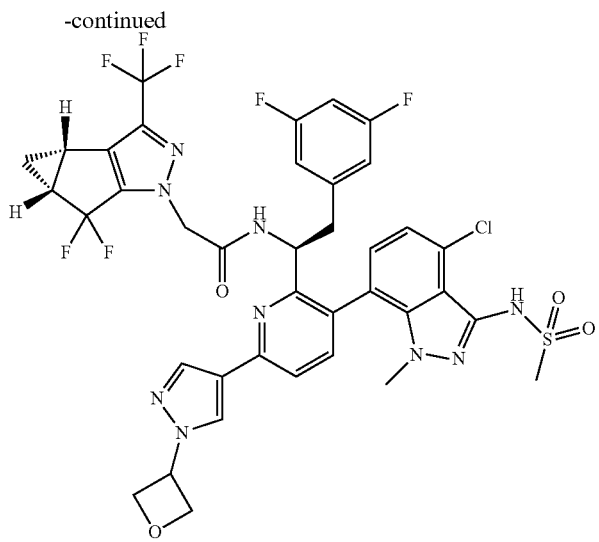

72

Synthesis of N—((S)-1-(3-(4-chloro-1-methyl-3-(methylsulfonamido)-1H-indazol-7-yl)-6-(1-(oxetan-3-yl)-1H-pyrazol-4-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (72): The title compound (72) was prepared according to the method presented for the synthesis of compound 71 of Example 71 utilizing N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (43F) and 1-(oxetan-3-yl)-4-(4,4,5,5-tetramethyl-1,3,2-dioxaborolan-2-yl)-1H-pyrazole. $^1$H NMR (400 MHz, Methanol-$d_4$) δ 8.61-8.54 (m), 8.40-8.31 (m), 7.77-7.60 (m), 7.18-7.00 (m), 6.85-6.57 (m), 6.51-6.33 (m), 5.68 (p), 5.30-4.95 (m), 3.48-3.36 (m), 3.27-3.18 (m), 3.09-2.94 (m), 2.60-2.39 (m), 1.52-1.34 (m), 1.21-0.98 (m). MS (m/z) 878.18 [M+H]$^+$.

Example 73

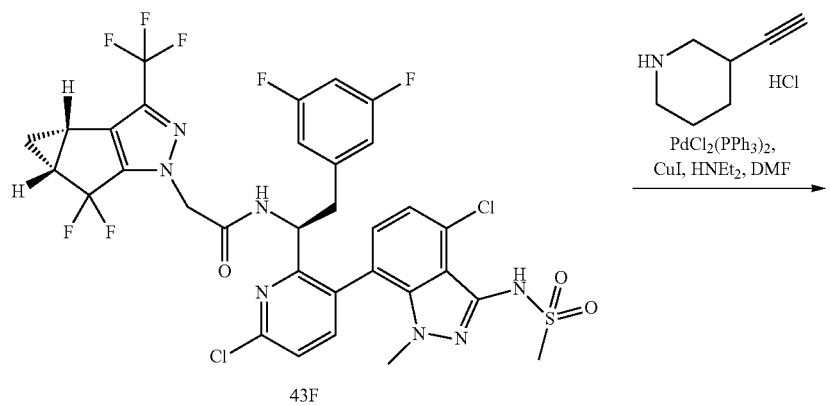

-continued

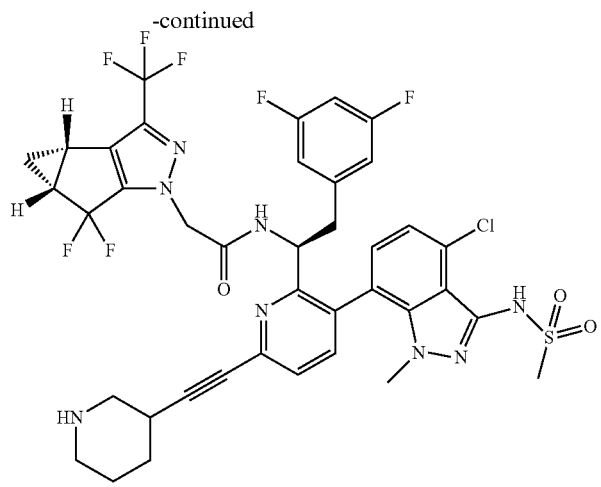

73

Synthesis of N-((1S)-1-(3-(4-chloro-1-methyl-3-(methylsulfonamido)-1H-indazol-7-yl)-6-(piperidin-3-ylethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (73): The title compound (73) was prepared according to the method presented for the synthesis of compound 57B of Example 57 utilizing N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (43F) and 3-ethynylpiperidine hydrochloride. $^1$H NMR (400 MHz, Methanol-$d_4$) δ 7.73 (dd), 7.58 (dd), 7.23-7.02 (m), 6.83-6.55 (m), 6.50-6.33 (m), 5.31-4.93 (m), 4.83-4.67 (m), 3.63-3.55 (m), 3.34-3.32 (m), 3.27-3.15 (m), 3.08-2.92 (m), 2.56-2.42 (m), 2.31-2.06 (m), 1.93-1.82 (m), 1.50-1.34 (m), 1.17-1.03 (m). MS (m/z) 863.20 [M+H]$^+$.

Example 74

Synthesis of N—((S)-1-(3-(4-chloro-1-methyl-3-(methylsulfonamido)-1H-indazol-7-yl)-6-((5-hydroxy-2,2-dimethyl-1,3-dioxan-5-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (74): The title compound (74) was prepared according to the method presented for the synthesis of compound 43G of Example 32 utilizing 5-ethynyl-2,2-dimethyl-1,3-dioxan-5-ol in place of 3-(2-methylbut-3-yn-2-yl)oxazolidin-2-one. $^1$H NMR (400 MHz, methanol-$d_4$) δ 7.71 (dd, 1H), 7.58 (dd, 1H), 7.21-7.06 (m, 2H), 6.76-6.63 (m, 1H), 6.45-6.31 (m, 2H), 5.28-4.98 (m, 1H), 4.77 (d, 2H), 4.15 (dd, 2H), 3.89 (dd, 2H), 3.36-3.29 (m, 3H), 3.24 (m, 3H), 3.15-2.90 (m, 1H), 3.06-2.91 (m, 2H), 2.49 (m, 2H), 1.55-1.33 (m, 7H), 1.15-1.01 (m, 1H). MS (m/z) 910.0 [M+H]$^+$ Example 75

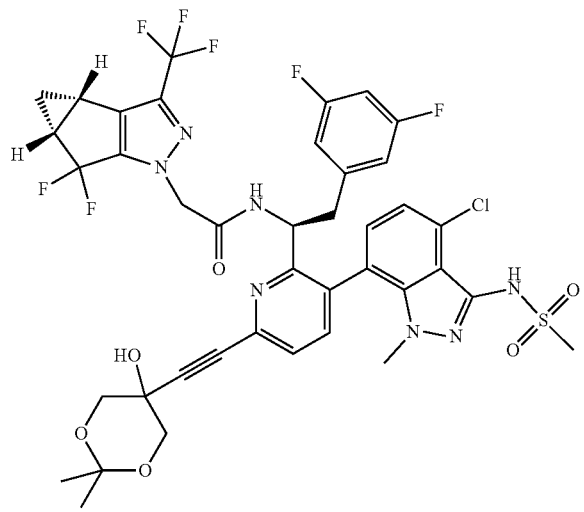

74

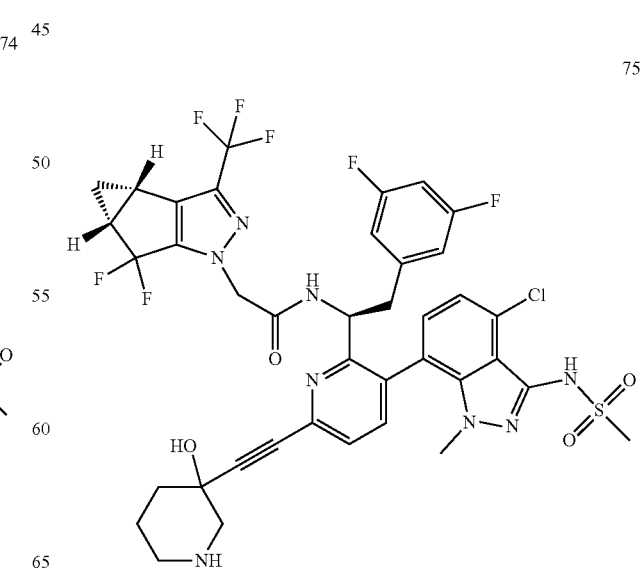

75

Synthesis of N-((1S)-1-(3-(4-chloro-1-methyl-3-(methylsulfonamido)-1H-indazol-7-yl)-6-((3-hydroxypiperidin-3-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (75): The title compound (75) was prepared according to the method presented for the synthesis of compound 43G of Example 43 utilizing tert-butyl 3-ethynyl-3-hydroxypiperidine-1-carboxylate in place of 3-(2-methylbut-3-yn-2-yl)oxazolidin-2-one. $^1$H NMR (400 MHz, methanol-d$_4$) δ 7.80-7.52 (m, 2H), 7.24-7.00 (m, 1H), 6.83-6.58 (m, 1H), 6.45-6.32 (m, 3H), 5.35-4.89 (m, 1H), 4.81-4.66 (m, 2H), 4.21-4.12 (m, 2H), 3.99-3.82 (m, 2H), 3.33-3.31 (m, 3H), 3.26-3.23 (m, 3H), 3.18-2.90 (m, 3H), 2.65-2.36 (m, 2H), 1.54-1.35 (m, 7H), 1.12-1.06 (m, 1H). MS (m/z) 879.4 [M+H]$^+$ Example 76

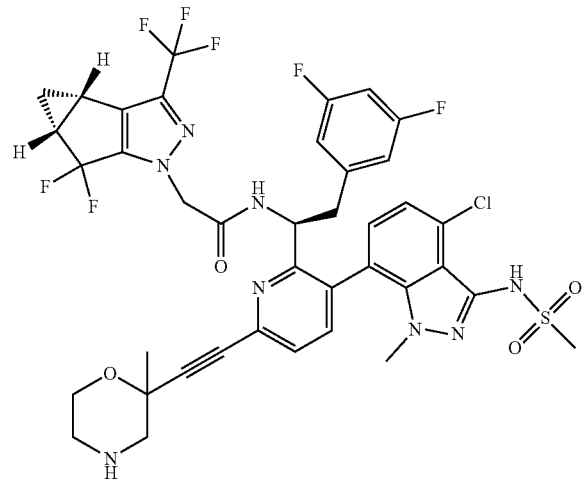

76

Synthesis of N-((1S)-1-(3-(4-chloro-1-methyl-3-(methylsulfonamido)-1H-indazol-7-yl)-6-((2-methylmorpholin-2-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (76): The title compound (76) was prepared according to the method presented for the synthesis of compound 43G of Example 43 utilizing tert-butyl 2-ethynyl-2-methylmorpholine-4-carboxylate in place of tert-butyl 2-ethynylpyrrolidine-1-carboxylate. $^1$H NMR (400 MHz, methanol-d$_4$) δ 8.74-8.69 (m, 1H), 7.86-7.60 (m, 2H), 7.32-7.02 (m, 2H), 6.88-6.59 (m, 1H), 6.48-6.33 (m, 3H), 5.38-4.91 (m, 1H), 4.78-4.64 (m, 2H), 4.48-4.30 (m, 1H), 4.11-4.06 (m, 1H), 3.64-3.61 (m, 1H), 3.33-3.31 (m, 4H), 3.26-3.23 (m, 5H), 3.12-2.92 (m, 2H), 2.49-2.42 (m, 2H), 1.93-1.72 (m, 3H), 1.59-1.29 (m, 1H), 1.12-1.06 (m, 1H). MS (m/z) 879.2 [M+H]$^+$ Example 77

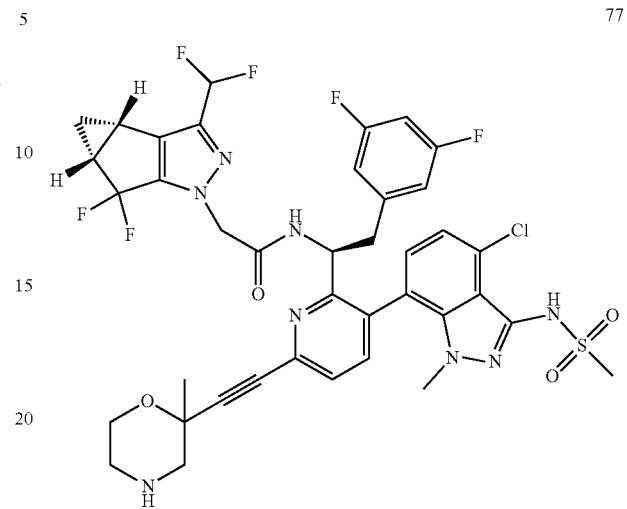

77

Synthesis of N-((1S)-1-(3-(4-chloro-1-methyl-3-(methylsulfonamido)-1H-indazol-7-yl)-6-((2-methylmorpholin-2-yl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (77): The title compound (77) was prepared according to the method presented for the synthesis of compound 60D of Example 60 utilizing tert-butyl 2-ethynyl-2-methylmorpholine-4-carboxylate in place of 3-(2-methylbut-3-yn-2-yl)oxazolidin-2-one and the addition of TFA (1 mL) before purification. $^1$H NMR (400 MHz, methanol-d$_4$) δ 8.66-8.58 (m, 1H), 7.81-7.68 (m, 2H), 7.24-7.07 (m, 1H), 6.85-6.54 (m, 2H), 6.44-6.32 (m, 3H), 5.32-4.96 (m, 1H), 4.75-4.66 (m, 2H), 4.44-4.38 (m, 1H), 4.11-4.06 (m, 1H), 3.64-3.61 (m, 1H), 3.33-3.31 (m, 4H), 3.26-3.23 (m, 4H), 3.02-2.97 (m, 3H), 2.49-2.42 (m, 2H), 1.93-1.72 (m, 3H), 1.41-1.35 (m, 1H), 1.07-1.01 (m, 1H). MS (m/z) 861.2 [M+H]$^+$ Example 78

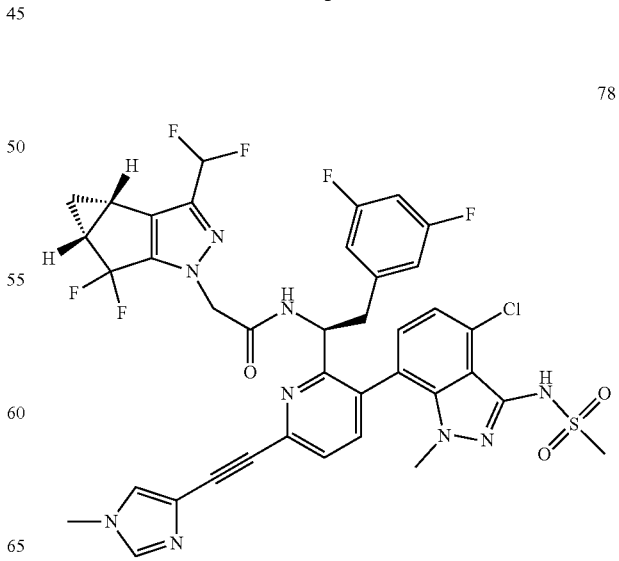

78

Synthesis of N—((S)-1-(3-(4-chloro-1-methyl-3-(methylsulfonamido)-1H-indazol-7-yl)-6-((1-methyl-1H-imidazol-4-yl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (78): The title compound (78) was prepared according to the method presented for the synthesis of compound 60X of Example 60 utilizing 4-ethynyl-1-methyl-1H-imidazole in place of 3-(2-methylbut-3-yn-2-yl)oxazolidin-2-one. MS (m/z) 842.1 [M+H]+ HPLC retention time 6.21 min and 6.34 min (2-98% acetonitrile: water with 0.1% trifluoroacetic acid, 8.5 min gradient on a Phenomonex Kinetex C18 column).

Example 79

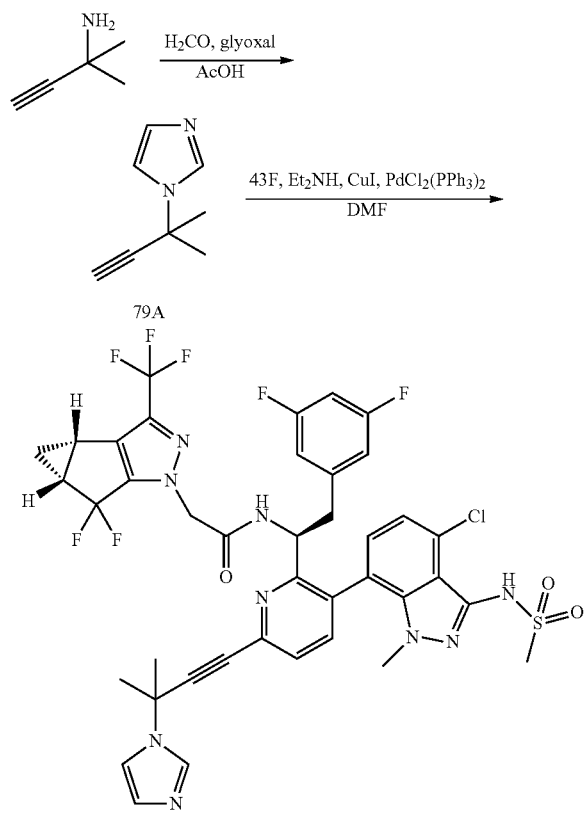

Synthesis of 1-(2-methylbut-3-yn-2-yl)-1H-imidazole (79A): A solution of 2-methylbut-3-yn-2-amine (0.51 ml, 4.82 mmol), 40% glyoxal in water (0.55 ml, 4.82 mmol), 36% formaldehyde in water (0.37 ml, 4.82 mmol), and acetic acid (0.28 ml, 4.82 mmol) was stirred at room temperature for 1 hour. 4M ammonium chloride in water (1.3 ml) was added and the reaction was heated in a microwave reactor at 120° C. for 20 minutes. The mixture was concentrated in vacuo, dissolved in dichloromethane, dried under sodium sulfate, and concentrated. The product was purified by silica chromatography to give the title compound 79A. MS (m/z) 135.0 [M+H]+.

Synthesis of N—((S)-1-(6-(3-(1H-imidazol-1-yl)-3-methylbut-1-yn-1-yl)-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (79B): A solution of 43F (20 mg, 25.3 µmol), 1-(2-methylbut-3-yn-2-yl)-1H-imidazole (6.79 mg, 50.6 mol), copper(I) iodide (0.5 mg, 2.5 µmol), Pd(Cl$_2$)(Ph$_3$) (1.8 mg, 2.5 µmol), and diethylamine (30 µl, 250 µmol) in DMF (0.2 ml) was degassed with argon and heated in a microwave reactor at 125° C. for 20 minutes. The excess diethylamine was removed under vacuum and the product was purified by reverse phase HPLC to give the title compound 79B as a mixture of atropisomers. $^1$H NMR (400 MHz, cd$_3$od) δ 8.57 (s), 8.00-7.93 (m), 7.31-7.27 (m), 7.00-6.94 (m), 6.93-6.85 (m), 6.44-6.36 (m), 6.28 (d), 6.01-5.93 (m), 5.87-5.79 (m), 5.65-5.53 (m), 4.54-4.46 (m), 4.22-4.15 (m), 4.00-3.88 (m), 2.51 (s), 2.45 (s), 2.42 (s), 2.38-2.29 (m), 2.26-2.14 (m), 1.76-1.60 (m), 1.34 (s), 0.65-0.53 (m), 0.34-0.28 (m), 0.27-0.20 (m). MS (m/z) 888.2 [M+H]+.

Example 80

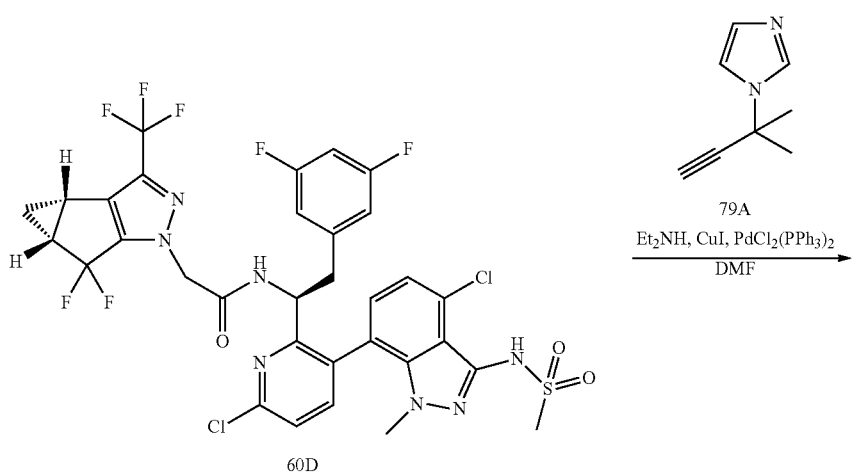

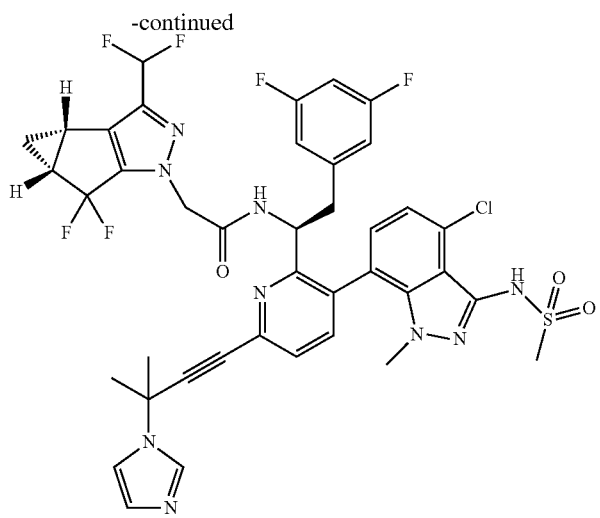

80

Synthesis of N—((S)-1-(6-(3-(1H-imidazol-1-yl)-3-methylbut-1-yn-1-yl)-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (80): The title compound (80) was prepared as a mixture of atropisomers according to the method presented for the synthesis of compound 79B of Example 79 utilizing compound 60D. $^1$H NMR (400 MHz, cd$_3$od) δ 8.57 (s), 7.92-7.83 (m), 7.29 (s), 7.00-6.78 (m), 6.77-6.69 (m), 6.44-6.34 (m), 6.28 (d), 6.05-5.70 (m), 5.66-5.52 (m), 4.55-4.45 (m), 4.22-4.15 (m), 3.93 (s), 3.89 (d), 2.51 (s), 2.45 (s), 2.42 (s), 2.33 (dd), 2.24-2.13 (m), 2.04 (s), 1.71-1.57 (m), 1.34 (s), 0.62-0.52 (m), 0.29-0.23 (m), 0.22-0.16 (m). MS (m/z) 870.2 [M+H]$^+$.

Example 81

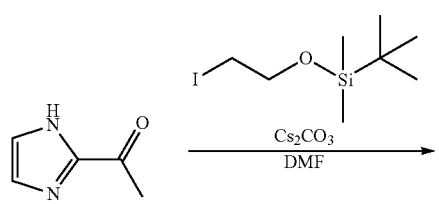

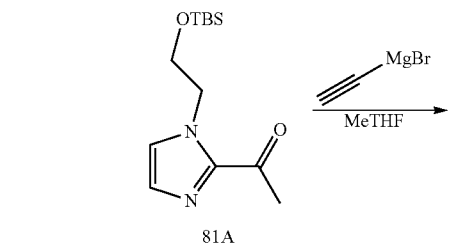

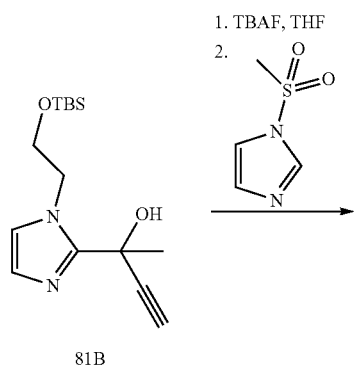

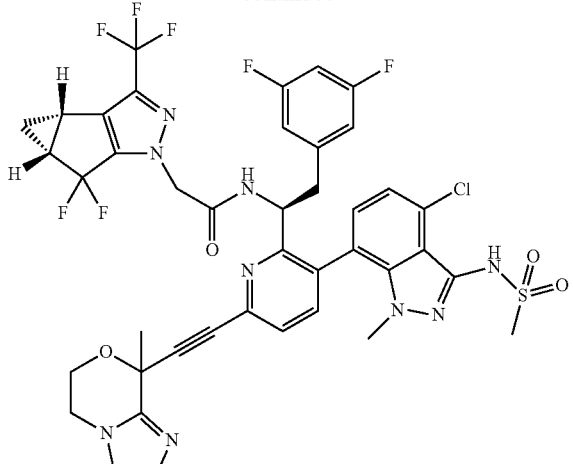

81E

Synthesis of 1-(1-(2-((tert-butyldimethylsilyl)oxy)ethyl)-1H-imidazol-2-yl)ethanone (81A) To a solution of 1-(1H-imidazol-2-yl)ethanone (0.31 g, 2.79 mmol) in DMF (3 ml) was added cesium carbonate (1.82 g, 5.59 mmol) followed by tert-butyl(2-iodoethoxy)dimethylsilane (0.8 g, 2.79 mmol). After stirring overnight at 40° C., the mixture was diluted with ethyl acetate and washed with water, followed by brine. The organic layer was dried with sodium sulfate, filtered, and concentrated. Product was purified by silica gel chromatography to give the title compound 81A. MS (m/z) 269.9 [M+H]⁺.

Synthesis of 2-(1-(2-((tert-butyldimethylsilyl)oxy)ethyl)-1H-imidazol-2-yl)but-3-yn-2-ol (81B): To a stirring solution of 0.5M ethynylmagnesium bromide in THF (2.4 ml) was added dropwise at 0° C. a solution of 1-(1-(2-((tert-butyldimethylsilyl)oxy)ethyl)-1H-imidazol-2-yl)ethanone in 2-MeTHF (7 ml). The reaction was warmed to room temperature and stirred for 1.5 hours. The resulting mixture was poured in a mixture of ice and 4.0M ammonium chloride. The organic layer was diluted with MeTHF, washed with water, dried with sodium sulfate, filtered, and concentrated. The product was purified by silica gel chromatography to give the title compound 81B. MS (m/z) 295.2 [M+H]⁺.

Synthesis of 2-(2-(2-hydroxybut-3-yn-2-yl)-1H-imidazol-1-yl)ethyl methanesulfonate (81C): To a solution of 81B (90 mg, 0.31 mmol) in THF (1.5 ml) was added 1.0M TBAF in THF (0.32 ml). After stirring for 30 minutes, 1-(methylsulfonyl)-1H-imidazole (44.61 mg, 0.31 mmol) was added and the mixture was sonicated until the solution became homogeneous. The reaction was stirred at room temperature for 3 hours. The resulting mixture was concentrated and the product was purified by silica gel chromatography to give the title compound 81C. MS (m/z) 259.5 [M+H]⁺.

Synthesis of 8-ethynyl-8-methyl-6,8-dihydro-5H-imidazo[2,1-c][1,4]oxazine (81D): To a solution of 81C (27 mg, 0.1 mmol) in THF (1 ml) was added sodium hydride (60% in mineral oil, 5.4 mg, 0.14 mmol). After stirring at room temperature for 24 hours, the reaction was diluted with methanol (1 ml), solid loaded onto silica gel, and purified by silica gel chromatography to give the title compound 81D. MS (m/z) 163.1 [M+H]⁺.

Synthesis of N—((S)-1-(6-(3-(1H-imidazol-1-yl)-3-methylbut-1-yn-1-yl)-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (81E): The title compound (81E) was prepared as a mixture of atropisomers according to the method presented for the synthesis of compound 79B of Example 79 utilizing 8-ethynyl-8-methyl-6,8-dihydro-5H-imidazo[2,1-c][1,4]oxazine. ¹H NMR (400 MHz, cd₃od) δ 7.90-7.82 (m), 7.16 (s), 6.98-6.91 (m), 6.91-6.78 (m), 6.42-6.33 (m), 6.27 (dd), 6.04-5.70 (m), 5.66-5.51 (m), 4.51-4.43 (m), 4.21-4.11 (m), 3.91 (s), 3.87 (d), 3.83-3.71 (m), 3.69-3.52 (m), 2.44 (s), 2.41 (s), 2.36-2.26 (m), 2.22-2.11 (m), 2.04 (s), 1.70-1.58 (m), 1.33 (s), 0.63-0.52 (m), 0.29-0.23 (m), 0.22-0.16 (m). MS (m/z) 916.3 [M+H]⁺.

Example 82

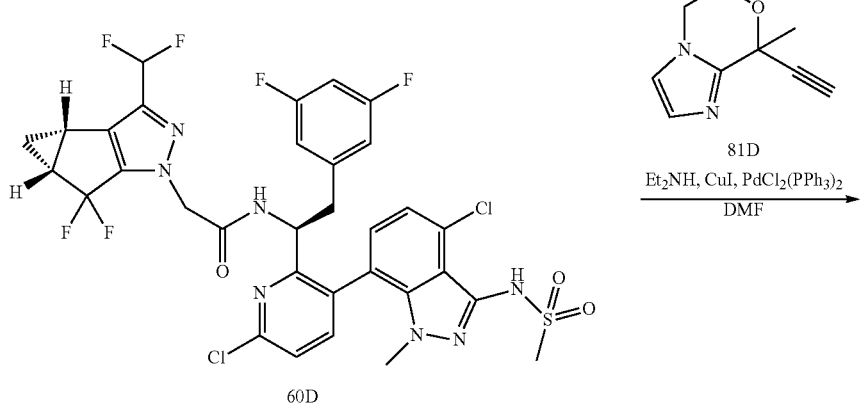

60D

81D

Et₂NH, CuI, PdCl₂(PPh₃)₂
DMF

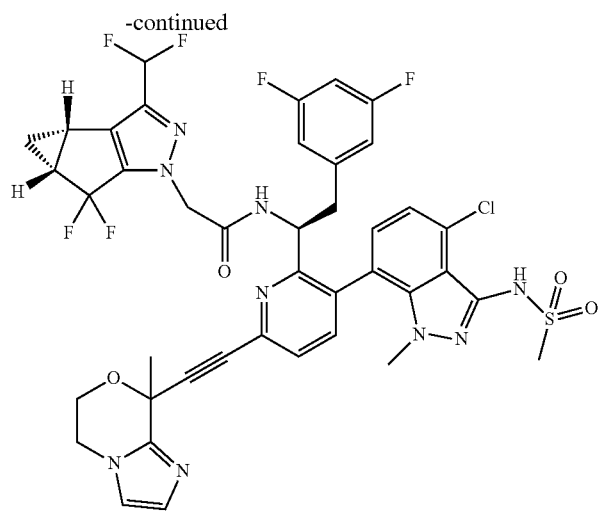

82

Synthesis of N-((1S)-1-(3-(4-chloro-1-methyl-3-(methylsulfonamido)-1H-indazol-7-yl)-6-((8-methyl-6,8-dihydro-5H-imidazo[2,1-c][1,4]oxazin-8-yl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (82): The title compound (82) was prepared as a mixture of atropisomers according to the method presented for the synthesis of compound 80 of Example 80 utilizing 8-ethynyl-8-methyl-6,8-dihydro-5H-imidazo[2,1-c][1,4]oxazine. $^1$H NMR (400 MHz, cd$_3$od) δ 7.99-7.92 (m), 7.16 (s), 6.98-6.90 (m), 6.90-6.78 (m), 6.42-6.33 (m), 6.29-6.24 (m), 6.01-5.91 (m), 5.86-5.78 (m), 5.65-5.51 (m), 4.47 (d), 4.21-4.11 (m), 3.99-3.86 (m), 3.84-3.71 (m), 3.68-3.52 (m), 2.44 (s), 2.41 (s), 2.36-2.27 (m), 2.24-2.13 (m), 2.04 (s), 1.76-1.60 (m), 1.33 (s), 0.65-0.55 (m), 0.33-0.28 (m), 0.25-0.20 (m). MS (m/z) 898.2 [M+H]$^+$.

Example 83

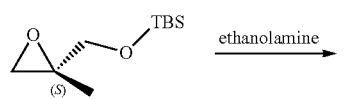

83A

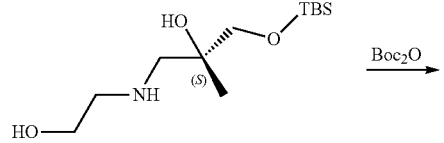

83B

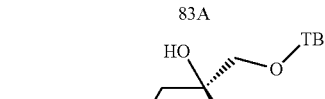

83C

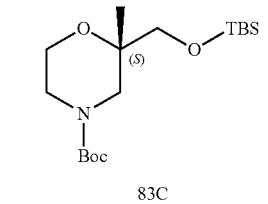

83D, 83E, 83F

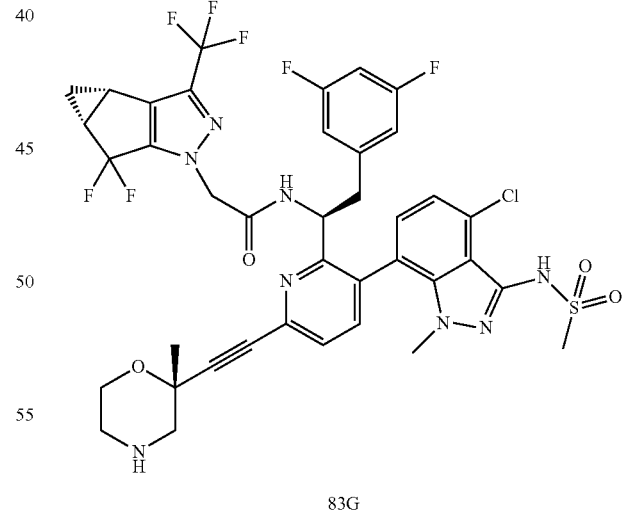

83G

Synthesis of (S)-1-((tert-butyldimethylsilyl)oxy)-3-((2-hydroxyethyl)amino)-2-methylpropan-2-ol (83A): A solution of (S)-tert-butyldimethyl((2-methyloxiran-2-yl)methoxy)silane (0.198 g, 0.97 mmol) in THF (1 mL) was treated with ethanolamine (0.58 mL, 9.7 mmol) and stirred at rt for 16 h. The reaction mixture was concentrated, dissolved in Me-THF then washed with brine. The organic phase was separated, dried over sodium sulfate, filtered and concentrated to give the title compound. MS (m/z) 264.3 [M+H]+.

Synthesis of (S)-tert-butyl(3-((tert-butyldimethylsilyl)oxy)-2-hydroxy-2-methylpropyl)(2-hydroxyethyl)carbamate (83B): The crude material 83A (~0.7 mmol) was dissolved in acetonitrile and treated with Boc anhydride for 1 h at it. The reaction was concentrated and the crude material was purified by silica gel to give the title compound. ¹H NMR (400 MHz, chloroform-d) δ 3.76-3.73 (m, 3H), 3.44-3.41 (m, 5H), 1.44 (s, 9H), 1.12 (s, 3H), 0.88 (s, 9H), 0.04 (s, 6H).

Synthesis of (S)-tert-butyl 2-(((tert-butyldimethylsilyl)oxy)methyl)-2-methylmorpholine-4-carboxylate (83C): A solution of 83B (0.12 g, 0.34 mmol) in toluene was treated with PPh₃ (0.10 g, 0.4 mmol) followed by a toluene solution of diisopropyl azodicarboxylate (0.08 g, 0.4 mmol) in toluene (1 mL) added dropwise. The reaction was stirred at rt for 16 h. The reaction mixture was poured onto brine, extracted with ethyl acetate, dried over sodium sulfate, filtered and concentrated. The crude material was purified by silica gel chromatography to give the title compound. ¹H NMR (400 MHz, chloroform-d) δ 3.72-3.15 (m, 8H), 1.43 (s, 9H), 1.15 (s, 3H), 0.87 (s, 9H), 0.04 (s, 6H).

Synthesis of (S)-tert-butyl 2-(hydroxymethyl)-2-methylmorpholine-4-carboxylate (83D): A solution of 83C (0.59 g, 1.7 mmol) in THF was treated with TBAF (3.42 mmol, 1 M in THF) at rt for 2 h. The reaction mixture was poured onto a saturated solution of ammonium chloride and the product was extracted with ethyl ether, dried over sodium sulfate, filtered and concentrated to give the crude title compound that was used as is for the next step.

Synthesis of (S)-tert-butyl 2-formyl-2-methylmorpholine-4-carboxylate (83E): A solution of crude 83C (0.39 g, 1.7 mmol) in DCM (10 mL) was treated with Dess-Martin reagent (1.0 g, 2.3 mmol) then stirred at rt for 1 h. The reaction mixture was poured onto ethyl ether, washed twice with a saturate sodium bicarbonate solution, then brine. The organic phase was then separated, dried over sodium sulfate, filtered and concentrated. The crude material was purified by silica gel chromatography to give the title compound. ¹H NMR (400 MHz, chloroform-d) δ 1H NMR (400 MHz, cdcl3) δ 9.55 (s, 1H), 4.10-4.03 (m, 3H), 3.83, 3.80-3.63 (m, 3H), 3.07-3.00 (m, 1H), 2.89-2.85 (d, 1H), 1.40 (s, 9H), 1.14 (s, 3H).

Synthesis of (S)-tert-butyl 2-formyl-2-methylmorpholine-4-carboxylate (83F): A solution of crude 83E (0.78 g, 3.4 mmol) in MeOH (10 mL) was treated with potassium carbonate (4.7 g, 34 mmol), cooled to 0° C., followed by the addition of dimethyl-1-diazo-2-oxopropylphosphonate (0.78 g, 4 mmol). The reaction was allowed to slowly reach rt and stirred for 16 h. The reaction mixture was then filtered through Celite, the filtrate was washed twice with water, then dried over sodium sulfate, filtered and concentrated. The crude material was purified by silica gel chromatography to give the title compound. ¹H NMR (400 MHz, chloroform-d) δ 1H NMR (400 MHz, cdcl3) δ 4.14-4.00 (m, 4H), 3.70-3.63 (m, 2H), 2.42 (s, 1H), 1.47 (s, 9H), 1.45 (s, 3H).

Synthesis of N—((S)-1-(3-(4-chloro-1-methyl-3-(methylsulfonamido)-1H-indazol-7-yl)-6-(((R)-2-methylmorpholin-2-yl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (83G): The title compound (83G) was prepared according to the method presented for the synthesis of compound 43G of Example 43 utilizing (S)-tert-butyl 2-formyl-2-methylmorpholine-4-carboxylate in place of tert-butyl 2-ethynylpyrrolidine-1-carboxylate. ¹H NMR (400 MHz, methanol-d₄) δ 8.74-8.69 (m, 1H), 7.86-7.60 (m, 2H), 7.32-7.02 (m, 2H), 6.88-6.59 (m, 1H), 6.48-6.33 (m, 3H), 5.38-4.91 (m, 1H), 4.78-4.64 (m, 2H), 4.48-4.30 (m, 1H), 4.11-4.06 (m, 1H), 3.64-3.61 (m, 1H), 3.33-3.31 (m, 4H), 3.26-3.23 (m, 51H), 3.12-2.92 (m, 2H), 2.49-2.42 (m, 2H), 1.93-1.72 (m, 3H), 1.59-1.29 (m, 1H), 1.12-1.06 (m, 1H). MS (m/z) 879.3 [M+H]+

Example 84

84

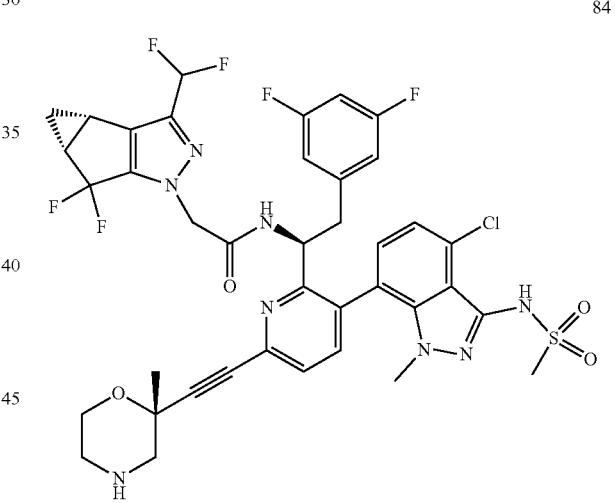

Synthesis of N—((S)-1-(3-(4-chloro-1-methyl-3-(methylsulfonamido)-1H-indazol-7-yl)-6-(((R)-2-methylmorpholin-2-yl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (84): The title compound (84) was prepared according to the method presented for the synthesis of compound 60D of Example 60 utilizing tert-butyl 2-ethynylpyrrolidine-1-carboxylate in place of 3-(2-methylbut-3-yn-2-yl)oxazolidin-2-one. ¹H NMR (400 MHz, methanol-d₄) δ 8.64-8.62 (m, 1H), 7.81-7.68 (m, 2H), 7.24-7.07 (m, 2H), 6.85-6.54 (m, 2H), 6.44-6.32 (m, 2H), 5.32-4.96 (m, 1H), 4.75-4.66 (m, 2H), 4.44-4.38 (m, 1H), 4.11-4.06 (m, 1H), 3.64-3.61 (m, 1H), 3.33-3.31 (m, 4H), 3.26-3.23 (m, 5H), 3.02-2.97 (m, 3H), 2.49-2.42 (m, 2H), 1.93-1.72 (m, 3H), 1.41-1.35 (m, 1H), 1.07-1.01 (m, 1H). MS (m/z) 861.2 [M+H]+.

Example 85

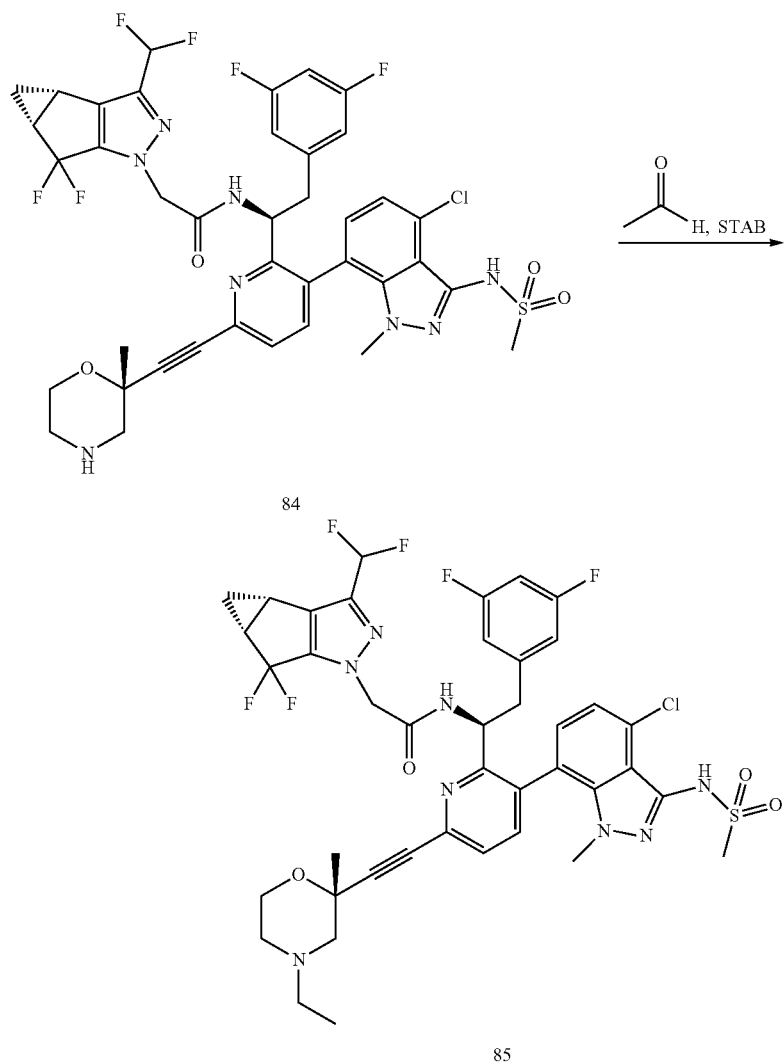

Synthesis of N—((S)-1-(3-(4-chloro-1-methyl-3-(methylsulfonamido)-1H-indazol-7-yl)-6-(((R)-4-ethyl-2-methylmorpholin-2-yl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1-cyclopropa[3,4]cyclopenta[1,2-c]pyrazol-1-yl)acetamide (85): To the reaction vial containing 84 (14 mg, 0.016 mmol) in DCM (0.25 mL) and acetic acid (0.25 ml) was added acetaldehyde (4 mg, 0.08 mmol)) followed by sodium triacetoxyborohydride (10 mg, 0.048 mmol) The reaction mixture was stirred for 2 h at rt, filtered and purified by reverse phase HPLC, eluting with 5-100% acetonitrile in water with 0.1% TFA. Fractions containing the product were pooled and lyophilized to provide the TFA salt of the title compound 85. $^1$H NMR (400 MHz, methanol-$d_4$) δ 8.63-8.61 (m, 1H), 7.82-7.67 (m, 2H), 7.26-7.07 (m, 2H), 6.85-6.54 (m, 2H), 6.44-6.32 (m, 2H), 5.35-4.97 (m, 1H), 4.69 (s, 2H), 4.44-4.37 (m, 1H), 4.18-4.15 (m, 1H), 3.89-3.86 (m, 1H), 3.56-3.47 (m, 1H), 3.33-3.31 (m, 5H), 3.26-3.12 (m, 6H), 3.02-2.97 (m, 1H), 2.48-2.42 (m, 2H), 1.93-1.75 (m, 3H), 1.45-1.37 (m, 4H), 1.03-1.01 (m, 1H). MS (m/z) 889.3 [M+H]$^+$.

Example 86

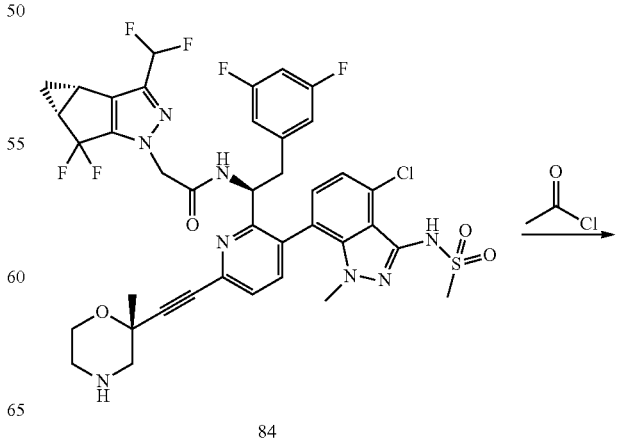

-continued

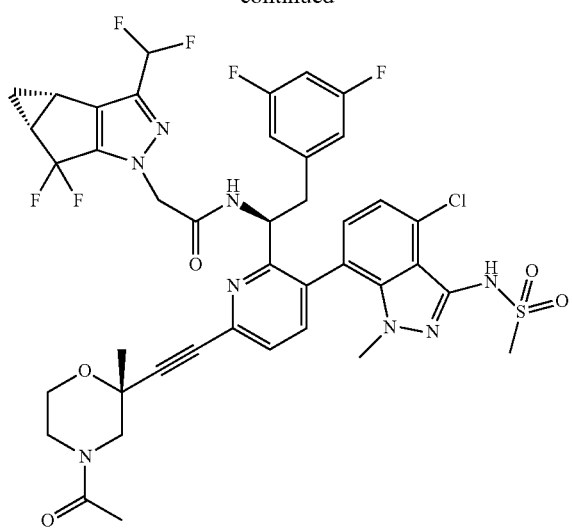

86

Synthesis of N—((S)-1-(6-(((R)-4-acetyl-2-methylmorpholin-2-yl)ethynyl)-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (86): To the reaction vial containing 84 (14 mg, 0.016 mmol) in DCM (1 mL) was treated with acetyl chloride (0.05 mg, 0.048 mmol)) The reaction mixture was stirred for 0.5 h at rt. The reaction was concentrated dissolve in methanol (1 mL) and treated with solid potassium carbonate (0.1 mmol) for 30 min at rt. The reaction was filtered and purified by reverse phase HPLC, eluting with 5-100% acetonitrile in water with 0.1% TFA. Fractions containing the product were pooled and lyophilized to provide the TFA salt of the title compound 86. $^1$H NMR (400 MHz, methanol-$d_4$) δ 8.68-8.66 (m, 1H), 7.81-7.49 (m, 2H), 7.27-7.00 (m, 1H), 6.93-6.52 (m, 2H), 6.51-6.32 (m, 3H), 5.36-4.92 (m, 1H), 4.82-4.59 (m, 2H), 4.52-4.48 (m, 1H), 4.25-4.01 (m, 2H), 3.86-3.81 (m, 1H), 3.34-3.33 (m, 4H), 3.25-3.23 (m, 3H), 3.15-3.11 (m, 1H), 3.03-2.79 (m, 3H), 2.51-2.40 (m, 2H), 2.34-2.14 (m, 3H), 2.00-1.56 (m, 3H), 1.39-1.34 (m, 1H), 1.08-1.01 (m, 1H). MS (m/z) 903.2 [M+H]$^+$.

Example 87

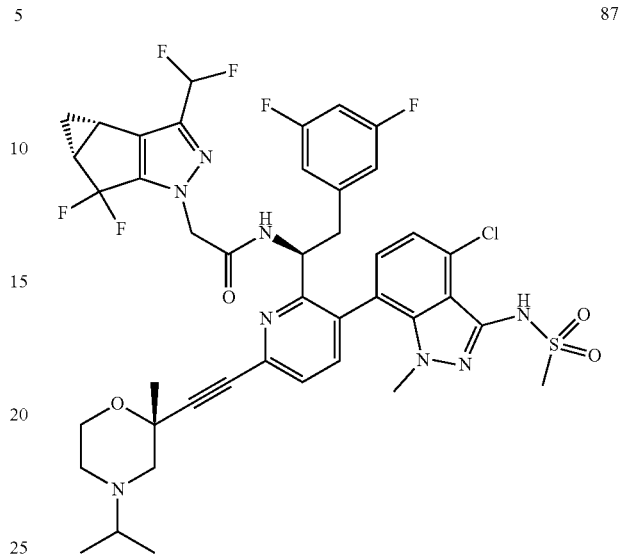

87

Synthesis of N—((S)-1-(3-(4-chloro-1-methyl-3-(methylsulfonamido)-1H-indazol-7-yl)-6-(((R)-4-isopropyl-2-methylmorpholin-2-yl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (87): The title compound (87) was prepared according to the method presented for the synthesis of compound 85 of Example 85 utilizing acetone in place of acetaldehyde and sodium cyanoborohydride in place of sodium triacetoxyborohydride. $^1$H NMR (400 MHz, methanol-$d_4$) δ 8.65-8.61 (m, 1H), 7.87-7.60 (m, 2H), 7.30-7.01 (m, 1H), 6.89-6.50 (m, 2H), 6.47-6.37 (m, 3H), 5.42-4.92 (m, 1H), 4.75-4.63 (m, 2H), 4.45-4.39 (m, 1H), 4.25-4.10 (m, 1H), 3.82-3.79 (m, 1H), 3.69-3.56 (m, 1H), 3.54-3.41 (m, 1H), 3.33 (s, 3H), 3.26-3.21 (m, 4H), 3.18-3.13 (m, 1H), 3.08-2.93 (m, 2H), 2.48-2.42 (m, 2H), 1.93-1.77 (m, 3H), 1.46 (dd, 6H), 1.38-1.37 (m, 1H), 1.16-0.95 (m, 1H). MS (m/z) 903.3 [M+H]$^+$ Example 88

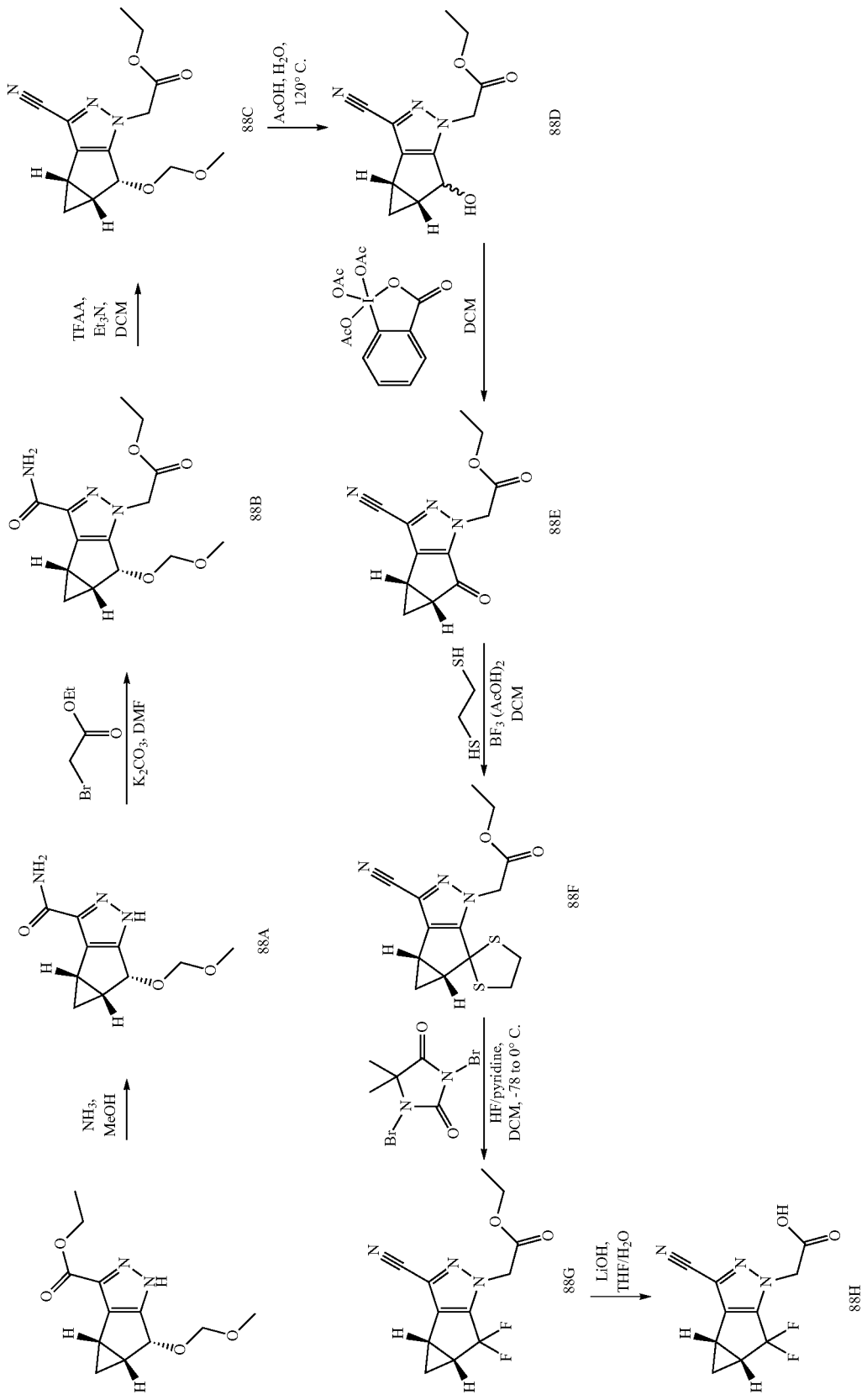

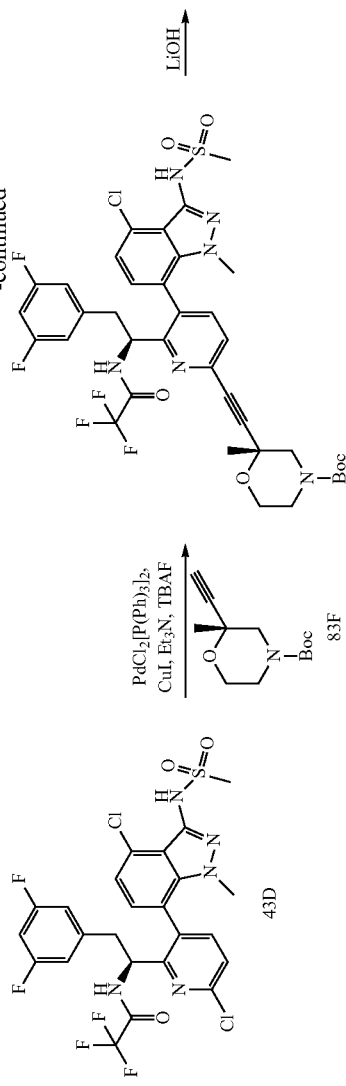
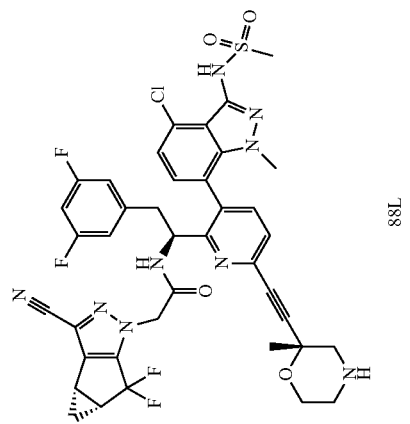
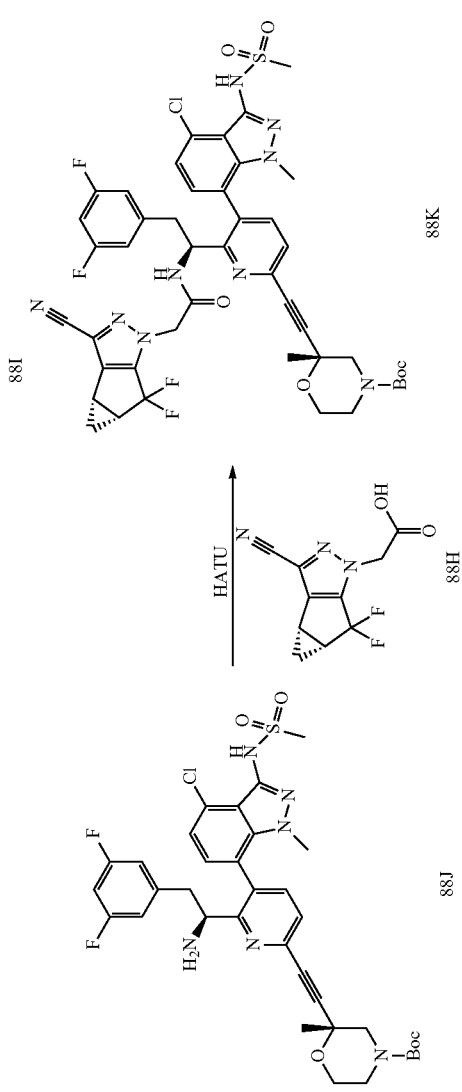

Synthesis of (3bS,4aR)-5-(methoxymethoxy)-3b,4,4a,5-tetrahydro-1H-cyclopropa[3,4]cyclopenta[1,2-c]pyrazole-3-carboxamide (88A): (3bS,4aR)-ethyl 5-(methoxymethoxy)-3b,4,4a,5-tetrahydro-1H-cyclopropa[3,4]cyclopenta[1,2-c]pyrazole-3-carboxylate (7.49 g, 29.7 mmol) was dissolved in 7N ammonia in methanol (20 mL). The solution was heated at 145° C. in a metal bomb overnight. After cooling, the volatiles were evaporated under vacuum and the residue was dissolved in 10% methanol in DCM. The solution was filtered through a plug of silica gel and eluted with 1 L 10% methanol in DCM. Evaporation of the solvents under vacuum gave the title compound. MS (m/z) 224.1 [M+H]+.

Synthesis of ethyl 2-((3bS,4aR)-3-carbamoyl-5-(methoxymethoxy)-3b,4,4a,5-tetrahydro-1H-cyclopropa[3,4]cyclopenta[1,2-c]pyrazol-1-yl)acetate (88B): (3bS,4aR)-5-(methoxymethoxy)-3b,4,4a,5-tetrahydro-1H-cyclopropa[3,4]cyclopenta[1,2-c]pyrazole-3-carboxamide (88A, 4.3 g, 19.26 mmol) was dissolved in DMF (30 mL) and potassium carbonate (8 g, 57.8 mmol) was added. Ethyl 2-bromoacetate (3.86 g, 23.1 mmol) was added dropwise. The mixture was stirred at ambient temperature for 4 hours. After dilution with ethyl acetate (200 mL), the solution was washed with water and brine, and evaporated under vacuum. Purification on 120 g silica gel, eluting with 50-100% ethyl acetate in hexane gave the title compound. MS (m/z) 310.2 [M+H]+.

Synthesis of ethyl 2-((3bS,4aR)-3-cyano-5-(methoxymethoxy)-3b,4,4a,5-tetrahydro-1H-cyclopropa[3,4]cyclopenta[1,2-c]pyrazol-1-yl)acetate (88C): To a solution of ethyl 2-((3bS,4aR)-3-carbamoyl-5-(methoxymethoxy)-3b,4,4a,5-tetrahydro-1H-cyclopropa[3,4]cyclopenta[1,2-c]pyrazol-1-yl)acetate (88B, 3.34 g, 10.8 mmol) in dichloromethane (100 mL) cooled in an ice bath was added triethylamine (3.31 mL, 24 mmol) followed by dropwise addition of trifluoroacetic acid anhydride (1.68 mL, 12 mmol). The mixture was stirred in ice bath for 30 min, then quenched with 100 mL water, extracted with ethyl acetate. The combined organic layers were washed with brine and evaporated under vacuum. Purification on 120 g silica gel, eluting with 10-60% ethyl acetate in hexane gave the title compound. MS (m/z) 292.1 [M+H]+.

Synthesis of ethyl 2-((3bS,4aR)-3-cyano-5-hydroxy-3b,4,4a,5-tetrahydro-1H-cyclopropa[3,4]cyclopenta[1,2-c]pyrazol-1-yl)acetate (88D): Ethyl 2-((3bS,4aR)-3-cyano-5-(methoxymethoxy)-3b,4,4a,5-tetrahydro-1H-cyclopropa[3,4]cyclopenta[1,2-c]pyrazol-1-yl)acetate (88C, 6.0 g, 20.6 mmol) was dissolved in acetonitrile (20 mL), water (10 mL), and acetic acid (1.5 mL). The mixture was heated in a microwave reactor at 125° C. for 2 hours. The volatiles were evaporated under vacuum and the title compound was obtained after purification on 120 g silica gel, 10-100% ethyl acetate in hexane. MS (m/z) 248.1 [M+H]+.

Synthesis of ethyl 2-((3bS,4aR)-3-cyano-5-oxo-3b,4,4a,5-tetrahydro-1H-cyclopropa[3,4]cyclopenta[1,2-c]pyrazol-1-yl)acetate (88E): To a solution of ethyl 2-((3bS,4aR)-3-cyano-5-hydroxy-3b,4,4a,5-tetrahydro-1H-cyclopropa[3,4]cyclopenta[1,2-c]pyrazol-1-yl)acetate (88D, 3.07 g, 12.42 mmol) in dichloromethane (60 mL) was added Dess-Martin periodinane (6.32 g, 15 mmol). The mixture was stirred at ambient temperature overnight, and then quenched with sodium thiosulfate solution and sodium bicarbonate solution. The mixture was extracted with dichloromethane, the organic phases washed with brine, and evaporated under vacuum. Purification on 80 g silica gel, eluting with 0-80% ethyl acetate in hexane gave the title compound. MS (m/z) 246.1 [M+H]+.

Synthesis of ethyl 2-((3bS,4aR)-3-cyano-4,4a-dihydrospiro[cyclopropa[3,4]cyclopenta[1,2-c]pyrazole-5,2'-[1,3]dithiolane]-1(3bH)-yl)acetate (88F): To a solution of ethyl 2-((3bS,4aR)-3-cyano-5-oxo-3b,4,4a,5-tetrahydro-1H-cyclopropa[3,4]cyclopenta[1,2-c]pyrazol-1-yl)acetate (88E, 2.48 g, 10.1 mmol) in dichloromethane (100 mL) was added ethanedithiol (1.45 mL, 17.2 mmol) followed by boron trifluoride acetic acid complex (2.39 mL, 17.2 mmol). The mixture was stirred at ambient temperature for 3 hours, and then quenched with aqu. sat. sodium bicarbonate solution. The mixture was extracted with ethyl acetate, the organic phases washed with brine, and evaporated under vacuum. Purification on 40 g silica gel, eluting with 0-50% ethyl acetate in hexane gave the title compound. MS (m/z) 322.1 [M+H]+.

Synthesis of ethyl 2-((3bS,4aR)-3-cyano-5,5-difluoro-3b,4,4a,5-tetrahydro-1H-cyclopropa[3,4]cyclopenta[1,2-c]pyrazol-1-yl)acetate (88G): In a Teflon bottle 1,3-Dibromo-5,5-dimethylhydantoin was suspended in dichloromethane (30 mL) and cooled to −78° C. HF/pyridine (8 mL) was added and the mixture was stirred for 10 min. A solution of ethyl 2-((3bS,4aR)-3-cyano-4,4a-dihydrospiro[cyclopropa[3,4]cyclopenta[1,2-c]pyrazole-5,2'-[1,3]dithiolane]-1(3bH)-yl)acetate (88F, 3.01 g, 9.36 mmol) in dichloromethane (15 mL) was added and stirred for 30 min at −78° C. Then the orange-red solution was warmed to 0° C. and stirred for 1 hour. The mixture was slowly poured into 400 mL sat. aqu. sodium bicarbonate, extracted with dichloromethane, the organic phases washed with brine, and evaporated under vacuum. Purification on 80 g silica gel, eluting with 0-50% ethyl acetate in hexane gave the title compound. MS (m/z) 268.2 [M+H]+.

Synthesis of 2-((3bS,4aR)-3-cyano-5,5-difluoro-3b,4,4a,5-tetrahydro-1H-cyclopropa[3,4]cyclopenta[1,2-c]pyrazol-1-yl)acetic acid (88H): Ethyl 2-((3bS,4aR)-3-cyano-5,5-difluoro-3b,4,4a,5-tetrahydro-1H-cyclopropa[3,4]cyclopenta[1,2-c]pyrazol-1-yl)acetate (88G, 1.92 g, 7.19 mmol) was dissolved in THF (20 mL), methanol (6 mL) and water (12 mL). After cooling to 0° C., lithium hydroxide (0.344 g, 14.37 mmol) was added and the mixture was stirred for 20 min. Acidification with 1N HCl was followed by extraction with ethyl acetate. The combined organic phases were washed with brine, dried with magnesium sulfate and evaporated under vacuum. Crystallization from ethyl acetate-hexane gave the title compound. $^1$H NMR (400 MHz, CDCl$_3$) δ 8.95 (br, 1H), 4.95 (s, 2H), 2.58-2.46 (m, 2H), 1.49-1.43 (m, 1H), 1.19-1.14 (m, 1H). MS (m/z) 240.1 [M+H]+.

Synthesis of (R)-tert-butyl 2-((5-(4-chloro-1-methyl-3-(methylsulfonamido)-1H-indazol-7-yl)-6-((S)-2-(3,5-difluorophenyl)-1-(2,2,2-trifluoroacetamido)ethyl)pyridin-2-yl)ethynyl)-2-methylmorpholine-4-carboxylate (88I): To 43D (60 mg, 0.096 mmol) in DMF (0.5 mL) was added (R)-tert-butyl 2-ethynyl-2-methylmorpholine-4-carboxylate (27 mg, 0.12 mmol), diethylamine (0.1 mL, 0.96 mmol), CuI (1.8 mg, 0.01 mmol) and PdCl$_2$[P(Ph)$_3$]$_2$ (7 mg, 0.01 mmol). The contents were flushed with argon gas for 5-10 min sealed and heated in a MW reactor at 125° C. for 20 min. The reaction mixture was poured onto brine, extracted with ethyl acetate, dried over sodium sulfate, filtered and concentrated to give the title compound 88I. This material was used for the next step with no further purification. MS (m/z) 811.0 [M+H]$^+$ Synthesis of (R)-tert-butyl 2-((6-((S)-1-amino-2-(3,5-difluorophenyl)ethyl)-5-(4-chloro-1-methyl-3-(methylsulfonamido)-1H-indazol-7-yl)pyridin-2-yl)ethynyl)-2-methylmorpholine-4-carboxylate (88J): To the reaction vial containing 88I (78 mg, 0.09 mmol) in ethanol (5 mL) was added lithium hydroxide (0.48 mL, 2M). The contents were sealed and heated in a MW reactor at 130° C. for 10 min. The reaction mixture was acidified with 2 M HCl, concentrated, dissolved in ethyl acetate, and the organic phase washed with a saturated solution of sodium bicarbonate. The organic phase was dried over sodium sulfate, filtered and concentrated to give the title compound 88J. This material was used for the next step with no further purification. MS (m/z) 717.1 [M+H]+

Synthesis of (R)-tert-butyl 2-((5-(4-chloro-1-methyl-3-(methylsulfonamido)-1H-indazol-7-yl)-6-((S)-1-(2-((3bS,4aR)-3-cyano-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)pyridin-2-yl)ethynyl)-2-methylmorpholine-4-carboxylate (88K): To a solution of 88J (0.09 mmol assuming 100% purity) in DMF (0.5 mL) was added triethylamine (0.012 mL, 0.08 mmol), followed by 2-((3bS,4aR)-3-cyano-5,5-difluoro-3b,4,4a,5-tetrahydro-1H-cyclopropa[3,4]cyclopenta[1,2-c]pyrazol-1-yl)acetic acid (20 mg, 0.08 mmol) and HATU (32 mg, 0.08 mmol). After stirring for 30 minutes, the reaction mixture was poured onto brine, extracted with ethyl acetate, dried over sodium sulfate, filtered and concentrated to give the title compound 88K. This material was used for the next step with no further purification. MS (m/z) 936.0 [M+H]+

Synthesis of N—((S)-1-(3-(4-chloro-1-methyl-3-(methylsulfonamido)-1H-indazol-7-yl)-6-(((R)-2-methylmorpholin-2-yl)ethynyl)pyridin-2-yl)-2-(3,5-difluorophenyl)ethyl)-2-((3bS,4aR)-3-cyano-5,5-difluoro-3b,4,4a,5-tetrahydro-1H-cyclopropa[3,4]cyclopenta[1,2-c]pyrazol-1-yl)acetamide (88L): To a solution of 88K (~0.09 mmol) in DCM (1 mL) was added neat TFA (1 mL). The reaction mixture was stirred at room temperature for 0.5 hours. After stirring, the reaction mixture was filtered and purified by reverse phase HPLC. Fractions containing the product were pooled and lyophilized to provide the product 88L. 1H NMR (400 MHz, methanol-d4) δ 8.77 (bs, 1H), 7.93-7.55 (m, 2H), 7.33-6.95 (m, 1H), 6.79 (td, 1H), 6.54-6.29 (m, 2H), 5.37-4.95 (m, 1H), 4.82-4.65 (m, 2H), 4.50-4.34 (m, 1H), 4.09 (dd, 1H), 3.90 (d, 1H), 3.64 (dd, 1H), 3.34-3.32 (m, 3H), 3.26-3.24 (3H), 3.22-3.12 (m 2H), 3.18-2.93 (m, 1H), 2.52 (b, 2H), 1.80-1.72 (m, 3H), 1.46-1.42 (m, 1H), 1.10-1.08 (m, 1H). MS (m/z) 836.2 [M+H]+.

Example 89

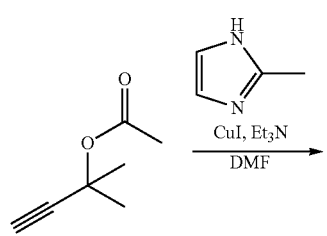

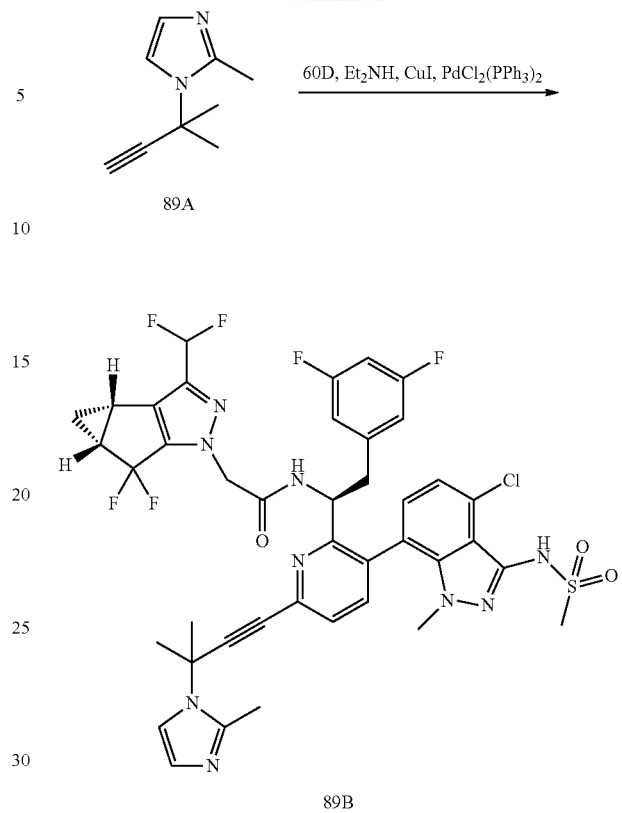

Synthesis of 2-methyl-1-(2-methylbut-3-yn-2-yl)-1H-imidazole (89A): A solution of 2-methylbut-3-yn-2-yl acetate (160 mg, 1.27 mmol), 2-methylimidazole (156 mg, 1.9 mmol), copper(I) chloride (13 mg, 0.13 mmol), and triethylamine (0.27 ml, 1.9 mmol) in DMF (0.5 ml) was degassed with argon. The mixture was heated in a microwave reactor at 125° C. for 10 minutes. The solvent was removed under vacuum and the product was purified by silica gel chromatography to give the title compound 89A. MS (m/z) 149.0 [M+H]+.

Synthesis of N-((1S)-1-(3-(4-chloro-1-methyl-3-(methylsulfonamido)-1H-indazol-7-yl)-6-((8-methyl-6,8-dihydro-5H-imidazo[2,1-c][1,4]oxazin-8-yl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (89B):

The title compound (89B) was prepared as a mixture of atropisomers according to the method presented for the synthesis of compound 80 of Example 80 utilizing 2-methyl-1-(2-methylbut-3-yn-2-yl)-1H-imidazole. 1H NMR (400 MHz, cd3od) δ 8.69-8.59 (m), 7.84 (d), 7.80-7.75 (m), 7.71-7.61 (m), 7.59-7.51 (m), 7.20 (q), 7.10 (d), 6.85-6.46 (m), 6.45-6.34 (m), 5.33-5.24 (m), 5.04-4.95 (m), 4.73 (s), 4.69 (d), 3.33 (s), 3.25 (s), 3.23 (s), 3.17-3.11 (m), 3.09 (s), 3.07 (s), 3.04-2.94 (m), 2.52-2.39 (m), 2.16 (s), 1.44-1.33 (m), 1.09-1.04 (m), 1.01-0.96 (m). MS (m/z) 884.4 [M+H]+.

Example 90

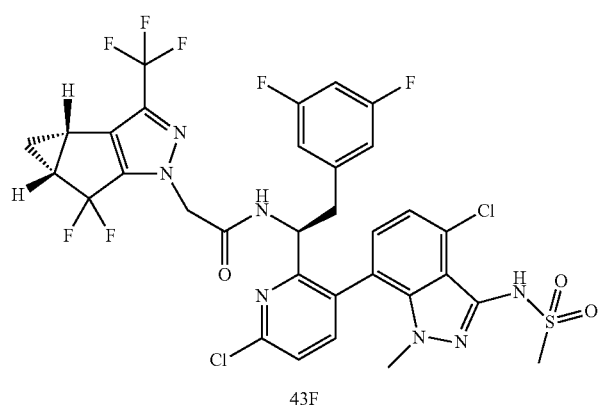
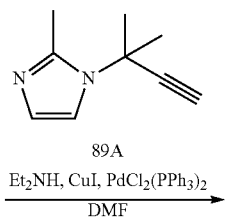
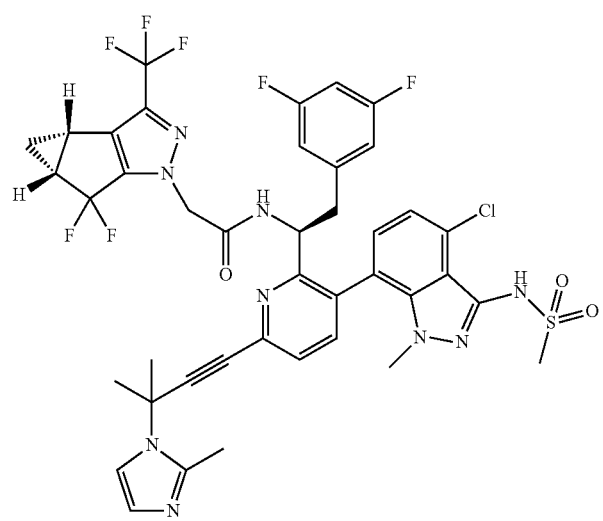

Synthesis of N—((S)-1-(3-(4-chloro-1-methyl-3-(methylsulfonamido)-1H-indazol-7-yl)-6-(3-methyl-3-(2-methyl-1H-imidazol-1-yl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (90): The title compound (90) was prepared as a mixture of atropisomers according to the method presented for the synthesis of compound 79B of Example 79 utilizing 2-methyl-1-(2-methylbut-3-yn-2-yl)-1H-imidazole. $^1$H NMR (400 MHz, cd$_3$od) δ 8.78-8.68 (m), 7.84 (d), 7.82-7.74 (m), 7.73-7.59 (m), 7.60-7.51 (m), 7.25-7.15 (m), 7.10 (d), 6.82-6.73 (m), 6.68-6.60 (m), 6.50-6.45 (m), 6.45-6.34 (m), 5.32-5.23 (m), 5.04-4.94 (m), 4.80-4.67 (m), 3.32 (s), 3.26 (s), 3.23 (s), 3.18-3.11 (m), 3.09 (s), 3.07 (s), 3.06-2.94 (m), 2.57-2.410 (m), 2.16 (s), 1.46-1.35 (m), 1.15-1.08 (m), 1.08-0.99 (m). MS (m/z) 902.3 [M+H]$^+$.

Example 91

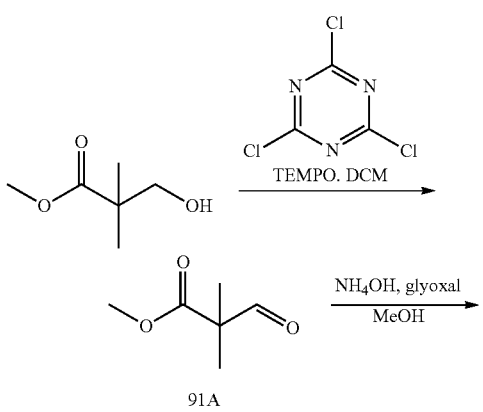

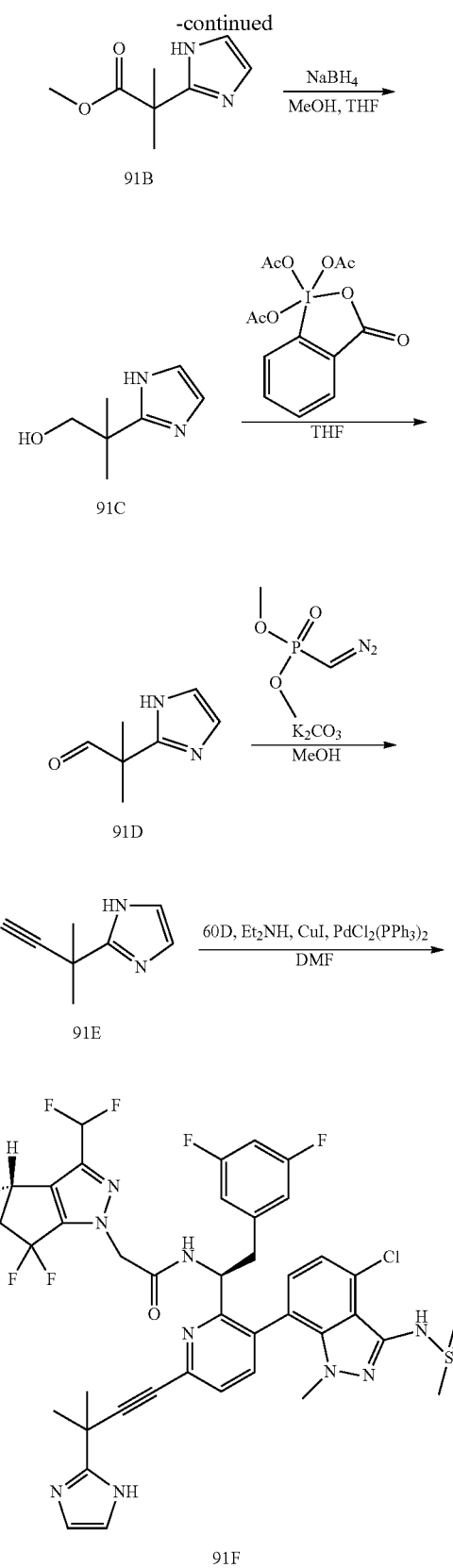

91B

91C

91D

91E

91F

Synthesis of methyl 2,2-dimethyl-3-oxopropanoate (91A): To a suspension of methyl 2,2-dimethyl-3-hydroxypropionate (1.93 ml, 15.1 mmol) and trichloroisocyanuric acid (3.52 g, 15.1 mmol) in dichloromethane (30 ml) was added TEMPO (50 mg, 0.3 mmol) at 0° C. The reaction was warmed to room temperature and stirred for 3 hours. The mixture was filtered and the filtrate was washed with 1M sodium bicarbonate (30 mL), followed by 1M HCl (30 mL), and brine (30 mL). The organic layer was dried with sodium sulfate, filtered, and concentrated under vacuum. The crude product was taken to the next step without further purification.

Synthesis of methyl 2-(1H-imidazol-2-yl)-2-methylpropanoate (91B): To a solution of 91A (1.96 g, 15.1 mmol, assuming 100% purity) in methanol (10 ml) was added concentrated ammonium hydroxide (3.2 ml) at 0° C. The resulting solution was stirred for 30 minutes at room temperature and a mixture of 40% glyoxal in water (40%, 2.19 g, 15.1 mmol) and methanol (5 ml) was added dropwise over 2 hours. The reaction was warmed to room temperature and stirred overnight. The mixture was concentrated, diluted with MeTHF (30 mL), and washed with brine (30 ml). The aqueous layer was back extracted with MeTHF (30 mL). The organic layers were combined, dried with sodium sulfate, filtered, and concentrated under vacuum. The crude product was suspended in EtOAc:hexanes (2:1) and filtered to give the title compound 91B. MS (m/z) 169.1 [M+H]$^+$.

Synthesis of 2-(1H-imidazol-2-yl)-2-methylpropan-1-ol (91C): To a solution of 91B (510 mg, 3.03 mmol) in THF (8 ml) and methanol (2 ml) was added in portions sodium borohydride (229.43 mg, 6.06 mmol). The reaction was stirred at room temperature overnight. The mixture was concentrated under vacuum, extracted twice with MeTHF (20 ml) and brine (20 ml). The organic layers were combined, dried with sodium sulfate, filtered, and concentrated under vacuum. The crude product was diluted with dichloromethane (5 ml) and the precipitate was filtered to give 91C. The product remaining in the filtrate was purified by silica gel chromatography and combined with the precipitate to give the title compound 91C. MS (m/z) 141.1 [M+H]$^+$.

Synthesis of 2-(1H-imidazol-2-yl)-2-methylpropanal (91D): To a solution of 91C (140 mg, 1.0 mmol) in THF (4 ml) was added Dess-Martin periodinane (467 mg, 1.1 mmol) and the mixture was stirred at room temperature for 2 hours. The reaction was concentrated under vacuum, diluted with 2MeTHF (10 ml) and washed with 1.0M sodium bicarbonate (10 ml) and water (10 ml). The precipitates were filtered through celite, the organic layer was dried with sodium sulfate, filtered, and concentrated under vacuum. Product was purified by silica gel chromatography to give the title compound 91D. MS (m/z) 139.1 [M+H]$^+$.

Synthesis of 2-(2-methylbut-3-yn-2-yl)-1H-imidazole (91E): To a solution of 91D (80 mg, 0.58 mmol) in methanol (3 ml) was added potassium carbonate (80 mg, 0.58 mmol) followed by a dropwise addition of dimethyl(1-diazo-2-oxopropyl)phosphonate (122 mg, 0.64 mmol). After stirring at room temperature overnight, the mixture was filtered through celite and concentrated under vacuum. The crude material taken up in methanol, solid loaded onto silica, and purified by silica gel chromatography to give the title compound 91E. MS (m/z) 135.1 [M+H]$^+$.

Synthesis of N—((S)-1-(6-(3-(1H-imidazol-2-yl)-3-methylbut-1-yn-1-yl)-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]

pyrazol-1-yl)acetamide (91F): The title compound (91F) was prepared as a mixture of atropisomers according to the method presented for the synthesis of compound 80 of Example 80 utilizing 2-(2-methylbut-3-yn-2-yl)-1H-imidazole. $^1$H NMR (400 MHz, cd$_3$od) δ 7.72-7.64 (m), 7.63-7.54 (m), 7.20-7.14 (m), 7.08-6.97 (m), 6.90-6.51 (m), 6.43-6.32 (m), 5.34-5.26 (m), 5.00-4.92 (m), 4.80-4.64 (m), 3.32 (s), 3.25 (s), 3.22 (s), 3.17-3.06 (in), 3.04-2.93 (m), 2.52-2.36 (m), 1.81 (s), 1.43-1.31 (m), 1.10-1.04 (m), 1.04-0.97 (m). MS (m/z) 870.4 [M+H]$^+$.

Example 92

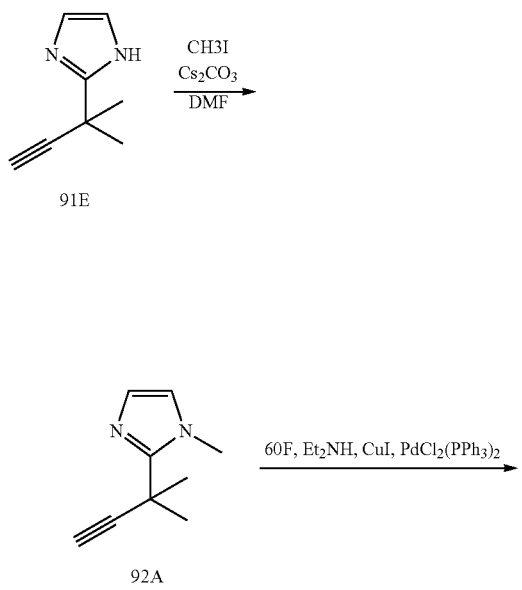

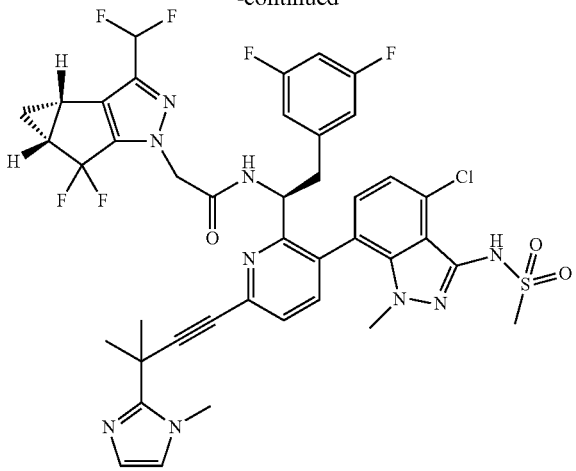

Synthesis of 1-methyl-2-(2-methylbut-3-yn-2-yl)-1H-imidazole (92A): A solution of 91E (10.4 mg, 0.08 mmol), cesium carbonate (30 mg, 0.09 mmol), and iodomethane (0.01 ml, 0.12 mmol) in DMF (0.2 mL) was stirred at room temperature overnight. The mixture was extracted with 2MeTHF and brine. The organic layer was dried with sodium sulfate, filtered, and concentrated under vacuum to give the title compound 91E. The crude product was taken to next step without further purification. MS (m/z) 149.1 [M+H]$^+$.

Synthesis of N—((S)-1-(3-(4-chloro-1-methyl-3-(methylsulfonamido)-1H-indazol-7-yl)-6-(3-methyl-3-(1-methyl-1H-imidazol-2-yl)but-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (92B): The title compound (92B) was prepared as a mixture of atropisomers according to the method presented for the synthesis of compound 80 of Example 80 utilizing 1-methyl-2-(2-methylbut-3-yn-2-yl)-1H-imidazole. $^1$H NMR (400 MHz, cd$_3$od) δ 7.66 (m), 7.59-7.52 (m), 7.21-7.14 (m), 7.12-7.07 (m), 6.91-6.87 (m), 6.84-6.34 (m), 5.27 (dd), 4.97 (t), 4.79-4.56 (m), 4.07 (s), 4.05 (s), 3.33 (s), 3.27-3.17 (m), 3.18-3.08 (m), 3.03-2.91 (m), 2.50-2.33 (m), 1.84 (s), 1.54 (d), 1.42-1.20 (m), 1.10-1.04 (m), 1.03-0.96 (m). MS (m/z) 884.3 [M+H]$^+$.

Example 93

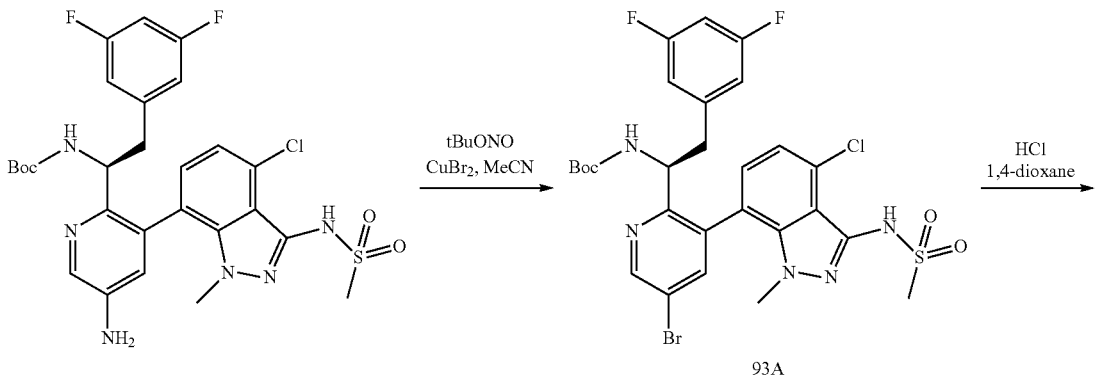

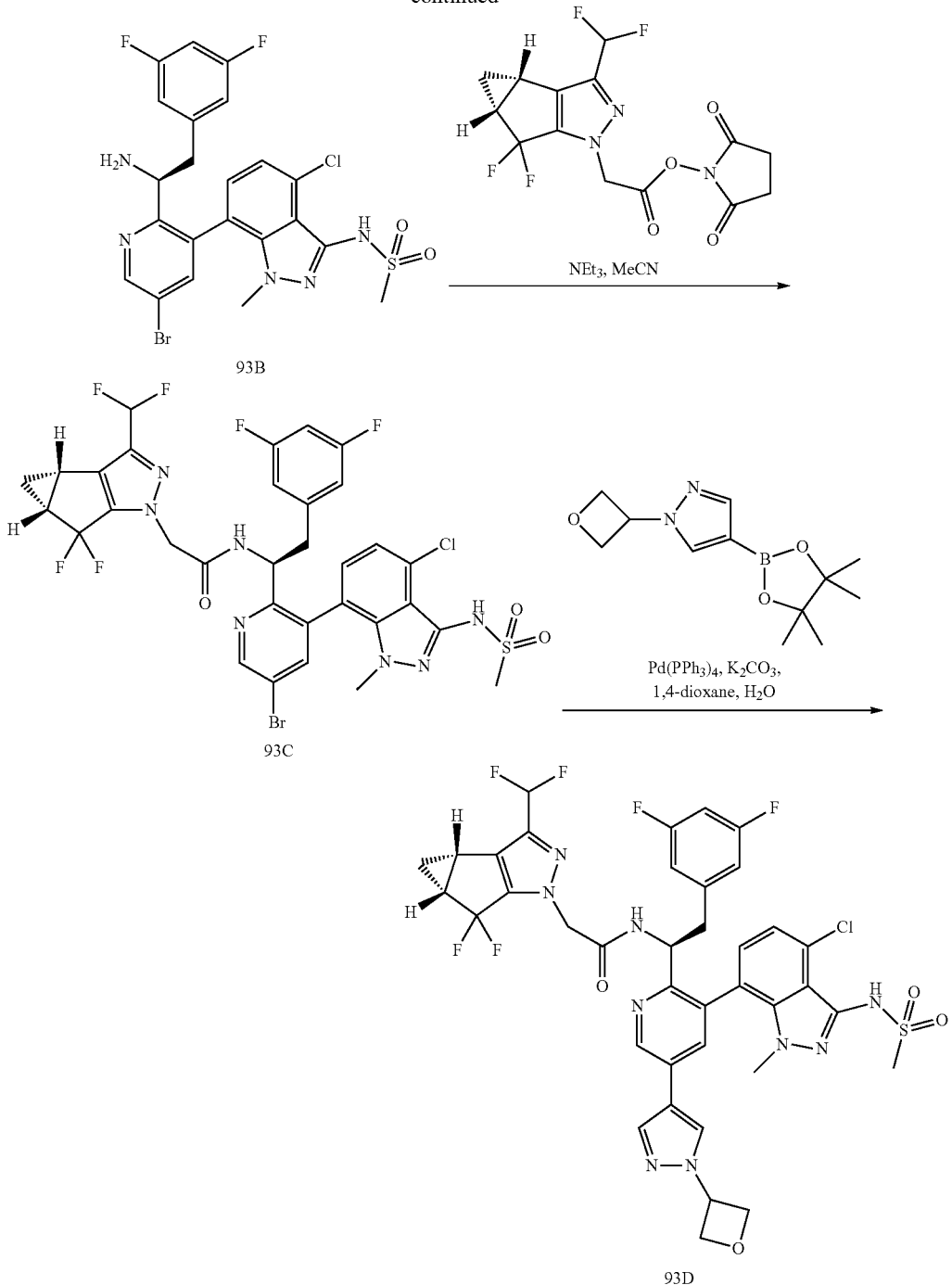

Synthesis of (S)-tert-butyl(1-(5-bromo-3-(4-chloro-1-methyl-3-(methylsulfonamido)-1H-indazol-7-yl)pyridin-2-yl)-2-(3,5-difluorophenyl)ethyl)carbamate (93A): To a stirred solution of tBuONO (0.15 mL, 1.24 mmol) and CuBr₂ (275.9 mg, 1.24 mmol) in MeCN (5 mL) at 0° C. was added (S)-tert-butyl(1-(5-amino-3-(4-chloro-1-methyl-3-(methylsulfonamido)-1H-indazol-7-yl)pyridin-2-yl)-2-(3,5-difluorophenyl)ethyl)carbamate (500.0 mg, 0.82 mmol). The suspension was warmed to room temperature and stirred at room temperature overnight. Upon completion, the reaction mixture was quenched with saturated aqueous ammonium chloride, and the aqueous layer was extracted with 3 portions of EtOAc. The combined organic layers were dried over Na₂SO₄, filtered, concentrated in vacuo, and purified by silica gel column chromatography to give the title compound 93A. MS (m/z) 668.85, 670.30 [M+H]⁺.

Synthesis of (S)—N-(7-(2-(1-amino-2-(3,5-difluorophenyl)ethyl)-5-bromopyridin-3-yl)-4-chloro-1-methyl-1H-indazol-3-yl)methanesulfonamide (93B): To a solution of (S)-tert-butyl(1-(5-bromo-3-(4-chloro-1-methyl-3-(methylsulfonamido)-1H-indazol-7-yl)pyridin-2-yl)-2-(3,5-difluorophenyl)ethyl)carbamate (93A, 359.6 mg, 0.54 mmol) in 1,4-dioxane (2 mL) was added HCl (4M in 1,4-dioxane, 1.34 mL, 5.4 mmol). The reaction mixture was heated to 35° C. for 4 hours. Upon completion, the reaction mixture was concentrated in vacuo, taken in DCM, and stirred with saturated aqueous sodium bicarbonate. The organic layer was collected and the aqueous layer was extracted with two portions of DCM. The combined organic layers were dried over $Na_2SO_4$, filtered, concentrated in vacuo to give the title compound 93B which was used without further purification. MS (m/z) 570.18, 572.02 $[M+H]^+$.

Synthesis of N—((S)-1-(5-bromo-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (93C): To a solution of (S)—N-(7-(2-(1-amino-2-(3,5-difluorophenyl)ethyl)-5-bromopyridin-3-yl)-4-chloro-1-methyl-1H-indazol-3-yl)methanesulfonamide (93B, 305.9 mg, 0.54 mmol) in MeCN (9 mL) was added triethylamine (0.08 mL, 0.56 mmol) followed by slow, portion-wise addition of 2,5-dioxopyrrolidin-1-yl 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetate (203.3 mg, 0.56 mmol). After the addition was complete, the reaction mixture was stirred at room temperature for 15 minutes. The reaction mixture was concentrated in vacuo and purified by silica gel column chromatography to give the title compound 93C. MS (m/z) 816.16, 818.06 $[M+H]^+$.

Synthesis of N—((S)-1-(3-(4-chloro-1-methyl-3-(methylsulfonamido)-1H-indazol-7-yl)-5-(1-(oxetan-3-yl)-1H-pyrazol-4-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (93D): N—((S)-1-(5-bromo-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (93C, 20 mg, 0.024 mmol), 1-(oxetan-3-yl)-4-(4,4,5,5-tetramethyl-1,3,2-dioxaborolan-2-yl)-1H-pyrazole (7.3 mg, 0.029 mmol), Pd(PPh$_3$)$_4$ (1.4 mg, 0.0012 mmol), and $K_2CO_3$ (10.2 mg, 0.073 mmol) were suspended in a mixture of 1,4-dioxane (0.2 mL) and water (0.05 mL). The reaction mixture was degassed with argon for 60 seconds, then heated at 120° C. for 20 minutes in a microwave reactor. Upon cooling, reaction mixture was filtered and concentrated in vacuo. The crude residue was taken in DMF, filtered, and purified by reverse phase HPLC to give the title compound 93D as a mixture of atropisomers. $^1$H NMR (400 MHz, Methanol-d$_4$) δ 9.08-9.02 (m), 8.37-8.31 (m), 8.27-8.22 (m), 8.12 (s), 8.11 (s), 8.05-8.02 (m), 7.96-7.86 (m), 7.20 (q), 7.10-7.03 (m), 6.89-6.53 (m), 6.47-6.35 (m), 5.71-5.49 (m), 5.32-5.23 (m), 5.10-5.03 (m), 5.01-4.92 (m), 4.78 (s), 4.75-4.72 (m), 4.01-3.87 (m), 3.37 (s), 3.26 (s), 3.24 (s), 3.22-3.11 (m), 3.08-2.93 (m), 2.54-2.35 (m), 1.49-1.32 (m), 1.14-0.98 (m). MS (m/z) 860.17 $[M+H]^+$.

Example 94

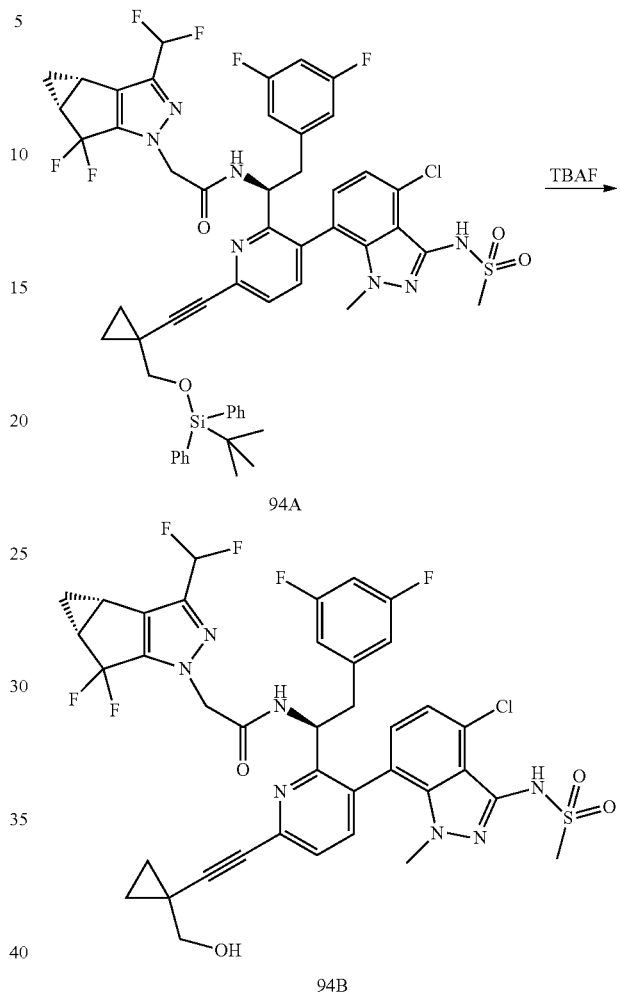

94A

94B

Synthesis of N—((S)-1-(6-((1-(((tert-butyldiphenylsilyl)oxy)methyl)cyclopropyl)ethynyl)-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (94A): The title compound (94A) was prepared according to the method presented for the synthesis of compound 60D of Example 60 utilizing tert-butyl((1-ethynylcyclopropyl)methoxy)diphenylsilane in place of 3-(2-methylbut-3-yn-2-yl)oxazolidin-2-one. MS (m/z) 1070.0 $[M+H]^+$ Synthesis of N—((S)-1-(3-(4-chloro-1-methyl-3-(methylsulfonamido)-1H-indazol-7-yl)-6-((1-(hydroxymethyl)cyclopropyl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (94B): To a solution of 94B (21 mg, 0.02 mmol) in THF (1 mL) was added TBAF (0.037 mL, 1M). The reaction mixture was stirred at room temperature for 0.5 hours. After stirring, the reaction mixture was concentrated, filtered and purified by reverse phase HPLC, eluting with 5-100% acetonitrile in water with 0.1% TFA. Fractions containing the product were pooled and lyophilized to provide the TFA salt of the product 94B. $^1$H NMR (400 MHz, methanol-d₄) δ 8.59 (bs, 1H), 7.65 (dd, 1H), 7.50 (dd, 1H), 7.23-6.98 (m, 1H), 6.90-6.50 (m, 2H), 6.46-6.21 (m, 3H), 5.34-4.94 (m, 1H), 4.80-4.58 (m, 2H), 3.62 (s, 2H), 3.25-3.22 (m, 3H), 3.29-3.18 (m, 3H), 3.19-3.05 (m, 1H), 3.04-2.81 (m, 2H), 2.45 (bs, 2H), 1.68-1.62 (m, 2H), 1.11-1.10 (m, 1H), 1.14-1.08 (m, 3H). MS (m/z) 832.1 [M+H]⁺.
Example 95
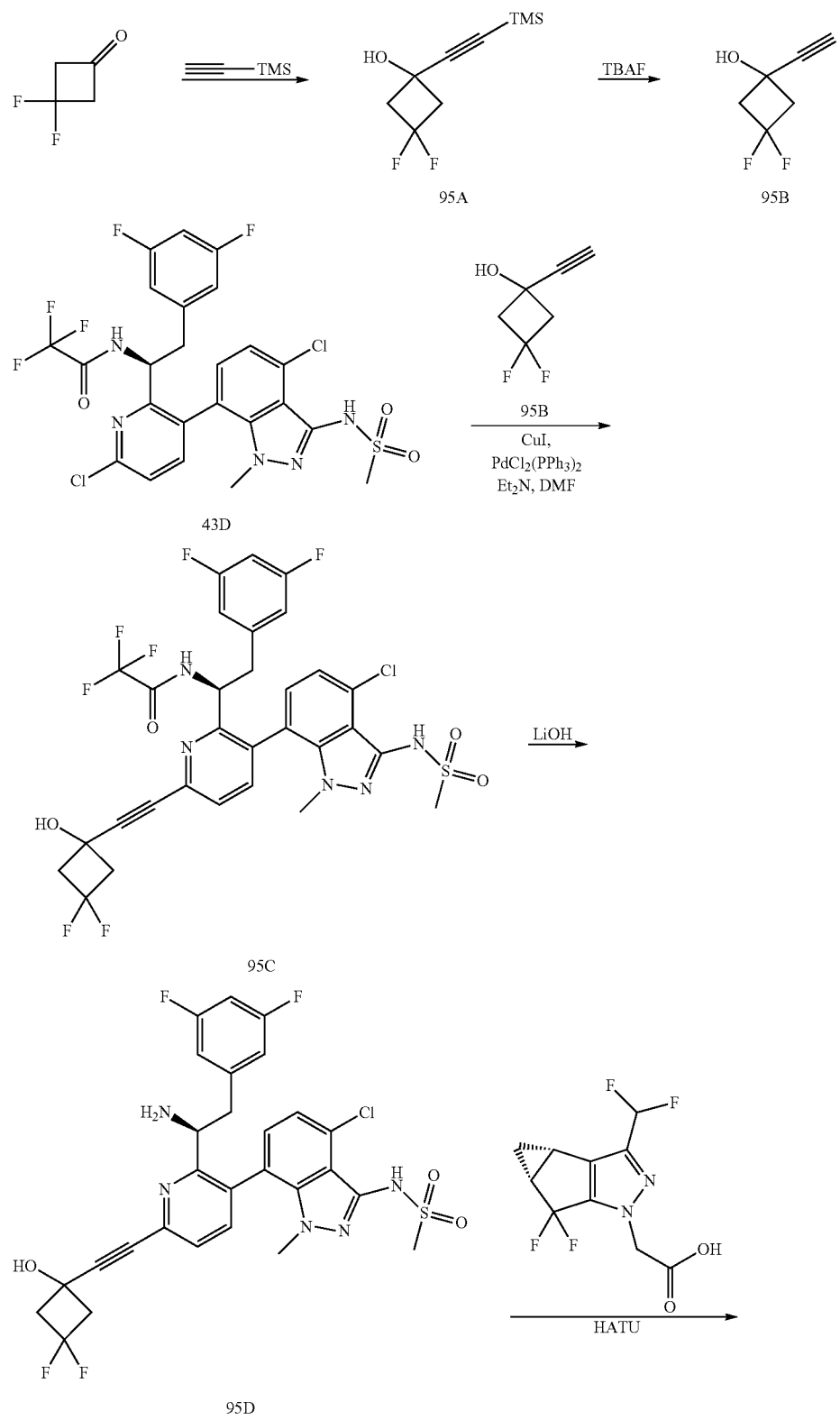

-continued

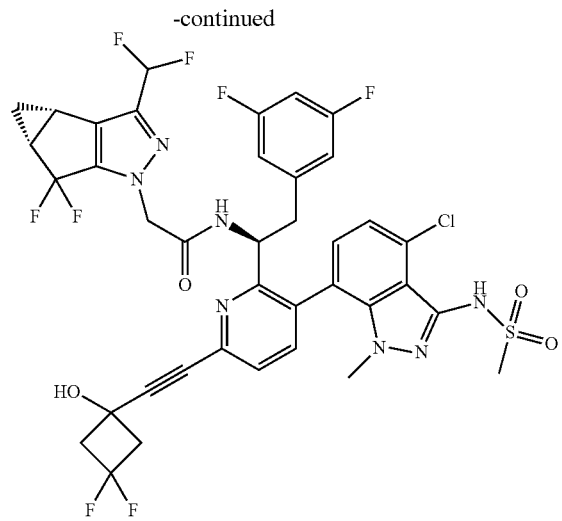

95E

Synthesis of 3,3-difluoro-1-((trimethylsilyl)ethynyl)cyclobutanol (95A): Trimethylsilylacetylene (2 ml, 0.01 mol) was dissolved in THF (15 ml) and cooled to −78° C. 1.6M nBuLi in hexanes (9.43 ml) was added dropwise and stirred 20 min at −78° C. This was transferred via cannula to a cooled solution (0° C.) of $CeCl_3$ (353 g, 14.33 mmol) in THF (20 ml). The slurry was stirred 20 min at 0° C. and then let warm to ambient and stirred for 4 h. After recooling to 0° C., a solution of 3,3-difluorocyclobutane (2200 mg, 0.02 mol) in THF (8 ml) was added to the organocerium reagent. The reaction was stirred at 0° C. for 30 min. Reaction was quenched with the addition of sat aq $NH_4Cl$. Reaction was partitioned between EtOAc and $H_2O$. Biphasic solution filtered over celite. Organics separated, washed, dried and solvents removed in vacuo. The residue was purified by column chromatography on silica to provide the desired product. $^1$H NMR (400 MHz, Chloroform-d) δ 2.88 (ddd, 2H), 2.78-2.56 (m, 2H), 0.13-0.14 (m, 9H).

Synthesis of 1-ethynyl-3,3-difluorocyclobutanol (95B): To compound 95A (455 mg, 2.23 mmol) in ether (10 mL) at 10° C. was added TBAF (2.23 mL, 1M in THF). The reaction was stirred 5 min then loaded directly onto a $SiO_2$ column and purified by column chromatography. TLC: 3:1 H/EA, rf 0.35, stain with $KMnO_4$.

Synthesis of (S)—N-(1-(3-(4-chloro-1-methyl-3-(methylsulfonamido)-1H-indazol-7-yl)-6-((3,3-difluoro-1-hydroxycyclobutyl)ethynyl)pyridin-2-yl)-2-(3,5-difluorophenyl)ethyl)-2,2,2-trifluoroacetamide (95C): The title compound (95C) was prepared according to the method presented for the synthesis of compound 88I of Example 88 utilizing 1-ethynyl-3,3-difluorocyclobutanol (95B). MS (m/z) 718.1 [M+H]$^+$.

Synthesis of (S)—N-(7-(2-(1-amino-2-(3,5-difluorophenyl)ethyl)-6-((3,3-difluoro-1-hydroxycyclobutyl)ethynyl)pyridin-3-yl)-4-chloro-1-methyl-1H-indazol-3-yl)methanesulfonamide (95D): The title compound (95D) was prepared according to the method presented for the synthesis of compound 88J of Example 88 utilizing 95C. MS (m/z) 622.1 [M+H]$^+$.

Synthesis of N—((S)-1-(3-(4-chloro-1-methyl-3-(methylsulfonamido)-1H-indazol-7-yl)-6-((3,3-difluoro-1-hydroxycyclobutyl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (95E): The title compound (95E) was prepared according to the method presented for the synthesis of compound 10A of Example 10 utilizing 95D and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. $^1$H NMR (400 MHz, Methanol-$d_4$) δ 7.72 (dd), 7.57 (dd), 7.17 (d), 7.07 (d), 6.88-6.50 (m), 6.48-6.31 (m), 5.33-5.22 (m), 4.98 (t), 4.77-4.61 (m), 3.51-3.45 (m), 3.30 (p), 3.27-3.07 (m), 3.07-2.88 (m), 2.45 (ddt), 1.38 (p), 1.27 (s), 1.05 (d). MS (m/z) 868.3 [M+H]$^+$.

Example 96

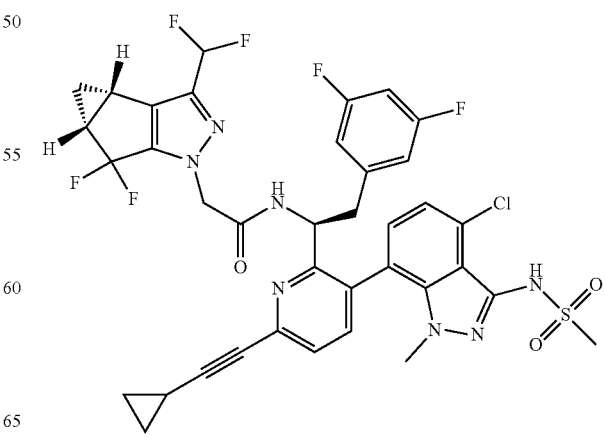

96

Synthesis of N—((S)-1-(3-(4-chloro-1-methyl-3-(methylsulfonamido)-1H-indazol-7-yl)-6-(cyclopropylethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (96): The title compound (96) was prepared according to the method presented for the synthesis of compound 60D of Example 60 utilizing ethynylcyclopropane in place of 3-(2-methylbut-3-yn-2-yl)oxazolidin-2-one. $^1$H NMR (400 MHz, methanol-$d_4$) δ 7.64 (dd, 1H), 7.44 (dd, 1H), 7.23-6.99 (m, 1H), 6.89-6.52 (m, 2H), 6.45-6.26 (m, 3H), 5.34-4.88 (m, 1H), 4.79-4.59 (m, 2H), 3.30 (d, 3H), 3.24 (d, 3H), 3.10 (dd, 1H), 3.02-2.88 (m, 2H), 2.45 (ddd, 2H), 1.71-1.48 (m, 1H), 1.38 (d, 1H), 1.09-0.92 (m, 3H), 0.89 (dt, 2H). MS (m/z) 802.2 [M+H]$^+$ Example 97

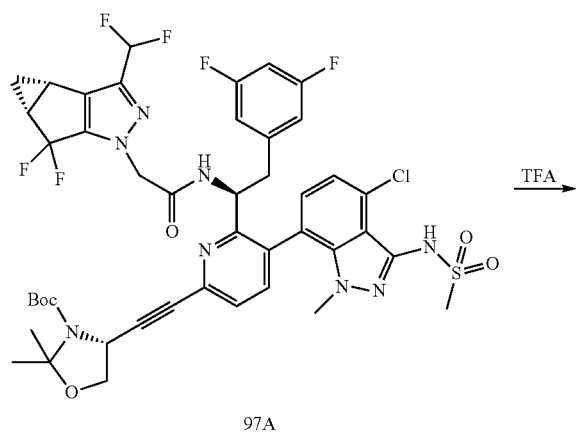

97A

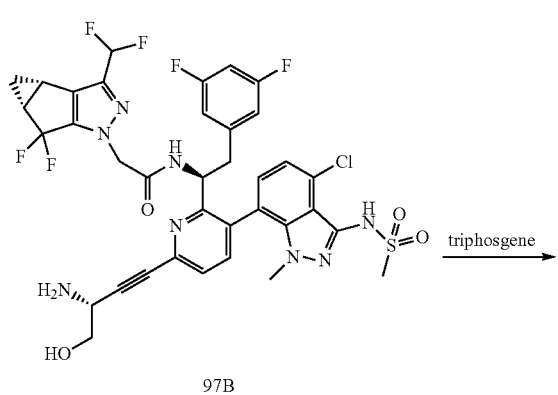

97B

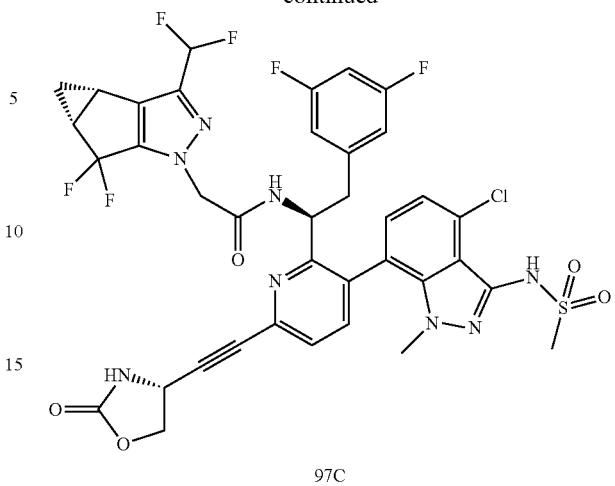

97C

Synthesis of (R)-tert-butyl 4-((5-(4-chloro-1-methyl-3-(methylsulfonamido)-1H-indazol-7-yl)-6-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)pyridin-2-yl)ethynyl)-2,2-dimethyloxazolidine-3-carboxylate (97A): The title compound (97A) was prepared according to the method presented for the synthesis of compound 60D of Example 60 utilizing (R)-tert-butyl 4-ethynyl-2,2-dimethyloxazolidine-3-carboxylate in place of 3-(2-methylbut-3-yn-2-yl)oxazolidin-2-one. MS (m/z) 961.0 [M+H]$^+$ Synthesis of N—((S)-1-(6-((R)-3-amino-4-hydroxybut-1-yn-1-yl)-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (97B): To a solution of 97B (35 mg, 0.03 mmol) in DCM (1 mL) was added TFA (1 mL). The reaction mixture was stirred at room temperature for 0.5 hours. After stirring, the reaction mixture was concentrated, filtered and purified by reverse phase HPLC. Fractions containing the product were pooled and lyophilized to provide the product 94B. MS (m/z) 821.3 [M+H]$^+$.

Synthesis of N—((S)-1-(3-(4-chloro-1-methyl-3-(methylsulfonamido)-1H-indazol-7-yl)-6-(((R)-2-oxooxazolidin-4-yl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (97C): To a solution of 97C (15 mg, 0.02 mmol) in DCM (1 mL) cooled to 0° C. was added triethylamine (6 mg, 0.06 mmol) followed by triphosgene (6 mg, 0.02 mmol). The reaction mixture was stirred at room temperature for 0.5 hours. After stirring, the reaction mixture was concentrated, filtered and purified by reverse phase HPLC. Fractions containing the product were pooled and lyophilized to provide the product 97C. $^1$H NMR (400 MHz, methanol-$d_4$) δ 7.71 (dd, 1H), 7.58 (dd, 1H), 7.21-7.06 (m, 2H), 6.76-6.63 (m, 1H), 6.45-6.31 (m, 2H), 5.28-4.98 (m, 1H), 4.77 (d, 2H), 3.64-3.60 (m, 2H), 3.49-3.45 (m, 1H), 3.36 m-3.29 (m, 3H), 3.24 (m, 3H), 3.15-2.90 (m, 1H), 3.06-2.91 (m, 2H), 2.49 (m, 2H), 1.55-1.33 (m, 7H), 1.15-1.01 (m, 1H). MS (m/z) 847.1 [M+H]$^+$.

Example 98
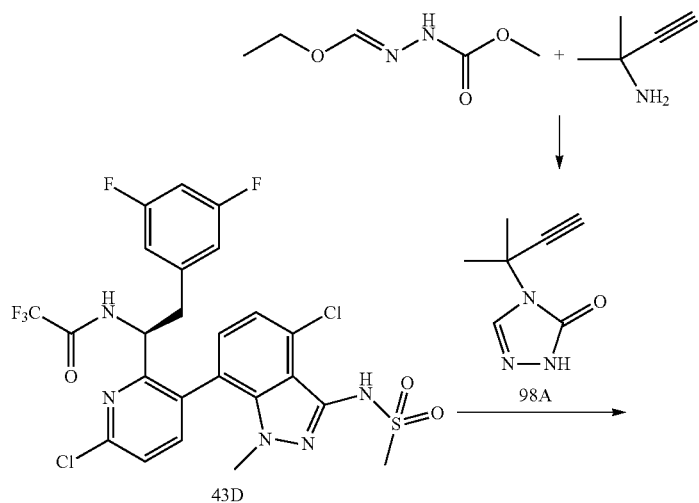
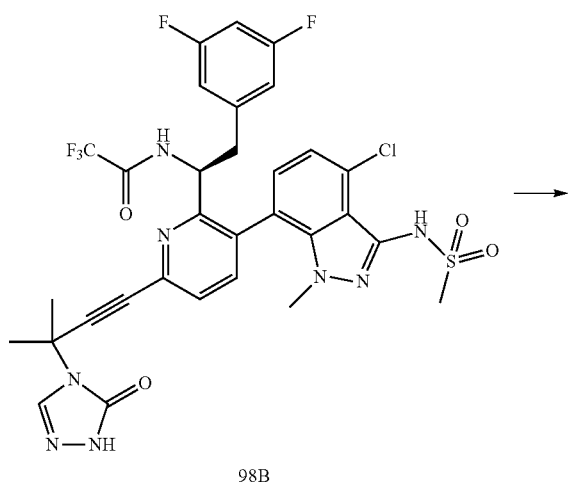
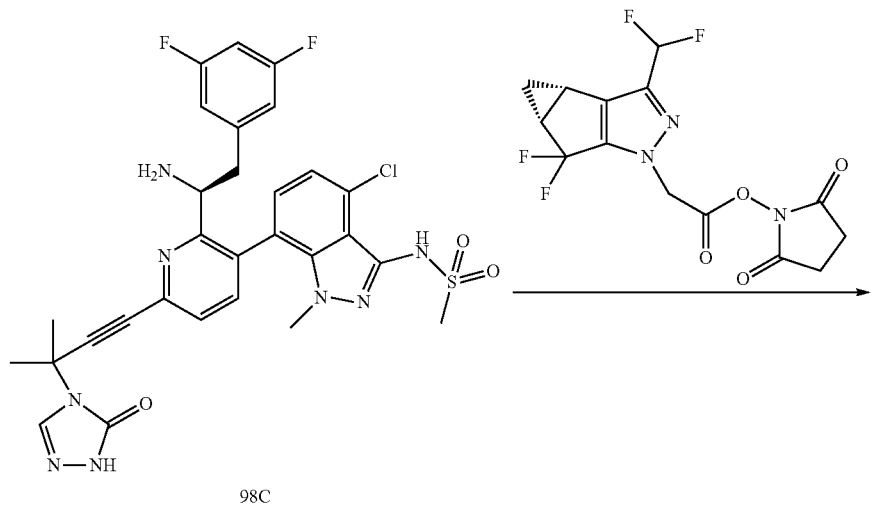

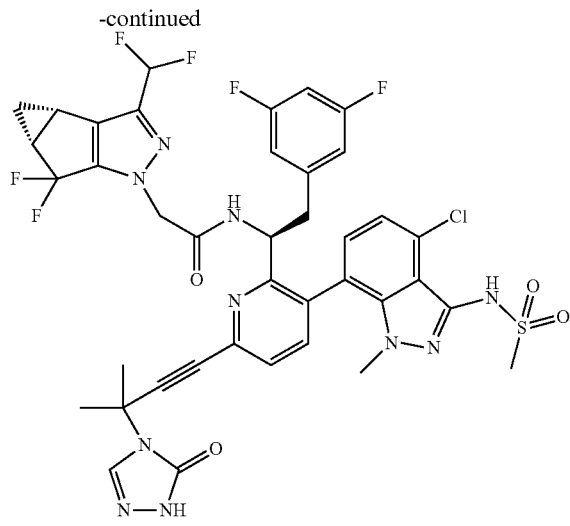

98D

Synthesis of 4-(2-methylbut-3-yn-2-yl)-1H-1,2,4-triazol-5(4H)-one (98A): The semicarbazide was synthesized according to the literature procedure (Tetrahedron Letters, 2006, 6743-6746). $^1$H NMR (400 MHz, Acetonitrile-d3) δ 8.21 (s, 1H), 7.91 (s, 1H), 4.10 (q, J=7.1 Hz, 2H), 3.66 (s, 3H), 1.29 (t, J=7.1 Hz, 3H). The terminal alkyne was synthesized according to the literature procedure (Tetrahedron Letters, 2006, 6743-6746). MS (m/z) 151.98 [M+H]$^+$ Synthesis of (S)—N-(1-(3-(4-chloro-1-methyl-3-(methylsulfonamido)-1H-indazol-7-yl)-6-(3-methyl-3-(5-oxo-1H-1,2,4-triazol-4(5H)-yl)but-1-yn-1-yl)pyridin-2-yl)-2-(3,5-difluorophenyl)ethyl)-2,2,2-trifluoroacetamide (98B): The title compound (98B) was prepared according to the method presented for the synthesis of compound 88I of Example 88 utilizing 98A.

Synthesis of (S)—N-(7-(2-(1-amino-2-(3,5-difluorophenyl)ethyl)-6-(3-methyl-3-(5-oxo-1H-1,2,4-triazol-4(5H)-yl)but-1-yn-1-yl)pyridin-3-yl)-4-chloro-1-methyl-1H-indazol-3-yl)methanesulfonamide (98C): The title compound (98C) was prepared according to the method presented for the synthesis of compound 88J of Example 88 utilizing 98B.

Synthesis of N—((S)-1-(3-(4-chloro-1-methyl-3-(methylsulfonamido)-1H-indazol-7-yl)-6-(3-methyl-3-(5-oxo-1H-1,2,4-triazol-4(5H)-yl)but-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4] cyclopenta[1,2-c]pyrazol-1-yl)acetamide (98D): The title compound (98D) was prepared according to the method presented for the synthesis of compound 93C of Example 93 utilizing 98C. $^1$H NMR (400 MHz, Methanol-d4) δ 8.95-8.60 (m, 1H), 8.07 (d, 1H), 7.90 (d, 3H), 7.83-7.50 (m, 3H), 7.28-6.95 (m, 2H), 6.89-6.50 (m, 3H), 6.52-6.26 (m, 4H), 5.43-4.92 (m, 1H), 4.80-4.63 (m, 4H), 3.24 (d, 5H), 3.14 (dd, 1H), 3.04-2.93 (m, 2H), 2.45 (d, 3H), 2.02 (d, 8H), 1.97-1.81 (m, 2H), 1.37 (m, 2H), 1.12-0.92 (m, 2H). MS (m/z) 887.13[M+H]$^+$ Example 99

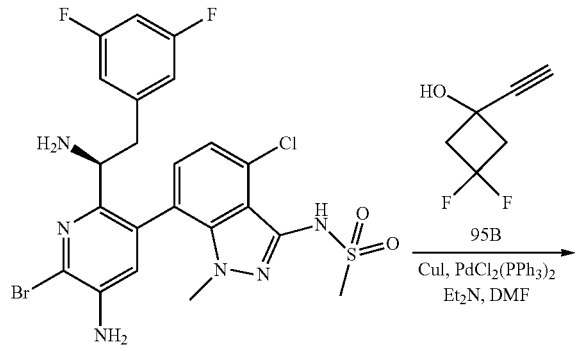

99A

-continued

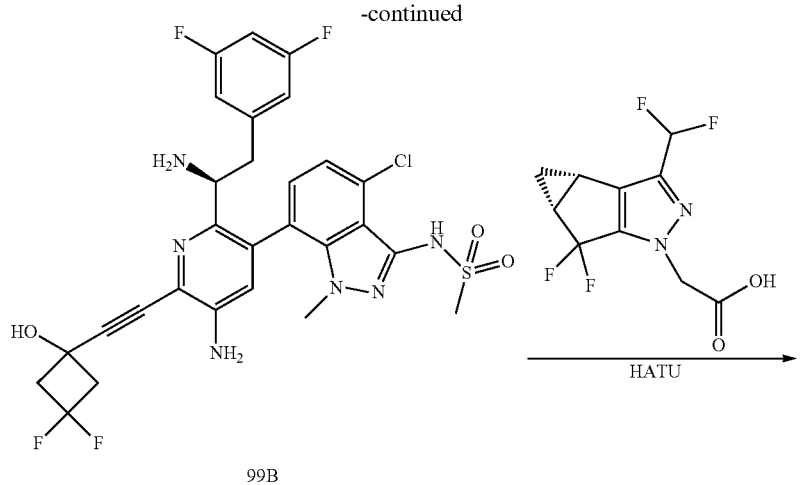

99B

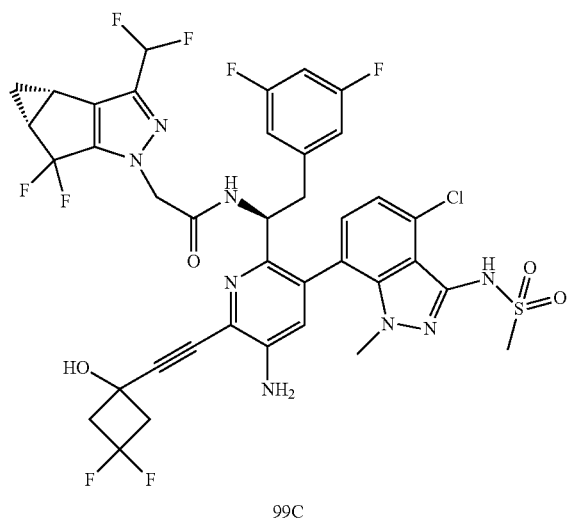

99C

Synthesis of (S)—N-(7-(5-amino-2-(1-amino-2-(3,5-difluorophenyl)ethyl)-6-((3,3-difluoro-1-hydroxycyclobutyl)ethynyl)pyridin-3-yl)-4-chloro-1-methyl-1H-indazol-3-yl)methanesulfonamide (99B): The title compound (99B) was prepared according to the method presented for the synthesis of compound 95C of Example 95 utilizing 99A. MS (m/z) 637.0 [M+H]$^+$.

Synthesis of N—((S)-1-(3-(4-chloro-1-methyl-3-(methylsulfonamido)-1H-indazol-7-yl)-6-((3,3-difluoro-1-hydroxycyclobutyl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (99C): The title compound (99C) was prepared according to the method presented for the synthesis of compound 10A of Example 10 utilizing 99B and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. MS (m/z) 883.0 [M+H]$^+$.

Example 100

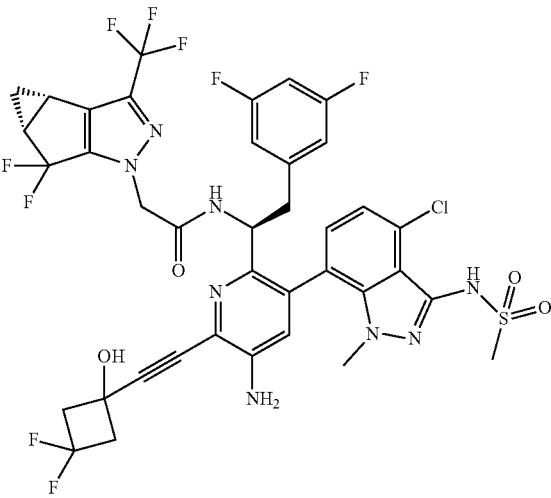

100

Synthesis of N—((S)-1-(5-amino-3-(4-chloro-1-methyl-3-(methylsulfonamido)-1H-indazol-7-yl)-6-((3,3-difluoro-1-hydroxycyclobutyl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (100): The title compound (100) was prepared according to the method presented for the synthesis of compound 99B of Example 99 utilizing 2-((3bS,4aR)-5,5-difluoro-3-(trifluoromethyl)-3b,4,4a,5-tetrahydro-1H-cyclopropa[3,4]cyclopenta[1,2-c]

pyrazol-1-yl)acetic acid. $^1$H NMR (400 MHz, Methanol-d4) δ 7.11 (d, 1H), 6.98 (dd, 2H), 6.85-6.70 (m, 1H), 6.69-6.56 (m, 1H), 6.44 (d, 1H), 6.41-6.31 (m, 2H), 6.23 (d, 1H), 5.07-4.93 (m, 1H), 4.81-4.68 (m, 3H), 3.40 (s, 3H), 3.24 (d, 6H), 3.16-2.85 (m, 7H), 2.61-2.42 (m, 3H), 1.41 (dt, 1H), 1.18-0.98 (m, 1H). MS (m/z) 901.19 [M+H]$^+$.

Example 101

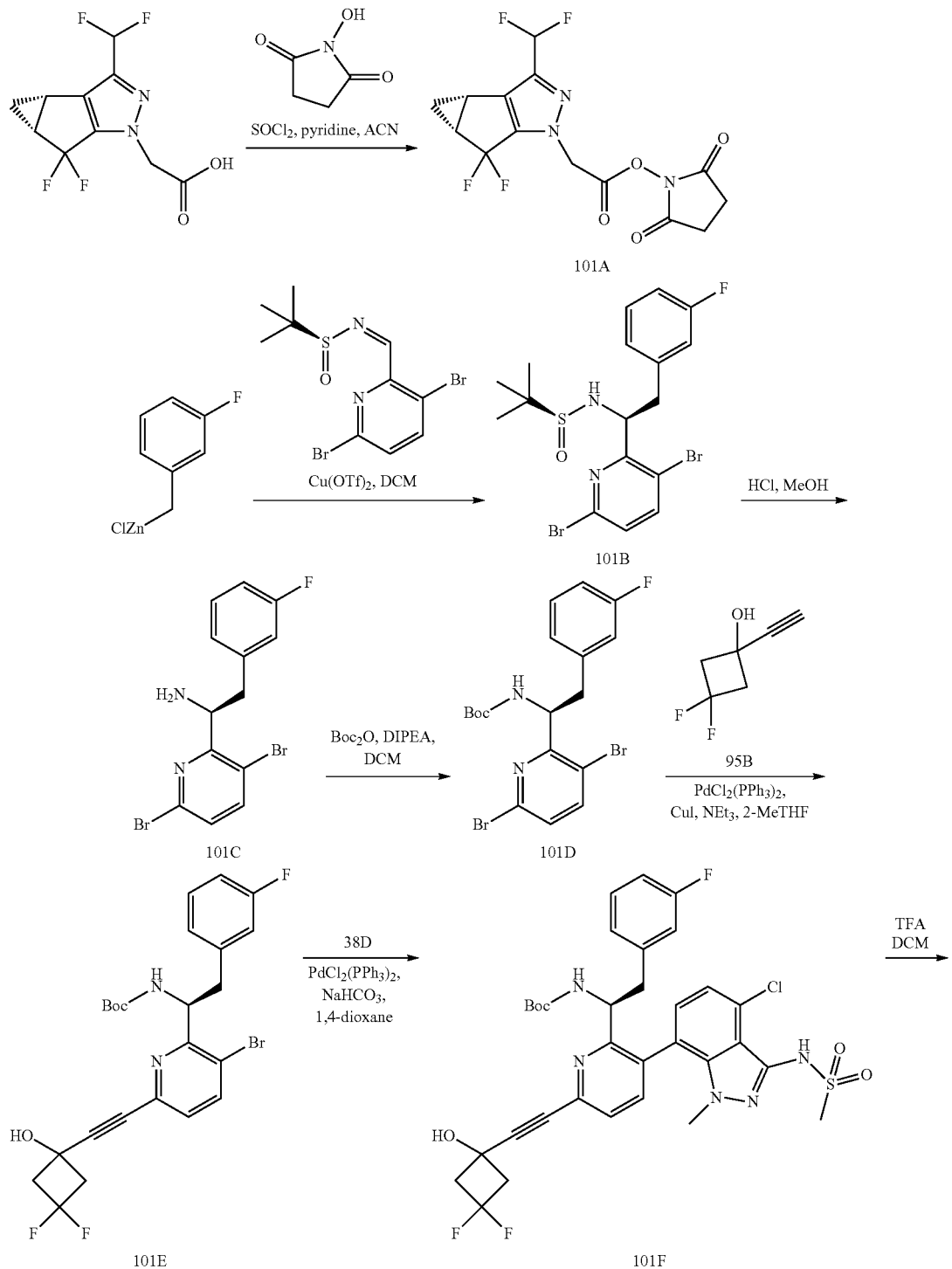

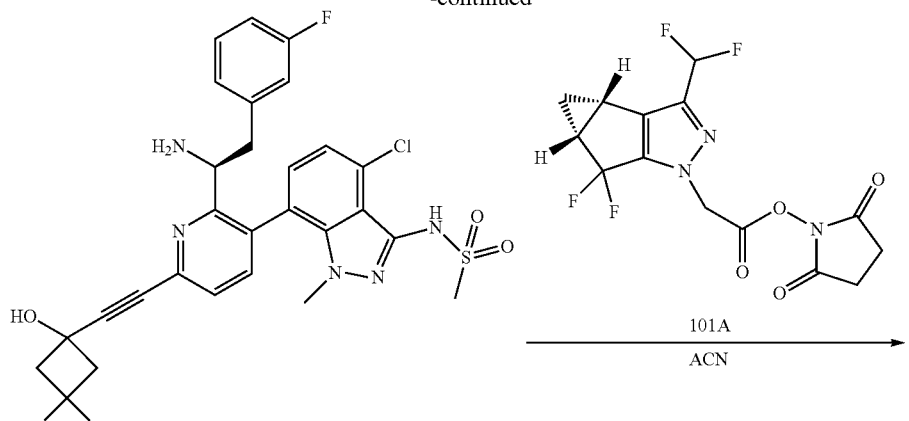

101G

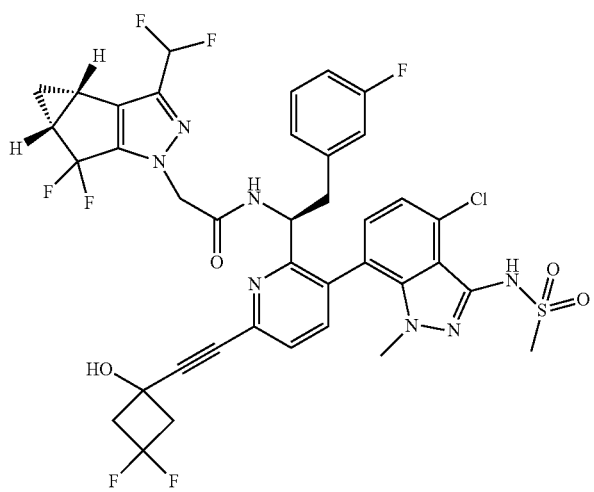

101A

101H

Synthesis of 2,5-dioxopyrrolidin-1-yl 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetate (101A): A solution of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (1.5 g, 5.68 mmol) and N-hydroxysuccinimide (0.98 g, 8.52 mmol) in acetonitrile (10 ml) was cooled to 0° C. To the reaction was added pyridine (1.56 ml) followed by dropwise addition of thionyl chloride (0.7 ml, 9.65 mmol). The reaction was stirred at 0° C. for 45 minutes. The reaction was concentrated under vacuum, taken up in dichloromethane, and purified by silica gel chromatography to give the title compound 101A. $^1$H NMR (400 MHz, Chloroform-d) δ 6.62 (t, J=54.7, 54.7 Hz, 1H), 5.17 (s, 2H), 2.84 (s, 4H), 2.52-2.42 (m, 2H), 1.42-1.34 (m, 1H), 1.17-1.10 (m, 1H).

Synthesis of (S)—N—((S)-1-(3,6-dibromopyridin-2-yl)-2-(3-fluorophenyl)ethyl)-2-methylpropane-2-sulfinamide (101B): To a solution of (S,Z)—N-((3,6-dibromopyridin-2-yl)methylene)-2-methylpropane-2-sulfinamide (1.0 g, 2.717 mmol) and Cu(OTf)$_2$ (49.1 mg, 0.136 mmol) in DCM (10 mL) was added 3-fluorobenzyl zinc chloride (0.5M in THF, 7.6 mL, 3.803 mmol) dropwise over 7 minutes at 0° C. The reaction mixture was stirred at 0° C. for 1 hour, then quenched with saturated aqueous NH$_4$Cl and diluted with EtOAc. The organic layer was collected, and the aqueous layer was extracted an additional time with EtOAc. The combined organic layers were dried over Na$_2$SO$_4$, filtered, concentrated, and purified by silica gel column chromatography to provide the title compound 101B. MS (m/z) 476.93, 478.84, 480.79 [M+H]$^+$.

Synthesis of(S)-1-(3,6-dibromopyridin-2-yl)-2-(3-fluorophenyl)ethanamine (101C): To a solution of 101B, 714.2 mg, 1.493 mmol) in MeOH (3.7 mL) was added HCl (4M in 1,4-dioxane, 3.7 mL, 14.93 mmol). The reaction mixture was stirred at room temperature for 30 minutes. Upon completion, the reaction mixture was concentrated in vacuo to provide the title compound 101C, which was used without purification. MS (m/z) 373.08, 374.92, 376.86 [M+H]$^+$.

Synthesis of (S)-tert-butyl(1-(3,6-dibromopyridin-2-yl)-2-(3-fluorophenyl)ethyl)carbamate (101D): To a solution of 101C (558.62 mg, 1.493 mmol) in DCM was added DIPEA (0.52 mL, 2.987 mmol). The reaction mixture was cooled to 0° C., then Boc$_2$O (358.6 mg, 1.643 mmol) was added. The reaction mixture was warmed to room temperature and stirred at room temperature for 2.5 hours. Upon completion, the reaction mixture was concentrated in vacuo and purified by silica gel column chromatography to provide the title compound 101D. MS (m/z) 472.71, 474.68, 476.68 [M+H]$^+$.

Synthesis of(S)-tert-butyl(1-(3-bromo-6-((3,3-difluoro-1-hydroxycyclobutyl)ethynyl)pyridin-2-yl)-2-(3-fluorophenyl)ethyl)carbamate (101E): A solution of 101D (240 mg, 0.51 mmol) in 2-MeTHF (2.5 mL) was degassed by bubbling argon for 60 seconds. To the degassed solution were added NEt₃ (0.21 ml, 1.52 mmol) and 95B (66.9 mg, 0.51 mmol) followed by CuI (2.9 mg, 0.02 mmol) and PdCl₂(PPh₃)₂ (10.7 mg, 0.02 mmol). The reaction mixture was stirred at room temperature for 30 minutes. Upon completion, the reaction mixture was diluted with water and extracted three times with EtOAc. The combined organic layers were dried over Na₂SO₄, filtered, concentrated in vacuo, and purified by silica gel column chromatography to provide the title compound 101E. MS (m/z) 424.9 [M+H]⁺.

Synthesis (S)-tert-butyl(1-(3-(4-chloro-1-methyl-3-(methylsulfonamido)-1H-indazol-7-yl)-6-((3,3-difluoro-1-hydroxycyclobutyl)ethynyl)pyridin-2-yl)-2-(3-fluorophenyl)ethyl)carbamate (101F): 101E (60 mg, 0.11 mmol), 38D (66 mg, 0.17 mmol), and PdCl₂(PPh₃)₂ (4.2 mg, 0.006 mmol) were taken in 1,4-dioxane (0.75 mL) and NaHCO₃ (1 M in water, 0.22 mL). The resulting solution was degassed by bubbling argon for 5 minutes, then the reaction flask was sealed and the reaction heated at 150° C. for 10 minutes in a microwave reactor. Upon cooling, the reaction mixture diluted with EtOAc and water. The organic layer was dried with sodium sulfate, filtered, concentrated in vacuo, and purified by silica gel column chromatography to provide the title compound 101F as a mixture of atropisomers. MS (m/z) 703.9 [M+H]⁺.

Synthesis of (S)—N-(7-(2-(1-amino-2-(3-fluorophenyl)ethyl)-6-(3-hydroxy-3-methylbut-1-yn-1-yl)pyridin-3-yl)-4-chloro-1-methyl-1H-indazol-3-yl)methanesulfonamide (101G): To a solution of 101F (80 mg, 0.39 mmol) in DCM (0.2 mL) was added TFA (0.1 mL). The reaction mixture was stirred at room temperature for 1 hour. Upon completion, the reaction mixture was concentrated in vacuo, diluted with EtOAc and washed twice with 1M NaHCO₃. The organic layer was dried with sodium sulfate, filtered and concentrated under vacuum. The product was purified by silica gel chromatography to provide the title compound 101G as a mixture of atropisomers. MS (m/z) 604.1 [M+H]⁺.

Synthesis of N—((S)-1-(3-(4-chloro-1-methyl-3-(methylsulfonamido)-1H-indazol-7-yl)-6-((3,3-difluoro-1-hydroxycyclobutyl)ethynyl)pyridin-2-yl)-2-(3-fluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (101H): To a solution of 101G (14 mg, 0.02 mmol) in acetonitrile (0.25 ml) was added 101A (8.37 mg, 0.02 mmol). After stirring for 2 hours, the reaction was concentrated under vacuum and was and purified by reverse phase HPLC to provide the title compound 10H as a mixture of atropisomers. ¹H NMR (400 MHz, Methanol-d₄) δ 7.62-7.54 (m), 7.49-7.42 (m), 7.12-7.03 (m), 6.91 (d), 6.89-6.79 (m), 6.77-6.57 (m), 6.51-6.38 (m), 6.07 (d), 5.25-5.19 (m), 4.92-4.84 (m), 4.70-4.57 (m), 3.23 (s), 3.18-3.02 (m), 2.94-2.82 (m), 2.74 (s), 2.44-2.28 (m), 1.37-1.16 (m), 1.02-0.96 (m), 0.94-0.89 (m). MS (m/z) 850.2 [M+H]⁺.

Example 102

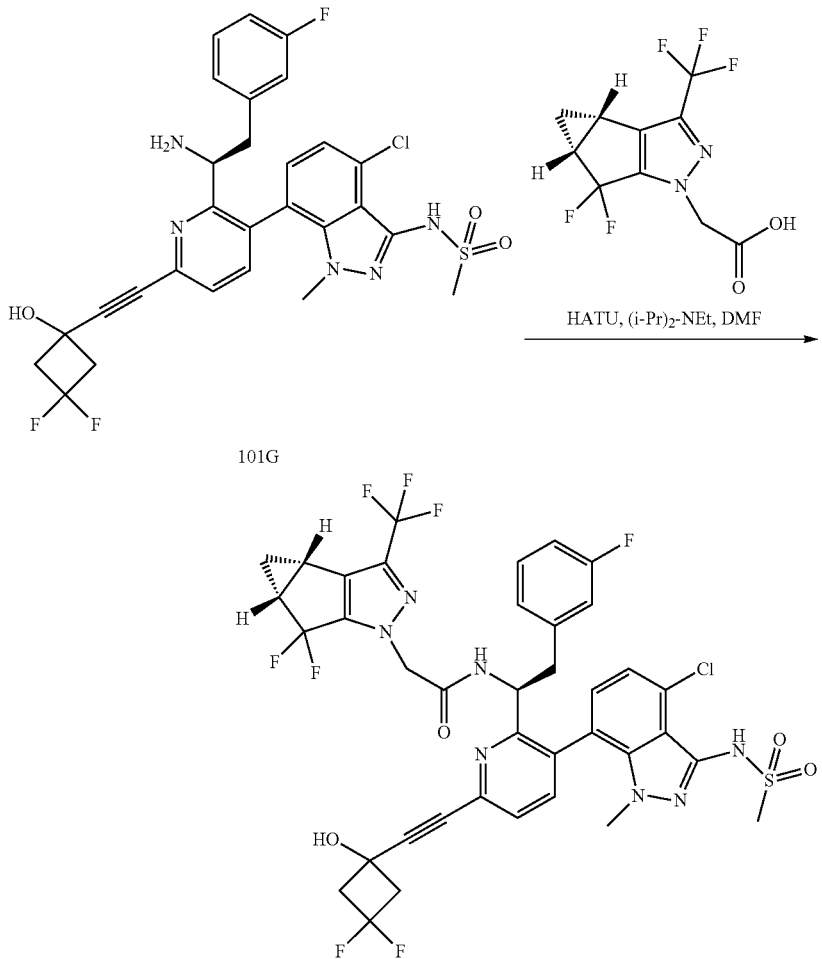

102

Synthesis of N—((S)-1-(3-(4-chloro-1-methyl-3-(methylsulfonamido)-1H-indazol-7-yl)-6-((3,3-difluoro-1-hydroxycyclobutyl)ethynyl)pyridin-2-yl)-2-(3-fluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (102): To a solution of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (6.5 mg, 0.023 mmol), 101G (14 mg, 0.023 mmol), and DIPEA (4.0 µl, 0.023 mmol) in DMF (0.1 ml) was added dropwise a solution of HATU (8.8 mg, 0.023 mmol) in DMF (0.2 ml). After stirring for 1 h, the product was purified by reverse phase HPLC to provide the title compound 102 as a mixture of atropisomers. $^1$H NMR (400 MHz, Methanol-$d_4$) δ 7.72-7.62 (m), 7.60-7.51 (m), 7.22-7.13 (m), 6.99 (d), 6.97-6.89 (m), 6.81-6.73 (m), 6.60-6.48 (m), 6.14 (d), 5.35-5.26 (m), 5.01-4.94 (m), 4.81-4.71 (m), 3.32 (s), 3.26 (s), 3.22 (s), 3.22-3.14 (m), 3.04-2.91 (m), 2.81 (s), 2.58-2.39 (m), 1.48-1.35 (m), 1.18-1.10 (m), 1.11-1.03 (m). MS (m/z) 868.2 [M+H]$^+$.

Example 103

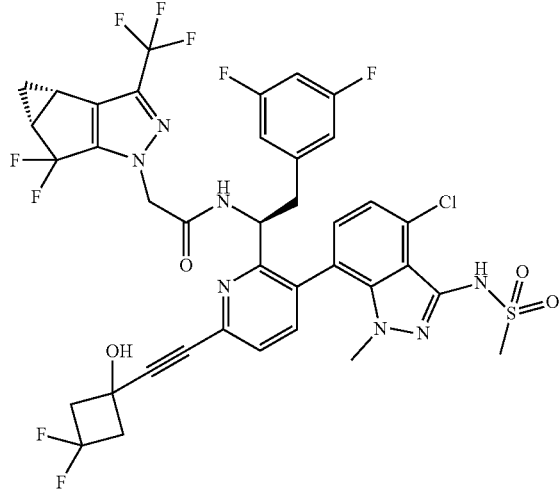

Synthesis of N—((S)-1-(3-(4-chloro-1-methyl-3-(methylsulfonamido)-1H-indazol-7-yl)-6-((3,3-difluoro-1-hydroxycyclobutyl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (103): The title compound (103) was prepared according to the method presented for the synthesis of compound 95E of Example 95 utilizing 95D and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. $^1$H NMR (400 MHz, Methanol-d4) δ 8.75 (d, 1H), 7.72 (dd, 2H), 7.57 (dd, 2H), 7.25-7.11 (m, 1H), 7.07 (d, 1H), 6.85-6.51 (m, 2H), 6.39 (dd, 4H), 5.35-4.93 (m, 1H), 4.77 (d, 2H), 3.24 (d, 6H), 3.07-2.88 (m, 5H), 2.58-2.39 (m, 1H), 1.41 (m, 2H), 1.18-1.01 (m, 2H). MS (m/z) 886.14 [M+H]$^+$.

Example 104

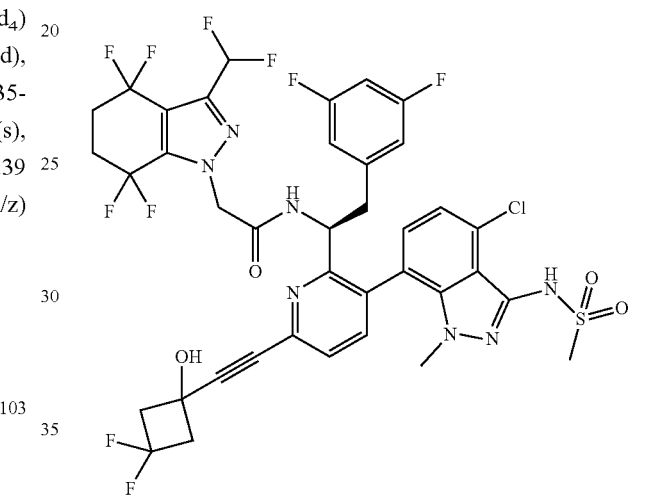

Synthesis of (S)—N-(1-(3-(4-chloro-1-methyl-3-(methylsulfonamido)-1H-indazol-7-yl)-6-((3,3-difluoro-1-hydroxycyclobutyl)ethynyl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (104):

The title compound (104) was prepared according to the method presented for the synthesis of compound 95E of Example 95 utilizing 95D and 2-(3-(difluoromethyl)-4,4,7,7-tetrafluoro-4,5,6,7-tetrahydro-1H-indazol-1-yl)acetic acid. $^1$H NMR (400 MHz, Methanol-d4) δ 8.84 (d, 1H), 7.73 (t, 1H), 7.58 (dd, 1H), 7.29-7.13 (m, 1H), 7.08 (d, 1H), 7.00-6.53 (m, 3H), 6.51-6.26 (m, 3H), 5.39-4.88 (m, 4H), 3.35 (s, 3H), 3.27-3.11 (m, 7H), 3.07-2.81 (m, 5H), 2.52 (dd, 8H). MS (m/z) 906.15 [M+H]$^+$.

Example 105
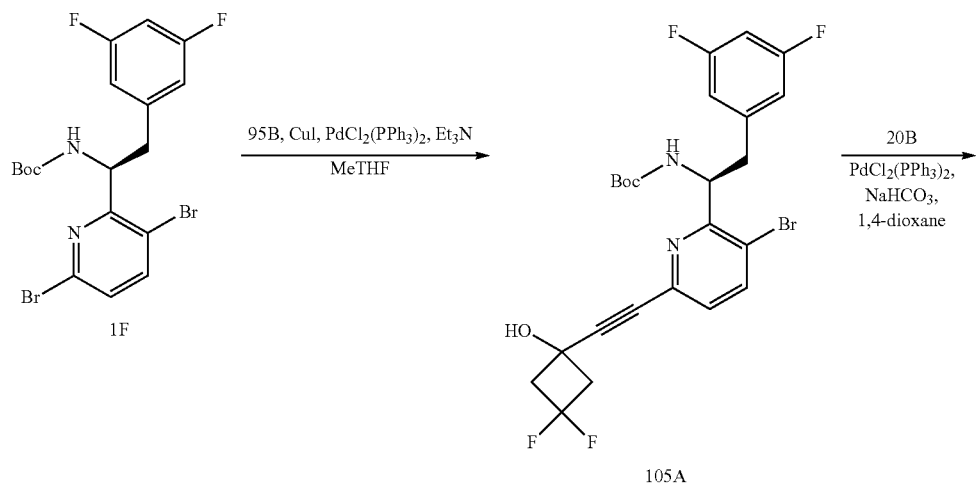
105A
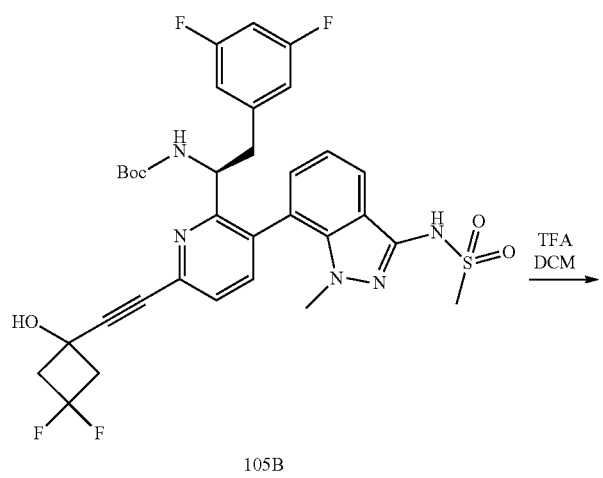
105B
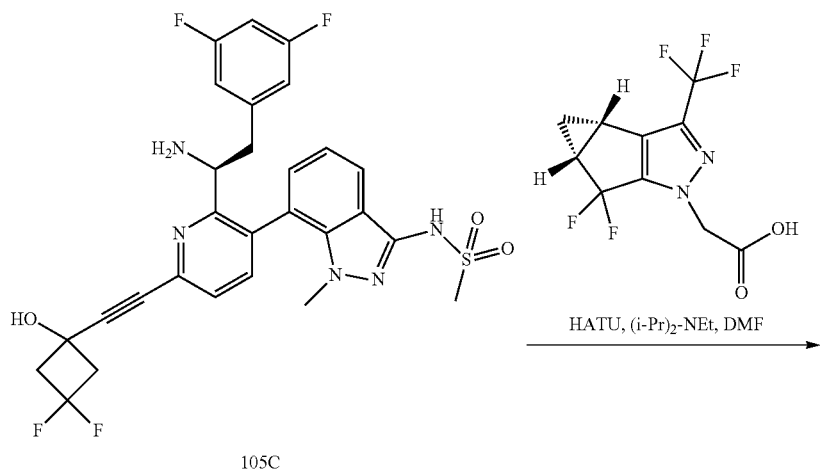
105C

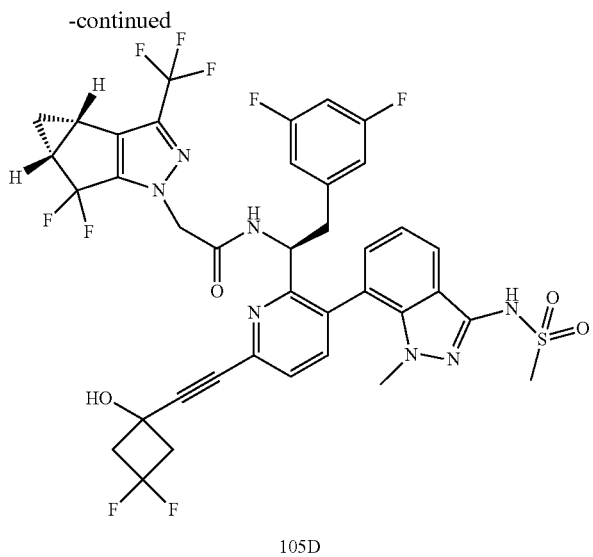

105D

Synthesis of (S)-tert-butyl(1-(3-bromo-6-((3,3-difluoro-1-hydroxycyclobutyl)ethynyl)pyridin-2-yl)-2-(3,5-difluorophenyl)ethyl)carbamate (105A): Argon was bubbled through a solution of 1F (850 mg, 1.73 mmol), 95B (228.2 mg, 1.73 mmol), Pd(Cl$_2$)(Ph$_3$)$_2$ (24.2 mg, 0.03 mmol), CuI (6.6 mg, 0.03 mmol), and triethylamine (0.72 ml, 5.18 mmol) in MeTHF (5 mL) for 1 minute. The reaction was stirred at room temperature overnight, the washed with water, the organic layer dried with sodium sulfate, filtered, and concentrated under vacuum. The product was purified by silica gel chromatography to give the title compound 105A. MS (m/z) 542.9 [M+H]$^+$.

Synthesis of (S)-tert-butyl(1-(6-((3,3-difluoro-1-hydroxycyclobutyl)ethynyl)-3-(1-methyl-3-(methylsulfonamido)-1H-indazol-7-yl)pyridin-2-yl)-2-(3,5-difluorophenyl)ethyl)carbamate (105B): Argon was bubbled through a suspension of 105A (50 mg, 0.09 mmol), the 20B (48 mg, 0.13 mmol), and PdCl$_2$(P(cy)$_3$)$_2$ (3.5 mg, 0.01 mmol) in dioxane (0.6 ml) and 1M NaHCO3 (0.2 ml) for 1 min. The mixture was heated at 150° C. for 10 minutes in a microwave reactor. The resulting solution was diluted with EtOAc (5 ml) and washed with brine (5 ml). The organic layer was dried with sodium sulfate, filtered, and concentrated under vacuum to give the title compound 105B. The crude product was taken to next step without further purification. MS (m/z) 687.9 [M+H]$^+$.

Synthesis of (S)—N-(7-(2-(1-amino-2-(3,5-difluorophenyl)ethyl)-6-((3,3-difluoro-1-hydroxycyclobutyl)ethynyl)pyridin-3-yl)-1-methyl-1H-indazol-3-yl)methanesulfonamide (105C): The title compound (105C) was prepared as a mixture of atropisomers according to the method presented for the synthesis of compound 101G of Example 101 utilizing compound 105B. MS (m/z) 588.2 [M+H]$^+$.

Synthesis of N—((S)-1-(3-(4-chloro-1-methyl-3-(methylsulfonamido)-1H-indazol-7-yl)-6-((3,3-difluoro-1-hydroxycyclobutyl)ethynyl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (105D): The title compound (105D) was prepared as a mixture of atropisomers according to the method presented for the synthesis of compound 102 of Example 102 utilizing compound 105C. $^1$H NMR (400 MHz, Methanol-d$_4$) δ 8.79-8.70 (m), 7.88-7.79 (m), 7.76-7.68 (m), 7.62-7.53 (m), 7.26 (d), 7.22-7.14 (m), 7.12-7.06 (m), 6.78-6.69 (m), 6.66-6.56 (m), 6.55-6.51 (m), 6.37-6.26 (m), 5.35-5.26 (m), 5.05-4.96 (m), 4.84-4.71 (m), 3.33 (s), 3.28-3.07 (m), 3.03-2.84 (m), 2.57-2.40 (m), 1.47-1.35 (m), 1.17-1.10 (m), 1.10-1.03 (m). MS (m/z) 852.2 [M+H]$^+$.

Example 106

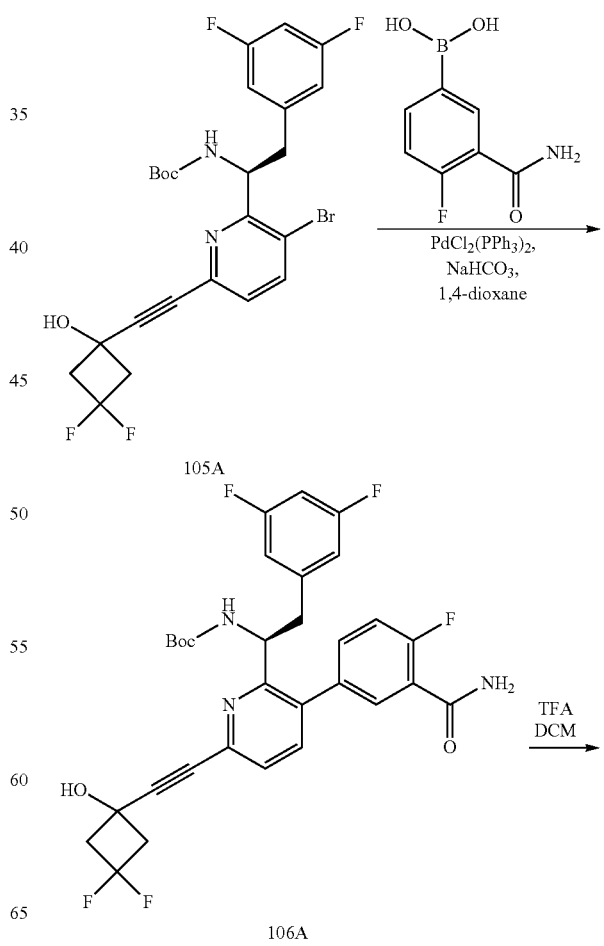

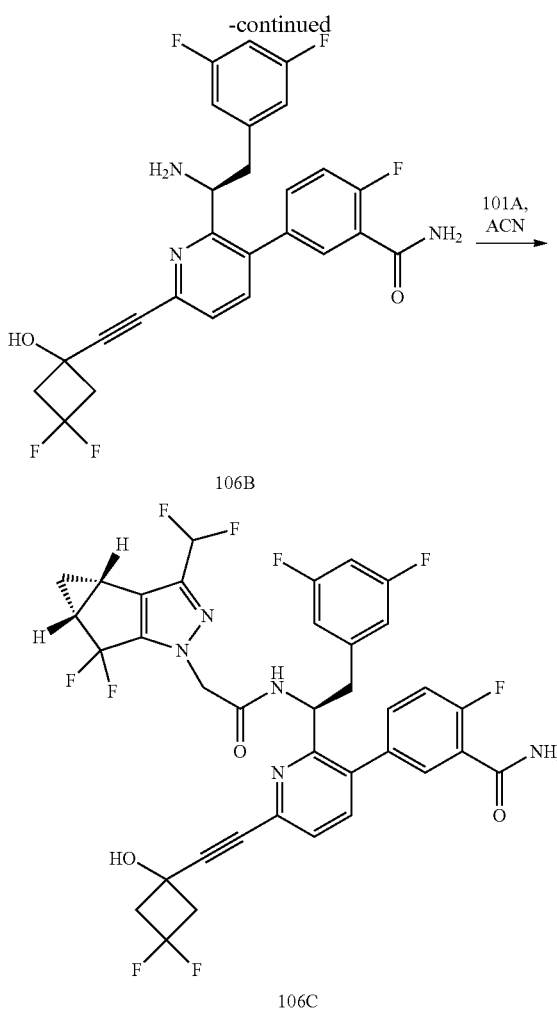

106B

106C

Synthesis of(S)-tert-butyl(1-(3-bromo-6-((3,3-difluoro-1-hydroxycyclobutyl)ethynyl)pyridin-2-yl)-2-(3,5-difluorophenyl)ethyl)carbamate (106A): The title compound (106A) was prepared as a mixture of atropisomers according to the method presented for the synthesis of compound 105B of Example 105 utilizing (3-carbamoyl-4-fluorophenyl)boronic acid. MS (m/z) 602.0 [M+H]$^+$.

Synthesis of(S)-5-(2-(1-amino-2-(3,5-difluorophenyl)ethyl)-6-((3,3-difluoro-1-hydroxycyclobutyl)ethynyl)pyridin-3-yl)-2-fluorobenzamide (106B): The title compound (106B) was prepared as a mixture of atropisomers according to the method presented for the synthesis of compound 105C of Example 105 utilizing compound 106A. MS (m/z) 502.0 [M+H]$^+$.

Synthesis of 5-(6-((3,3-difluoro-1-hydroxycyclobutyl)ethynyl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (106C): The title compound (106C) was prepared as a mixture of atropisomers according to the method presented for the synthesis of compound 101H of Example 101 utilizing compound 106B. $^1$H NMR (400 MHz, Methanol-d$_4$) δ 7.59-7.48 (m), 7.41-7.35 (m), 7.35-7.28 (m), 7.27-7.19 (m), 6.83 (s), 6.71-6.63 (m), 6.56 (s), 6.38-6.28 (m), 5.40-5.33 (m), 4.80 (s), 3.25-3.11 (m), 3.12-2.84 (m), 2.51-2.42 (m), 1.42-1.33 (m), 1.10-1.03 (m). MS (m/z) 748.2 [M+H]$^+$.

Example 107

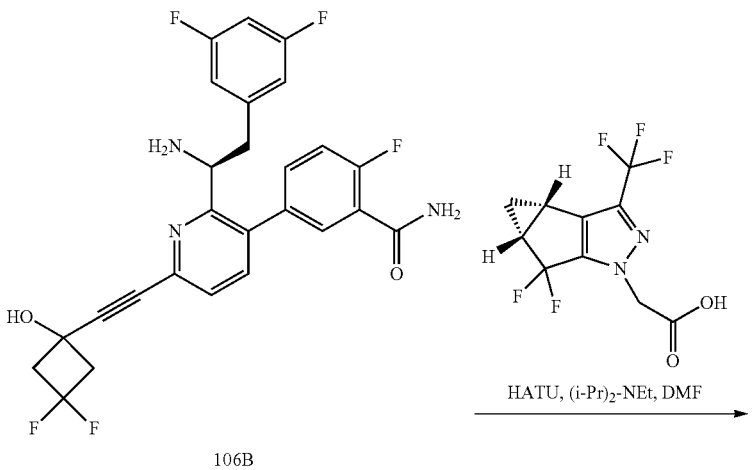

106B

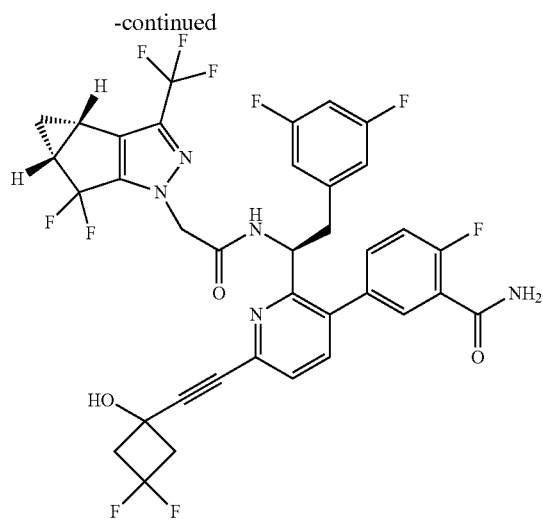

107

Synthesis of 5-(6-((3,3-difluoro-1-hydroxycyclobutyl)ethynyl)-2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (107): The title compound (107) was prepared as a mixture of atropisomers according to the method presented for the synthesis of compound 102 of Example 102 utilizing compound 106B.

$^1$H NMR (400 MHz, Methanol-$d_4$) δ 7.56 (d), 7.50 (d), 7.42-7.35 (m), 7.35-7.27 (m), 7.22 (dd), 6.72-6.61 (m), 6.40-6.30 (m), 5.43-5.31 (m), 3.26-3.11 (m), 3.11-3.00 (m), 3.00-2.83 (m), 2.58-2.42 (m), 1.46-1.34 (m), 1.15-1.06 (m). MS (m/z) 766.2 [M+H]$^+$.

Example 108

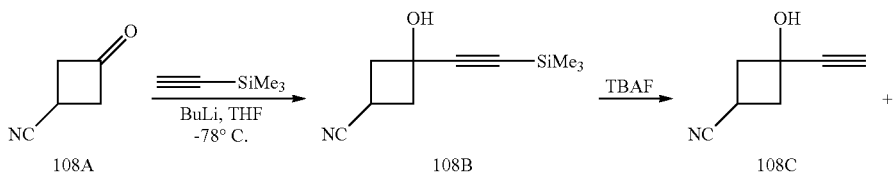

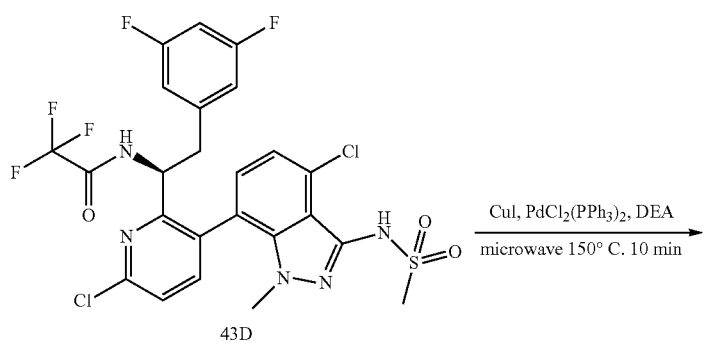

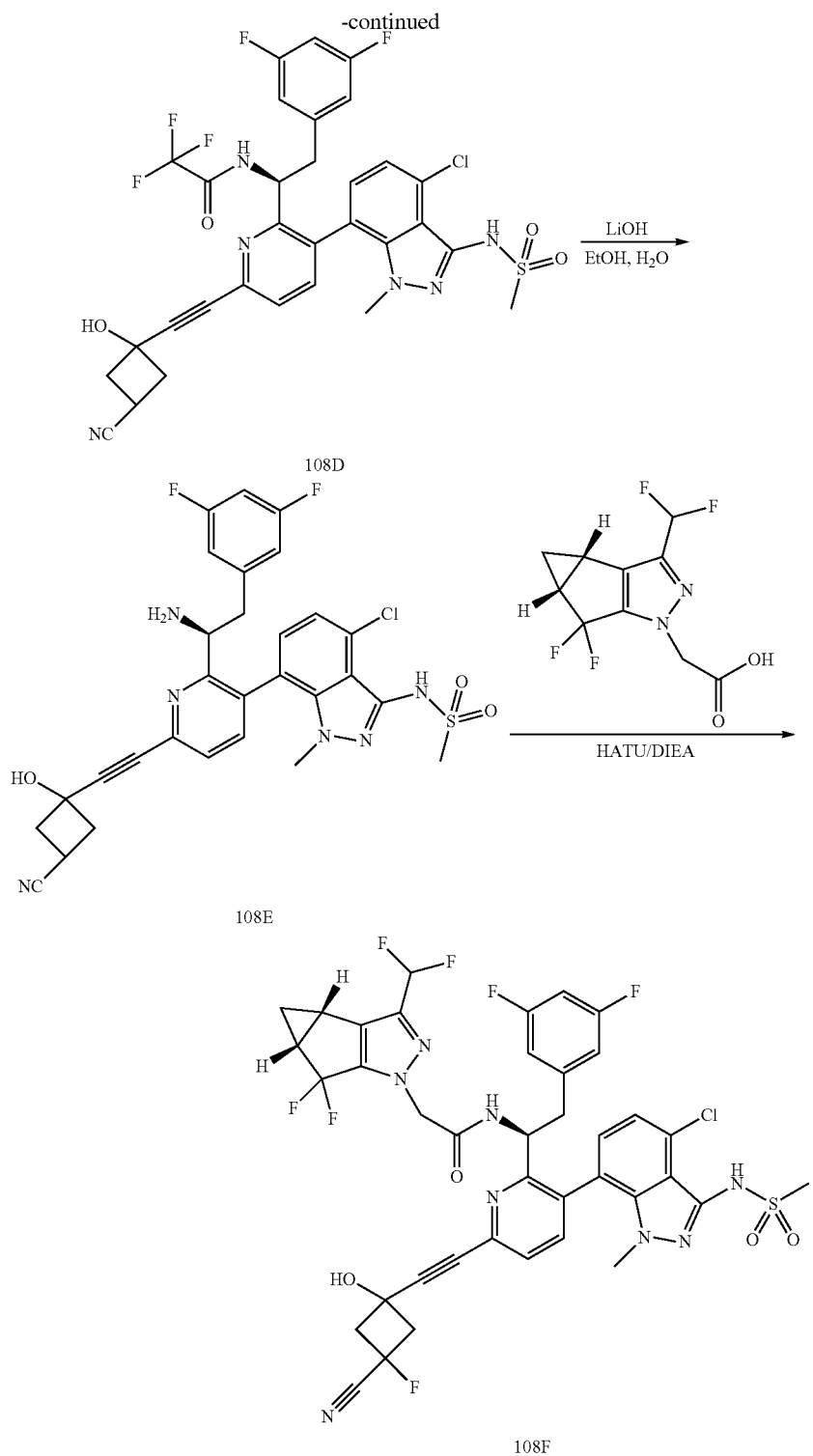

Synthesis of 3-hydroxy-3-((trimethylsilyl)ethynyl)cyclobutanecarbonitrile (108B): At −78° C., n-BuLi (1.6M in hexane, 3.8 ml) was added dropwise to a stirred solution of trimethylsilylacetylene (0.99 ml, 7.0 mmol) in THF (4 ml) over 3 minutes. The reaction was stirred for 55 min at −78 C. Compound 108A in 1 ml THF was added. The reaction was stirred at −78° C. for 2 hours. The reaction was quenched with saturated aqueous NH$_4$Cl solution, extracted with EtOAc. The organic layer was dried with MgSO$_4$ and concentrated. The resultant crude was purified by column chromatography on silica to afford compound 108B.

Synthesis of 3-ethynyl-3-hydroxycyclobutanecarbonitrile (108C): Compound 108B (53.5 mg, 0.28 mmol) was dissolved in 1 ml of THF, then treated with TBAF (1M in THF, 0.33 ml, 0.33 mmol). The reaction was stirred at room temperature overnight, poured reaction into saturated aqueous ammonium chloride solution, extracted with EtOAc, The organic layer was dried with MgSO₄ and concentrated. The resultant crude was purified by column chromatography on silica to afford compound 108C.

Synthesis of (S)—N-(1-(3-(4-chloro-1-methyl-3-(methylsulfonamido)-1H-indazol-7-yl)-6-((3-cyano-1-hydroxycyclobutyl)ethynyl)pyridin-2-yl)-2-(3,5-difluorophenyl)ethyl)-2,2,2-trifluoroacetamide (108D): Compound 43D (75 mg, 0.12 mmol) and compound 108C (54 ul, 0.39 mmol) were dissolved in DMF. Diethylamine (125 ul, 1.2 mmol) was added followed by CuI (16 mg, 0.08 mmol) and PdCl₂(PPh₃)₂ (59 mg, 0.08 mmol). The reaction mixture was bubbled with N₂ for 1 minute. Reaction was micro waved at 150° C. for 10 minutes. The reaction was diluted with EtOAc and washed with brine. The organic layer was dried with MgSO₄ and concentrated. The resultant crude was purified by column chromatography on silica (40-90% EtOAc/hexane) to afford compound 108D as a mixture of atropisomers. MS (m/z) 707 [M+H]⁺.

Synthesis of(S)—N-(7-(2-(1-amino-2-(3,5-difluorophenyl)ethyl)-6-((3-cyano-1-hydroxycyclobutyl)ethynyl)pyridin-3-yl)-4-chloro-1-methyl-1H-indazol-3-yl)methanesulfonamide (108E): Compound 108D (28 mg, 0.04 mmol) was dissolved in EtOH. 2M aqueous solution of lithium hydroxide (0.20 ml, 0.40 mmol) was added. The reaction mixture was stirred at 80° C. for 1 hour. Upon completion, the reaction was neutralized with 1N HCl, diluted with EtOAc and washed with aqueous NaHCO₃. The organic layer was dried with MgSO₄ and concentrated to provide crude compound 108E as a mixture of atropisomers. MS (m/z) 611 [M+H]⁺.

Synthesis of N—((S)-1-(3-(4-chloro-1-methyl-3-(methylsulfonamido)-1H-indazol-7-yl)-6-((3-cyano-1-hydroxycyclobutyl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (108F): Crude compound 108E, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (9 mg, 0.035 mmol) was dissolved in DMF. DIEA (30 ul, 0.18 mmol) and HATU (16 mg, 0.042 mmol) were added. The reaction mixture was stirred for 2 minutes. The reaction was diluted with EtOAc, washed with brine. The organic layer was dried with MgSO₄ and concentrated. The resultant crude was purified by HPLC to provide compound 108F as a mixture of atropisomers. 1H NMR (400 MHz, Acetonitrile-d3) δ 7.82 (d), 7.72 (dd), 7.58 (dd), 7.37 (d), 7.27-7.17 (m), 7.13 (d), 6.85-6.73 (m), 6.69-6.53 (m), 6.46-6.35 (m), 5.26 (q), 4.92 (q), 4.74-4.60 (m), 3.34-2.87 (m), 2.77-2.66 (m), 2.55-2.40 (m), 2.02-1.97 (m), 1.45-1.34 (m), 1.05-0.96 (m). MS (m/z) 857 [M+H]⁺.

Example 109

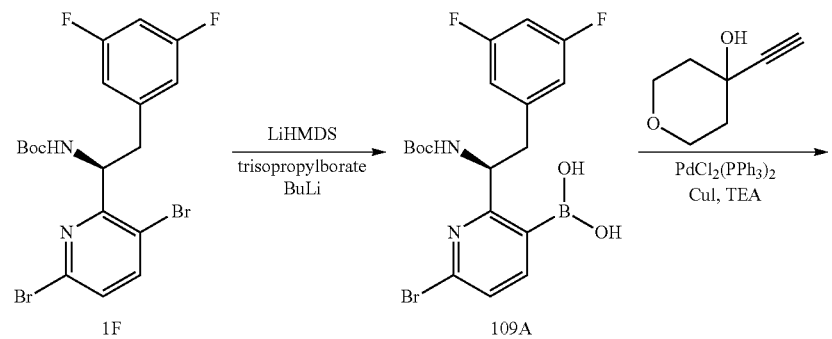

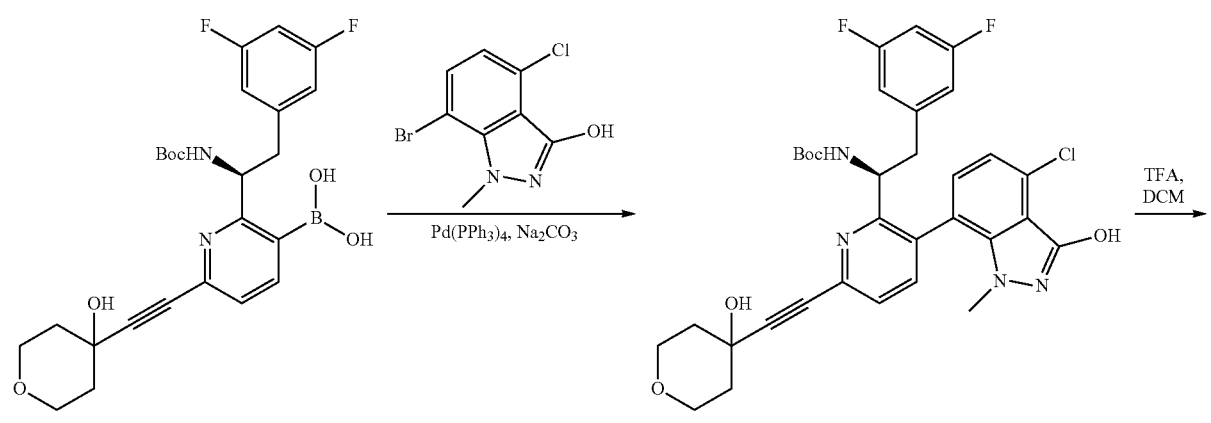

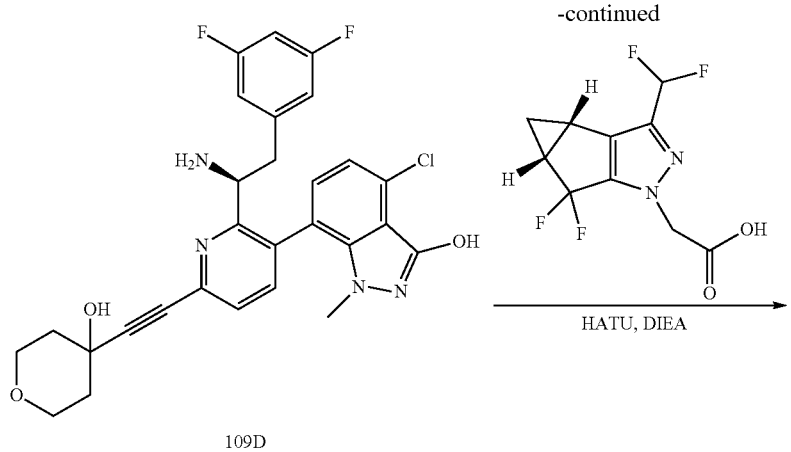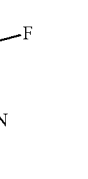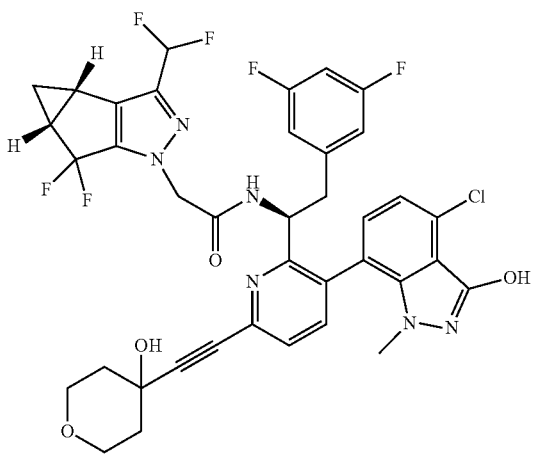

109D

109E

Synthesis of (S)-(6-bromo-2-(1-((tert-butoxycarbonyl)amino)-2-(3,5-difluorophenyl)ethyl)pyridin-3-yl)boronic acid (109A): To a solution of compound 1F (6.2 g, 12.6 mmol) in 2-methyltetrahydrofuran (25 ml) was added dropwise 1M LiHMDS in THF (12.6 ml) at 0° C. After stirring at room temperature for 20 minutes, the reaction was concentrated in vacuo, dissolved in toluene (30 mL), concentrated in vacuo, and re-dissolved in 2-MeTHF (25 ml). To the resulting solution was added triisopropyl borate (7.11 ml, 37.8 mmol) at −78° C. followed by the dropwise addition of 1M n-butyllithium in hexanes (20 ml) over 15 minutes. After stirring for 5 minutes, the reactions were gradually warmed to 0° C., and quenched with 4M aqueous NH$_4$Cl (75 mL). Additional 2-MeTHF (25 mL) was added and the organic layer was dried with Na$_2$SO$_4$, filtered, and concentrated in vacuo to afford crude compound 109A. MS (m/z) 457 [M+H]$^+$.

Synthesis of (S)-(2-(1-((tert-butoxycarbonyl)amino)-2-(3,5-difluorophenyl)ethyl)-6-((4-hydroxytetrahydro-2H-pyran-4-yl)ethynyl)pyridin-3-yl)boronic acid (109B): Compound 109A (154 mg, 0.34 mmol) was dissolved in degassed THF (1.7 ml), TEA (0.14 ml) and 4-ethynyltetrahydro-2H-pyran-4-ol (64 mg, 0.51 mmol) were added followed by CuI (13 mg, 0.067 mmol) and PdCl$_2$(PPh$_3$)$_2$ (47 mg, 0.067 mmol). The reaction was stirred for 30 minutes and then partitioned between EtOAc and water. The organics were separated, dried with MgSO$_4$ and concentrated. The residue was purified by column chromatography on silica to afford the compound 109B. MS (m/z) 503 [M+H]$^+$.

Synthesis of (S)-tert-butyl(1-(3-(4-chloro-3-hydroxy-1-methyl-1H-indazol-7-yl)-6-((4-hydroxytetrahydro-2H-pyran-4-yl)ethynyl)pyridin-2-yl)-2-(3,5-difluorophenyl)ethyl)carbamate (109C): 7-bromo-4-chloro-1-methyl-1H-indazol-3-ol (91 mg, 0.35 mmol), Na$_2$CO$_3$ (31 mg, 0.29 mmol), Pd(PPh$_3$)$_4$ (7 mg, 0.006 mmol) were added to a microwave tube. Compound 109B (29 mg, 0.058 mmol) in degassed 1,4-dioxane (2.5 ml) was added, water (0.5 ml) was added. The reaction mixture was bubbled with N$_2$ for 2 minutes, microwaved at 150° C. for 14 minutes. The reaction was diluted with EtOAc, washed with brine. The organics was dried with Na$_2$SO$_4$, filtered and concentrated to afford crude compound 109C as a mixture of atropisomers. MS (m/z) 639 [M+H]$^+$.

Synthesis of (S)-7-(2-(1-amino-2-(3,5-difluorophenyl)ethyl)-6-((4-hydroxytetrahydro-2H-pyran-4-yl)ethynyl)pyridin-3-yl)-4-chloro-1-methyl-1H-indazol-3-ol (109D): The compound 109D was prepared as a mixture of atropisomers according to the method presented for the synthesis of compound 3C of Example 3 utilizing compound 109C. MS (m/z) 539 [M+H]$^+$.

Synthesis of N—((S)-1-(3-(4-chloro-3-hydroxy-1-methyl-1H-indazol-7-yl)-6-((4-hydroxytetrahydro-2H-pyran-4-yl)ethynyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (109E): The compound 109E was prepared as a mixture of atropisomers according to the method presented for the synthesis of compound 108F of Example 108 utilizing compound 109C. 1H NMR (400 MHz, Acetonitrile-d3) δ 7.68 (dd), 7.56 (dd), 7.30 (d), 7.20-6.88 (m), 6.87-6.72 (m), 6.71-6.60 (m), 6.52 (d), 6.48-6.30 (m), 5.47 (s), 5.25 (q), 4.98 (dt), 4.75-4.64 (m), 3.97-3.87 (m), 3.79-3.68 (m), 3.30 (s), 3.09 (s), 3.05-2.83 (m), 2.55-2.41 (m), 2.13-2.01 (m), 1.99 (s), 1.87 (ddd), 1.80-1.71 (m), 1.48-1.20 (m), 1.08-0.96 (m), 0.95-0.70 (m). MS (m/z) 785 [M+H]$^+$.

Example 110

The following illustrate representative pharmaceutical dosage forms, containing a compound of formula I ('Compound X'), for therapeutic or prophylactic use in humans.

| (i) Tablet 1 | mg/tablet |
|---|---|
| Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X' (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All references, including publications, patents, and patent documents are incorporated by reference herein, as though individually incorporated by reference. The present disclosure provides reference to various specific and preferred embodiments and techniques. However, it should be understood that many variations and modifications may be made while remaining within the spirit and scope of the present disclosure.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein. Of these, variations of the disclosed embodiments will become apparent to those of ordinary skill in the art upon reading the foregoing disclosure. Skilled artisans are expected employ such variations as appropriate (e.g., altering or combining features or embodiments), and it is expected that the subject matter of the present disclosure to be practiced otherwise than as specifically described herein.

Accordingly, this disclosure includes all modifications and equivalents of the subject matter recited in the claims appended hereto as permitted by applicable law. Moreover, any combination of the above described elements in all possible variations thereof is encompassed by the present disclosure unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein. In one aspect, about a value includes and intends that value per se. For example, about x includes and intends x per se.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. A compound of formula I:

wherein
$A^1$ is C—$Z^3$ or nitrogen;
$A^2$ is C—$Z^3$ or nitrogen;
$R^1$ is 6-12 membered aryl, 5-12 membered heteroaryl, or 3-12 membered heterocycle, wherein any 6-12 membered aryl, 5-12 membered heteroaryl, or 3-12 membered heterocycle of $R^1$ is optionally substituted with 1, 2, 3, 4 or 5 $Z^4$ groups, wherein the $Z^4$ groups are the same or different;
each $R^{3a}$ and $R^{3b}$ is independently H or $(C_1$-$C_3)$alkyl;
$Z^1$ is 6-12 membered aryl, 5-14 membered heteroaryl, or 3-14 membered heterocycle, wherein any 6-12 membered aryl, 5-14 membered heteroaryl, or 3-14 membered heterocycle of $Z^1$ is optionally substituted with 1, 2, 3, 4 or 5 $Z^{1a}$ or $Z^{1b}$, wherein the $Z^{1a}$ and $Z^{1b}$ groups are the same or different;
each $Z^{1a}$ is independently oxo, $(C_3$-$C_7)$carbocycle, 5-12 membered heteroaryl, 3-12 membered heterocycle, halogen, —CN, —$OR^{n1}$, —$OC(O)R^{p1}$, —$OC(O)NR^{q1}R^{r1}$, —$SR^{n1}$, —$S(O)R^{p1}$, —$S(O)_2OH$, —$S(O)_2R^{p1}$, —$S(O)_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2OR^{p1}$, —$NR^{n1}S(O)_2NR^{q1}R^{r1}$, —$C(O)R^{n1}$, —$C(O)OR^{n1}$, —$C(O)NR^{q1}R^{r1}$ and —$S(O)_2NR^{n1}COR^{p1}$, wherein any $(C_3$-$C_7)$carbocycle, 5-12 membered heteroaryl and 3-12 membered heterocycle of $Z^{1a}$ is optionally substituted with 1, 2, 3, 4 or 5 $Z^{1c}$ or $Z^{1d}$ groups, wherein the $Z^{1c}$ and $Z^{1d}$ groups are the same or different;
each $Z^{1b}$ is independently $(C_1$-$C_8)$alkyl optionally substituted with 1, 2, 3, 4 or 5 halogen, which are the same or different;
each $Z^{1c}$ is independently halogen, —CN, —OH, —$NH_2$, —$C(O)NR^{q2}R^{r2}$, or $(C_1$-$C_8)$heteroalkyl;

each $Z^{1d}$ is independently $(C_1$-$C_8)$alkyl or $(C_1$-$C_8)$haloalkyl;
each $R^{n1}$ is independently H, $(C_1$-$C_8)$alkyl, $(C_3$-$C_7)$carbocycle, 3-7 membered heterocycle, or 5-6 membered monocyclic-heteroaryl, wherein any $(C_3$-$C_7)$carbocycle, 3-7 membered heterocycle, or 5-6 membered monocyclic-heteroaryl of $R^{n1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1$-$C_8)$alkyl of $R^{n1}$ is optionally substituted with 1, 2, 3, 4 or 5 $Z^{1c}$ groups, wherein the $Z^{1c}$ groups are the same or different;
each $R^{p1}$ is independently $(C_1$-$C_8)$alkyl, $(C_3$-$C_7)$carbocycle, 3-7 membered heterocycle, or 5-6 membered monocyclic-heteroaryl, wherein any $(C_3$-$C_7)$carbocycle, 3-7 membered heterocycle, or 5-6 membered monocyclic-heteroaryl of $R^{p1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1$-$C_8)$alkyl of $R^{p1}$ is optionally substituted with 1, 2, 3, 4 or 5 $Z^{1c}$ groups, wherein the $Z^{1c}$ groups are the same or different;
each $R^{q1}$ and $R^{r1}$ is independently H, $(C_1$-$C_8)$alkyl, $(C_3$-$C_7)$carbocycle, 3-7 membered heterocycle, or 5-6 membered monocyclic-heteroaryl, wherein any $(C_3$-$C_7)$carbocycle, 3-7 membered heterocycle, or 5-6 membered monocyclic-heteroaryl of $R^{q1}$ or $R^{r1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1$-$C_8)$alkyl of $R^{q1}$ or $R^{r1}$ is optionally substituted with 1, 2, 3, 4 or 5 $Z^{1c}$ groups, wherein the $Z^{1c}$ groups are the same or different, or $R^{q1}$ and $R^{r1}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups, wherein the $Z^{1c}$ and $Z^{1d}$ groups are the same or different;
each $R^{q2}$ and $R^{r2}$ is independently H, $(C_1$-$C_8)$alkyl, $(C_3$-$C_7)$carbocycle, or $R^{q2}$ and $R^{r2}$ together with the nitrogen to which they are attached form a 5, 6, or 7-membered heterocycle;
$Z^2$ is $(C_2$-$C_8)$alkenyl, $(C_2$-$C_8)$alkynyl, 6-12 membered aryl, 5-12 membered heteroaryl, 3-12 membered heterocycle, wherein any $(C_2$-$C_8)$alkenyl, $(C_2$-$C_8)$alkynyl, 6-12 membered aryl, 5-12 membered heteroaryl, or 3-12 membered heterocycle of $Z^2$ is substituted with 1 or 2 $Z^{2b}$ groups and optionally 1, 2, or 3 $Z^{2c}$ groups, wherein the $Z^{2b}$ and $Z^{2c}$ groups are the same or different;
each $R^{n3}$ is independently H or $(C_1$-$C_4)$alkyl;
each $R^{q3}$ and $R^{r3}$ is independently H or $(C_1$-$C_4)$alkyl;
each $Z^{2b}$ is independently 6-12 membered aryl, 5-12 membered heteroaryl, 3-9 membered carbocycle, 3-12 membered heterocycle, or amino substituted with 3-12 membered heterocycle, 5-12 membered heteroaryl, 3-9 membered carbocycle, or 3-12 membered heterocycle, wherein any 6-12 membered aryl, 5-12 membered heteroaryl, 3-9 membered carbocycle, or 3-12 membered heterocycle of $Z^{2b}$ is optionally substituted with 1, 2, 3, 4, or 5 $Z^{2d}$ groups;
each $Z^{2c}$ is independently oxo, halogen, —CN, —$OR^{n4}$, —$OC(O)R^{p4}$, —$OC(O)NR^{q4}R^{r4}$, —$SR^{n4}$, —$S(O)R^{p4}$, —$S(O)_2OH$, —$S(O)_2R^{p4}$, —$S(O)_2NR^{q4}R^{r4}$, —$NR^{q4}R^{r4}$, —$NR^{n4}COR^{p4}$, —$NR^{n4}CO_2R^{p4}$, —$NR^{n4}CONR^{q4}R^{r4}$, —$NR^{n4}S(O)_2R^{p4}$, —$NR^{n4}S(O)_2OR^{p4}$, —$NR^{n4}S(O)_2NR^{q4}R^{r4}$, —$NO_2$, —$C(O)R^{n4}$, —C(O)OR$^{n4}$, —C(O)NR$^{q4}$R$^{r4}$, or (C$_1$-C$_4$) alkyl optionally substituted with 1, 2, or 3 halogen or —OR$^{n4}$;

each Z$^{2d}$ is independently oxo, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, —C(O)NR$^{q4}$R$^{r4}$, or (C$_1$-C$_4$) alkyl optionally substituted with 1, 2, or 3 halogen or —OR$^{n4}$;

each R$^{n4}$ is independently H, (C$_1$-C$_4$)alkyl optionally substituted with 1, 2, or 3 —OH groups, (C$_1$-C$_4$) haloalkyl, or (C$_1$-C$_4$)heteroalkyl;

each R$^{p4}$ is independently (C$_1$-C$_8$)alkyl, (C$_1$-C$_4$)haloalkyl, or (C$_1$-C$_4$)heteroalkyl;

each R$^{q4}$ and R$^{r4}$ is independently H, (C$_1$-C$_4$)alkyl, (C$_1$-C$_4$)haloalkyl, or (C$_1$-C$_4$)heteroalkyl;

each Z$^3$ is independently H or —NR$^{q4}$R$^{r4}$;

each Z$^4$ is independently oxo, (C$_1$-C$_8$)alkyl, (C$_3$-C$_7$)carbocycle, halogen, —CN, —OR$^{n5}$, —NR$^{q5}$R$^{r5}$, —NR$^{n5}$COR$^{p5}$, —NR$^{n5}$CO$_2$R$^{p5}$, —C(O)R$^{n5}$, —C(O)OR$^{n5}$, or —C(O)NR$^{q5}$R$^{r5}$, wherein any (C$_3$-C$_7$)carbocycle or (C$_1$-C$_8$)alkyl of Z$^4$ is optionally substituted with 1, 2, 3, 4 or 5 Z$^{4a}$ groups, wherein the Z$^{4a}$ groups are the same or different;

each Z$^{4a}$ is independently halogen, —CN, or —OR$^{n6}$;

each R$^{n5}$, R$^{p5}$, R$^{q5}$, R$^{r5}$, and R$^{n6}$ is independently H or (C$_1$-C$_4$)alkyl;

each Z$^5$ is independently halogen, which may be same or different; and n is 0, 1, 2, or 3;

or a pharmaceutically acceptable salt thereof.

2. The compound of claim 1, or a pharmaceutically acceptable salt thereof, wherein the moiety

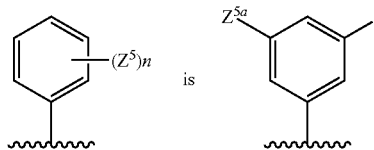

is wherein Z$^{5a}$ is H or halogen.

3. The compound of claim 1, or a pharmaceutically acceptable salt thereof, wherein R$^{3a}$ and R$^{3b}$ are each H.

4. The compound of claim 1, or a pharmaceutically acceptable salt thereof, which is a compound of formula II

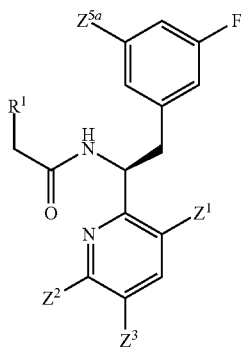

wherein Z$^3$ is H or —NH$_2$ and Z$^{5a}$ is H or halogen.

5. The compound of claim 1, or a pharmaceutically acceptable salt thereof, wherein Z$^2$ is (C$_2$-C$_8$)alkynyl or 5-6 membered C-linked-monocyclic-heteroaryl, wherein any (C$_2$-C$_8$)alkynyl or 5-6 membered C-linked-monocyclic-heteroaryl of Z$^2$ is substituted with 1 or 2 Z$^{2b}$ groups and optionally substituted with 1, 2, or 3 Z$^{2c}$ groups.

6. The compound of claim 5, or a pharmaceutically acceptable salt thereof, wherein Z$^2$ is (C$_2$-C$_8$)alkynyl substituted with 1 or 2 Z$^{2b}$ groups and optionally substituted with 1, 2, or 3 Z$^{2c}$ groups.

7. The compound of claim 1, or a pharmaceutically acceptable salt thereof, wherein each Z$^{2c}$ is independently halogen, —OR$^{n4}$, NR$^{q4}$R$^{r4}$, —NR$^{n4}$CO$_2$R$^{p4}$, —C(O)OR$^{n4}$, or —C(O)NR$^{q4}$R$^{r4}$.

8. The compound of claim 7, or a pharmaceutically acceptable salt thereof, wherein each Z$^{2c}$ is independently halogen or —OR$^{n4}$.

9. The compound of claim 1, or a pharmaceutically acceptable salt thereof, wherein each Z$^{2b}$ is independently phenyl, 5-10 membered C-linked-heteroaryl, 3-7 membered carbocycle, 4-6 membered C-linked-heterocycle or amino substituted with 4-5 membered heterocycle, wherein any phenyl, 5-10 membered C-linked-heteroaryl, 3-7 membered carbocycle, 4-6 membered C-linked-heterocycle, or 4-5 membered heterocycle of Z$^{2b}$ is optionally substituted with 1, 2, 3, 4, or 5 Z$^{2d}$ groups, wherein each Z$^{2d}$ is independently oxo, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, —C(O)NR$^{q4}$R$^{r4}$, or (C$_1$-C$_4$) alkyl optionally substituted with 1, 2, or 3 halogen or —OR$^{n4}$.

10. The compound of claim 1, or a pharmaceutically acceptable salt thereof, which is a compound of formula III

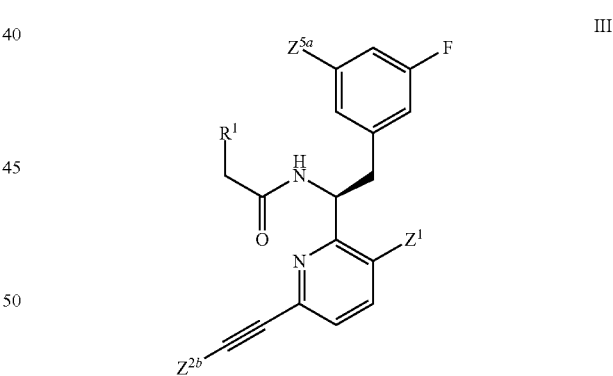

wherein the Z$^{2b}$ is optionally substituted with 1, 2 or 3 Z$^{2d}$ groups, and Z$^{5a}$ is H or halogen.

11. The compound of claim 10, or a pharmaceutically acceptable salt thereof, wherein Z$^{2b}$ is cyclopropyl, cyclobutyl, cyclopentyl, cyclohexyl, dihydroquinolinyl, dihydropyridinyl, oxetanyl, azetidinyl, pyrrolidinyl, tetrahydropyranyl, tetrahydrofuranyl, piperidinyl, piperazinyl, morpholinyl, hexahydrofuro[2,3-b]furanyl, oxaspiro[3.3]heptanyl, oxazolidinyl, dioxanyl, dihydroimidazo[2,1-c][1,4]oxazinyl, oxotriazolyl, phenyl, pyridinyl, pyrimidinyl, pyrrolo[2,3-b]pyridinyl, imidazolyl, furanyl, or triazolyl, wherein Z$^{2b}$ is optionally substituted with 1, 2 or 3 Z$^{2d}$ groups.

12. The compound of claim 11, or a pharmaceutically acceptable salt thereof, wherein $Z^{2b}$ is optionally substituted with 1, 2 or 3 $Z^{2d}$ groups, wherein each $Z^{2d}$ group is independently halogen, —CN, $OR^{n4}$, —$NR^{q4}R^{r4}$, oxo, ($C_1$-$C_4$)alkyl optionally substituted with —OH, $C(O)R^{n4}$, where $R^{n4}$ is ($C_1$-$C_4$)alkyl optionally substituted with 1, 2, or 3 —OH groups.

13. The compound of claim 11, or a pharmaceutically acceptable salt thereof, wherein $Z^{2b}$ is cyclopropyl, cyclobutyl, cyclopentyl, or cyclohexyl, optionally substituted with 1, 2, or 3 $Z^{2d}$ groups, wherein each $Z^{2d}$ group is independently —CN, halogen or —OH.

14. The compound of claim 10, or a pharmaceutically acceptable salt thereof, wherein $Z^{2b}$ optionally substituted with 1, 2 or 3 $Z^{2d}$ groups is

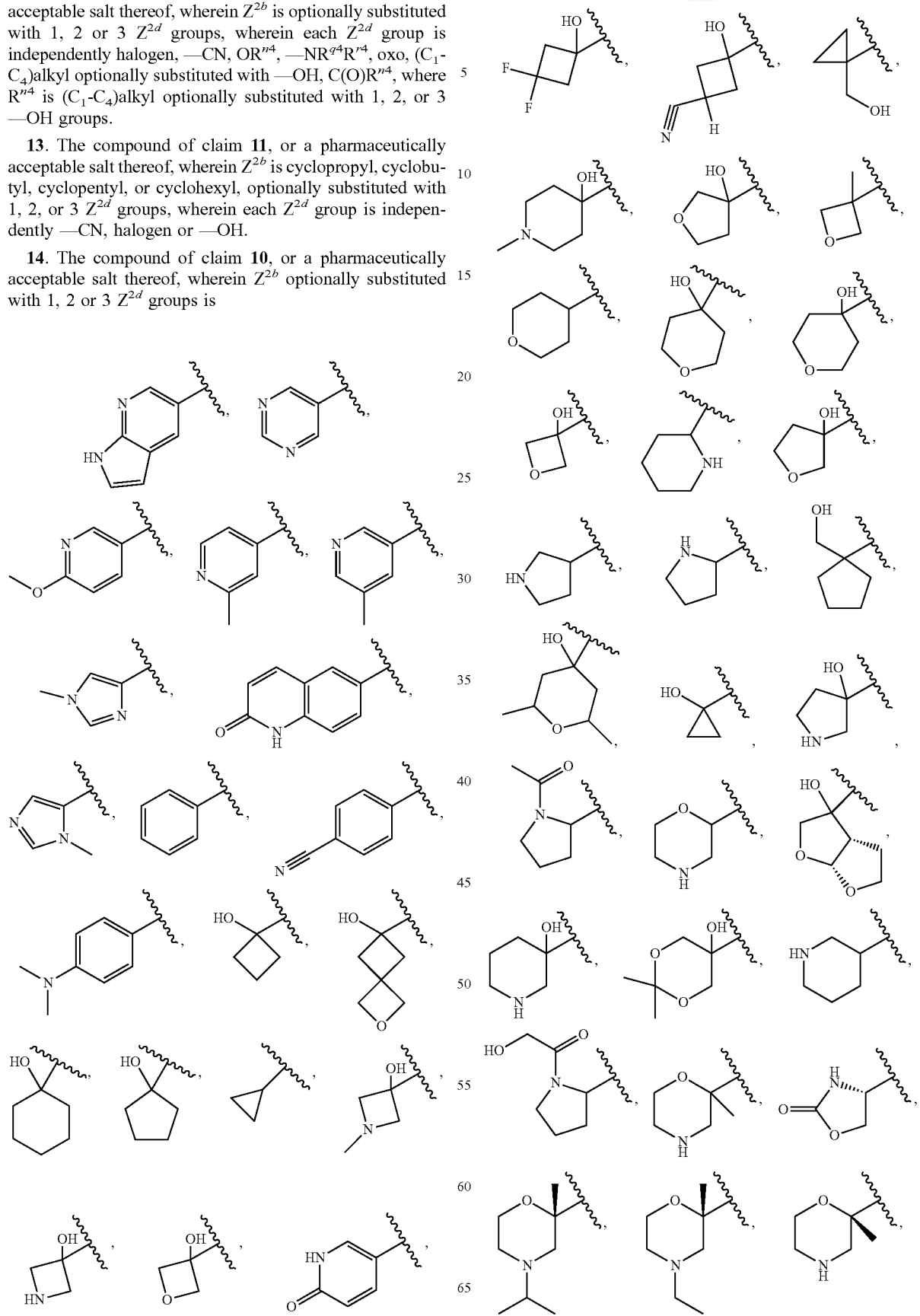

-continued

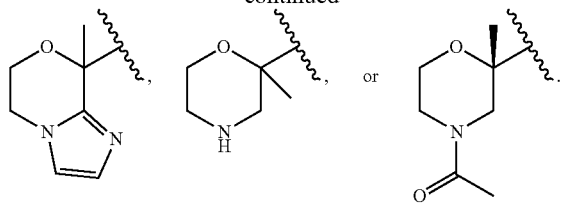

15. The compound of claim 1, or a pharmaceutically acceptable salt thereof, which is a compound of formula IV

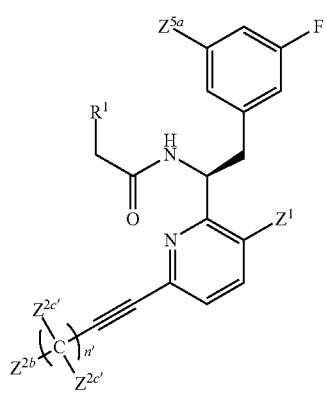

Formula IV wherein each $Z^{2c'}$ is independently hydrogen, $(C_1-C_4)$alkyl, or $OR^{n4}$ where $R^{n4}$ is hydrogen or $(C_1-C_4)$ alkyl, and where n' is 1, 2, or 3; and $Z^{5a}$ is H or halogen.

16. The compound of claim 15, or a pharmaceutically acceptable salt thereof, wherein each $Z^{2c'}$ is independently hydrogen, methyl, or —OH.

17. The compound of claim 16, or a pharmaceutically acceptable salt thereof, wherein $Z^{2b}$ is phenyl, piperazinyl, morpholinyl, triazolyl, azetidinyl, imidazoyl, furanyl, cyclopropyl, oxazolidinyl, or amino substituted with azetidinyl, wherein each $Z^{2b}$ is optionally substituted with 1, 2 or 3 $Z^{2d}$ groups, wherein each $Z^{2d}$ group is independently halogen, oxo, or $(C_1-C_4)$alkyl.

18. The compound of claim 15, or a pharmaceutically acceptable salt thereof, wherein the moiety

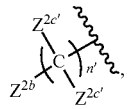

wherein $Z^{2b}$ is optionally substituted with 1, 2 or 3 $Z^{2d}$ groups, is

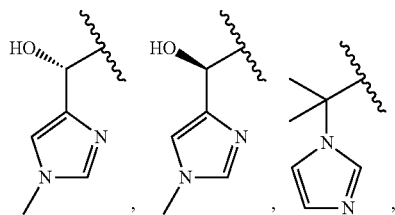

-continued

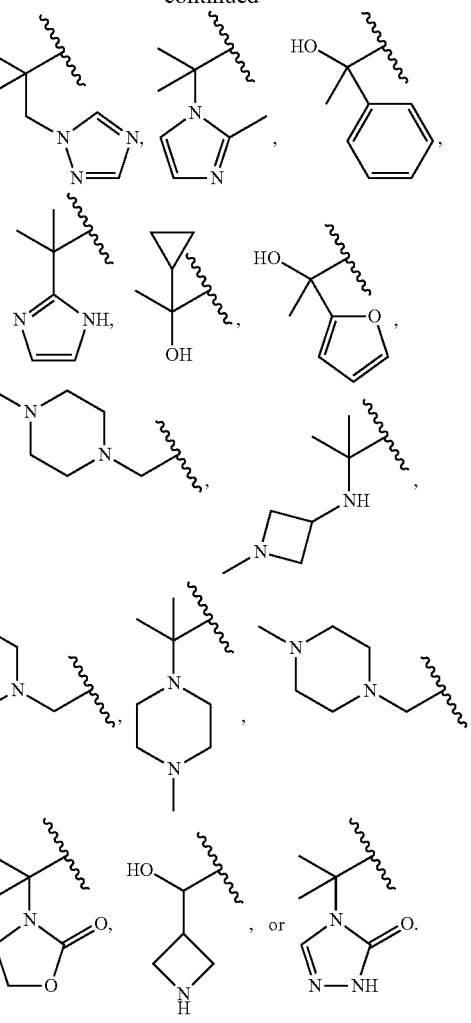

19. The compound of claim 1, or a pharmaceutically acceptable salt thereof, wherein $R^1$ is

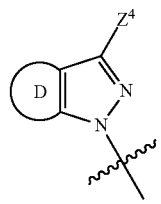

wherein
D, together with the two carbon atoms to which it is attached, forms a 3-7 membered monocyclic-carbocycle, 6 membered aryl, 6 membered heteroaryl, or 5-9 membered bicyclic-carbocycle, wherein any 3-7 membered monocyclic-carbocycle, 6 membered aryl, 6 membered heteroaryl, or 5-9 membered bicyclic-carbocycle of D is optionally substituted with 1, 2, 3, 4 or 5 $Z^4$ groups, wherein the $Z^4$ groups are the same or different.

20. The compound of claim 19, or a pharmaceutically acceptable salt thereof, wherein D, together with the two carbon atoms to which it is attached, forms a 5-6 membered monocyclic-carbocycle, 6 membered aryl, or 6 membered bicyclic-carbocycle, wherein any 5-6 membered monocyclic-carbocycle, 6 membered aryl, or 6 membered bicyclic-carbocycle of D is optionally substituted with 1, 2, 3, 4 or 5 $Z^4$ groups, wherein the $Z^4$ groups are the same or different.

21. The compound of claim 20, or a pharmaceutically acceptable salt thereof, wherein D, together with the two carbon atoms to which it is attached, forms a phenyl, cyclohexyl, cyclopentyl, or bicyclohexyl group, wherein any phenyl, cyclohexyl, cyclopentyl, or bicyclohexyl group of D is optionally substituted with 1, 2, 3, 4 or 5 $Z^4$ groups, wherein the $Z^4$ groups are the same or different.

22. The compound of claim 19, or a pharmaceutically acceptable salt thereof, wherein each $Z^4$ is independently ($C_1$-$C_6$)alkyl, —CN, or halogen, wherein any ($C_1$-$C_6$)alkyl of $Z^4$ is optionally substituted with 1, 2, 3, 4 or 5 halogen, which may be the same or different.

23. The compound of claim 22, or a pharmaceutically acceptable salt thereof, wherein each $Z^4$ is independently ($C_1$-$C_3$)alkyl, —CN, or halogen, wherein any ($C_1$-$C_3$)alkyl of $Z^4$ is optionally substituted with 1, 2, 3, 4 or 5 halogen, which may be the same or different.

24. The compound of claim 19, or a pharmaceutically acceptable salt thereof, wherein $R^1$ is

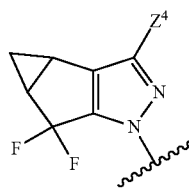 or 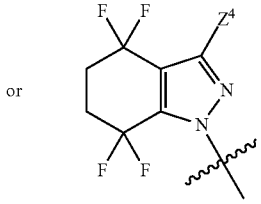.

25. The compound of claim 19, or a pharmaceutically acceptable salt thereof, wherein $R^1$ optionally substituted with 1, 2, 3, 4, or 5 $Z^4$ groups is

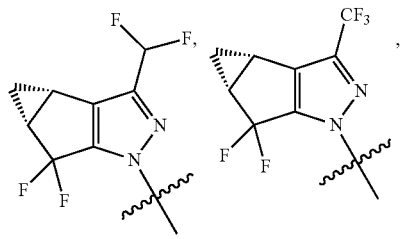

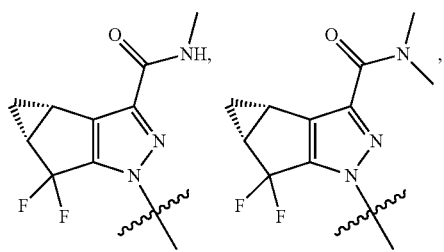

-continued

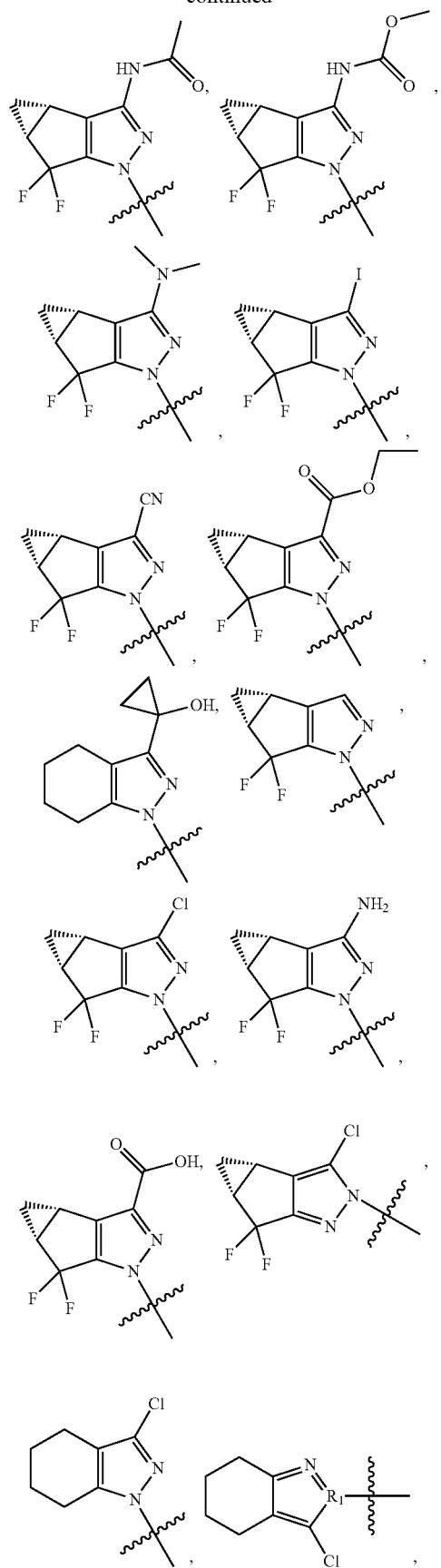

315
-continued
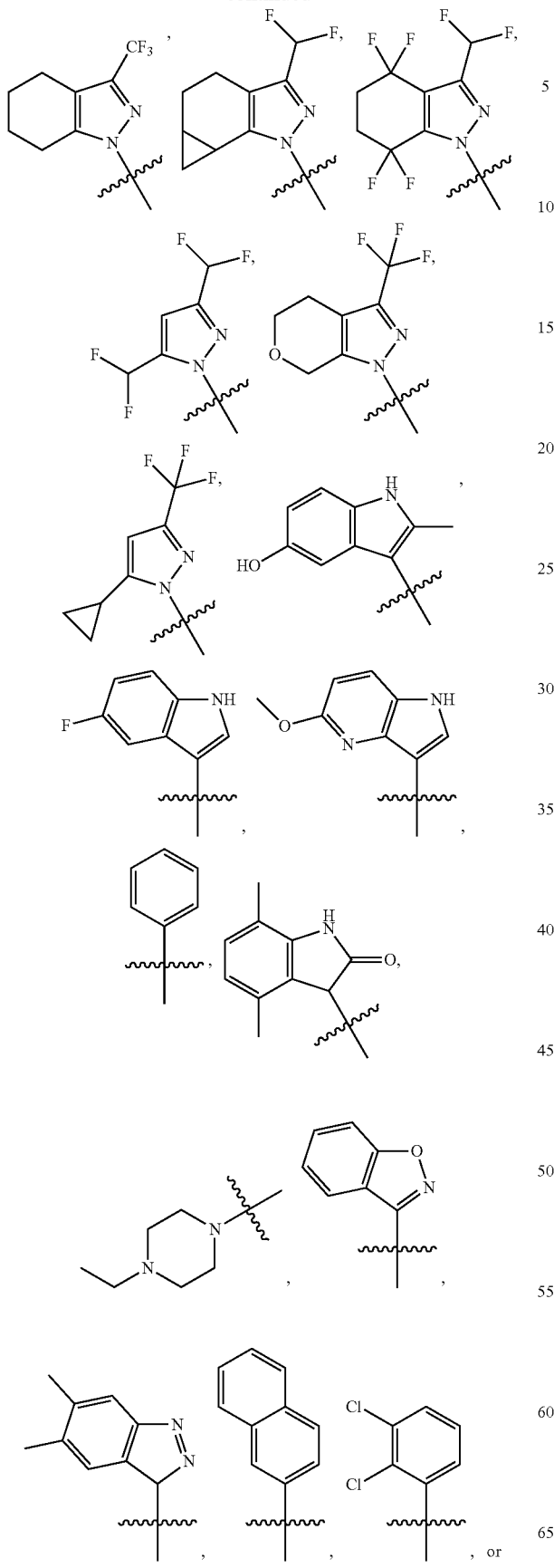
, or
316
-continued
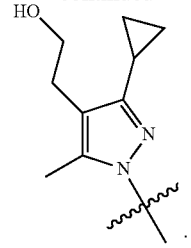
26. The compound of claim 19, or a pharmaceutically acceptable salt thereof, wherein $R^1$ optionally substituted with 1, 2, 3, 4, or 5 $Z^4$ groups is
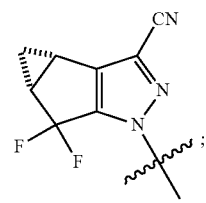
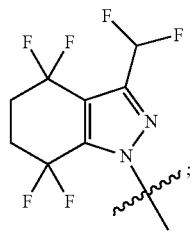
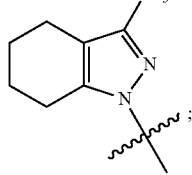
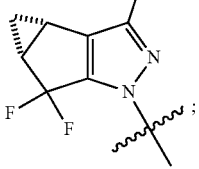
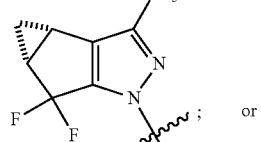
; or
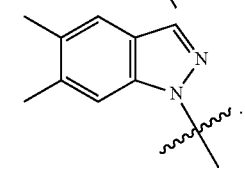
27. The compound of claim 1, or a pharmaceutically acceptable salt thereof, wherein $Z^1$ is phenyl, 8-10 membered bicyclic-heteroaryl, 8-10 membered bicyclic-heterocycle, or 9-12 membered tricyclic-heterocycle, wherein any phenyl, 8-10 membered bicyclic-heteroaryl, 8-10 membered bicyclic-heterocycle, or 9-12 membered tricyclic-heterocycle of $Z^1$ is optionally substituted with 1, 2, 3, 4, or 5 $Z^{1a}$ or $Z^{1b}$ groups.

28. The compound of claim 27, or a pharmaceutically acceptable salt thereof, wherein $Z^1$ is phenyl, 8-10 membered bicyclic-heteroaryl or 8-10 membered bicyclic-heterocycle, wherein any 8-10 membered bicyclic-heteroaryl or 8-10 membered bicyclic-heterocycle has 3-9 carbon atoms and 1-5 heteroatoms in the ring system, and wherein any phenyl, 8-10 membered bicyclic-heteroaryl, or 8-10 membered bicyclic-heterocycle of $Z^1$ is optionally substituted with 1, 2, 3, 4, or 5 $Z^{1a}$ or $Z^{1b}$ groups.

29. The compound of any claim 28, or a pharmaceutically acceptable salt thereof, wherein each $Z^{1a}$ is independently oxo, $(C_3-C_7)$carbocycle, halogen, —CN, —OH, —O—$(C_1-C_8)$alkyl, —NR$^{q1}$R$^{r1}$, —NR$^{n1}$COR$^{p1}$, —NR$^{n1}$CO$_2$R$^{p1}$, —NR$^{n1}$CONR$^{q1}$, —NR$^{n1}$S(O)$_2$R$^{p1}$, —NR$^{n1}$S(O)$_2$NR$^{q1}$R$^{r1}$, or —C(O)NR$^{q1}$R$^{r1}$.

30. The compound of claim 28, or a pharmaceutically acceptable salt thereof, wherein each $Z^{1b}$ is independently methyl or difluoromethyl.

31. The compound of claim 28, or a pharmaceutically acceptable salt thereof, wherein $Z^1$ is

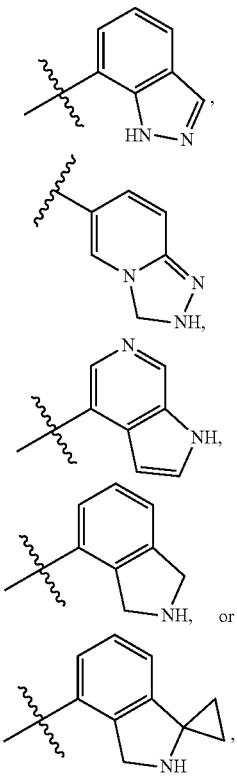

optionally substituted with 1, 2, 3, 4 or 5 $Z^{1a}$ or $Z^{1b}$.

32. The compound of claim 31, or a pharmaceutically acceptable salt thereof, wherein each $Z^{1a}$ is independently oxo, —NR$^{q1}$R$^{r1}$, —OH, halogen, or —NR$^{n1}$S(O)$_2$R$^{p1}$.

33. The compound of claim 28, or a pharmaceutically acceptable salt thereof, wherein $Z^1$ optionally substituted with 1, 2, 3, 4 or 5 $Z^{1a}$ or $Z^{1b}$ groups is

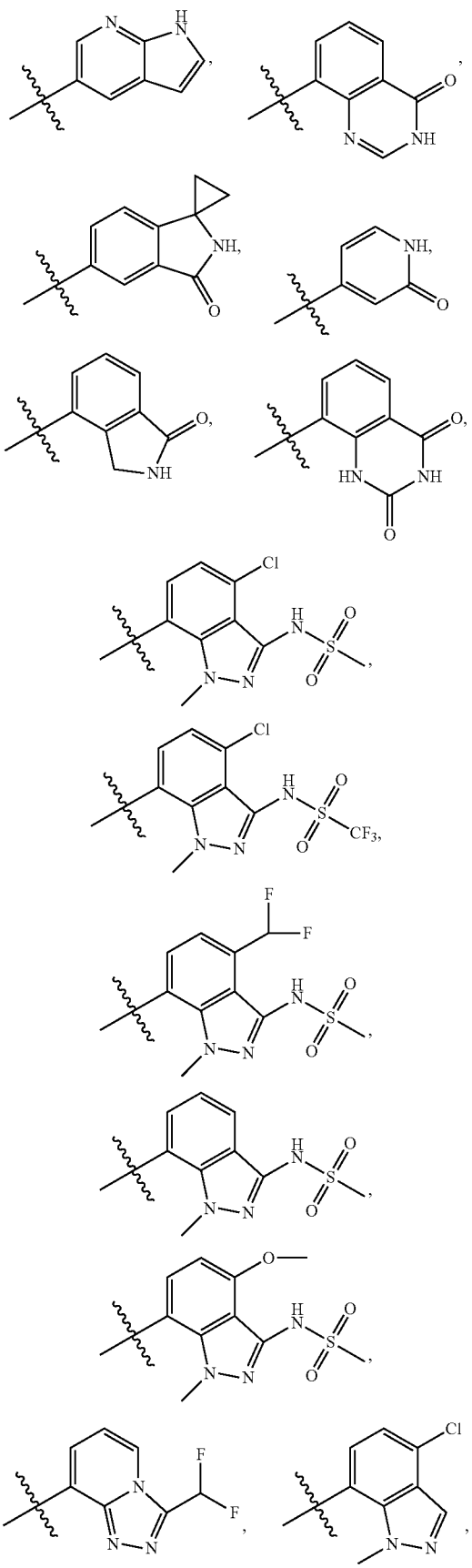

-continued
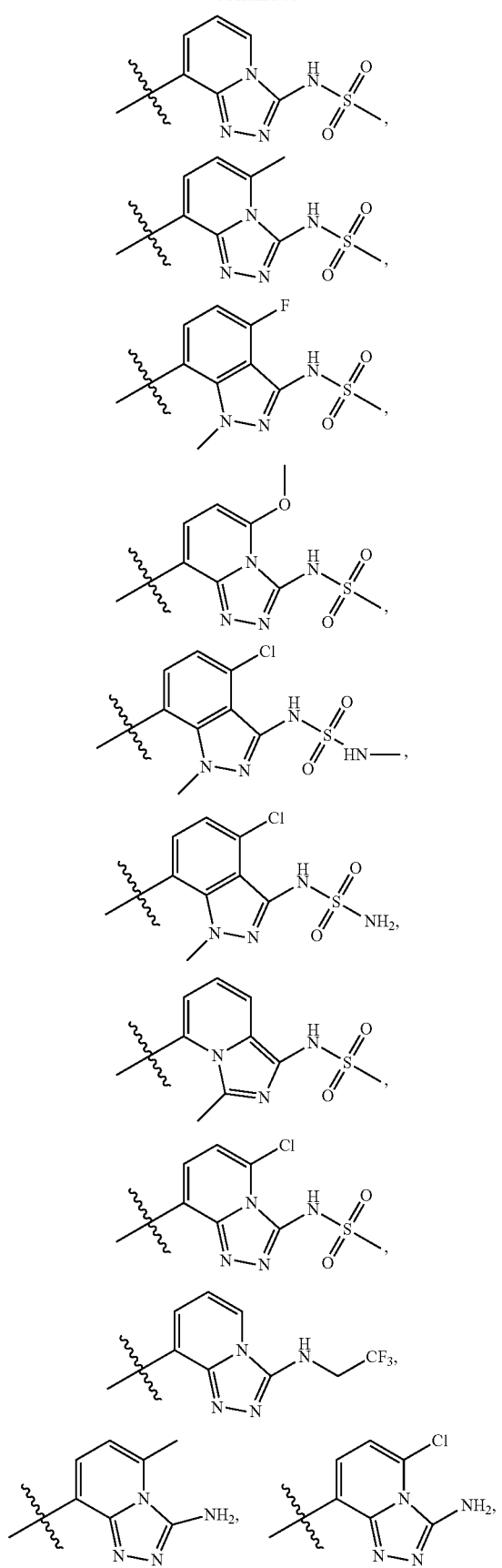
-continued
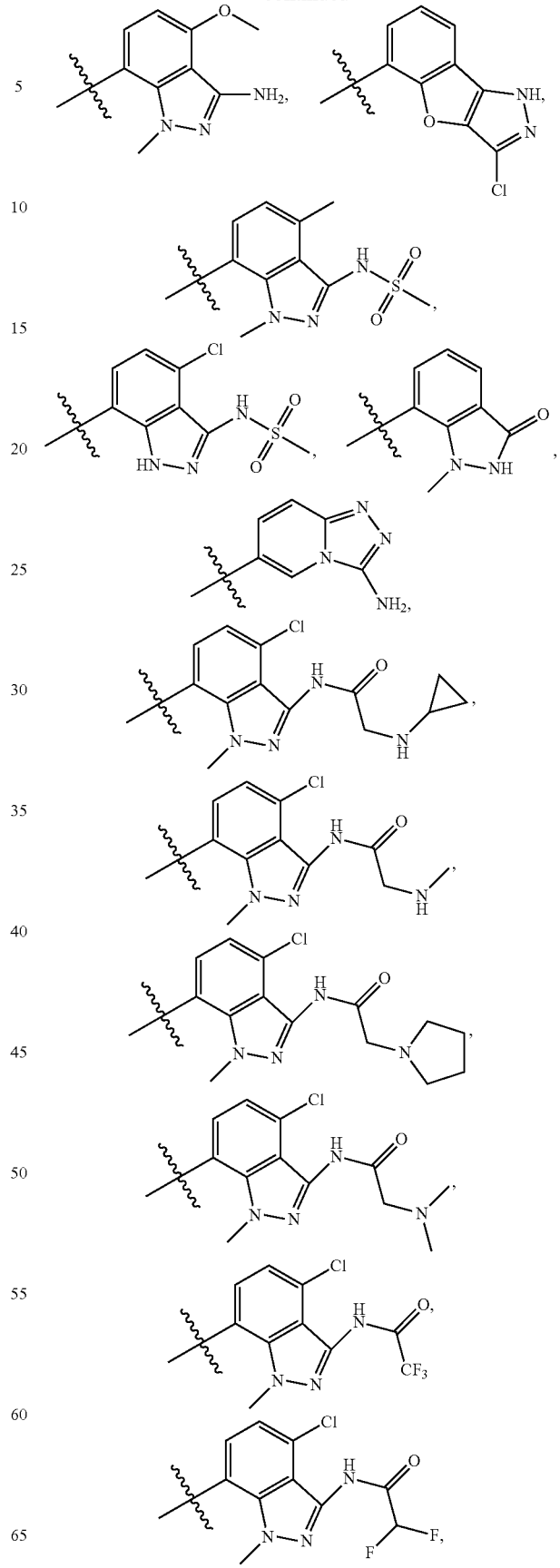

321
-continued
322
-continued
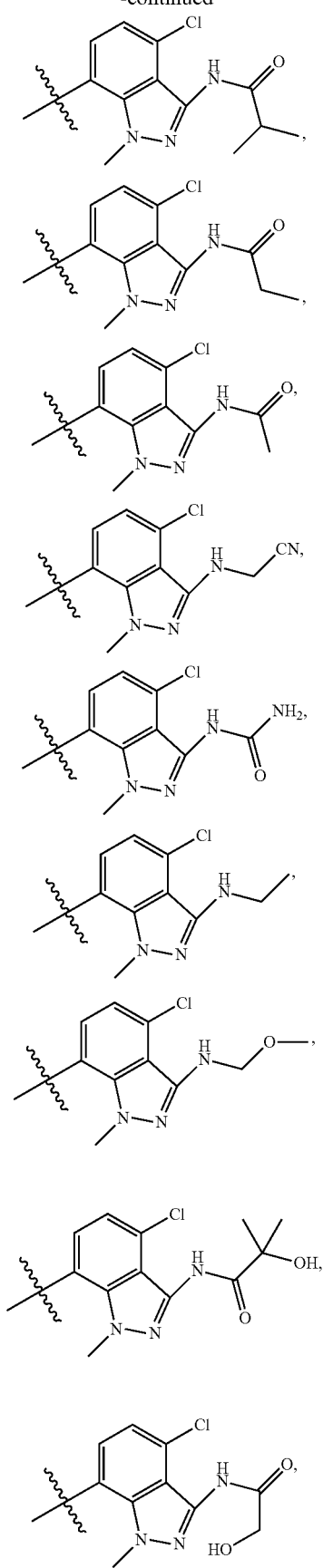
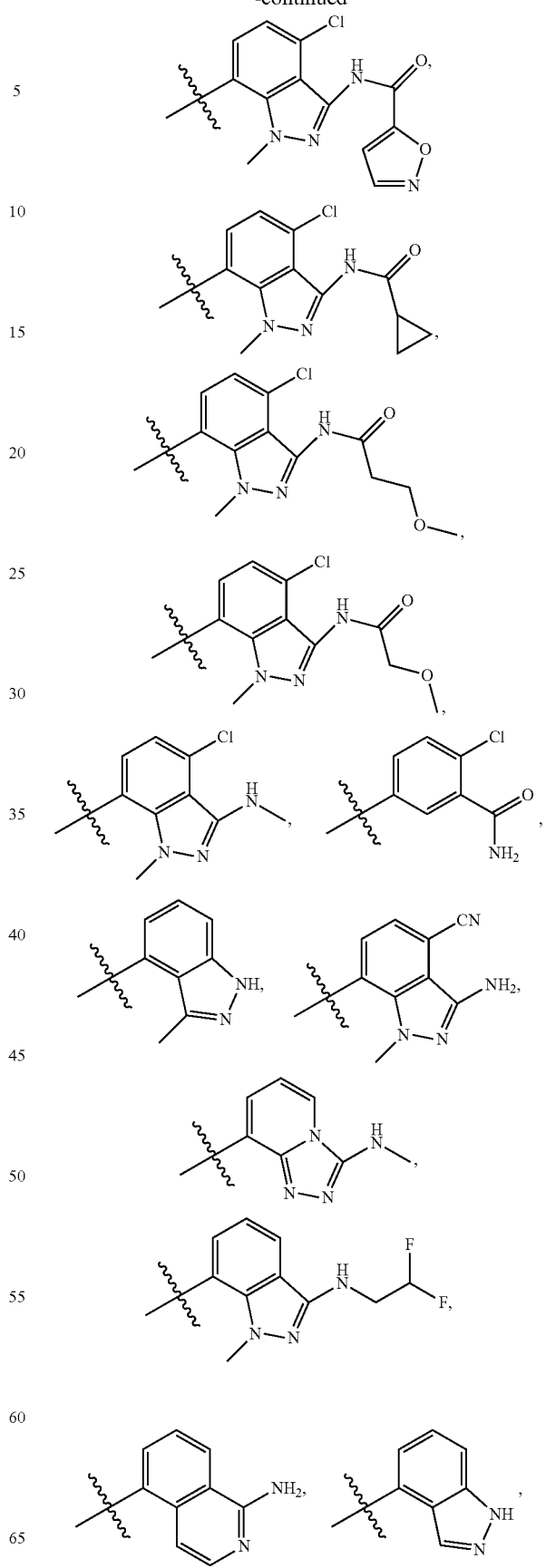

323
-continued
324
-continued
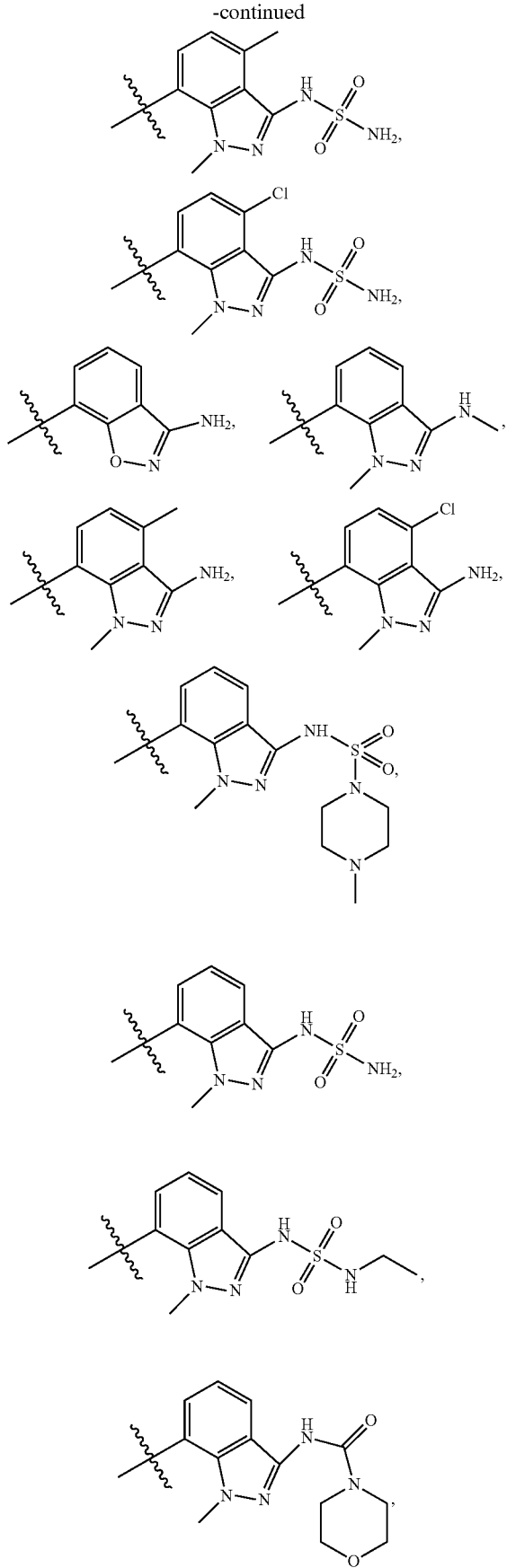
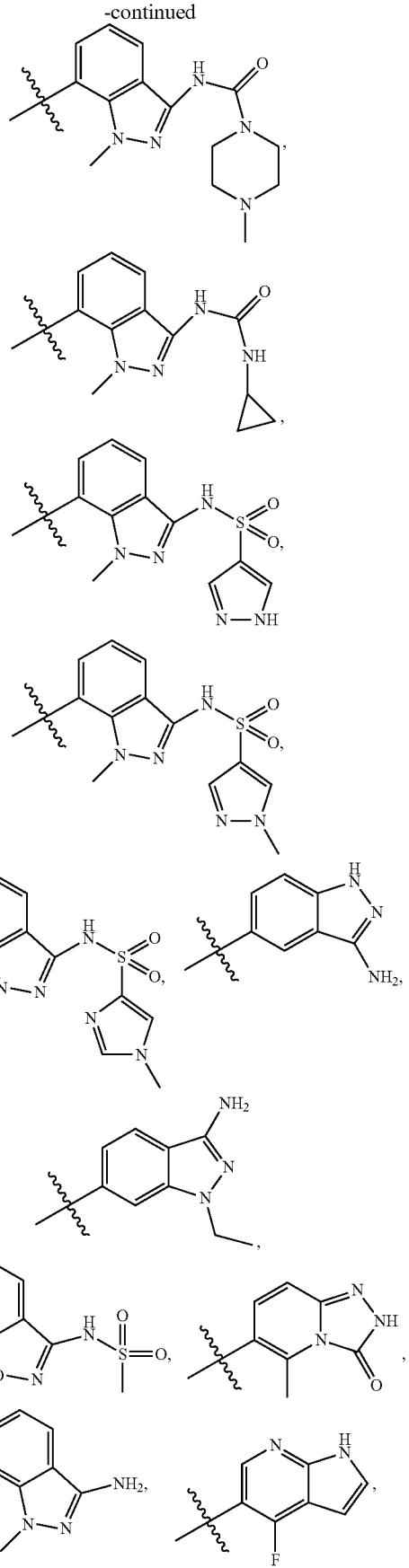

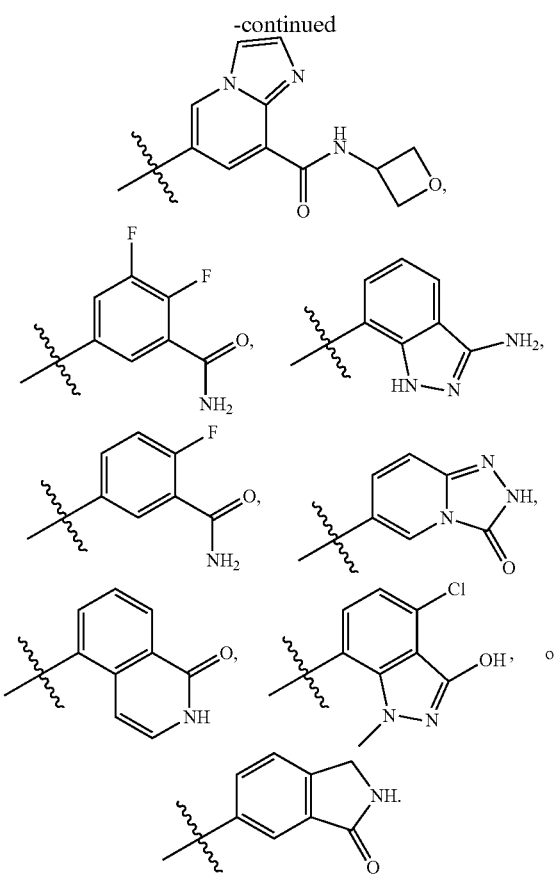
34. The compound of claim 1, or a pharmaceutically acceptable salt thereof, wherein $Z^2$ substituted with 1 or 2 $Z^{2b}$ groups, and optionally 1, 2, or 3 $Z^{2c}$ groups is selected from
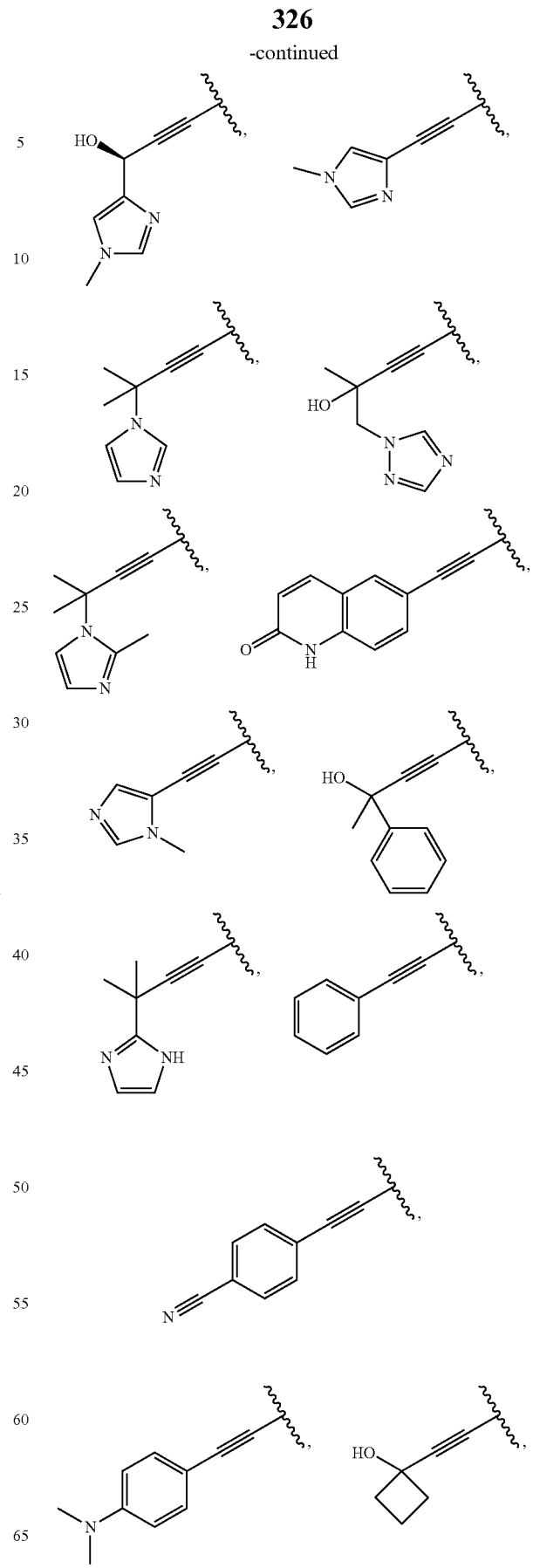

327
-continued
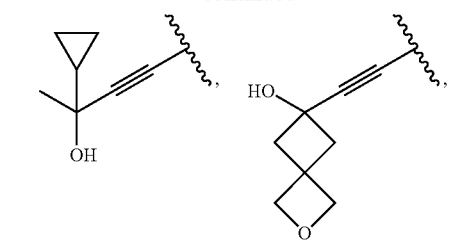
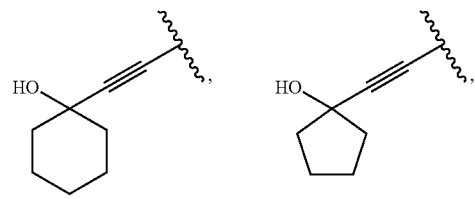
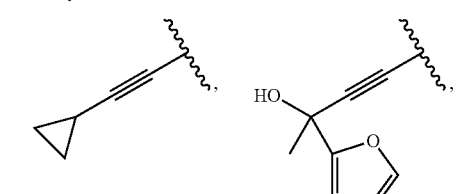
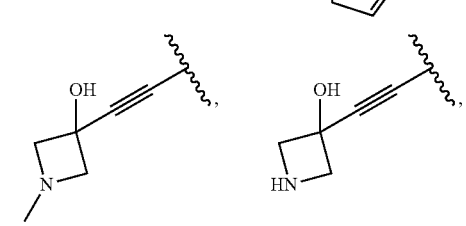
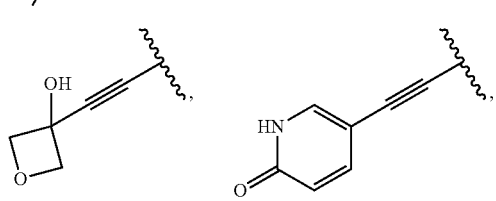
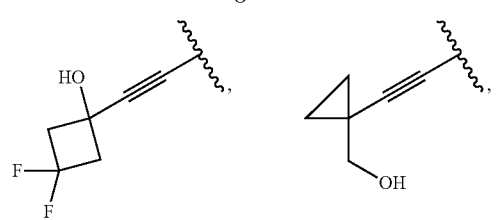
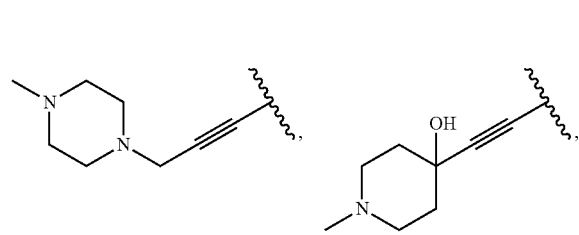
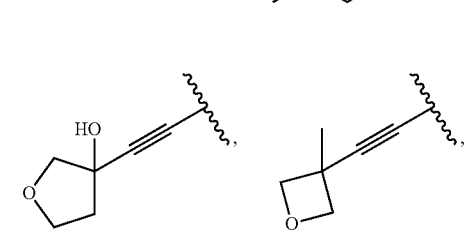
328
-continued
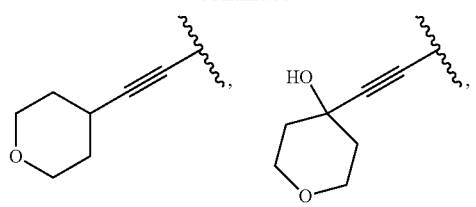
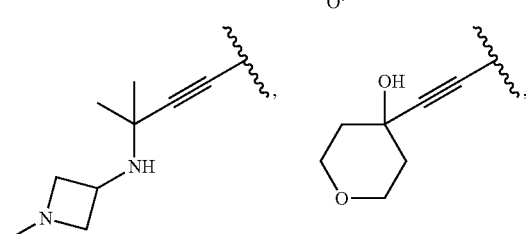
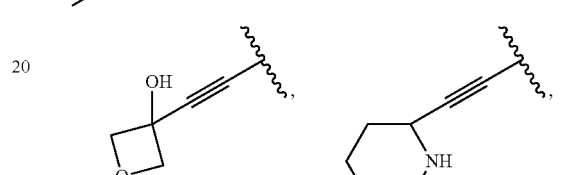
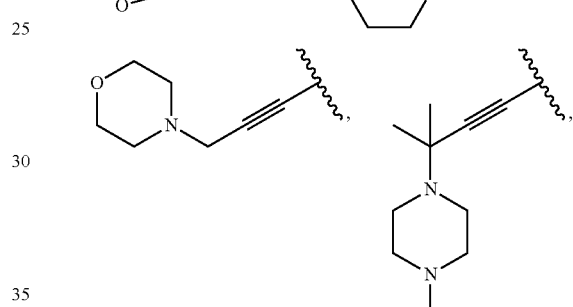
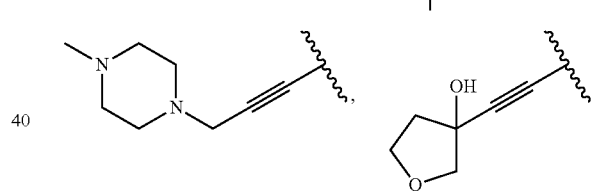
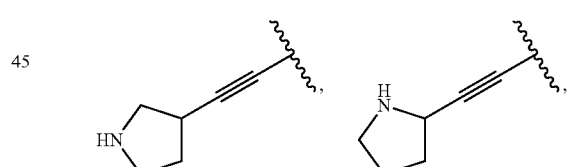
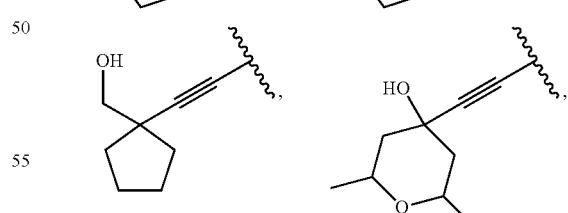
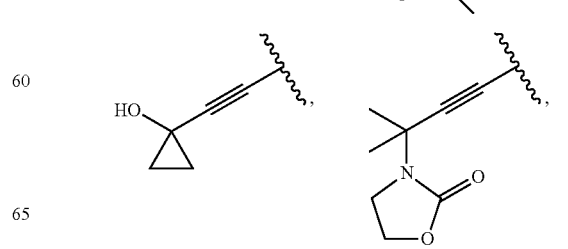

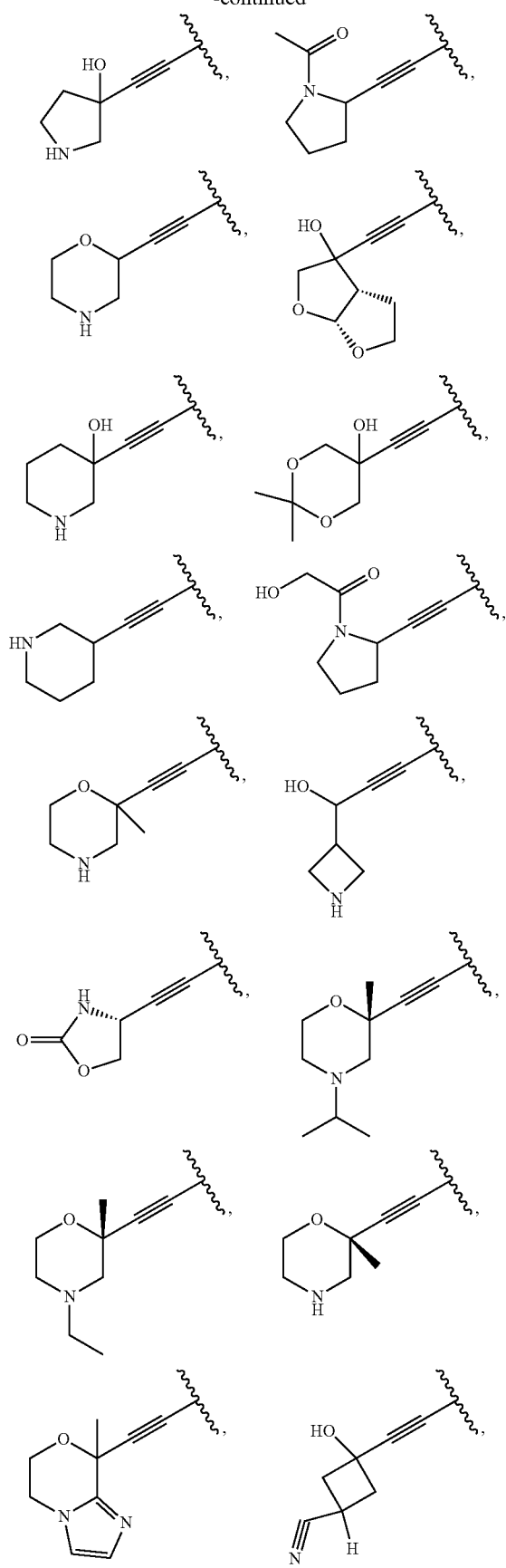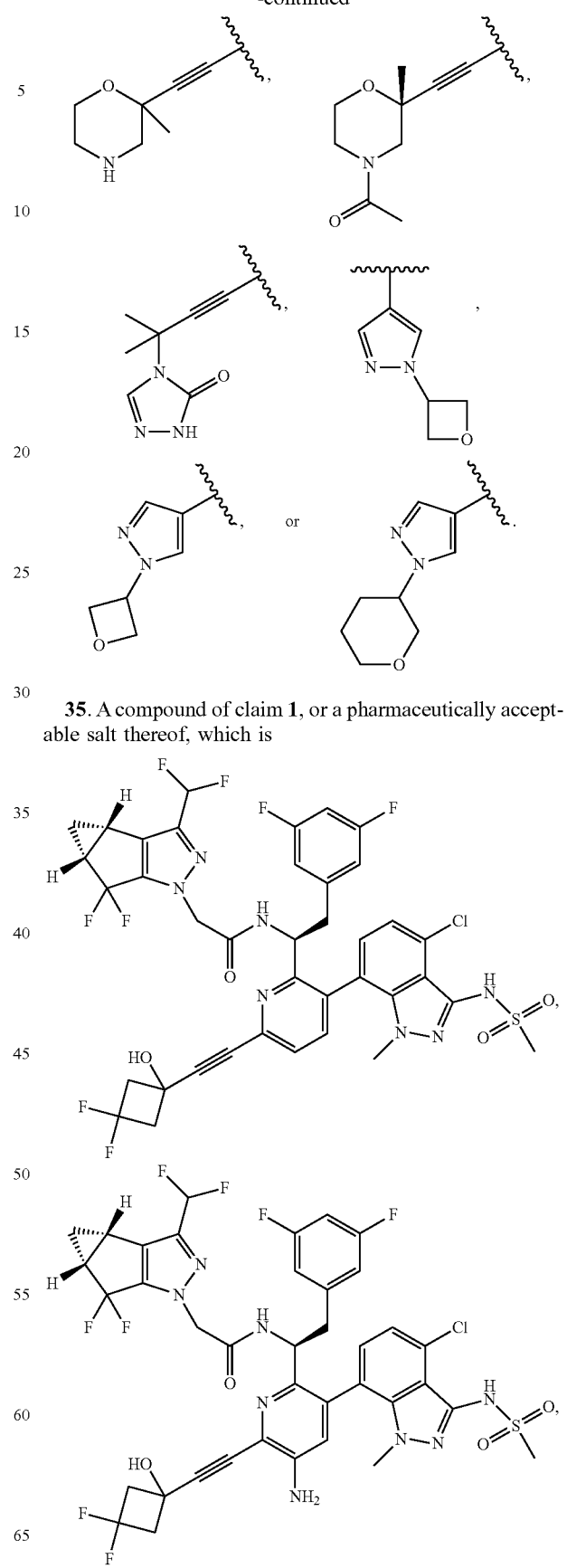
35. A compound of claim 1, or a pharmaceutically acceptable salt thereof, which is
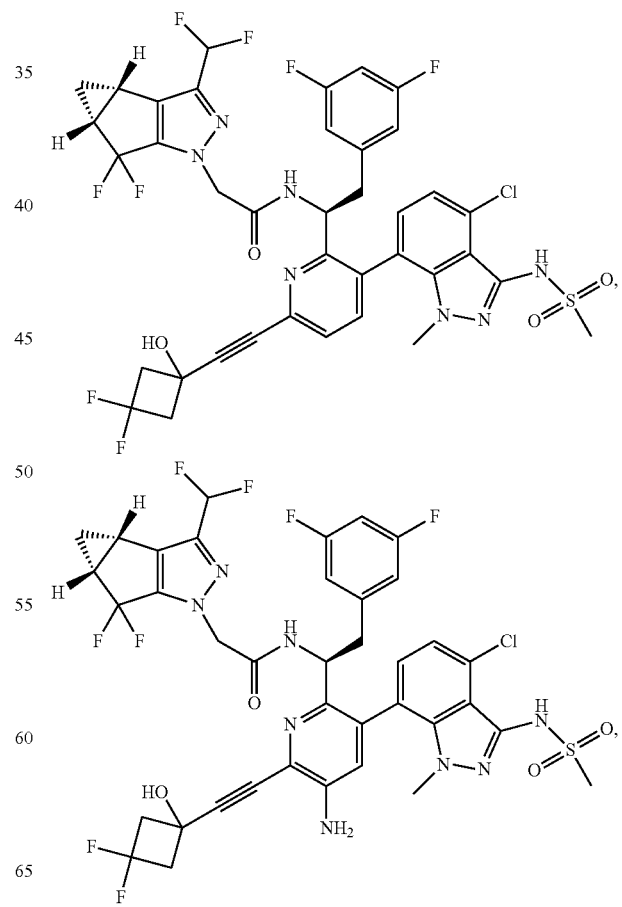

331
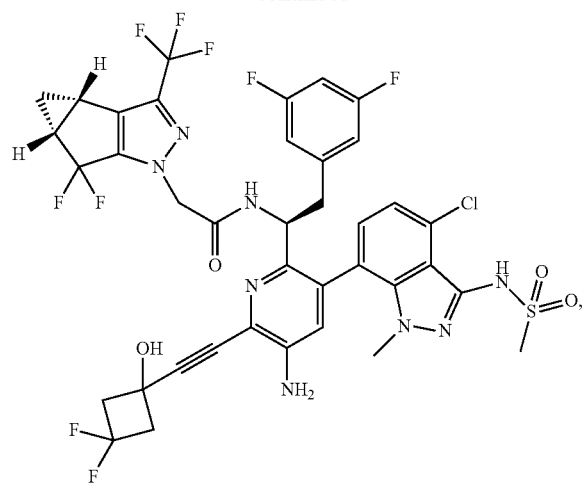
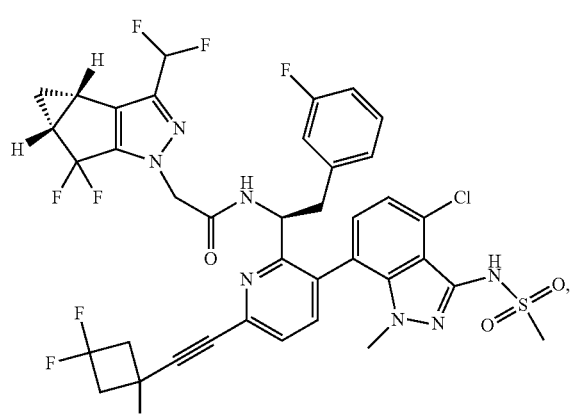
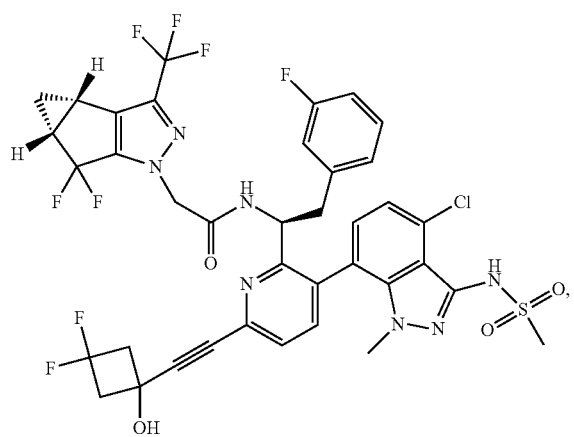
332
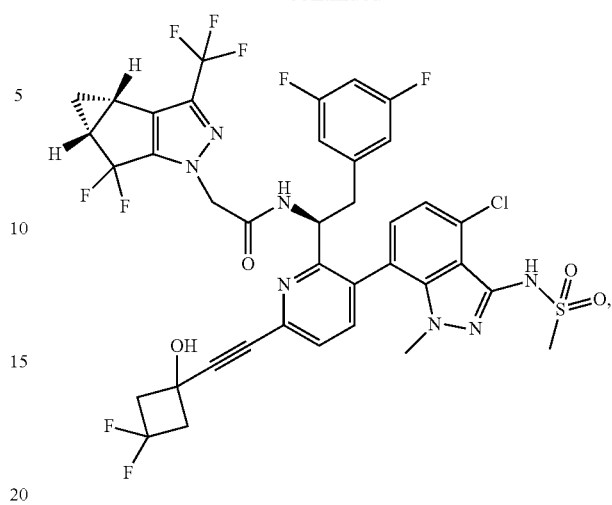
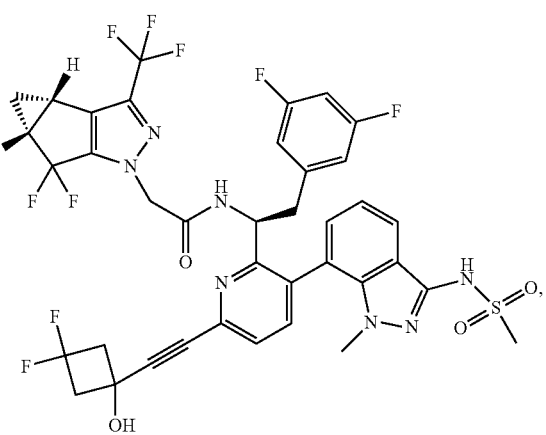

333
-continued
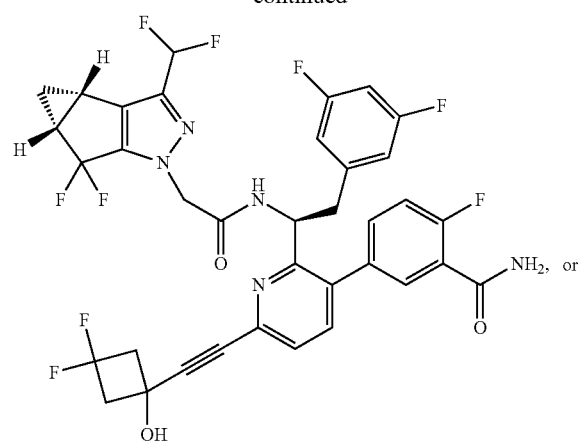
334
-continued
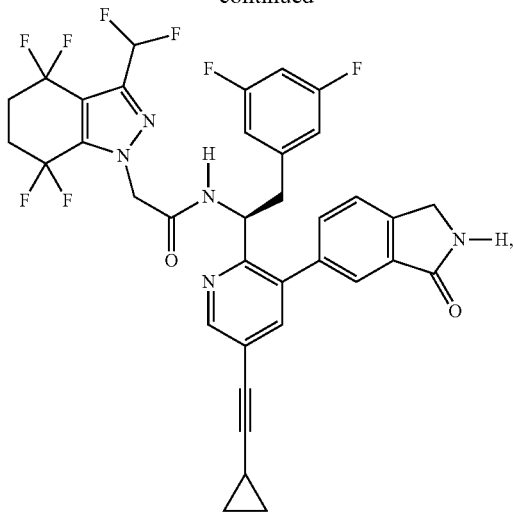
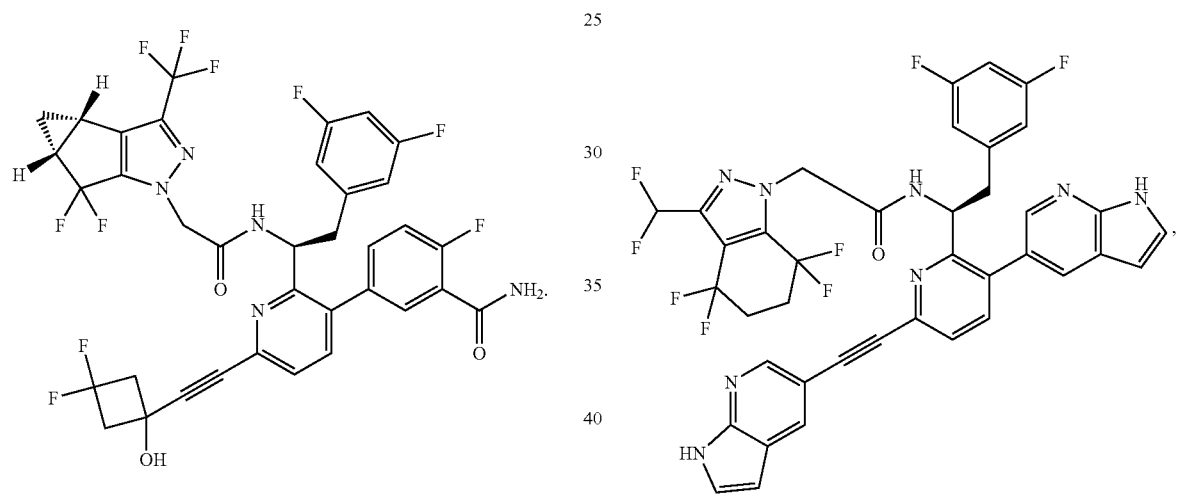
36. A compound of claim 1, or a pharmaceutically acceptable salt thereof, which is
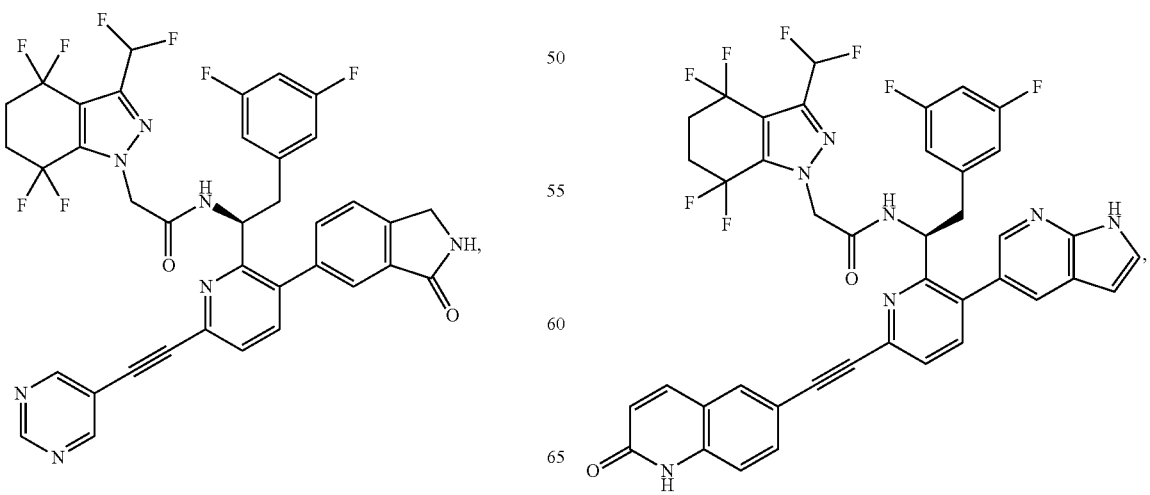

335
-continued
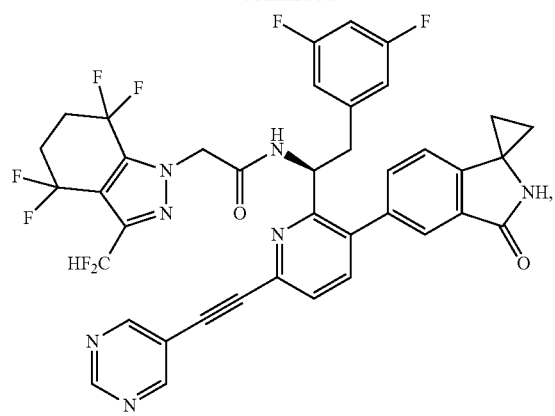
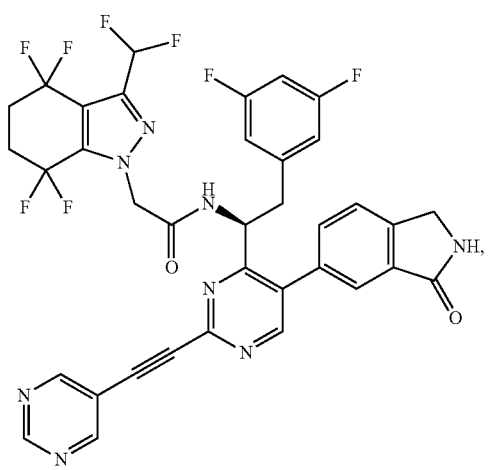
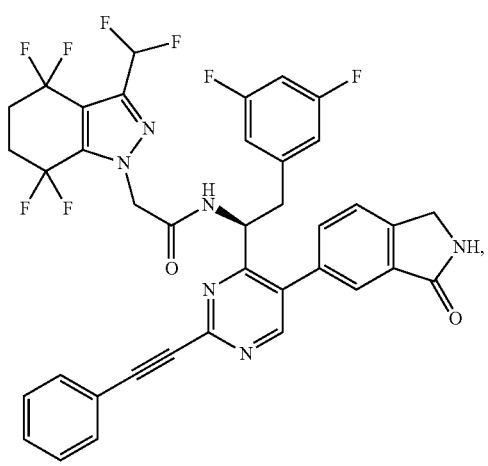
336
-continued
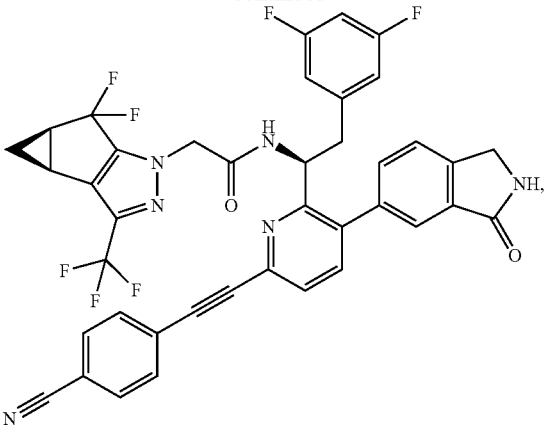
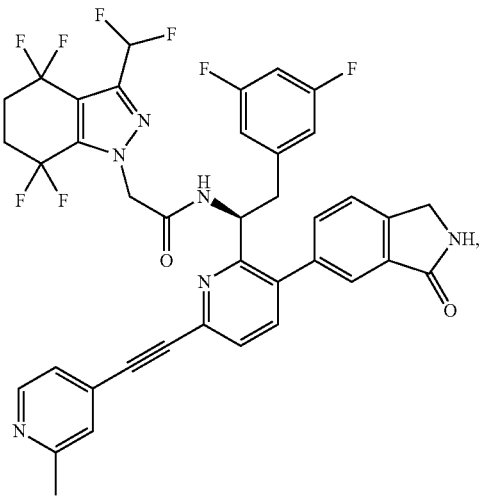
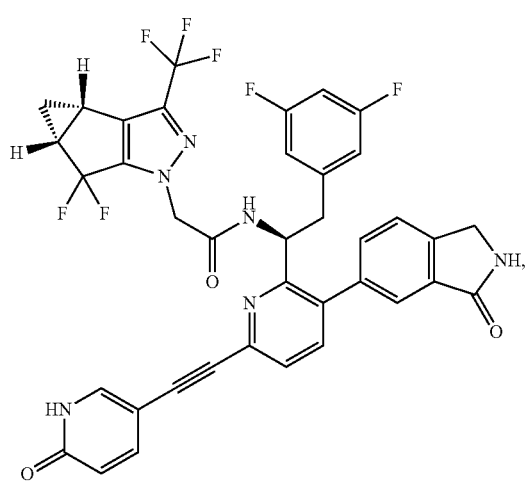

337
-continued
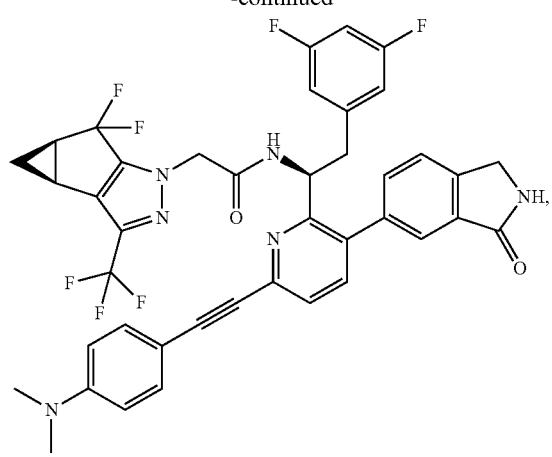
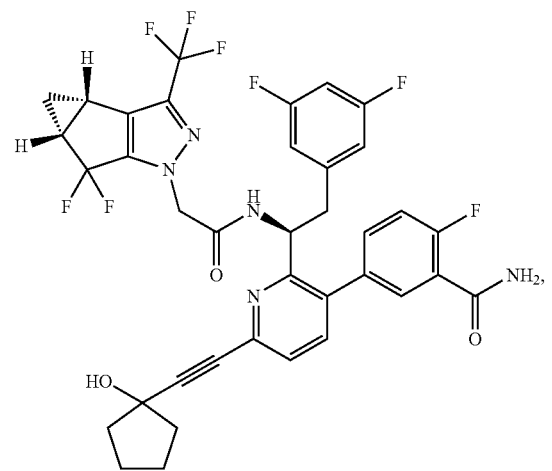
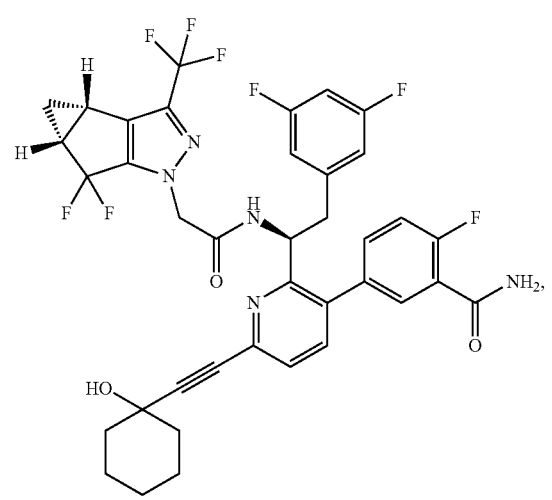
338
-continued
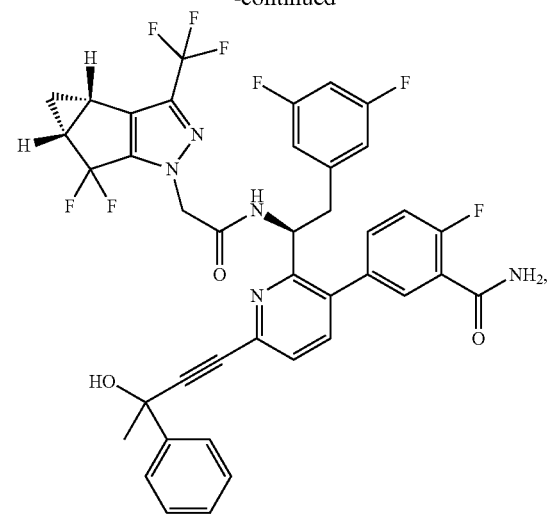
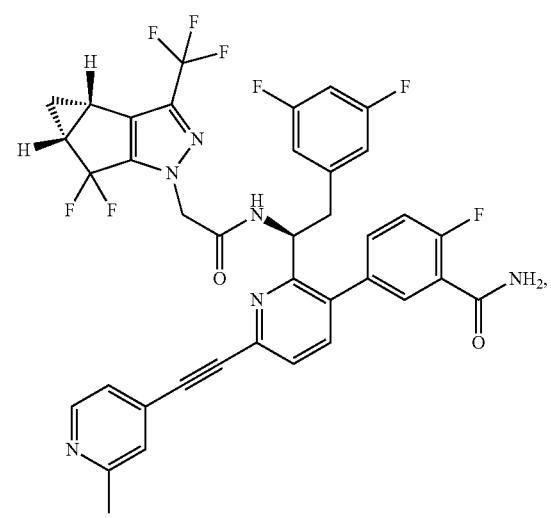

339
-continued
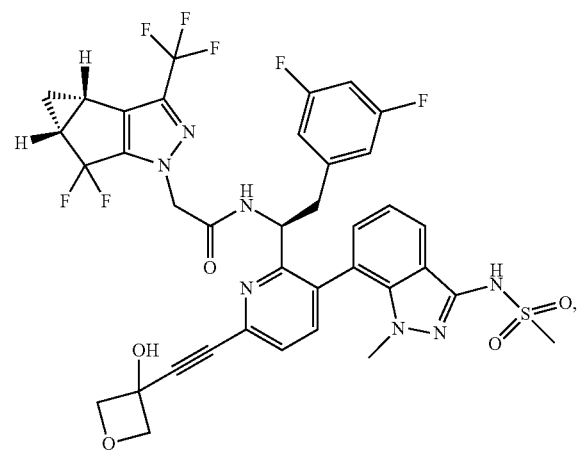
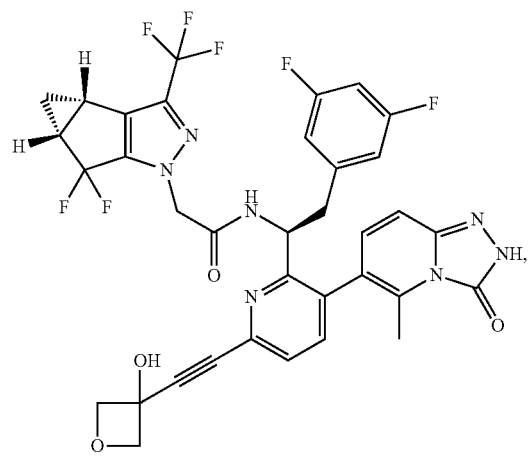
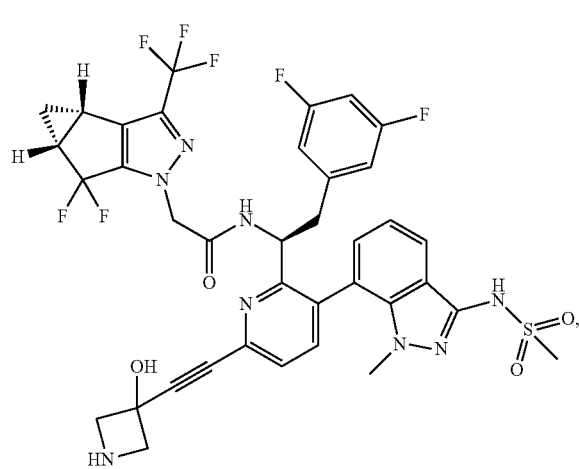
340
-continued
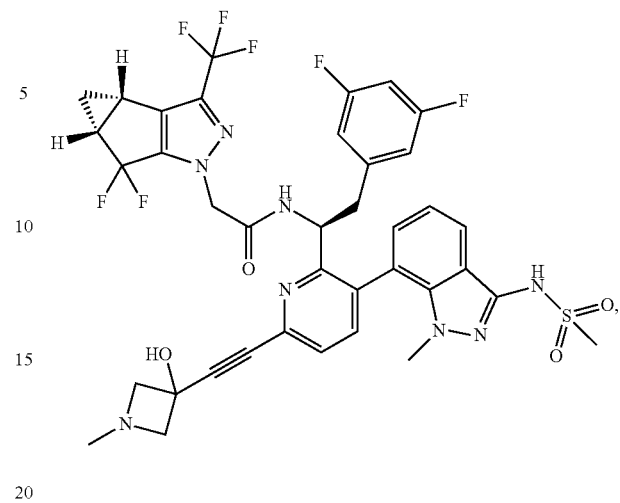
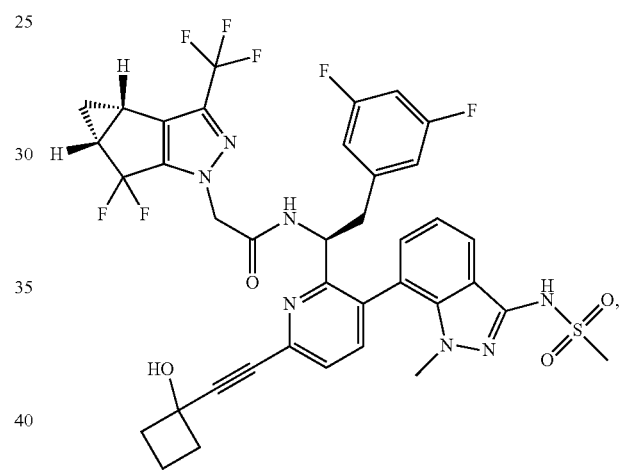
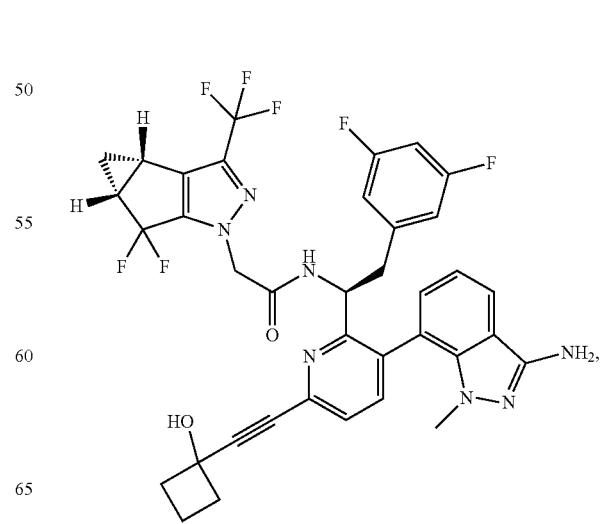

341
-continued
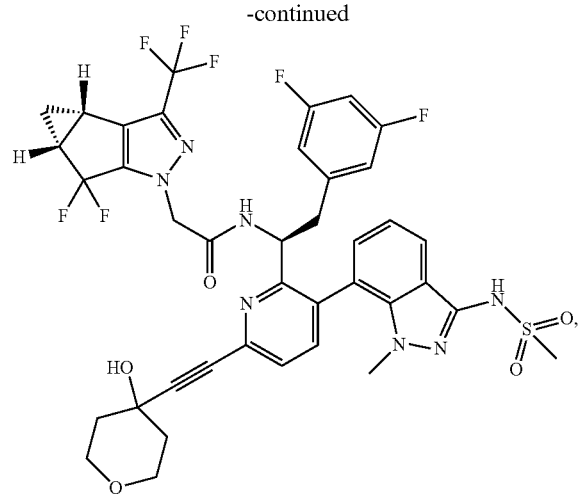
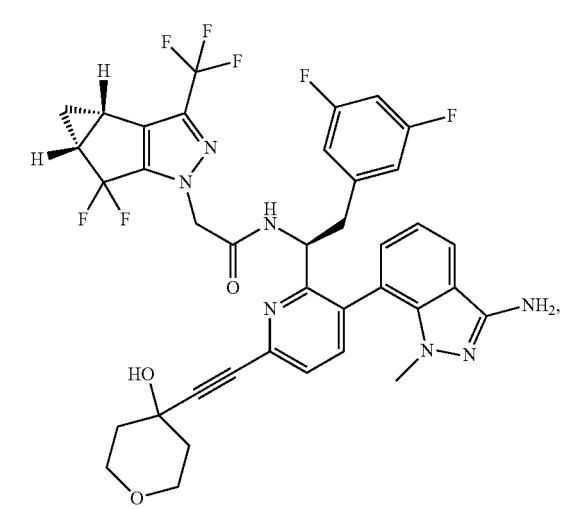
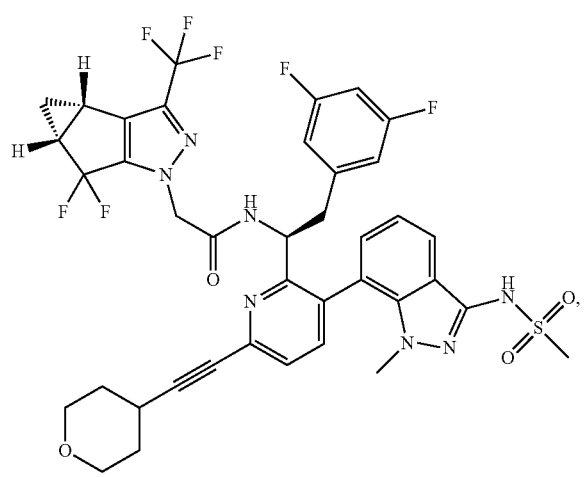
342
-continued
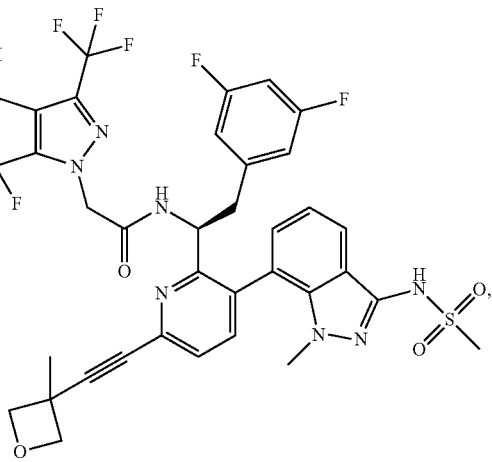
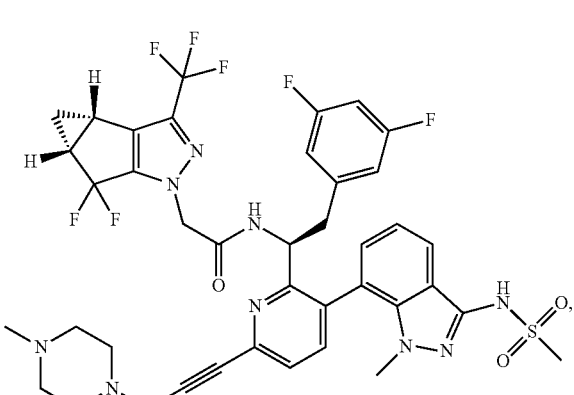

343
-continued
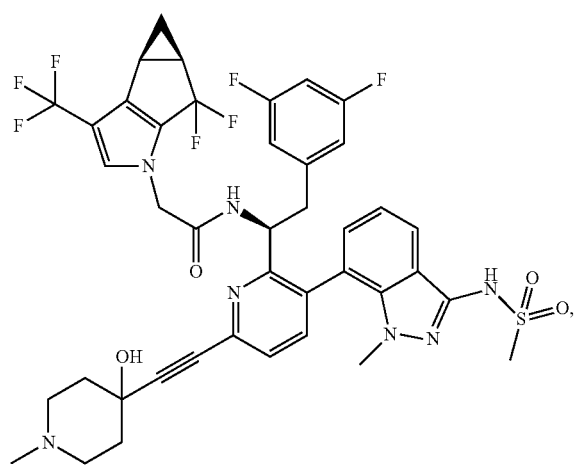
344
-continued
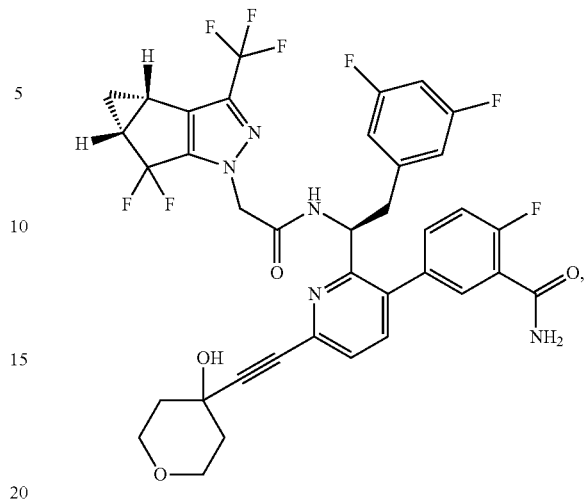
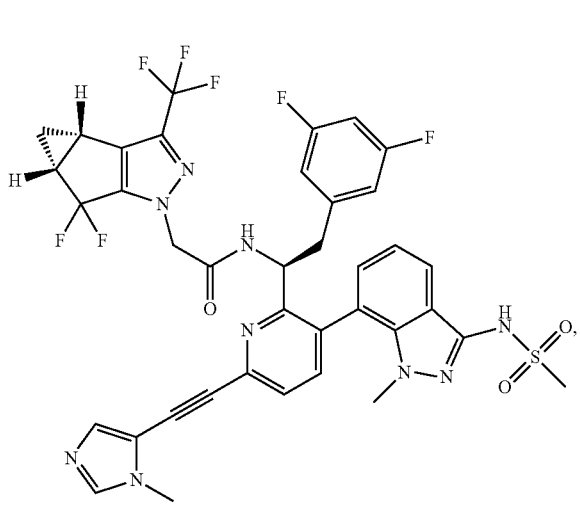
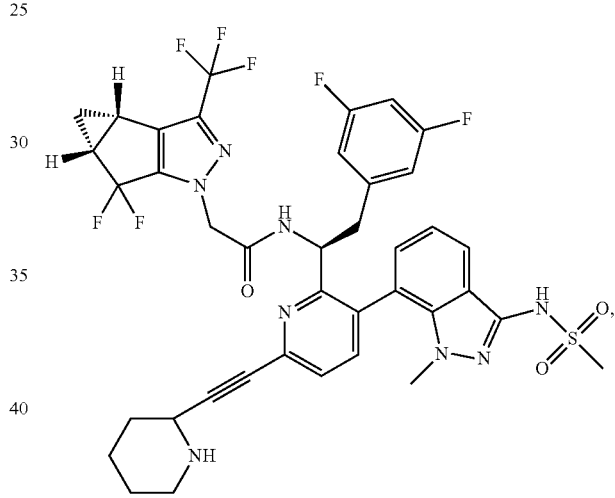
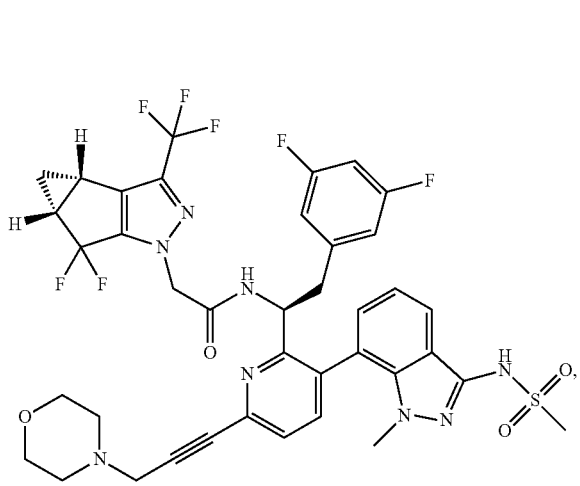
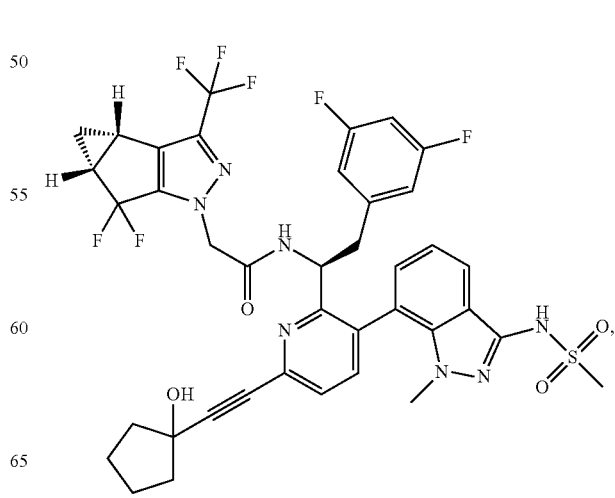

345
-continued
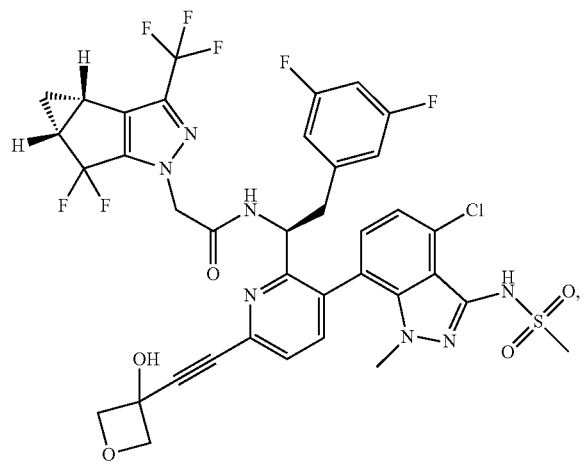
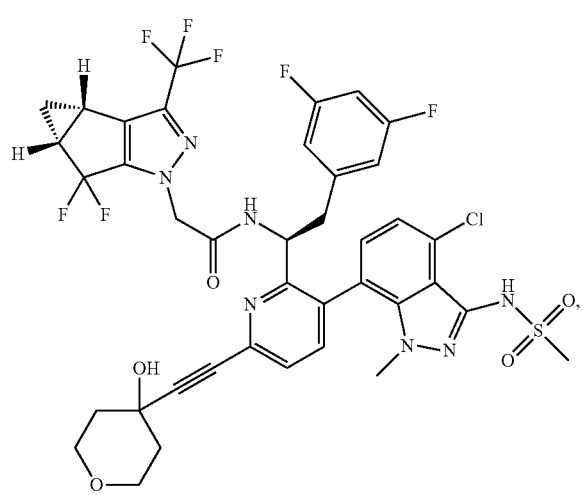
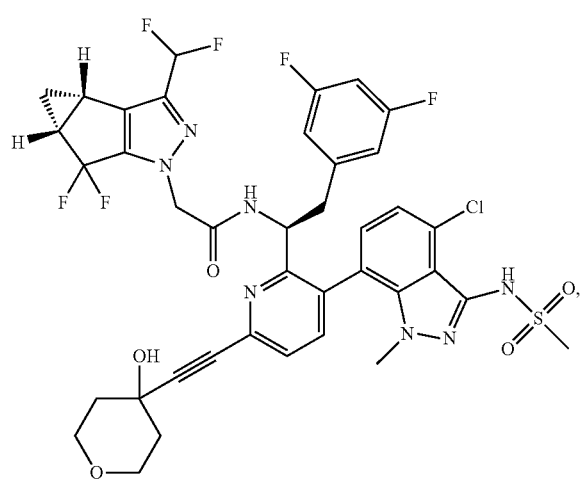
346
-continued
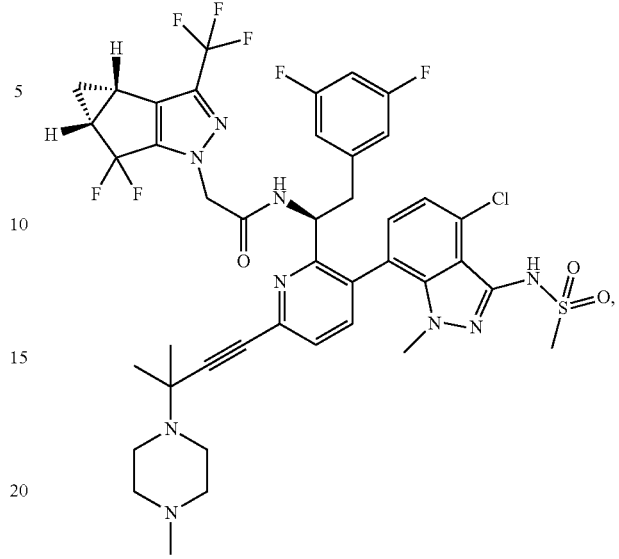
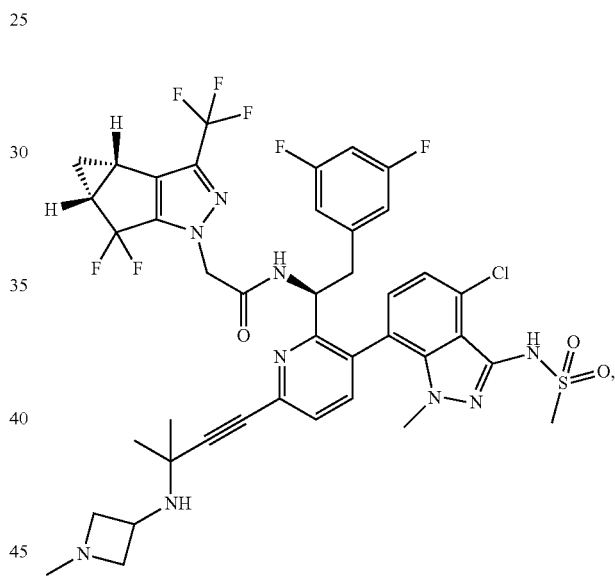
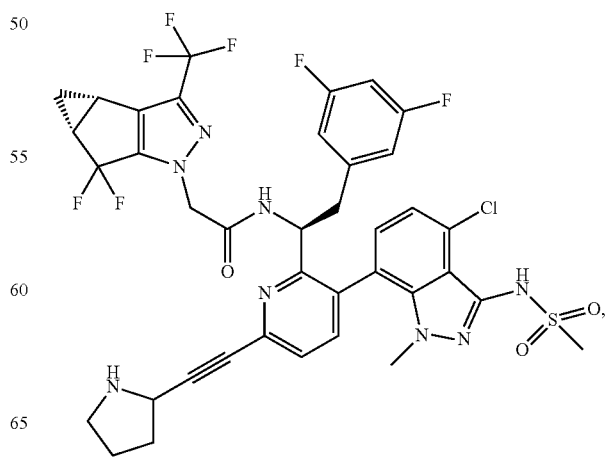

347
-continued
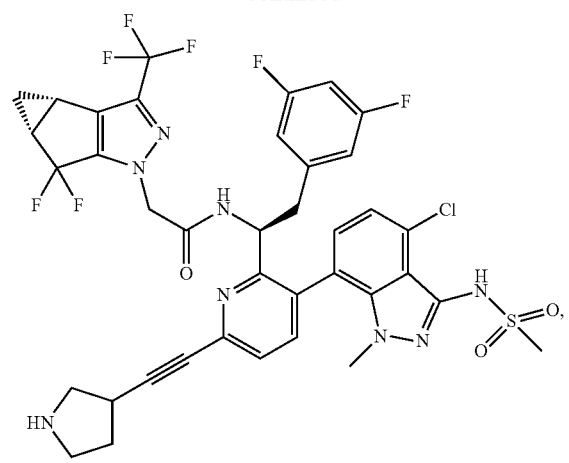
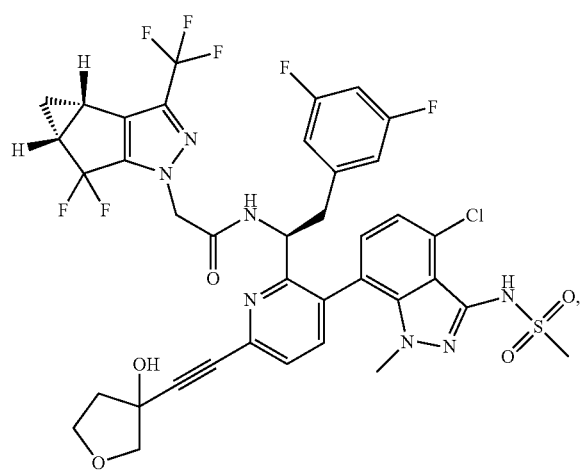
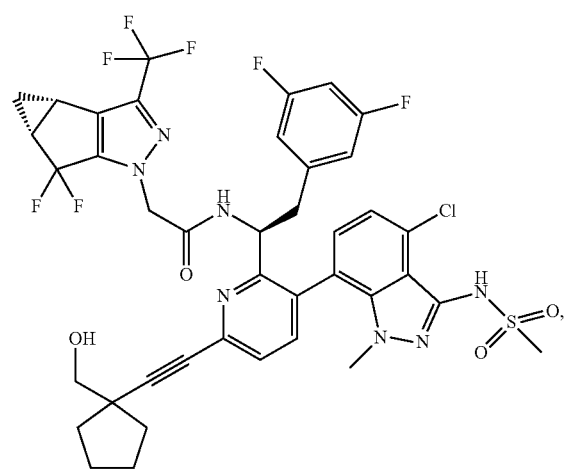
348
-continued
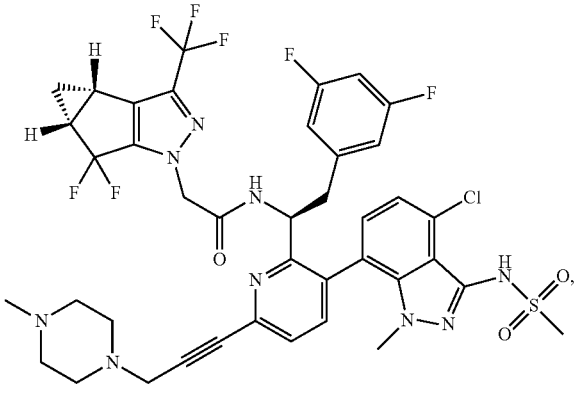
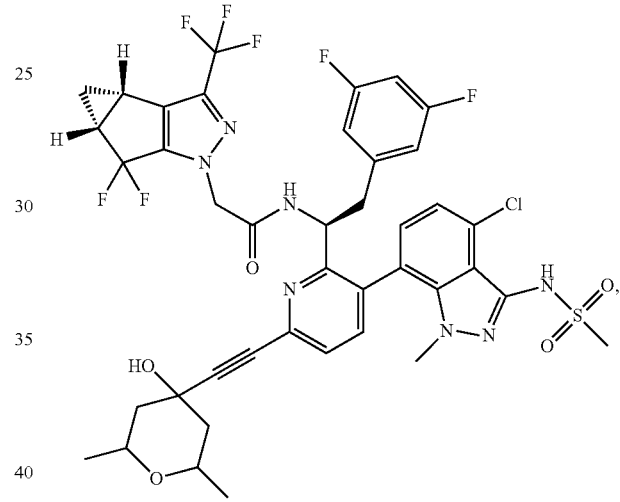
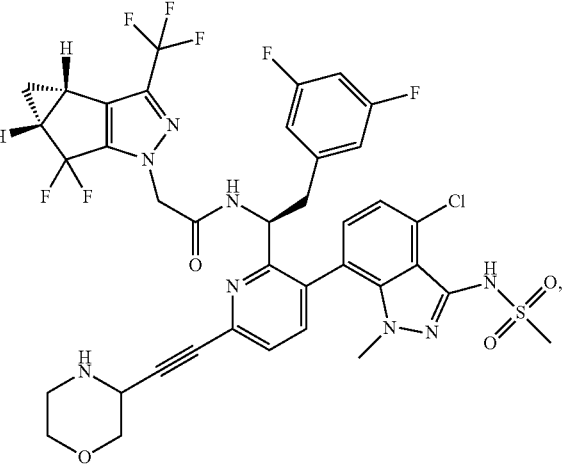

349
-continued
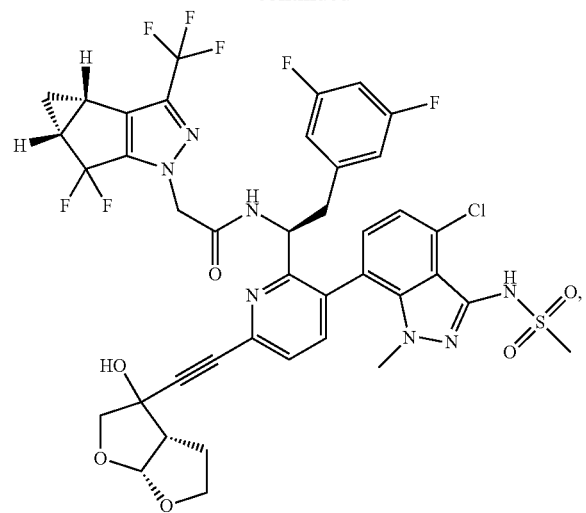
350
-continued
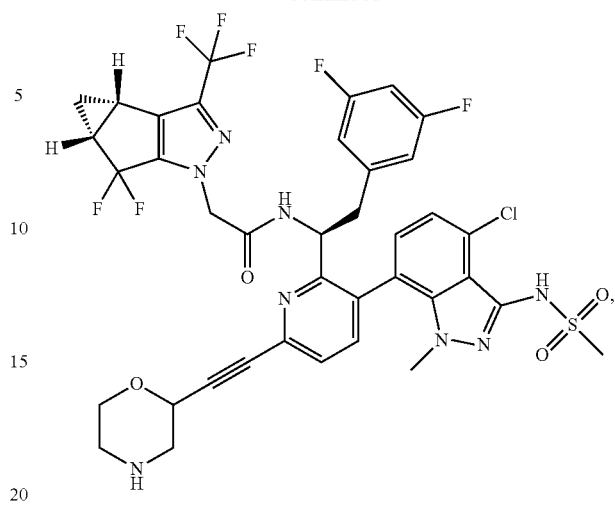
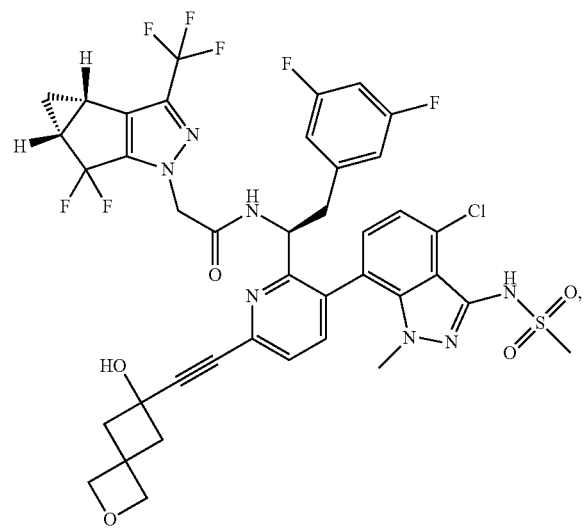
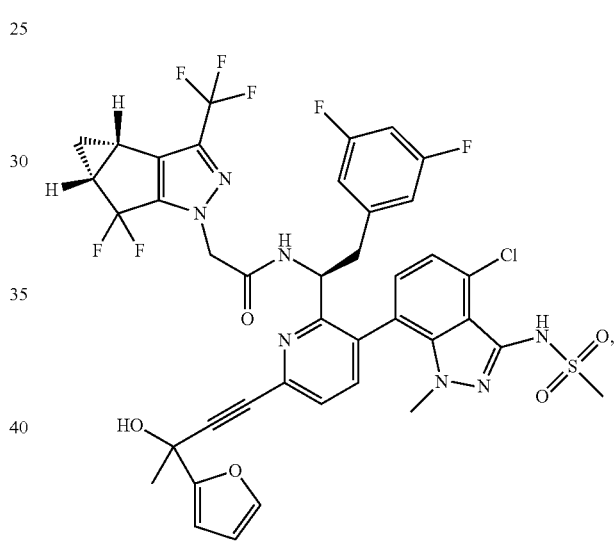
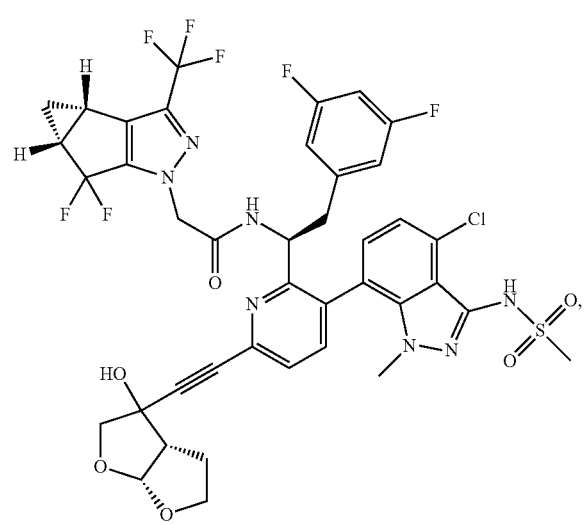
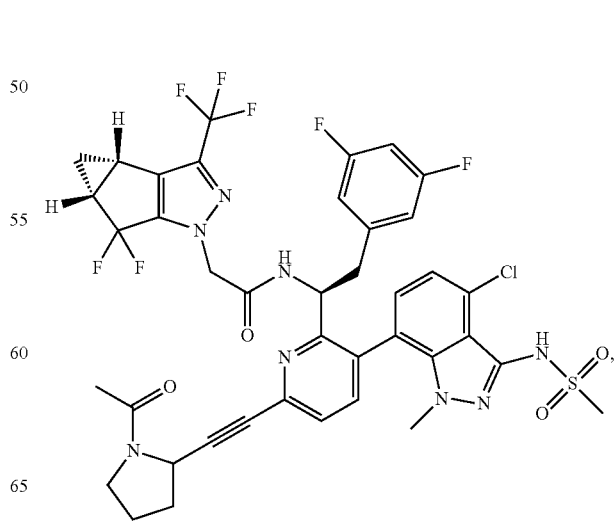

351
-continued
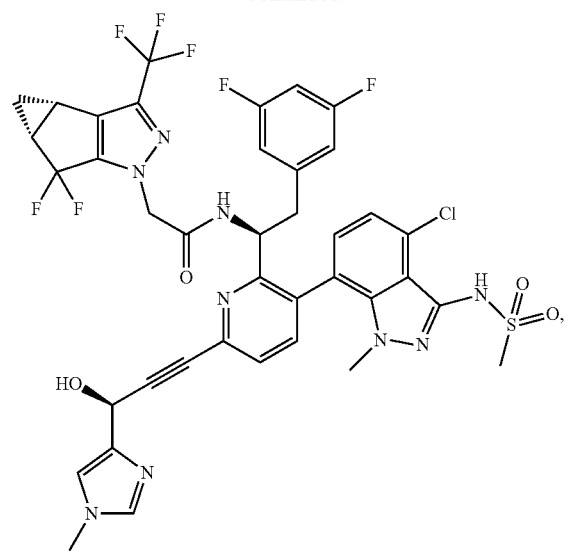
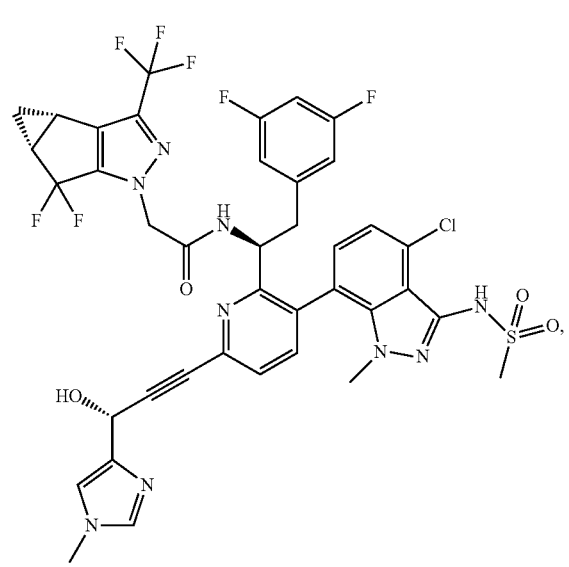
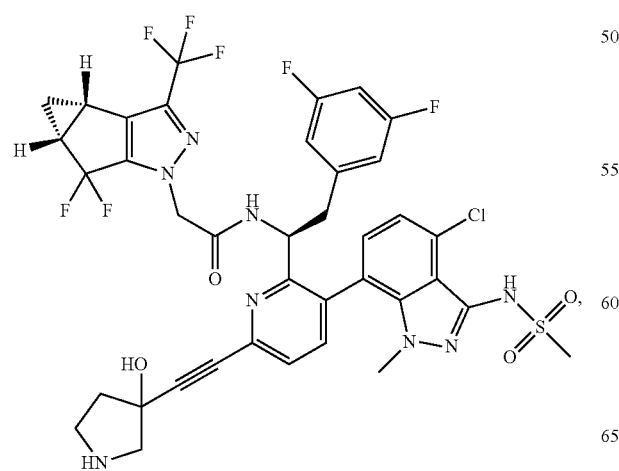
352
-continued
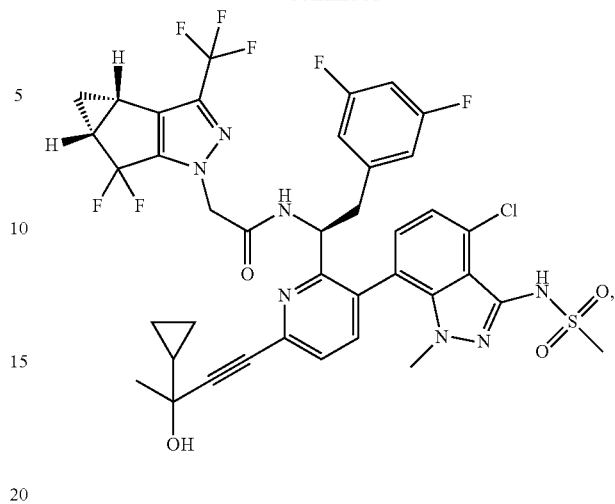
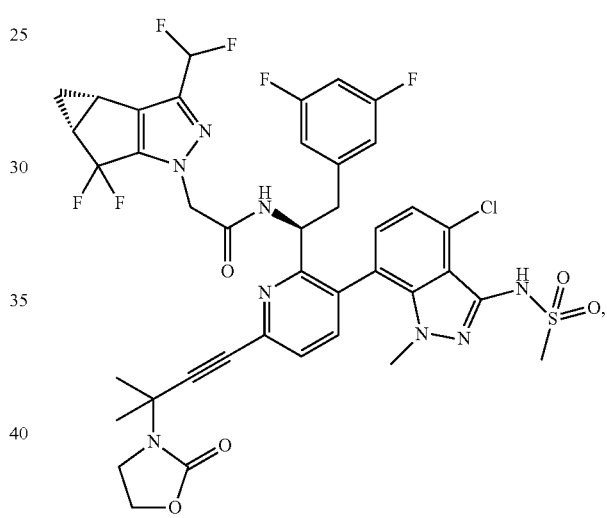
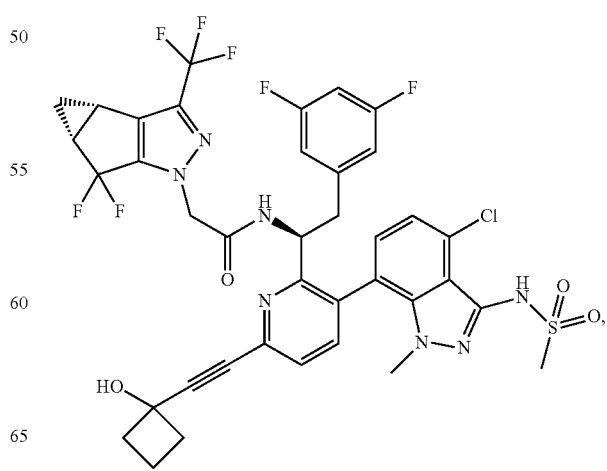

353
-continued
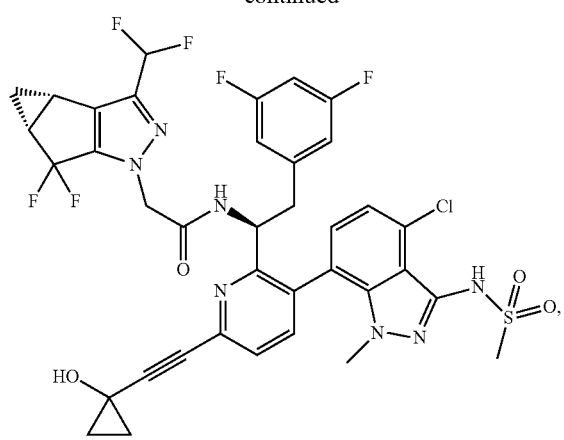
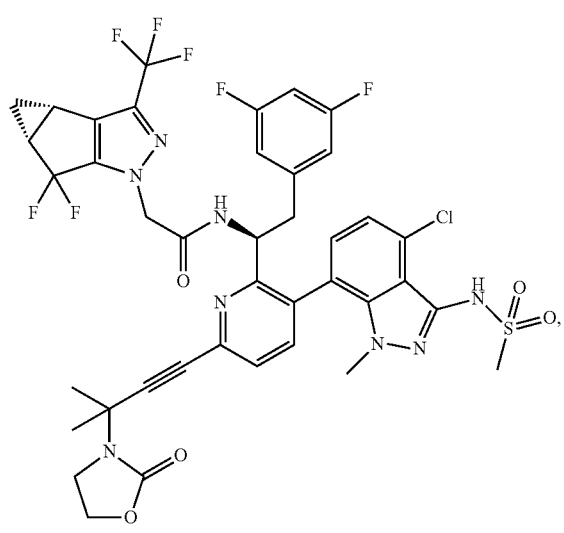
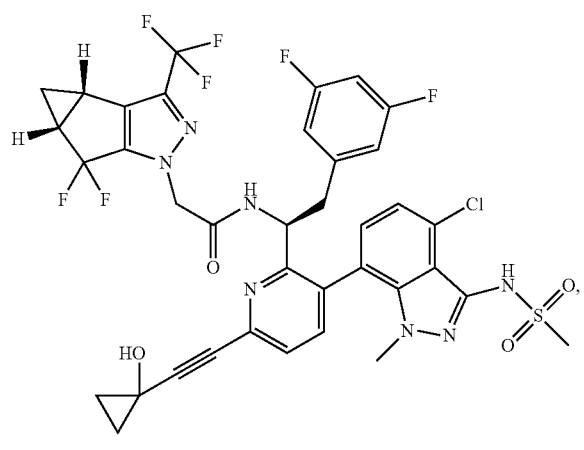
354
-continued
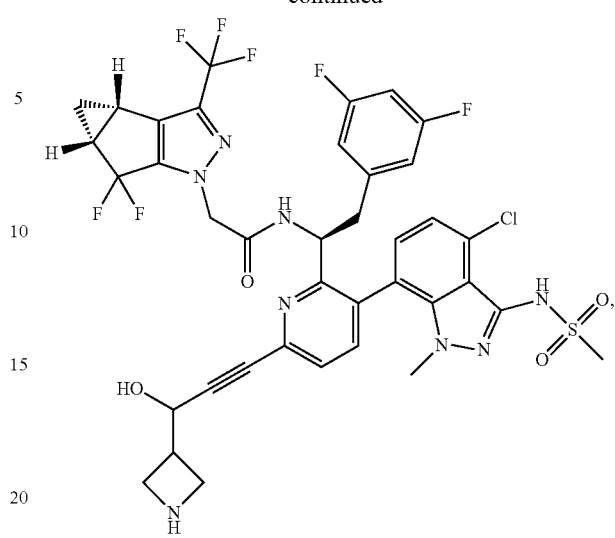
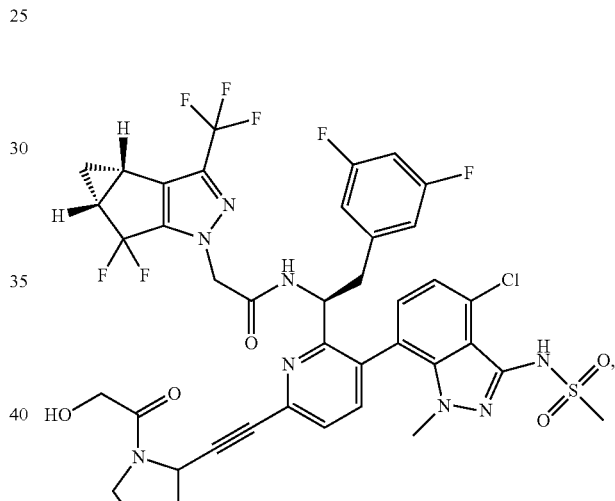
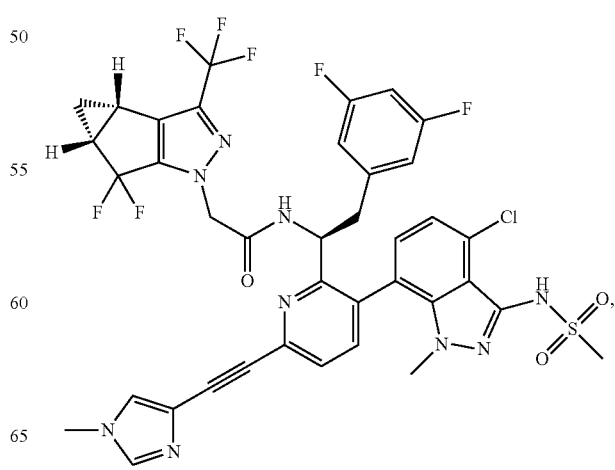

355
-continued
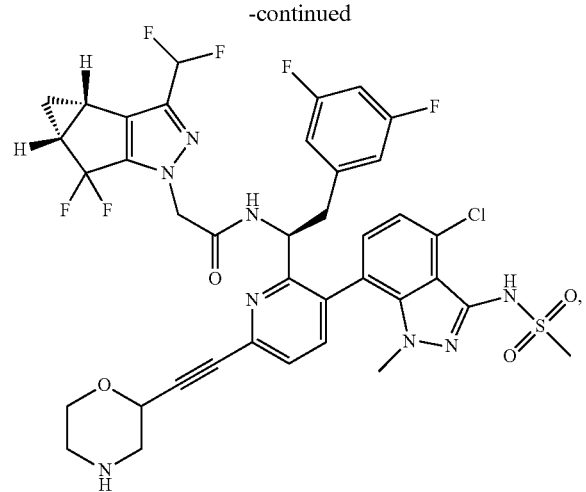
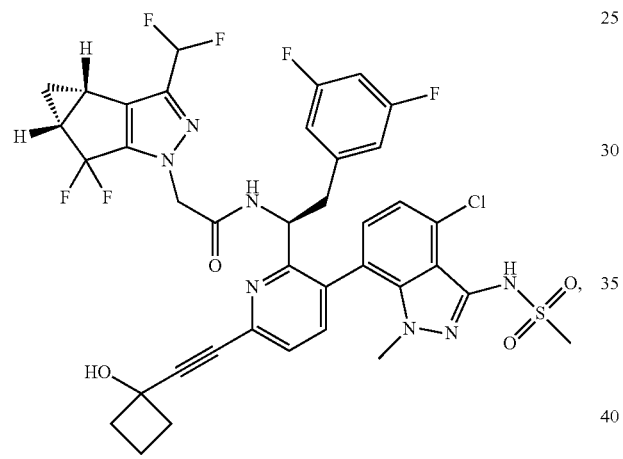
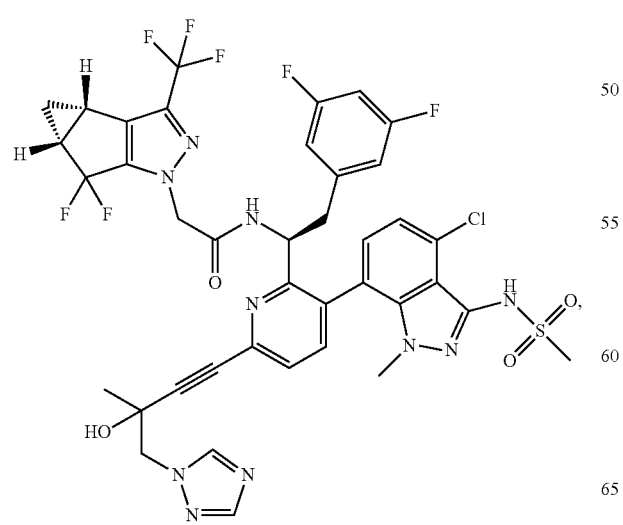
356
-continued
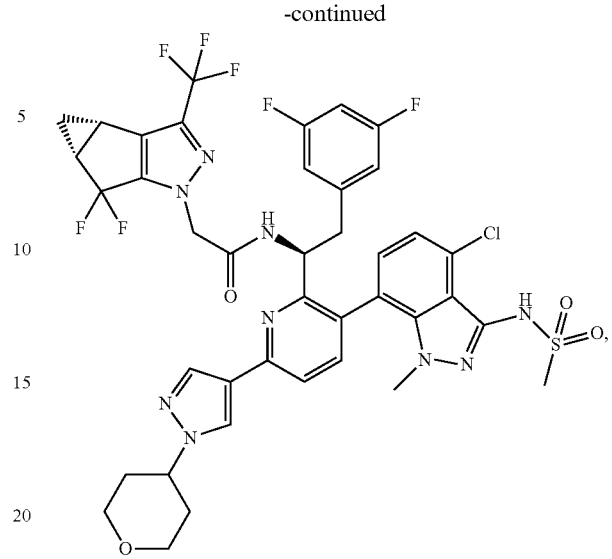
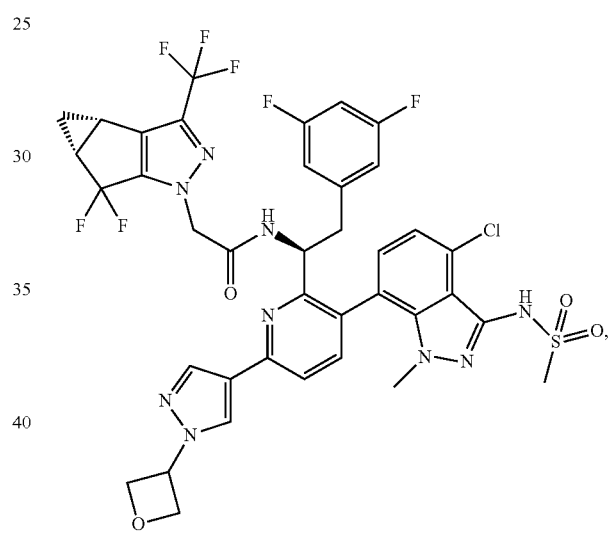
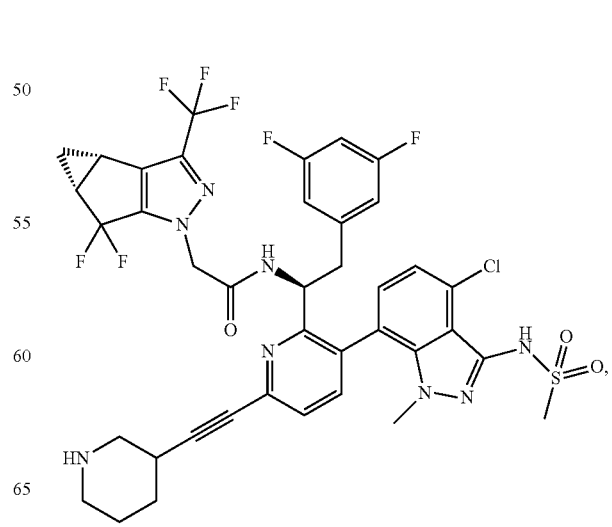

357
-continued
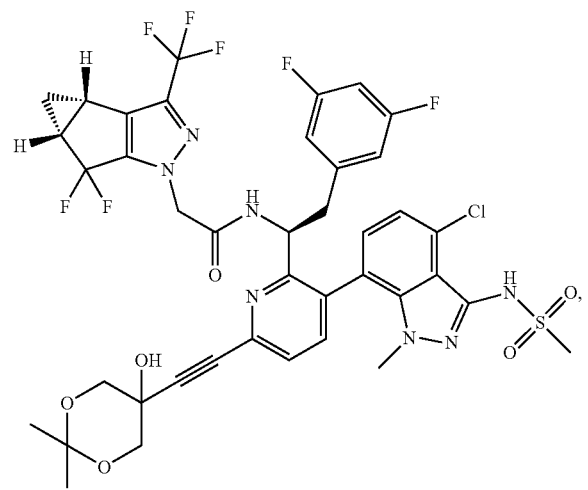
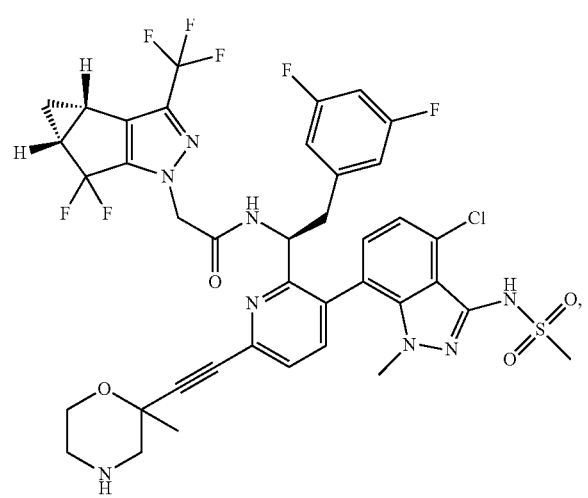
358
-continued
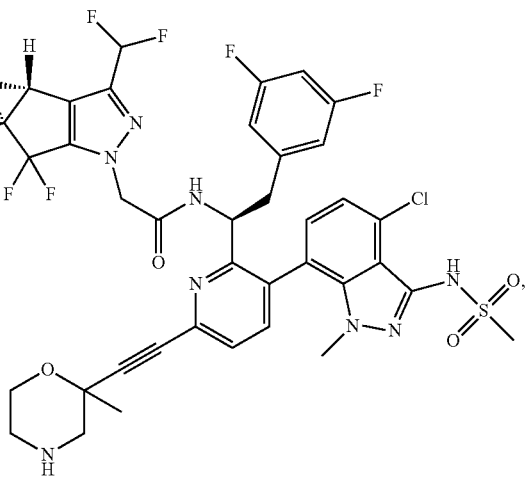
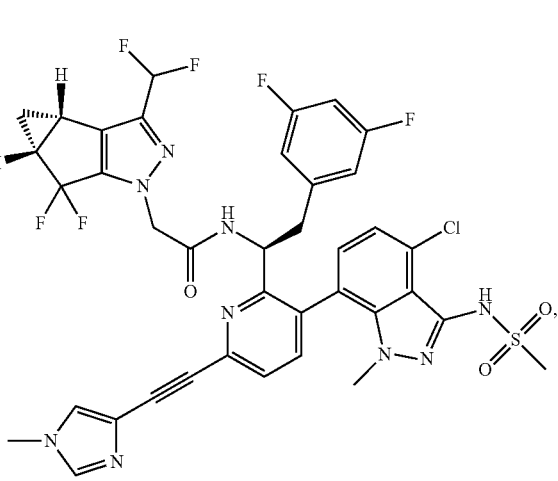

359
-continued
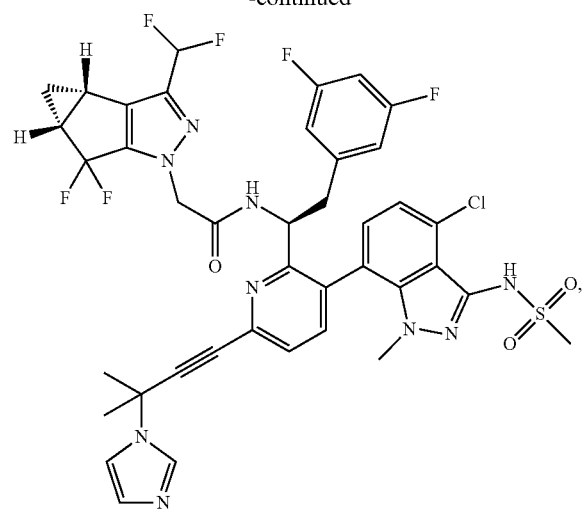
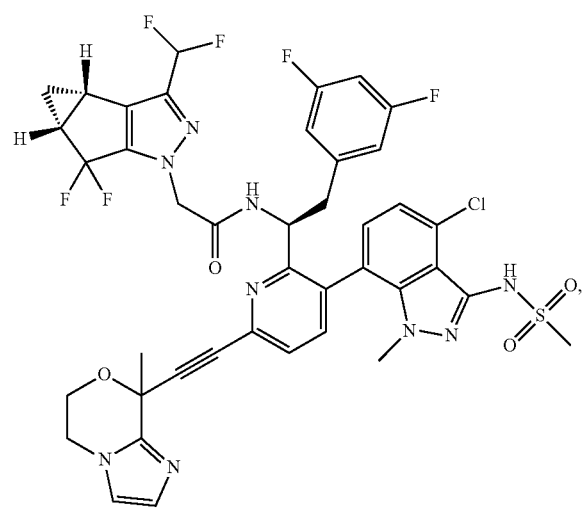
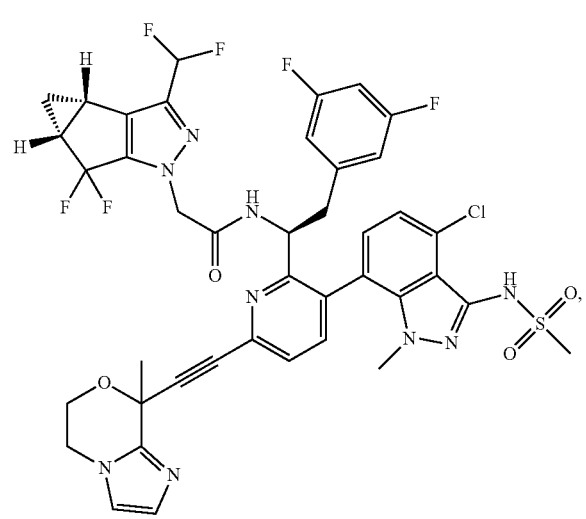
360
-continued
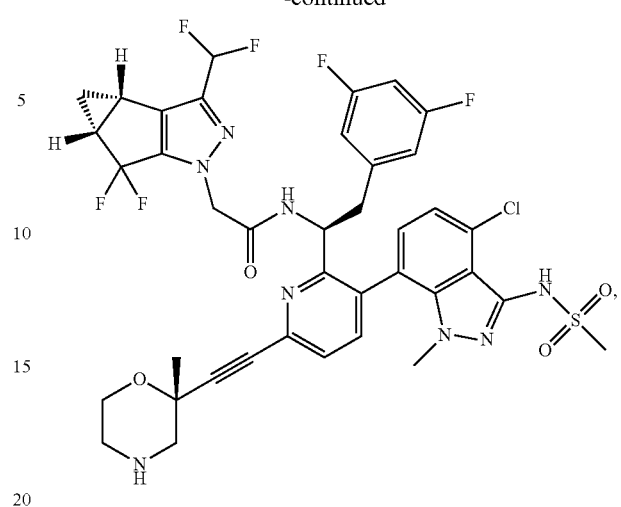
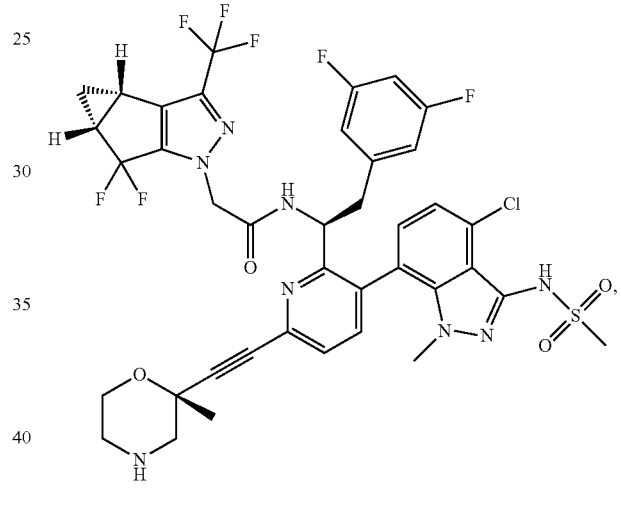
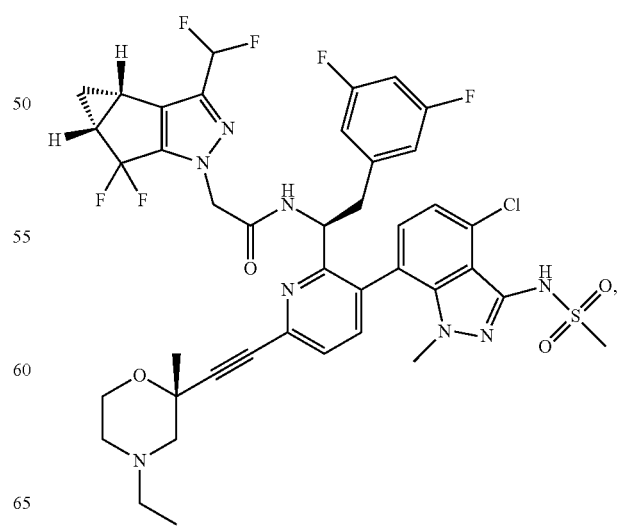

361
-continued
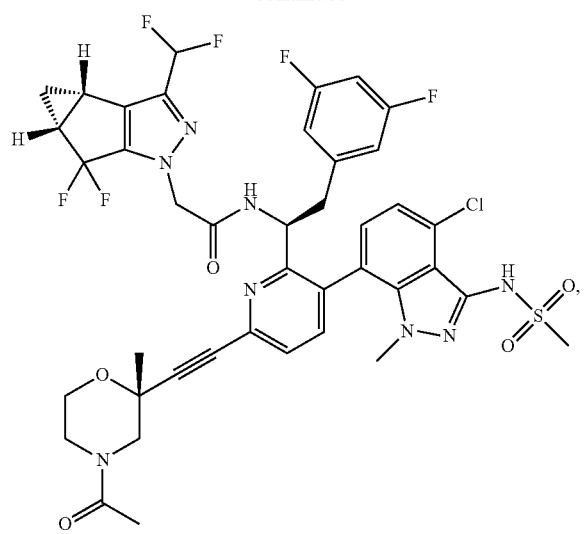
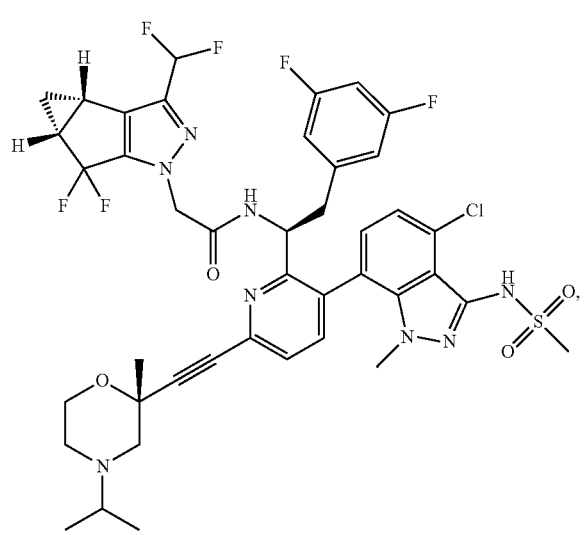
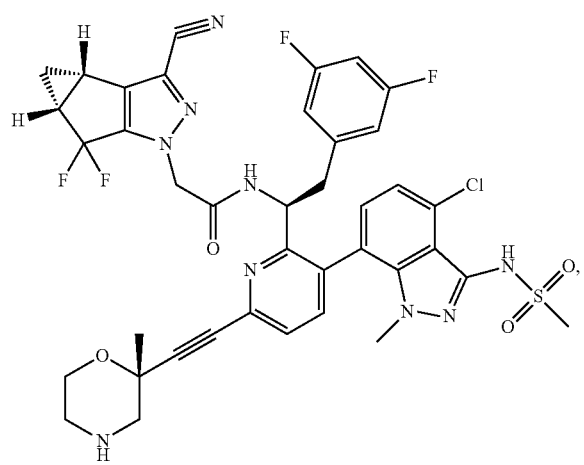
362
-continued
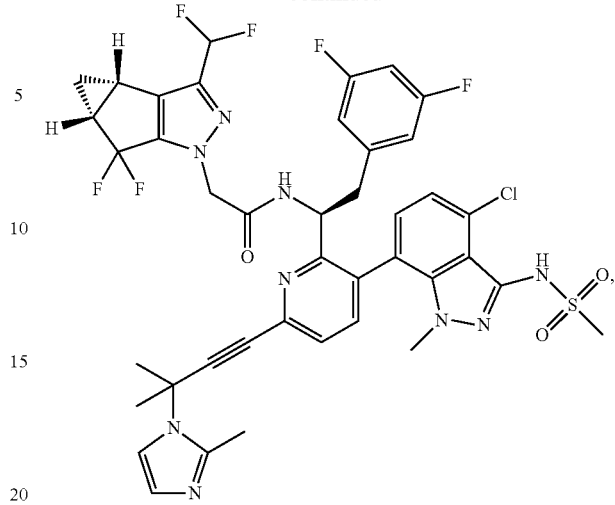
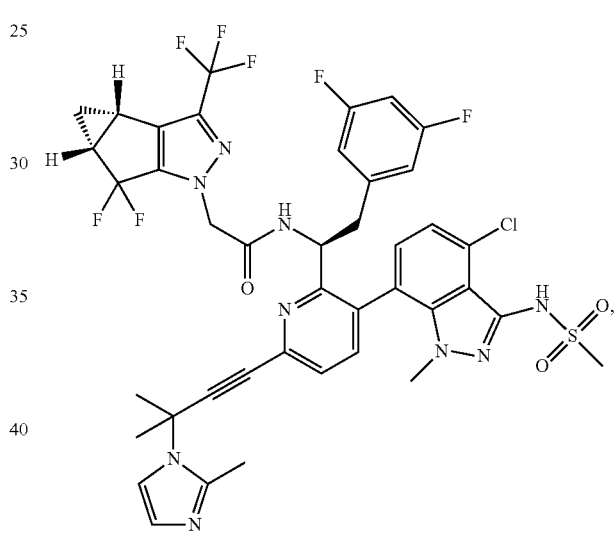
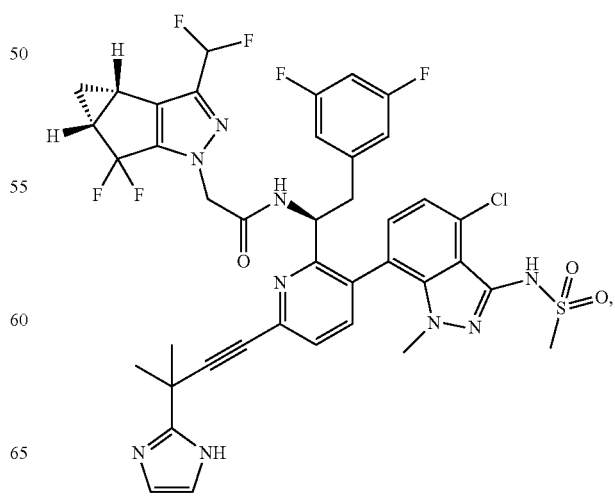

363
-continued
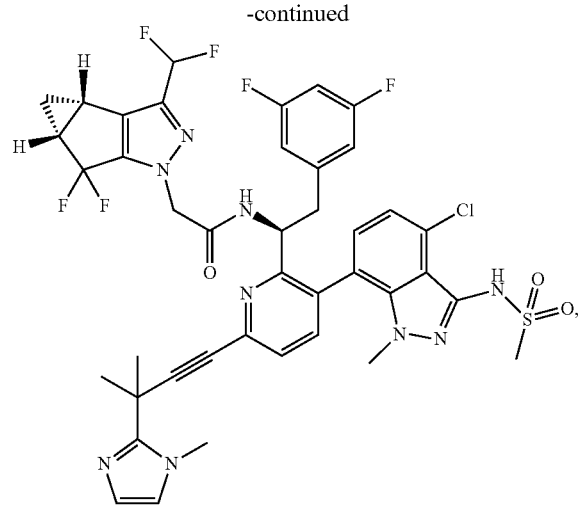
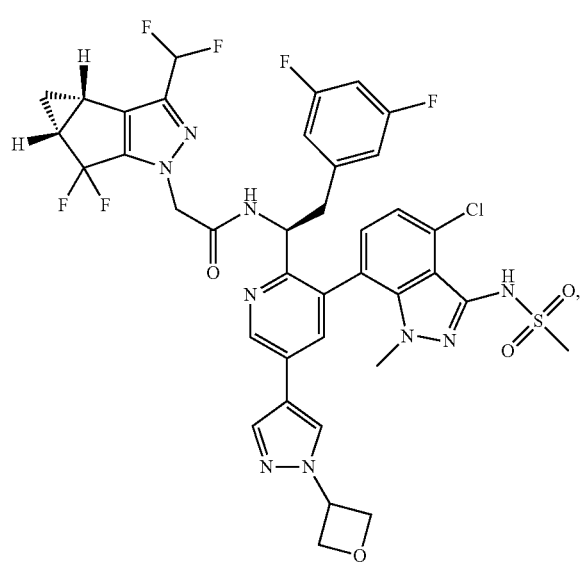
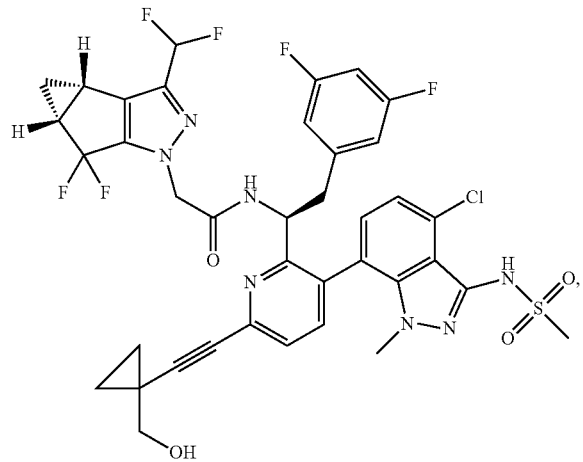
364
-continued
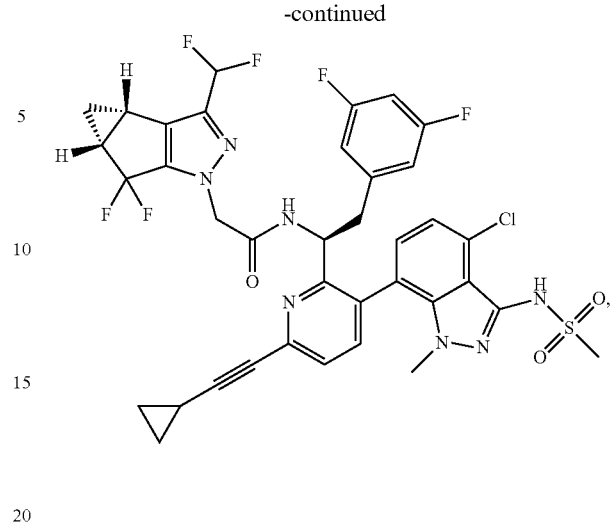
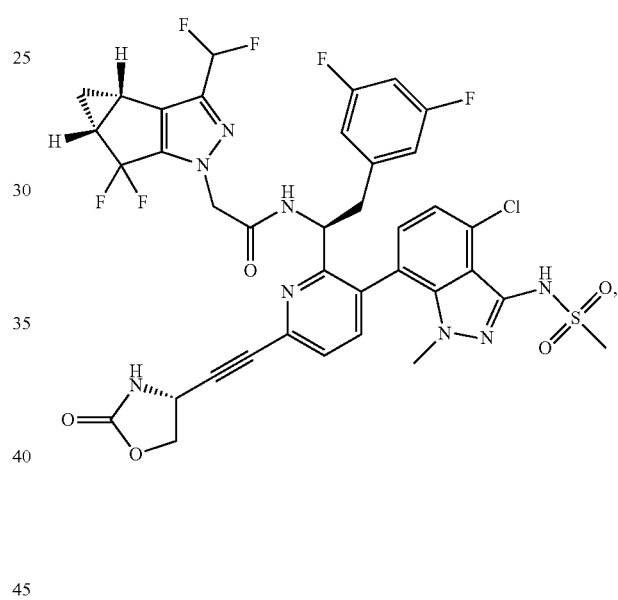
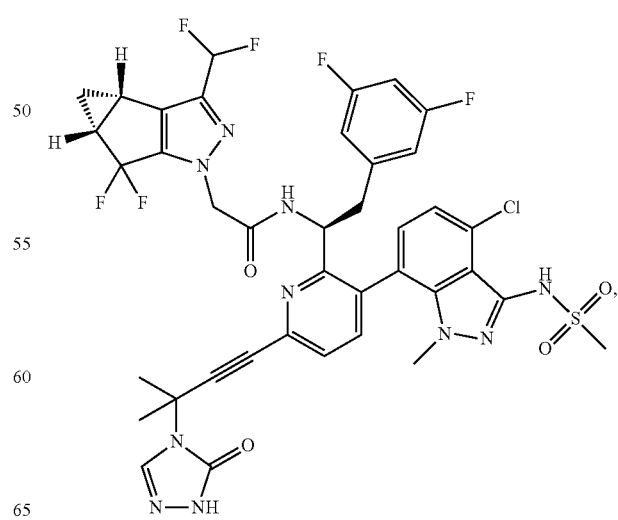

365
-continued

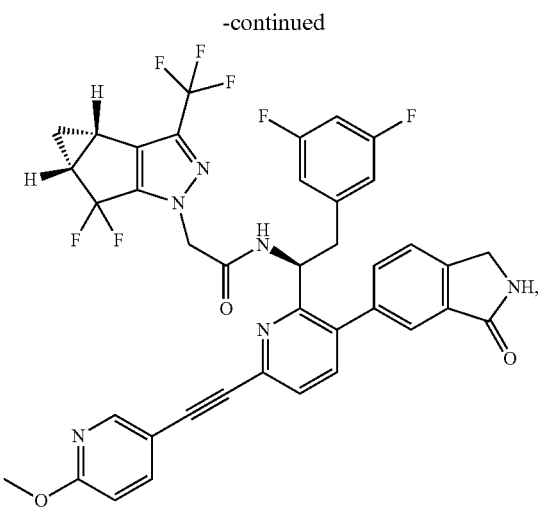

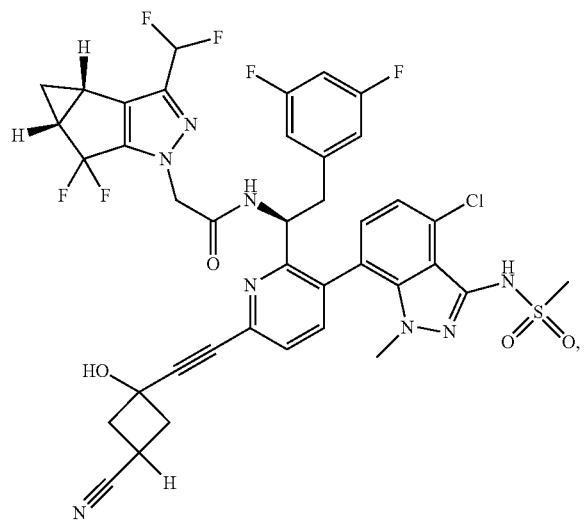

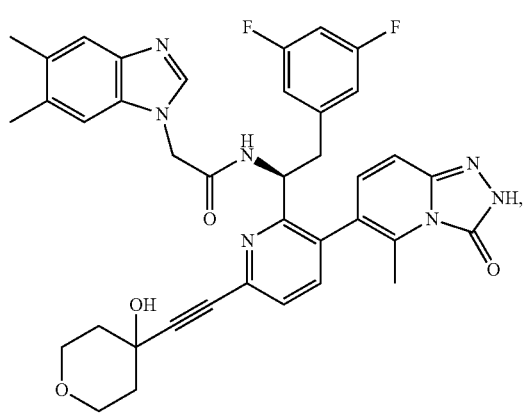

366
-continued

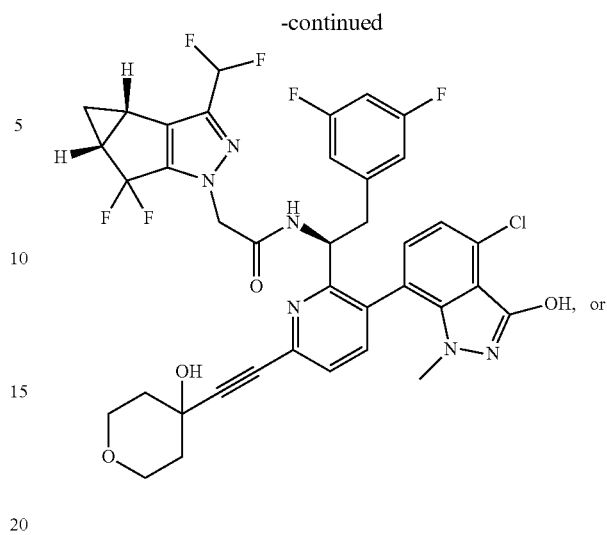

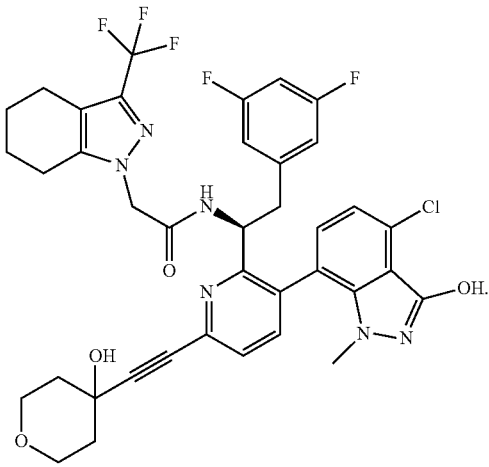

37. A pharmaceutical composition comprising a compound of claim 1, or a pharmaceutically acceptable salt thereof, and a pharmaceutically acceptable carrier.

38. A pharmaceutical composition comprising a compound of claim 1, or a pharmaceutically acceptable salt thereof, and an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor and combinations thereof.

39. A method for treating a HIV infection in a patient having a HIV infection comprising administering a therapeutically effective amount of a compound of claim 1, or a pharmaceutically acceptable salt thereof, to the patient.

40. A method for treating an HIV infection in a patient having a HIV infection comprising administering to the patient a therapeutically effective amount of a compound of claim 1, or a pharmaceutically acceptable salt thereof, in combination with a therapeutically effective amount of an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor and combinations thereof.

\* \* \* \* \*